United States Patent
Davies et al.

(10) Patent No.: US 10,144,731 B2
(45) Date of Patent: Dec. 4, 2018

(54) NRF2 REGULATORS

(71) Applicants: GlaxoSmithKline Intellectual Property Development Limited, Brentford, Middlesex (TW); Astex Therapeutics, Ltd, Milton Road, Cambridge (GB)

(72) Inventors: Thomas Glanmor Davies, Cambridgeshire (GB); Alison Jo-anne Woolford, Cambridgeshire (GB); Hendrika Maria Gerarda Willems, Cambridgeshire (GB); David Norton, Cambridgeshire (GB); Thomas Daniel Heightman, Cambridgeshire (GB); Jeffrey K. Kerns, King of Prussia, PA (US)

(73) Assignees: GlaxoSmithKline Intellectual Property Development Limited, Brentford, Middlesex (GB); Astex Therapeutics, Ltd, Cambridge (GB)

( * ) Notice: Subject to any disclaimer, the term of this patent is extended or adjusted under 35 U.S.C. 154(b) by 0 days.

(21) Appl. No.: 15/105,306

(22) PCT Filed: Dec. 17, 2014

(86) PCT No.: PCT/IB2014/067027
§ 371 (c)(1),
(2) Date: Jun. 16, 2016

(87) PCT Pub. No.: WO2015/092713
PCT Pub. Date: Jun. 25, 2015

(65) Prior Publication Data
US 2016/0318917 A1    Nov. 3, 2016

Related U.S. Application Data

(60) Provisional application No. 61/980,091, filed on Apr. 16, 2014, provisional application No. 61/917,466, filed on Dec. 18, 2013.

(51) Int. Cl.
| | |
|---|---|
| *C07D 249/18* | (2006.01) |
| *C07D 417/10* | (2006.01) |
| *C07D 281/02* | (2006.01) |
| *C07D 291/08* | (2006.01) |
| *C07D 401/12* | (2006.01) |
| *C07D 403/12* | (2006.01) |
| *C07D 405/12* | (2006.01) |
| *C07D 417/14* | (2006.01) |
| *C07D 419/10* | (2006.01) |
| *C07D 419/14* | (2006.01) |
| *C07D 471/04* | (2006.01) |
| *C07D 513/04* | (2006.01) |
| *C07D 515/04* | (2006.01) |

(52) U.S. Cl.
CPC .......... *C07D 417/10* (2013.01); *C07D 249/18* (2013.01); *C07D 281/02* (2013.01); *C07D 291/08* (2013.01); *C07D 401/12* (2013.01); *C07D 403/12* (2013.01); *C07D 405/12* (2013.01); *C07D 417/14* (2013.01); *C07D 419/10* (2013.01); *C07D 419/14* (2013.01); *C07D 471/04* (2013.01); *C07D 513/04* (2013.01); *C07D 515/04* (2013.01)

(58) Field of Classification Search
None
See application file for complete search history.

(56) References Cited

U.S. PATENT DOCUMENTS

| | | |
|---|---|---|
| 2003/0191115 A1 | 10/2003 | Pinto et al. |
| 2004/0157919 A1 | 8/2004 | Wu et al. |
| 2015/0018422 A1 | 1/2015 | Miwatashi et al. |

FOREIGN PATENT DOCUMENTS

| | | |
|---|---|---|
| EP | 478328 | 9/1991 |
| EP | 528586 | 8/1992 |
| JP | WO 93/12075 | 12/1991 |
| JP | WO 2001/25181 | 4/2001 |
| JP | WO 2001/53267 | 7/2001 |
| JP | WO 2002/80899 | 10/2002 |
| JP | WO 2002/100812 | 12/2002 |
| JP | WO 2004/07464 | 1/2004 |
| JP | WO 2006/118320 | 11/2006 |
| WO | WO 95/32710 | 12/1995 |
| WO | WO 2002/59080 | 8/2002 |
| WO | WO 2003/26652 | 4/2003 |
| WO | WO 2006/44133 | 4/2006 |
| WO | WO 2008/2490 | 1/2008 |
| WO | WO 2010/05922 | 1/2010 |
| WO | WO 2011/97300 | 8/2011 |
| WO | WO 2012/68589 | 5/2012 |
| WO | WO 2013/067036 A | 5/2013 |
| WO | WO 2013/122028 | 8/2013 |
| WO | WO 2013/155528 | 10/2013 |

*Primary Examiner* — Svetlana M Ivanova
(74) *Attorney, Agent, or Firm* — Nora L. Stein; Edward R. Gimmi

(57) ABSTRACT

The present invention relates to bis aryl analogs, pharmaceutical compositions containing them and their use as Nrf2 regulators.

12 Claims, No Drawings

NRF2 REGULATORS

This application is a 371 national phase entry of International Application No. PCT/IB2014/067027, filed Dec. 17, 2014, which claims the benefit of U.S. Provisional Application No. 61/980,091, filed Apr. 16, 2014 and U.S. Provisional Application No. 61/917,466, filed Dec. 18, 2013, which is incorporated herein in their entirety.

FIELD OF THE INVENTION

The present invention relates to bis aryl analogs, pharmaceutical compositions containing them and their use as Nrf2 regulators.

BACKGROUND OF THE INVENTION

Nrf2 (NF-E2 related factor 2) is a member of the cap-n-collar (CNC) family of transcription factors containing a characteristic basic-leucine zipper motif. Under basal conditions, Nrf2 levels are tightly controlled by the cytosolic actin-bound repressor, KEAP1 (Kelch-like ECH associating protein 1), which binds to Nrf2 and targets it for ubiquitylation and proteasomal degradation via the Cul3-based E3-ubiquitin ligase complex. Under conditions of oxidative stress, DJ1 (PARK7) is activated and stabilizes Nrf2 protein by preventing Nrf2 from interacting with KEAP1. Also, modification of reactive cysteines on KEAP1 can cause a conformational change in KEAP1 that alters Nrf2 binding and promotes Nrf2 stabilization. Thus, the levels of Nrf2 in the cytosol are low in normal conditions but the system is designed to respond immediately to environmental stress by increasing Nrf2 activity.

Inappropriately low Nrf2 activity in the face of on-going oxidative stress appears to be a pathological mechanism underlying chronic obstructive pulmonary disease (COPD). This may be a result of an altered equilibrium between Nrf2 regulators with both inappropriate lack of positive regulators such as DJ1, and overabundance of negative regulators such as Keap1 and Bach1. Therefore, restoration of Nrf2 activity in the lungs of COPD patients should result in repair of the imbalance and mitigation of deleterious processes such as apoptosis of structural cells (including alveolar epithelial and endothelial cells) and inflammation. The results of these effects would be enhanced cytoprotection, preservation of lung structure, and structural repair in the COPD lung, thus slowing disease progression. Therefore, Nrf2 modulators may treat COPD (Boutten, A., et al. 2011. *Trends Mol. Med.* 17:363-371) and other respiratory diseases, including asthma and pulmonary fibrosis (Cho, H. Y., and Kleeberger, S. R. 2010. *Toxicol. Appl. Pharmacol.* 244:43-56).

An example of inappropriately low Nrf2 activity is found in pulmonary macrophages from COPD patients. These cells have impaired bacterial phagocytosis compared with similar cells from control patients, and this effect is reversed by the addition of Nrf2 activators in vitro. Therefore, in addition to the effects mentioned above, restoration of appropriate Nrf2 activity could also rescue COPD exacerbations by reducing lung infections. This is demonstrated by the Nrf2 activator, Sulforaphane, which increases the expression of Macrophage Receptor with Collagenous structure (MARCO) by COPD macrophages and alveolar macrophages from cigarette smoke-exposed mice, thereby improving in these cells bacterial phagocytosis (*Pseudomonas aeruginosa*, non-typable *Haemophilus influenzae*) and bacterial clearance both ex vivo and in vivo. (Harvey, C. J., et al. 2011. *Sci. Transl. Med.* 3:78ra32).

The therapeutic potential of targeting Nrf2 in the lung is not limited to COPD. Rather, targeting the Nrf2 pathway could provide treatments for other human lung and respiratory diseases that exhibit oxidative stress components such as chronic and acute asthma, lung disease secondary to environmental exposures including but not limited to ozone, diesel exhaust and occupational exposures, fibrosis, acute lung infection (e.g., viral (Noah, T. L. et al. 2014. PLoS ONE 9(6): e98671), bacterial or fungal), chronic lung infection, α1 antitrypsin disease, and cystic fibrosis (C F, Chen, J. et al. 2008. *PLoS One.* 2008; 3(10):e3367).

A therapy that targets the Nrf2 pathway also has many potential uses outside the lung and respiratory system. Many of the diseases for which an Nrf2 activator may be useful are autoimmune diseases (psoriasis, IBD, MS), suggesting that an Nrf2 activator may be useful in autoimmune diseases in general.

In the clinic, a drug targeting the Nrf2 pathway (bardoxolone methyl) has shown efficacy in diabetic patients with diabetic nephropathy/chronic kidney disease (CKD) (Aleksunes, L. M., et al. 2010. *J. Pharmacol. Exp. Ther.* 335:2-12), though phase III trials with this drug in patients with the most severe stage of CKD were terminated. Furthermore, there is evidence to suspect that such a therapy would be effective in sepsis-induced acute kidney injury, other acute kidney injury (AKI) (Shelton, L. M., et al. 2013. *Kidney International.* 84(6), 1090-1095), and kidney disease or malfunction seen during kidney transplantation.

In the cardiac area, bardoxolone methyl is currently under investigation in patients with Pulmonary Arterial Hypertension and so a drug targeting Nrf2 by other mechanisms may also be useful in this disease. Also, it may be useful in a variety of cardiovascular diseases including but not limited to atherosclerosis, hypertension, and heart failure (Oxidative Medicine and Cellular Longevity Volume 2013 (2013), Article ID 104308, 10 pages).

A drug activating the Nrf2 pathway could also be useful for treatment of several neurodegenerative diseases including Parkinson's disease (PD), Alzheimer's disease (AD), amyotrophic lateral sclerosis (ALS) (Brain Res. 2012 Mar. 29; 1446:109-18. 2011.12.064. Epub 2012 Jan. 12.), autism (Singh, K., et al. 2014. *Proc Natl Acad Sci USA* 111(43): 15550-15555.), and multiple sclerosis (MS). Multiple in vivo models have shown that Nrf2 KO mice are more sensitive to neurotoxic insults than their wild-type counterparts. Treatment of rats with the Nrf2 activator tert-butylhydroquinone (tBHQ) reduced cortical damage in rats in a cerebral ischemia-reperfusion model, and cortical glutathione levels were increased in Nrf2 wild-type but not KO mice after administration of tBHQ (Shih, A. Y., et al. 2005. *J. Neurosci.* 25: 10321-10335). Tecfidera™ (dimethyl fumarate), which activates Nrf2 among other targets, is approved in the U.S. to treat relapsing-remitting multiple sclerosis (MS). Activation of Nrf2 may also help treat cases of Friedreich's Ataxia, where increased sensitivity to oxidative stress and impaired Nrf2 activation has been reported (Paupe V., et al, 2009. PLoS One; 4(1):e4253.

There is preclinical evidence of the specific protective role of the Nrf2 pathway in models of inflammatory bowel disease (IBD, Crohn's Disease and Ulcerative Colitis) and/or colon cancer (Khor, T. O., et al 2008. *Cancer Prev. Res.* (*Phila*) 1:187-191).

Age-related macular degeneration (AMD) is a common cause of vision loss in people over the age of 50. Cigarette smoking is a major risk factor for the development of non-neovascular (dry) AMD and perhaps also neovascular (wet) AMD. Findings in vitro and in preclinical species support the notion that the Nrf2 pathway is involved in the antioxidant response of retinal epithelial cells and modulation of inflammation in pre-clinical models of eye injury (Schimel, et al. 2011. *Am. J. Pathol.* 178:2032-2043). Fuchs Endothelial Corneal Dystrophy (FECD) is a progressive, blinding disease characterized by corneal endothelial cells apoptosis. It is a disease of aging and increased oxidative stress related to low levels of Nrf2 expression and/or function (Bitar, M. S., et al. 2012. *Invest Ophthalmol. Vis. Sci. Aug.* 24, 2012 vol. 53 no. 9 5806-5813). In addition, an Nrf2 activator may be useful in uveitis or other inflammatory eye conditions.

Nonalcoholic steatohepatitis (NASH) is a disease of fat deposition, inflammation, and damage in the liver that occurs in patients who drink little or no alcohol. In pre-clinical models, development of NASH is greatly accelerated in KO mice lacking Nrf2 when challenged with a methionine- and choline-deficient diet (Chowdhry S., et al. 2010. *Free Rad. Biol. & Med.* 48:357-371). Administration of the Nrf2 activators oltipraz and NK-252 in rats on a choline-deficient L-amino acid-defined diet significantly attenuated progression of histologic abnormalities, especially hepatic fibrosis (Shimozono R. et al. 2012. *Molecular Pharmacology.* 84:62-70). Other liver diseases that may be amenable to Nrf2 modulation are toxin-induced liver disease (e.g., acetaminophen-induced hepatic disease), viral hepatitis, and cirrhosis (Oxidative Medicine and Cellular Longevity Volume 2013 (2013), Article ID 763257, 9 page).

Recent studies have also begun to elucidate the role of ROS in skin diseases such as psoriasis. A study in psoriasis patients showed an increase in serum malondialdehyde and nitric oxide end products and a decrease in erythrocyte-superoxide dismutase activity, catalase activity, and total antioxidant status that correlated in each case with disease severity index (Dipali P. K., et al. Indian J Clin Biochem. 2010 October; 25(4): 388-392). Also, an Nrf2 modulator may be useful in treating the dermatitis/topical effects of radiation (Schäfer, M. et al. 2010. *Genes & Devl.* 24:1045-1058), and the immunosuppression due to radiation exposure (Kim J H et al, J. Clin. Invest. 2014 Feb. 3; 124(2): 730-41).

There are also data suggesting that an Nrf2 activator may be beneficial in preeclampsia, a disease that occurs in 2-5% of pregnancies and involves hypertension and proteinuria (*Annals of Anatomy—Anatomischer Anzeiger Volume* 196, Issue 5, September 2014, Pages 268-277).

Preclinical data has shown that compounds with Nrf2 activating activity are better at reversing high altitude-induced damage than compounds without Nrf2 activity, using animal and cellular models of Acute Mountain Sickness (Lisk C. et al, 2013, Free Radic Biol Med. October 2013; 63: 264-273.)

SUMMARY OF THE INVENTION

In one aspect this invention provides for the compounds of Formula (I), pharmaceutically acceptable salts thereof, and pharmaceutical compositions containing them.

In a second aspect, this invention provides for the use of the compounds of Formula (I) as Nrf2 regulators.

In another aspect, this invention provides for the use of the compounds of Formula (I) for treating and preventing conditions associated with Nrf2 imbalance.

In a further aspect, this invention provides for a method of treating respiratory and non-respiratory disorders, including COPD, asthma, fibrosis, chronic and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, Parkinson's disease (PD), Alzheimer's disease (AD), autism, Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Nonalcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness, which comprises administering to a human in need thereof, a compound of formula (I).

In yet another aspect, this invention provides for the use of the compounds of Formula (I) for the treatment of respiratory and non-respiratory disorders, including COPD, asthma, fibrosis, chronic and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, Parkinson's disease (PD), Alzheimer's disease (AD), autism, Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Nonalcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In a further aspect, this invention relates to use of a compound of Formula (I) or a pharmaceutically acceptable salt thereof in the manufacture of a medicament for the treatment of respiratory and non-respiratory disorders, including COPD, asthma, fibrosis, chronic and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, Parkinson's disease (PD), Alzheimer's disease (AD), autism, Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Nonalcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In a further aspect, this invention relates to a compound of formula (I) or a pharmaceutically acceptable salt thereof, for use in medical therapy.

In a further aspect, this invention relates to a compound of formula (I) or a pharmaceutically acceptable salt thereof, for use in the treatment of respiratory and non-respiratory disorders, including COPD, asthma, fibrosis, chronic and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, Parkinson's disease (PD), Alzheimer's disease (AD), autism, Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Nonalcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In a further aspect, this invention relates to a compound of formula (I) or a pharmaceutically acceptable salt thereof, for use in the treatment COPD.

The compounds of formula (I) and pharmaceutically acceptable salts thereof may be used in combination with one or more other agents which may be useful in the prevention or treatment of allergic disease, inflammatory disease, autoimmune disease, for example; antigen immunotherapy, anti-histamines, corticosteroids, (eg fluticasone propionate, fluticasone furoate, beclomethasone dipropionate, budesonide, ciclesonide, mometasone furoate, triamcinolone, flunisolide), NSAIDs, leukotriene modulators (e.g. montelukast, zafirlukast, pranlukast), iNOS inhibitors, tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g. sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

The compounds may also be used in combination with agents for aiding transplantation including Cyclosporines, Tacrolimus, Mycophenolate mofetil, Prednisone, Azathioprine, Sirolimus, Daclizumab, Basiliximab, or OKT3.

They may also be used in combination with agents for Diabetes: metformin (biguanides), meglitinides, sulfonylureas, DPP-4 inhibitors, Thiazolidinediones, Alpha-glucosidase inhibitors, Amylin mimetics, Incretin mimetics, insulin.

The compounds may be used in combination with antihypertensives such as diuretics, ACE inhibitors, ARBS, calcium channel blockers, and beta blockers.

Other aspects and advantages of the present invention are described further in the following detailed description of the preferred embodiments thereof.

DETAILED DESCRIPTION OF THE INVENTION

The present invention provides for compounds of Formula (I):

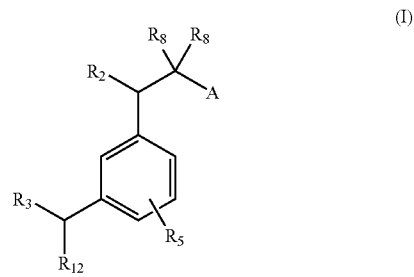

wherein:
A is —C(O)OR$_1$ or tetrazolyl;
R$_1$ is hydrogen, —CH$_2$C(O)N(R$_7$)$_2$, —CH$_2$-(4-methyl-1,3-dioxol-2-one), —C$_{2-3}$ alkyl-OH, C$_{1-3}$ alkyl, —C$_{2-5}$ alkyl-N(R$_7$)$_2$, —(CH$_2$)$_n$-morpholinyl, —(CH$_2$)$_n$-furyl, —CH$_2$—O—C(O)—C$_{1-5}$ alkyl, —(CH$_2$)$_n$-imidazolyl, —(CH$_2$)$_n$-pyrrolidinyl, —(CH$_2$)$_n$-piperidyl, or 2-oxotetrahydrofuran-3-yl; wherein the morpholinyl and piperidyl may be substituted by one or two C$_{1-3}$ alkyl; and the pyrrolidinyl, imidazolyl, and furyl may be substituted by one or two groups independently selected from C$_{1-3}$ alkyl, halo, and —O—C$_{1-3}$ alkyl;
R$_2$ is:
—(CH$_2$)$_n$-phenyl, which may be substituted by one, two, or three groups independently selected from —CN, —F, —Cl, —C(O)N(R$_7$)$_2$, —O(O)OH, —C(O)CH$_3$, —O—C$_{1-3}$ alkyl, —S—C$_{1-3}$ alkyl, C$_{1-3}$ alkyl, —C$_{1-3}$ alkyl-N(R$_7$)$_2$, —CF$_3$, and —OCF$_3$;
benzotriazolyl, which may be substituted by one, two, or three groups independently selected from —O—C$_{1-3}$ alkyl, —F, —Cl, —CF$_3$, —OCF$_3$, C$_{1-3}$ alkyl, and —C$_{2-3}$ alkyl-NH—C(O)—O—C$_{1-4}$ alkyl, or may be substituted by R$_{13}$ and optionally by one or two additional groups independently selected from —O—C$_{1-3}$ alkyl, —F, —Cl, —CF$_3$, —OCF$_3$, and C$_{1-3}$ alkyl;
—(CH$_2$)$_n$-triazolyl, which may be substituted by one or two groups independently selected from C$_{1-3}$ alkyl and —CH$_2$-phenyl;
—C$_{3-6}$ cycloalkyl-triazolyl, which may be substituted by one or two groups independently selected from C$_{1-3}$ alkyl and —CH$_2$-phenyl;
—(CH$_2$)$_n$-imidazolyl, which may be substituted by one or two groups independently selected from C$_{1-3}$ alkyl and —CH$_2$-phenyl;
—(CH$_2$)$_n$-pyrazolyl, which may be substituted by one or two groups independently selected from C$_{1-3}$ alkyl and —CH$_2$-phenyl;
dihydroindenyl, which may be substituted by one, two, or three groups independently selected from C$_{1-3}$ alkyl, —F, —OCH$_3$, and =O;
isoindolinyl, which may be substituted by one, two, or three groups independently selected from C$_{1-3}$ alkyl, —F, —OCH$_3$, and =O;

—(CH$_2$)$_n$-pyridyl, which may be substituted by one, two, or three groups independently selected from C$_{1-3}$ alkyl, —F, —OCH$_3$, and =O;

triazolopyridyl, which may be substituted by one or two groups independently selected from —O—C$_{1-3}$ alkyl, —F, and C$_{1-3}$ alkyl;

tetrazolopyridyl, which may be substituted by —O—C$_{1-3}$ alkyl, —F, or C$_{1-3}$ alkyl;

1,2,3,4-tetrahydroisoquinolinyl, which may be substituted by one or two groups independently selected from —O—C$_{1-3}$ alkyl, —F, —Cl, —CF$_3$, —OCF$_3$, and C$_{1-3}$ alkyl;

C$_{1-6}$ alkyl, —(CH$_2$)$_n$—C$_{3-6}$ cycloalkyl, —C$_{1-3}$ alkyl-O—C$_{1-3}$ alkyl, or —C$_{1-3}$ alkyl-C(O)N(R$_{14}$)$_2$;

R$_3$ is R$_4$—SO$_2$—N(R$_6$)—;

R$_4$ is phenyl, C$_{5-6}$ cycloalkyl, thienyl, imidazolyl, pyrazolyl, pyridyl, piperidyl, tetrahydro-2H-pyranyl, C$_{1-3}$ alkyl, or

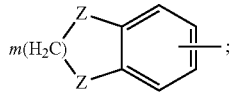

each of which may be substituted by one or two groups independently selected from C$_{1-3}$ alkyl, —NH—C(O)—CH$_3$, —O—C$_{1-3}$alkyl, —C(O)—CH$_3$, =O, and OH;

or R$_3$ is

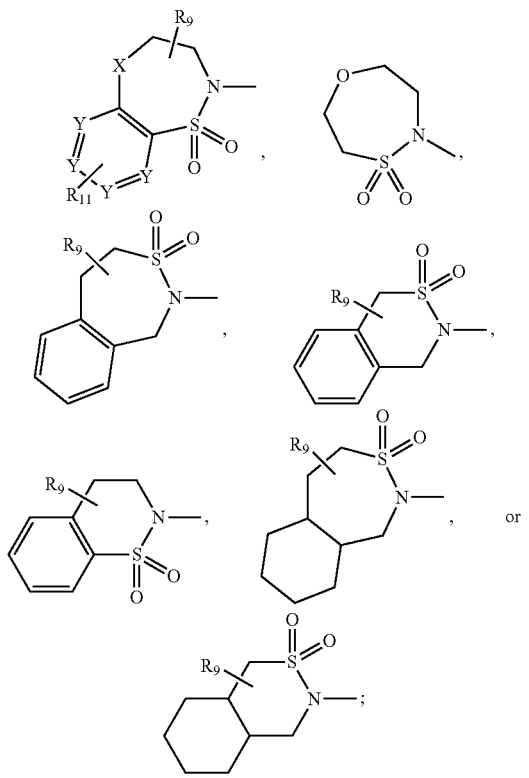

X is CH$_2$, NR$_9$ or O;
each Y is independently N or CH; provided that not more than one Y is N;
each Z is independently O, CH$_2$, or NR$_{10}$;
R$_5$ is hydrogen, —F, —Cl, C$_{1-3}$ alkyl, or —CF$_3$;
R$_6$ is hydrogen, C$_{1-3}$ alkyl, or —C$_{2-3}$ alkyl-OH;

each R$_7$ is independently hydrogen or C$_{1-3}$ alkyl;
each R$_8$ is independently hydrogen, —NH$_2$, or C$_{1-3}$ alkyl, provided that at least one R$_8$ is hydrogen or C$_{1-3}$ alkyl;
each R$_9$ is independently hydrogen or C$_{1-3}$ alkyl;
or R$_9$ and R$_{13}$ taken together represent —CH$_2$—CH=CH—(CH$_2$)$_2$— or —(CH$_2$)$_5$—;
R$_{10}$ is —C(O)—CH$_3$;
R$_{11}$ is hydrogen, halo, —CF$_3$, —CN, —C(O)N(R$_7$)$_2$, —C$_{1-3}$ alkyl-N(R$_7$)$_2$, or —C$_{1-3}$ alkyl-NH—C(O)—O—C$_{1-4}$ alkyl;
R$_{12}$ is hydrogen;
or R$_5$ and R$_{12}$ taken together represent —CH$_2$CH$_2$—;
each R$_{14}$ is independently hydrogen, C$_{1-3}$ alkyl, or —CH$_2$-phenyl;
each n is independently 0, 1, 2, or 3; and
m is 1 or 2;
or a pharmaceutically acceptable salt thereof.

"Alkyl" refers to a monovalent saturated hydrocarbon chain having the specified number of carbon member atoms. For example, C$_{1-4}$ alkyl refers to an alkyl group having from 1 to 4 carbon member atoms. Alkyl groups may be straight or branched. Representative branched alkyl groups have one, two, or three branches. Alkyl includes but is not limited to methyl, ethyl, propyl (n-propyl and isopropyl), and butyl (n-butyl, isobutyl, s-butyl, and t-butyl).

"Cycloalkyl" refers to a monovalent saturated or unsaturated hydrocarbon ring having the specified number of carbon member atoms. For example, C$_{3-6}$ cycloalkyl refers to a cycloalkyl group having from 3 to 6 carbon member atoms. Unsaturated cycloalkyl groups have one or more carbon-carbon double bonds within the ring. Cycloalkyl groups are not aromatic. Cycloalkyl includes but is not limited to cyclopropyl, cyclopropenyl, cyclobutyl, cyclobutenyl, cyclopentyl, cyclopentenyl, cyclohexyl, and cyclohexenyl.

When used herein, the terms 'halogen' and 'halo' include fluorine, chlorine, bromine and iodine, and fluoro, chloro, bromo, and iodo, respectively.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

The term "independently" means that where more than one substituent is selected from a number of possible substituents, those substituents may be the same or different. That is, each substituent is separately selected from the entire group of recited possible substituents.

The invention also includes various isomers of the compounds of Formula (I) and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers). The compounds according to Formula (I) contain one or more asymmetric centers, also referred to as chiral centers, and may, therefore, exist as individual enantiomers, diastereomers, or other stereoisomeric forms, or as mixtures thereof. All such isomeric forms are included within the present invention, including mixtures thereof.

Chiral centers may also be present in a substituent such as an alkyl group. Where the stereochemistry of a chiral center present in Formula (I), or in any chemical structure illustrated herein, is not specified the structure is intended to encompass any stereoisomer and all mixtures thereof. Thus, compounds according to Formula (I) containing one or more chiral centers may be used as racemic mixtures, enantiomerically enriched mixtures, or as enantiomerically pure individual stereoisomers.

Individual stereoisomers of a compound according to Formula (I) which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

As used herein, "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The skilled artisan will appreciate that pharmaceutically acceptable salts of the compounds according to Formula (I) may be prepared. These pharmaceutically acceptable salts may be prepared in situ during the final isolation and purification of the compound, or by separately treating the purified compound in its free acid or free base form with a suitable base or acid, respectively.

In certain embodiments, compounds according to Formula (I) may contain an acidic functional group and are, therefore, capable of forming pharmaceutically acceptable base addition salts by treatment with a suitable base. Examples of such bases include a) hydroxides, carbonates, and bicarbonates of sodium, potassium, lithium, calcium, magnesium, aluminum, and zinc; and b) primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically acceptable acid addition salts by treatment with a suitable acid. Suitable acids include pharmaceutically acceptable inorganic acids and organic acids. Representative pharmaceutically acceptable acids include hydrogen chloride, hydrogen bromide, nitric acid, sulfuric acid, sulfonic acid, phosphoric acid, acetic acid, hydroxyacetic acid, phenylacetic acid, propionic acid, butyric acid, valeric acid, maleic acid, acrylic acid, fumaric acid, succinic acid, malic acid, malonic acid, tartaric acid, citric acid, salicylic acid, benzoic acid, tannic acid, formic acid, stearic acid, lactic acid, ascorbic acid, methylsulfonic acid, p-toluenesulfonic acid, oleic acid, lauric acid, and the like.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed from crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and hence, may be preferred in some circumstances. Isotopically labeled compounds of Formula (I) and following of this invention can generally be prepared by carrying out the procedures disclosed in the Schemes and/or in the Examples below, by substituting a readily available isotopically labeled reagent for a non-isotopically labeled reagent.

Representative Embodiments

In one embodiment:

A is —C(O)OR$_1$ or tetrazolyl;

R$_1$ is hydrogen, —CH$_2$C(O)N(R$_7$)$_2$, —CH$_2$-(4-methyl-1,3-dioxol-2-one), —C$_{2-3}$ alkyl-OH, C$_{1-3}$ alkyl, —C$_{2-5}$ alkyl-N(R$_7$)$_2$, —(CH$_2$)$_n$-morpholinyl, —(CH$_2$)$_n$-furyl, —CH$_2$—O—C(O)—C$_{1-5}$ alkyl, —(CH$_2$)$_n$-imidazolyl, —(CH$_2$)$_n$-pyrrolidinyl, —(CH$_2$)$_n$-piperidyl, or 2-oxotetrahydrofuran-3-yl; wherein the morpholinyl and piperidyl may be substituted by one or two C$_{1-3}$ alkyl; and the pyrrolidinyl, imidazolyl, and furyl may be substituted by one or two groups independently selected from C$_{1-3}$ alkyl, halo, and —O—C$_{1-3}$ alkyl;

R$_2$ is:

—(CH$_2$)$_n$-phenyl, which may be substituted by one, two, or three groups independently selected from —CN, —F, —Cl, —C(O)N(R$_7$)$_2$, —C(O)OH, —C(O)CH$_3$, —O—C$_{1-3}$ alkyl, —S—C$_{1-3}$ alkyl, C$_{1-3}$ alkyl, —C$_{1-3}$ alkyl-N(R$_7$)$_2$, —CF$_3$, and —OCF$_3$;

benzotriazolyl, which may be substituted by one, two, or three groups independently selected from —O—C$_{1-3}$ alkyl, —F, —Cl, —CF$_3$, —OCF$_3$, C$_{1-3}$ alkyl, and —C$_{2-3}$ alkyl-NH—C(O)—O—C$_{1-4}$ alkyl, or may be substituted by R$_{13}$ and optionally by one or two additional groups independently selected from —O—C$_{1-3}$ alkyl, —F, —Cl, —CF$_3$, —OCF$_3$, and C$_{1-3}$ alkyl;

—(CH$_2$)$_n$-triazolyl, which may be substituted by one or two groups independently selected from C$_{1-3}$ alkyl and —CH$_2$-phenyl;

—C$_{3-6}$ cycloalkyl-triazolyl, which may be substituted by one or two groups independently selected from C$_{1-3}$ alkyl and —CH$_2$-phenyl;

—(CH$_2$)$_n$-imidazolyl, which may be substituted by one or two groups independently selected from C$_{1-3}$ alkyl and —CH$_2$-phenyl;

—(CH$_2$)$_n$-pyrazolyl, which may be substituted by one or two groups independently selected from C$_{1-3}$ alkyl and —CH$_2$-phenyl;

dihydroindenyl, which may be substituted by one, two, or three groups independently selected from C$_{1-3}$ alkyl, —F, —OCH$_3$, and =O;

isoindolinyl, which may be substituted by one, two, or three groups independently selected from C$_{1-3}$ alkyl, —F, —OCH$_3$, and =O;

—(CH$_2$)$_n$-pyridyl, which may be substituted by one, two, or three groups independently selected from C$_{1-3}$ alkyl, —F, —OCH$_3$, and =O;

triazolopyridyl, which may be substituted by one or two groups independently selected from —O—C$_{1-3}$ alkyl, —F, and C$_{1-3}$ alkyl;

tetrazolopyridyl, which may be substituted by —O—C$_{1-3}$ alkyl, —F, or C$_{1-3}$ alkyl;

1,2,3,4-tetrahydroisoquinolinyl, which may be substituted by one or two groups independently selected from —O—C$_{1-3}$ alkyl, —F, —Cl, —CF$_3$, —OCF$_3$, and C$_{1-3}$ alkyl;

C$_{1-6}$ alkyl, —(CH$_2$)$_n$—C$_{3-6}$cycloalkyl, —C$_{1-3}$ alkyl-O—C$_{1-3}$ alkyl, or —C$_{1-3}$ alkyl-C(O)N(R$_{14}$)$_2$;

R$_3$ is R$_4$—SO$_2$—N(R$_6$)—;

R$_4$ is phenyl, C$_{5-6}$ cycloalkyl, thienyl, imidazolyl, pyrazolyl, pyridyl, piperidyl, tetrahydro-2H-pyranyl, C$_{1-3}$ alkyl, or

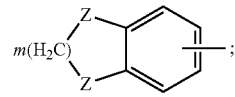

each of which may be substituted by one or two groups independently selected from C$_{1-3}$ alkyl, —NH—C(O)—CH$_3$, —O—C$_{1-3}$alkyl, —C(O)—CH$_3$, =O, and OH;

or R$_3$ is

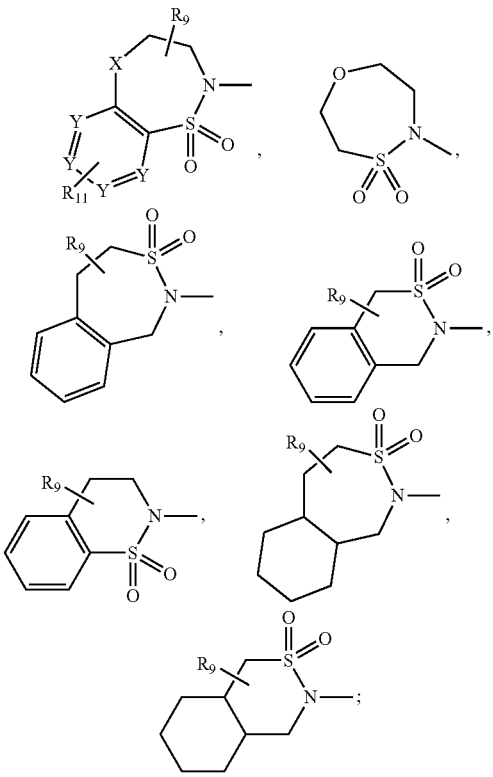

X is CH$_2$, NR$_9$ or O;

each Y is independently N or CH; provided that not more than one Y is N;

each Z is independently O, CH$_2$, or NR$_{10}$;

R$_5$ is hydrogen, —F, C$_{1-3}$ alkyl, or —CF$_3$;

R$_6$ is hydrogen, C$_{1-3}$ alkyl, or —C$_{2-3}$ alkyl-OH;

each R$_7$ is independently hydrogen or C$_{1-3}$ alkyl;

each R$_8$ is independently hydrogen, —NH$_2$, or C$_{1-3}$ alkyl, provided that at least one R$_8$ is hydrogen or C$_{1-3}$ alkyl;

each R$_9$ is independently hydrogen or C$_{1-3}$ alkyl;

or R$_9$ and R$_{13}$ taken together represent —CH$_2$—CH=CH—(CH$_2$)$_2$— or —(CH$_2$)$_5$—;

$R_{10}$ is —C(O)—CH$_3$;

$R_{11}$ is hydrogen, halo, —CF$_3$, —CN, —C(O)N(R$_7$)$_2$, —C$_{1-3}$ alkyl-N(R$_7$)$_2$, or —C$_{1-3}$ alkyl-NH—C(O)—O—C$_{1-4}$ alkyl;

$R_{12}$ is hydrogen;

or $R_5$ and $R_{12}$ taken together represent —CH$_2$CH$_2$—;

each $R_{14}$ is independently hydrogen, C$_{1-3}$ alkyl, or —CH$_2$-phenyl;

each n is independently 0, 1, 2, or 3; and m is 1 or 2;

In another embodiment A is —C(O)OR$_1$.

In another embodiment $R_1$ is hydrogen, —C$_{1-5}$ alkyl-N(R$_7$)$_2$, —(CH$_2$)$_n$-morpholinyl, —(CH$_2$)$_n$-imidazolyl, —(CH$_2$)$_n$-pyrolidinyl, or —(CH$_2$)$_n$-piperidyl. In a specific embodiment $R_1$ is hydrogen.

In another embodiment $R_2$ is:

phenyl substituted by one, two, or three groups independently selected from —CN, —F, —Cl, C$_{1-3}$ alkyl, and —O—C$_{1-3}$ alkyl;

benzotriazolyl substituted by one, two, or three groups independently selected from —O—C$_{1-3}$alkyl and C$_{1-3}$ alkyl; or —(CH$_2$)$_2$-triazolyl substituted by one or two groups independently selected from C$_{1-3}$ alkyl or —CH$_2$-phenyl;

In another embodiment $R_2$ is:

phenyl substituted with —CN, —F, —Cl, C$_{1-3}$ alkyl, or —O—C$_{1-3}$ alkyl;

benzotriazolyl substituted with —O—C$_{1-3}$alkyl or C$_{1-3}$ alkyl; or —(CH$_2$)$_2$-triazolyl substituted with C$_{1-3}$ alkyl or —CH$_2$-phenyl;

In another embodiment $R_2$ is benzotriazolyl, which may be substituted by one, two, or three groups independently selected from —O—C$_{1-3}$ alkyl, —F, —Cl, —CF$_3$, —OCF$_3$, and C$_{1-3}$ alkyl. In another embodiment $R_2$ is benzotriazolyl substituted by one or two groups independently selected from —O—C$_{1-3}$ alkyl and C$_{1-3}$ alkyl. In another embodiment $R_2$ is benzotriazolyl substituted by one or two groups which are each independently methyl, ethyl, or methoxy. In another embodiment $R_2$ is benzotriazolyl substituted by one or two groups which are each independently C$_{1-3}$ alkyl. In another embodiment $R_2$ is benzotriazolyl substituted by one or two groups which are each independently methyl or ethyl.

In another embodiment X is CH$_2$, N(CH$_3$), or O. In another embodiment X is CH$_2$ or O. In a specific embodiment X is CH$_2$. In another specific embodiment X is N(CH$_3$). In another specific embodiment X is O.

In another embodiment $R_3$ is

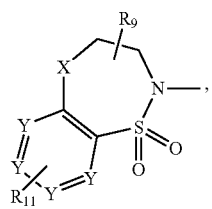

wherein X is CH$_2$, N(CH$_3$), or O and each Y is independently N or CH, provided that not more than one Y is N. In another embodiment $R_3$ is

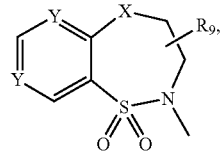

wherein X is CH$_2$ or O and each Y is independently N or CH, provided that one Y is CH.

In a specific embodiment $R_5$ is hydrogen, —F, —Cl, methyl, ethyl, or —CF$_3$. In another embodiment $R_5$ is hydrogen, —Cl, C$_{1-3}$ alkyl, or —CF$_3$. In a specific embodiment $R_5$ is —Cl, methyl, or —CF$_3$. In another embodiment $R_5$ is hydrogen or C$_{1-3}$ alkyl. In a specific embodiment $R_5$ is methyl. In another specific embodiment $R_5$ is —CF$_3$. In another specific embodiment $R_5$ is —Cl.

In another embodiment $R_6$ is C$_{1-3}$ alkyl. In a specific embodiment $R_6$ is methyl, ethyl, or n-propyl. In another embodiment $R_6$ is —C$_{2-3}$ alkyl-OH. In a specific embodiment $R_6$ is 2-hydroxyethyl.

In another embodiment each $R_7$ is independently C$_{1-3}$ alkyl.

In another embodiment each $R_8$ is independently hydrogen or C$_{1-3}$ alkyl. In a specific embodiment each $R_8$ is hydrogen. In another specific embodiment each $R_8$ is methyl. In another embodiment one $R_8$ is hydrogen and the other $R_8$ is hydrogen, —NH$_2$, or C$_{1-3}$ alkyl. In a specific embodiment one $R_8$ is hydrogen and the other $R_8$ is hydrogen, —NH$_2$, or methyl. In another specific embodiment one $R_8$ is hydrogen and the other $R_8$ is —NH$_2$. In another specific embodiment one $R_8$ is hydrogen and the other $R_8$ is methyl.

In another embodiment $R_9$ is C$_{1-3}$ alkyl. In another embodiment $R_9$ is methyl or ethyl. In a specific embodiment $R_9$ is ethyl.

In another embodiment $R_9$ and $R_{13}$ taken together represent —CH$_2$—CH=CH—(CH$_2$)$_2$— or —(CH$_2$)$_5$—.

In another embodiment $R_{12}$ is hydrogen.

In another embodiment $R_5$ and $R_{12}$ taken together represent —CH$_2$CH$_2$—.

In another embodiment each n is independently 2 or 3. In another embodiment each n is 2. In another embodiment each n is 0.

In another embodiment the present invention provides for compounds of Formula (Ia):

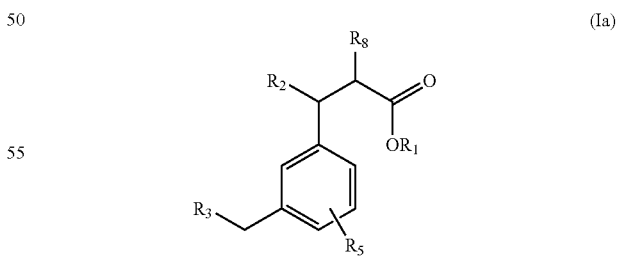

wherein:

$R_1$ is hydrogen, —CH$_2$C(O)N(R$_7$)$_2$, —CH$_2$-(4-methyl-1,3-dioxol-2-one), —C$_{1-3}$ alkyl-OH, C$_{1-3}$ alkyl, —C$_{1-5}$ alkyl-N(R$_7$)$_2$, —(CH$_2$)$_n$-morpholinyl, —(CH$_2$)$_n$-furyl, —CH$_2$—O—C(O)—C$_{1-6}$ alkyl, —(CH$_2$)$_n$-imidazolyl, —(CH$_2$)$_n$-pyrrolidinyl, —(CH$_2$)$_n$-piperidyl, or 2-oxotetrahydrofuran-3-yl; wherein the morpholinyl and piperidyl may be substituted by one or two C$_{1-3}$ alkyl; and the pyrrolidinyl, imidazolyl, and furyl may be substituted by one or two groups independently selected from C$_{1-3}$ alkyl, halo, and —O—C$_{1-3}$ alkyl;

R$_2$ is:

phenyl, which may be substituted by one, two, or three groups independently selected from —CN, —F, —C(O)NH$_2$, —C(O)CH$_3$, —O—C$_{1-3}$ alkyl, C$_{1-3}$ alkyl, —CF$_3$, and —OCF$_3$;

benzotriazolyl, which may be substituted by one, two, or three groups independently selected from —O—C$_{1-3}$ alkyl, —F, —Cl, —CF$_3$, —OCF$_3$, and C$_{1-3}$ alkyl;

—(CH$_2$)$_n$-triazolyl, which may be substituted by one or two groups independently selected from C$_{1-3}$ alkyl and —CH$_2$-phenyl;

pyridyl, which may be substituted by one, two, or three groups independently selected from C$_{1-3}$ alkyl, —F, —OCH$_3$, and =O;

or triazolopyridyl, which may be substituted by one or two groups independently selected from —O—C$_{1-3}$ alkyl, —F, and C$_{1-3}$ alkyl;

R$_3$ is R$_4$—SO$_2$—N(R$_6$)—;

R$_4$ is phenyl, C$_{5-6}$ cycloalkyl, thienyl, imidazolyl, pyridyl, piperidyl, tetrahydro-2H-pyranyl, C$_{1-3}$ alkyl, or

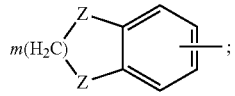

each of which may be substituted by one or two groups independently selected from C$_{1-3}$ alkyl, —NH—C(O)—CH$_3$, —O—C$_{1-3}$alkyl, —C(O)—CH$_3$, =O, and OH;

or R$_3$ is

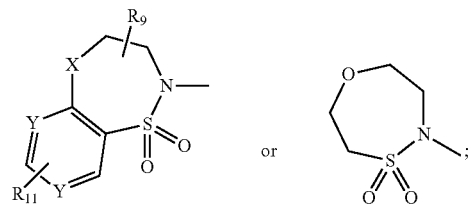

X is CH$_2$, NR$_6$ or O;

each Y is independently N or CH; provided one Y is CH;

each Z is independently O, CH$_2$, or NR$_{10}$;

R$_5$ is hydrogen, C$_{1-3}$ alkyl, —Cl, —F, or —CF$_3$;

R$_6$ is hydrogen or C$_{1-3}$ alkyl;

each R$_7$ is independently hydrogen or C$_{1-3}$ alkyl;

R$_8$ is hydrogen or C$_{1-3}$ alkyl;

R$_9$ is hydrogen or C$_{1-3}$ alkyl;

R$_{10}$ is —C(O)—CH$_3$;

R$_{11}$ is hydrogen or —F;

each n is independently 0, 1, 2, or 3; and m is 1 or 2;

or a pharmaceutically acceptable salt thereof.

In another embodiment the present invention provides for compounds of Formula (Ib):

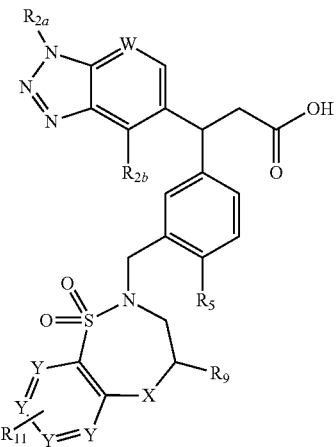

(Ib)

wherein:

W is N or CR$_{2c}$;

X is CH$_2$, NR$_9$ or O;

each Y is independently N or CH; provided that not more than one Y is N;

R$_{2a}$ is methyl or ethyl;

R$_{2b}$ is hydrogen, —F, methyl, or —CF$_3$;

R$_2$ is hydrogen or methoxy;

R$_5$ is hydrogen, —F, —Cl, methyl, ethyl, or —CF$_3$;

each R$_9$ is independently hydrogen, methyl, or ethyl; and

R$_{11}$ is hydrogen, halo, —CF$_3$, —CN, —C(O)NH$_2$, —C$_{1-3}$ alkyl-NH$_2$, —C$_{1-3}$ alkyl-N(C$_{1-3}$ alkyl)$_2$, or —C$_{1-3}$ alkyl-NH—C(O)—O—C$_{1-4}$ alkyl;

or a pharmaceutically acceptable salt thereof.

It is to be understood that the present invention covers all combinations of the embodiments and particular groups described hereinabove.

Specific examples of compounds of the present invention include the following:

3-(7-methoxy-1-methyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid;

3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid;

3-(1,4-dimethyl-1H-benzo[d][1,2,3]triazol-5-yl)-3-(3-((1,1-dioxido-3,4-dihydro-2H-benzo[b][1,4,5]oxathiazepin-2-yl)methyl)-4-methylphenyl)propanoic acid;

3-(7-methoxy-1-methyl-1H-benzo[d][1,2,3]triazol-5-yl)-3-(4-methyl-3-((3-methyl-1,1-dioxido-3,4-dihydro-2H-benzo[b][1,4,5]oxathiazepin-2-yl)methyl)phenyl)propanoic acid;

3-(7-methoxy-1-methyl-1H-benzo[d][1,2,3]triazol-5-yl)-3-(4-methyl-3-((4-methyl-1,1-dioxido-3,4-dihydro-2H-benzo[b][1,4,5]oxathiazepin-2-yl)methyl)phenyl)propanoic acid;

3-(3-((1,1-dioxido-3,4-dihydro-2H-pyrido[2,3-b][1,4,5]oxathiazepin-2-yl)methyl)-4-methylphenyl)-3-(7-methoxy-1-methyl-1H-benzo[d][1,2,3]triazol-5-yl)propanoic acid;

3-(3-((N-(2-hydroxyethyl)-2-methoxypyridine-3-sulfonamido)methyl)-4-methylphenyl)-3-(7-methoxy-1-methyl-1H-benzo[d][1,2,3]triazol-5-yl)propanoic acid;

3-(1,4-dimethyl-1H-benzo[d][1,2,3]triazol-5-yl)-3-(3-((1,1-dioxido-3,4-dihydro-2H-pyrido[2,3-b][1,4,5]oxathiazepin-2-yl)methyl)-4-methylphenyl)propanoic acid;

3-(1,4-dimethyl-1H-benzo[d][1,2,3]triazol-5-yl)-3-(3-((N-(2-hydroxyethyl)-2-methoxypyridine-3-sulfonamido)methyl)-4-methylphenyl)propanoic acid;

3-(1,4-dimethyl-1H-benzo[d][1,2,3]triazol-5-yl)-3-(4-methyl-3-((4-methyl-1,1-dioxido-3,4-dihydro-2H-benzo[b][1,4,5]oxathiazepin-2-yl)methyl)phenyl)propanoic acid;

3-(1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(1,4-dimethyl-1H-benzo[d][1,2,3]triazol-5-yl)-3-(4-methyl-3-(((S)-4-methyl-1,1-dioxido-3,4-dihydro-2H-benzo[b][1,4,5]oxathiazepin-2-yl)methyl)phenyl)propanoic acid;

3-(7-methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(7-methoxy-1-methyl-1H-benzo[d][1,2,3]triazol-5-yl)-3-(4-methyl-3-(((S)-4-methyl-1,1-dioxido-3,4-dihydro-2H-benzo[b][1,4,5]oxathiazepin-2-yl)methyl)phenyl)propanoic acid;

3-(3-((5-ethyl-1,1-dioxido-4,5-dihydrobenzo[f][1,2,5]thiadiazepin-2(3H)-yl)methyl)-4-methylphenyl)-3-(7-methoxy-1-methyl-1H-benzo[d][1,2,3]triazol-5-yl)propanoic acid;

3-(1,4-dimethyl-1H-benzo[d][1,2,3]triazol-5-yl)-3-(3-((5-ethyl-1,1-dioxido-4,5-dihydrobenzo[f][1,2,5]thiadiazepin-2(3H)-yl)methyl)-4-methylphenyl)propanoic acid;

3-(7-methoxy-1-methyl-1H-benzo[d][1,2,3]triazol-5-yl)-3-(4-methyl-3-(((S)-4-methyl-1,1-dioxido-3,4-dihydro-2H-pyrido[2,3-b][1,4,5]oxathiazepin-2-yl)methyl)phenyl)propanoic acid;

3-(7-methoxy-1-methyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid;

(S)-3-(1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

(R)-3-(1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(1,4-dimethyl-1H-benzo[d][1,2,3]triazol-5-yl)-3-(3-((4-ethyl-1,1-dioxido-3,4-dihydro-2H-benzo[b][1,4,5]oxathiazepin-2-yl)methyl)-4-methylphenyl)propanoic acid;

3-(1,4-dimethyl-1H-benzo[d][1,2,3]triazol-5-yl)-3-(3-((4-ethyl-1,1-dioxido-3,4-dihydro-2H-pyrido[2,3-b][1,4,5]oxathiazepin-2-yl)methyl)-4-methylphenyl)propanoic acid;

3-(3-((4-ethyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid;

3-(3-((4-ethyl-1,1-dioxido-3,4-dihydro-2H-pyrido[2,3-b][1,4,5]oxathiazepin-2-yl)methyl)-4-methylphenyl)-3-(7-methoxy-1-methyl-1H-benzo[d][1,2,3]triazol-5-yl)propanoic acid;

3-(1,4-dimethyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid;

3-(1,4-dimethyl-1H-benzo[d][1,2,3]triazol-5-yl)-3-(3-((5-ethyl-1,1-dioxido-4,5-dihydropyrido[2,3-f][1,2,5]thiadiazepin-2(3H)-yl)methyl)-4-methylphenyl)propanoic acid;

3-(3-((5-ethyl-1,1-dioxido-4,5-dihydropyrido[2,3-f][1,2,5]thiadiazepin-2(3H)-yl)methyl)-4-methylphenyl)-3-(7-methoxy-1-methyl-1H-benzo[d][1,2,3]triazol-5-yl)propanoic acid;

3-(1-methyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid;

3-(1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(3-((5-ethyl-1,1-dioxido-4,5-dihydrobenzo[f][1,2,5]thiadiazepin-2(3H)-yl)methyl)-4-methylphenyl)-3-(1-methyl-1H-benzo[d][1,2,3]triazol-5-yl)propanoic acid;

3-(3-((4-ethyl-1,1-dioxido-3,4-dihydro-2H-pyrido[2,3-b][1,4,5]oxathiazepin-2-yl)methyl)-4-methylphenyl)-3-(1-methyl-1H-benzo[d][1,2,3]triazol-5-yl)propanoic acid;

3-(3-((4-ethyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoic acid;

3-(3-((5-ethyl-1,1-dioxido-4,5-dihydropyrido[2,3-f][1,2,5]thiadiazepin-2(3H)-yl)methyl)-4-methylphenyl)-3-(1-methyl-1H-benzo[d][1,2,3]triazol-5-yl)propanoic acid;

(3R)-3-(7-methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

(3S)-3-(7-methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(3-((4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic acid;

3-(1-ethyl-4-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(1-ethyl-4-methyl-1H-benzo[d][1,2,3]triazol-5-yl)-3-(4-methyl-3-(((R)-4-methyl-1-dioxido-3,4-dihydro-2H-pyrido[2,3-b][1,4,5]oxathiazepin-2-yl)methyl)phenyl)propanoic acid;

3-(3-((4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid;

3-(3-((5-ethyl-1,1-dioxido-4,5-dihydropyrido[2,3-f][1,2,5]thiadiazepin-2(3H)-yl)methyl)-4-methylphenyl)-3-(1-ethyl-4-methyl-1H-benzo[d][1,2,3]triazol-5-yl)propanoic acid;

3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid;

3-(1,4-dimethyl-1H-benzo[d][1,2,3]triazol-5-yl)-3-(3-(((R)-4-ethyl-1-dioxido-3,4-dihydro-2H-pyrido[2,3-b][1,4,5]oxathiazepin-2-yl)methyl)-4-methylphenyl)propanoic acid;

3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic acid;

3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid;

3-(3-(((R)-4-ethyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid;

3-(3-(((R)-4-ethyl-1,1-dioxido-3,4-dihydro-2H-pyrido[2,3-b][1,4,5]oxathiazepin-2-yl)methyl)-4-methylphenyl)-3-(7-methoxy-1-methyl-1H-benzo[d][1,2,3]triazol-5-yl)propanoic acid;

3-(4-ethyl-3-(((R)-4-ethyl-1,1-dioxido-3,4-dihydro-2H-benzo[b][1,4,5]oxathiazepin-2-yl)methyl)phenyl)-3-(3-methoxyphenyl)propanoic acid;

3-(4-chloro-3-((N,4-dimethylphenylsulfonamido)methyl)phenyl)-3-(1-methyl-1H-benzo[d][1,2,3]triazol-5-yl)propanoic acid;

3-(4-chloro-3-((N,3-dimethylphenylsulfonamido)methyl)phenyl)-3-(1-methyl-1H-benzo[d][1,2,3]triazol-5-yl)propanoic acid;

3-(4-chloro-3-((N-methyl-2,3-dihydro-1H-indene-5-sulfonamido)methyl)phenyl)-3-(1-methyl-1H-benzo[d][1,2,3]triazol-5-yl)propanoic acid;

3-(3-((3-acetamido-N-methylphenylsulfonamido)methyl)-4-chlorophenyl)-3-(1-methyl-1H-benzo[d][1,2,3]triazol-5-yl)propanoic acid;

3-(4-chloro-3-((N-methylcyclohexanesulfonamido)methyl)phenyl)-3-(1-methyl-1H-benzo[d][1,2,3]triazol-5-yl)propanoic acid;

3-(4-chloro-3-((N-methyl-2,3-dihydrobenzo[b][1,4]dioxine-6-sulfonamido)methyl)phenyl)-3-(1-methyl-1H-benzo[d][1,2,3]triazol-5-yl)propanoic acid;

(3R)-3-{4-chloro-3-[(N-methylbenzenesulfonamido)methyl]phenyl}-3-(1-methyl-1H-1,2,3-benzotriazol-5-yl)propanoic acid;

(3S)-3-{4-chloro-3-[(N-methylbenzenesulfonamido)methyl]phenyl}-3-(1-methyl-1H-1,2,3-benzotriazol-5-yl)propanoic acid;

(3R)-3-(1,4-dimethyl-1H-1,2,3-benzotriazol-5-yl)-3-{4-methyl-3-[(N-methylbenzenesulfonamido)methyl]phenyl}propanoic acid;

(3S)-3-(1,4-dimethyl-1H-1,2,3-benzotriazol-5-yl)-3-{4-methyl-3-[(N-methylbenzenesulfonamido)methyl]phenyl}propanoic acid;

3-(3-((1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid;

3-(3-((1,1-dioxido-3,4-dihydro-2H-benzo[b][1,4,5]oxathiazepin-2-yl)methyl)-4-methylphenyl)-3-(tetrazolo[1,5-a]pyridin-7-yl)propanoic acid;

3-(3-((4,4-dioxido-1,4,5-oxathiazepan-5-yl)methyl)-4-methylphenyl)-3-(7-methoxy-1-methyl-1H-benzo[d][1,2,3]triazol-5-yl)propanoic acid;

3-(3-((1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoic acid;

3-(7-methoxy-1-methyl-1H-benzo[d][1,2,3]triazol-5-yl)-3-(3-(((R)-4-methyl-1,1-dioxido-3,4-dihydro-2H-pyrido[2,3-b][1,4,5]oxathiazepin-2-yl)methyl)phenyl)propanoic acid;

3-(7-methoxy-1-methyl-1H-benzo[d][1,2,3]triazol-5-yl)-3-(3-((4-methyl-1,1-dioxido-3,4-dihydro-2H-benzo[b][1,4,5]oxathiazepin-2-yl)methyl)phenyl)propanoic acid;

3-(7-methoxy-1-methyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)phenyl)propanoic acid;

3-(3-((4-ethyl-1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoic acid;

3-(3-((4-ethyl-1,1-dioxido-3,4-dihydro-2H-pyrido[2,3-b][1,4,5]oxathiazepin-2-yl)methyl)phenyl)-3-(7-methoxy-1-methyl-1H-benzo[d][1,2,3]triazol-5-yl)propanoic acid;

3-(1,4-dimethyl-1H-benzo[d][1,2,3]triazol-5-yl)-3-(3-((1,1-dioxido-3,4-dihydro-2H-benzo[b][1,4,5]oxathiazepin-2-yl)methyl)-4-fluorophenyl)propanoic acid;

3-(1,4-dimethyl-1H-benzo[d][1,2,3]triazol-5-yl)-3-(4-fluoro-3-(((R)-4-methyl-1,1-dioxido-3,4-dihydro-2H-benzo[b][1,4,5]oxathiazepin-2-yl)methyl)phenyl)propanoic acid;

3-(1,4-dimethyl-1H-benzo[d][1,2,3]triazol-5-yl)-3-(3-((4-ethyl-1,1-dioxido-3,4-dihydro-2H-benzo[b][1,4,5]oxathiazepin-2-yl)methyl)-4-fluorophenyl)propanoic acid;

3-(1,4-dimethyl-1H-benzo[d][1,2,3]triazol-5-yl)-3-(4-fluoro-3-(((R)-4-methyl-1,1-dioxido-3,4-dihydro-2H-pyrido[2,3-b][1,4,5]oxathiazepin-2-yl)methyl)phenyl)propanoic acid;

3-(1,4-dimethyl-1H-benzo[d][1,2,3]triazol-5-yl)-3-(3-((1,1-dioxido-3,4-dihydro-2H-pyrido[4,3-b][1,4,5]oxathiazepin-2-yl)methyl)-4-methylphenyl)propanoic acid;

Ethyl 3-(1,4-dimethyl-1H-benzo[d][1,2,3]triazol-5-yl)-3-(4-methyl-3-((5-methyl-1,1-dioxido-4,5-dihydropyrido[4,3-f][1,2,5]thiadiazepin-2(3H)-yl)methyl)phenyl)propanoate;

3-(4-chloro-3-(((R)-4-methyl-1,1-dioxido-3,4-dihydro-2H-benzo[b][1,4,5]oxathiazepin-2-yl)methyl)phenyl)-3-(1,4-dimethyl-1H-benzo[d][1,2,3]triazol-5-yl)propanoic acid;

3-(4-chloro-3-(((R)-4-methyl-1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoic acid;

3-(3-methoxyphenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(4-chloro-3-(((R)-4-methyl-1,1-dioxido-3,4-dihydro-2H-benzo[b][1,4,5]oxathiazepin-2-yl)methyl)phenyl)-3-(1-methyl-1H-benzo[d][1,2,3]triazol-5-yl)propanoic acid;

3-(3-methoxy-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(4-methyl-3-(((R)-4-methyl-1,1-dioxido-3,4-dihydro-2H-benzo[b][1,4,5]oxathiazepin-2-yl)methyl)phenyl)-3-(3-methyl-3H-[1,2,3]triazolo[4,5-b]pyridin-6-yl)propanoic acid;

3-(1-methyl-2-oxo-1,2-dihydropyridin-4-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(3,7-dimethyl-3H-[1,2,3]triazolo[4,5-b]pyridin-6-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(3,5-dimethoxyphenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(5-methoxypyridin-3-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(3-methoxy-5-(trifluoromethoxy)phenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(3-((4-ethyl-1,1-dioxido-3,4-dihydro-2H-benzo[b][1,4,5]oxathiazepin-2-yl)methyl)-4-methylphenyl)-3-(1-methyl-2-oxo-1,2-dihydropyridin-4-yl)propanoic acid;

3-(1-methyl-2-oxo-1,2-dihydropyridin-4-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid;

3-(4-chloro-3-(((R)-4-methyl-1,1-dioxido-3,4-dihydro-2H-benzo[b][1,4,5]oxathiazepin-2-yl)methyl)phenyl)-3-(1-methyl-2-oxo-1,2-dihydropyridin-4-yl)propanoic acid;

3-(1-methyl-2-oxo-1,2-dihydropyridin-4-yl)-3-(4-methyl-3-((5-methyl-1,1-dioxido-4,5-dihydrobenzo[f][1,2,5]thiadiazepin-2(3H)-yl)methyl)phenyl)propanoic acid;

3-(4-fluoro-1,7-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(4-fluoro-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(3-((((cyclopentyloxy)carbonyl)(methyl)amino)methyl)-4-methylphenyl)-3-(7-methoxy-1,4-dimethyl-1H-benzo[d][1,2,3]triazol-5-yl)propanoic acid;

3-(1,4-Dimethyl-1H-benzo[d][1,2,3]triazol-5-yl)-3-(4-methyl-3-((N-methylcyclopentanesulfonamido)methyl)phenyl)propanoic acid;

2-(Dimethylamino)-2-oxoethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

(5-Methyl-2-oxo-1,3-dioxol-4-yl)methyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

2-Hydroxyethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

Ethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

2-(Dimethylamino)ethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

2-Morpholinoethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

3-(Dimethylamino)propyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

2-Oxotetrahydrofuran-3-yl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

((3-(1,4-Dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoyl)oxy)methyl pivalate;

2-(1H-Imidazol-1-yl)ethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

3-(Diethylamino)propyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

4-(Dimethylamino)butyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

3-(Dimethylamino)-2,2-dimethylpropyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

3-(Pyrrolidin-1-yl)propyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

1-(Dimethylamino)propan-2-yl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

3-morpholinopropyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

2-(5-(1-(1,4-dimethyl-1H-benzo[d][1,2,3]triazol-5-yl)-3-hydroxypropyl)-2-methylbenzyl)-5-methyl-2,3,4,5-tetrahydrobenzo[f][1,2,5]thiadiazepine 1,1-dioxide;

Methyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

Methylpyrrolidin-3-yl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

1-Methylpiperidin-3-yl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

((S)-1-Methylpyrrolidin-2-yl)methyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

Pyrrolidin-3-ylmethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

1-Methylpiperidin-4-yl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate;

3-(4-Methyl-3-(((R)-4-methyl-1,1-dioxido-3,4-dihydro-2H-benzo[b][1,4,5]oxathiazepin-2-yl)methyl)phenyl)-3-(3-methyl-[1,2,3]triazolo[1,5-a]pyridin-6-yl)propanoic acid;

Ethyl 3-(3-((N-isopropylphenylsulfonamido)methyl)-4-methylphenyl)-3-(7-methoxy-1-methyl-1H-benzo[d][1,2,3]triazol-5-yl)propanoate;

3-(1,4-dimethyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl)propanoic acid;

3-(4-Chloro-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

2-Methyl-3-(1-methyl-1H-benzo[d][1,2,3]triazol-5-yl)-3-(4-methyl-3-((N-methylphenylsulfonamido)methyl)phenyl)propanoic acid;

2-methyl-3-(1-methyl-1H-benzo[d][1,2,3]triazol-5-yl)-3-(4-methyl-3-((N-methylphenylsulfonamido)methyl)phenyl)propanoic acid;

3-(4-Methyl-3-(((R)-4-methyl-1,1-dioxido-3,4-dihydro-2H-benzo[b][1,4,5]oxathiazepin-2-yl)methyl)phenyl)-5-(1H-1,2,3-triazol-4-yl)pentanoic acid;

5-(1-Benzyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid;

5-(2-Methyl-2H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid;

5-(1-Methyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid;

5-(1-Ethyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid;

3-(7-Methoxy-1-methyl-1H-benzo[d][1,2,3]triazol-5-yl)-3-(4-methyl-3-(((R)-4-methyl-1,1-dioxido-3,4-dihydro-2H-pyrido[4,3-b][1,4,5]oxathiazepin-2-yl)methyl)phenyl)propanoic acid;

3-(1,4-Dimethyl-1H-benzo[d][1,2,3]triazol-5-yl)-3-(4-methyl-3-(((R)-4-methyl-1,1-dioxido-3,4-dihydro-2H-pyrido[4,3-b][1,4,5]oxathiazepin-2-yl)methyl)phenyl)propanoic acid;

3-(4-methyl-3-(((R)-4-methyl-1,1-dioxido-3,4-dihydro-2H-benzo[b][1,4,5]oxathiazepin-2-yl)methyl)phenyl)-3-(1-methyl-4-(trifluoromethyl)-1H-benzo[d][1,2,3]triazol-5-yl)propanoic acid;

3-(7-methoxy-1-methyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl)propanoic acid;

3-(7-Methoxy-1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(1-Ethyl-2-oxo-1,2-dihydropyridin-4-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(4-Methyl-3-(((R)-4-methyl-1,1-dioxido-3,4-dihydro-2H-benzo[b][1,4,5]oxathiazepin-2-yl)methyl)phenyl)-3-(2-oxo-1-propyl-1,2-dihydropyridin-4-yl)propanoic acid;

3-(4-Methyl-3-(((R)-4-methyl-1,1-dioxido-3,4-dihydro-2H-benzo[b][1,4,5]oxathiazepin-2-yl)methyl)phenyl)-3-(1-methyl-6-oxo-1,6-dihydropyridin-2-yl)propanoic acid;

3-{4-chloro-3-[(N-methylmethanesulfonamido)methyl]phenyl}-3-(1-methyl-1H-1,2,3-benzotriazol-5-yl)propanoic acid;

Methyl 3-{4-chloro-3-[(N-propylpyridine-3-sulfonamido)methyl]phenyl}-3-(1-methyl-1H-1,2,3-benzotriazol-5-yl)propanoate;

3-{4-chloro-3-[(N-propylpyridine-3-sulfonamido)methyl]phenyl}-3-(1-methyl-1H-1,2,3-benzotriazol-5-yl)propanoic acid;

3-{4-chloro-3-[(N-ethylpyridine-3-sulfonamido)methyl]phenyl}-3-(1-methyl-1H-1,2,3-benzotriazol-5-yl)propanoic acid;

3-{4-chloro-3-[(N-methylpyridine-3-sulfonamido)methyl]phenyl}-3-(1-methyl-1H-1,2,3-benzotriazol-5-yl)propanoic acid;

3-{4-chloro-3-[(N-methyl-1,5-dimethyl-1H-pyrazole-4-sulfonamido)methyl]phenyl}-3-(1-methyl-1H-1,2,3-benzotriazol-5-yl)propanoic acid;

3-(4-chloro-3-((5-methyl-1,1-dioxido-4,5-dihydrobenzo[f][1,2,5]thiadiazepin-2(3H)-yl)methyl)phenyl)-3-(1-methyl-1H-benzo[d][1,2,3]triazol-5-yl)propanoic acid;

3-(1-methyl-1H-1,2,3-benzotriazol-5-yl)-3-{4-methyl-3-[(N-methylbenzenesulfonamido)methyl]phenyl}propanoic acid;

3-(1-methyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid;

3-(7-methoxy-1-methyl-1H-1,2,3-benzotriazol-5-yl)-3-{4-methyl-3-[(N-methylbenzenesulfonamido)methyl]phenyl}propanoic acid;

3-(1-Ethyl-4-methyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl)propanoic acid;

(4R)-2-(5-(1-(1,4-Dimethyl-1H-benzo[d][1,2,3]triazol-5-yl)-2-(1H-tetrazol-5-yl)ethyl)-2-methylbenzyl)-4-methyl-3,4-dihydro-2H-benzo[b][1,4,5]oxathiazepine 1,1-dioxide;

3-(1,4-Dimethyl-1H-benzo[d][1,2,3]triazol-5-yl)-3-(4-methyl-3-(((R)-4-methyl-1,1-dioxido-3,4-dihydro-2H-pyrido[3,2-b][1,4,5]oxathiazepin-2-yl)methyl)phenyl)propanoic acid;

5-(1-Ethyl-1H-1,2,3-triazol-4-yl)-3-(4-methyl-3-(((R)-4-methyl-1,1-dioxido-3,4-dihydro-2H-pyrido[3,2-b][1,4,5]oxathiazepin-2-yl)methyl)phenyl)pentanoic acid;

5-(1-Ethyl-1H-1,2,3-triazol-4-yl)-3-(4-methyl-3-((4-methyl-1,1-dioxido-4,5-dihydropyrido[2,3-f][1,2]thiazepin-2(3H)-yl)methyl)phenyl)pentanoic acid;

5-(1-Ethyl-1H-1,2,3-triazol-4-yl)-3-(4-methyl-3-((4-methyl-1,1-dioxido-4,5-dihydropyrido[4,3-f][1,2]thiazepin-2(3H)-yl)methyl)phenyl)pentanoic acid;

5-(1-Ethyl-1H-1,2,3-triazol-4-yl)-3-(4-methyl-3-(((R)-4-methyl-1,1-dioxido-3,4-dihydro-2H-pyrido[3,4-b][1,4,5]oxathiazepin-2-yl)methyl)phenyl)pentanoic acid;

3-(1,4-Dimethyl-1H-benzo[d][1,2,3]triazol-5-yl)-3-(4-methyl-3-(((R)-4-methyl-1,1-dioxido-3,4-dihydro-2H-pyrido[3,4-b][1,4,5]oxathiazepin-2-yl)methyl)phenyl)propanoic acid;

3-(7-Methoxy-1-methyl-1H-benzo[d][1,2,3]triazol-5-yl)-3-(4-methyl-3-((4-methyl-1,1-dioxido-3,4-dihydro-2H-benzo[e][1,2]thiazin-2-yl)methyl)phenyl)propanoic acid;

3-(3-((4-Ethyl-1,1-dioxido-3,4-dihydro-2H-benzo[e][1,2]thiazin-2-yl)methyl)-4-methylphenyl)-3-(7-methoxy-1-methyl-1H-benzo[d][1,2,3]triazol-5-yl)propanoic acid;

6-(Benzyl(methyl)amino)-3-(4-methyl-3-(((S)-4-methyl-1,1-dioxido-3,4-dihydro-2H-benzo[b][1,4,5]oxathiazepin-2-yl)methyl)phenyl)-6-oxohexanoic acid;

3-(3-((7-(3-(Dimethylamino)propyl)-4-methyl-1,1-dioxido-4,5-dihydrobenzo[f][1,2]thiazepin-2(3H)-yl)methyl)-4-methylphenyl)-3-(4-fluoro-2-methylphenyl)propanoic acid;

3-(4-Methyl-3-(((S)-4-methyl-1,1-dioxido-3,4-dihydro-2H-benzo[b][1,4,5]oxathiazepin-2-yl)methyl)phenyl)-6-(methylamino)-6-oxohexanoic acid;

3-(2-((Dimethylamino)methyl)-4-fluoro-6-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid;

3-(5-Methoxy-2-methylpyridin-3-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(4-Methyl-3-(((R)-4-methyl-1,1-dioxido-3,4-dihydro-2H-benzo[b][1,4,5]oxathiazepin-2-yl)methyl)phenyl)-5-(o-tolyl)pentanoic acid;

3-(1-Ethyl-1H-imidazol-4-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

5-(1-Ethyl-1H-pyrazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid;

6-Methoxy-3-(4-methyl-3-(((R)-4-methyl-1,1-dioxido-3,4-dihydro-2H-benzo[b][1,4,5]oxathiazepin-2-yl)methyl)phenyl)hexanoic acid;

3-(3-((7-(3-((tert-Butoxycarbonyl)amino)propyl)-4-methyl-1,1-dioxido-4,5-dihydrobenzo[f][1,2]thiazepin-2(3H)-yl)methyl)-4-methylphenyl)-3-(1-methyl-1H-benzo[d][1,2,3]triazol-5-yl)propanoic acid;

3-(3-(((R)-4-Ethyl-1,1-dioxido-3,4-dihydro-2H-benzo[b][1,4,5]oxathiazepin-2-yl)methyl)-4-methylphenyl)-3-(2-methyl-1,2,3,4-tetrahydroisoquinolin-6-yl)propanoic acid;

5-(1-Ethyl-1H-imidazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid;

3-(4-Methyl-3-(((R)-4-methyl-1,1-dioxido-3,4-dihydro-2H-benzo[b][1,4,5]oxathiazepin-2-yl)methyl)phenyl)-5-(pyridin-3-yl)pentanoic acid;

3-(4-Methyl-3-(((R)-4-methyl-1,1-dioxido-3,4-dihydro-2H-benzo[b][1,4,5]oxathiazepin-2-yl)methyl)phenyl)-5-(o-tolyl)pentanoic acid;

3-(5-(2-(Dimethylamino)ethyl)-4-fluoro-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(3-(((R)-4-Ethyl-1,1-dioxido-3,4-dihydro-2H-benzo[b][1,4,5]oxathiazepin-2-yl)methyl)-4-methylphenyl)-3-(2-methylisoindolin-5-yl)propanoic acid;

3-(5-(3-(Dimethylamino)propyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid;

6-Methyl-3-(4-methyl-3-(((R)-4-methyl-1,1-dioxido-3,4-dihydro-2H-benzo[b][1,4,5]oxathiazepin-2-yl)methyl)phenyl)heptanoic acid;

3-(3-(((R)-8-Chloro-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoic acid;

3-(3-(((R)-8-Cyano-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoic acid;

3-(3-(((R)-8-carbamoyl-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoic acid;

3-(5-((Dimethylamino)methyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid;

3-(5-(2-(Dimethylamino)ethyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid;

2-Amino-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid;

3-(1,4-dimethyl-1H-benzo[d][1,2,3]triazol-5-yl)-3-(3-((3,3-dioxido-4,5-dihydrobenzo[d][1,2]thiazepin-2(1H)-yl)methyl)-4-methylphenyl)propanoic acid;

3-(1,4-Dimethyl-1H-benzo[d][1,2,3]triazol-5-yl)-3-(3-((2,2-dioxidohexahydro-1H-benzo[d][1,2]thiazin-3(4H)-yl)methyl)-4-methylphenyl)propanoic acid;

3-(1,4-Dimethyl-1H-benzo[d][1,2,3]triazol-5-yl)-3-(3-((2,2-dioxido-1H-benzo[d][1,2]thiazin-3(4H)-yl)methyl)-4-methylphenyl)propanoic acid;

3-(1,4-Dimethyl-1H-benzo[d][1,2,3]triazol-5-yl)-3-(3-((3,3-dioxidooctahydrobenzo[d][1,2]thiazepin-2(1H)-yl)methyl)-4-methylphenyl)propanoic acid;

3-(4-Methyl-3-(((R)-4-methyl-1,1-dioxido-3,4-dihydro-2H-benzo[b][1,4,5]oxathiazepin-2-yl)methyl)phenyl)-5-(p-tolyl)pentanoic acid;

3-(2,4-Difluorophenyl)-3-(3-((7-(3-(dimethylamino)propyl)-4-methyl-1,1-dioxido-4,5-dihydrobenzo[f][1,2]thiazepin-2(3H)-yl)methyl)-4-methylphenyl)propanoic acid;

3-(3-(((R)-4-Ethyl-1,1-dioxido-3,4-dihydro-2H-benzo[b][1,4,5]oxathiazepin-2-yl)methyl)-4-methylphenyl)-3-(2-methyl-1,2,3,4-tetrahydroisoquinolin-7-yl)propanoic acid;

3-(2-(1-Methyl-1H-1,2,3-triazol-4-yl)cyclopropyl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(1,4-dimethyl-1H-benzo[d][1,2,3]triazol-5-yl)-2-methyl-3-(4-methyl-3-((5-methyl-1,1-dioxido-4,5-dihydrobenzo[f][1,2,5]thiadiazepin-2(3H)-yl)methyl)phenyl)propanoic acid;

3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid;

3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid;

3-(3-(((R)-4-Ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoic acid;

3-(3-(((R)-4-Ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoic acid;

3-(3-(((R)-4-Ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)pentanoic acid;

5-Methoxy-3-(4-methyl-3-(((R)-4-methyl-1,1-dioxido-3,4-dihydro-2H-benzo[b][1,4,5]oxathiazepin-2-yl)methyl)phenyl)pentanoic acid;

5-Cyclopentyl-3-(4-methyl-3-(((R)-4-methyl-1,1-dioxido-3,4-dihydro-2H-benzo[b][1,4,5]oxathiazepin-2-yl)methyl)phenyl)pentanoic acid;

3-(3-(((R)-4-Ethyl-1,1-dioxido-3,4-dihydro-2H-pyrido[4,3-b][1,4,5]oxathiazepin-2-yl)methyl)-4-(trifluoromethyl)phenyl)-5-(1-ethyl-1H-1,2,3-triazol-4-yl)pentanoic acid;

5-(1-Ethyl-1H-1,2,3-triazol-4-yl)-3-(3-((4-methyl-1,1-dioxido-4,5-dihydrobenzo[f][1,2]thiazepin-2(3H)-yl)methyl)-4-(trifluoromethyl)phenyl)pentanoic acid;

3-(3-(((R)-4-Ethyl-1,1-dioxido-3,4-dihydro-2H-pyrido[4,3-b][1,4,5]oxathiazepin-2-yl)methyl)-4-methylphenyl)-5-(1-ethyl-1H-1,2,3-triazol-4-yl)pentanoic acid;

3-(3-(((R)-4-Ethyl-1,1-dioxido-3,4-dihydro-2H-benzo[b][1,4,5]oxathiazepin-2-yl)methyl)-4-(trifluoromethyl)phenyl)-5-(1-ethyl-1H-1,2,3-triazol-4-yl)pentanoic acid;

3-(4-methyl-3-(((R)-4-methyl-1,1-dioxido-3,4-dihydro-2H-benzo[b][1,4,5]oxathiazepin-2-yl)methyl)phenyl)-5-(1-propyl-1H-1,2,3-triazol-4-yl)pentanoic acid;

3-(3-(((R)-4-Ethyl-1,1-dioxido-3,4-dihydro-2H-benzo[b][1,4,5]oxathiazepin-2-yl)methyl)-4-methylphenyl)-5-(1-propyl-1H-1,2,3-triazol-4-yl)pentanoic acid;

5-(1-Isopropyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid;

3-(3-(((R)-4-Ethyl-1,1-dioxido-3,4-dihydro-2H-benzo[b][1,4,5]oxathiazepin-2-yl)methyl)-4-methylphenyl)-5-(1-isopropyl-1H-1,2,3-triazol-4-yl)pentanoic acid;

3-(3-(((R)-4-Ethyl-1,1-dioxido-3,4-dihydro-2H-pyrido[4,3-b][1,4,5]oxathiazepin-2-yl)methyl)-4-methylphenyl)-5-(1-propyl-1H-1,2,3-triazol-4-yl)pentanoic acid;

3-(3-(((R)-4-Ethyl-1,1-dioxido-3,4-dihydro-2H-pyrido[4,3-b][1,4,5]oxathiazepin-2-yl)methyl)-4-methylphenyl)-5-(1-isopropyl-1H-1,2,3-triazol-4-yl)pentanoic acid;

3-(3-(((R)-4-Ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)hexanoic acid;

3-(1,4-Dimethyl-1H-benzo[d][1,2,3]triazol-5-yl)-3-(3-((1,1-dioxido-4,5-dihydrobenzo[f][1,2]thiazepin-2(3H)-yl)methyl)-4-methylphenyl)propanoic acid;

3-(1,4-Dimethyl-1H-benzo[d][1,2,3]triazol-5-yl)-3-(4-methyl-3-((4-methyl-1,1-dioxido-4,5-dihydrobenzo[f][1,2]thiazepin-2(3H)-yl)methyl)phenyl)propanoic acid;

3-(1,4-Dimethyl-1H-benzo[d][1,2,3]triazol-5-yl)-3-(3-(((R)-9-fluoro-4-methyl-1,1-dioxido-3,4-dihydro-2H-benzo[b][1,4,5]oxathiazepin-2-yl)methyl)-4-methylphenyl)propanoic acid;

(S)-3-(7-Methoxy-1-methyl-1H-benzo[d][1,2,3]triazol-5-yl)-3-(4-methyl-3-(((R)-4-methyl-1,1-dioxido-4,5-dihydrobenzo[f][1,2]thiazepin-2(3H)-yl)methyl)phenyl)propanoic acid;

(S)-3-(7-Methoxy-1-methyl-1H-benzo[d][1,2,3]triazol-5-yl)-3-(4-methyl-3-(((S)-4-methyl-1,1-dioxido-4,5-dihydrobenzo[f][1,2]thiazepin-2(3H)-yl)methyl)phenyl)propanoic acid;

3-(4-Cyano-2-methylphenyl)-3-(4-methyl-3-((4-methyl-1,1-dioxido-4,5-dihydrobenzo[f][1,2]thiazepin-2(3H)-yl)methyl)phenyl)propanoic acid;

3-(4-Cyano-2-methylphenyl)-3-(3-((7-fluoro-4-methyl-1,1-dioxido-4,5-dihydrobenzo[f][1,2]thiazepin-2(3H)-yl)methyl)-4-methylphenyl)propanoic acid;

3-(4-Cyano-2-methylphenyl)-3-(3-((7-methoxy-4-methyl-1,1-dioxido-4,5-dihydrobenzo[f][1,2]thiazepin-2(3H)-yl)methyl)-4-methylphenyl)propanoic acid;

3-(4-Cyano-2-methylphenyl)-3-(4-methyl-3-((4-methyl-1,1-dioxido-7-(trifluoromethyl)-4,5-dihydrobenzo[f][1,2]thiazepin-2(3H)-yl)methyl)phenyl)propanoic acid;

3-(4-Cyano-2-methylphenyl)-3-(4-methyl-3-((4-methyl-1,1-dioxido-7-(trifluoromethoxy)-4,5-dihydrobenzo[f][1,2]thiazepin-2(3H)-yl)methyl)phenyl)propanoic acid;

3-(4-Cyano-2-methoxyphenyl)-3-(3-(((R)-4-ethyl-1,1-dioxido-3,4-dihydro-2H-benzo[b][1,4,5]oxathiazepin-2-yl)methyl)-4-methylphenyl)propanoic acid;

3-(4-Cyano-3-methoxyphenyl)-3-(3-(((R)-4-ethyl-1,1-dioxido-3,4-dihydro-2H-benzo[b][1,4,5]oxathiazepin-2-yl)methyl)-4-methylphenyl)propanoic acid;

3-(4-Cyano-2-fluorophenyl)-3-(3-(((R)-4-ethyl-1,1-dioxido-3,4-dihydro-2H-benzo[b][1,4,5]oxathiazepin-2-yl)methyl)-4-methylphenyl)propanoic acid;

5-(1-Ethyl-1H-1,2,3-triazol-4-yl)-3-(4-methyl-3-(((S)-4-methyl-1,1-dioxido-4,5-dihydrobenzo[f][1,2]thiazepin-2(3H)-yl)methyl)phenyl)pentanoic acid;

3-(3-(((R)-4-Ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)pentanoic acid;

3-(3-((1,1-Dioxido-4,5-dihydrobenzo[f][1,2]thiazepin-2(3H)-yl)methyl)-4-methylphenyl)-5-(1-ethyl-1H-1,2,3-triazol-4-yl)pentanoic acid;

3-(3-(((R)-4-Ethyl-1,1-dioxido-3,4-dihydro-2H-pyrido[2,3-b][1,4,5]oxathiazepin-2-yl)methyl)-4-methylphenyl)-5-(1-ethyl-1H-1,2,3-triazol-4-yl)pentanoic acid;

5-(1-Ethyl-1H-1,2,3-triazol-4-yl)-3-(4-methyl-3-(((R)-4-methyl-1,1-dioxido-4,5-dihydrobenzo[f][1,2]thiazepin-2(3H)-yl)methyl)phenyl)pentanoic acid;

5-(1-Ethyl-1H-1,2,3-triazol-4-yl)-3-(3-((8-fluoro-4-methyl-1,1-dioxido-4,5-dihydrobenzo[f][1,2]thiazepin-2(3H)-yl)methyl)-4-methylphenyl)pentanoic acid;

3-(3-((7-(3-Aminopropyl)-4-methyl-1,1-dioxido-4,5-dihydrobenzo[f][1,2]thiazepin-2(3H)-yl)methyl)-4-methylphenyl)-3-(1-methyl-1H-benzo[d][1,2,3]triazol-5-yl)propanoic acid;

3-(4-Cyano-2-methylphenyl)-3-(3-((4-ethyl-1,1-dioxido-3,4-dihydro-2H-benzo[b][1,4,5]oxathiazepin-2-yl)methyl)-4-methylphenyl)propanoic acid;

3-(4-Cyano-2-methylphenyl)-3-(3-((4-ethyl-1,1-dioxido-3,4-dihydro-2H-pyrido[2,3-b][1,4,5]oxathiazepin-2-yl)methyl)-4-methylphenyl)propanoic acid;

3-(4-Cyano-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(3,4-Difluorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(4-Methyl-3-(((R)-4-methyl-1,1-dioxido-3,4-dihydro-2H-benzo[b][1,4,5]oxathiazepin-2-yl)methyl)phenyl)-3-(3,4,5-trifluorophenyl)propanoic acid;

3-(3-Fluorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(4-Methyl-3-(((R)-4-methyl-1,1-dioxido-3,4-dihydro-2H-benzo[b][1,4,5]oxathiazepin-2-yl)methyl)phenyl)-3-phenylpropanoic acid;

3-(4-Methyl-3-(((R)-4-methyl-1,1-dioxido-3,4-dihydro-2H-benzo[b][1,4,5]oxathiazepin-2-yl)methyl)phenyl)-3-(o-tolyl)propanoic acid;

3-(4-Fluorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(4-Fluoro-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(4-Chloro-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(4-Chlorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(4-Carbamoyl-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid;

3-(4-Acetylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

4-(2-Carboxy-1-(4-methyl-3-(((R)-4-methyl-1,1-dioxido-3,4-dihydro-2H-benzo[b][1,4,5]oxathiazepin-2-yl)methyl)phenyl)ethyl)-2-(ethylcarbamoyl)benzoic acid;

5-(2-carboxy-1-(4-methyl-3-(((R)-4-methyl-1,1-dioxido-3,4-dihydro-2H-benzo[b][1,4,5]oxathiazepin-2-yl)methyl)phenyl)ethyl)-2-(ethylcarbamoyl)benzoic acid;

3-(1-(2-((Tert-butoxycarbonyl)amino)ethyl)-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(4-Methyl-3-(((R)-4-methyl-1,1-dioxido-3,4-dihydro-2H-benzo[b][1,4,5]oxathiazepin-2-yl)methyl)phenyl)-3-(3-oxo-2,3-dihydro-1H-inden-5-yl)propanoic acid;

3-(1-(3-((Tert-butoxycarbonyl)amino)propyl)-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(4-Methyl-3-(((R)-4-methyl-1,1-dioxido-3,4-dihydro-2H-benzo[b][1,4,5]oxathiazepin-2-yl)methyl)phenyl)-3-(4-(methylthio)phenyl)propanoic acid;

3-(4-Methyl-3-(((R)-4-methyl-1,1-dioxido-3,4-dihydro-2H-benzo[b][1,4,5]oxathiazepin-2-yl)methyl)phenyl)-3-(1-oxo-2,3-dihydro-1H-inden-5-yl)propanoic acid;

3-(2,4-Difluorophenyl)-3-(3-(((R)-4-ethyl-1,1-dioxido-3,4-dihydro-2H-benzo[b][1,4,5]oxathiazepin-2-yl)methyl)-4-methylphenyl)propanoic acid;

3-(2,4-Difluorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

Methyl 3-(1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate;

3-(4-Acetyl-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(4-Acetyl-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid;

3-(2-Methyl-1-oxoisoindolin-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(2,2-Dimethyl-1-oxo-2,3-dihydro-1H-inden-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(2-Ethyl-1,3-dioxoisoindolin-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid;

3-(3-(((R)-4-ethyl-1,1-dioxido-3,4-dihydro-2H-benzo[b][1,4,5]oxathiazepin-2-yl)methyl)-4-methylphenyl)-3-(2-ethyl-1,3-dioxoisoindolin-5-yl)propanoic acid;

3-(1,4-Dimethyl-1H-benzo[d][1,2,3]triazol-5-yl)-3-(3-((R)-4-methyl-1,1-dioxido-3,4-dihydro-2H-benzo[b][1,4,5]oxathiazepin-2-yl)-2,3-dihydro-1H-inden-5-yl)propanoic acid;

3-(1,4-Dimethyl-1H-benzo[d][1,2,3]triazol-5-yl)-3-(3-((R)-4-ethyl-1,1-dioxido-3,4-dihydro-2H-benzo[b][1,4,5]oxathiazepin-2-yl)-2,3-dihydro-1H-inden-5-yl)propanoic acid;

3-(1,4-Dimethyl-1H-benzo[d][1,2,3]triazol-5-yl)-3-(3-(4-methyl-1,1-dioxido-4,5-dihydrobenzo[f][1,2]thiazepin-2(3H)-yl)-2,3-dihydro-1H-inden-5-yl)propanoic acid;

3-(3-(8-Bromo-4-methyl-1,1-dioxido-4,5-dihydrobenzo[f][1,2]thiazepin-2(3H)-yl)-2,3-dihydro-1H-inden-5-yl)-3-(1,4-dimethyl-1H-benzo[d][1,2,3]triazol-5-yl)propanoic acid;

3-(3-(8-Bromo-4-methyl-1,1-dioxido-4,5-dihydrobenzo[f][1,2]thiazepin-2(3H)-yl)-2,3-dihydro-1H-inden-5-yl)-3-(1,4-dimethyl-1H-benzo[d][1,2,3]triazol-5-yl)propanoic acid;

2-{34-Methyl-3,3-dioxo-10-oxa-3$\lambda^6$-thia-2,17,18,19-tetraazaheptacyclo[24.5.2.1$^{2,11}$.1$^{2^0,2^4}$.0$^{4,9}$.0$^{17,21}$.0$^{2^9,32}$]pentatriaconta-4(9),5,7,18,20(34),21,23,26(33),27,29(32)-decaen-25-yl}acetic acid;

2-{4,32-Dimethyl-30,30-dioxo-23-oxa-30$\lambda^6$-thia-1,14,15,16-tetraazahexacyclo[20.8.1.1$^{3,7}$.1$^{9,13}$.0$^{12,16}$.0$^{2^4,2^9}$]tritriaconta-3,5,7(33),9,11,13(32),14,24(29),25,27-decaen-8-yl}acetic acid;

2-{4,32-Dimethyl-30,30-dioxo-23-oxa-30$\lambda^6$-thia-1,14,15,16-tetraazahexacyclo[20.8.1.1$^{3,7}$.1$^{9,13}$.0$^{12,16}$.0$^{2^4,2^9}$]tritriaconta-3,5,7(33),9,11,13(32),14,18,24(29),25,27-undecaen-8-yl}acetic acid;

2-{34-Methyl-3,3-dioxo-10-oxa-3$\lambda^6$-thia-2,17,18,19-tetraazaheptacyclo[24.5.2.1$^{2,11}$.1$^{2^0,2^4}$.0$^{4,9}$.0$^{17,21}$.0$^{2^9,32}$]pentatriaconta-4(9),5,7,14,18,20(34),21,23,26(33),27,29(32)-undecaen-25-yl}acetic acid;

3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid;

(S)-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid; and (R)-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid;

or pharmaceutically acceptable salts thereof.

Compounds of the present invention also include:

3-Aminopropyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate, trifluoroacetic acid salt; and 2-Amino-3-methylbutyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate, trifluoroacetic acid salt.

Compound Preparation

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compounds of the general formula (I) and pharmaceutically acceptable derivatives and salts thereof may be accomplished as outlined below in Schemes 1-15. In the following description, the groups are as defined above for compounds of formula (I) unless otherwise indicated. Abbreviations are as defined in the Examples section. Starting materials are commercially available or are made from commercially available starting materials using methods known to those skilled in the art.

Scheme 1

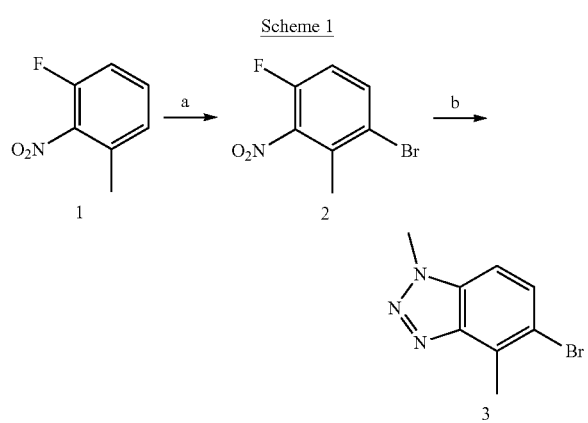

Conditions: a) NBS, TFA, H$_2$SO$_4$; b) i) MeNH$_2$, THF; ii) Zn, HOAc; iii) NaNO$_2$, H$_2$SO$_4$ Scheme 1 shows a general scheme for the preparation of 5-bromo-4-methyl-1-methyl-1H-benzo[d][1,2,3]triazole. Starting with commercially available 1-fluoro-3-methyl-2-nitrobenzene, bromination with NBS provides intermediate 2. Displacement of the fluoride using methylamine followed by zinc metal reduction of the nitro to the aniline and diazotization and cyclization provides the required triazole 3. Completion of the fully elaborated analog can be accomplished in a fashion analogous to that shown in Scheme 9.

Scheme 2

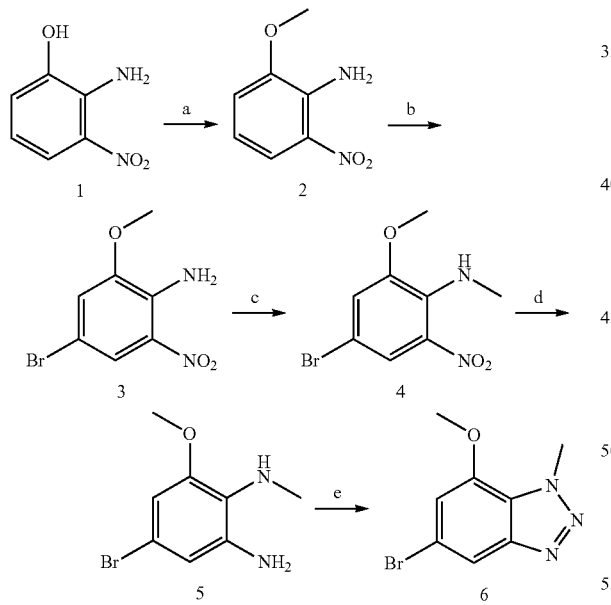

Conditions: a) K$_2$CO$_3$, MeI, DMF; b) Br$_2$, acetic acid; c) NaH, MeI, DMF; d) Zinc, acetic acid; e) NaNO$_2$, H$_2$SO$_4$ Scheme 2 shows a general scheme for the preparation of 5-bromo-7-methoxy-1-methyl-1H-benzo[d][1,2,3]triazole. Starting with commercially available 2-amino-3-nitrophenol, methylation of the phenol using K$_2$CO$_3$ and MeI (step a) provides intermediate 2 which can be brominated with NBS (step c). Methylation of the aniline (step d) followed by reduction of the nitro group (step d) and diazotization and cyclization (step e) provide the required triazole 5. Completion of the fully elaborated analog can be accomplished in a fashion analogous to that shown in Scheme 9.

Scheme 3

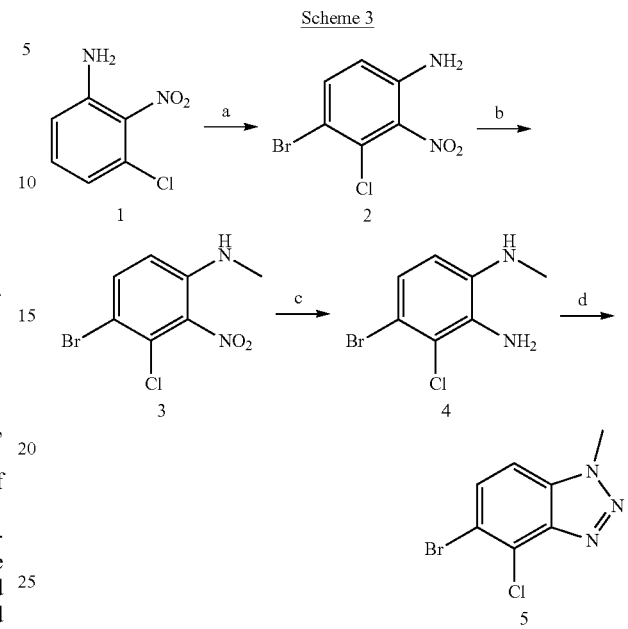

Conditions: a) NBS, acetic acid; b) NaH, MeI, DMF; c) Zinc, acetic acid; d) NaNO$_2$, H$_2$SO$_4$ Scheme 3 shows a general scheme for the preparation of 5-bromo-4-chloro-1-methyl-1H-benzo[d][1,2,3]triazole. Starting with commercially available 3-chloro-2-nitroaniline, bromination with NBS provides intermediate 2. Methylation of the aniline (step b) followed by reduction of the nitro group (step c) and diazotization and cyclization (step d) provide the required triazole 5. Completion of the fully elaborated analog can be accomplished in a fashion analogous to that shown in scheme 9.

Scheme 4

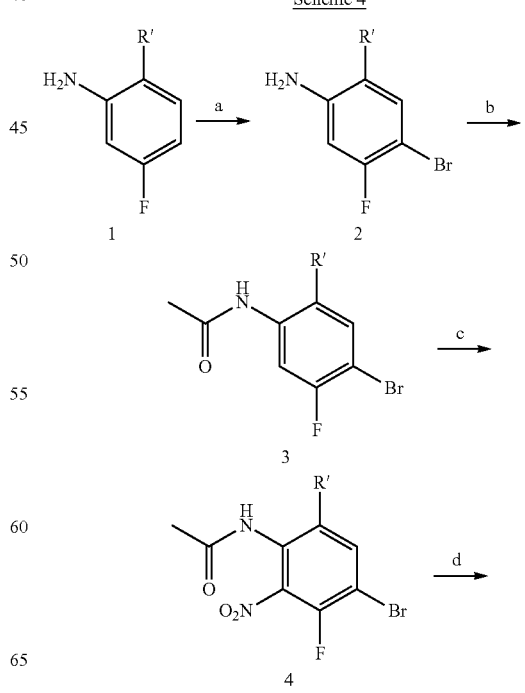

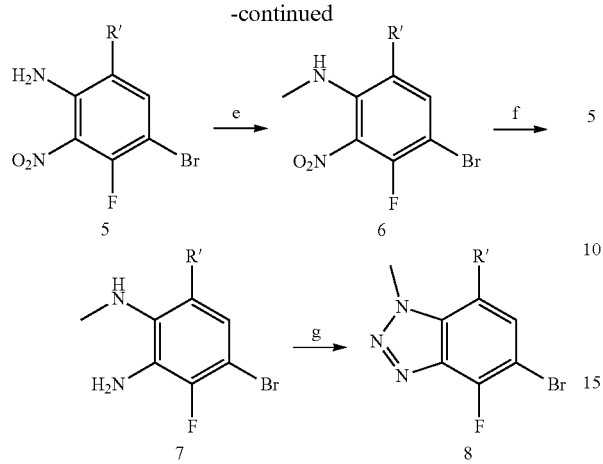

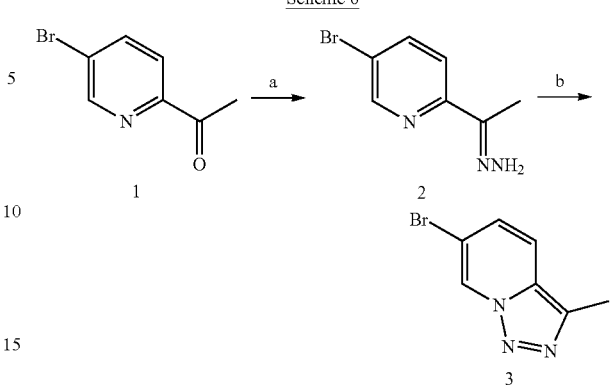

Conditions: a) hydrazine hydrate, MeOH; b) MnO$_2$, CHCl$_3$;

Scheme 6 represents a general scheme for the preparation of 6-Bromo-3-methyl-[1,2,3]triazolo[1,5-a]pyridine starting material. Treatment of 1-(5-bromopyridin-2-yl)ethanone 1 with hydrazine hydrate in MeOH provides intermediate 2 Intermediate 2 can be oxidized with MnO$_2$ to provide bromide intermediate 3. Completion of the fully elaborated analog can be accomplished in a fashion analogous to that shown in Scheme 9.

Conditions: a) NBS, DMF; b) acetic anhydride; c) HNO$_3$, H$_2$SO$_4$; d) HCl; e) NaH, MeI, DMF; f) Zinc, acetic acid; g) NaNO$_2$, H$_2$SO$_4$;

Scheme 4 represents a general scheme for the preparation of analogs containing 4-fluoro-1-methyl-1H-benzo[d][1,2,3]triazole or 4-fluoro-1,7-dimethyl-1H-benzo[d][1,2,3]triazole where R' is hydrogen or methyl. Starting with commercially available 3-fluoroaniline or 5-fluoro-2-methylaniline, bromination can be accomplished via treatment with NBS. Protection of the aniline as the acetamide, nitration and removal of the acetyl group provides intermediate 5. Conversion to the requisite triazole 8 is achieved via methylation, reduction of the nitro group followed by diazotization and cyclization. Completion of the fully elaborated analog can be accomplished in a fashion analogous to that shown in Scheme 9.

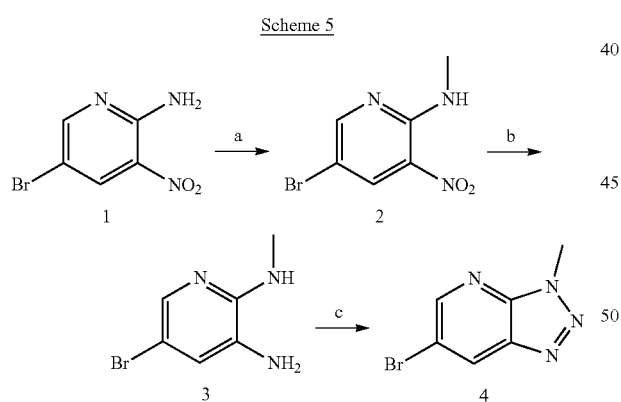

Conditions: a) NaH, MeI, DMF; b) TiCl$_2$, EtOH; c) NaNO$_2$, H$_2$SO$_4$;

Scheme 5 represents a general scheme for the preparation of 3-methyl-3H-[1,2,3]triazolo[4,5-b]pyridine. 5-bromo-3-nitropyridin-2-amine, which is commercially available, is methylated by deprotonation with sodium hydride followed by reaction with methyl iodide to afford intermediate 2. The nitro group can be reduced using TiCl$_2$ and triazole formation accomplished via diazotization and cyclization to provide intermediate 4. Completion of the fully elaborated analog can be accomplished in a fashion analogous to that shown in scheme 9.

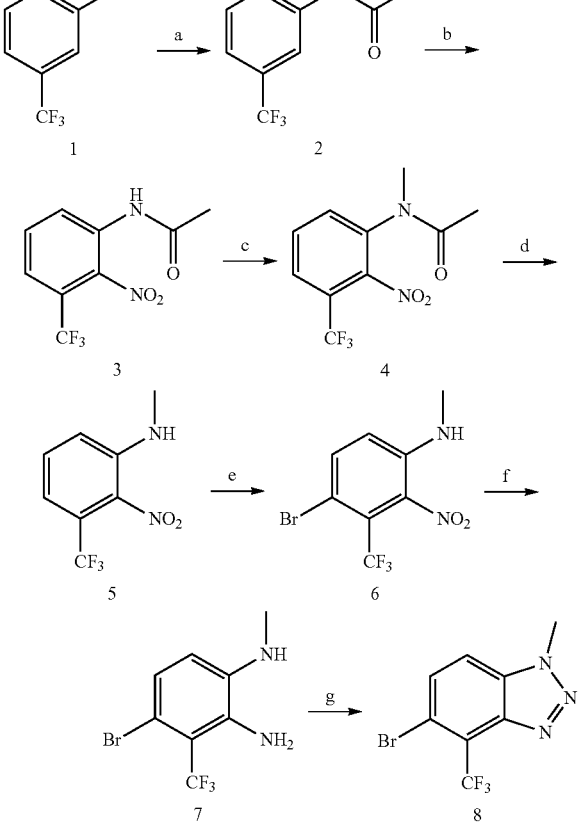

Conditions: a) acetic anhydride; b) HNO$_3$; c) NaH, MeI, DMF; d) NaOH, EtOH; e) NBS, DMF; f) Zinc, acetic acid; g) NaNO$_2$, H$_2$SO$_4$;

Scheme 7 represents a general scheme for the preparation of 5-bromo-1-methyl-4-(trifluoromethyl)-1H-benzo[d][1,2,3]triazole starting material. Starting with 3-(trifluoromethyl) aniline which is commercially available, acetylation of the aniline nitrogen provides acetamide 2. A three step sequence involving nitration, methylation of the acetamide and deprotection provides intermediate 5. This intermediate can be brominated using NBS to provide 6. Reduction of the nitro to the aniline followed by diazotization and cyclization gives the requisite triazole. Completion of the fully elaborated analog can be accomplished in a fashion analogous to that shown in Scheme 9.

Scheme 8

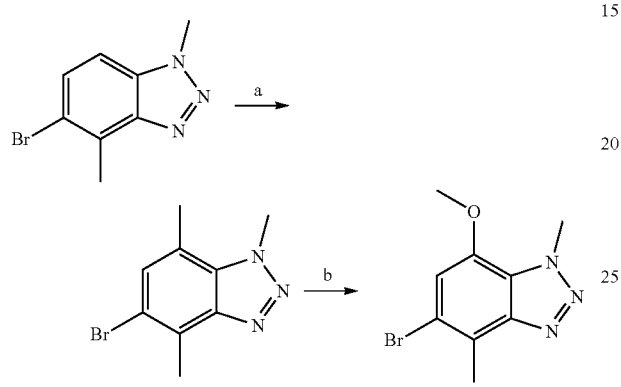

Conditions: a) NaIO$_4$/H$_2$SO$_4$, I$_2$, Ac$_2$O/AcOH; b) CuI, Cs$_2$CO$_3$, MeOH;

Scheme 8 shows a general scheme for the preparation of 5-bromo-7-methoxy-1,4-dimethyl-1H-benzo[d][1,2,3]triazole This two step process starts with iodination at C7 of 5-bromo-1,4-dimethyl-1H-benzo[d][1,2,3]triazole. Copper mediated replacement of the iodide with MeOH provides the desired material. Completion of the fully elaborated analog can be accomplished in a fashion analogous to that shown in Scheme 9.

Scheme 9

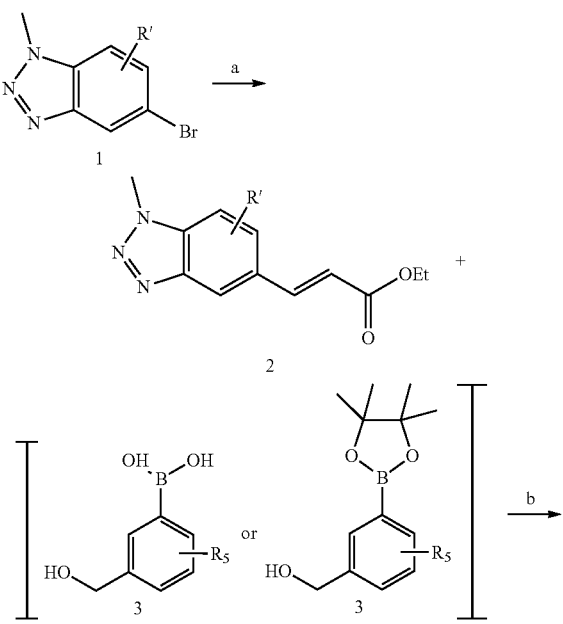

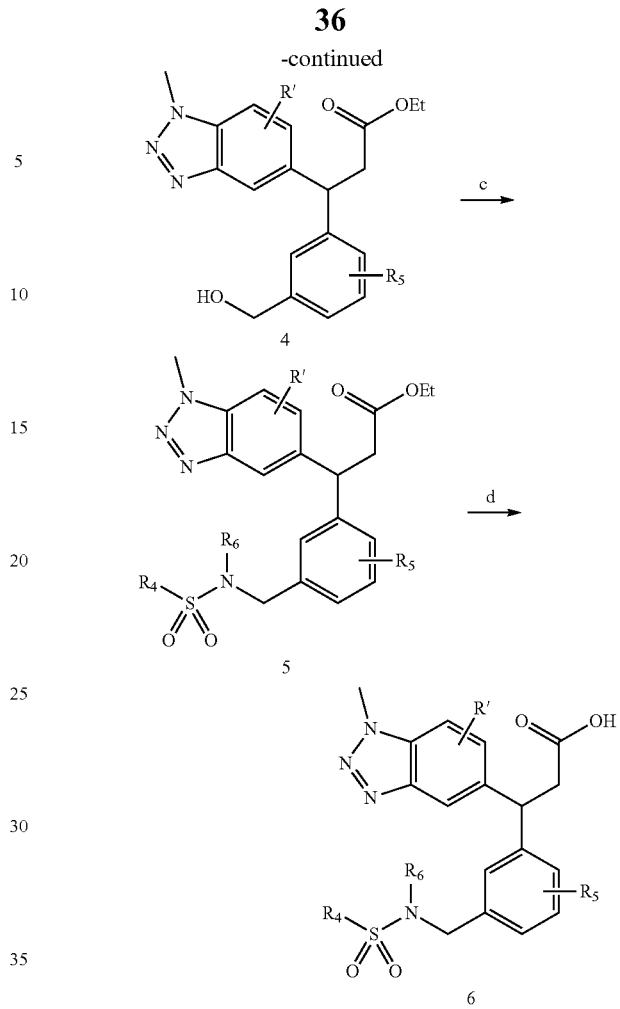

Conditions: a) Ethyl acrylate, Pd(OAc)$_2$, DIPEA, DMF; b) [RhCl(cod)]$_2$, TEA, H$_2$O, 1,4-dioxane; c) R$_7$SO$_2$NHR$_6$, Bu$_3$P, 1,1'-(Azodicarbonyl)dipiperidine, THF; d) LiOH, MeOH, THF.

Scheme 9 represents a general scheme for the preparation of compounds according to Formula (I). In Scheme 9, R$_4$, R$_5$, and R$_6$ are as defined for Formula (I); R' is O—C$_{1-3}$ alkyl or C$_{1-3}$ alkyl. The triazole depicted as starting material is either commercially available or may be synthesized from readily available materials. Reaction conditions are as described above in the scheme; however, the skilled artisan will appreciate that certain modifications in the reaction conditions and/or reagents used are possible.

Treatment of triazole 1 with ethyl acrylate in the presence of palladium (II) acetate and diisopropylethyl amine in presence of a suitable solvent produces the desired Heck cross-coupling product 2. It will appreciated by the skilled artisan that compound 2 may also be obtained via a Homer Wadsworth Emmons or Wittig olefination reaction starting from the appropriate aldehyde of compound 1. Further transformation of the olefin 2 can be achieved through rhodium mediated addition of the appropriate boronic acid or boronic ester 3 in the presence of triethylamine. Completion of the analog synthesis is accomplished via Mitsunobu reaction with the requisite sulfonamide followed by hydrolysis of the ester to produce 6. It will appreciated by the skilled artisan that sulfonamides like 5, may be synthesized via conversion of the benzylic alcohol of 4 to a leaving group such as, but not limited to, mesylate, tosylate, chloride, bromide, or iodide followed by reaction with the requisite amine NHR$_6$ and subsequent reaction with a sulfonylating reagent such as a sulfonyl chloride.

Scheme 10

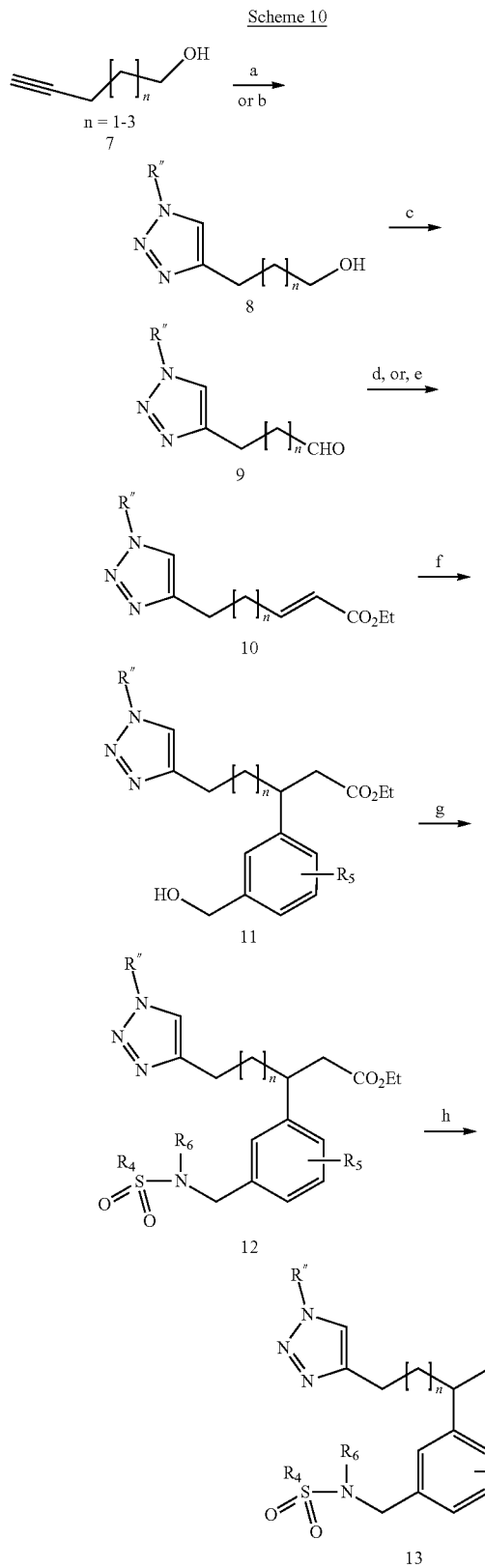

Conditions: a) R″—I, NaN$_3$, CuI; b) R″—N3, CuSO$_4$, sodium ascorbate; c) oxalyl chloride, DMSO, triethylamine, −78° C.; d) EtO$_2$CCH$_2$PO(OEt)$_2$, NaH, DCM, 23° C., 1 h; e) CO$_2$EtCH=PPh$_3$, DCM, reflux, 16 h; f) (Rh[COD]Cl)$_2$, 3-(Hydroxymethyl)-phenyl boronic acids; triethylamine, 1,4-dioxane, water; g) 1,1'-(Azodicarbonyl)dipiperidine, tri-n-butylphosphine, R$_4$SO$_2$NHR$_6$, THF; h) LiOH, H$_2$O, MeOH, THF.

Scheme 10 represents a general scheme for the preparation of compounds according to formula I. In scheme 10, R″ is C$_{1-3}$ alkyl or —CH$_2$-phenyl; R$_4$, R$_5$, and R$_6$ are defined as above for Formula (I). The acetylenic alkyl alcohols 7 depicted are commercially available. Reaction conditions are as described above in the scheme; however, the skilled artisan will appreciate that certain modifications in the reaction conditions and/or reagents used are possible. The triazines 8 are prepared by standard click conditions either using commercially available organo-azides, Cu(II), and a suitable reducing agent such as sodium ascorbate to generate the Cu(I) catalyst or alternatively by in situ formation of an alkyl azide by reaction of an alkyl halide with sodium azide followed by reaction in the presence of a commercially available source of Cu(I) such as CuI. Aldehydes such as 9 are best obtained from the triazine alcohols by a Swern oxidation. Other well known methods for oxidation of alkyl alcohols to aldehydes, such as pyridinium chlorochromate oxidation or use of the Dess Martin reagent may also be applied. It will be appreciated by the skilled artisan that compound 10 may be obtained by either the Horner Wadsworth Emmons reaction or a Wittig olefination reaction starting from the appropriate aldehyde 9 and the stabilized phosphonium ylide as shown in the scheme. Both procedures generally afford the trans olefin though that is irrelevant to the subsequent reaction. Further transformation of the olefin 10 can be achieved through rhodium mediated cross-coupling of the appropriate boronic acid or boronic ester in the presence of triethylamine to afford the methyl-phenyl alcohol 11. Completion of the analog synthesis is accomplished via Mitsunobu reaction with the requisite sulfonamide followed by hydrolysis of the ester to produce 12. It will appreciated by the skilled artisan that the sulfonamides in the scheme may be synthesized via conversion of the benzylic alcohol of 11 to a leaving group such as, but not limited to, mesylate, tosylate, chloride, bromide, or iodide followed by reaction with the requisite amine NH R$_6$ and subsequent reaction with a sulfonylating reagent such as a sulfonyl chloride. Standard aqueous LiOH hydrolysis of the ester in the presence of suitable co-solvents to assure adequate solubility of the reactants affords the final target carboxylic acids.

Scheme 11

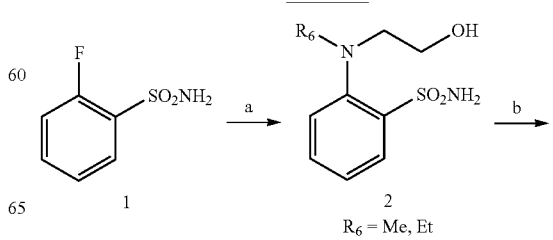

R$_6$ = Me, Et

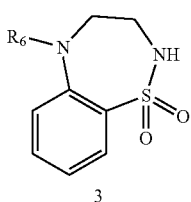

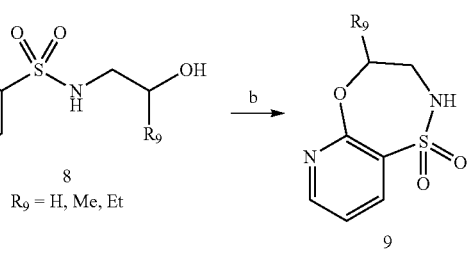

Conditions: a) R₁NHCH₂CH₂NH₂; b) DIAD, PS—PPh₃, THF

Scheme 11 represents a general scheme for the preparation of 5-methyl-2,3,4,5-tetrahydrobenzo[f][1,2,5]thiadiazepine 1,1-dioxide and 5-ethyl-2,3,4,5-tetrahydrobenzo[f][1,2,5]thiadiazepine 1,1-dioxide used in the invention. In this, 2-fluorobenzenesulfonamide depicted as starting material is commercially available. Displacement of the fluorine with the appropriate ethylenediamine followed by Mitsunobu reaction provides the required intermediate 3.

Conditions: a) H₂NCH₂CH(R₃)OH, K₂CO₃, THF/H₂O; b) t-BuOK, DMSO

Scheme 13 represents a general scheme for the preparation of 3,4-dihydro-2H-pyrido[2,3-b][1,4,5]oxathiazepine 1,1-dioxide, 4-methyl-3,4-dihydro-2H-pyrido[2,3-b][1,4,5]oxathiazepine 1,1-dioxide, and 4-ethyl-3,4-dihydro-2H-pyrido[2,3-b][1,4,5]oxathiazepine 1,1-dioxide used in the invention. In this, 2-fluoro-pyridine-3-sulfonyl chloride depicted as starting material is commercially available. Reaction with the appropriate aminoalcohol followed by displacement of the fluoride provides the required intermediate 9.

Scheme 12

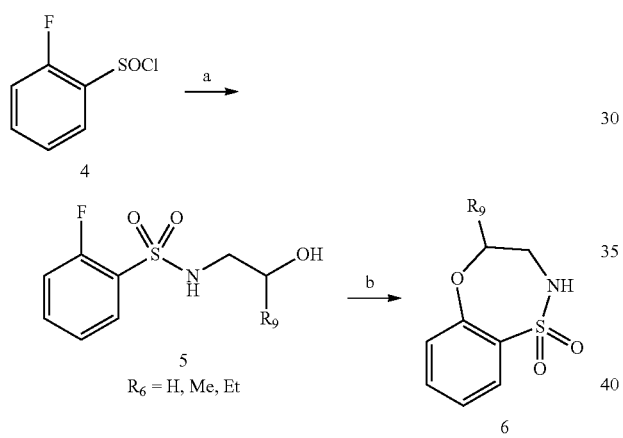

Conditions: a) H₂NCH₂CH(R²)OH, K₂CO₃, THF/H₂O; b) t-BuOK, DMSO

Scheme 12 represents a general scheme for the preparation of 3,4-dihydro-2H-benzo[b][1,4,5]oxathiazepine 1,1-dioxide, 4-methyl-3,4-dihydro-2H-benzo[b][1,4,5]oxathiazepine 1,1-dioxide, and 4-ethyl-3,4-dihydro-2H-benzo[b][1,4,5]oxathiazepine 1,1-dioxide used in the invention. In this, 2-fluorobenzenesulfonylchloride depicted as starting material is commercially available. Reaction with the appropriate aminoalcohol followed by displacement of the fluoride provides the required intermediate 6.

Scheme 13

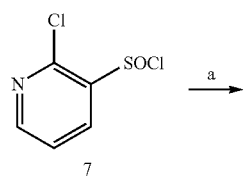

Scheme 14

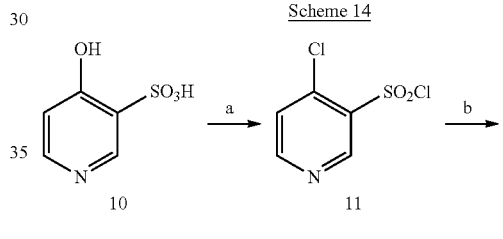

Conditions: a) POCl₃, PCl₅; b) H₂NCH₂CH(R₄)OH, K₂CO₃, THF/H₂O; c) t-BuOK, DMSO

Scheme 14 represents a general scheme for the preparation of 3,4-dihydro-2H-pyrido[4,3-b][1,4,5]oxathiazepine 1,1-dioxide, 4-methyl-3,4-dihydro-2H-pyrido[4,3-b][1,4,5]oxathiazepine 1,1-dioxide, and 4-ethyl-3,4-dihydro-2H-pyrido[4,3-b][1,4,5]oxathiazepine 1,1-dioxide used in the invention. In this, 4-hydroxypyridine-3-sulfonic acid depicted as starting material is commercially available. Reaction with the appropriate aminoalcohol followed by displacement of the fluoride provides the required intermediate 13.

Scheme 15

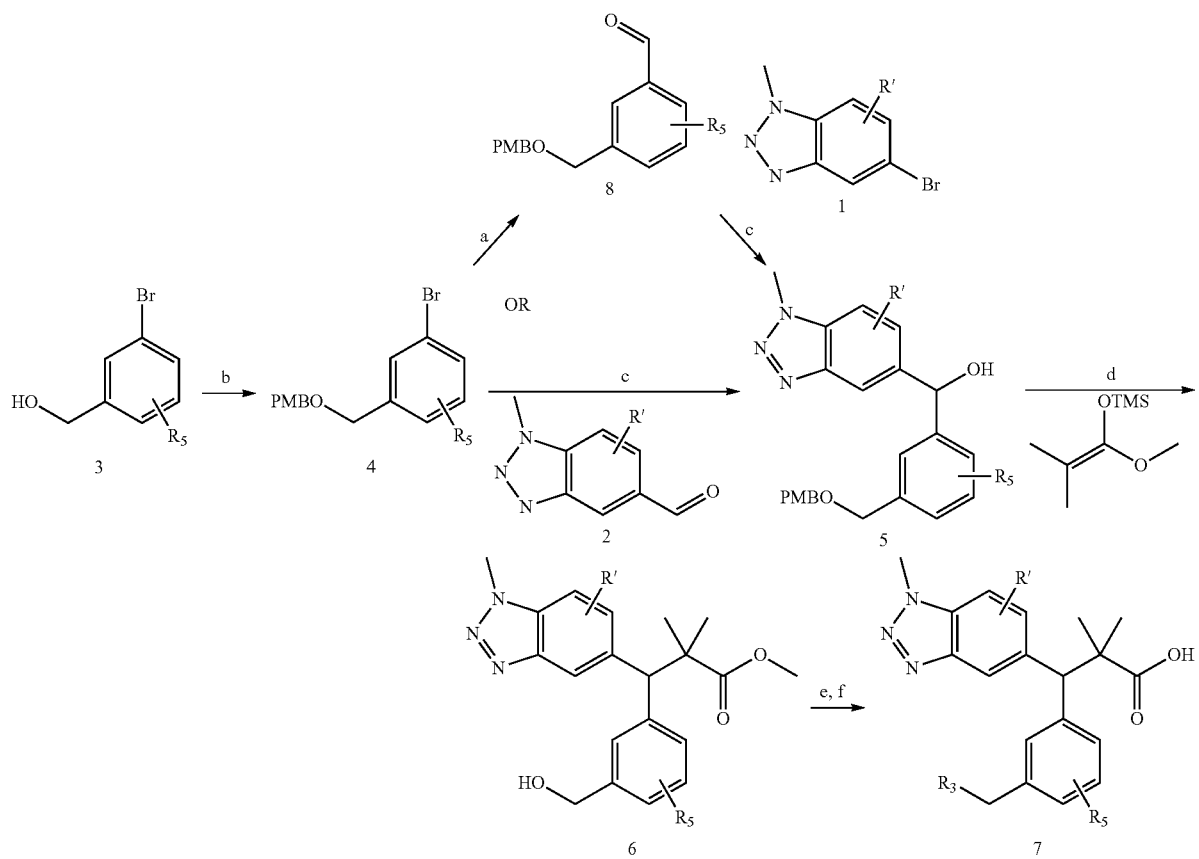

Conditions: a) n-BuLi, DMF, THF b) NaH, PMBCl, DMF t-BuLi, THF d). TiCl₄, DCM e) R₃H, Bu₃P, 1,1'-(azodicarbonyl)dipiperidine, THF; f) LiOH, MeOH, THF.

Scheme 15 represents a general scheme for the preparation of compounds according to Formula (I). In Scheme 15, $R_3$ and $R_5$ are as defined for Formula (I); R' is O—$C_{1-3}$ alkyl or $C_{1-3}$ alkyl. Triazole 1 is either commercially available or may be synthesized from readily available materials. Reaction conditions are as described above in the scheme; however, the skilled artisan will appreciate that certain modifications in the reaction conditions and/or reagents used are possible.

Treatment of triazole 1 with n-butyl lithium and DMF in presence of a suitable solvent produces the desired aldehyde product 2. The coupling partner for aldehyde 2 is obtained by first protecting the benzylic alcohol 3 as its paramethoxybenzylether. It will be appreciated that alternative protecting groups are possible. Coupling of the aldehyde 2 and bromide 4 can be accomplished via treatment of the bromide first with t-butyl lithium followed by addition of the aldehyde. Intermediate alcohol 6, arises from treatment of alcohol 5 with the appropriate silylketene acetal in the presence of a Lewis acid. Completion of the synthesis can be accomplished via Mitsunobu reaction with the requisite sulfonamide followed by hydrolysis of the ester to produce 7. It will be appreciated by the skilled artisan that sulfonamides like 7, may be synthesized via conversion of the benzylic alcohol of 6 to a leaving group such as, but not limited to, mesylate, tosylate, chloride, bromide, or iodide followed by reaction with the requisite amine $NHR_6$ and subsequent reaction with a sulfonylating reagent such as a sulfonyl chloride.

It will be also be appreciated by the skilled artisan that intermediate 5 may be prepared by coupling bromide 1 with aldehyde 8.

Biological Activity

As stated above, the compounds according to Formula I are Nrf2 regulators, and are useful in the treatment or prevention of human diseases that exhibit oxidative stress components such as respiratory disorders, diabetic nephropathy/chronic kidney disease, autoimmune diseases (e.g., multiple sclerosis and inflammatory bowel disease), eye diseases (e.g., AMD) Fuchs, and uveitis), cardiovascular diseases, acute kidney injury, topical effects of radiation, and kidney transplant.

The biological activity of the compounds according to Formula I can be determined using any suitable assay for determining the activity of a candidate compound as a Nrf2 antagonist, as well as tissue and in vivo models.

The biological activity of the compounds of Formula (I) are demonstrated by the following tests.

BEAS-2B NQO1 MTT Assay

NAD(P)H:quinone oxidoreductase 1 (NQO1), also called DT diaphorase, is a homodimeric FAD-containing enzyme that catalyzes obligatory NAD(P)H-dependent two-electron reductions of quinones and protects cells against the toxic and neoplastic effects of free radicals and reactive oxygen species arising from one-electron reductions. The transcription of NQO1 is finely regulated by Nrf2, and thus NQO1 activity is a good marker for Nrf2 activation. On day one, frozen BEAS-2B cells (ATCC) are thawed in a water bath, counted, and re-suspended at a concentration of 250,000 cells/mL. Fifty microliters of cells are plated in 384 well black clear-bottomed plates. Plates are incubated at 37° C., 5% $CO_2$ overnight. On day two, plates are centrifuged and 50 nL of compound or controls are added to the cells. Plates are then incubated at 37° C., 5% $CO_2$ for 48 h. On day four, medium is aspirated from the plate and crude cell lysates are made by adding 13 μL of 1× Cell Signaling Technologies lysis buffer with 1 Complete, Mini, EDTA-free Protease Inhibitor Tablet (Roche) for each 10 mL of lysis buffer. After lysis plates are incubated for 20 min at room temperature. Two microliters of lysate are removed for use in Cell Titer Glo assay (Promega) and MTT cocktail is prepared (Prochaska et. al. 1998) for measurement of NQO1 activity. Fifty microliters of MTT cocktail is added to each well, plate is centrifuged, and analyzed on an Envision plate reader (Perkin Elmer) using Absorbance 570 nm label for 30 min. Product formation is measured kinetically and the $pEC_{50}$ of NQO1 specific activity induction is calculated by plotting the change in absorbance (Delta OD/min) versus the log of compound concentration followed by 3-parameter fitting.

All examples described herein possessed NQO1 specific enzyme activity in BEAS-2B cells with $EC_{50}$s between >10 μM-<10 nM unless otherwise noted (see table below). $EC_{50}$s<10 nM (++++), $EC_{50}$s 10-100 nM (+++), $EC_{50}$s 100 nM-1 μM (++), $EC_{50}$s 1-10 μM (+), $EC_{50}$s>10 μM (X), or were not determined (ND).

| Ex # | $EC_{50}$ |
|---|---|
| 1 | ++ |
| 2 | ++ |
| 3 | ++ |
| 4 | + |
| 5 | +++ |
| 6 | + |
| 7 | − |
| 8 | ++ |
| 9 | − |
| 10 | +++ |
| 11 | ++++ |
| 12 | ++ |
| 13 | ++++ |
| 14 | ++ |
| 15 | +++ |
| 16 | +++ |
| 17 | + |
| 18 | +++ |
| 19 | ++++ |
| 20 | ++++ |
| 21 | ++++ |
| 22 | ++++ |
| 23 | ++++ |
| 24 | ++++ |
| 25 | +++ |
| 26 | +++ |
| 27 | +++ |
| 28 | ++ |
| 29 | ++ |
| 30 | ++ |
| 31 | ++ |
| 32 | +++ |
| 33 | ++ |
| 34a | +++ |
| 34b | +++ |
| 35 | ++++ |
| 36 | ++++ |
| 37 | +++ |
| 38 | ++++ |
| 39 | +++ |
| 40 | ++++ |
| 41 | ++++ |
| 42 | ++++ |
| 43 | ++++ |
| 44 | ++++ |
| 45 | ++++ |
| 46 | ++ |
| 47 | − |
| 48 | + |
| 49 | ND |
| 50 | + |
| 51 | − |
| 52 | + |
| 53 | + |
| 54 | − |
| 55 | ++ |
| 56 | ++ |
| 57 | + |
| 58 | − |
| 59 | − |
| 60 | ND |
| 61 | ++++ |
| 62 | + |
| 63 | + |
| 64 | ++ |
| 65 | + |
| 66 | + |
| 67 | ++ |
| 68 | +++ |
| 69 | + |
| 70 | − |
| 71 | − |
| 72 | +++ |
| 73 | +++ |
| 74 | ++ |
| 75 | ++ |
| 76 | ++ |
| 77 | ++ |
| 78 | + |
| 79 | +++ |
| 80 | − |
| 81 | + |
| 82 | − |
| 83 | + |
| 84 | + |
| 85 | − |
| 86 | − |
| 87 | ++++ |
| 88 | +++ |
| 89 | ++ |
| 90 | + |
| 91 | ++ |
| 92 | ++ |
| 93 | ++ |
| 94 | − |
| 95 | ++ |
| 96 | ++ |
| 97 | + |
| 98 | + |
| 99 | ++ |
| 100 | + |
| 101 | ++ |
| 102 | + |
| 103 | + |
| 104 | + |
| 105 | + |
| 106 | + |
| 107 | ++ |
| 108 | + |
| 109 | + |
| 110 | ND |
| 111 | ++ |
| 112 | ++ |
| 113 | ++ |
| 114 | + |
| 115 | + |
| 116 | + |

| Ex # | EC$_{50}$ |
|---|---|
| 117 | + |
| 118 | +++ |
| 119 | ++++ |
| 120 | ++ |
| 121 | + |
| 122 | + |
| 123 | +++ |
| 124 | + |
| 125 | +++ |
| 126 | ++ |
| 127 | ++ |
| 128 | ++ |
| 129 | ++ |
| 130 | +++ |
| 131 | + |
| 132 | ++ |
| 133 | ++++ |
| 134 | + |
| 135 | + |
| 136 | − |
| 137 | ND |
| 138 | ND |
| 139 | − |
| 140 | ND |
| 141 | − |
| 142 | − |
| 143 | ND |
| 144 | + |
| 145 | ++ |
| 146 | ++ |
| 147 | ++ |
| 148 | ++ |
| 149 | +++ |
| *150 | ++ |
| 151 | +++ |
| 152 | +++ |
| 153 | ++ |
| 154 | +++ |
| 155 | +++ |
| 156 | ++++ |
| 157 | + |
| 158 | ++ |
| 159 | + |
| 160 | ++ |
| 161 | + |
| 162 | ++ |
| *163 | + |
| 164 | ++ |
| 165 | + |
| 166 | ++++ |
| 167 | + |
| *168 | + |
| 169 | + |
| 170 | ++ |
| 171 | + |
| 172 | + |
| 173 | ++ |
| 174 | ++ |
| 175 | ++++ |
| 176 | ++ |
| 177 | ++ |
| 178 | ++ |
| 179 | ++ |
| 180 | ++ |
| 181 | +++ |
| 182 | ++++ |
| 183 | +++ |
| 184 | ++++ |
| 185 | ++ |
| 186 | ++ |
| 187 | + |
| 188 | ++ |
| 189 | ++ |
| 189 isomer M1 | |
| 189 isomer N1 | +++ |
| 190 | +++++ |
| 190 isomer M1 | ++++ |
| 191 isomer M1 | ++++ |
| 191 isomer N1 | ++++ |
| 192 | +++++ |
| 193 | +++++ |
| 194 | +++ |
| 195 | + |
| 196 | ++ |
| 197 | + |
| 198 | ++ |
| 199 | +++ |
| 200 | ++ |
| 201 | +++ |
| 202 | ++++ |
| 203 | +++ |
| 204 | +++ |
| 205 | +++ |
| 206 | +++ |
| 207 | ++ |
| 208 | ++ |
| 208 isomer M1 | |
| 208 isomer N1 | ++ |
| 209 | +++ |
| 210 | ++++ |
| 211 | +++ |
| 212 | +++ |
| 213 | ++++ |
| 214 | +++ |
| 215 | ++++ |
| 216 | ++++ |
| 217 | +++ |
| 218 | +++ |
| 219 | ++ |
| 220 | +++ |
| 221 | +++ |
| 222 | ++++ |
| 223 | +++ |
| 224 | + |
| 225 | ++ |
| 226 | + |
| 227 | ++++ |
| 228 | ++ |
| 229 | +++ |
| 230 | +++ |
| 231 | +++ |
| 232 | ++ |
| 233 | ++ |
| 234 | + |
| 235 | + |
| 236 | ++ |
| 237 | ++ |
| 238 | ++ |
| 239 | +++ |
| 240 | ++ |
| 241 | + |
| 242 | ++ |
| 243 | + |
| 244 | + |
| 245 | ++ |
| 246 | ++ |
| 247 | ++ |
| 248 | ++ |
| 249 | +++ |
| 250 | +++ |

-continued

| Ex # | EC$_{50}$ |
|---|---|
| 251 | + |
| 252 | +++ |
| 253 | +++ |
| 254 | + |
| 255 | +++ |
| 256 | ++ |
| 257 | ++++ |
| 258 | + |
| 259 | + |
| 260 | ++ |
| 261 | ++ |
| 262 | ++ |
| 263 | + |
| 264 | + |
| 265 | +++ |
| 266 | ++ |
| 267 | + |
| 268 | ++++ |
| 269 | ++++ |
| 270 | ++++ |

*in some determinations EC$_{50}$s were >10 μM

Nrf2-Keap1 FP Assay

One model for the Nrf2-Keap1 interaction is through two binding sites in the Neh2 domain on Nrf2. The two sites are referred to as the DLG binding motif (latch domain, μM affinity) and the ETGE binding motif (hinge domain, nM affinity). The Keap1 protein consists of an N-terminal region (NTR), a broad complex, tramtrack, and brick a' brac domain (BTB), an intervening region (IVR), a double glycine repeat domain (DGR or Kelch), and a C-terminal region. The DLG and ETGE motifs of Nrf2's Neh2 domain bind to the Kelch domain of Keap1 at different affinities. In the Keap1 Kelch fluorescence polarization (FP) assay, a TAMRA-labeled 16 mer peptide (AFFAQLQLDEETGEFL) containing the ETGE motif of Nrf2 and the Kelch domain (321-609) of Keap1 is used. The assay determines if a compound interferes with the binding between Keap1 (361-609) and the TAMRA-labeled peptide. Binding of TAMRA-labeled Nrf2 peptide to Keap1 (321-609) results in a high FP signal. If a compound interferes with the binding between the peptide and the protein, it will cause the assay signal to decrease. Thus, assay signal is inversely proportional to binding inhibition.

FP Assay #1:

100 nL of 100× compound dose response curves (serial 3-fold dilutions) in DMSO are stamped using an Echo liquid handling system (Labcyte) into 384-well low volume black assay plates (Greiner, #784076), with DMSO in columns 6 and 18. The top concentration of compound is located in columns 1 and 13. Keap1 (321-609) is diluted to 40 nM (2×) in 1× assay buffer (50 mM Tris, pH 8.0, 100 mM NaCl, 5 mM MgCl$_2$, 1 mM DTT, 2 mM CHAPS, and 0.005% BSA) and 5 ul is added using a Multidrop Combi (Thermo Electron Corporation) equipped with a metal tip dispenser to all wells of the compound plate, except column 18. Column 18 receives only 5 ul of assay buffer. Immediately, 5 μL of 16 nM (2×) of Tamra labeled peptide (AFFAQLQLDEET-GEFL, 21$^{st}$ Century Biochemicals) is added to all wells of the plate. The plates are spun at 500 rpm for 1 min, incubated for 1 h at room temperature, and read on an Analyst GT (Molecular Devices) equipped with excitation (530/25 nm) and emission (580/10 nm) filters designed for Tamra probes. A 561 nm dichroic mirror is also used in the Analyst. The final assay concentrations of Keap1 (321-609) and Tamra labeled peptide are 20 nM and 8 nM, respectively. Fluorescence measurements, represented as mP, are used in the transformation of the data. Compound activity is calculated based on percent inhibition, normalized against controls in the assay (Control 1 contains the Tamra peptide and Keap1 (321-609) together (0% response) and control 2 contains the Tamra peptide alone (100% response)). Data analysis is handled using the software package Abase XE (Surrey, United Kingdom. The % inhibition values are calculated by the equation:

100−(100*((compound response−average control 2)/(average control 1−average control 2))).

For calculation of pIC$_{50}$s, Abase XE uses a four parameter equation.

All examples described herein possessed activity in the Keap1/Nrf2 FP assay as listed (see table below) unless otherwise noted. IC$_{50}$s<10 nM (+++++), IC$_{50}$s 10-100 nM (++++), IC$_{50}$s 100 nM-1 μM (+++), IC$_{50}$s 1-10 μM (++), IC$_{50}$s 10-100 μM (+), IC$_{50}$s>100 μM (X), or were not determined (ND).

| Ex # | IC$_{50}$ |
|---|---|
| 1 | ++++ |
| 2 | ++++ |
| 3 | ++++ |
| 4 | +++ |
| 5 | ++++ |
| 6 | ++++ |
| 7 | ++ |
| 8 | ++++ |
| 9 | ++ |
| 10 | ++++ |
| 11 | +++++ |
| 12 | ++++ |
| 13 | +++++ |
| 14 | ++++ |
| 15 | ++++ |
| 16 | +++++ |
| 17 | ++++ |
| 18 | +++++ |
| 19 | ++++ |
| 20 | +++++ |
| 21 | ++++ |
| 22 | +++++ |
| 23 | +++++ |
| 24 | +++++ |
| 25 | ++++ |
| 26 | +++++ |
| 27 | ++++ |
| 28 | ++++ |
| 29 | ++++ |
| 30 | ++++ |
| 31 | ++++ |
| 32 | ++++ |
| 33 | ++++ |
| 34a | ++++ |
| 34b | ++++ |
| 35 | ++++ |
| 36 | ++++ |
| 37 | ++++ |
| 38 | ++++ |
| 39 | ++++ |
| 40 | ++++ |
| 41 | ++++ |
| 42 | ++++ |
| 43 | ++++ |
| 44 | ++++ |
| 45 | ++++ |
| 46 | +++ |
| 47 | +++ |
| 48 | +++ |
| 49 | ND |
| 50 | +++ |
| 51 | ++ |
| 52 | +++ |
| 53 | +++ |

| Ex # | IC$_{50}$ |
|---|---|
| 54 | +++ |
| 55 | ++++ |
| 56 | ++++ |
| 57 | ++++ |
| 58 | +++ |
| 59 | ++++ |
| 60 | ND |
| 61 | ++++ |
| 62 | +++ |
| 63 | ++++ |
| 64 | ++++ |
| 65 | ++++ |
| 66 | +++ |
| 67 | ++++ |
| 68 | ++++ |
| 69 | ++++ |
| 70 | ++++ |
| 71 | ++++ |
| 72 | ++++ |
| 73 | ++++ |
| 74 | +++ |
| 75 | ++++ |
| 76 | +++ |
| 77 | ++++ |
| 78 | ++++ |
| 79 | ++++ |
| 80 | ++ |
| 81 | ++++ |
| 82 | ++ |
| 83 | ++++ |
| 84 | ++++ |
| 85 | ++++ |
| 86 | +++ |
| 87 | ++++ |
| 88 | ++++ |
| 89 | ++++ |
| 90 | +++ |
| 91 | + |
| 92 | ++++ |
| 93 | ++ |
| 94 | − |
| 95 | +++ |
| 96 | ++ |
| 97 | ++ |
| 98 | ++ |
| 99 | + |
| 100 | ++ |
| 101 | +++ |
| 102 | ++ |
| 103 | ++ |
| 104 | + |
| 105 | ++ |
| 106 | ++ |
| 107 | +++ |
| 108 | +++ |
| 109 | ++ |
| 110 | ND |
| 111 | ++ |
| 112 | +++ |
| 113 | ++ |
| 114 | ++ |
| 115 | ++++ |
| 116 | ++++ |
| 117 | ++++ |
| 118 | ++++ |
| 119 | ++++ |
| 120 | ++++ |
| 121 | +++ |
| 122 | +++ |
| 123 | ++++ |
| 124 | ++++ |
| 125 | ++++ |
| 126 | +++ |
| 127 | ++++ |
| 128 | ++++ |
| 129 | ++++ |
| 130 | ++++ |
| 131 | ++++ |
| 132 | ++++ |
| 133 | ++++ |
| 134 | ++++ |
| 135 | ++++ |
| 136 | ++++ |
| 145 | ++++ |
| 146 | ++++ |
| 147 | ++++ |
| 148 | ++++ |
| 149 | ++++ |
| 150 | ++++ |
| 151 | ++++ |
| 152 | ++++ |
| 153 | ++++ |
| 154 | ++++ |
| 155 | ++++ |
| 156 | ++++ |
| 157 | +++ |
| 158 | ++++ |
| 159 | ++++ |
| 160 | ++++ |
| 161 | +++ |
| 162 | +++ |
| 163 | ++ |
| 164 | ++++ |
| 165 | +++ |
| 166 | ++++ |
| 167 | +++ |
| 168 | ++++ |
| 169 | +++ |
| 170 | +++ |
| 171 | ++++ |
| 172 | +++ |
| 173 | ++++ |
| 174 | +++ |
| 175 | ++++ |
| 176 | ++++ |
| 177 | ++++ |
| 178 | ++++ |
| 179 | ++++ |
| 180 | ++++ |
| 181 | ++++ |
| 182 | ++++ |
| 183 | ++++ |
| 184 | ++++ |
| 185 | +++ |
| 186 | ++++ |
| 187 | +++ |
| 188 | ++++ |
| 189 isomer M1 | ++++ |
| 189 isomer N1 | ++++ |
| 190 isomer M1 | ++++ |
| 190 isomer N1 | ++++ |
| 191 isomer M1 | ++++ |
| 191 isomer N1 | +++++ |
| 192 | +++++ |
| 193 | ++++ |
| 194 | ++++ |
| 195 | +++ |
| 196 | +++ |
| 197 | ++++ |
| 198 | ++++ |
| 199 | ++++ |
| 200 | ++++ |

-continued

| Ex # | IC$_{50}$ |
|---|---|
| 201 | ++++ |
| 202 | ++++ |
| 203 | ++++ |
| 204 | ++++ |
| 205 | ++++ |
| 206 | ++++ |
| 207 | ++++ |
| 208 isomer M1 | ++++ |
| 208 isomer N1 | ++++ |
| 209 | ++++ |
| 210 | ++++ |
| 211 | ++++ |
| 212 | ++++ |
| 213 | ++++ |
| 214 | ++++ |
| 215 | ++++ |
| 216 | ++++ |
| 217 | ++++ |
| 218 | ++++ |
| 219 | +++ |
| 220 | ++++ |
| 221 | ++++ |
| 222 | ++++ |
| 223 | ++++ |
| 224 | ++++ |
| 225 | +++ |
| 226 | ++++ |
| 227 | ++++ |
| 228 | ++++ |
| 229 | ++++ |
| 230 | ++++ |
| 231 | ++++ |
| 232 | ++++ |
| 233 | +++ |
| 234 | +++ |
| 235 | +++ |
| 236 | +++ |
| 237 | +++ |
| 238 | ++++ |
| 239 | ++++ |
| 240 | ++++ |
| 241 | ++++ |
| 242 | ++++ |
| 243 | +++ |
| 244 | ++++ |
| 245 | ++++ |
| 246 | ++++ |
| 247 | ++++ |
| 248 | ++++ |
| 249 | ++++ |
| 250 | ++++ |
| 251 | + |
| 252 | ++++ |
| 253 | ++++ |
| 254 | ++++ |
| 255 | ++++ |
| 256 | ++++ |
| 257 | ++++ |
| 258 | +++ |
| 259 | +++ |
| 260 | +++ |
| 261 | +++ |
| 262 | +++ |
| 263 | ++ |
| 264 | ++ |
| 265 | ++++ |
| 266 | +++ |
| 267 | ++ |
| 268 | ++++ |
| 269 | ++++ |
| 270 | +++ |

FP Assay #2

10-point semi-log dilution curves in DMSO are prepared in 96-well polypropylene plates to 100× final assay concentration. Compound curves are then diluted 10-fold in assay buffer (50 mM Tris, pH 8.0, 100 mM NaCl, 5 mM MgCl$_2$, 1 mM DTT, 2 mM CHAPS, and 0.005% BSA). To a Costar 384-well black polystyrene assay plate (Corning, #3573), 5 µL of the 10× compound dose response curves are added, with columns 1, 12, 13, and 24 receiving only DMSO. The top concentration of compound is located in columns 2 and 14. Keap1 (321-609) is diluted to 17.5 nM (2.5×) in assay buffer and 20 µL is added to all wells except columns 12 and 24 (rows A-H), which get 20 µL of assay buffer instead. Immediately, 25 µL of 4 nM (2×) Tam$_a$ra labeled peptide (AFFAQLQLDEETGEFL, 21$^{st}$ Century Biochemicals) in assay buffer is added to all wells except columns 12 and 24 (rows I-P), which get 25 µL of assay buffer instead. The assay plate is sealed with a foil film, shaken at 600 rpm for 1 h at room temperature and then read on a Pherastar (BMG), equipped with a TAMRA FP optic module (540/20 nm excitation and 590/20 nm emission filters). Fluorescence measurements, represented as mP, are used in the transformation of the data. The final assay concentrations of Keap1 (321-609) and Tamra labeled peptide are 7 nM and 2 nM, respectively. For each plate, the Pherastar's gain is adjusted after setting the min to 35 mP. The average background reading is automatically subtracted from each sample. Compound activity is calculated based on percent inhibition, normalized against controls in the assay (Control 1 contains the Tamra peptide and Keap1 (321-609) together (0% response) and Control 2 contains the Tamra peptide alone (100% response)). Control 3, containing only Keap1 (321-609) in columns 12 and 24 (rows I-P) are used for background. Data analysis is handled in Prism by first transforming the % inhibition values using x=log x and then using the nonlinear regression equation sigmoidal dose-response curve (variable slope) to determine the pIC$_{50}$ values. The % inhibition=100*(1−((compound response−average min)/(average max−average min))).

All examples described herein possessed activity in the Keap1/Nrf2 FP assay as listed unless otherwise noted (see table below). IC$_{50}$s <10 nM (+++++), IC$_{50}$s 10-100 nM (++++), IC$_{50}$s 100 nM-1 µM (+++), IC$_{50}$s 1-10 µM (++). IC$_{50}$s 10-100 µM (+), IC$_{50}$ s>100 µM (X), or were not determined (ND).

| Ex # | IC$_{50}$ |
|---|---|
| 137 | ++ |
| 138 | +++ |
| 139 | +++ |
| 140 | +++ |
| 141 | +++ |
| 142 | +++ |
| 143 | ND |

Methods of Use

The compounds of the invention are Nrf2 regulators, and are useful in the treatment or prevention of respiratory and non-respiratory disorders, including COPD, asthma, fibrosis, chronic and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, Parkinson's disease (PD), Alzheimer's disease (AD), autism, Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Nonalcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

Accordingly, in another aspect the invention is directed to methods of treating such conditions.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1,000 mg per person per day. Preferred dosages are 1-500 mg once daily, more preferred is 1-100 mg per person per day. IV dosages range form 0.1-1,000 mg/day, preferred is 0.1-500 mg/day, and more preferred is 0.1-100 mg/day. Inhaled daily dosages range from 10 µg-10 mg/day, with preferred 10 µg-2 mg/day, and more preferred 50 µg-500 µg/day.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, ethers, esters, thioesters, carbonates, and carbamates, are well known to those skilled in the art.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In another aspect, the invention is directed to a dosage form adapted for administration to a patient parenterally including subcutaneous, intramuscular, intravenous or intradermal. Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides.

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 µg-10 mg of the compound of the invention.

Aerosols may be formed by suspending or dissolving a compound of the invention in a liquefied propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically acceptable excipients typically used with multiple dose inhalers such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically acceptable liquid such as water, aqueous saline, alcohols or glycols, e.g., ethanol, isopropyl alcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically acceptable excipients may be added to the suspension or solution. The compound of the invention may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

The compounds of formula (I) and pharmaceutically acceptable salts thereof may be used in combination with one or more other agents which may be useful in the prevention or treatment of allergic disease, inflammatory disease, autoimmune disease, for example; antigen immunotherapy, anti-histamines, corticosteroids, NSAIDs, leukotriene modulators, iNOS inhibitors, tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors, DP1 antagonists, DP2 antagonists, PI3K delta inhibitors, ITK inhibitors, LP (lysophosphatidic) inhibitors or FLAP (5-lipoxygenase activating protein) inhibitors, bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

The compounds may also be used in combination with agents for aiding transplantation including Cyclosporines, Tacrolimus, Mycophenolate mofetil, Prednisone, Azathioprine, Sirolimus, Daclizumab, Basiliximab, or OKT3.

They may also be used in combination with agents for Diabetes: metformin (biguanides), meglitinides, sulfonylureas, DPP-4 inhibitors, Thiazolidinediones, Alpha-glucosidase inhibitors, Amylin mimetics, Incretin mimetics, insulin.

The compounds may be used in combination with anti-hypertensives such as diuretics, ACE inhibitors, ARBS, calcium channel blockers, and beta blockers.

One embodiment of the invention encompasses combinations comprising one or two other therapeutic agents. It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation.

Appropriate doses of known therapeutic agents will readily be appreciated by those skilled in the art.

The invention thus provides, in a further aspect, a pharmaceutical composition comprising a combination of a compound of the invention together with another therapeutically active agent.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

All temperatures are given in degrees Celsius, all solvents are highest available purity and all reactions run under anhydrous conditions in an argon (Ar) or nitrogen ($N_2$) atmosphere where necessary.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. The CombiFlash® system used for purification in this application was purchased from Isco, Inc. CombiFlash® purification was carried out using prepacked silica gel columns, a detector with UV wavelength at 254 nm and a variety of solvents or solvent combinations.

Preparative HPLC was performed using a Gilson Preparative System with variable wavelength UV detection or an Agilent Mass Directed AutoPrep (MDAP) system with both mass and variable wavelength UV detection. A variety of reverse phase columns, e.g., Luna 5m C18(2) 100 A, SunFire C18, XBridge C18, Atlantics T3 were used in the purification with the choice of column support dependent upon the conditions used in the purification. The compounds are eluted using a gradient of $CH_3CN$ and water. Neutral conditions used an $CH_3CN$ and water gradient with no additional modifier, acidic conditions used an acid modifier, usually 0.1% TFA (added to both the $CH_3CN$ and water) and basic conditions used a basic modifier, usually 0.1% $NH_4OH$ (added to the water). Analytical HPLC was run using an Agilent system, Shimadzu/Sciex LCMS with variable wavelength UV detection using reverse phase chromatography with a $CH_3CN$ and water gradient with a 0.02 or 0.1% TFA modifier (added to each solvent). LC-MS was determined using either a PE Sciex Single Quadrupole 150EX LC-MS, or Waters ZQ Single Quadrupole LC-MS instruments. The compound is analyzed using a reverse phase column, e.g., Thermo Hypersil Gold C18, eluted using a gradient of $CH_3CN$ and water with a low percentage of an acid modifier such as 0.02% TFA.

Preparative Chiral SFC was performed using a Thar/Waters Preparative SFC System with single wavelength UV detection system. A variety of chiral SFC columns, e.g. Chiralpak IA, IC, AY, AD were used in the purification. The compounds are eluted using supercritical fluid $CO_2$ and co-solvents, such as MeOH, EtOH, IPA, and combination of these solvent in different ratio based on the compound selectivity. Modifiers (0.1% of TFA, $NH_4OH$, DEA) would be used as needed.

Analytical Chiral SFC was run using a Thar/Waters SFC system with variable wavelength UV detection. A variety of chiral SFC columns, e.g. Chiralpak IA, IB, IC, ID, AY, AD, AS, CCL4 were used in the purification. The compounds are eluted using supercritical fluid $CO_2$ and co-solvents, such as MeOH, EtOH, IPA, and combination of these solvent in different ratio based on the compound selectivity. Modifiers (0.1% of TFA, $NH_4OH$, DEA) would be used as needed.

Celite® is a filter aid composed of acid-washed diatomaceous silica, and is a registered trademark of Manville Corp., Denver, Colo. Isolute® is a functionalized silica gel based sorbent, and is a registered trademark of Biotage AB Corp., Sweden.

Nuclear magnetic resonance spectra were recorded at 400 MHz using a Bruker AVANCE 400 or Brucker DPX400 spectrometer. $CDCl_3$ is deuteriochloroform, DMSO-$D_6$ is hexadeuteriodimethylsulfoxide, and MeOD is tetradeuteriomethanol, $CD_2Cl_2$ is deuteriodichloromethane. Chemical shifts are reported in parts per million (δ) downfield from the internal standard tetramethylsilane (TMS) or calibrated to the residual proton signal in the NMR solvent (e.g., $CHCl_3$ in $CDCl_3$). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz.

Heating of reaction mixtures with microwave irradiations was carried out on a Biotage Initiator® microwave reactor, typically employing the high absorbance setting.

Cartridges or columns containing polymer based functional groups (acid, base, metal chelators, etc) can be used as part of compound workup. The "amine" columns or cartridges are used to neutralize or basify acidic reaction mixtures or products. These include $NH_2$ Aminopropyl SPE-ed SPE Cartridges available from Applied Separations and diethylamino SPE cartridges available from United Chemical Technologies, Inc.

Abbreviations are listed in the table below. All other abbreviations are as described in the ACS Style Guide (American Chemical Society, Washington, D.C., 1986).

| Table of Abbreviations | |
|---|---|
| $Pd_2(dba)_3$: tris(dibenzylideneacetone)-dipalladium(0) | $Pd(OAc)_2$: palladium(II) acetate |
| $PdCl_2(dppf)$: [1,1'-bis(diphenylphosphino)-ferrocene] dichloropalladium(II) | $(PPh_3)_2PdCl_2$: bis(triphenylphosphine)palladium(II) dichloride |
| Pd/C: palladium on carbon | $Pd(OH)_2$/C: palladium hydroxide on carbon |
| $[RhCl(cod)]_2$: chloro(1,5-cyclooctadiene)rhodium(I) dimer | $Rh_2(OAc)_4$: rhodium(II) acetate dimer |
| $Cs_2CO_3$: cesium carbonate | NaH: sodium hydride |
| $CH_3CN$ or MeCN: acetonitrile | DMSO: dimethyl sulfoxide |
| $Et_3N$ or TEA: triethylamine | THF: tetrahydrofuran |
| TFA: trifluoroacetic acid | HCl: hydrochloric acid |

Table of Abbreviations

| | |
|---|---|
| MeI: iodomethane | H₂SO₄: sulfuric acid |
| K₂CO₃: potassium carbonate | DMF: N,N-dimethylformamide |
| NaOH: sodium hydroxide | NaNO₂: sodium nitrite |
| NaOMe: sodium methoxide | NaN₃: sodium azide |
| NaOAc: sodium acetate | EtOAc: ethyl acetate |
| NaHCO₃: sodium bicarbonate | NaCl: sodium chloride |
| Na₂SO₄: sodium sulfate | Et₂O: diethyl ether |
| NaIO₄: sodium periodate | Na(OAc)₃BH: sodium triacetoxyborohydride |
| MgSO₄: magnesium sulfate | NH₄Cl: ammonium chloride |
| CH₂Cl₂ or DCM: dichloromethane | NH₄OH: ammonium hydroxide |
| MeOH: methanol | NH₄OAc: ammonium acetate |
| EtOH: ethanol | SnCl₂·2 H₂O: tin(II) chloride dihydrate |
| LiHMDS: lithium hexamethyldisilazane | LDA: lithium diisopropylamide |
| LiOH: lithium hydroxide | LAH: lithium aluminum hydride |
| DCE: 1,2-dichloroethane | n-BuLi: n-butyllithium |
| PS-PPh₃: polymer supported triphenylphosphine | m-CPBA: m-chloroperbenzoic acid |
| ADDP: (E)-diazene-1,2-diylbis(piperidin-1-ylmethanone) | NBS: N-Bromosuccinimide |
| DIAD: diisopropyl azodicarboxylate | DTBAD: di-tert-butyl azodicarboxylate |
| DIPEA: diisopropylethylamine | KOt-Bu: potassium tert-butoxide |
| AcOH: acetic acid | N₂: nitrogen gas |
| mL: milliliter(s) | TBAF: tetrabutylammonium fluoride |
| g: gram(s) | mmol: millimole(s) |
| RT: room temperature | mg: milligram(s) |
| h: hour(s) | min: minute(s) |

Example 1

3-(7-methoxy-1-methyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid

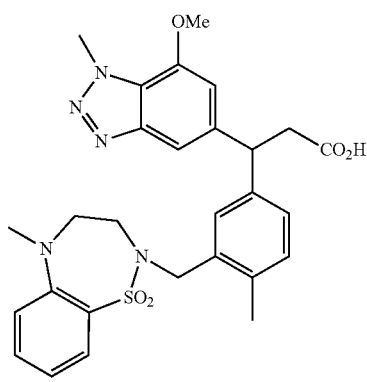 [SMILES: COc1cc(C(CC(=O)O)c2ccc(C)c(CN3CCN(C)c4ccccc4S3(=O)=O)c2)cc2nnn(C)c12]

2-((2-hydroxyethyl)(methyl)amino)benzenesulfonamide

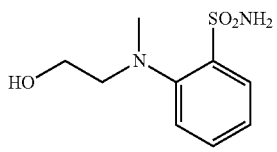

The solution of 2-fluorobenzenesulfonamide (2.102 g, 12 mmol) in 2-(methylamino)ethanol (9.64 mL, 120 mmol) was heated with microwave irradiation at 130° C. for 30 min, heated again with microwave at 130° C. for 30 min. The reaction mixture was diluted with H₂O (100 mL), adjusted pH to ~5 with HCl (6 N then 1 N), extracted with EtOAc (3×100 mL). The organic layer was washed with brine (50 mL), dried over MgSO₄, filtered, concentrated under reduced pressure, to afford the desired product 2-((2-hydroxyethyl)(methyl)amino)benzenesulfonamide (2.4151 g, 10.49 mmol, 87% yield). LC-MS m/z 231 (M+H)⁺, 0.55 (ret. time).

5-methyl-2,3,4,5-tetrahydrobenzo[f][1,2,5]thiadiazepine 1,1-dioxide

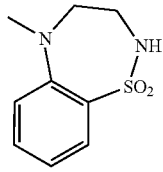

To the solution of 2-((2-hydroxyethyl)(methyl)amino) benzenesulfonamide (461 mg, 2 mmol) in THF (100 mL) was added DIAD (0.778 mL, 4.00 mmol), PS—PPh₃ (1818 mg, 4.00 mmol). The resulting reaction mixture was stirred at RT for 17 h. The reaction mixture was filtered, concentrated under reduced pressure, purified by silica gel chromatography to afford the desired product 5-methyl-2,3,4,5-tetrahydrobenzo[f][1,2,5]thiadiazepine 1,1-dioxide (310.1 mg, 1.461 mmol, 73.0% yield). LC-MS m/z 213 (M+H)⁺, 0.59 (ret. time).

(E)-Ethyl 3-(7-methoxy-1-methyl-1H-benzo[d][1,2,3]triazol-5-yl)acrylate

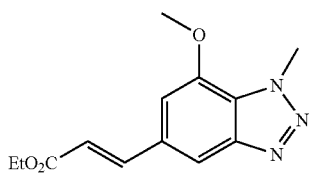

2-Methoxy-6-nitroaniline

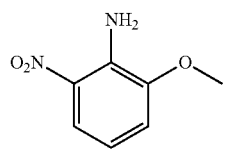

To a solution of 2-amino-3-nitrophenol (35 g, 227 mmol) in DMF (400 mL), K$_2$CO$_3$ (37.7 g, 273 mmol) and MeI (17.04 mL, 273 mmol) were added at RT. The reaction mixture was stirred at RT for 16 h. Then it was poured into water. The resulting precipitate was collected by filtration and the solid was washed with water to give 35 g (89%) of the title compound. LC-MS m/z 168.9 (M+H)$^+$, 1.71 (ret. time).

4-Bromo-2-methoxy-6-nitroaniline

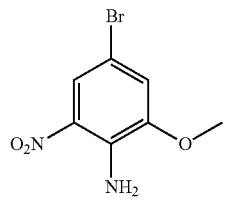

To a solution of 2-methoxy-6-nitroaniline (35 g, 208 mmol) in Acetic Acid (500 mL), NaOAc (27.3 g, 333 mmol) and bromine (11.80 mL, 229 mmol) were added. Then the reaction mixture was stirred at RT for 20 min. The resulting precipitate was filtered and washed with water and dried in-vacuum pump to give 50 g (95%) of the title compound. LC-MS m/z 248.9 (M+H)$^+$, 1.78 (ret. time).

4-Bromo-2-methoxy-N-methyl-6-nitroaniline

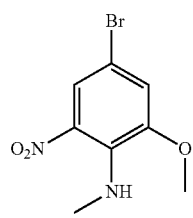

To a solution of 4-bromo-2-methoxy-6-nitroaniline (50 g, 202 mmol) in DMF (400 mL) at 0° C., NaH (5.83 g, 243 mmol) was added. After 30 min, MeI (13.92 mL, 223 mmol) was added and the reaction mixture was stirred 30 min further. Water (1000 mL) was added. The red precipitate was collected by filtration and washed with water, dried to give 50 g (71.8%) of the title compound. LC-MS m/z 263.0 (M+H)$^+$, 1.86 (ret. time).

4-Bromo-6-methoxy-N1-methylbenzene-1,2-diamine

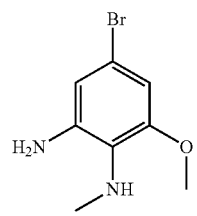

To 4-bromo-2-methoxy-N-methyl-6-nitroaniline (25 g, 96 mmol) in Acetic Acid (300 mL), zinc (18.78 g, 287 mmol) was added in small portions. Then the reaction mixture was stirred at RT for 10 h. The reaction mixture was filtered through celite and the solid was washed copiously with EtOAc. The combined solutions were concentrated to give 20 g (27.6%) of the title compound. LC-MS m/z 233.0 (M+H)$^+$, 1.25 (ret. time).

5-Bromo-7-methoxy-1-methyl-1H-benzo[d][1,2,3]triazole

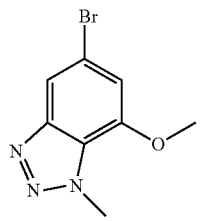

To 4-bromo-6-methoxy-N1-methylbenzene-1,2-diamine (40 g, 173 mmol) in 100 mL of 10% H$_2$SO$_4$ at 0° C., NaNO$_2$ (16.72 g, 242 mmol) was added in small portions over a 20 minute period. After the reaction mixture was stirred for 30 min further, 200 mL of water was added. The resulting precipitate was collected by filtration, washed with water and dried. The mother liquid was left to stand 16 h and a second batch of precipitate formed, which was collected as before. The combined solids were columned in EtOAc to remove inorganic salts, to give 15 g (35.8%) of the title compound. LC-MS m/z 244.0 (M+H)$^+$, 1.68 (ret. time).

(E)-Ethyl 3-(7-methoxy-1-methyl-1H-benzo[d][1,2,3]triazol-5-yl)acrylate

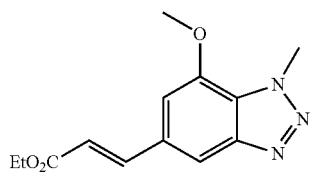 [SMILES: CCOC(=O)/C=C/c1cc(OC)c2c(c1)nnn2C]

To a solution of 5-bromo-7-methoxy-1-methyl-1H-benzo[d][1,2,3]triazole (10 g, 41.3 mmol) in dry DMF (10 mL), ethyl acrylate (20.68 g, 207 mmol), DIPEA (18.04 mL, 103 mmol), and tri-o-tolylphosphine (2.51 g, 8.26 mmol) were added, followed by Pd(OAc)$_2$ (0.927 g, 4.13 mmol). The reaction was heated to 95° C. under a nitrogen atmosphere for 4 h. The reaction mixture was diluted with water and extracted with EtOAc (×3). Combined organic fractions were dried over MgSO$_4$ and concentrated. The residue was purified by silica gel chromatography (10-50% EtOAc/Petrol) to give 9.2 g (83%) of the title compound. LC-MS m/z 262.1 (M+H)$^+$, 1.70 (ret. time).

Ethyl 3-(3-(hydroxymethyl)-4-methylphenyl)-3-(7-methoxy-1-methyl-1H-benzo[d][1,2,3]triazol-5-yl) propanoate

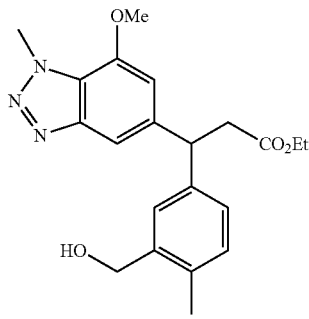 [SMILES: CCOC(=O)CC(c1ccc(C)c(CO)c1)c1cc(OC)c2c(c1)nnn2C]

To the solution of (E)-ethyl 3-(7-methoxy-1-methyl-1H-benzo[d][1,2,3]triazol-5-yl)acrylate (0.390 g, 1.493 mmol) in 1,4-dioxane (10 mL) and water (5 mL) was added (3-(hydroxymethyl)-4-methylphenyl)boronic acid (0.372 g, 2.239 mmol), Et$_3$N (0.312 mL, 2.239 mmol) and [RhCl(cod)]$_2$ (0.041 g, 0.075 mmol). The resulting reaction mixture was stirred at 95° C. for 1 h. The reaction mixture was extracted with EtOAc (3×10 mL). The combined organic layer was dried over MgSO$_4$, filtered, concentrated under reduced pressure, purified by silica gel chromatography to afford the desired product ethyl 3-(3-(hydroxymethyl)-4-methylphenyl)-3-(7-methoxy-1-methyl-1H-benzo[d][1,2,3]triazol-5-yl)propanoate (354.5 mg, 0.925 mmol, 61.9% yield). LC-MS m/z 384 (M+H)$^+$, 0.88 (ret. time).

3-(7-methoxy-1-methyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid

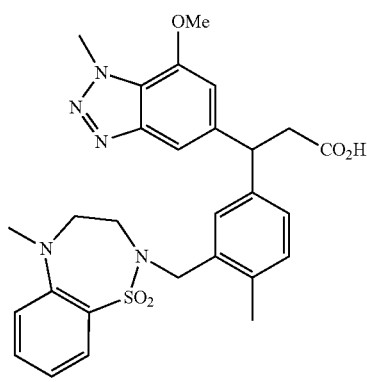 [SMILES: COc1cc(C(CC(=O)O)c2ccc(C)c(CN3CCN(C)c4ccccc4S3(=O)=O)c2)cc2nnn(C)c12]

To the solution of ethyl 3-(3-(hydroxymethyl)-4-methylphenyl)-3-(7-methoxy-1-methyl-1H-benzo[d][1,2,3]triazol-5-yl)propanoate (77 mg, 0.2 mmol) in THF (2 mL) was added 5-methyl-2,3,4,5-tetrahydrobenzo[f][1,2,5]thiadiazepine 1,1-dioxide (63.7 mg, 0.300 mmol), PS—PPh$_3$ (136 mg, 0.300 mmol) and DIAD (0.058 mL, 0.300 mmol). The resulting reaction mixture was stirred at RT for 160 min before was added more PS—PPh$_3$ (45.5 mg, 0.100 mmol) and DIAD (0.019 mL, 0.100 mmol) then stirred at RT for 15 min. The reaction mixture was then filtered, concentrated under reduced pressure, purified by silica gel chromatography to afford desired intermediate ethyl 3-(7-methoxy-1-methyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate (43.6 mg, 0.075 mmol, 37.7% yield). This intermediate was redissolved in MeOH (2.000 mL) then was added NaOH (2 N) (0.500 mL, 1.000 mmol). The resulting reaction mixture was heated with microwave irradiation at 100° C. for 1 h. The reaction mixture was acidified with HCl (1 N) to pH ~3, concentrated under reduced pressure, purified with reverse phase HPLC to afford the desired product 3-(7-methoxy-1-methyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (37.6 mg, 0.068 mmol, 34.2% yield). LC-MS m/z 550 (M+H)$^+$, 0.98 (ret. time).

Example 2

3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid

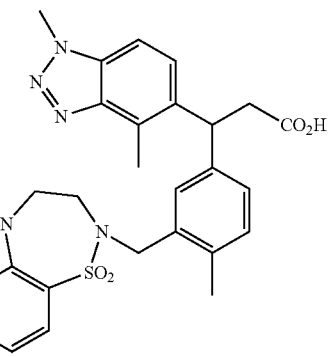

(E)-Ethyl 3-(1-methyl-1H-benzo[d][1,2,3]triazol-5-yl)acrylate 3-Methyl-2-nitrobenzamide

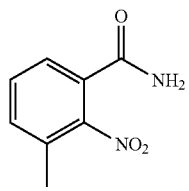

To a solution of 3-methyl-2-nitrobenzoic acid (100 g, 552 mmol) in DCM (1000 mL), oxalyl chloride (72.5 mL, 828 mmol) was added at 25° C. The reaction mixture was stirred at RT for 1 h. The solvent was removed under reduced pressure. The residue was dissolved in $CH_2Cl_2$ (100 mL). The solvent was added to $NH_4OH$ (1000 mL, 7704 mmol) at RT and was stirred for 30 min. Then the reaction mixture was extracted with EtOAc (3×500 mL). The combined organic layer was dried over MgSO4 and concentrated to give 67 g (60.6%) of the title compound. LC-MS m/z 181.1 $(M+H)^+$, 1.40 (ret. time).

3-Methyl-2-nitroaniline

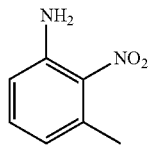

To a mixture of NaOH (2.220 g, 55.5 mmol) in water (12 mL), $Br_2$ (0.322 mL, 6.26 mmol) was added at 0° C. Then 3-methyl-2-nitrobenzamide (1 g, 5.55 mmol) was added in one portion, and the mixture is warmed slowly in a water bath. The material soon darkens in color, and at 50-55° C. (internal temperature) oil droplets begin to separate. The temperature is raised gradually to 70° and maintained at this point for 1 h. A solution of 0.7 g. of NaOH in 4 cc. of water was added slowly and the temperature is increased to 80° C. for an additional hour. The reaction was cooled to RT and extracted with EtOAc (3×50 mL). The combined organic layer was dried and concentrated to give 0.7 g (90%) of the title compound. LC-MS m/z 153.1 $(M+H)^+$, 1.65 (ret. time).

4-bromo-3-methyl-2-nitroaniline

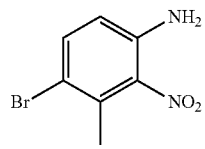

A mixture of NBS (51.5 g, 289 mmol), 3-methyl-2-nitroaniline (44 g, 289 mmol) and AcOH (450 mL) was stirred at 110° C. for 1 h. The mixture was cooled to RT and poured into water (100 mL). The solid was collected to give 55 g (78%) of the title compound. LC-MS m/z 230.9 $(M+H)^+$, 1.78 (ret. time).

4-Bromo-N,3-dimethyl-2-nitroaniline

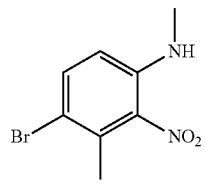

To a solution of 4-bromo-3-methyl-2-nitroaniline (20 g, 87 mmol) in DMF (200 mL), NaH (3.81 g, 95 mmol) was added at 25° C. The reaction mixture was stirred at 25° C. for 30 min. Then MeI (12.90 g, 91 mmol) was added. The reaction mixture was stirred for 12 h. The reaction mixture was poured into water and the solid was collected to give 18 g (59.4%) of the title compound. LC-MS m/z 247.0 $(M+H)^+$, 1.90 (ret. time).

4-Bromo-$N^1$,3-dimethylbenzene-1,2-diamine

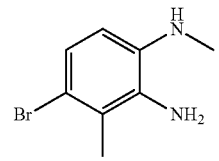

To a solution of 4-Bromo-N,3-dimethyl-2-nitroaniline (30 g, 122 mmol) in EtOH (600 mL), $SnCl_2.2H_2O$ (93 g, 490 mmol), was added. The reaction mixture was stirred at 75° C. for 2 h. Then the solvent was adjusted to pH=14 by using 40% NaOH. It was extracted with EtOAc (3×500 mL). The combined organic layer was dried over $MgSO_4$ and concentrated to give 26 g (39.5%) of the title compound.

5-bromo-1,4-dimethyl-1H-benzo[d][1,2,3]triazole

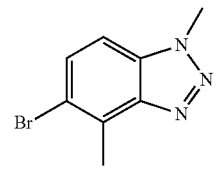

To 4-bromo-$N^1$,3-dimethylbenzene-1,2-diamine (30 g, 139 mmol) in 17 mL of 10% $H_2SO_4$ at 0° C., $NaNO_2$ (13.47 g, 195 mmol) was added in small portions over a 20 minute period. After the reaction mixture was stirred for 30 min further, 200 mL of water was added. The resulting precipitate was collected by filtration, washed with water and dried. The mother liquid was left to stand 16 h and a second batch of precipitate formed, which was collected as before. The combined solids were columned in EtOAc to remove inorganic salts to give 10 g (21.57%) of the title compound. LC-MS m/z 226.0 $(M+H)^+$, 1.71 (ret. time).

(E)-ethyl 3-(1,4-dimethyl-1H-benzo[d][1,2,3]triazol-5-yl)acrylate

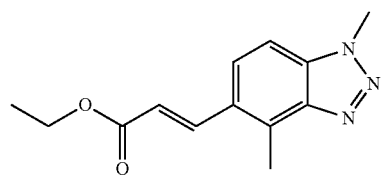 [SMILES: CCOC(=O)/C=C/c1ccc2c(nnn2C)c1C]

To a solution of 5-bromo-1,4-dimethyl-1H-benzo[d][1,2,3]triazole (10 g, 44.2 mmol) in DMF (20 mL), tri-o-tolylphosphine (2.69 g, 8.85 mmol), methyl acrylate (7.62 g, 88 mmol) and DIPEA (23.18 mL, 133 mmol) were added. Then $Pd(OAc)_2$ (0.993 g, 4.42 mmol) was added. The reaction mixture was stirred at 100° C. for 12 h. The mixture was poured into water and extracted with EtOAc (30 mL). The organic layer was dried and concentrated to get crude product. It was purified by silica gel chromatography column (petroleum ether:EtOAc=4:1) to give 8.2 g (76%) of the title compound. LC-MS m/z 246.1 (M+H)+, 1.68 (ret. time).

Ethyl 3-(1,4-dimethyl-1H-benzo[d][1,2,3]triazol-5-yl)-3-(3-(hydroxymethyl)-4-methylphenyl)propanoate

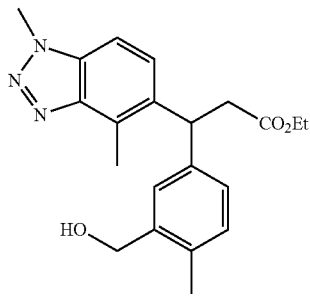 [SMILES: CCOC(=O)CC(c1ccc(C)c(CO)c1)c1ccc2c(nnn2C)c1C]

To the solution of (E)-ethyl 3-(1,4-dimethyl-1H-benzo[d][1,2,3]triazol-5-yl)acrylate (1 g, 4.08 mmol) in 1,4-dioxane (30 mL) and water (10 mL) was added (3-(hydroxymethyl)-4-methylphenyl)boronic acid (1.015 g, 6.12 mmol), Et₃N (0.852 mL, 6.12 mmol) and [RhCl(cod)]₂ (0.113 g, 0.204 mmol). The resulting reaction mixture was stirred at 90° C. for 18.5 h. The reaction mixture was extracted with EtOAc (3×30 mL). The combined organic layer was dried over MgSO₄, filtered, concentrated under reduced pressure, purified by silica gel chromatography to afford the desired product ethyl 3-(1,4-dimethyl-1H-benzo[d][1,2,3]triazol-5-yl)-3-(3-(hydroxymethyl)-4-methylphenyl)propanoate (1.1954 g, 3.25 mmol, 80% yield). LC-MS m/z 368 (M+H)+, 0.88 (ret. time).

3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid

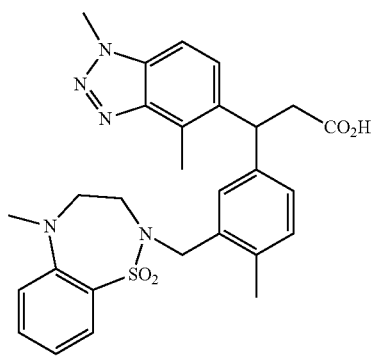 [SMILES: Cc1ccc(C(CC(=O)O)c2ccc3c(nnn3C)c2C)cc1CN1CCN(C)c2ccccc2S1(=O)=O]

To the solution of 2-((2-hydroxyethyl)(methyl)amino)benzenesulfonamide (46.1 mg, 0.2 mmol) in THF (10 mL) was added DIAD (0.078 mL, 0.400 mmol), PS—PPh₃ (182 mg, 0.400 mmol). The resulting reaction mixture was stirred at RT for 2 h. To this reaction mixture was added ethyl 3-(1,4-dimethyl-1H-benzo[d][1,2,3]triazol-5-yl)-3-(3-(hydroxymethyl)-4-methylphenyl)propanoate (73.5 mg, 0.200 mmol) then stirred at RT for 16.5 h. The reaction mixture was then filtered, concentrated under reduced pressure, redissolved in THF (2 mL), then was added PS—PPh₃ (182 mg, 0.400 mmol), DIAD (0.078 mL, 0.400 mmol) and stirred at RT for 40 min. The reaction mixture was filtered. To the filtrate was added NaOH (1 N) (1.000 mL, 1.000 mmol). The resulting reaction mixture was heated with microwave irradiation at 100° C. for 30 min, heated again at 100° C. for 1 h. To the reaction mixture was added more NaOH (6 N) (0.167 mL, 1.000 mmol) then heated with microwave irradiation at 100° C. for 30 min. The reaction mixture was acidified with HCl (1 N) to pH ~5, extracted with EtOAc (3×5 mL). The combine organic layer was dried over Na₂SO₄, filtered, concentrated under reduced pressure, purified with reverse phase HPLC to afford the desired product 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (35.7 mg, 0.067 mmol, 33.4% yield). LC-MS m/z 534 (M+H)+, 0.96 (ret. time).

Example 3

3-(1,4-dimethyl-1H-benzo[d][1,2,3]triazol-5-yl)-3-(3-((1,1-dioxido-3,4-dihydro-2H-benzo[b][1,4,5]oxathiazepin-2-yl)methyl)-4-methylphenyl)propanoic acid

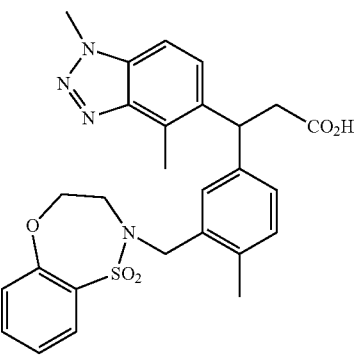 [SMILES: Cc1ccc(C(CC(=O)O)c2ccc3c(nnn3C)c2C)cc1CN1CCOc2ccccc2S1(=O)=O]

2-fluoro-N-(2-hydroxyethyl)benzenesulfonamide

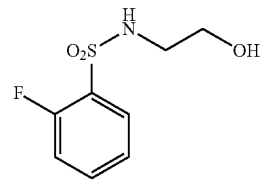 [SMILES: O=S(=O)(NCCO)c1ccccc1F]

To the solution of ethanolamine (1.210 mL, 20.00 mmol) in THF (40 mL) and water (10 mL) was added K₂CO₃ (2.76 g, 20.00 mmol) and then 2-fluorobenzene-1-sulfonyl chloride (2.65 mL, 20 mmol) slowly. The resulting reaction mixture was stirred at RT for 18 h. The reaction mixture was diluted with H₂O (20 mL), extracted with EtOAc (40+2×20 mL). The combined organic layer was washed with brine (30 mL), dried over MgSO₄, filtered, concentrated under reduced pressure, to afford the desired product 2-fluoro-N-(2-hydroxyethyl)benzenesulfonamide (4.4966 g, 20.51 mmol, 103% yield). LC-MS m/z 220 (M+H)⁺, 0.49 (ret. time).

3,4-dihydro-2H-benzo[b][1,4,5]oxathiazepine 1,1-dioxide

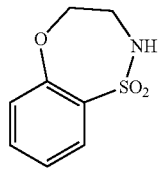

To the solution of 2-fluoro-N-(2-hydroxyethyl)benzenesulfonamide (1315 mg, 6 mmol) in DMSO (20 mL) was added KOtBu (2020 mg, 18.00 mmol). The resulting reaction mixture was heated with microwave irradiation at 80° C. for 60 min. The reaction mixture was diluted with H₂O (30 mL), adjusted pH to ~6 with HCl(1 N), extracted with EtOAc (80+2×40 mL). The combined organic layer was washed with brine (30 mL), dried over MgSO₄, filtered, concentrated under reduced pressure, purified by flash chromatography over silica gel column to afford the desired product 3,4-dihydro-2H-benzo[b][1,4,5]oxathiazepine 1,1-dioxide (962.3 mg, 4.83 mmol, 81% yield). LC-MS m/z 200 (M+H)⁺, 0.52 (ret. time).

3-(1,4-dimethyl-1H-benzo[d][1,2,3]triazol-5-yl)-3-(3-((1,1-dioxido-3,4-dihydro-2H-benzo[b][1,4,5]oxathiazepin-2-yl)methyl)-4-methylphenyl)propanoic acid To the solution of ethyl 3-(1,4-dimethyl-1H-benzo[d][1,2,3]triazol-5-yl)-3-(3-(hydroxymethyl)-4-methylphenyl)propanoate (90 mg, 0.245 mmol) in THF (2.5 mL) was added 3,4-dihydro-2H-benzo[b][1,4,5]oxathiazepine 1,1-dioxide (73.2 mg, 0.367 mmol), PS—PPh₃ (167 mg, 0.367 mmol) and then DIAD (0.071 mL, 0.367 mmol). The resulting reaction mixture was stirred at RT for 17 h. The reaction mixture was filtered, concentrated under reduced pressure. This crude intermediate was redissolved in MeOH (1.2 mL) then was added NaOH (2 N) (0.612 mL, 1.225 mmol). The resulting reaction mixture was heated with microwave irradiation at 100° C. for 30 min. The reaction mixture was acidified with HCl (1 N) to pH ~3, concentrated under reduced pressure, purified by reverse phase HPLC to afford the desired product 3-(1,4-dimethyl-1H-benzo[d][1,2,3]triazol-5-yl)-3-(3-((1,1-dioxido-3,4-dihydro-2H-benzo[b][1,4,5]oxathiazepin-2-yl)methyl)-4-methylphenyl)propanoic acid (95.3 mg, 0.183 mmol, 74.7% yield). LC-MS m/z 521 (M+H)⁺, 0.94 (ret. time).

Example 4

3-(7-methoxy-1-methyl-1H-benzo[d][1,2,3]triazol-5-yl)-3-(4-methyl-3-((3-methyl-1,1-dioxido-3,4-dihydro-2H-benzo[b][1,4,5]oxathiazepin-2-yl)methyl)phenyl)propanoic acid

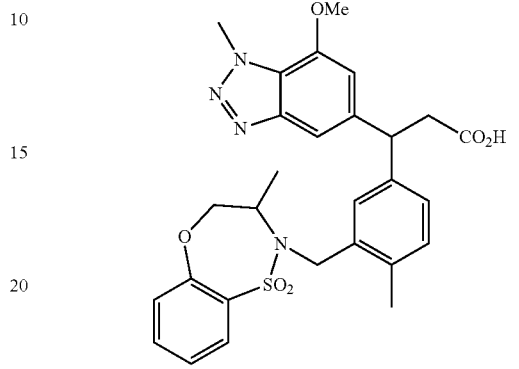

2-fluoro-N-(1-hydroxypropan-2-yl)benzenesulfonamide

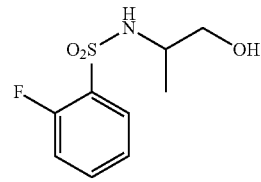

To the solution of 2-amino-1-propanol (0.390 mL, 5.00 mmol) in THF (10 mL) and water (2 mL) was added K₂CO₃ (0.691 g, 5.00 mmol) and then 2-fluorobenzene-1-sulfonyl chloride (0.662 mL, 5 mmol) slowly. The resulting reaction mixture was stirred at RT for 17 h. The reaction mixture was diluted with H₂O (3 mL), extracted with EtOAc (2×10 mL). The combined organic layer was washed with brine (10 mL), dried over MgSO₄, filtered, concentrated under reduced pressure, to afford the desired product 2-fluoro-N-(1-hydroxypropan-2-yl)benzenesulfonamide (1.2145 g, 5.21 mmol, 104% yield). LC-MS m/z 234 (M+H)⁺, 0.57 (ret. time).

3-methyl-3,4-dihydro-2H-benzo[b][1,4,5]oxathiazepine 1,1-dioxide

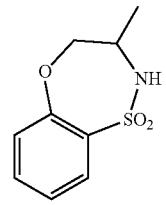

To the solution of 2-fluoro-N-(1-hydroxypropan-2-yl)benzenesulfonamide (1.166 g, 5 mmol) in DMSO (20 mL)

was added KOt-Bu (1.683 g, 15.00 mmol). The resulting reaction mixture was heated with microwave irradiation at 100° C. for 30 min. The reaction mixture was concentrated under reduced pressure, then was added H$_2$O (10 mL), and adjusted pH ~7 with HCl (1 N), extracted with EtOAc (3×20 mL). The combined organic layer was washed with brine (20 mL), dried over MgSO$_4$, filtered, concentrated under reduced pressure, purified by silica gel chromatography to afford desired product 3-methyl-3,4-dihydro-2H-benzo[b][1,4,5]oxathiazepine 1,1-dioxide (1.0843 g, 5.08 mmol, 102% yield). LC-MS m/z 214 (M+H)$^+$, 0.48 (ret. time).

3-(7-methoxy-1-methyl-1H-benzo[d][1,2,3]triazol-5-yl)-3-(4-methyl-3-((3-methyl-1,1-dioxido-3,4-dihydro-2H-benzo[b][1,4,5]oxathiazepin-2-yl)methyl)phenyl)propanoic acid

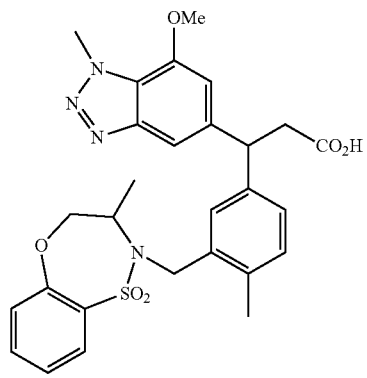 [SMILES: COc1cc(C(CC(=O)O)c2ccc(C)c(CN3C(C)COc4ccccc4S3(=O)=O)c2)cc2nnn(C)c12]

To the solution of ethyl 3-(3-(hydroxymethyl)-4-methylphenyl)-3-(7-methoxy-1-methyl-1H-benzo[d][1,2,3]triazol-5-yl)propanoate (77 mg, 0.2 mmol) in THF (2 mL) was added 3-methyl-3,4-dihydro-2H-benzo[b][1,4,5]oxathiazepine 1,1-dioxide (64.0 mg, 0.300 mmol), PS—PPh$_3$ (136 mg, 0.300 mmol) and DIAD (0.058 mL, 0.300 mmol). The resulting reaction mixture was stirred at RT for 92 h. To this reaction mixture was added more PS—PPh$_3$ (45.5 mg, 0.100 mmol) and DIAD (0.019 mL, 0.100 mmol) then stirred at RT for 90 min. To the reaction mixture was added more PS—PPh$_3$ (136 mg, 0.300 mmol) and DIAD (0.058 mL, 0.300 mmol) then stirred at RT for 35 min. The reaction mixture was filtered, concentrated under reduced pressure to afford desired intermediate ethyl 3-(7-methoxy-1-methyl-1H-benzo[d][1,2,3]triazol-5-yl)-3-(4-methyl-3-((3-methyl-1,1-dioxido-3,4-dihydro-2H-benzo[b][1,4,5]oxathiazepin-2-yl)methyl)phenyl)propanoate. This intermediate was redissolved in MeOH (2.000 mL) then was added NaOH (2 N) (0.500 mL, 1.000 mmol). The resulting reaction mixture was heated with microwave irradiation at 100° C. for 30 min. The reaction mixture was acidified with HCl (1 N) to pH ~3, evaporated under vacuum, purified reverse phase HPLC to afford the desired product 3-(7-methoxy-1-methyl-1H-benzo[d][1,2,3]triazol-5-yl)-3-(4-methyl-3-((3-methyl-1,1-dioxido-3,4-dihydro-2H-benzo[b][1,4,5]oxathiazepin-2-yl)methyl)phenyl)propanoic acid (62.1 mg, 0.113 mmol, 56.4% yield). LC-MS m/z 551 (M+H)$^+$, 1.07 (ret. time).

Example 5

3-(7-methoxy-1-methyl-1H-benzo[d][1,2,3]triazol-5-yl)-3-(4-methyl-3-((4-methyl-1,1-dioxido-3,4-dihydro-2H-benzo[b][1,4,5]oxathiazepin-2-yl)methyl)phenyl)propanoic acid

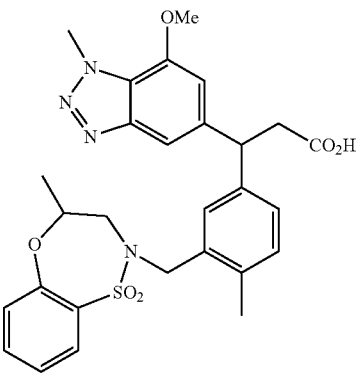

2-fluoro-N-(2-hydroxypropyl)benzenesulfonamide

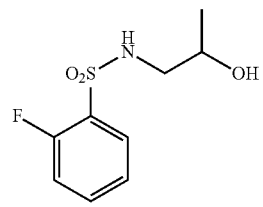

To the solution of 1-Amino-2-propanol (0.386 mL, 5.00 mmol) in THF (10 mL) and water (2.5 mL) was added K$_2$CO$_3$ (0.691 g, 5.00 mmol) and then 2-fluorobenzene-1-sulfonyl chloride (0.662 mL, 5 mmol) slowly. The resulting reaction mixture was stirred at RT for 24 h. The reaction mixture was diluted with H$_2$O (10 mL), extracted with EtOAc (20+2×10 mL). The combined organic layer was washed with brine (15 mL), dried over MgSO$_4$, filtered, evaporated down over under vacuum, to afford the desired product 2-fluoro-N-(2-hydroxypropyl)benzenesulfonamide (1.2272 g, 5.26 mmol, 105% yield). LC-MS m/z 234 (M+H)$^+$, 0.64 (ret. time).

4-methyl-3,4-dihydro-2H-benzo[b][1,4,5]oxathiazepine 1,1-dioxide

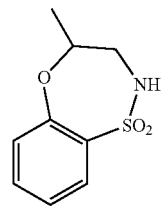

To the solution of 2-fluoro-N-(2-hydroxypropyl)benzenesulfonamide (1.166 g, 5 mmol) in DMSO (20 mL) was added KOt-Bu (1.683 g, 15.00 mmol). The resulting reaction mixture was heated with microwave irradiation at 100° C. for 30 min. The reaction mixture was diluted with H₂O (30 mL), acidified with HCl (1 N) to pH ~6, extracted with EtOAc (3×50 mL). The combined organic layer was washed with brine (50 mL), dried over MgSO₄, filtered, concentrated under reduced pressure, purified by silica gel chromatography to afford the desired product 4-methyl-3,4-dihydro-2H-benzo[b][1,4,5]oxathiazepine 1,1-dioxide (0.9423 g, 4.42 mmol, 88% yield). LC-MS m/z 214 (M+H)⁺, 0.61 (ret. time).

3-(7-methoxy-1-methyl-1H-benzo[d][1,2,3]triazol-5-yl)-3-(4-methyl-3-((4-methyl-1,1-dioxido-3,4-dihydro-2H-benzo[b][1,4,5]oxathiazepin-2-yl)methyl)phenyl)propanoic acid

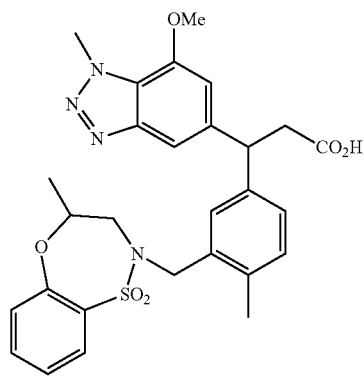 [SMILES: COc1cc(C(CC(=O)O)c2ccc(C)c(CN3CC(C)Oc4ccccc4S3(=O)=O)c2)cc2nnn(C)c12]

To the solution of ethyl 3-(3-(hydroxymethyl)-4-methylphenyl)-3-(7-methoxy-1-methyl-1H-benzo[d][1,2,3]triazol-5-yl)propanoate (77 mg, 0.2 mmol) in THF (2 mL) was added 4-methyl-3,4-dihydro-2H-benzo[b][1,4,5]oxathiazepine 1,1-dioxide (64.0 mg, 0.300 mmol), PS—PPh₃ (136 mg, 0.300 mmol) and DIAD (0.058 mL, 0.300 mmol). The resulting reaction mixture was stirred at RT for 1 h. The reaction mixture was filtered, concentrated under reduced pressure, purified by silica gel chromatography to afford desired intermediate ethyl 3-(7-methoxy-1-methyl-1H-benzo[d][1,2,3]triazol-5-yl)-3-(4-methyl-3-((4-methyl-1,1-dioxido-3,4-dihydro-2H-benzo[b][1,4,5]oxathiazepin-2-yl)methyl)phenyl)propanoate This intermediate was redissolved in MeOH (2.000 mL) then was added NaOH (2 N) (0.500 mL, 1.000 mmol). The resulting reaction mixture was heated with microwave irradiation at 100° C. for 30 min. The reaction mixture was acidified with HCl (1 N) to pH ~3, concentrated under reduced pressure, purified by reverse phase HPLC to afford the desired product 3-(7-methoxy-1-methyl-1H-benzo[d][1,2,3]triazol-5-yl)-3-(4-methyl-3-((4-methyl-1,1-dioxido-3,4-dihydro-2H-benzo[b][1,4,5]oxathiazepin-2-yl)methyl)phenyl)propanoic acid (66.9 mg, 0.121 mmol, 60.7% yield). LC-MS m/z 551 (M+H)⁺, 1.00 (ret. time).

Example 6

3-(3-((1,1-dioxido-3,4-dihydro-2H-pyrido[2,3-b][1,4,5]oxathiazepin-2-yl)methyl)-4-methylphenyl)-3-(7-methoxy-1-methyl-1H-benzo[d][1,2,3]triazol-5-yl)propanoic acid

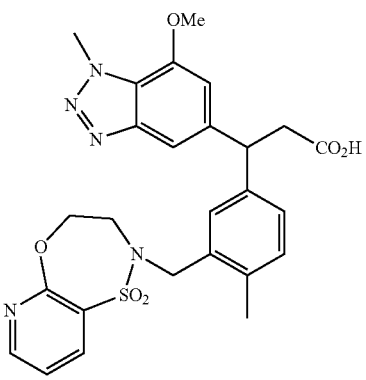 [SMILES: COc1cc(C(CC(=O)O)c2ccc(C)c(CN3CCOc4ncccc4S3(=O)=O)c2)cc2nnn(C)c12]

2-chloro-N-(2-hydroxyethyl)pyridine-3-sulfonamide

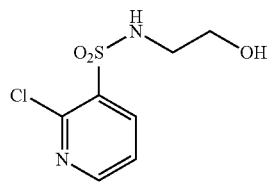 [SMILES: O=S(=O)(NCCO)c1cccnc1Cl]

To the solution of ethanolamine (0.121 mL, 2.000 mmol) in THF (2 mL) and water (1 mL) was added K₂CO₃ (276 mg, 2.000 mmol) and then 2-chloropyridine-3-sulfonyl chloride (424 mg, 2 mmol) in THF (2 mL) slowly. The resulting reaction mixture was stirred at RT for 19 h. The reaction mixture was diluted with H₂O (2 mL), extracted with EtOAc (4+2×2 mL). The combined organic layer was washed with brine (3 mL), dried over MgSO₄, filtered, concentrated under reduced pressure, to afford the desired product 2-chloro-N-(2-hydroxyethyl)pyridine-3-sulfonamide (458.4 mg, 1.937 mmol, 97% yield). LC-MS m/z 237 (M+H)⁺, 0.47 (ret. time).

3,4-dihydro-2H-pyrido[2,3-b][1,4,5]oxathiazepine 1,1-dioxide

To the solution of 2-chloro-N-(2-hydroxyethyl)pyridine-3-sulfonamide (450 mg, 1.901 mmol) in DMSO (8 mL) was added KOt-Bu (640 mg, 5.70 mmol) then heated at 80° C. for 2 h. The reaction mixture was diluted with $H_2O$ (10 mL), acidified with HCl (1 N) to pH ~7, extracted with EtOAc (3×20 mL). The combined organic layer was washed with brine (20 mL), dried over $MgSO_4$, filtered, concentrated under reduced pressure, purified by silica gel chromatography to afford the desired product 3,4-dihydro-2H-pyrido[2,3-b][1,4,5]oxathiazepine 1,1-dioxide (116.7 mg, 0.583 mmol, 30.7% yield). LC-MS m/z 201 (M+H)$^+$, 0.29 (ret. time).

3-(3-((1,1-dioxido-3,4-dihydro-2H-pyrido[2,3-b][1,4,5]oxathiazepin-2-yl)methyl)-4-methylphenyl)-3-(7-methoxy-1-methyl-1H-benzo[d][1,2,3]triazol-5-yl)propanoic acid

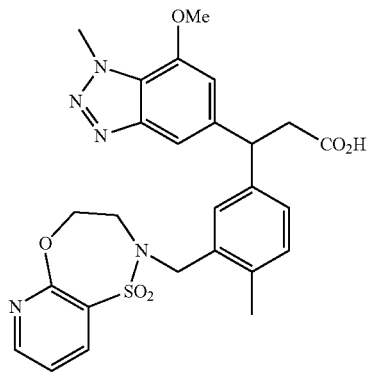 [SMILES: COc1cc(C(CC(=O)O)c2ccc(C)c(CN3CCOc4ncccc4S3(=O)=O)c2)cc2nnn(C)c12]

To the solution of ethyl 3-(3-(hydroxymethyl)-4-methylphenyl)-3-(7-methoxy-1-methyl-1H-benzo[d][1,2,3]triazol-5-yl)propanoate (0.120 g, 0.313 mmol) in THF (4 mL) was added 3,4-dihydro-2H-pyrido[2,3-b][1,4,5]oxathiazepine 1,1-dioxide (0.094 g, 0.469 mmol), PS—PPh$_3$ (0.285 g, 0.626 mmol) and DIAD (0.122 mL, 0.626 mmol). The resulting reaction mixture was stirred at RT for 30 min. The reaction mixture was filtered, concentrated under reduced pressure to afford crude desired intermediate ethyl 3-(3-((1,1-dioxido-3,4-dihydro-2H-pyrido[2,3-b][1,4,5]oxathiazepin-2-yl)methyl)-4-methylphenyl)-3-(7-methoxy-1-methyl-1H-benzo[d][1,2,3]triazol-5-yl)propanoate. This intermediate was redissolved in MeOH (4.00 mL) then was added NaOH (2 N) (0.782 mL, 1.565 mmol). The resulting reaction mixture was heated with microwave irradiation at 100° C. for 30 min. The reaction mixture was acidified with HCl (1 N) to pH ~3, concentrated under reduced pressure, purified with reverse phase HPLC to afford the desired product 3-(3-((1,1-dioxido-3,4-dihydro-2H-pyrido[2,3-b][1,4,5]oxathiazepin-2-yl)methyl)-4-methylphenyl)-3-(7-methoxy-1-methyl-1H-benzo[d][1,2,3]triazol-5-yl)propanoic acid (28.2 mg, 0.052 mmol, 16.76% yield) LC-MS m/z 538 (M+H)$^+$, 0.87 (ret. time).

Example 7

3-(3-((N-(2-hydroxyethyl)-2-methoxypyridine-3-sulfonamido)methyl)-4-methylphenyl)-3-(7-methoxy-1-methyl-1H-benzo[d][1,2,3]triazol-5-yl)propanoic acid

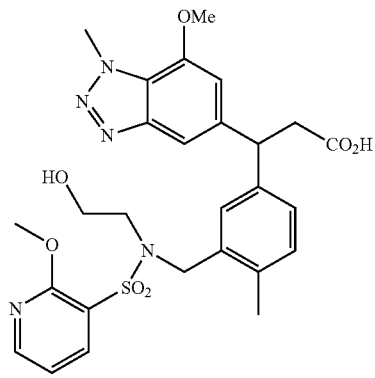 [SMILES: COc1ncccc1S(=O)(=O)N(CCO)Cc1cc(C(CC(=O)O)c2cc(OC)c3c(c2)nnn3C)ccc1C]

3-(3-((N-(2-hydroxyethyl)-2-methoxypyridine-3-sulfonamido)methyl)-4-methylphenyl)-3-(7-methoxy-1-methyl-1H-benzo[d][1,2,3]triazol-5-yl)propanoic acid was isolated from the purification of 3-(3-((1,1-dioxido-3,4-dihydro-2H-pyrido[2,3-b][1,4,5]oxathiazepin-2-yl)methyl)-4-methylphenyl)-3-(7-methoxy-1-methyl-1H-benzo[d][1,2,3]triazol-5-yl)propanoic acid (45.9 mg, 0.081 mmol, 25.7% yield). LC-MS m/z 570 (M+H)$^+$, 0.85 (ret. time).

Example 8

3-(1,4-dimethyl-1H-benzo[d][1,2,3]triazol-5-yl)-3-(3-((1,1-dioxido-3,4-dihydro-2H-pyrido[2,3-b][1,4,5]oxathiazepin-2-yl)methyl)-4-methylphenyl)propanoic acid

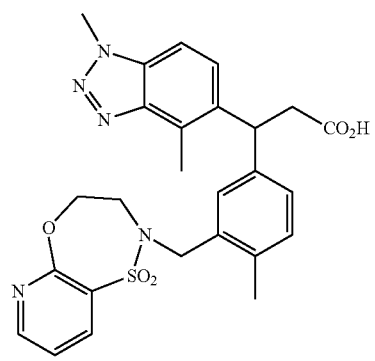 [SMILES: Cc1ccc(C(CC(=O)O)c2ccc3c(nnn3C)c2C)cc1CN1CCOc2ncccc2S1(=O)=O]

To the solution of ethyl 3-(1,4-dimethyl-1H-benzo[d][1,2,3]triazol-5-yl)-3-(3-(hydroxymethyl)-4-methylphenyl)propanoate (0.055 g, 0.150 mmol) in THF (2 mL) was added 3,4-dihydro-2H-pyrido[2,3-b][1,4,5]oxathiazepine 1,1-dioxide (0.045 g, 0.225 mmol), PS—PPh$_3$ (0.136 g, 0.299 mmol) and DIAD (0.058 mL, 0.299 mmol). The resulting reaction mixture was stirred at RT for 30 min. The reaction mixture was filtered, concentrated under reduced pressure to afford desired intermediate ethyl 3-(1,4-dimethyl-1H-benzo[d][1,2,3]triazol-5-yl)-3-(3-((1,1-dioxido-3,4-dihydro-2H- pyrido[2,3-b][1,4,5]oxathiazepin-2-yl)methyl)-4-methylphenyl)propanoate This intermediate was redissolved in MeOH (2.000 mL) then was added NaOH (2 N) (0.374 mL, 0.748 mmol). The resulting reaction mixture was heated with microwave irradiation at 100° C. for 30 min. The reaction mixture was acidified with HCl (1 N) to pH ~3, concentrated under reduced pressure, purified by reverse phase HPLC to afford the desired product 3-(1,4-dimethyl-1H-benzo[d][1,2,3]triazol-5-yl)-3-(3-((1,1-dioxido-3,4-dihydro-2H-pyrido[2,3-b][1,4,5]oxathiazepin-2-yl)methyl)-4-methylphenyl)propanoic acid (14.5 mg, 0.028 mmol, 18.57% yield) LC-MS m/z 522 (M+H)$^+$, 0.84 (ret. time).

Example 9

3-(1,4-dimethyl-1H-benzo[d][1,2,3]triazol-5-yl)-3-(3-((N-(2-hydroxyethyl)-2-methoxypyridine-3-sulfonamido)methyl)-4-methylphenyl)propanoic acid

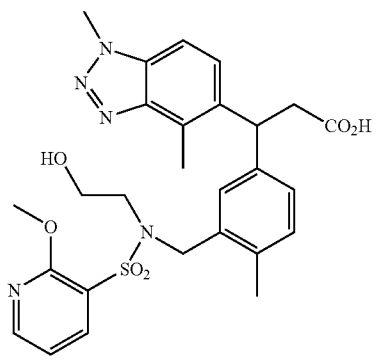 [SMILES: COc1ncccc1S(=O)(=O)N(CCO)Cc1cc(C(CC(=O)O)c2ccc3c(nnn3C)c2C)ccc1C]

3-(1,4-dimethyl-1H-benzo[d][1,2,3]triazol-5-yl)-3-(3-((N-(2-hydroxyethyl)-2-methoxypyridine-3-sulfonamido)methyl)-4-methylphenyl)propanoic acid was isolated from the purification of 3-(1,4-dimethyl-1H-benzo[d][1,2,3]triazol-5-yl)-3-(3-((1,1-dioxido-3,4-dihydro-2H-pyrido[2,3-b][1,4,5]oxathiazepin-2-yl)methyl)-4-methylphenyl)propanoic acid (34.0 mg, 0.061 mmol, 41.0% yield). LC-MS m/z 554 (M+H)$^+$, 0.82 (ret. time).

Example 10

3-(1,4-dimethyl-1H-benzo[d][1,2,3]triazol-5-yl)-3-(4-methyl-3-((4-methyl-1,1-dioxido-3,4-dihydro-2H-benzo[b][1,4,5]oxathiazepin-2-yl)methyl)phenyl)propanoic acid

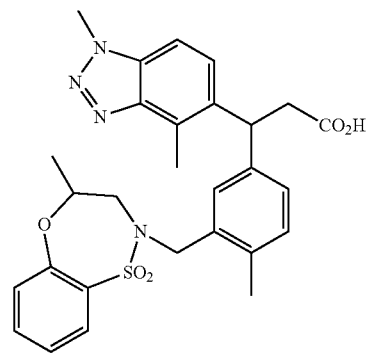 [SMILES: Cc1ccc(C(CC(=O)O)c2ccc3c(nnn3C)c2C)cc1CN1CC(C)Oc2ccccc2S1(=O)=O]

To the solution of ethyl 3-(1,4-dimethyl-1H-benzo[d][1,2,3]triazol-5-yl)-3-(3-(hydroxymethyl)-4-methylphenyl)propanoate (0.055 g, 0.150 mmol) in THF (2 mL) was added 4-methyl-3,4-dihydro-2H-benzo[b][1,4,5]oxathiazepine 1,1-dioxide (0.048 g, 0.225 mmol), PS—PPh$_3$ (0.136 g, 0.299 mmol) and DIAD (0.058 mL, 0.299 mmol). The resulting reaction mixture was stirred at RT for 1 h. The reaction mixture was filtered, concentrated under reduced pressure to afford desired intermediate ethyl 3-(1,4-dimethyl-1H-benzo[d][1,2,3]triazol-5-yl)-3-(4-methyl-3-((4-methyl-1,1-dioxido-3,4-dihydro-2H-benzo[b][1,4,5]oxathiazepin-2-yl)methyl)phenyl)propanoate This intermediate was redissolved in MeOH (2.000 mL) then was added NaOH (2 N) (0.374 mL, 0.748 mmol). The resulting reaction mixture was heated with microwave irradiation at 100° C. for 30 min. The reaction mixture was acidified with HCl (1 N) to pH ~3, concentrated under reduced pressure, purified by reverse phase HPLC to afford the desired product 3-(1,4-dimethyl-1H-benzo[d][1,2,3]triazol-5-yl)-3-(4-methyl-3-((4-methyl-1,1-dioxido-3,4-dihydro-2H-benzo[b][1,4,5]oxathiazepin-2-yl)methyl)phenyl)propanoic acid (60.5 mg, 0.113 mmol, 76% yield). LC-MS m/z 535 (M+H)$^+$, 0.96 (ret. time).

Example 11

3-(1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

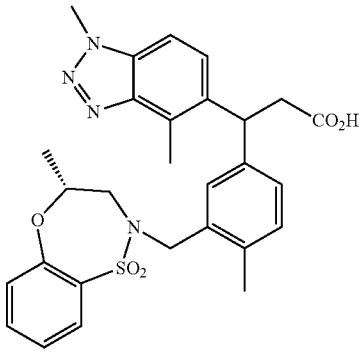 [SMILES: Cc1ccc(C(CC(=O)O)c2ccc3c(nnn3C)c2C)cc1CN1C[C@@H](C)Oc2ccccc2S1(=O)=O]

(R)-2-fluoro-N-(2-hydroxypropyl)benzenesulfonamide

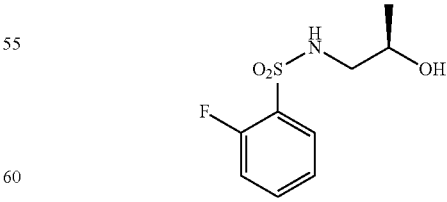

To the solution of (R)-1-Amino-2-propanol (0.386 mL, 5.00 mmol) in THF (10 mL) and water (2.5 mL) was added K$_2$CO$_3$ (0.691 g, 5.00 mmol) and then 2-fluorobenzene-1-sulfonyl chloride (0.662 mL, 5 mmol) slowly. The resulting reaction mixture was stirred at RT for 66 h. The reaction mixture was diluted with H₂O (10 mL), extracted with EtOAc (20+2×10 mL). The combined organic layer was washed with brine (15 mL), dried over MgSO₄, filtered, concentrated under reduced pressure, to afford the desired product (R)-2-fluoro-N-(2-hydroxypropyl)benzenesulfonamide (1.2159 g, 5.21 mmol, 104% yield). LC-MS m/z 234 (M+H)⁺, 0.65 (ret. time).

(R)-4-methyl-3,4-dihydro-2H-benzo[b][1,4,5]oxathiazepine 1,1-dioxide

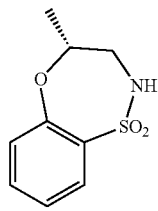

To the solution of (R)-2-fluoro-N-(2-hydroxypropyl)benzenesulfonamide (1166 mg, 5 mmol) in DMSO (20 mL) was added KOt-Bu (1683 mg, 15.00 mmol). The resulting reaction mixture was heated with at 100° C. for 20 min. The reaction mixture was diluted with H₂O (30 mL), acidified with HCl (1 N) to pH ~6, extracted with EtOAc (3×50 mL). The combined organic layer was washed with brine (50 mL), dried over MgSO₄, filtered, concentrated under reduced pressure, purified by silica gel chromatography to afford the desired product (R)-4-methyl-3,4-dihydro-2H-benzo[b][1,4,5]oxathiazepine 1,1-dioxide (841.6 mg, 3.95 mmol, 79% yield). LC-MS m/z 214 (M+H)⁺, 0.73 (ret. time).

3-(1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

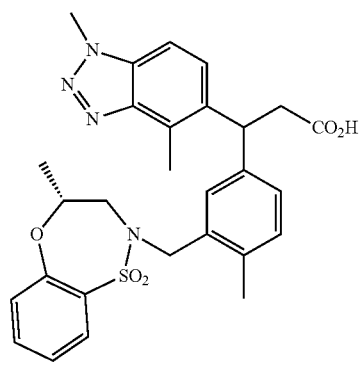

To the solution of ethyl 3-(1,4-dimethyl-1H-benzo[d][1,2,3]triazol-5-yl)-3-(3-(hydroxymethyl)-4-methylphenyl)propanoate (100 mg, 0.272 mmol) in THF (4 mL) was added (R)-4-methyl-3,4-dihydro-2H-benzo[b][1,4,5]oxathiazepine 1,1-dioxide (87 mg, 0.408 mmol), PS—PPh₃ (247 mg, 0.544 mmol) and DIAD (0.106 mL, 0.544 mmol). The resulting reaction mixture was stirred at RT for 30 min. The reaction mixture was filtered and the filtrate was evaporated down to afford desired crude intermediate ethyl 3-(1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate. To this intermediate was added MeOH (4 mL) then NaOH (2 N) (0.680 mL, 1.361 mmol). The resulting reaction mixture was heated with microwave irradiation at 80° C. for 30 min. The reaction mixture was acidified with HCl (1 N) to pH ~3, concentrated under reduced pressure, purified by reverse phase HPLC to afford the desired product 3-(1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid (95.2 mg, 0.178 mmol, 65.4% yield). LC-MS m/z 535 (M+H)⁺, 0.97 (ret. time).

Example 12

3-(1,4-dimethyl-1H-benzo[d][1,2,3]triazol-5-yl)-3-(4-methyl-3-(((S)-4-methyl-1,1-dioxido-3,4-dihydro-2H-benzo[b][1,4,5]oxathiazepin-2-yl)methyl)phenyl)propanoic acid

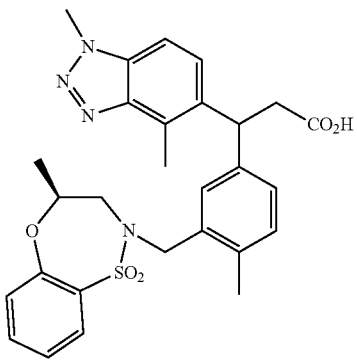 [SMILES: Cc1ccc(C(CC(=O)O)c2ccc3c(nnn3C)c2C)cc1CN1C[C@H](C)Oc2ccccc2S1(=O)=O]

(S)-2-fluoro-N-(2-hydroxypropyl)benzenesulfonamide

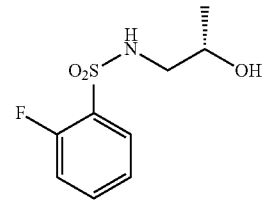

To the solution of (s)-1-Amino-2-propanol (0.386 mL, 5.00 mmol) in THF (10 mL) and water (2.5 mL) was added K₂CO₃ (0.691 g, 5.00 mmol) and then 2-fluorobenzene-1-sulfonyl chloride (0.662 mL, 5 mmol) slowly. The resulting reaction mixture was stirred at RT for 21 h. The reaction mixture was diluted with H₂O (10 mL), extracted with EtOAc (20+2×10 mL). The combined organic layer was washed with brine (15 mL), dried over MgSO₄, filtered, concentrated under reduced pressure, to afford the desired product (S)-2-fluoro-N-(2-hydroxypropyl)benzenesulfonamide (1.1981 g, 5.14 mmol, 103% yield). LC-MS m/z 234 (M+H)⁺, 0.63 (ret. time).

(S)-4-methyl-3,4-dihydro-2H-benzo[b][1,4,5]oxathiazepine 1,1-dioxide

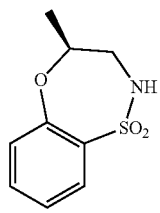

To the solution of (S)-2-fluoro-N-(2-hydroxypropyl)benzenesulfonamide (1166 mg, 5 mmol) in DMSO (20 mL) was added KOt-Bu (1683 mg, 15.00 mmol). The resulting reaction mixture was heated at 100° C. for 30 min. The reaction mixture was diluted with $H_2O$ (30 mL), acidified with HCl (1 N) to pH ~6, extracted with EtOAc (3×50 mL). The combined organic layer was washed with brine (50 mL), dried over $MgSO_4$, filtered, concentrated under reduced pressure, purified by silica gel chromatography to afford the desired product (S)-4-methyl-3,4-dihydro-2H-benzo[b][1,4,5]oxathiazepine 1,1-dioxide (911.2 mg, 4.27 mmol, 85% yield). LC-MS m/z 214 $(M+H)^+$, 0.71 (ret. time).

3-(1,4-dimethyl-1H-benzo[d][1,2,3]triazol-5-yl)-3-(4-methyl-3-(((S)-4-methyl-1,1-dioxido-3,4-dihydro-2H-benzo[b][1,4,5]oxathiazepin-2-yl)methyl)phenyl)propanoic acid

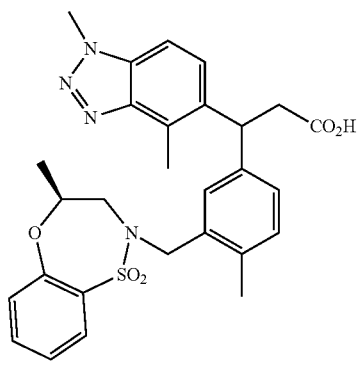 [SMILES: Cc1ccc(C(CC(=O)O)c2ccc3c(nnn3C)c2C)cc1CN1C[C@H](C)Oc2ccccc2S1(=O)=O]

To the solution of ethyl 3-(1,4-dimethyl-1H-benzo[d][1,2,3]triazol-5-yl)-3-(3-(hydroxymethyl)-4-methylphenyl)propanoate (100 mg, 0.272 mmol) in THF (4 mL) was added (S)-4-methyl-3,4-dihydro-2H-benzo[b][1,4,5]oxathiazepine 1,1-dioxide (87 mg, 0.408 mmol), PS—$PPh_3$ (247 mg, 0.544 mmol) and DIAD (0.106 mL, 0.544 mmol). The resulting reaction mixture was stirred at RT for 30 min. The reaction mixture was filtered and the filtrate was evaporated down to afford desired crude intermediate ethyl 3-(1,4-dimethyl-1H-benzo[d][1,2,3]triazol-5-yl)-3-(4-methyl-3-(((S)-4-methyl-1,1-dioxido-3,4-dihydro-2H-benzo[b][1,4,5]oxathiazepin-2-yl)methyl)phenyl)propanoate. To this intermediate was added MeOH (4 mL) then NaOH (2 N) (0.680 mL, 1.361 mmol). The resulting reaction mixture was heated with microwave irradiation at 80° C. for 30 min. The reaction mixture was acidified with HCl (1 N) to pH ~3, concentrated under reduced pressure, purified by reverse phase HPLC to afford the desired product 3-(1,4-dimethyl-1H-benzo[d][1,2,3]triazol-5-yl)-3-(4-methyl-3-(((S)-4-methyl-1,1-dioxido-3,4-dihydro-2H-benzo[b][1,4,5]oxathiazepin-2-yl)methyl)phenyl)propanoic acid (97.9 mg, 0.183 mmol, 67.3% yield). LC-MS m/z 535 $(M+H)^+$, 0.97 (ret. time).

Example 13

3-(7-methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

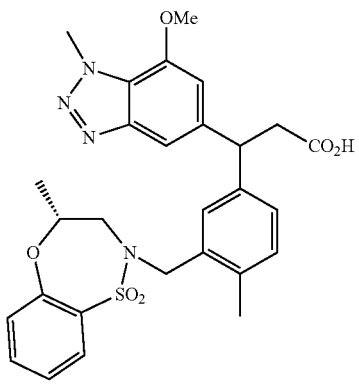 [SMILES: COc1cc(C(CC(=O)O)c2ccc(C)c(CN3C[C@@H](C)Oc4ccccc4S3(=O)=O)c2)cc2nnn(C)c12]

To the solution of ethyl 3-(3-(hydroxymethyl)-4-methylphenyl)-3-(7-methoxy-1-methyl-1H-benzo[d][1,2,3]triazol-5-yl)propanoate (100 mg, 0.261 mmol) in THF (4 mL) was added (R)-4-methyl-3,4-dihydro-2H-benzo[b][1,4,5]oxathiazepine 1,1-dioxide (83 mg, 0.391 mmol), PS—$PPh_3$ (237 mg, 0.522 mmol) and DIAD (0.101 mL, 0.522 mmol). The resulting reaction mixture was stirred at RT for 25 min. The reaction mixture was filtered and the filtrate was evaporated down over glass-col evaporator to afford desired crude intermediate ethyl 3-(7-methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate. To this intermediate was added MeOH (4 mL) then NaOH (2 N) (0.652 mL, 1.304 mmol). The resulting reaction mixture was heated with microwave irradiation at 80° C. for 30 min. The reaction mixture was acidified with HCl (1 N) to pH ~3, concentrated under reduced pressure, purified by reverse phase HPLC to afford the desired product 3-(7-methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid (58.1 mg, 0.106 mmol, 40.5% yield). LC-MS m/z 551 $(M+H)^+$, 0.98 (ret. time).

Example 14

3-(7-methoxy-1-methyl-1H-benzo[d][1,2,3]triazol-5-yl)-3-(4-methyl-3-(((S)-4-methyl-1,1-dioxido-3,4-dihydro-2H-benzo[b][1,4,5]oxathiazepin-2-yl)methyl)phenyl)propanoic acid

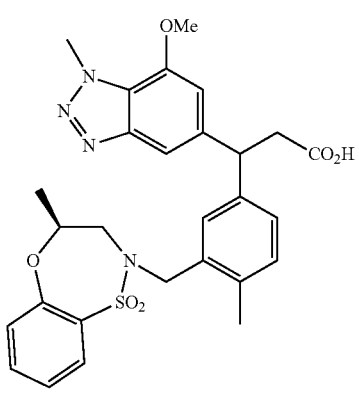 [SMILES: COc1cc(C(CC(=O)O)c2ccc(C)c(CN3C[C@H](C)Oc4ccccc4S3(=O)=O)c2)cc2nnn(C)c12]

To the solution of ethyl 3-(3-(hydroxymethyl)-4-methylphenyl)-3-(7-methoxy-1-methyl-1H-benzo[d][1,2,3]triazol-5-yl)propanoate (100 mg, 0.261 mmol) in THF (4 mL) was added (S)-4-methyl-3,4-dihydro-2H-benzo[b][1,4,5]oxathiazepine 1,1-dioxide (83 mg, 0.391 mmol), PS—PPh$_3$ (237 mg, 0.522 mmol) and DIAD (0.101 mL, 0.522 mmol). The resulting reaction mixture was stirred at RT for 25 min. The reaction mixture was filtered and the filtrate was evaporated down over glass-col evaporator to afford desired crude intermediate ethyl 3-(7-methoxy-1-methyl-1H-benzo[d][1,2,3]triazol-5-yl)-3-(4-methyl-3-(((S)-4-methyl-1,1-dioxido-3,4-dihydro-2H-benzo[b][1,4,5]oxathiazepin-2-yl)methyl)phenyl)propanoate. To this intermediate was added MeOH (4 mL) then NaOH (2 N) (0.652 mL, 1.304 mmol). The resulting reaction mixture was heated with microwave irradiation at 80° C. for 30 min. The reaction mixture was acidified with HCl (1 N) to pH ~3, concentrated under reduced pressure, purified by reverse phase HPLC to afford the desired product 3-(7-methoxy-1-methyl-1H-benzo[d][1,2,3]triazol-5-yl)-3-(4-methyl-3-(((S)-4-methyl-1,1-dioxido-3,4-dihydro-2H-benzo[b][1,4,5]oxathiazepin-2-yl)methyl)phenyl)propanoic acid (37.2 mg, 0.068 mmol, 25.9% yield). LC-MS m/z 551 (M+H)$^+$, 0.97 (ret. time).

Example 15

3-(3-((5-ethyl-1,1-dioxido-4,5-dihydrobenzo[f][1,2,5]thiadiazepin-2(3H)-yl)methyl)-4-methylphenyl)-3-(7-methoxy-1-methyl-1H-benzo[d][1,2,3]triazol-5-yl)propanoic acid

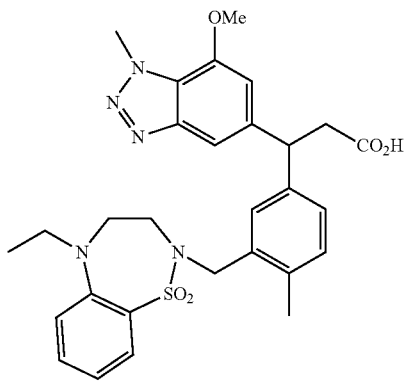 [SMILES: CCN1CCN(Cc2cc(C(CC(=O)O)c3cc(OC)c4c(c3)nnn4C)ccc2C)S(=O)(=O)c2ccccc21]

To the solution of 2-(ethyl(2-hydroxyethyl)amino)benzenesulfonamide (0.053 g, 0.215 mmol) in THF (2 mL) was added PS—PPh$_3$ (0.196 g, 0.430 mmol) and DTBAD (0.099 g, 0.430 mmol). The resulting reaction mixture was stirred at RT for 15 min. To this reaction mixture was then added ethyl 3-(3-(hydroxymethyl)-4-methylphenyl)-3-(7-methoxy-1-methyl-1H-benzo[d][1,2,3]triazol-5-yl)propanoate (0.055 g, 0.143 mmol) before was stirred at RT for 20 min. The reaction mixture was filtered, concentrated to afford desired intermediate ethyl 3-(3-((5-ethyl-1,1-dioxido-4,5-dihydrobenzo[f][1,2,5]thiadiazepin-2(3H)-yl)methyl)-4-methylphenyl)-3-(7-methoxy-1-methyl-1H-benzo[d][1,2,3]triazol-5-yl)propanoate. This intermediate was redissolved in MeOH (2.000 mL) then was added NaOH (2 N) (0.359 mL, 0.717 mmol). The resulting reaction mixture was heated with microwave irradiation at 80° C. for 30 min.

The reaction mixture was acidified with HCl (1 N) to pH ~3, concentrated under reduced pressure, purified by reverse phase HPLC to afford the desired product 3-(3-((5-ethyl-1,1-dioxido-4,5-dihydrobenzo[f][1,2,5]thiadiazepin-2(3H)-yl)methyl)-4-methylphenyl)-3-(7-methoxy-1-methyl-1H-benzo[d][1,2,3]triazol-5-yl)propanoic acid (29.9 mg, 0.053 mmol, 37.0% yield). LC-MS m/z 564 (M+H)$^+$, 1.04 (ret. time).

Example 16

3-(1,4-dimethyl-1H-benzo[d][1,2,3]triazol-5-yl)-3-(3-((5-ethyl-1,1-dioxido-4,5-dihydrobenzo[f][1,2,5]thiadiazepin-2(3H)-yl)methyl)-4-methylphenyl)propanoic acid

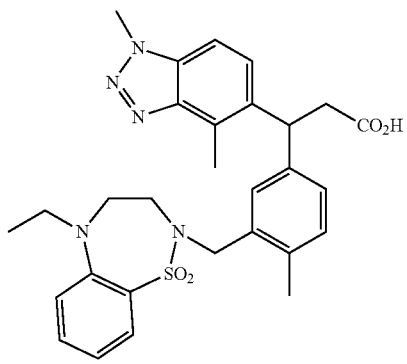 [SMILES: CCN1CCN(Cc2cc(C(CC(=O)O)c3ccc4c(nnn4C)c3C)ccc2C)S(=O)(=O)c2ccccc21]

2-(ethyl(2-hydroxyethyl)amino)benzenesulfonamide

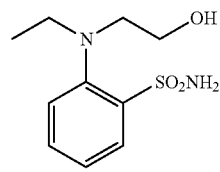

To the solution of 2-fluorobenzenesulfonamide (1051 mg, 6 mmol) in 2-(ethylamino)ethanol (2.93 mL, 30.0 mmol) was heated with microwave irradiation at 130° C. for 30 min, heated again with microwave at 130° C. for 30 min (71-1), heated again with microwave at 150° C. for 30 min. To the reaction mixture was added DMSO (2 mL) and water (0.2 mL) then heated with microwave irradiation at 130° C. for 2 h, heated again with microwave at 140° C. for 1 h, heated again with microwave at 150° C. for 1 h, heated again at 150° C. for 5 h. The reaction mixture was diluted with H$_2$O (30 mL), adjusted pH to ~5 with HCl (6 N then 1 N), extracted with EtOAc (3×30 mL). The organic layer was washed with brine (30 mL), dried over MgSO$_4$, filtered, concentrated under reduced pressure, purified by silica gel chromatography, to afford the desired product 2-(ethyl(2-hydroxyethyl)amino)benzenesulfonamide (923.0 mg, 3.78 mmol, 63.0% yield). LC-MS m/z 245 (M+H)$^+$, 0.94 (ret. time).

3-(1,4-dimethyl-1H-benzo[d][1,2,3]triazol-5-yl)-3-(3-((5-ethyl-1,1-dioxido-4,5-dihydrobenzo[f][1,2,5]thiadiazepin-2(3H)-yl)methyl)-4-methylphenyl)propanoic acid

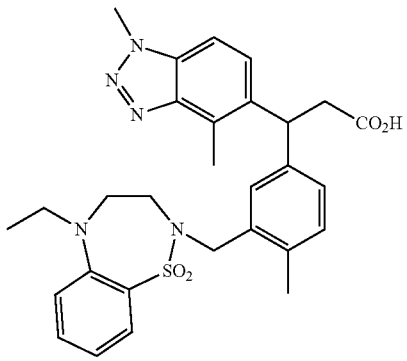 [SMILES: CCN1CCN(Cc2cc(C(CC(=O)O)c3ccc4c(nnn4C)c3C)ccc2C)S(=O)(=O)c2ccccc21]

To the solution of 2-(ethyl(2-hydroxyethyl)amino)benzenesulfonamide (0.055 g, 0.225 mmol) in THF (2 mL) was added PS—PPh$_3$ (0.204 g, 0.449 mmol) and DTBAD (0.103 g, 0.449 mmol). The resulting reaction mixture was stirred at RT for 40 min. To this reaction mixture was then added ethyl 3-(1,4-dimethyl-1H-benzo[d][1,2,3]triazol-5-yl)-3-(3-(hydroxymethyl)-4-methylphenyl)propanoate (0.055 g, 0.150 mmol) before was stirred at RT for 30 min. The reaction mixture was filtered, concentrated to afford desired intermediate ethyl 3-(1,4-dimethyl-1H-benzo[d][1,2,3]triazol-5-yl)-3-(3-((5-ethyl-1,1-dioxido-4,5-dihydrobenzo[f][1,2,5]thiadiazepin-2(3H)-yl)methyl)-4-methylphenyl)propanoate This intermediate was redissolved in MeOH (2.000 mL) then was added NaOH (2 N) (0.374 mL, 0.748 mmol). The resulting reaction mixture was heated with microwave irradiation at 80° C. for 30 min. The reaction mixture was acidified with HCl (1 N) to pH ~3, concentrated under reduced pressure, purified by reverse phase HPLC to afford the desired product 3-(1,4-dimethyl-1H-benzo[d][1,2,3]triazol-5-yl)-3-(3-((5-ethyl-1,1-dioxido-4,5-dihydrobenzo[f][1,2,5]thiadiazepin-2(3H)-yl)methyl)-4-methylphenyl)propanoic acid (20.4 mg, 0.037 mmol, 24.89% yield). LC-MS m/z 548 (M+H)$^+$, 1.00 (ret. time).

Example 17

3-(7-methoxy-1-methyl-1H-benzo[d][1,2,3]triazol-5-yl)-3-(4-methyl-3-(((S)-4-methyl-1,1-dioxido-3,4-dihydro-2H-pyrido[2,3-b][1,4,5]oxathiazepin-2-yl)methyl)phenyl)propanoic acid

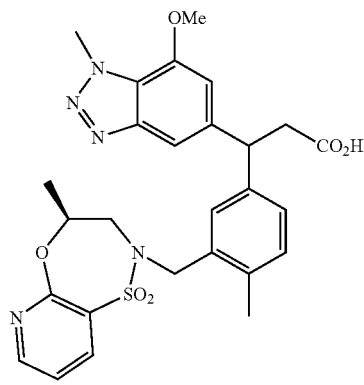 [SMILES: COc1cc(C(CC(=O)O)c2ccc(C)c(CN3C[C@H](C)Oc4ncccc4S3(=O)=O)c2)cc2nnn(C)c12]

(S)-2-chloro-N-(2-hydroxypropyl)pyridine-3-sulfonamide

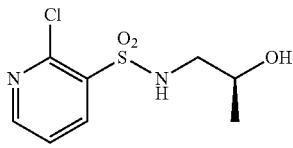

To the solution of (S)-1-aminopropan-2-ol (0.354 g, 4.72 mmol) in THF (10 mL) and water (2.5 mL) was added K$_2$CO$_3$ (0.652 g, 4.72 mmol) and stirred for 5 min before was added 2-chloropyridine-3-sulfonyl chloride (1.0 g, 4.72 mmol). The resulting reaction mixture was stirred at RT for 17 h. The reaction mixture was diluted with EtOAc (20 mL), separated layers and the organic layer was washed with brine (10 mL), dried over MgSO$_4$, filtered, concentrated under reduced pressure, to afford the desired product (S)-2-chloro-N-(2-hydroxypropyl)pyridine-3-sulfonamide (1.1678 g, 4.66 mmol, 99% yield). LC-MS m/z 251 (M+H)$^+$, 0.48 (ret. time).

(S)-4-methyl-3,4-dihydro-2H-pyrido[2,3-b][1,4,5]oxathiazepine 1,1-dioxide

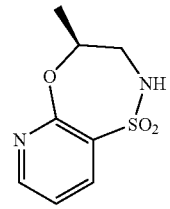

To the solution of (S)-2-chloro-N-(2-hydroxypropyl)pyridine-3-sulfonamide (1.16 g, 4.63 mmol) in DMSO (15 mL) was added KOt-Bu (1.558 g, 13.88 mmol) then heated at 80° C. for 30 min. The reaction mixture was diluted with H$_2$O (25 mL), acidified with HCl (1 N) to pH ~7, extracted with EtOAc (3×50 mL). The combined organic layer was washed with brine (50 mL), dried over MgSO$_4$, filtered, concentrated under reduced pressure, purified by silica gel chromatography to afford the desired product (S)-4-methyl-3,4-dihydro-2H-pyrido[2,3-b][1,4,5]oxathiazepine 1,1-dioxide (374.8 mg, 1.749 mmol, 37.8% yield). LC-MS m/z 215 (M+H)$^+$, 0.44 (ret. time).

3-(7-methoxy-1-methyl-1H-benzo[d][1,2,3]triazol-5-yl)-3-(4-methyl-3-(((S)-4-methyl-1,1-dioxido-3,4-dihydro-2H-pyrido[2,3-b][1,4,5]oxathiazepin-2-yl)methyl)phenyl)propanoic acid

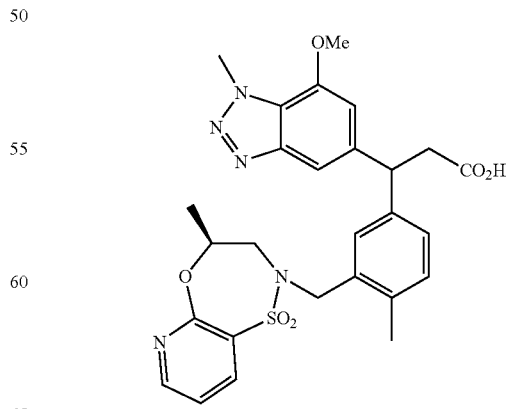

To the solution of ethyl 3-(3-(hydroxymethyl)-4-methylphenyl)-3-(7-methoxy-1-methyl-1H-benzo[d][1,2,3]triazol- 5-yl)propanoate (55 mg, 0.143 mmol) in THF (2 mL) was added (S)-4-methyl-3,4-dihydro-2H-pyrido[2,3-b][1,4,5] oxathiazepine 1,1-dioxide (46.1 mg, 0.215 mmol), PS—PPh$_3$ (130 mg, 0.287 mmol) and ADDP (72.4 mg, 0.287 mmol). The resulting reaction mixture was stirred at RT for 30 min. To this reaction mixture was added DIAD (0.056 mL, 0.287 mmol) then stirred at RT for 25 min. The reaction mixture was filtered, concentrated to afford crude desired intermediate ethyl 3-(7-methoxy-1-methyl-1H-benzo[d][1,2,3]triazol-5-yl)-3-(4-methyl-3-(((S)-4-methyl-1,1-dioxido-3,4-dihydro-2H-pyrido[2,3-b][1,4,5]oxathiazepin-2-yl)methyl)phenyl)propanoate. This intermediate was redissolved in MeOH (2.000 mL) then was added NaOH (2 N) (0.359 mL, 0.717 mmol). The resulting reaction mixture was heated with microwave irradiation at 60° C. for 30 min, heated again with microwave at 60° C. for 30 min, heated again with microwave at 80° C. for 10 min, heated again with microwave at 90° C. for 10 min. To this reaction mixture was added more NaOH (1 N) (0.287 mL, 0.287 mmol) then heated with microwave irradiation at 80° C. for 10 min. The reaction mixture was acidified with HCl (1 N) to pH ~5, concentrated under reduced pressure, purified by reverse phase HPLC to afford the desired product 3-(7-methoxy-1-methyl-1H-benzo[d][1,2,3]triazol-5-yl)-3-(4-methyl-3-(((S)-4-methyl-1,1-dioxido-3,4-dihydro-2H-pyrido[2,3-b][1,4,5]oxathiazepin-2-yl)methyl)phenyl)propanoic acid (36.6 mg, 0.066 mmol, 46.3% yield). LC-MS m/z 552 (M+H)$^+$, 0.89 (ret. time).

Example 18

3-(7-methoxy-1-methyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid

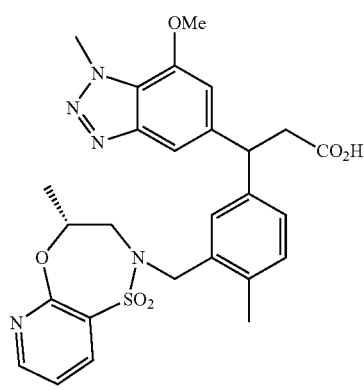 [SMILES: COc1cc(C(CC(=O)O)c2ccc(C)c(CN3C[C@@H](C)Oc4ncccc4S3(=O)=O)c2)cc2nnn(C)c12]

(R)-2-chloro-N-(2-hydroxypropyl)pyridine-3-sulfonamide

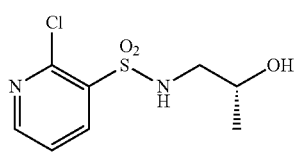

To the solution of (R)-1-aminopropan-2-ol (0.354 g, 4.72 mmol) in THF (10 mL) and water (2.5 mL) was added K$_2$CO$_3$ (0.652 g, 4.72 mmol) and stirred at RT for 5 min before was added 2-chloropyridine-3-sulfonyl chloride (1.0 g, 4.72 mmol). The resulting reaction mixture was stirred at RT for 17 h. The reaction mixture was diluted with EtOAc (20 mL), separated layers and organic layer was washed with brine (10 mL), dried over MgSO$_4$, filtered, concentrated under reduced pressure, to afford the desired product (R)-2-chloro-N-(2-hydroxypropyl)pyridine-3-sulfonamide (1.1486 g, 4.58 mmol, 97% yield). LC-MS m/z 251 (M+H)$^+$, 0.45 (ret. time).

(R)-4-methyl-3,4-dihydro-2H-pyrido[2,3-b][1,4,5]oxathiazepine 1,1-dioxide

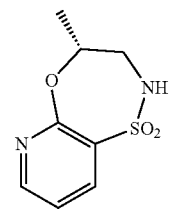

To the solution of (R)-2-chloro-N-(2-hydroxypropyl)pyridine-3-sulfonamide (1.15 g, 4.59 mmol) in DMSO (15 mL) was added KOt-Bu (1.544 g, 13.76 mmol) then heated at 80° C. for 1 h. The reaction mixture was diluted with H$_2$O (25 mL), acidified with HCl (1 N) to pH ~7, extracted with EtOAc (3×50 mL). The combined organic layer was washed with brine (50 mL), dried over MgSO$_4$, filtered, concentrated under reduced pressure, purified by silica gel chromatography to afford the desired product (R)-4-methyl-3,4-dihydro-2H-pyrido[2,3-b][1,4,5]oxathiazepine 1,1-dioxide (607.5 mg, 2.84 mmol, 61.8% yield). LC-MS m/z 215 (M+H)$^+$, 0.44 (ret. time).

3-(7-methoxy-1-methyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid

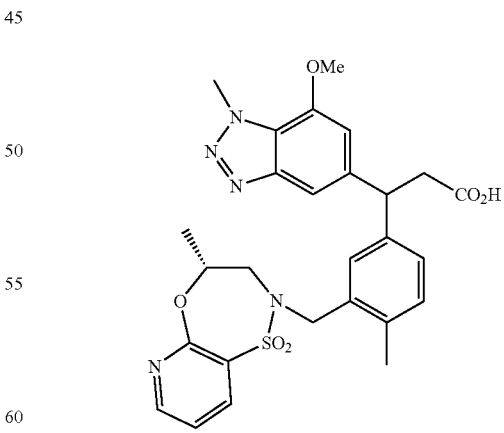

To the solution of ethyl 3-(3-(hydroxymethyl)-4-methylphenyl)-3-(7-methoxy-1-methyl-1H-benzo[d][1,2,3]triazol-5-yl)propanoate (55 mg, 0.143 mmol) in THF (2 mL) was added (R)-4-methyl-3,4-dihydro-2H-pyrido[2,3-b][1,4,5] oxathiazepine 1,1-dioxide (46.1 mg, 0.215 mmol), PS—

PPh₃ (130 mg, 0.287 mmol) and DIAD (0.056 mL, 0.287 mmol). The resulting reaction mixture was stirred at RT for 20 min. The reaction mixture was filtered, concentrated to afford crude desired intermediate ethyl 3-(7-methoxy-1-methyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoate. This intermediate was redissolved in MeOH (2.000 mL) then was added NaOH (2 N) (0.359 mL, 0.717 mmol). The resulting reaction mixture was heated with microwave irradiation at 80° C. for 30 min. The reaction mixture was acidified with HCl (1 N) to pH ~5, concentrated under reduced pressure, purified by reverse phase HPLC to afford the desired product 3-(7-methoxy-1-methyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid (42.4 mg, 0.077 mmol, 53.6% yield). LC-MS m/z 552 (M+H)⁺, 0.89 (ret. time).

Example 19

(S)-3-(1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

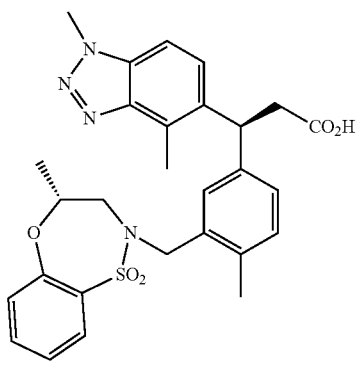 [SMILES: Cc1ccc([C@H](CC(=O)O)c2ccc3c(nnn3C)c2C)cc1CN1C[C@@H](C)Oc2ccccc2S1(=O)=O]

To the solution of ethyl 3-(1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate (1.00 g, 1.777 mmol) in MeOH (40 mL) was added NaOH (3 N) (2.96 mL, 8.89 mmol). The resulting reaction mixture was stirred at 60° C. for 3 h. The reaction mixture was acidified to pH ~3 with HCl (1 N), concentrated under reduced pressure, extracted with EtOAc (3×30 mL), dried over MgSO₄, filtered, concentrated under reduced pressure, purified by silica gel chromatography to afford the desired product 3-(1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid (812.3 mg, 1.519 mmol, 85% yield). This product which is a diastereomeric mixture was further purified by SFC chiral purification to afford the title compound (276.3 mg, 0.517 mmol, 29.1% yield) LC-MS m/z 535 (M+H)⁺, 0.93 (ret. time).

Example 20

(R)-3-(1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

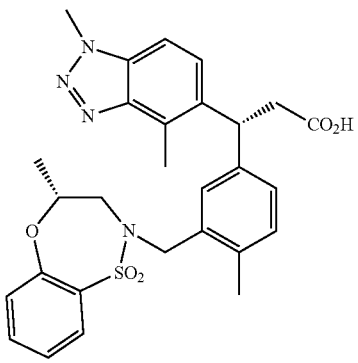 [SMILES: Cc1ccc([C@@H](CC(=O)O)c2ccc3c(nnn3C)c2C)cc1CN1C[C@@H](C)Oc2ccccc2S1(=O)=O]

To the solution of ethyl 3-(1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate (1.00 g, 1.777 mmol) in MeOH (40 mL) was added NaOH (3 N) (2.96 mL, 8.89 mmol). The resulting reaction mixture was stirred at 60° C. for 3 h. The reaction mixture was acidified to pH ~3 with HCl (1 N), concentrated under reduced pressure, extracted with EtOAc (3×30 mL), dried over MgSO₄, filtered, concentrated under reduced pressure, purified by silica gel chromatography to afford the desired product 3-(1,4-dimethyl-1H-benzo[d][1,2,3]triazol-5-yl)-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid (812.3 mg, 1.519 mmol, 85% yield). This product which is a diastereomeric mixture was further purified by SFC chiral purification to afford the title compound (286.2 mg, 0.535 mmol, 30.1% yield). LC-MS m/z 535 (M+H)⁺, 0.94 (ret. time).

Example 21

3-(1,4-dimethyl-1H-benzo[d][1,2,3]triazol-5-yl)-3-(3-((4-ethyl-1,1-dioxido-3,4-dihydro-2H-benzo[b][1,4,5]oxathiazepin-2-yl)methyl)-4-methylphenyl)propanoic acid

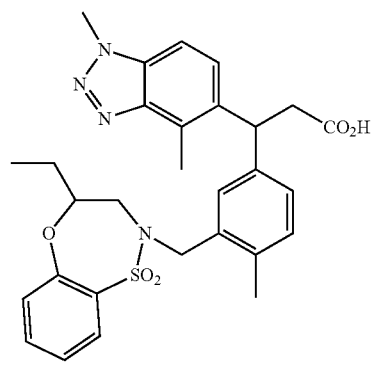 [SMILES: CCC1CN(Cc2cc(C(CC(=O)O)c3ccc4c(nnn4C)c3C)ccc2C)S(=O)(=O)c2ccccc2O1]

4-ethyl-3,4-dihydro-2H-benzo[b][1,4,5]oxathiazepine 1,1-dioxide

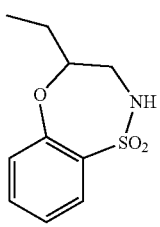

To the solution of 1-amino-2-butanol (0.446 g, 5.00 mmol) in THF (10 mL) and water (2.5 mL) was added K$_2$CO$_3$ (0.691 g, 5.00 mmol) then 2-fluorobenzene-1-sulfonyl chloride (0.662 mL, 5 mmol). The resulting reaction mixture was stirred at RT for 90 min. The reaction mixture was diluted with H$_2$O (10 mL), extracted with EtOAc (20+2×10 mL). The combined organic layer was washed with brine (15 mL), dried over MgSO$_4$, filtered, concentrated under reduced pressure, to afford the desired intermediate 2-fluoro-N-(2-hydroxybutyl)benzenesulfonamide (1.4313 g, 5.79 mmol, 116% yield). This intermediate was dissolved in DMSO (20 mL) and KOtBu (1.683 g, 15.00 mmol) was added to the resulting solution. The resulting reaction was stirred at 80° C. for 20 min. The reaction mixture was diluted with H$_2$O (20 mL), then added HCl (10 mL, 1 N), extracted with EtOAc (50+2×30 mL). The combined organic layer was washed with brine (30 mL), dried over MgSO$_4$, filtered, concentrated under reduced pressure, purified by silica gel chromatography to afford the desired product 4-ethyl-3,4-dihydro-2H-benzo[b][1,4,5]oxathiazepine 1,1-dioxide (1.1158 g, 4.91 mmol, 98% yield). LC-MS m/z 228 (M+H)$^+$, 0.69 (ret. time).

3-(1,4-dimethyl-1H-benzo[d][1,2,3]triazol-5-yl)-3-(3-((4-ethyl-1,1-dioxido-3,4-dihydro-2H-benzo[b][1,4,5]oxathiazepin-2-yl)methyl)-4-methylphenyl)propanoic acid

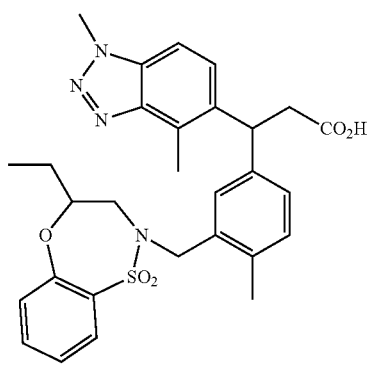 [SMILES: CCC1CN(Cc2cc(C(CC(=O)O)c3ccc4c(nnn4C)c3C)ccc2C)S(=O)(=O)c2ccccc2O1]

To the solution of ethyl 3-(1,4-dimethyl-1H-benzo[d][1,2,3]triazol-5-yl)-3-(3-(hydroxymethyl)-4-methylphenyl)propanoate (50 mg, 0.136 mmol) in THF (2 mL) was added 4-ethyl-3,4-dihydro-2H-benzo[b][1,4,5]oxathiazepine 1,1-dioxide (46.4 mg, 0.204 mmol), PS—PPh$_3$ (124 mg, 0.272 mmol) and DIAD (0.053 mL, 0.272 mmol). The resulting reaction mixture was stirred at RT for 30 min. The reaction mixture was filtered and the filtrate was concentrated to afford desired crude intermediate ethyl 3-(1,4-dimethyl-1H-benzo[d][1,2,3]triazol-5-yl)-3-(3-((4-ethyl-1,1-dioxido-3,4-dihydro-2H-benzo[b][1,4,5]oxathiazepin-2-yl)methyl)-4-methylphenyl)propanoate. To this intermediate was added MeOH (2 mL) then NaOH (2 N) (0.340 mL, 0.680 mmol). The resulting reaction mixture was heated with microwave irradiation at 80° C. for 20 min. The reaction mixture was acidified with HCl (1 N) to pH ~3, concentrated under reduced pressure, purified by reverse phase HPLC to afford the desired product 3-(1,4-dimethyl-1H-benzo[d][1,2,3]triazol-5-yl)-3-(3-((4-ethyl-1,1-dioxido-3,4-dihydro-2H-benzo[b][1,4,5]oxathiazepin-2-yl)methyl)-4-methylphenyl)propanoic acid (45.6 mg, 0.083 mmol, 61.1% yield). LC-MS m/z 549 (M+H)$^+$, 0.99 (ret. time).

Example 22

3-(1,4-dimethyl-1H-benzo[d][1,2,3]triazol-5-yl)-3-(3-((4-ethyl-1,1-dioxido-3,4-dihydro-2H-pyrido[2,3-b][1,4,5]oxathiazepin-2-yl)methyl)-4-methylphenyl)propanoic acid

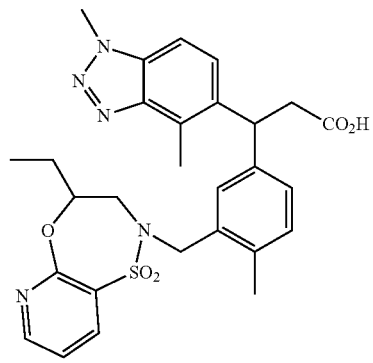 [SMILES: CCC1CN(Cc2cc(C(CC(=O)O)c3ccc4c(nnn4C)c3C)ccc2C)S(=O)(=O)c2cccnc2O1]

4-ethyl-3,4-dihydro-2H-pyrido[2,3-b][1,4,5]oxathiazepine 1,1-dioxide

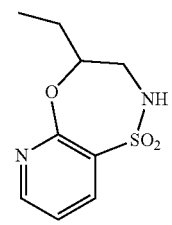

To the solution of 1-amino-2-butanol (0.446 g, 5.00 mmol) in THF (10 mL) and water (2.5 mL) was added K$_2$CO$_3$ (0.691 g, 5.00 mmol) then 2-chloropyridine-3-sulfonyl chloride (1.060 g, 5.00 mmol). The resulting reaction mixture was stirred at RT for 90 min. The reaction mixture was diluted with H$_2$O (10 mL), extracted with EtOAc (20+2×10 mL). The combined organic layer was washed with brine (15 mL), dried over MgSO$_4$, filtered, concentrated under reduced pressure, to afford the desired intermediate 2-chloro-N-(2-hydroxybutyl)pyridine-3-sulfonamide (1.6582 g, 6.26 mmol, 125% yield). This intermediate was dissolved in DMSO (20 mL) and was added KOtBu (1.683 g, 15.00 mmol). The resulting reaction was stirred at 80° C. for 30 min. The reaction mixture was diluted with H$_2$O (20 mL), was added HCl (10 mL, 1 N), extracted with EtOAc (50+2×30 mL). The combined organic layer was washed with brine (30 mL), dried over MgSO$_4$, filtered, concentrated under reduced pressure, purified by silica gel chromatography to afford the desired product 4-ethyl-3,4-dihydro-2H-pyrido[2,3-b][1,4,5]oxathiazepine 1,1-dioxide (1.2522 g, 5.10 mmol, 102% yield). LC-MS m/z 229 (M+H)$^+$, 0.52 (ret. time).

3-(1,4-dimethyl-1H-benzo[d][1,2,3]triazol-5-yl)-3-(3-((4-ethyl-1,1-dioxido-3,4-dihydro-2H-pyrido[2,3-b][1,4,5]oxathiazepin-2-yl)methyl)-4-methylphenyl)propanoic acid

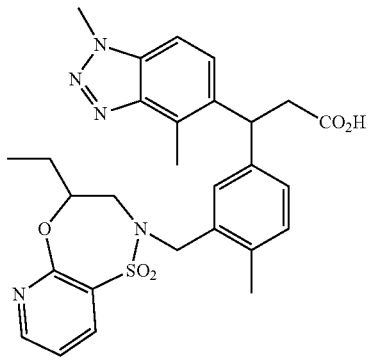 [SMILES: CCC1CN(Cc2cc(C(CC(=O)O)c3ccc4c(nnn4C)c3C)ccc2C)S(=O)(=O)c2cccnc2O1]

To the solution of ethyl 3-(1,4-dimethyl-1H-benzo[d][1,2,3]triazol-5-yl)-3-(3-(hydroxymethyl)-4-methylphenyl)propanoate (50 mg, 0.136 mmol) in THF (2 mL) was added 4-ethyl-3,4-dihydro-2H-pyrido[2,3-b][1,4,5]oxathiazepine 1,1-dioxide (46.6 mg, 0.204 mmol), PS—PPh₃ (124 mg, 0.272 mmol) and DIAD (0.053 mL, 0.272 mmol). The resulting reaction mixture was stirred at RT for 30 min. The reaction mixture was filtered and the filtrate was concentrated to afford desired crude intermediate ethyl 3-(1,4-dimethyl-1H-benzo[d][1,2,3]triazol-5-yl)-3-(3-((4-ethyl-1,1-dioxido-3,4-dihydro-2H-pyrido[2,3-b][1,4,5]oxathiazepin-2-yl)methyl)-4-methylphenyl)propanoate. To this intermediate was added MeOH (2 mL) then NaOH (2 N) (0.340 mL, 0.680 mmol). The resulting reaction mixture was heated with microwave irradiation at 80° C. for 20 min. The reaction mixture was acidified with HCl (1 N) to pH ~3, concentrated under reduced pressure, purified by reverse phase HPLC to afford the desired product 3-(1,4-dimethyl-1H-benzo[d][1,2,3]triazol-5-yl)-3-(3-((4-ethyl-1,1-dioxido-3,4-dihydro-2H-pyrido[2,3-b][1,4,5]oxathiazepin-2-yl)methyl)-4-methylphenyl)propanoic acid (41.0 mg, 0.075 mmol, 54.8% yield). LC-MS m/z 550 (M+H)⁺, 0.89 (ret. time).

Example 23

3-(3-((4-ethyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid

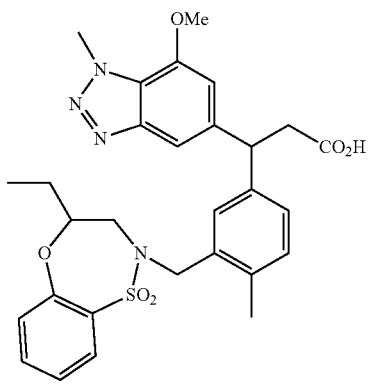 [SMILES: CCC1CN(Cc2cc(C(CC(=O)O)c3cc(OC)c4c(c3)nnn4C)ccc2C)S(=O)(=O)c2ccccc2O1]

To the solution of ethyl 3-(3-(hydroxymethyl)-4-methylphenyl)-3-(7-methoxy-1-methyl-1H-benzo[d][1,2,3]triazol-5-yl)propanoate (50 mg, 0.130 mmol) in THF (2 mL) was added 4-ethyl-3,4-dihydro-2H-benzo[b][1,4,5]oxathiazepine 1,1-dioxide (44.5 mg, 0.196 mmol), PS—PPh₃ (119 mg, 0.261 mmol) and DIAD (0.051 mL, 0.261 mmol). The resulting reaction mixture was stirred at RT for 70 min. The reaction mixture was filtered and the filtrate was evaporated down over glass-col evaporator to afford desired crude intermediate ethyl 3-(3-((4-ethyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoate. To this intermediate was added MeOH (2 mL) then NaOH (2 N) (0.326 mL, 0.652 mmol). The resulting reaction mixture was heated with microwave irradiation at 80° C. for 20 min. The reaction mixture was acidified with HCl (1 N) to pH ~3, concentrated under reduced pressure, purified by reverse phase HPLC to afford the desired product 3-(3-((4-ethyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid (36.0 mg, 0.064 mmol, 48.9% yield). LC-MS m/z 565 (M+H)⁺, 1.01 (ret. time).

Example 24

3-(3-((4-ethyl-1,1-dioxido-3,4-dihydro-2H-pyrido[2,3-b][1,4,5]oxathiazepin-2-yl)methyl)-4-methylphenyl)-3-(7-methoxy-1-methyl-1H-benzo[d][1,2,3]triazol-5-yl)propanoic acid

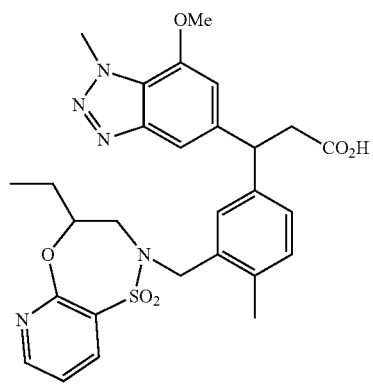 [SMILES: CCC1CN(Cc2cc(C(CC(=O)O)c3cc(OC)c4c(c3)nnn4C)ccc2C)S(=O)(=O)c2cccnc2O1]

To the solution of ethyl 3-(3-(hydroxymethyl)-4-methylphenyl)-3-(7-methoxy-1-methyl-1H-benzo[d][1,2,3]triazol-5-yl)propanoate (50 mg, 0.130 mmol) in THF (2 mL) was added 4-ethyl-3,4-dihydro-2H-pyrido[2,3-b][1,4,5]oxathiazepine 1,1-dioxide (44.6 mg, 0.196 mmol), PS—PPh₃ (119 mg, 0.261 mmol) and DIAD (0.051 mL, 0.261 mmol). The resulting reaction mixture was stirred at RT for 70 min. The reaction mixture was filtered and the filtrate was concentrated to afford desired crude intermediate ethyl 3-(3-((4-ethyl-1,1-dioxido-3,4-dihydro-2H-pyrido[2,3-b][1,4,5]oxathiazepin-2-yl)methyl)-4-methylphenyl)-3-(7-methoxy-1-methyl-1H-benzo[d][1,2,3]triazol-5-yl)propanoate. To this intermediate was added MeOH (2 mL) then NaOH (2 N) (0.326 mL, 0.652 mmol). The resulting reaction mixture was heated with microwave irradiation at 80° C. for 20 min. The reaction mixture was acidified with HCl (1 N) to pH ~3, concentrated under reduced pressure, purified by reverse phase HPLC to afford the desired product 3-(3-((4-ethyl-1,1-dioxido-3,4-dihydro-2H-pyrido[2,3-b][1,4,5]oxathiazepin-2-yl)methyl)-4-methylphenyl)-3-(7-methoxy-1-methyl-1H-benzo[d][1,2,3]triazol-5-yl)propanoic acid (37.5 mg, 0.066 mmol, 50.8% yield). LC-MS m/z 566 (M+H)⁺, 0.91 (ret. time).

Example 25

3-(1,4-dimethyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid

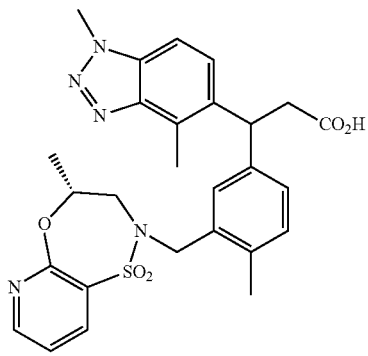 [SMILES: Cc1ccc(C(CC(=O)O)c2ccc3c(nnn3C)c2C)cc1CN1C[C@@H](C)Oc2ncccc2S1(=O)=O]

To the solution of ethyl 3-(1,4-dimethyl-1H-benzo[d][1,2,3]triazol-5-yl)-3-(3-(hydroxymethyl)-4-methylphenyl)propanoate (50 mg, 0.136 mmol) in THF (2 mL) was added (R)-4-methyl-3,4-dihydro-2H-pyrido[2,3-b][1,4,5]oxathiazepine 1,1-dioxide (43.7 mg, 0.204 mmol), PS—PPh$_3$ (170 mg, 0.272 mmol) and DIAD (0.053 mL, 0.272 mmol). The resulting reaction mixture was stirred at RT for 90 min. The reaction mixture was filtered, concentrated under reduced pressure to afford crude desired intermediate ethyl 3-(1,4-dimethyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoate. This intermediate was redissolved in MeOH (2.000 mL) then was added NaOH (2 N) (0.340 mL, 0.680 mmol). The resulting reaction mixture was heated with microwave irradiation at 80° C. for 20 min. The reaction mixture was acidified with HCl (1 N) to pH ~5, concentrated under reduced pressure, purified by reverse phase HPLC to afford the desired product 3-(1,4-dimethyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid (39.5 mg, 0.074 mmol, 54.2% yield). LC-MS m/z 536 (M+H)$^+$, 0.90 (ret. time).

Example 26

3-(1,4-dimethyl-1H-benzo[d][1,2,3]triazol-5-yl)-3-(3-((5-ethyl-1,1-dioxido-4,5-dihydropyrido[2,3-f][1,2,5]thiadiazepin-2(3H)-yl)methyl)-4-methylphenyl)propanoic acid

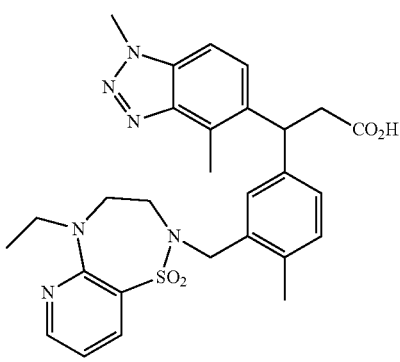 [SMILES: CCN1CCN(Cc2cc(C(CC(=O)O)c3ccc4c(nnn4C)c3C)ccc2C)S(=O)(=O)c2cccnc21]

5-ethyl-2,3,4,5-tetrahydropyrido[2,3-f][1,2,5]thiadiazepine 1,1-dioxide

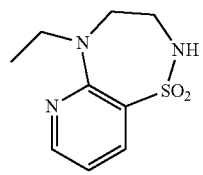

To the solution of N-ethyl ethylenediamine (0.790 mL, 7.50 mmol) in THF (25 mL) was added DIPEA (1.747 mL, 10.00 mmol) then 2-chloropyridine-3-sulfonyl chloride (1060 mg, 5 mmol). The resulting reaction mixture was stirred at RT for 90 min then heated at 50° C. for 17 d. The reaction mixture was filtered, washed with THF (~10 mL). The filtrate was concentrated under reduced pressure, purified by silica gel chromatography to afford the desired product 5-ethyl-2,3,4,5-tetrahydropyrido[2,3-f][1,2,5]thiadiazepine 1,1-dioxide (331.5 mg, 1.459 mmol, 29.2% yield). LC-MS m/z 228 (M+H)$^+$, 0.53 (ret. time).

3-(1,4-dimethyl-1H-benzo[d][1,2,3]triazol-5-yl)-3-(3-((5-ethyl-1,1-dioxido-4,5-dihydropyrido[2,3-f][1,2,5]thiadiazepin-2(3H)-yl)methyl)-4-methylphenyl)propanoic acid

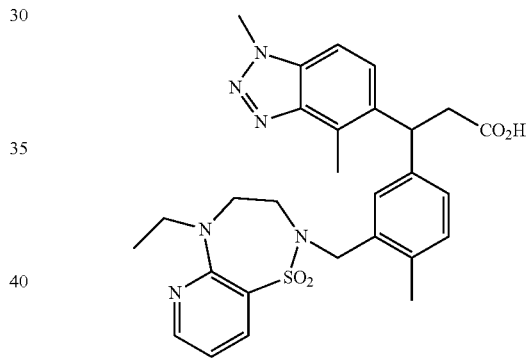

To the solution of ethyl 3-(1,4-dimethyl-1H-benzo[d][1,2,3]triazol-5-yl)-3-(3-(hydroxymethyl)-4-methylphenyl)propanoate (0.050 g, 0.136 mmol) in THF (2 mL) was added 5-ethyl-2,3,4,5-tetrahydropyrido[2,3-f][1,2,5]thiadiazepine 1,1-dioxide (0.046 g, 0.204 mmol), PS—PPh$_3$ (0.170 g, 0.272 mmol) and then DIAD (0.053 mL, 0.272 mmol). The resulting reaction was stirred at RT for 1 h. The reaction mixture was filtered and the filtrate was evaporated down over glass-col evaporator to afford desired crude intermediate ethyl 3-(1,4-dimethyl-1H-benzo[d][1,2,3]triazol-5-yl)-3-(3-((5-ethyl-1,1-dioxido-4,5-dihydropyrido[2,3-f][1,2,5]thiadiazepin-2(3H)-yl)methyl)-4-methylphenyl)propanoate. To this intermediate was added MeOH (2.000 mL) then NaOH (2 N) (0.340 mL, 0.680 mmol). The resulting reaction mixture was heated with microwave irradiation at 80° C. for 20 min. The reaction mixture was acidified with HCl (1 N) to pH ~3, concentrated under reduced pressure, purified by reverse phase HPLC to afford the desired product 3-(1,4-dimethyl-1H-benzo[d][1,2,3]triazol-5-yl)-3-(3-((5-ethyl-1,1-dioxido-4,5-dihydropyrido[2,3-f][1,2,5]thiadiazepin-2(3H)-yl)methyl)-4-methylphenyl)propanoic acid (44.0 mg, 0.080 mmol, 58.9% yield). LC-MS m/z 549 (M+H)$^+$, 0.97 (ret. time).

Example 27

3-(3-((5-ethyl-1,1-dioxido-4,5-dihydropyrido[2,3-f]
[1,2,5]thiadiazepin-2(3H)-yl)methyl)-4-methylphe-
nyl)-3-(7-methoxy-1-methyl-1H-benzo[d][1,2,3]
triazol-5-yl)propanoic acid

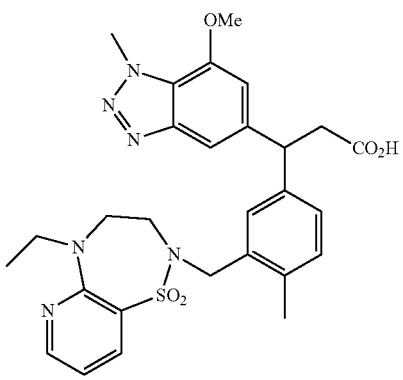 [SMILES: CCN1CCN(Cc2cc(C(CC(=O)O)c3cc(OC)c4c(c3)nnn4C)ccc2C)S(=O)(=O)c2cccnc21]

To the solution of ethyl 3-(3-(hydroxymethyl)-4-methylphenyl)-3-(7-methoxy-1-methyl-1H-benzo[d][1,2,3]triazol-5-yl)propanoate (0.050 g, 0.130 mmol) in THF (2 mL) was added 5-ethyl-2,3,4,5-tetrahydropyrido[2,3-f][1,2,5]thiadiazepine 1,1-dioxide (0.044 g, 0.196 mmol), PS—PPh$_3$ (0.163 g, 0.261 mmol) and then DIAD (0.051 mL, 0.261 mmol). The resulting reaction was stirred at RT for 1 h. The reaction mixture was filtered and the filtrate was concentrated to afford desired crude intermediate ethyl 3-(3-((5-ethyl-1,1-dioxido-4,5-dihydropyrido[2,3-f][1,2,5]thiadiazepin-2(3H)-yl)methyl)-4-methylphenyl)-3-(7-methoxy-1-methyl-1H-benzo[d][1,2,3]triazol-5-yl)propanoate. To this intermediate was added MeOH (2.000 mL) then NaOH (2 N) (0.326 mL, 0.652 mmol). The resulting reaction mixture was heated with microwave irradiation at 80° C. for 20 min. The reaction mixture was acidified with HCl (1 N) to pH ~3, concentrated under reduced pressure, purified by reverse phase HPLC to afford the desired product 3-(3-((5-ethyl-1,1-dioxido-4,5-dihydropyrido[2,3-f][1,2,5]thiadiazepin-2(3H)-yl)methyl)-4-methylphenyl)-3-(7-methoxy-1-methyl-1H-benzo[d][1,2,3]triazol-5-yl)propanoic acid (57.4 mg, 0.102 mmol, 78% yield). LC-MS m/z 565 (M+H)$^+$, 1.00 (ret. time).

Example 28

3-(1-methyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid

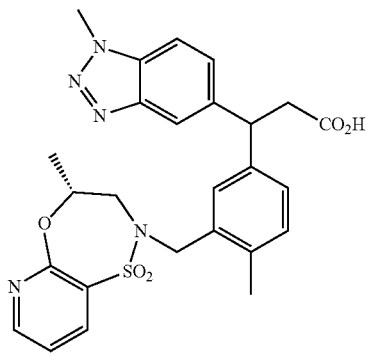 [SMILES: Cc1ccc(C(CC(=O)O)c2ccc3c(c2)nnn3C)cc1CN1C[C@@H](C)Oc2ncccc2S1(=O)=O]

Methyl 3-(3-(hydroxymethyl)-4-methylphenyl)-3-(1-methyl-1H-benzo[d][1,2,3]triazol-5-yl)propanoate

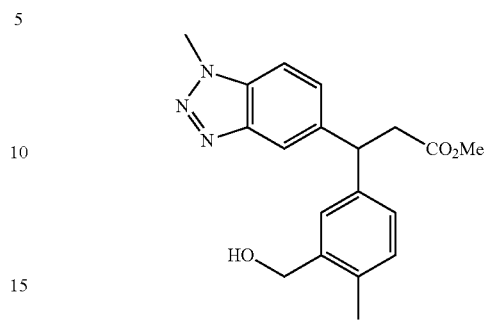

To the solution of methyl diethylphosphonoacetate (2.495 mL, 13.65 mmol) in THF (50 mL) was added KOtBu (1.532 g, 13.65 mmol) and stirred at RT for 10 min before was added 1-methyl-1H-benzo[d][1,2,3]triazole-5-carbaldehyde (2.0 g, 12.41 mmol) in THF (10 mL). The resulting reaction mixture was stirred at RT for 30 min. The reaction mixture was added H$_2$O (30 mL), extracted with EtOAc (3×50 mL). The combined organic layer was washed with brine (30 mL), dried over MgSO$_4$, filtered, concentrated under reduced pressure to afford desired intermediate (E)-methyl 3-(1-methyl-1H-benzo[d][1,2,3]triazol-5-yl)acrylate. To this intermediate was added 1,4-dioxane (90 mL) and water (30 mL) then (3-(hydroxymethyl)-4-methylphenyl)boronic acid (4.12 g, 24.82 mmol), TEA (5.19 mL, 37.2 mmol) and [Rh(cod)Cl]$_2$ (0.306 g, 0.620 mmol). The resulting reaction mixture was stirred at 90° C. for 45 min. The reaction mixture was extracted with EtOAc (100+2×50 mL). The combined organic layer was washed with brine (50 mL), dried over MgSO$_4$, filtered, concentrated under reduced pressure, purified by silica gel chromatography to afford the desired product methyl 3-(3-(hydroxymethyl)-4-methylphenyl)-3-(1-methyl-1H-benzo[d][1,2,3]triazol-5-yl)propanoate (3.2661 g, 9.62 mmol, 78% yield). LC-MS m/z 340 (M+H)$^+$, 0.77 (ret. time).

3-(1-methyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid

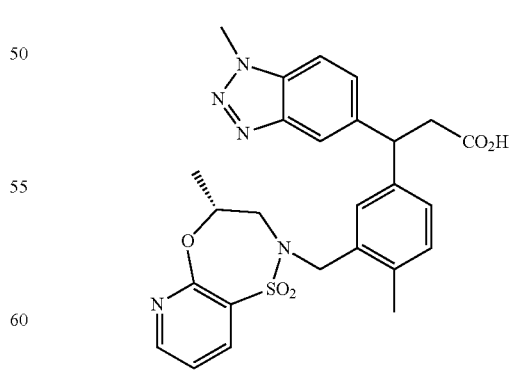

To the solution of methyl 3-(3-(hydroxymethyl)-4-methylphenyl)-3-(1-methyl-1H-benzo[d][1,2,3]triazol-5-yl)propanoate (50 mg, 0.147 mmol) in THF (2 mL) was added (R)-4-methyl-3,4-dihydro-2H-pyrido[2,3-b][1,4,5]oxathiazepine 1,1-dioxide (47.3 mg, 0.221 mmol), PS—PPh₃ (134 mg, 0.295 mmol) and DIAD (0.057 mL, 0.295 mmol). The resulting reaction mixture was stirred at RT for 30 min. The reaction mixture was filtered and the filtrate was evaporated down over glass-col evaporator to afford desired crude intermediate methyl 3-(1-methyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoate. To this intermediate was added MeOH (2 mL) then NaOH (2 N) (0.368 mL, 0.737 mmol). The resulting reaction mixture was heated with microwave irradiation at 80° C. for 20 min. The reaction mixture was acidified with HCl (1 N) to pH ~3, concentrated under reduced pressure, purified by reverse phase HPLC to afford the desired product 3-(1-methyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid (45.0 mg, 0.086 mmol, 58.6% yield). LC-MS m/z 522 (M+H)⁺, 0.88 (ret. time).

Example 29

3-(1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

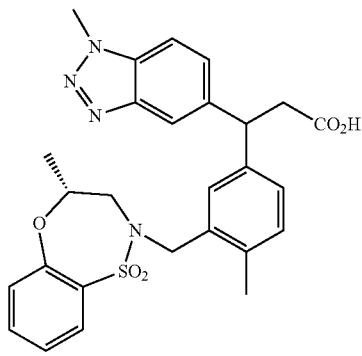 [SMILES: Cc1ccc(C(CC(=O)O)c2ccc3c(c2)nnn3C)cc1CN1C[C@@H](C)Oc2ccccc2S1(=O)=O]

To the solution of methyl 3-(3-(hydroxymethyl)-4-methylphenyl)-3-(1-methyl-1H-benzo[d][1,2,3]triazol-5-yl)propanoate (50 mg, 0.147 mmol) in THF (2 mL) was added (R)-4-methyl-3,4-dihydro-2H-benzo[b][1,4,5]oxathiazepine 1,1-dioxide (47.1 mg, 0.221 mmol), PS—PPh₃ (134 mg, 0.295 mmol) and DIAD (0.057 mL, 0.295 mmol). The resulting reaction mixture was stirred at RT for 30 min. The reaction mixture was filtered and the filtrate was evaporated down over glass-col evaporator to afford desired crude intermediate methyl 3-(1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate. To this intermediate was added MeOH (2 mL) then NaOH (2 N) (0.368 mL, 0.737 mmol). The resulting reaction mixture was heated with microwave irradiation at 80° C. for 20 min. The reaction mixture was acidified with HCl (1 N) to pH ~3, concentrated under reduced pressure, purified by reverse phase HPLC to afford the desired product 3-(1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid (51.7 mg, 0.099 mmol, 67.4% yield). LC-MS m/z 521 (M+H)⁺, 0.97 (ret. time).

Example 30

3-(3-((5-ethyl-1,1-dioxido-4,5-dihydrobenzo[f][1,2,5]thiadiazepin-2(3H)-yl)methyl)-4-methylphenyl)-3-(1-methyl-1H-benzo[d][1,2,3]triazol-5-yl)propanoic acid

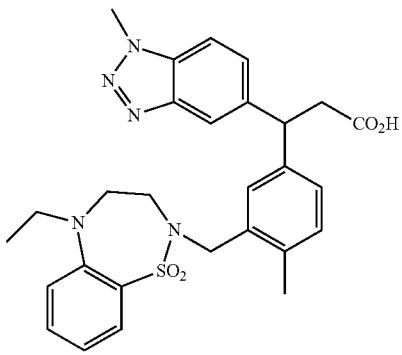 [SMILES: CCN1CCN(Cc2cc(C(CC(=O)O)c3ccc4c(c3)nnn4C)ccc2C)S(=O)(=O)c2ccccc21]

To the solution of 2-(ethyl(2-hydroxyethyl)amino)benzenesulfonamide (54.0 mg, 0.221 mmol) in THF (2 mL) was added PS—PPh₃ (276 mg, 0.442 mmol) and DIAD (0.086 mL, 0.442 mmol). The resulting reaction mixture was stirred at RT for 20 min. To this reaction mixture was then added methyl 3-(3-(hydroxymethyl)-4-methylphenyl)-3-(1-methyl-1H-benzo[d][1,2,3]triazol-5-yl)propanoate (50 mg, 0.147 mmol) before was stirred at RT for 90 min. The reaction mixture was filtered, evaporated down over glass-col evaporator to afford desired intermediate methyl 3-(3-((5-ethyl-1,1-dioxido-4,5-dihydrobenzo[f][1,2,5]thiadiazepin-2(3H)-yl)methyl)-4-methylphenyl)-3-(1-methyl-1H-benzo[d][1,2,3]triazol-5-yl)propanoate. This intermediate was redissolved in MeOH (2.000 mL) then was added NaOH (2 N) (0.368 mL, 0.737 mmol). The resulting reaction mixture was heated with microwave irradiation at 80° C. for 20 min. The reaction mixture was acidified with HCl (1 N) to pH ~3, concentrated under reduced pressure, purified by reverse phase HPLC to afford the desired product 3-(3-((5-ethyl-1,1-dioxido-4,5-dihydrobenzo[f][1,2,5]thiadiazepin-2(3H)-yl)methyl)-4-methylphenyl)-3-(1-methyl-1H-benzo[d][1,2,3]triazol-5-yl)propanoic acid (54.1 mg, 0.101 mmol, 68.8% yield). LC-MS m/z 534 (M+H)⁺, 1.00 (ret. time).

Example 31

3-(3-((4-ethyl-1,1-dioxido-3,4-dihydro-2H-pyrido[2,3-b][1,4,5]oxathiazepin-2-yl)methyl)-4-methylphenyl)-3-(1-methyl-1H-benzo[d][1,2,3]triazol-5-yl)propanoic acid

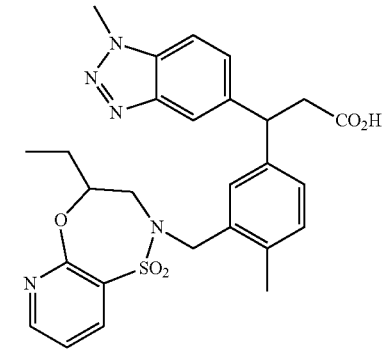 [SMILES: CCC1CN(Cc2cc(C(CC(=O)O)c3ccc4c(c3)nnn4C)ccc2C)S(=O)(=O)c2cccnc2O1]

To the solution of methyl 3-(3-(hydroxymethyl)-4-methylphenyl)-3-(1-methyl-1H-benzo[d][1,2,3]triazol-5-yl)propanoate (50 mg, 0.147 mmol) in THF (2 mL) was added 4-ethyl-3,4-dihydro-2H-pyrido[2,3-b][1,4,5]oxathiazepine 1,1-dioxide (50.4 mg, 0.221 mmol), PS—PPh₃ (134 mg, 0.295 mmol) and DIAD (0.057 mL, 0.295 mmol). The resulting reaction mixture was stirred at RT for 30 min. The reaction mixture was filtered and the filtrate was evaporated down over glass-col evaporator to afford desired crude intermediate methyl 3-(3-((4-ethyl-1,1-dioxido-3,4-dihydro-2H-pyrido[2,3-b][1,4,5]oxathiazepin-2-yl)methyl)-4-methylphenyl)-3-(1-methyl-1H-benzo[d][1,2,3]triazol-5-yl)propanoate. To this intermediate was added MeOH (2 mL) then NaOH (2 N) (0.368 mL, 0.737 mmol). The resulting reaction mixture was heated with microwave irradiation at 80° C. for 20 min. The reaction mixture was acidified with HCl (1 N) to pH ~3, concentrated under reduced pressure, purified by reverse phase HPLC to afford the desired product 3-(3-((4-ethyl-1,1-dioxido-3,4-dihydro-2H-pyrido[2,3-b][1,4,5]oxathiazepin-2-yl)methyl)-4-methylphenyl)-3-(1-methyl-1H-benzo[d][1,2,3]triazol-5-yl)propanoic acid (50.1 mg, 0.094 mmol, 63.5% yield). LC-MS m/z 536 (M+H)⁺, 0.91 (ret. time).

Example 32

3-(3-((4-ethyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoic acid

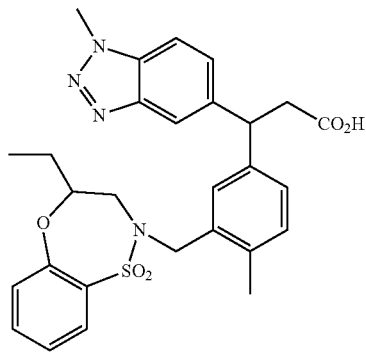 [SMILES: CCC1CN(Cc2cc(C(CC(=O)O)c3ccc4c(c3)nnn4C)ccc2C)S(=O)(=O)c2ccccc2O1]

To the solution of methyl 3-(3-(hydroxymethyl)-4-methylphenyl)-3-(1-methyl-1H-benzo[d][1,2,3]triazol-5-yl)propanoate (50 mg, 0.147 mmol) in THF (2 mL) was added 4-ethyl-3,4-dihydro-2H-benzo[b][1,4,5]oxathiazepine 1,1-dioxide (50.2 mg, 0.221 mmol), PS—PPh₃ (134 mg, 0.295 mmol) and DIAD (0.057 mL, 0.295 mmol). The resulting reaction mixture was stirred at RT for 30 min. The reaction mixture was filtered and the filtrate was evaporated down over glass-col evaporator to afford desired crude intermediate methyl 3-(3-((4-ethyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoate. To this intermediate was added MeOH (2 mL) then NaOH (2 N) (0.368 mL, 0.737 mmol). The resulting reaction mixture was heated with microwave irradiation at 80° C. for 20 min. The reaction mixture was acidified with HCl (1 N) to pH ~3, concentrated under reduced pressure, purified by reverse phase HPLC to afford the desired product 3-(3-((4-ethyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoic acid (60.9 mg, 0.114 mmol, 77% yield). LC-MS m/z 535 (M+H)⁺, 1.02 (ret. time).

Example 33

3-(3-((5-ethyl-1,1-dioxido-4,5-dihydropyrido[2,3-f][1,2,5]thiadiazepin-2(3H)-yl)methyl)-4-methylphenyl)-3-(1-methyl-1H-benzo[d][1,2,3]triazol-5-yl)propanoic acid

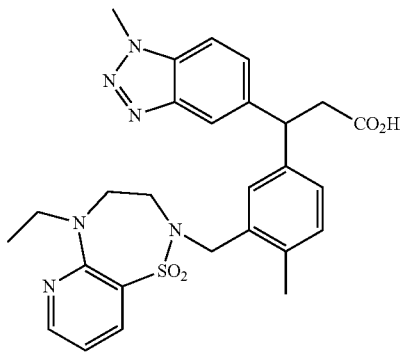 [SMILES: CCN1CCN(Cc2cc(C(CC(=O)O)c3ccc4c(c3)nnn4C)ccc2C)S(=O)(=O)c2cccnc21]

To the solution of methyl 3-(3-(hydroxymethyl)-4-methylphenyl)-3-(1-methyl-1H-benzo[d][1,2,3]triazol-5-yl)propanoate (0.050 g, 0.147 mmol) in THF (2 mL) was added 5-ethyl-2,3,4,5-tetrahydropyrido[2,3-f][1,2,5]thiadiazepine 1,1-dioxide (0.050 g, 0.221 mmol), PS—PPh₃ (0.184 g, 0.295 mmol) and then DIAD (0.057 mL, 0.295 mmol). The resulting reaction was stirred at RT for 1 h. The reaction mixture was filtered and the filtrate was evaporated down over glass-col evaporator to afford desired crude intermediate methyl 3-(3-((5-ethyl-1,1-dioxido-4,5-dihydropyrido[2,3-f][1,2,5]thiadiazepin-2(3H)-yl)methyl)-4-methylphenyl)-3-(1-methyl-1H-benzo[d][1,2,3]triazol-5-yl)propanoate. To this intermediate was added MeOH (2.000 mL) then NaOH (2 N) (0.368 mL, 0.737 mmol). The resulting reaction mixture was heated with microwave irradiation at 80° C. for 20 min. The reaction mixture was acidified with HCl (1 N) to pH ~3, concentrated under reduced pressure, purified by reverse phase HPLC to afford the desired product 3-(3-((5-ethyl-1,1-dioxido-4,5-dihydropyrido[2,3-f][1,2,5]thiadiazepin-2(3H)-yl)methyl)-4-methylphenyl)-3-(1-methyl-1H-benzo[d][1,2,3]triazol-5-yl)propanoic acid (52.2 mg, 0.098 mmol, 66.3% yield). LC-MS m/z 535 (M+H)⁺, 0.97 (ret. time).

Example 34

(3R)-3-(7-methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

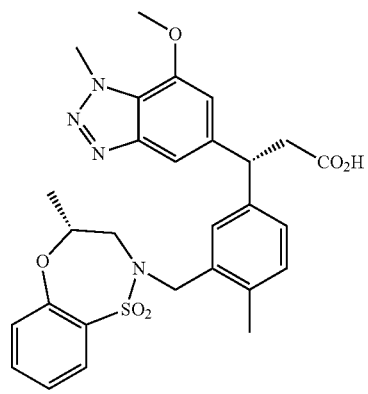 [SMILES: COc1cc([C@H](CC(=O)O)c2ccc(C)c(CN3C[C@@H](C)Oc4ccccc4S3(=O)=O)c2)cc2nnn(C)c12]

To the solution of ethyl 3-(3-(hydroxymethyl)-4-methylphenyl)-3-(7-methoxy-1-methyl-1H-benzo[d][1,2,3]triazol-5-yl)propanoate (980 mg, 2.56 mmol) in THF (30 mL) was added (R)-4-methyl-3,4-dihydro-2H-benzo[b][1,4,5]oxathiazepine 1,1-dioxide (818 mg, 3.83 mmol), PS—PPh₃ (3195 mg, 5.11 mmol) and then was added DIAD (0.994 mL, 5.11 mmol) in THF (10 mL). The resulting reaction mixture was stirred at RT for 30 min.

The reaction mixture was filtered and the filtrate was concentrated under reduced pressure, purified with flash chromatograph over Silica gel column to afford desired crude intermediate ethyl 3-(7-methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate (1.2990 g, 2.245 mmol, 88% yield). This crude intermediate was dissolved in MeOH (30.0 mL) then was added NaOH (2 N) (6.39 mL, 12.78 mmol). The resulting reaction mixture was stirred at 80° C. for 40 min. The reaction mixture was acidified with HCl (1 N) to pH ~3, concentrated under reduced pressure, extracted with EtOAc (3×50 mL). The combined organic layer was washed with brine (50 mL), dried over MgSO₄, filtered, concentrated under reduced pressure to afford the desired product 3-(7-methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid (1.4075 g, 2.56 mmol, 100% yield). The title compound was obtained by SFC chiral purification (400 mg, 0.726 mmol, 28.4% yield) LC-MS m/z 551 (M+H)⁺, 1.02 (ret. time).

(3S)-3-(7-methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

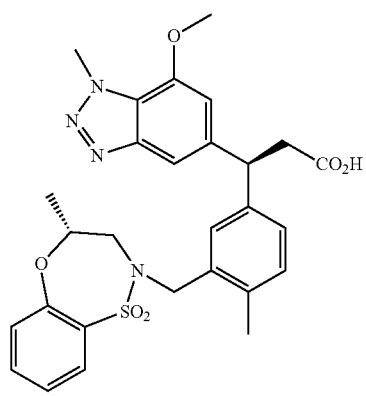 [SMILES: COc1cc([C@@H](CC(=O)O)c2ccc(C)c(CN3C[C@@H](C)Oc4ccccc4S3(=O)=O)c2)cc2nnn(C)c12]

To the solution of ethyl 3-(3-(hydroxymethyl)-4-methylphenyl)-3-(7-methoxy-1-methyl-1H-benzo[d][1,2,3]triazol-5-yl)propanoate (980 mg, 2.56 mmol) in THF (30 mL) was added (R)-4-methyl-3,4-dihydro-2H-benzo[b][1,4,5]oxathiazepine 1,1-dioxide (818 mg, 3.83 mmol), PS—PPh₃ (3195 mg, 5.11 mmol) and then was added DIAD (0.994 mL, 5.11 mmol) in THF (10 mL). The resulting reaction mixture was stirred at RT for 30 min. The reaction mixture was filtered and the filtrate was concentrated under reduced pressure, purified with flash chromatograph over Silica gel column to afford desired crude intermediate ethyl 3-(7-methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate (1.2990 g, 2.245 mmol, 88% yield). This crude intermediate was dissolved in MeOH (30.0 mL) then was added NaOH (2 N) (6.39 mL, 12.78 mmol). The resulting reaction mixture was stirred at 80° C. for 40 min. The reaction mixture was acidified with HCl (1 N) to pH ~3, concentrated under reduced pressure, extracted with EtOAc (3×50 mL). The combined organic layer was washed with brine (50 mL), dried over MgSO₄, filtered, concentrated under reduced pressure to afford the desired product 3-(7-methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid (1.4075 g, 2.56 mmol, 100% yield). The title compound was obtained by SFC chiral purification to afford desired enantiomeric pure product (367 mg, 0.667 mmol, 26.1% yield). LC-MS m/z 551 (M+H)⁺, 1.02 (ret. time).

Example 35

3-(3-((4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic acid

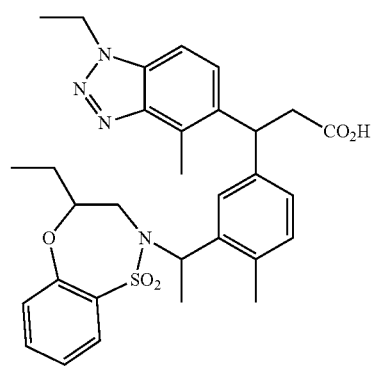 [SMILES: CCC1CN(C(C)c2cc(C(CC(=O)O)c3ccc4c(nnn4CC)c3C)ccc2C)S(=O)(=O)c2ccccc2O1]

(E)-Ethyl 3-(1-ethyl-4-methyl-1H-benzo[d][1,2,3]triazol-5-yl)acrylate

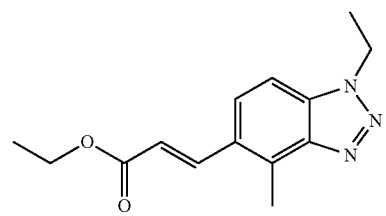 [SMILES: CCOC(=O)/C=C/c1ccc2c(nnn2CC)c1C]

Fluoro-3-methyl-2-nitrobenzene

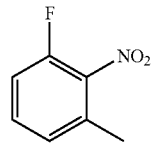

To a solution of 2-fluoro-6-methylaniline (8.5 g, 67.9 mmol) in DCE (150 mL), m-CPBA (58.6 g, 272 mmol) was added slowly under nitrogen at RT. The reaction mixture was stirred at 70° C. for 4 h. DCM (500 mL) was added. Then it was washed with 1N NaOH (200 mL×4). The combined organic layers was dried and concentrated under a stream of nitrogen at 50° C. to give 11.2 g (65.9%) of the title compound.

N-Ethyl-3-methyl-2-nitroaniline

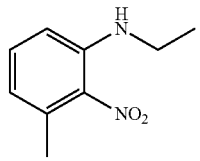

To a solution of 1-fluoro-3-methyl-2-nitrobenzene (11.2 g, 72.2 mmol) in EtOH (80 mL), ethanamine (80 mL, 911 mmol) was added slowly under nitrogen at RT. The reaction mixture was stirred at 60° C. for 16 h. Water (100 mL) was added. Then it was extracted with EtOAc (3×80 mL). The combined organic layers was dried and concentrated under a stream of nitrogen at 50° C. The crude product was purified by silica gel chromatography (hexane:EtOAc=100:1) to give 11.9 g (85%) of the title compound. LC-MS m/z 181.2 (M+H)$^+$, 1.81 (ret. time).

4-Bromo-N-ethyl-3-methyl-2-nitroaniline

To a solution of N-ethyl-3-methyl-2-nitroaniline (11.9 g, 66.0 mmol) in DMF (100 mL), NBS (11.75 g, 66.0 mmol) in 100 mL of DMF was added dropwise. Then the reaction mixture was stirred at RT for 16 h. 800 mL of water was added. The solid was filtered and dried to give 16 g (78%) of the title compound. LC-MS m/z 2.02 (M+H)$^+$, 260.9 (ret. time).

4-Bromo-N1-ethyl-3-methylbenzene-1,2-diamine

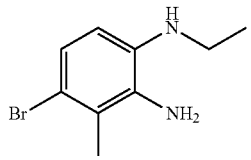

To 4-bromo-N-ethyl-3-methyl-2-nitroaniline (16 g, 61.8 mmol) in AcOH (100 mL), zinc (12.11 g, 185 mmol) was added in small portions. The reaction mixture was stirred at RT for 10 h. The reaction mixture was filtered through celite and the solid was washed with EtOAc (3×). The combined organic was concentrated. The crude product was purified by silica gel chromatography (hexane:EtOAc=10:1) to give 4.0 g (16.96%) of the title compound. LC-MS m/z 231.0 (M+H)$^+$, 1.51 (ret. time).

5-Bromo-1-ethyl-4-methyl-1H-benzo[d][1,2,3]triazole

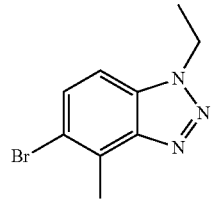

To H$_2$SO$_4$ (1.954 mL, 36.7 mmol) in water (30 mL), 4-bromo-N1-ethyl-3-methylbenzene-1,2-diamine (4 g, 10.48 mmol) was added. Then NaNO$_2$ (1.445 g, 20.95 mmol) in water (20 mL) was added by dropwise at 0° C. The reaction mixture was stirred at 0° C. for 16 h. 200 mL of water was added. The solid was filtered. The solid was dissolved in 500 mL of DCM, washed with aqueous NaCl (50 mL×2), dried with MgSO$_4$ and concentrated to give 2.4 g (76%) of the title compound. LC-MS m/z 242.0 (M+H)$^+$, 1.80 (ret. time).

(E)-Ethyl 3-(1-ethyl-4-methyl-1H-benzo[d][1,2,3]triazol-5-yl)acrylate

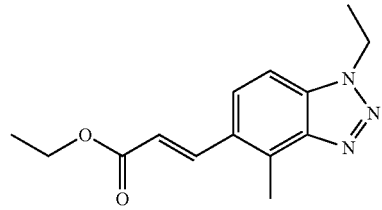 [SMILES: CCOC(=O)/C=C/c1ccc2c(nnn2CC)c1C]

To a solution of 5-bromo-1-ethyl-4-methyl-1H-benzo[d][1,2,3]triazole (2.4 g, 7.00 mmol) in DMF (100 mL), tri-o-tolylphosphine (0.426 g, 1.399 mmol), ethyl acrylate (1.401 g, 13.99 mmol) and DIPEA (3.67 mL, 20.99 mmol) were added. Then Pd(OAc)$_2$ (0.157 g, 0.700 mmol) was added. The reaction mixture was stirred at 100° C. for 12 h. The reaction mixture was poured into water (30 mL) and extracted with EtOAc (3×30 mL). The combined organic layers was dried and concentrated. The crude product was purified by silica gel chromatography (hexane:EtOAc=4:1) to give 1.75 g (87%) of the title compound. LC-MS m/z 260.1 (M+H)$^+$, 1.75 (ret. time).

Ethyl 3-(1-ethyl-4-methyl-1H-benzo[d][1,2,3]triazol-5-yl)-3-(3-(hydroxymethyl)-4-methylphenyl)propanoate

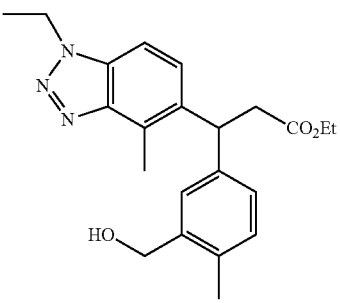 [SMILES: CCOC(=O)CC(c1ccc(C)c(CO)c1)c1ccc2c(nnn2CC)c1C]

To the solution of (E)-ethyl 3-(1-ethyl-4-methyl-1H-benzo[d][1,2,3]triazol-5-yl)acrylate (1 g, 3.86 mmol) in 1,4-dioxane (30 mL) and water (10 mL) was added (3-(hydroxymethyl)-4-methylphenyl)boronic acid (1.280 g, 7.71 mmol), Et$_3$N (1.613 mL, 11.57 mmol) and then [RhCl(cod)]$_2$ (0.095 g, 0.193 mmol). The resulting reaction mixture was stirred at 90° C. for 2 h. The reaction mixture was extracted with EtOAc (3×30 mL). The combined organic layer was dried over MgSO$_4$, filtered, concentrated under reduced pressure, purified by silica gel chromatography to afford the desired product ethyl 3-(1-ethyl-4-methyl-1H-benzo[d][1,2,3]triazol-5-yl)-3-(3-(hydroxymethyl)-4-methylphenyl)propanoate (1.3764 g, 3.61 mmol, 94% yield). LC-MS m/z 382 (M+H)$^+$, 0.96 (ret. time).

3-(3-((4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic acid

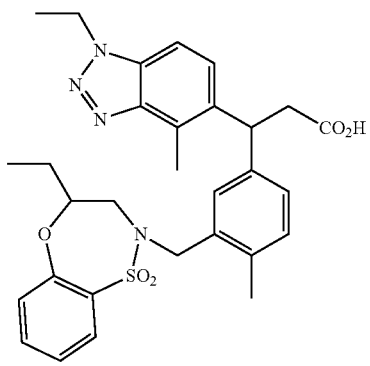 [SMILES: CCC1CN(Cc2cc(C(CC(=O)O)c3ccc4c(nnn4CC)c3C)ccc2C)S(=O)(=O)c2ccccc2O1]

To the solution of ethyl 3-(1-ethyl-4-methyl-1H-benzo[d][1,2,3]triazol-5-yl)-3-(3-(hydroxymethyl)-4-methylphenyl)propanoate (50 mg, 0.131 mmol) in CH$_3$CN (2 mL) was added 4-ethyl-3,4-dihydro-2H-benzo[b][1,4,5]oxathiazepine 1,1-dioxide (44.7 mg, 0.197 mmol), PS—PPh$_3$ (164 mg, 0.262 mmol) and then DIAD (0.051 mL, 0.262 mmol). The resulting reaction mixture was stirred at RT for 1 h. The reaction mixture was then filtered, concentrated under reduced pressure, redissolved in THF (2.000 mL). To this solution was added PS—PPh$_3$ (164 mg, 0.262 mmol), DIAD (0.051 mL, 0.262 mmol). The resulting reaction mixture was stirred at RT for 35 min. The reaction mixture was filtered, evaporated down over glass-col evaporator, redissolved in MeOH (2.000 mL). To the solution was added NaOH (2 N) (0.328 mL, 0.655 mmol). The resulting reaction mixture was heated with microwave irradiation at 80° C. for 30 min, heated again with microwave at 80° C. for 30 min. To the reaction mixture was added more H$_2$O (0.1 mL) then heated with microwave irradiation at 80° C. for 30 min. To the reaction mixture was added more NaOH (1 N) (0.262 mL, 0.262 mmol) and then heated with microwave irradiation at 80° C. for 30 min. The reaction mixture was acidified with HCl (3 N) to pH ~5, concentrated under reduced pressure, purified by reverse phase HPLC to afford the desired product 3-(3-((4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic acid (49.5 mg, 0.088 mmol, 67.1% yield). LC-MS m/z 563 (M+H)$^+$, 1.08 (ret. time).

Example 36

3-(1-ethyl-4-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

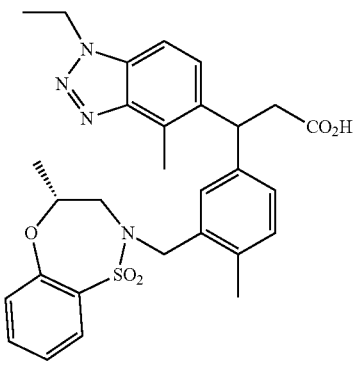 [SMILES: CCn1nnc2c(C)c(C(CC(=O)O)c3ccc(C)c(CN4C[C@@H](C)Oc5ccccc5S4(=O)=O)c3)ccc21]

To the solution of methyl 3-(1-ethyl-4-methyl-1H-benzo[d][1,2,3]triazol-5-yl)-3-(3-(hydroxymethyl)-4-methylphenyl)propanoate (50 mg, 0.136 mmol) in THF (2 mL) was added (R)-4-methyl-3,4-dihydro-2H-benzo[b][1,4,5]oxathiazepine 1,1-dioxide (43.5 mg, 0.204 mmol), PS—PPh$_3$ (170 mg, 0.272 mmol) and DIAD (0.053 mL, 0.272 mmol). The resulting reaction mixture was stirred at RT for 30 min. The reaction mixture was filtered and the filtrate was concentrated to afford desired crude intermediate methyl 3-(1-ethyl-4-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate. To this intermediate was added MeOH (2 mL) then NaOH (2 N) (0.340 mL, 0.680 mmol). The resulting reaction mixture was heated with microwave irradiation at 80° C. for 20 min. The reaction mixture was acidified with HCl (1 N) to pH ~3, concentrated under reduced pressure, purified by reverse phase HPLC to afford the desired product 3-(1-ethyl-4-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid (37.3 mg, 0.068 mmol, 50.0% yield). LC-MS m/z 549 (M+H)$^+$, 1.04 (ret. time).

Example 37

3-(1-ethyl-4-methyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid

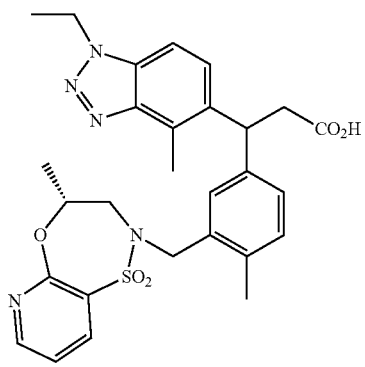 [SMILES: CCn1nnc2c(C)c(C(CC(=O)O)c3ccc(C)c(CN4C[C@@H](C)Oc5ncccc5S4(=O)=O)c3)ccc21]

To the solution of 1) methyl 3-(1-ethyl-4-methyl-1H-benzo[d][1,2,3]triazol-5-yl)-3-(3-(hydroxymethyl)-4-methylphenyl)propanoate (50 mg, 0.136 mmol) in THF (2 mL) was added (R)-4-methyl-3,4-dihydro-2H-pyrido[2,3-b][1,4,5]oxathiazepine 1,1-dioxide (43.7 mg, 0.204 mmol), PS—PPh$_3$ (170 mg, 0.272 mmol) and DIAD (0.053 mL, 0.272 mmol). The resulting reaction mixture was stirred at RT for 30 min. The reaction mixture was filtered and the filtrate was evaporated down over glass-col evaporator to afford desired crude intermediate methyl 3-(1-ethyl-4-methyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoate. To this intermediate was added MeOH (2 mL) then NaOH (2 N) (0.340 mL, 0.680 mmol). The resulting reaction mixture was heated with microwave irradiation at 80° C. for 20 min. The reaction mixture was acidified with HCl (1 N) to pH ~3, concentrated under reduced pressure, purified by reverse phase HPLC to afford the desired product 3-(1-ethyl-4-methyl-1H-benzo[d][1,2,3]triazol-5-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid (34.2 mg, 0.062 mmol, 45.7% yield). LC-MS m/z 550 (M+H)$^+$, 0.95 (ret. time).

Example 38

3-(3-((4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid

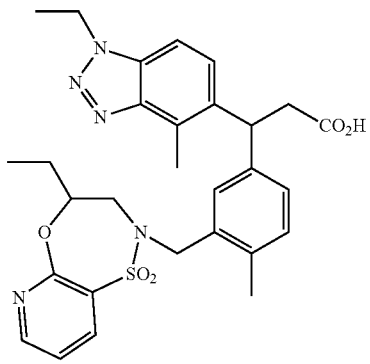 [SMILES: CCC1CN(Cc2cc(C(CC(=O)O)c3ccc4c(nnn4CC)c3C)ccc2C)S(=O)(=O)c2cccnc2O1]

To the solution of ethyl 3-(1-ethyl-4-methyl-1H-benzo[d][1,2,3]triazol-5-yl)-3-(3-(hydroxymethyl)-4-methylphenyl)propanoate (50 mg, 0.131 mmol) in THF (2 mL) was added 4-ethyl-3,4-dihydro-2H-pyrido[2,3-b][1,4,5]oxathiazepine 1,1-dioxide (44.9 mg, 0.197 mmol), PS—PPh$_3$ (164 mg, 0.262 mmol) and then DIAD (0.051 mL, 0.262 mmol). The resulting reaction mixture was stirred at RT for 30 min. The reaction mixture was filtered, evaporated down over glass-col evaporator, redissolved in MeOH (2.000 mL). To the solution was added NaOH (2 N) (0.328 mL, 0.655 mmol). The resulting reaction mixture was heated with microwave irradiation at 80° C. for 20 min. The reaction mixture was acidified with HCl (3 N) to pH ~5, concentrated under reduced pressure, purified by reverse phase HPLC to afford the desired product 3-(3-((4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (32.9 mg, 0.058 mmol, 44.5% yield). LC-MS m/z 564 (M+H)$^+$, 0.97 (ret. time).

Example 39

3-(3-((5-ethyl-1,1-dioxido-4,5-dihydropyrido[2,3-f][1,2,5]thiadiazepin-2(3H)-yl)methyl)-4-methylphenyl)-3-(1-ethyl-4-methyl-1H-benzo[d][1,2,3]triazol-5-yl)propanoic acid

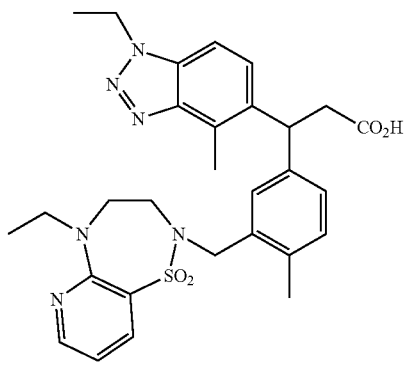 [SMILES: CCN1CCN(Cc2cc(C(CC(=O)O)c3ccc4c(nnn4CC)c3C)ccc2C)S(=O)(=O)c2cccnc21]

To the solution of ethyl 3-(1-ethyl-4-methyl-1H-benzo[d][1,2,3]triazol-5-yl)-3-(3-(hydroxymethyl)-4-methylphenyl)propanoate (50 mg, 0.131 mmol) in THF (2 mL) was added 5-ethyl-2,3,4,5-tetrahydropyrido[2,3-f][1,2,5]thiadiazepine 1,1-dioxide (44.7 mg, 0.197 mmol), PS—PPh$_3$ (164 mg, 0.262 mmol) and then DIAD (0.051 mL, 0.262 mmol). The resulting reaction mixture was stirred at RT for 1 h. The reaction mixture was filtered, concentrated, and re-dissolved in MeOH (2.000 mL). To the solution was added NaOH (2 N) (0.328 mL, 0.655 mmol). The resulting reaction mixture was heated with microwave irradiation at 80° C. for 20 min. The reaction mixture was acidified with HCl (3 N) to pH ~5, concentrated under reduced pressure, purified by reverse phase HPLC to afford the desired product 3-(3-((5-ethyl-1,1-dioxido-4,5-dihydropyrido[2,3-f][1,2,5]thiadiazepin-2(3H)-yl)methyl)-4-methylphenyl)-3-(1-ethyl-4-methyl-1H-benzo[d][1,2,3]triazol-5-yl)propanoic acid (41.5 mg, 0.074 mmol, 56.3% yield). LC-MS m/z 563 (M+H)$^+$, 1.04 (ret. time).

Example 40

3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid

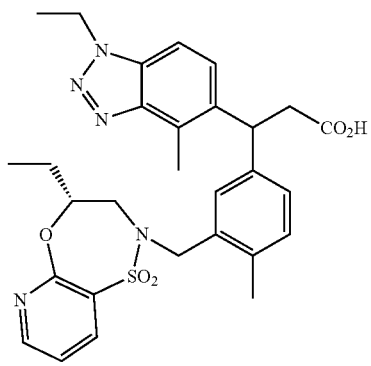 [SMILES: CC[C@@H]1CN(Cc2cc(C(CC(=O)O)c3ccc4c(nnn4CC)c3C)ccc2C)S(=O)(=O)c2cccnc2O1]

(R)-1-aminobutan-2-ol

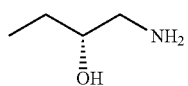

To the solution of NH₄OH (~28% solution in H₂O) (36.3 mL, 261 mmol) was added (R)-2-ethyloxirane (2.246 mL, 26.1 mmol). The resulting reaction mixture was stirred at RT for 18 h. The reaction mixture was concentrated under reduced pressure to afford the desired product (R)-1-aminobutan-2-ol (2.4880 g, 19.54 mmol, 74.9% yield). ¹H NMR (400 MHz, CHLOROFORM-d) δ ppm 0.97 (t, J=7.53 Hz, 3H) 1.42-1.53 (m, 2H) 1.71 (br. s., 3H) 2.47-2.59 (m, 1H) 2.85 (dd, J=12.80, 3.26 Hz, 1H) 3.39-3.49 (m, 1H).

(R)-4-ethyl-3,4-dihydro-2H-pyrido[2,3-b][1,4,5]oxathiazepine 1,1-dioxide

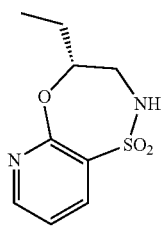

To the solution of (R)-1-amino-2-butanol (468 mg, 5.25 mmol) in THF (10 mL) and water (2.5 mL) was added K₂CO₃ (691 mg, 5.00 mmol) then 2-chloropyridine-3-sulfonyl chloride (1060 mg, 5 mmol). The resulting reaction mixture was stirred at RT for 5 h. The reaction mixture was diluted with H₂O (10 mL), extracted with EtOAc (20+2×10 mL). The combined organic layer was washed with brine (15 mL), dried over MgSO₄, filtered, concentrated under reduced pressure, to afford desired intermediate 2-chloro-N-(2-hydroxybutyl)pyridine-3-sulfonamide. This intermediate was dissolved in DMSO (20 mL) and was added KOtBu (1683 mg, 15.00 mmol). The resulting reaction was stirred at 80° C. for 1 h. The reaction mixture was diluted with H₂O (20 mL), then added HCl (10 mL, 1 N), extracted with EtOAc (50+2×25 mL). The combined organic layer was washed with brine (250 mL), dried over MgSO₄, filtered, concentrated under reduced pressure, purified by silica gel chromatography to afford the desired product (R)-4-ethyl-3,4-dihydro-2H-pyrido[2,3-b][1,4,5]oxathiazepine 1,1-dioxide (443.0 mg, 1.941 mmol, 38.8% yield). LC-MS m/z 229 (M+H)⁺, 0.58 (ret. time).

3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid

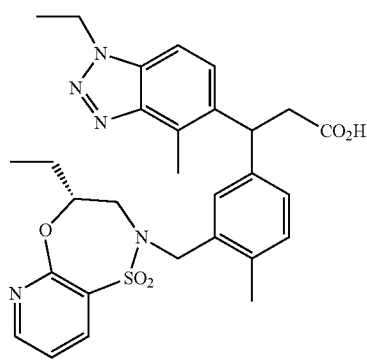 [SMILES: CC[C@@H]1CN(Cc2cc(C(CC(=O)O)c3ccc4c(nnn4CC)c3C)ccc2C)S(=O)(=O)c2cccnc2O1]

To the solution of ethyl 3-(1-ethyl-4-methyl-1H-benzo[d][1,2,3]triazol-5-yl)-3-(3-(hydroxymethyl)-4-methylphenyl)propanoate (50 mg, 0.131 mmol) in THF (2 mL) was added (R)-4-ethyl-3,4-dihydro-2H-pyrido[2,3-b][1,4,5]oxathiazepine 1,1-dioxide (44.9 mg, 0.197 mmol), PS—PPh₃ (164 mg, 0.262 mmol) and then DIAD (0.051 mL, 0.262 mmol). The resulting reaction mixture was stirred at RT for 1 h. The reaction mixture was filtered, evaporated down over glasscol evaporator, redissolved in MeOH (2.000 mL). To the solution was added NaOH (2 N) (0.328 mL, 0.655 mmol). The resulting reaction mixture was heated with microwave irradiation at 80° C. for 20 min. The reaction mixture was acidified with HCl (3 N) to pH ~5, concentrated under reduced pressure, purified by reverse phase HPLC to afford the desired product 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (29.4 mg, 0.052 mmol, 39.8% yield). LC-MS m/z 564 (M+H)⁺, 0.98 (ret. time).

Example 41

3-(1,4-dimethyl-1H-benzo[d][1,2,3]triazol-5-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic acid

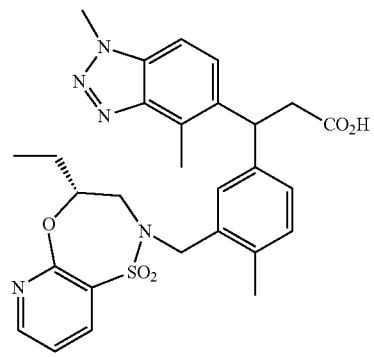 [SMILES: CC[C@@H]1CN(Cc2cc(C(CC(=O)O)c3ccc4c(nnn4C)c3C)ccc2C)S(=O)(=O)c2cccnc2O1]

To the solution of ethyl 3-(1,4-dimethyl-1H-benzo[d][1,2,3]triazol-5-yl)-3-(3-(hydroxymethyl)-4-methylphenyl)propanoate (50 mg, 0.136 mmol) in THF (2 mL) was added (R)-4-ethyl-3,4-dihydro-2H-pyrido[2,3-b][1,4,5]oxathiazepine 1,1-dioxide (46.6 mg, 0.204 mmol), PS—PPh₃ (170 mg, 0.272 mmol) and then DIAD (0.053 mL, 0.272 mmol). The resulting reaction mixture was stirred at RT for 1 h. The reaction mixture was filtered, concentrated, and re-dissolved in MeOH (2.000 mL). To the solution was added NaOH (2 N) (0.340 mL, 0.680 mmol). The resulting reaction mixture was heated with microwave irradiation at 80° C. for 20 min The reaction mixture was acidified with HCl (3 N) to pH ~5, concentrated under reduced pressure, purified by reverse phase HPLC to afford the desired product 3-(1,4-dimethyl-1H-benzo[d][1,2,3]triazol-5-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic acid (30.8 mg, 0.056 mmol, 41.2% yield). LC-MS m/z 550 (M+H)⁺, 0.95 (ret. time).

Example 42

3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic acid

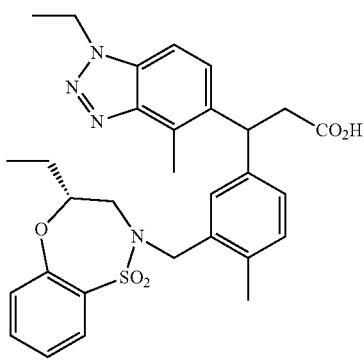 [SMILES: CC[C@@H]1CN(Cc2cc(C(CC(=O)O)c3ccc4c(nnn4CC)c3C)ccc2C)S(=O)(=O)c2ccccc2O1]

(R)-4-ethyl-3,4-dihydro-2H-benzo[b][1,4,5]oxathiazepine 1,1-dioxide

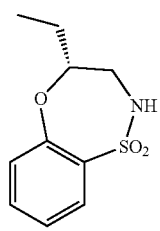

To the solution of (R)-1-amino-2-butanol (579 mg, 6.50 mmol) in THF (10 mL) and water (2.5 mL) was added $K_2CO_3$ (691 mg, 5.00 mmol) then 2-fluorobenzene-1-sulfonyl chloride (0.662 mL, 5 mmol). The resulting reaction mixture was stirred at RT for 80 min. To the reaction mixture was added more (R)-1-amino-2-butanol (134 mg, 1.500 mmol) then stirred at RT for 66 h. The reaction mixture was diluted with $H_2O$ (10 mL), extracted with EtOAc (20+2×10 mL). The combined organic layer was washed with brine (15 mL), dried over $MgSO_4$, filtered, concentrated under reduced pressure, to afford desired intermediate 2-fluoro-N-(2-hydroxybutyl)benzenesulfonamide. This intermediate was dissolved in DMSO (20 mL) then was added KOtBu (1683 mg, 15.00 mmol). The resulting reaction was stirred at 80° C. for 1 h. The reaction mixture was diluted with $H_2O$ (20 mL) then added HCl (10 mL, 1 N), extracted with EtOAc (50+2×25 mL). The combined organic layer was washed with brine (250 mL), dried over $MgSO_4$, filtered, concentrated under reduced pressure, purified by silica gel chromatography to afford the desired product (R)-4-ethyl-3,4-dihydro-2H-benzo[b][1,4,5]oxathiazepine 1,1-dioxide (822.8 mg, 3.62 mmol, 72.4% yield). LC-MS m/z 228 $(M+H)^+$, 0.74 (ret. time).

3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic acid

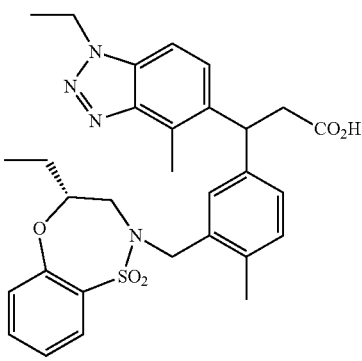 [SMILES: CC[C@@H]1CN(Cc2cc(C(CC(=O)O)c3ccc4c(nnn4CC)c3C)ccc2C)S(=O)(=O)c2ccccc2O1]

To the solution of ethyl 3-(1-ethyl-4-methyl-1H-benzo[d][1,2,3]triazol-5-yl)-3-(3-(hydroxymethyl)-4-methylphenyl)propanoate (50 mg, 0.131 mmol) in THF (2 mL) was added (R)-4-ethyl-3,4-dihydro-2H-benzo[b][1,4,5]oxathiazepine 1,1-dioxide (44.7 mg, 0.197 mmol), PS—$PPh_3$ (164 mg, 0.262 mmol) and then DIAD (0.051 mL, 0.262 mmol). The resulting reaction mixture was stirred at RT for 40 min. The reaction mixture was filtered, evaporated down over glasscol evaporator, redissolved in MeOH (2.000 mL). To the solution was added NaOH (2 N) (0.328 mL, 0.655 mmol). The resulting reaction mixture was heated with microwave irradiation at 80° C. for 20 min. The reaction mixture was acidified with HCl (3 N) to pH ~5, concentrated under reduced pressure, purified by reverse phase HPLC to afford the desired product 3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic acid (42.3 mg, 0.075 mmol, 57.4% yield). LC-MS m/z 563 $(M+H)^+$, 1.09 (ret. time).

Example 43

3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid

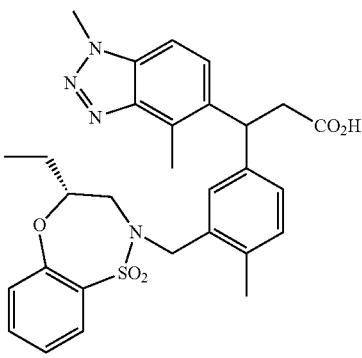 [SMILES: CC[C@@H]1CN(Cc2cc(C(CC(=O)O)c3ccc4c(nnn4C)c3C)ccc2C)S(=O)(=O)c2ccccc2O1]

To the solution of ethyl 3-(1,4-dimethyl-1H-benzo[d][1,2,3]triazol-5-yl)-3-(3-(hydroxymethyl)-4-methylphenyl)propanoate (50 mg, 0.136 mmol) in THF (2 mL) was added (R)-4-ethyl-3,4-dihydro-2H-benzo[b][1,4,5]oxathiazepine 1,1-dioxide (46.4 mg, 0.204 mmol), PS—PPh$_3$ (170 mg, 0.272 mmol) and then DIAD (0.053 mL, 0.272 mmol). The resulting reaction mixture was stirred at RT for 30 min. The reaction mixture was filtered, evaporated down over glasscol evaporator, redissolved in MeOH (2.000 mL). To the solution was added NaOH (2 N) (0.340 mL, 0.680 mmol). The resulting reaction mixture was heated with microwave irradiation at 80° C. for 20 min. The reaction mixture was acidified with HCl (3 N) to pH ~5, concentrated under reduced pressure, purified by reverse phase HPLC to afford the desired product 3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid (30.6 mg, 0.056 mmol, 41.0% yield). LC-MS m/z 549 (M+H)$^+$, 1.05 (ret. time).

Example 44

3-(3-(((R)-4-ethyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid

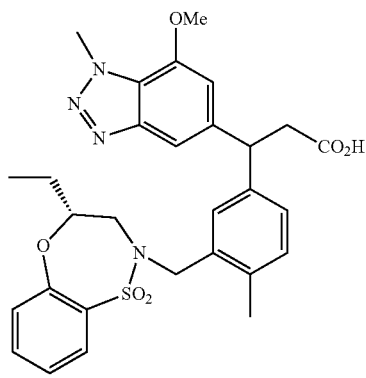 [SMILES: CC[C@@H]1CN(Cc2cc(C(CC(=O)O)c3cc(OC)c4c(c3)nnn4C)ccc2C)S(=O)(=O)c2ccccc2O1]

To the solution of ethyl 3-(3-(hydroxymethyl)-4-methylphenyl)-3-(7-methoxy-1-methyl-1H-benzo[d][1,2,3]triazol-5-yl)propanoate (50 mg, 0.130 mmol) in THF (2 mL) was added (R)-4-ethyl-3,4-dihydro-2H-benzo[b][1,4,5]oxathiazepine 1,1-dioxide (44.5 mg, 0.196 mmol), PS—PPh$_3$ (163 mg, 0.261 mmol) and then DIAD (0.051 mL, 0.261 mmol). The resulting reaction mixture was stirred at RT for 30 min. The reaction mixture was filtered, concentrated, and re-dissolved in MeOH (2.000 mL). To the solution was added NaOH (2 N) (0.326 mL, 0.652 mmol). The resulting reaction mixture was heated with microwave irradiation at 80° C. for 20 min. The reaction mixture was acidified with HCl (3 N) to pH ~5, concentrated under reduced pressure, purified by reverse phase HPLC to afford the desired product 3-(3-(((R)-4-ethyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid (35.4 mg, 0.063 mmol, 48.1% yield). LC-MS m/z 565 (M+H)$^+$, 1.07 (ret. time).

Example 45

3-(3-(((R)-4-ethyl-1,1-dioxido-3,4-dihydro-2H-pyrido[2,3-b][1,4,5]oxathiazepin-2-yl)methyl)-4-methylphenyl)-3-(7-methoxy-1-methyl-1H-benzo[d][1,2,3]triazol-5-yl)propanoic acid

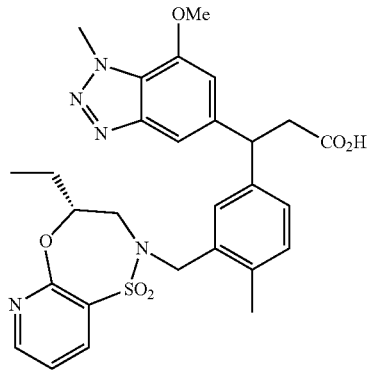 [SMILES: CC[C@@H]1CN(Cc2cc(C(CC(=O)O)c3cc(OC)c4c(c3)nnn4C)ccc2C)S(=O)(=O)c2cccnc2O1]

To the solution of ethyl 3-(3-(hydroxymethyl)-4-methylphenyl)-3-(7-methoxy-1-methyl-1H-benzo[d][1,2,3]triazol-5-yl)propanoate (50 mg, 0.130 mmol) in THF (2 mL) was added (R)-4-ethyl-3,4-dihydro-2H-pyrido[2,3-b][1,4,5]oxathiazepine 1,1-dioxide (44.6 mg, 0.196 mmol), PS—PPh$_3$ (163 mg, 0.261 mmol) and then DIAD (0.051 mL, 0.261 mmol). The resulting reaction mixture was stirred at RT for 30 min. The reaction mixture was filtered, concentrated, and re-dissolved in MeOH (2.000 mL). To the solution was added NaOH (2 N) (0.326 mL, 0.652 mmol). The resulting reaction mixture was heated with microwave irradiation at 80° C. for 20 min. The reaction mixture was acidified with HCl (3 N) to pH ~5, concentrated under reduced pressure, purified by reverse phase HPLC to afford the desired product 3-(3-(((R)-4-ethyl-1,1-dioxido-3,4-dihydro-2H-pyrido[2,3-b][1,4,5]oxathiazepin-2-yl)methyl)-4-methylphenyl)-3-(7-methoxy-1-methyl-1H-benzo[d][1,2,3]triazol-5-yl)propanoic acid (23.8 mg, 0.042 mmol, 32.3% yield). LC-MS m/z 566 (M+H)$^+$, 0.97 (ret. time).

Example 46

3-(4-ethyl-3-(((R)-4-ethyl-1,1-dioxido-3,4-dihydro-2H-benzo[b][1,4,5]oxathiazepin-2-yl)methyl)phenyl)-3-(3-methoxyphenyl)propanoic acid

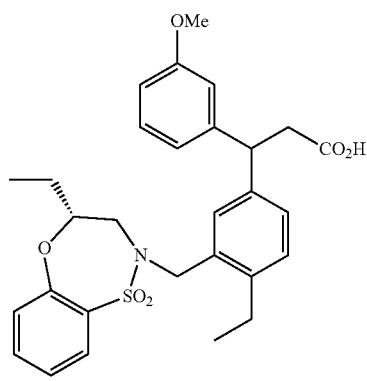 [SMILES: CCc1ccc(C(CC(=O)O)c2cccc(OC)c2)cc1CN1C[C@@H](CC)Oc2ccccc2S1(=O)=O]

2-ethyl-5-iodobenzoic acid

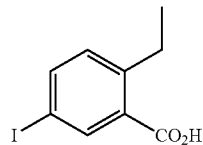

NaIO$_4$ (5.56 g, 26.0 mmol) and 12 (4.31 g, 17.00 mmol) was ground together then was added AcOH (37.2 mL, 650 mmol) and Ac$_2$O (18.87 mL, 200 mmol). To this mixture was then slowly added H$_2$SO$_4$ (conc.) (18.66 mL, 350 mmol) in ice-water bath to keep temperature below 5° C. while adding. To the above reaction mixture was added 2-ethylbenzoic acid (7.51 g, 50 mmol) (ground). The resulting reaction mixture was stirred at RT for 19 h. The reaction mixture was poured into ice-water (150/150 g) and stirred at RT for 30 min before was filtered, washed with H$_2$O (2×30 mL), to afford 2-ethyl-5-iodobenzoic acid (14.7552 g, 53.4 mmol, 107% yield). LC-MS m/z 277 (M+H)$^+$, 0.95 (ret. time).

(2-ethyl-5-iodophenyl)methanol

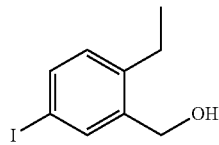

To 2-ethyl-5-iodobenzoic acid (2.76 g, 10 mmol) was added BH$_3$.THF (1.0 M in THF) (20.00 mL, 20.00 mmol) slowly. The resulting reaction mixture was stirred at RT for 130 min. The reaction mixture was then heated at 60° C. for 105 min. To the reaction mixture was added more BH$_3$.THF (1.0 M in THF) (0.430 g, 5.00 mmol) then heated at 60° C. for another 140 min. To the reaction was added more BH$_3$.THF (1.0 M in THF) (0.430 g, 5.00 mmol) then heated at 60° C. for another 16 h. The reaction mixture was quenched by adding NaHCO$_3$ (20 mL, sat. aq.) slowly then was added H$_2$O (20 mL) and extracted with EtOAc (3×50 mL). The combined organic layer was washed with brine (30 mL), dried over MgSO$_4$, filtered, concentrated under reduced pressure, purified by silica gel chromatography to afford the desired product (2-ethyl-5-iodophenyl)methanol (1.6081 g, 6.14 mmol, 61.4% yield). LC-MS m/z 245 (M−OH)$^+$, 0.92 (ret. time).

(E)-methyl 3-(4-ethyl-3-(hydroxymethyl)phenyl)acrylate

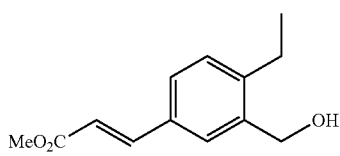 [SMILES: CCc1ccc(/C=C/C(=O)OC)cc1CO]

To the solution of (2-ethyl-5-iodophenyl)methanol (1.337 g, 5.1 mmol) in DMF (20 mL) was added methyl acrylate (2.311 mL, 25.5 mmol), DIPEA (2.227 mL, 12.75 mmol), Pd(OAc)$_2$ (0.114 g, 0.510 mmol) and tri-o-tolylphosphine (0.310 g, 1.020 mmol). The reaction mixture was then heated with microwave irradiation at 130° C. under N$_2$ atmosphere for 1 h. The reaction mixture was diluted with H$_2$O (20 mL), extracted with EtOAc (3×40 mL). The combined organic layer was washed with brine (50 mL), dried over MgSO$_4$, filtered, concentrated under reduced pressure, purified by silica gel chromatography to afford the desired product (E)-methyl 3-(4-ethyl-3-(hydroxymethyl)phenyl)acrylate (1.0220 g, 4.64 mmol, 91% yield). LC-MS m/z 221 (M+H)$^+$, 0.87 (ret. time).

(R,E)-methyl 3-(4-ethyl-3-((4-ethyl-1,1-dioxido-3,4-dihydro-2H-benzo[b][1,4,5]oxathiazepin-2-yl)methyl)phenyl)acrylate

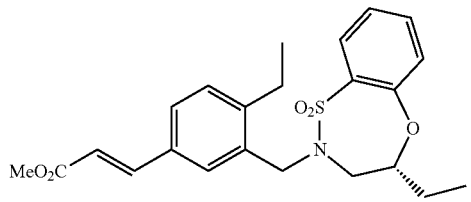 [SMILES: CCc1ccc(/C=C/C(=O)OC)cc1CN1C[C@@H](CC)Oc2ccccc2S1(=O)=O]

To the solution of (E)-methyl 3-(4-ethyl-3-(hydroxymethyl)phenyl)acrylate (0.441 g, 2 mmol) in THF (40 mL) was added (R)-4-ethyl-3,4-dihydro-2H-benzo[b][1,4,5]oxathiazepine 1,1-dioxide (0.591 g, 2.60 mmol), PS—PPh$_3$ (1.875 g, 3.00 mmol) then DIAD (0.583 mL, 3.00 mmol). The resulting reaction mixture was stirred at RT for 30 min. The reaction was filtered. The filtrate was concentrated under reduced pressure, purified by silica gel chromatography to afford the desired product (R,E)-methyl 3-(4-ethyl-3-((4-ethyl-1,1-dioxido-3,4-dihydro-2H-benzo[b][1,4,5]oxathiazepin-2-yl)methyl)phenyl)acrylate (1.0258 g, 2.388 mmol, 119% yield). LC-MS m/z 430 (M+H)$^+$, 1.25 (ret. time).

3-(4-ethyl-3-(((R)-4-ethyl-1,1-dioxido-3,4-dihydro-2H-benzo[b][1,4,5]oxathiazepin-2-yl)methyl)phenyl)-3-(3-methoxyphenyl)propanoic acid

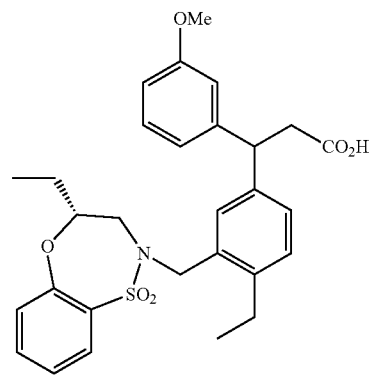 [SMILES: CCc1ccc(C(CC(=O)O)c2cccc(OC)c2)cc1CN1C[C@@H](CC)Oc2ccccc2S1(=O)=O]

To the solution of 1) (R,E)-methyl 3-(4-ethyl-3-((4-ethyl-1,1-dioxido-3,4-dihydro-2H-benzo[b][1,4,5]oxathiazepin-2-yl)methyl)phenyl)acrylate (64.4 mg, 0.15 mmol) in 1,4-dioxane (2 mL) and water (0.7 mL) was added (3-methoxyphenyl)boronic acid (34.2 mg, 0.225 mmol), Et$_3$N (0.063 mL, 0.450 mmol) and [RhCl(cod)]$_2$ (3.70 mg, 7.50 μmol). The resulting reaction mixture was stirred at 90°

C. for 90 min. The reaction mixture was extracted with EtOAc (2×3 mL). The combined organic layer was washed with brine (3 mL), dried over MgSO$_4$, filtered, concentrated to afford crude intermediate ethyl 3-(4-ethyl-3-(((R)-4-ethyl-1,1-dioxido-3,4-dihydro-2H-benzo[b][1,4,5]oxathiazepin-2-yl)methyl)phenyl)-3-(3-methoxyphenyl)propanoate. This intermediate was redissolved in MeOH (2 mL) then was added NaOH (2 N) (0.375 mL, 0.750 mmol). The resulting reaction mixture was heated with microwave irradiation at 60° C. for 20 min. The reaction mixture was acidified with HCl (3 N) to pH 4-5, concentrated under reduced pressure, purified by reverse phase HPLC to afford the desired product 3-(4-ethyl-3-(((R)-4-ethyl-1,1-dioxido-3,4-dihydro-2H-benzo[b][1,4,5]oxathiazepin-2-yl)methyl)phenyl)-3-(3-methoxyphenyl)propanoic acid (24.8 mg, 0.047 mmol, 31.6% yield). LC-MS m/z 524 (M+H)$^+$, 1.20 (ret. time).

Example 47

3-(4-chloro-3-((N,4-dimethylphenylsulfonamido) methyl)phenyl)-3-(1-methyl-1H-benzo[d][1,2,3] triazol-5-yl)propanoic acid

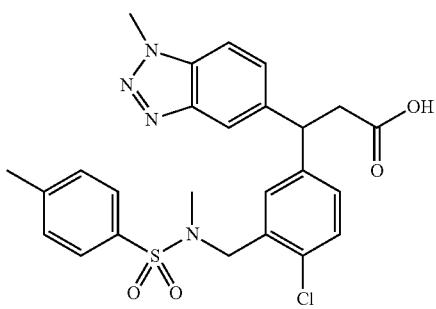 [SMILES: Cc1ccc(S(=O)(=O)N(C)Cc2cc(C(CC(=O)O)c3ccc4c(c3)nnn4C)ccc2Cl)cc1]

(E)-methyl 3-(1-methyl-1H-benzo[d][1,2,3]triazol-5-yl)acrylate

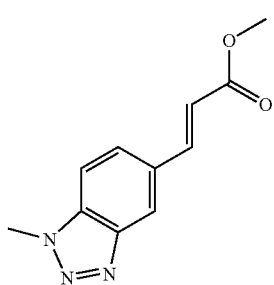

To a suspension of KOt-Bu (108 mg, 0.96 mmol) in THF (4 mL) stirred at 0° C. was added methyl 2-(dimethoxyphosphoryl)acetate (0.18 mL, 1.12 mmol) in THF (4 mL). The reaction mixture was stirred at 0° C. for 1.5 h. Then 1-methyl-1H-benzo[d][1,2,3]triazole-5-carbaldehyde (100 mg, 0.62 mmol) was added in one portion. The suspension was stirred at 0° C. for 1.5 h. The reaction was quenched via addition of saturated NH$_4$Cl solution and diluted with water. A precipitate formed which was filtered and dried to give 105 mg (78%) of the title compound. LC-MS m/z 218.0 (M+H)$^+$, 0.68 min (ret. time).

Methyl 3-(4-chloro-3-(hydroxymethyl)phenyl)-3-(1-methyl-1H-benzo[d][1,2,3]triazol-5-yl)propanoate

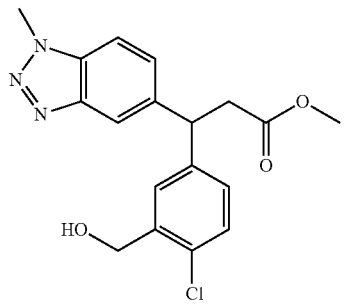 [SMILES: COC(=O)CC(c1ccc(Cl)c(CO)c1)c1ccc2c(c1)nnn2C]

To a suspension of (2-chloro-5-(4,4,5,5-tetramethyl-1,3,2-dioxaborolan-2-yl)phenyl)methanol (500 mg, 1.86 mmol), (E)-methyl 3-(1-methyl-1H-benzo[d][1,2,3]triazol-5-yl)acrylate (640 mg, 2.95 mmol) and [RhCl(cod)]$_2$ (92 mg, 0.19 mmol) in water (8 mL) and 1,4-dioxane (1.5 mL) with stirring at room temp Et$_3$N was added (0.5 mL, 3.61 mmol). The reaction mixture was stirred at 95° C. for 2 h and then at RT for 17 h. The reaction was diluted with water and EtOAc. The organic phase was washed with water and brine, dried over MgSO$_4$, then filtered. The filtrate was adsorbed onto isolute and purified by silica gel chromatography to give 98 mg (15%) of title compound. LC-MS m/z 360.0 (M+H)$^+$, 0.81 min (ret. time).

N,4-dimethylbenzenesulfonamide

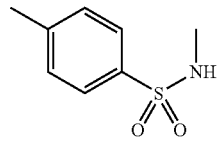

Methylamine (2.0 M in THF) (10.0 mL, 19.93 mmol) was added to a solution of 4-methylbenzene-1-sulfonyl chloride (1.9 g, 9.97 mmol) in dichloromethane (15 mL) at 0° C., during which time a white precipitate formed. The suspension was stirred for 2 h, then the white solid was filtered and the filtrate was concentrated under reduced pressure to give 2.14 g crude product as white solid. Then the crude product was dissolved in EtOAc and washed by 15% NaHCO$_3$ solution and brine. The organic layer was dried by MgSO$_4$ and filtered then concentrated under reduced pressure to give 1.82 g (99%) of title product. LC-MS m/z 185.9 (M+H)$^+$, 0.65 min (ret. time).

Methyl 3-(4-chloro-3-((N,4-dimethylphenylsulfonamido)methyl)phenyl)-3-(1-methyl-1H-benzo[d][1,2,3]triazol-5-yl)propanoate

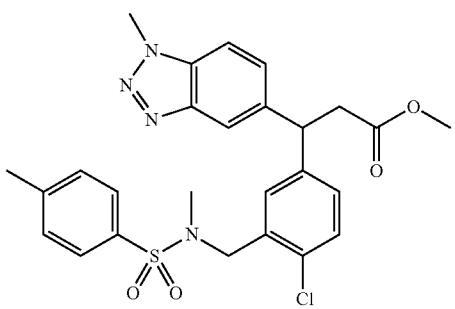

To a solution of methyl 3-(4-chloro-3-(hydroxymethyl)phenyl)-3-(1-methyl-1H-benzo[d][1,2,3]triazol-5-yl)propanoate (113 mg, 0.31 mmol), N,4-dimethylbenzenesulfonamide (87 mg, 0.47 mmol) and ADDP (238 mg, 0.94 mmol) under nitrogen in THF (5 mL) at 0° C. was added tributylphosphine (0.23 mL, 0.94 mmol). The reaction mixture was stirred at 0° C. for 40 min, during which a precipitate generated. The mixture was stirred at RT for 19 h. Most solvent was removed under reduced pressure. The residue was dissolved in EtOAc, washed with brine (2×20 mL) and dried with MgSO$_4$. The mixture was filtered and concentrated under reduced pressure to give 312 mg of crude product. The crude product was purified by flash chromatography to give 171 mg (87%) of the title compound. LC-MS m/z 527.3 (M+H)$^+$, 1.16 min (ret. time).

3-(4-chloro-3-((N,4-dimethylphenylsulfonamido)methyl)phenyl)-3-(1-methyl-1H-benzo[d][1,2,3]triazol-5-yl)propanoic acid

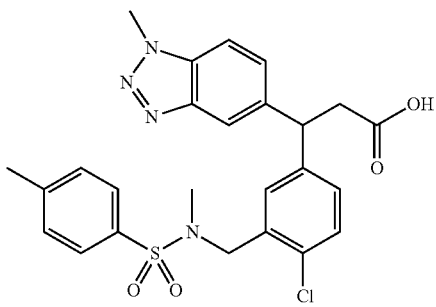 [SMILES: Cc1ccc(S(=O)(=O)N(C)Cc2cc(C(CC(=O)O)c3ccc4c(c3)nnn4C)ccc2Cl)cc1]

To a solution of methyl 3-(4-chloro-3-((N,4-dimethylphenylsulfonamido)methyl)phenyl)-3-(1-methyl-1H-benzo[d][1,2,3]triazol-5-yl)propanoate (171 mg, 0.32 mmol) in MeOH (15 mL) and THF (1 mL) stirred at RT was added a solution of LiOH (16 mL, 16.00 mmol) in water (16 mL). The solution became an suspension and then diluted with MeOH (10 mL). The reaction mixture was stirred at RT for 1 h 10 min. The pH of the reaction mixture was adjusted to 2 with 1 N HCl solution and diluted with EtOAc. The organic layer was washed by brine (2×10 mL), dried over MgSO$_4$, filtered and concentrated to give 174 mg crude product. The crude product was dissolved in DMSO (1 mL), filtered through a 0.45 μm acrodisc, and purified by reverse phase HPLC (YMC C18 S-5 μm/12 nm 50×20 mm preparatory column), eluting at 20 mL/min with a linear gradient running from 10% CH$_3$CN/H$_2$O (0.1% TFA) to 90% CH$_3$CN/H$_2$O (0.1% TFA) over 10 min. The desired fractions were concentrated under a stream of nitrogen at 50° C., giving 25 mg title compound. LC-MS m/z 513.3 (M+H)$^+$, 1.04 min (ret. time). $^1$H NMR (400 MHz, CDCl$_3$) δ ppm 7.94 (s, 1H); 7.74 (d, J=8.03 Hz, 2H); 7.43-7.49 (m, 2H); 7.34-7.40 (m, 3H); 7.26 (d, J=8.28 Hz, 1H); 7.08 (dd, J=8.28, 2.01 Hz, 1H); 4.72 (t, J=7.78 Hz, 1H); 4.29 (s, 2H); 4.28 (s, 3H) 3.08-3.23 (m, 2H); 2.63 (s, 3H); 2.47 (s, 3H).

Example 48

3-(4-chloro-3-((N,3-dimethylphenylsulfonamido)methyl)phenyl)-3-(1-methyl-1H-benzo[d][1,2,3]triazol-5-yl)propanoic acid

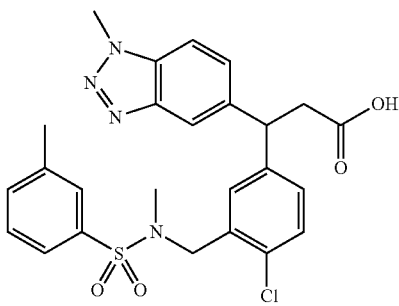 [SMILES: Cc1cccc(S(=O)(=O)N(C)Cc2cc(C(CC(=O)O)c3ccc4c(c3)nnn4C)ccc2Cl)c1]

N,3-dimethylbenzenesulfonamide

Methylamine (2.0 M in THF) (10.0 mL, 19.93 mmol) was added to a solution of 3-methylbenzene-1-sulfonyl chloride (1.45 mL, 9.97 mmol) in dichloromethane (15 mL) at 0° C., during which time white precipitate formed. The suspension was stirred for 2 h, then the white solid was filtered and the filtrate was washed by 10% NaHCO$_3$ solution and the organic layer was dried by MgSO$_4$ then concentrated under reduced pressure to give 1.63 g (89%) title compound. LC-MS m/z 185.9 (M+H)$^+$, 0.63 min (ret. time).

Methyl 3-(4-chloro-3-((N,3-dimethylphenylsulfonamido)methyl)phenyl)-3-(1-methyl-1H-benzo[d][1,2,3]triazol-5-yl)propanoate

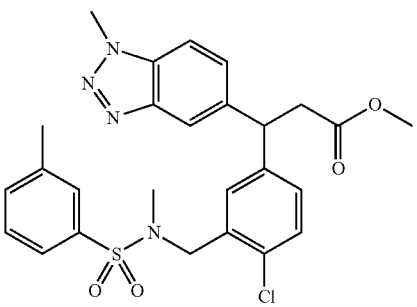 [SMILES: COC(=O)CC(c1ccc(Cl)c(CN(C)S(=O)(=O)c2cccc(C)c2)c1)c1ccc2c(c1)nnn2C]

To a solution of methyl 3-(4-chloro-3-(hydroxymethyl)phenyl)-3-(1-methyl-1H-benzo[d][1,2,3]triazol-5-yl)propanoate (101 mg, 0.28 mmol), N,3-dimethylbenzenesulfonamide (78 mg, 0.42 mmol) and ADDP (212 mg, 0.84 mmol) protected by nitrogen in THF (5 mL) stirred at 0° C. was added tributylphosphine (0.20 mL, 0.84 mmol). The reaction mixture was stirred at 0° C. for 24 min, during which a precipitate generated. The mixture was stirred at RT for another 19 h. Most solvent was removed under reduced pressure, then dissolved in EtOAc, washed with brine (2×20 mL), and dried by MgSO$_4$. The mixture was filtered, adsorbed onto isolute and purified by silica gel chromatography (Combiflash, 12 g), eluting at 30 mL/min with a gradient running from 100% hexanes to 70% EtOAc/hexanes over 30 min. Product containing fractions were combined and concentrated to give 130 mg (11%) title compound.

LC-MS m/z 527.4 (M+H)$^+$, 1.16 min (ret. time)

3-(4-chloro-3-((N,3-dimethylphenylsulfonamido)methyl)phenyl)-3-(1-methyl-1H-benzo[d][1,2,3]triazol-5-yl)propanoic acid

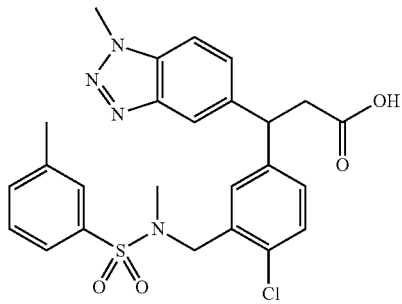 [SMILES: Cc1cccc(S(=O)(=O)N(C)Cc2cc(C(CC(=O)O)c3ccc4c(c3)nnn4C)ccc2Cl)c1]

To a solution of methyl 3-(4-chloro-3-((N,3-dimethylphenylsulfonamido)methyl)phenyl)-3-(1-methyl-1H-benzo[d][1,2,3]triazol-5-yl)propanoate (130 mg, 0.25 mmol) in MeOH (15 mL) and THF (1 mL) stirred at RT was added a solution of LiOH (16 mL, 16.00 mmol) in water (16 mL). The solution became a suspension and was diluted with MeOH (10 mL). The reaction mixture was stirred at RT for 1 h 13 min. Most of the MeOH was removed under the reduced pressure. The resulting mixture was diluted by water, extracted by EtOAc (2×20 mL). The pH of the aqueous layer was adjusted to 2 with 1N HCl solution and extracted with EtOAc (2×20 mL). The organic layers were combined, dried over MgSO$_4$, filtered and concentrated to give 21 mg crude product. The crude product was dissolved in DMSO (1 mL), filtered through a 0.45 μm acrodisc, and purified by reverse phase HPLC (YMC C18 S-5 μm/12 nm 50×20 mm preparatory column), eluting at 20 mL/min with a linear gradient running from 10% CH$_3$CN/H$_2$O (0.1% TFA) to 90% CH$_3$CN/H$_2$O (0.1% TFA) over 10 min. The desired fractions were concentrated under a stream of nitrogen at 50° C., giving 18 mg (14%) of title compound. LC-MS m/z 513.3 (M+H)$^+$, 1.05 min (ret. time). $^1$H NMR (400 MHz, CDCl$_3$-d) δ ppm 7.94 (s, 1H); 7.63-7.70 (m, 2H); 7.43-7.51 (m, 4H); 7.35-7.40 (m, 1H); 7.27 (d, J=8.28 Hz, 1H); 7.09 (d, J=8.28 Hz, 1H); 4.73 (t, J=7.78 Hz, 1H); 4.32 (s, 2H); 4.29 (s, 3H); 3.16 (t, J=7.91 Hz, 2H); 2.66 (s, 3H); 2.48 (s, 3H).

Example 49

3-(4-chloro-3-((N-methyl-2,3-dihydro-1H-indene-5-sulfonamido)methyl)phenyl)-3-(1-methyl-1H-benzo[d][1,2,3]triazol-5-yl)propanoic acid

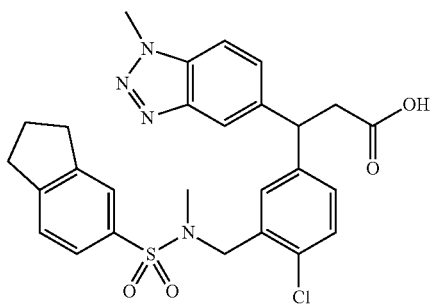 [SMILES: CN(Cc1cc(C(CC(=O)O)c2ccc3c(c2)nnn3C)ccc1Cl)S(=O)(=O)c1ccc2c(c1)CCC2]

N-methyl-2,3-dihydro-1H-indene-5-sulfonamide

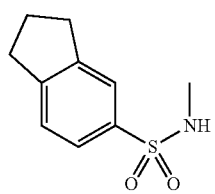

Methylamine (2.0 M in THF) (2.5 mL, 2.2 mmol) was added to a solution of 2,3-dihydro-1H-indene-5-sulfonyl chloride (500 mg, 2.31 mmol) in dichloromethane (5 mL) at 0° C., during which time white precipitate formed. The suspension was stirred for 2 h, then the white solid was filtered and the filtrate was concentrated under reduced pressure to give 535 mg crude product. The crude product was dissolved in EtOAc and washed by 15% NaHCO$_3$ solution and brine. The organic phase was dried over MgSO$_4$, filtered and concentrated under reduced pressure to give 285 mg (59%) of title compound. LC-MS m/z 212.0 (M+H)$^+$, 0.79 min (ret. time).

Methyl 3-(4-chloro-3-((N-methyl-2,3-dihydro-1H-indene-5-sulfonamido)methyl)phenyl)-3-(1-methyl-1H-benzo[d][1,2,3]triazol-5-yl)propanoate

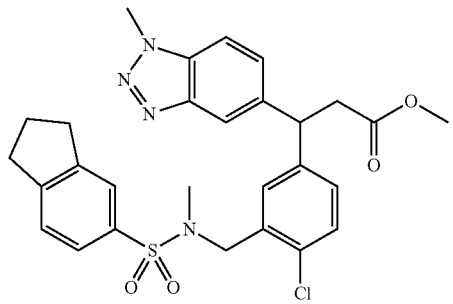 [SMILES: COC(=O)CC(c1ccc(Cl)c(CN(C)S(=O)(=O)c2ccc3c(c2)CCC3)c1)c1ccc2c(c1)nnn2C]

To a solution of methyl 3-(4-chloro-3-(hydroxymethyl)phenyl)-3-(1-methyl-1H-benzo[d][1,2,3]triazol-5-yl)propanoate (111 mg, 0.31 mmol), N-methyl-2,3-dihydro-1H-indene-5-sulfonamide (123 mg, 0.58 mmol) and ADDP (156 mg, 0.61 mmol) under nitrogen in THF (5 mL) stirred at 0° C. was added tributylphosphine (0.15 mL, 0.61 mmol). The reaction mixture was stirred at 0° C. for 40 min, during which a precipitate generated. The mixture was stirred at RT for 89 h. Most solvent was removed under reduced pressure. The residue was dissolved in EtOAc, washed with brine and dried with $MgSO_4$. The mixture was filtered and the filtrate was adsorbed onto isolute and purified by silica gel chromatography (Combiflash, 12 g), eluting at 20 mL/min with a gradient running from 100% hexane to 80% EtOAc/hexane over 35 min. Product containing fractions were combined and concentrated to give 65 mg (22%) of title compound. LC-MS m/z 553.2 $(M+H)^+$, 1.23 min (ret. time)

3-(4-chloro-3-((N-methyl-2,3-dihydro-1H-indene-5-sulfonamido)methyl)phenyl)-3-(1-methyl-1H-benzo[d][1,2,3]triazol-5-yl)propanoic acid

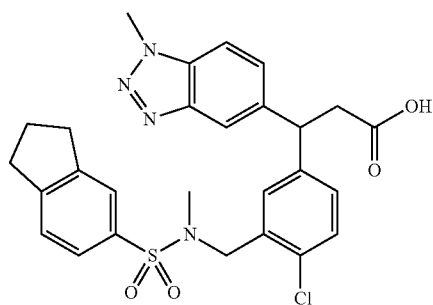 [SMILES: CN(Cc1cc(C(CC(=O)O)c2ccc3c(c2)nnn3C)ccc1Cl)S(=O)(=O)c1ccc2c(c1)CCC2]

To a solution of methyl 3-(4-chloro-3-((N-methyl-2,3-dihydro-1H-indene-5-sulfonamido)methyl)phenyl)-3-(1-methyl-1H-benzo[d][1,2,3]triazol-5-yl)propanoate (65 mg, 0.12 mmol) in MeOH (5 mL) stirred at RT was added a solution of LiOH (10 mL, 10.00 mmol). The solution became an suspension and then diluted with MeOH (5 mL). The reaction mixture was stirred at RT for 3 h. Most of the MeOH was removed under the reduced pressure. Then the solution was diluted by water, extracted by $Et_2O$ (12×10 mL) until LCMS showed that most of the byproduct was removed from the aqueous layer. The pH of the aqueous layer was adjusted to 2 with 1N HCl solution and extracted with EtOAc (2×15 mL). The organic layers were combined, dried over $MgSO_4$, filtered and concentrated to give 51 mg crude product. The crude product was dissolved in DMSO (1 mL), filtered through a 0.45 μm acrodisc, and purified by reverse phase HPLC (YMC C18 S-5 μm/12 nm 50×20 mm preparatory column), eluting at 20 mL/min with a linear gradient running from 10% $CH_3CN/H_2O$ (0.1% TFA) to 90% $CH_3CN/H_2O$ (0.1% TFA) over 10 min. The desired fractions were concentrated under a stream of nitrogen at 50° C., giving 40 mg (62%) of title compound. LC-MS m/z 539.3 $(M+H)^+$, 1.10 min (ret. time). $^1H$ NMR (400 MHz, $CDCl_3$-d) δ ppm 7.95 (s, 1H); 7.69 (s, 1H); 7.63 (d, J=7.78 Hz, 1H); 7.45-7.51 (m, 2H); 7.36-7.43 (m, 2H); 7.24-7.31 (m, 2H); 7.08 (dd, J=8.28, 1.76 Hz, 1H); 4.73 (t, J=7.78 Hz, 1H); 4.30 (br. s., 2H); 4.29 (s, 3H) 3.10-3.22 (m, 2H); 3.01 (t, J=6.78 Hz, 4H); 2.65 (s, 3H); 2.13-2.23 (m, 2H).

Example 50

3-(3-((3-acetamido-N-methylphenylsulfonamido)methyl)-4-chlorophenyl)-3-(1-methyl-1H-benzo[d][1,2,3]triazol-5-yl)propanoic acid

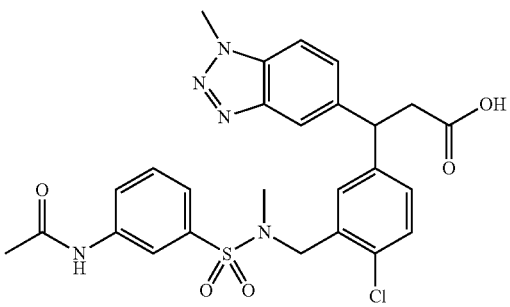 [SMILES: CC(=O)Nc1cccc(S(=O)(=O)N(C)Cc2cc(C(CC(=O)O)c3ccc4c(c3)nnn4C)ccc2Cl)c1]

N-(3-(N-methylsulfamoyl)phenyl)acetamide

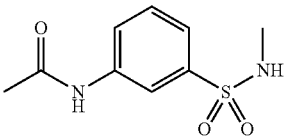

Methylamine (2.0 M in THF) (2.5 mL, 5 mmol) was added to a solution of 3-acetamidobenzene-1-sulfonyl chloride (500 mg, 2.14 mmol) in dichloromethane (5 mL) at 0° C. The solution was stirred for 2 h. All solvent was removed under reduced pressure and the residue was dissolved in EtOAc. The solution was washed by water, dried via $MgSO_4$, filtered and the filtrate was concentrated under reduced pressure to give 256 mg (52%) of title compound. LC-MS m/z 229.0 $(M+H)^+$, 0.46 min (ret. time).

Methyl 3-(3-((3-acetamido-N-methylphenylsulfonamido)methyl)-4-chlorophenyl)-3-(1-methyl-1H-benzo[d][1,2,3]triazol-5-yl)propanoate

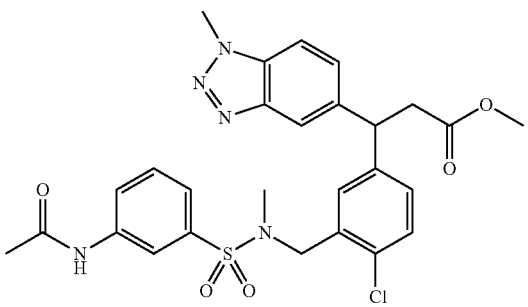 [SMILES: COC(=O)CC(c1ccc(Cl)c(CN(C)S(=O)(=O)c2cccc(NC(C)=O)c2)c1)c1ccc2c(c1)nnn2C]

To a solution of methyl 3-(4-chloro-3-(hydroxymethyl)phenyl)-3-(1-methyl-1H-benzo[d][1,2,3]triazol-5-yl)propanoate (285 mg, 0.79 mmol), N-(3-(N-methylsulfamoyl)

phenyl)acetamide (256 mg, 1.12 mmol) and ADDP (400 mg, 1.58 mmol) under nitrogen in THF (7 mL) stirred at 0° C. was added tributylphosphine (0.4 mL, 1.62 mmol). The reaction mixture was stirred at 0° C. for 40 min, during which a precipitate generated. The mixture was stirred at RT for another 21 h. Most solvent was removed under reduced pressure, the residue was dissolved in EtOAc, washed by brine (2×20 mL), and dried with MgSO$_4$. The mixture was filtered and the filtrated was adsorbed onto isolute and then purified by silica gel chromatography (Combiflash, 12 g), eluting at 20 mL/min with a gradient running from 100% hexane to 70% EtOAc/hexane over 35 min. Product containing fractions were combined and concentrated to give 592 mg (63%) of title compound. LC-MS m/z 570.1 (M+H)$^+$, 0.96 min (ret. time).

3-(3-((3-acetamido-N-methylphenylsulfonamido)methyl)-4-chlorophenyl)-3-(1-methyl-1H-benzo[d][1,2,3]triazol-5-yl)propanoic acid

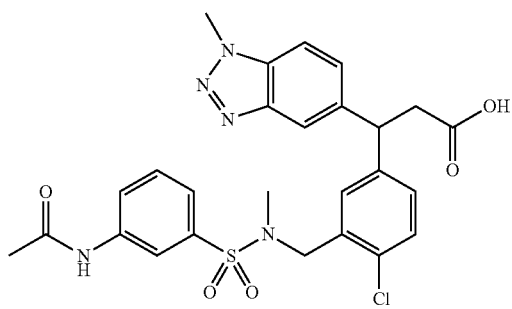 [SMILES: CC(=O)Nc1cccc(S(=O)(=O)N(C)Cc2cc(C(CC(=O)O)c3ccc4c(c3)nnn4C)ccc2Cl)c1]

To a solution of methyl 3-(3-((3-acetamido-N-methylphenylsulfonamido)methyl)-4-chlorophenyl)-3-(1-methyl-1H-benzo[d][1,2,3]triazol-5-yl)propanoate (592 mg, 0.50 mmol) in MeOH (15 mL) stirred at RT was added a solution of LiOH (20 mL, 20.00 mmol). The solution became a suspension and was diluted with MeOH (10 mL). The reaction mixture was stirred at RT for 1 h. Most of the MeOH was removed under the reduced pressure. Then the mixture was diluted with water, extracted by Et$_2$O (12×15 mL) until most of the by-product (m/z 219 and 235) was removed from the aqueous layer as determined by LCMS. The pH of aqueous layer was adjusted to 2 with 1N HCl solution and extracted with EtOAc (2×20 mL). The organic layers were combined, dried over MgSO$_4$, filtered and concentrated to give 172 mg crude product. The crude product was dissolved in DMSO (1 mL), filtered through a 0.45 µm acrodisc, and purified by reverse phase HPLC (YMC C18 S-5 µm/12 nm 50×20 mm preparatory column), eluting at 20 mL/min with a linear gradient running from 10% CH$_3$CN/H$_2$O (0.1% TFA) to 90% CH$_3$CN/H$_2$O (0.1% TFA) over 10 min. The desired fractions were concentrated under a stream of nitrogen at 50° C., giving 136 mg (49%) of the title compound. LC-MS m/z 556.5 (M+H)$^+$, 0.89 min (ret. time). $^1$H NMR (400 MHz, CDCl$_3$-d) δ ppm 8.34 (s, 1H); 8.04 (d, J=8.28 Hz, 1H); 7.87 (s, 2H); 7.44-7.62 (m, 3H); 7.34 (d, J=8.53 Hz, 1H); 7.25 (d, J=8.28 Hz, 1H); 7.07 (d, J=8.03 Hz, 1H); 4.68 (t, J=7.78 Hz, 1H); 4.39 (s, 2H); 4.30 (s, 3H); 3.06-3.19 (m, 2H); 2.71 (s, 3H); 2.24 (s, 3H).

Example 51

3-(4-chloro-3-((N-methylcyclohexanesulfonamido)methyl)phenyl)-3-(1-methyl-1H-benzo[d][1,2,3]triazol-5-yl)propanoic acid

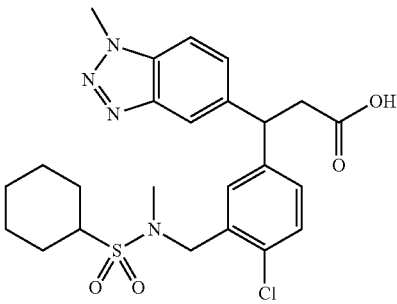 [SMILES: CN(Cc1cc(C(CC(=O)O)c2ccc3c(c2)nnn3C)ccc1Cl)S(=O)(=O)C1CCCCC1]

N-methylcyclohexanesulfonamide

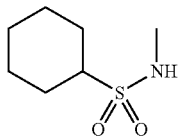

Methylamine (2.0 M in THF) (2.5 mL, 5 mmol) was added to a solution of cyclohexanesulfonyl chloride (0.40 mL, 2.46 mmol) in dichloromethane (5 mL) at 0° C. The solution was stirred for 20 h. The mixture was diluted by DCM and washed by 10% NaHCO$_3$ solution and brine, the organic layer was dried via MgSO$_4$, filtered and the filtrate was concentrated under reduced pressure to give 380 mg (87%) of title compound. LC-MS m/z 177.9 (M+H)$^+$, 0.57 min (ret. time).

Methyl 3-(4-chloro-3-((N-methylcyclohexanesulfonamido)methyl)phenyl)-3-(1-methyl-1H-benzo[d][1,2,3]triazol-5-yl)propanoate

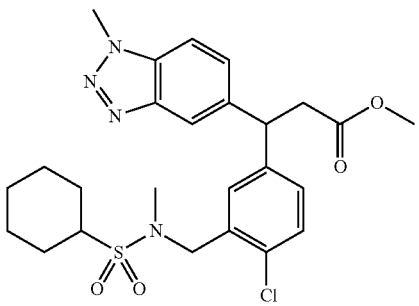 [SMILES: COC(=O)CC(c1ccc(Cl)c(CN(C)S(=O)(=O)C2CCCCC2)c1)c1ccc2c(c1)nnn2C]

To a solution of methyl 3-(4-chloro-3-(hydroxymethyl)phenyl)-3-(1-methyl-1H-benzo[d][1,2,3]triazol-5-yl)propanoate (137 mg, 0.38 mmol), N-methylcyclohexanesulfonamide (183 mg, 1.03 mmol) and ADDP (207 mg, 0.82 mmol) under nitrogen in THF (5 mL) stirred at 0° C. was added tributylphosphine (0.2 mL, 0.81 mmol). The reaction mixture was stirred at 0° C. for 40 min, during which a precipitate generated. The mixture was stirred at RT for 66 h. Most solvent was removed under reduced pressure, the residue was dissolved in EtOAc, washed with brine and dried with MgSO$_4$. The mixture was filtered and the filtrate was adsorbed onto isolute and purified by silica gel chromatography (Combiflash, 12 g), eluting at 20 mL/min with a gradient running from 100% hexane to 80% EtOAc/hexane over 35 min. Product containing fractions were combined and concentrated to give 82 mg (42%) of title compound. LC-MS m/z 519.1 (M+H)$^+$, 1.16 min (ret. time).

131

3-(4-chloro-3-((N-methylcyclohexanesulfonamido)methyl)phenyl)-3-(1-methyl-1H-benzo[d][1,2,3]triazol-5-yl)propanoic acid

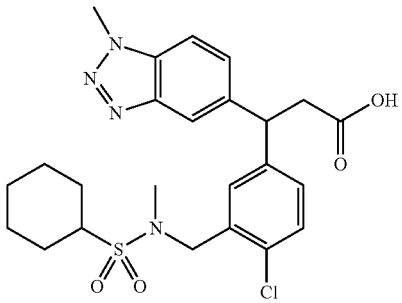 [SMILES: CN(Cc1cc(C(CC(=O)O)c2ccc3c(c2)nnn3C)ccc1Cl)S(=O)(=O)C1CCCCC1]

To a solution of methyl 3-(4-chloro-3-((N-methylcyclohexanesulfonamido)methyl)phenyl)-3-(1-methyl-1H-benzo[d][1,2,3]triazol-5-yl)propanoate (82 mg, 0.15 mmol) in MeOH (4 mL) stirred at RT was added a solution of LiOH (10 mL, 10.00 mmol). The solution became a suspension and then diluted with MeOH (6 mL). The reaction mixture was stirred at RT for 1 h 40 min. Most of the MeOH was removed under the reduced pressure. The pH of the aqueous layer was adjusted to 2 with 1N HCl solution and extracted with EtOAc (2×20 mL). The organic layers were combined, dried over MgSO₄, filtered and the filtrate was concentrated to give 93 mg crude product. The crude product was dissolved in DMSO (4 mL), filtered through a 0.45 μm acrodisc, and purified by reverse phase HPLC (YMC C18 S-5 μm/12 nm 50×20 mm preparatory column), eluting at 20 mL/min with a linear gradient running from 10% CH₃CN/H₂O (0.1% TFA) to 90% CH₃CN/H₂O (0.1% TFA) over 10 min. The desired fractions were concentrated under a stream of nitrogen at 50° C., giving 55 mg (69%) of title compound. LC-MS m/z 505.1 (M+H)⁺, 1.06 min (ret. time). ¹H NMR (400 MHz, CDCl₃-d) δ ppm 7.95 (s, 1H); 7.51 (d, J=1.76 Hz, 1H); 7.42-7.47 (m, 1H); 7.35-7.40 (m, 1H); 7.26-7.31 (m, 1H); 7.08 (dd, J=8.28, 2.01 Hz, 1H); 4.74 (t, J=7.91 Hz, 1H); 4.50 (s, 2H); 4.26 (s, 3H); 3.10-3.24 (m, 2H); 2.99 (tt, J=12.02, 3.29 Hz, 1H); 2.81 (s, 3H); 2.14 (d, J=11.80 Hz, 2H); 1.90 (d, J=11.29 Hz, 2H); 1.72 (d, J=8.28 Hz, 1H); 1.52-1.65 (m, 2H); 1.17-1.35 (m, 3H).

Example 52

3-(4-chloro-3-((N-methyl-2,3-dihydrobenzo[b][1,4]dioxine-6-sulfonamido)methyl)phenyl)-3-(1-methyl-1H-benzo[d][1,2,3]triazol-5-yl)propanoic acid

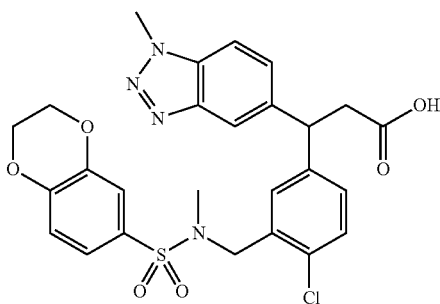 [SMILES: CN(Cc1cc(C(CC(=O)O)c2ccc3c(c2)nnn3C)ccc1Cl)S(=O)(=O)c1ccc2c(c1)OCCO2]

132

N-methyl-2,3-dihydrobenzo[b][1,4]dioxine-6-sulfonamide

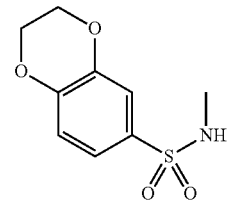

Methylamine (2.0 M in THF) (2.5 mL, 5 mmol) was added to a solution of 2,3-dihydrobenzo[b][1,4]dioxine-6-sulfonyl chloride (500 mg, 1.92 mmol) in dichloromethane (5 mL) at 0° C. The solution was stirred for 2 h. The mixture was diluted by DCM and washed by 10% NaHCO₃ solution and brine, the organic layer was dried via MgSO₄, filtered and the filtrate was concentrated under reduced pressure to give 436 mg of crude product. This was adsorbed onto isolute and purified via combiflash (12 g), eluting at 20 mL/min with a gradient running from 100% hexane to 80% EtOAc/hexane over 35 min. Product containing fractions were combined and concentrated to give 403 mg (85%) of title compound. LC-MS m/z 229.9 (M+H)⁺, 0.60 min (ret. time).

Methyl 3-(4-chloro-3-((N-methyl-2,3-dihydrobenzo[b][1,4]dioxine-6-sulfonamido)methyl)phenyl)-3-(1-methyl-1H-benzo[d][1,2,3]triazol-5-yl)propanoate

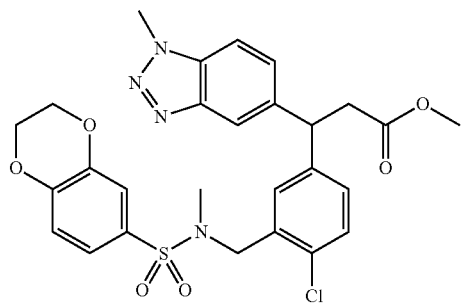 [SMILES: COC(=O)CC(c1ccc(Cl)c(CN(C)S(=O)(=O)c2ccc3c(c2)OCCO3)c1)c1ccc2c(c1)nnn2C]

To a solution of methyl 3-(4-chloro-3-(hydroxymethyl)phenyl)-3-(1-methyl-1H-benzo[d][1,2,3]triazol-5-yl)propanoate (106 mg, 0.30 mmol), N-methyl-2,3-dihydrobenzo[b][1,4]dioxine-6-sulfonamide (136 mg, 0.59 mmol) and ADDP (158 mg, 0.62 mmol) under nitrogen in THF (5 mL) stirred at 0° C. was added tributylphosphine (0.2 mL, 0.81 mmol). The reaction mixture was stirred at 0° C. for 40 min, during which a precipitate formed. The mixture was stirred at RT for 63 h. Most solvent was removed under reduced pressure, the residue was dissolved in EtOAc, washed with brine (2×15 mL) and dried with MgSO₄ and filtered. The filtrate was adsorbed onto isolute and purified by silica gel chromatography (Combiflash, 12 g), eluting at 20 mL/min with a gradient running from 100% hexane to 80% EtOAc/hexane over 40 min. Product containing fractions were combined and concentrated to give 45 mg (27%) of title compound. LC-MS m/z 571.1 (M+H)⁺, 1.11 min (ret. time).

133

3-(4-chloro-3-((N-methyl-2,3-dihydrobenzo[b][1,4]
dioxine-6-sulfonamido)methyl)phenyl)-3-(1-methyl-
1H-benzo[d][1,2,3]triazol-5-yl)propanoic acid

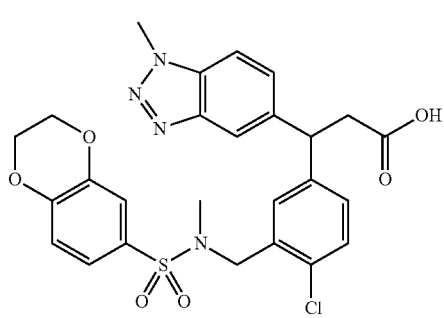 [SMILES: CN(Cc1cc(C(CC(=O)O)c2ccc3c(c2)nnn3C)ccc1Cl)S(=O)(=O)c1ccc2c(c1)OCCO2]

To a solution of methyl 3-(4-chloro-3-((N-methyl-2,3-dihydrobenzo[b][1,4]dioxine-6-sulfonamido)methyl)phenyl)-3-(1-methyl-1H-benzo[d][1,2,3]triazol-5-yl)propanoate (45 mg, 0.08 mmol) in MeOH (5 mL) stirred at room temp was added a solution of LiOH (5 mL, 5.00 mmol). The solution became an suspension and then diluted with MeOH (5 mL). The reaction mixture was stirred at RT for 1 h 40 min. Most of the MeOH was removed under the reduced pressure. Water was added to dilute the solution and then extracted with Et$_2$O (4×15 mL) until LCMS showed the by-products (m/z:219 and 235) were removed from the aqueous layer. Then the pH of the aqueous layer was adjusted to 2 with 1N HCl solution and diluted with EtOAc (3×20 mL). The organic layer was combined, dried over MgSO$_4$, filtered and the filtrated was concentrated to give 32 mg crude product. The crude product was dissolved in DMSO (3 mL), filtered through a 0.45 μm acrodisc, and purified by reverse phase HPLC (YMC C18 S-5 μm/12 nm 50×20 mm preparatory column), eluting at 20 mL/min with a linear gradient running from 10% CH$_3$CN/H$_2$O (0.1% TFA) to 90% CH$_3$CN/H$_2$O (0.1% TFA) over 10 min. The desired fractions were concentrated under a stream of nitrogen at 50° C., giving 16 mg (37%) of title compound. LC-MS m/z 557.1 (M+H)$^+$, 1.01 min (ret. time). $^1$H NMR (400 MHz, CDCl$_3$-d) δ ppm 7.98 (s, 1H); 7.46-7.52 (m, 2H); 7.33-7.42 (m, 3H); 7.26 (s, 1H); 7.08 (dd, J=8.28, 2.01 Hz, 1H); 7.02 (d, J=8.53 Hz, 1H); 4.74 (t, J=7.78 Hz, 1H); 4.32-4.39 (m, 4H); 4.31 (s, 5H); 3.11-3.25 (m, 2H); 2.66 (s, 3H).

Example 53

(3R)-3-{4-chloro-3-[(N-methylbenzenesulfonamido)
methyl]phenyl}-3-(1-methyl-1H-1,2,3-benzotriazol-
5-yl)propanoic acid

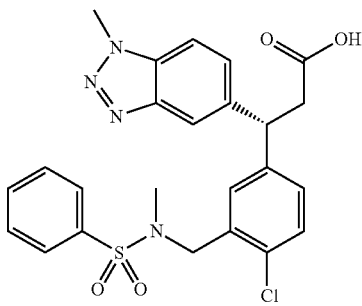 [SMILES: CN(Cc1cc([C@@H](CC(=O)O)c2ccc3c(c2)nnn3C)ccc1Cl)S(=O)(=O)c1ccccc1]

134

(R)-methyl 3-(4-chloro-3-((N-methylphenylsulfona-
mido)methyl)phenyl)-3-(1-methyl-1H-benzo[d][1,2,
3]triazol-5-yl)propanoate

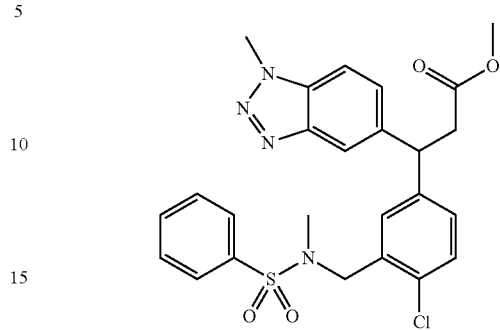

To a solution of methyl 3-(4-chloro-3-(hydroxymethyl)phenyl)-3-(1-methyl-1H-benzo[d][1,2,3]triazol-5-yl)propanoate (0.485 g, 1.348 mmol), N-methylbenzenesulfonamide (0.243 g, 1.419 mmol), and ADDP (0.715 g, 2.83 mmol) in THF (18 mL) at 0° C. was added tributylphosphine (0.75 mL, 3.04 mmol). Upon addition the color turned from deep orange to a lighter yellow. The ice-bath was removed and the solution allowed stirred at RT for 15 h during which time a precipitate formed. The supernatant was removed and the solution diluted with acetone and EtOAc and washed with water (2×), brine (1×), dried over MgSO$_4$, filtered and concentrated to give 1.427 g of a yellow oil. This was adsorbed onto isolute and purified by silica gel chromatography to give 0.522 g of a white solid.

This was subjected to chiral SFC HPLC resolution of to give 0.106 g of (R)-methyl 3-(4-chloro-3-((N-methylphenylsulfonamido)methyl)phenyl)-3-(1-methyl-1H-benzo[d][1,2,3]triazol-5-yl)propanoate as a white solid. LC-MS m/z 513.2 (M+H)$^+$, 515.2 (M+H+2)$^+$, 1.07 min (ret. time).

(3R)-3-{4-chloro-3-[(N-methylbenzenesulfonamido)
methyl]phenyl}-3-(1-methyl-1H-1,2,3-benzotriazol-
5-yl)propanoic acid

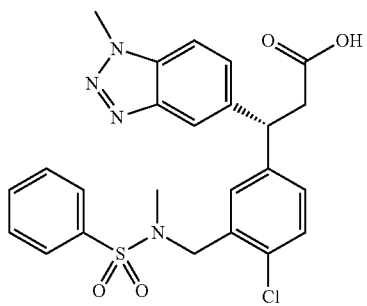 [SMILES: CN(Cc1cc([C@@H](CC(=O)O)c2ccc3c(c2)nnn3C)ccc1Cl)S(=O)(=O)c1ccccc1]

To a solution of (R)-methyl 3-(4-chloro-3-((N-methylphenylsulfonamido)methyl)phenyl)-3-(1-methyl-1H-benzo[d][1,2,3]triazol-5-yl)propanoate (0.177 g, 0.345 mmol) in MeOH (15 mL) and THF (1 mL) at RT was added a 1M LiOH solution (16 mL, 16.00 mmol). After the addition, MeOH (10 mL) was added. The resulting suspension was kept at RT. After 1 h 20 mins the reaction mixture was acidified to pH 1-2 and the solution diluted with EtOAc. The organic phase was washed with water (2×), dried over MgSO$_4$, filtered, and concentrated to give 0.148 g of a light yellow solid. This material was dissolved in chloroform and concentrated (3×) to give 0.137 g of the title compound as a light yellow solid. LC-MS m/z 499.4 (M+H)$^+$, 501.4 (M+H+2)$^+$, 1.03 min (ret. time).

Example 54

(3S)-3-{4-chloro-3-[(N-methylbenzenesulfonamido)methyl]phenyl}-3-(1-methyl-1H-1,2,3-benzotriazol-5-yl)propanoic acid

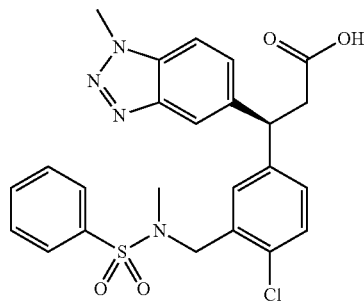 [SMILES: CN(Cc1cc([C@H](CC(=O)O)c2ccc3c(c2)nnn3C)ccc1Cl)S(=O)(=O)c1ccccc1]

(S)-methyl 3-(4-chloro-3-((N-methylphenylsulfonamido)methyl)phenyl)-3-(1-methyl-1H-benzo[d][1,2,3]triazol-5-yl)propanoate

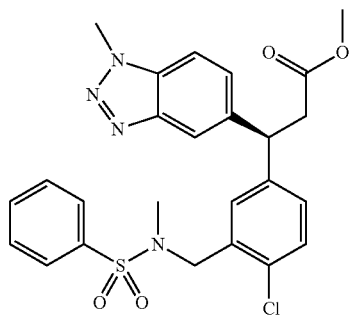 [SMILES: COC(=O)C[C@@H](c1ccc(Cl)c(CN(C)S(=O)(=O)c2ccccc2)c1)c1ccc2c(c1)nnn2C]

Chiral SFC HPLC resolution of Methyl 3-(4-chloro-3-((N-methylphenylsulfonamido)methyl)phenyl)-3-(1-methyl-1H-benzo[d][1,2,3]triazol-5-yl)propanoate provided 0.113 g of (S)-methyl 3-(4-chloro-3-((N-methylphenylsulfonamido)methyl)phenyl)-3-(1-methyl-1H-benzo[d][1,2,3]triazol-5-yl)propanoate as a white solid. LC-MS m/z 513.2 (M+H)$^+$, 515.2 (M+H+2)$^+$, 1.08 min (ret. time).

(3S)-3-{4-chloro-3-[(N-methylbenzenesulfonamido)methyl]phenyl}-3-(1-methyl-1H-1,2,3-benzotriazol-5-yl)propanoic acid

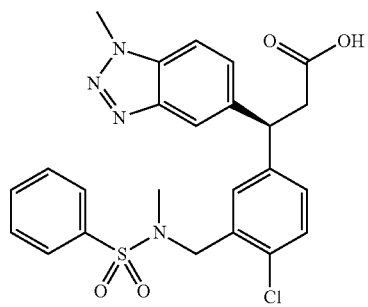 [SMILES: CN(Cc1cc([C@H](CC(=O)O)c2ccc3c(c2)nnn3C)ccc1Cl)S(=O)(=O)c1ccccc1]

To a solution of (S)-methyl 3-(4-chloro-3-((N-methylphenylsulfonamido)methyl)phenyl)-3-(1-methyl-1H-benzo[d][1,2,3]triazol-5-yl)propanoate (0.180 g, 0.351 mmol) in MeOH (15 mL) and THF (1 mL) at RT was added a 1M solution of LiOH (16 mL, 16.00 mmol). The resulting suspension was diluted with MeOH (10 mL). After 1 hr 20 mins at RT the reaction mixture was acidified to pH 1-2 and the solution diluted with EtOAc. The organic phase was washed with water (2×), dried over MgSO$_4$, filtered, and concentrated to give 0.156 g of a light yellow solid. This material was dissolved in chloroform and concentrated (3×) to give 0.141 g of the title compound as a light yellow solid. LC-MS m/z 499.4 (M+H)$^+$, 501.4 (M+H+2)$^+$, 1.03 min (ret. time).

Example 55

(3R)-3-(1,4-dimethyl-1H-1,2,3-benzotriazol-5-yl)-3-{4-methyl-3-[(N-methylbenzenesulfonamido)methyl]phenyl}propanoic acid

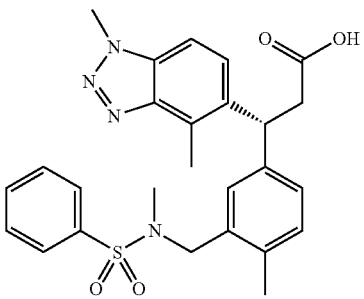 [SMILES: Cc1ccc([C@@H](CC(=O)O)c2ccc3c(nnn3C)c2C)cc1CN(C)S(=O)(=O)c1ccccc1]

Ethyl 3-(1,4-dimethyl-1H-benzo[d][1,2,3]triazol-5-yl)-3-(4-methyl-3-((N-methylphenylsulfonamido)methyl)phenyl)propanoate

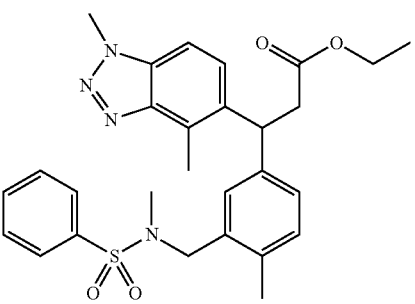 [SMILES: CCOC(=O)CC(c1ccc(C)c(CN(C)S(=O)(=O)c2ccccc2)c1)c1ccc2c(nnn2C)c1C]

To a solution of ethyl 3-(1,4-dimethyl-1H-benzo[d][1,2,3]triazol-5-yl)-3-(3-(hydroxymethyl)-4-methylphenyl)propanoate (0.5 g, 1.361 mmol), N-methylbenzenesulfonamide (0.238 g, 1.390 mmol), and 1,1'-(Azodicarbonyl)dipiperidine (0.689 g, 2.73 mmol) in THF (15 mL) at 0° C. was added tri-n-butylphosphine (0.7 mL, 2.84 mmol). After the addition the ice-bath was removed and stirring continued at RT. After 16 h the reaction mixture was diluted with EtOAc and acetone and adsorbed onto isolute purified by silica gel chromatography to give 0.578 g of a white solid. LC-MS m/z 521.4 (M+H)$^+$, 1.16 min (ret. time)

3-(1,4-dimethyl-1H-1,2,3-benzotriazol-5-yl)-3-{4-methyl-3-[(N-methylbenzenesulfonamido)methyl]phenyl}propanoic acid

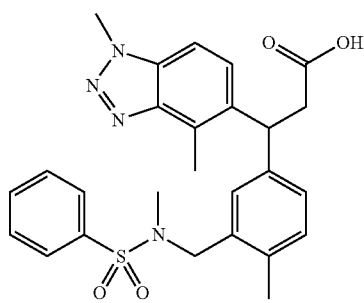

To a solution of ethyl 3-(1,4-dimethyl-1H-benzo[d][1,2,3]triazol-5-yl)-3-(4-methyl-3-((N-methylphenylsulfonamido)methyl)phenyl)propanoate (0.578 g, 1.110 mmol) in MeOH (50 mL) at RT was added a 1M solution of LiOH (50 mL, 50.0 mmol). The resulting suspension was diluted with MeOH (50.0 mL) to give a nearly homogeneous solution. The resultant mixture was allowed to stir at RT. After 1 hr 15 min the mixture was acidified to pH 1-2 and diluted with EtOAc. The solution was extracted with water and the organic phase was washed with brine (1×), dried over MgSO$_4$ and concentrated to give 0.587 g of a white solid. This was taken into EtOAc and extracted with saturated NaHCO$_3$ solution. The aqueous phase was extracted further with EtOAc then acidified to pH 1-2 with 6N HCl and extracted with EtOAc. The organic phase was washed with brine, dried over MgSO$_4$ and concentrated to give 0.513 g of white solid. This was subjected to chiral SFC HPLC resolution without further purification.

(3R)-3-(1,4-dimethyl-1H-1,2,3-benzotriazol-5-yl)-3-{4-methyl-3-[(N-methylbenzenesulfonamido)methyl]phenyl}propanoic acid

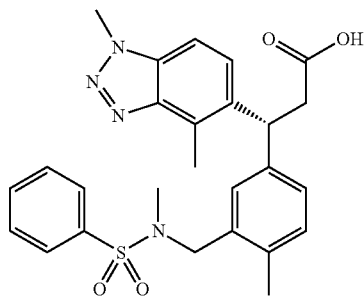 [SMILES: Cc1ccc([C@@H](CC(=O)O)c2ccc3c(nnn3C)c2C)cc1CN(C)S(=O)(=O)c1ccccc1]

The title compound was obtained by chiral SFC resolution of 3-(1,4-dimethyl-1H-1,2,3-benzotriazol-5-yl)-3-{4-methyl-3-[(N-methylbenzenesulfonamido)methyl]phenyl}propanoic acid to give 0.156 g as an off-white solid. LC-MS m/z 493.4 (M+H)$^+$, 0.98 min (ret. time).

Example 56

(3S)-3-(1,4-dimethyl-1H-1,2,3-benzotriazol-5-yl)-3-{4-methyl-3-[(N-methylbenzenesulfonamido)methyl]phenyl}propanoic acid

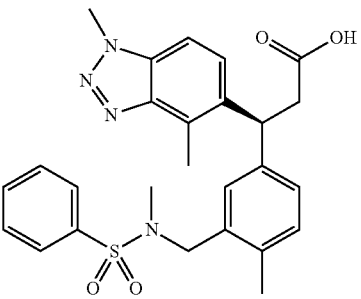 [SMILES: Cc1ccc([C@H](CC(=O)O)c2ccc3c(nnn3C)c2C)cc1CN(C)S(=O)(=O)c1ccccc1]

The title compound was obtained by chiral SFC resolution of 3-(1,4-dimethyl-1H-1,2,3-benzotriazol-5-yl)-3-{4-methyl-3-[(N-methylbenzenesulfonamido)methyl]phenyl}propanoic acid to give 0.156 g as an off-white solid. LC-MS m/z 493.4 (M+H)$^+$, 0.98 min (ret. time).

Example 57

3-(3-((1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid

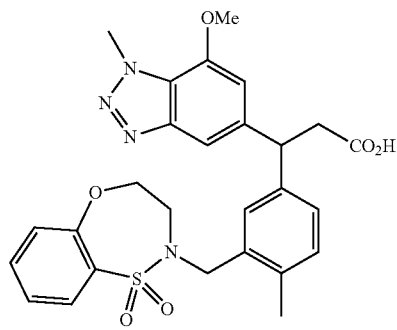 [SMILES: COc1cc(C(CC(=O)O)c2ccc(C)c(CN3CCOc4ccccc4S3(=O)=O)c2)cc2nnn(C)c12]

2-methoxy-6-nitroaniline

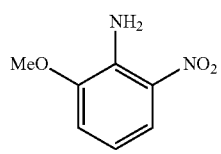

To a solution of 2-amino-3-nitrophenol (2.55 g, 16.55 mmol) dissolved in DMF (35 mL) was added potassium carbonate (2.52 g, 18.20 mmol). The mixture was stirred for 5 min before was added MeI (1.138 mL, 18.20 mmol) and let the reaction stir at RT for 2 h. water (75 mL) was added to quench the reaction and the precipitate product was collected by filtration, washed with water to give 2.26 g of 2-methoxy-6-nitroaniline (81%). LC-MS m/z 168.9 (M+H)⁺, 0.74 (ret. time)

4-bromo-2-methoxy-6-nitroaniline

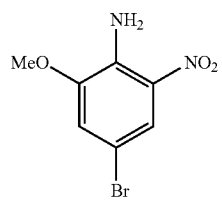 [SMILES: COc1cc(Br)cc([N+](=O)[O-])c1N]

To a solution of 2-methoxy-6-nitroaniline (2.26 g, 13.44 mmol) dissolved in AcOH (50 mL) was added NaOAc (1.654 g, 20.16 mmol) and bromine (0.762 mL, 14.78 mmol) and the mixture was stirred at RT for 30 min. water was added (75 mL) to quench the reaction and the precipitate product was collected by filtration, washed with water and dried over vacuum to give 2.78 g of 4-bromo-2-methoxy-6-nitroaniline (84%). LC-MS m/z 246.9/248.9 (M+H)⁺, 0.93 (ret. time).

4-bromo-2-methoxy-N-methyl-6-nitroaniline

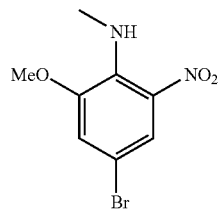

To a solution of 4-bromo-2-methoxy-6-nitroaniline (2.76 g, 11.17 mmol) dissolved in DMF (50 mL) was added NaH (300 mg, 12.50 mmol) slowly at 0° C. and the reaction mixture was stirred for 30 min. Then methyl iodide (0.768 mL, 12.29 mmol) was added. Water was added (60 mL) to quench the reaction and the precipitate product was collected by filtration, washed with water and dried over vacuum to give 2.82 g of 4-bromo-2-methoxy-N-methyl-6-nitroaniline (97%). LC-MS m/z 260.9/263 (M+H)⁺, 1.03 (ret. time).

5-bromo-7-methoxy-1-methyl-1H-benzo[d][1,2,3]triazole

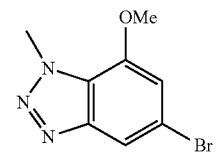

To a solution of 4-bromo-2-methoxy-N-methyl-6-nitroaniline (2.82 g, 10.80 mmol) dissolved in glacial AcOH (100 mL, 1747 mmol) was added zinc (4.94 g, 76 mmol) and the reaction mixture was stirred at RT for 2 h, 30 min. zinc (150 mg, 2.294 mmol) was added to the mixture and let the solution being stirred until the orange color disappeared (around 30 min). The mixture was filtrated and the solid was copiously washed with EtOAc, then the filtrate was concentrated to get the diamine compound. The crude product was dissolved into H₂SO₄ (10%) (50 mL, 10.80 mmol), NaNO₂ was added (0.745 g, 10.80 mmol) in small portions at 0° C. and the mixture was stirred at 0° C. for 1 h, 45 min. Water (100 mL) was added to quench the reaction and the precipitate product was collected by filtration, washed with water and dried under vacuum to give 1.28 g of 5-bromo-7-methoxy-1-methyl-1H-benzo[d][1,2,3]triazole (49%). LC-MS m/z 241.9/243.9 (M+H)⁺, 0.83 (ret. time).

(E)-ethyl 3-(7-methoxy-1-methyl-1H-benzo[d][1,2,3]triazol-5-yl)acrylate

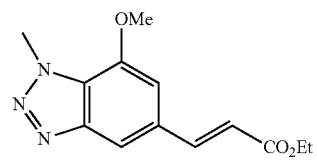

To a solution of 5-bromo-7-methoxy-1-methyl-1H-benzo[d][1,2,3]triazole (974 mg, 4.02 mmol) dissolved into DMF (15 mL) were added N,N-diisopropylethylamine (2.108 mL, 12.07 mmol), ethyl acrylate (4.29 mL, 40.2 mmol), Pd(OAc)₂ (271 mg, 1.207 mmol) and tri-o-tolylphosphine (980 mg, 3.22 mmol) and the reaction mixture was put in microwave at 150° C. for 2 h. water was added (50 mL) to quench the reaction. EtOAc was added and the layers were separated. The aqueous layer was then extracted with EtOAc twice and the combined organic layer was dried with MgSO₄, concentrated then purified by silica gel chromatography to give 820 mg of (E)-ethyl 3-(7-methoxy-1-methyl-1H-benzo[d][1,2,3]triazol-5-yl)acrylate (78%). LC-MS m/z 262 (M+H)⁺, 0.90 (ret. time).

Ethyl 3-(3-(hydroxymethyl)-4-methylphenyl)-3-(7-methoxy-1-methyl-1H-benzo[d][1,2,3]triazol-5-yl)propanoate

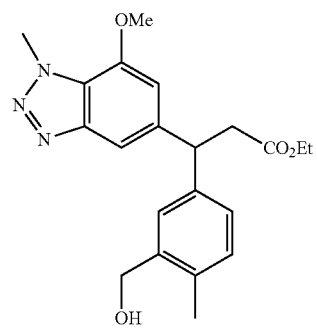 [SMILES: CCOC(=O)CC(c1ccc(C)c(CO)c1)c1cc(OC)c2c(c1)nnn2C]

To a solution of (E)-ethyl 3-(7-methoxy-1-methyl-1H-benzo[d][1,2,3]triazol-5-yl)acrylate (790 mg, 3.02 mmol) dissolved in 1,4-dioxane (10 mL) and water (10 mL) were added [RhCl(cod)]₂ (502 mg, 0.907 mmol), (3-(hydroxymethyl)-4-methylphenyl)boronic acid (1506 mg, 9.07 mmol) and Et₃N (0.969 mL, 6.95 mmol) and the mixture was heated in microwave at 150° C. for 45 min. The mixture was dissolved into water (25 mL) and EtOAc (25 mL) and the layers were separated. The aqueous layer was extracted with EtOAc thrice, then the combined organic layer was dried with MgSO$_4$, filtered, concentrated and purified by silica gel chromatography to give 560 mg of ethyl 3-(3-(hydroxymethyl)-4-methylphenyl)-3-(7-methoxy-1-methyl-1H-benzo[d][1,2,3]triazol-5-yl)propanoate (48%). LC-MS m/z 384.1 (M+H)$^+$, 0.91 (ret. time).

Ethyl 3-(3-((1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoate

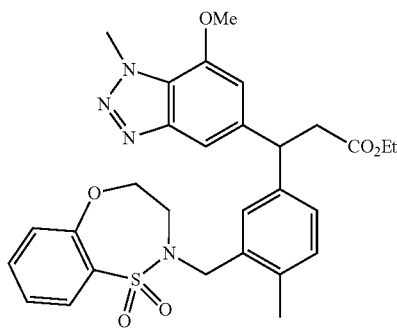 [SMILES: CCOC(=O)CC(c1ccc(C)c(CN2CCOc3ccccc3S2(=O)=O)c1)c1cc(OC)c2c(c1)nnn2C]

To a solution of ethyl 3-(3-(hydroxymethyl)-4-methylphenyl)-3-(7-methoxy-1-methyl-1H-benzo[d][1,2,3]triazol-5-yl)propanoate (483 mg, 1.260 mmol) dissolved in dry THF (15 mL) were added 3,4-dihydro-2H-benzo[b][1,4,5]oxathiazepine 1,1-dioxide (376 mg, 1.889 mmol), (E)-1,1'-(azodicarbonyl)dipiperidine (636 mg, 2.52 mmol) and tributylphosphine (0.622 mL, 2.52 mmol) at 0° C. The ice bath was removed once addition is over and the reaction mixture was stirred at RT for 21 h. The solution was dissolved in EtOAc and acetone (50/50 20 mL), adsorbed in isolute and the solvent was removed. The mixture was then purified by silica gel chromatography to give 365 mg of ethyl 3-(3-((1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoate (51%). LC-MS m/z 565.4 (M+H)$^+$, 1.15 (ret. time).

3-(3-((1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid

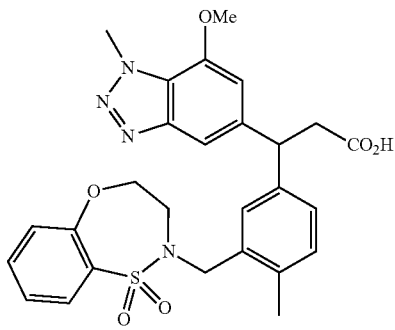 [SMILES: COc1cc(C(CC(=O)O)c2ccc(C)c(CN3CCOc4ccccc4S3(=O)=O)c2)cc2nnn(C)c12]

To a solution of ethyl 3-(3-((1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoate (365 mg, 0.646 mmol) dissolved in MeOH (20 mL) was added NaOH (1 N) (1.293 mL, 1.293 mmol) and the mixture was heated in microwave at 100° C. for 1 h. The solution was acidified with HCl 1N until pH ~2-3, and the mixture was filtered to give 3-(3-((1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid (311 mg, 0.580 mmol, 90% yield). LC-MS m/z 537.4 (M+H)$^+$, 0.98 (ret. time).

Example 58

3-(3-((1,1-dioxido-3,4-dihydro-2H-benzo[b][1,4,5]oxathiazepin-2-yl)methyl)-4-methylphenyl)-3-(tetrazolo[1,5-a]pyridin-7-yl)propanoic acid

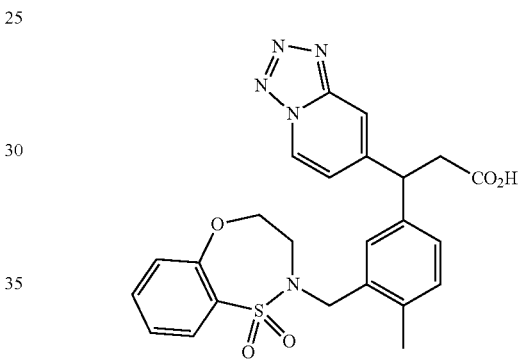

(E)-methyl 3-(pyridin-4-yl)acrylate

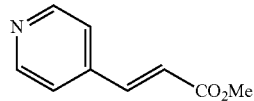 [SMILES: COC(=O)/C=C/c1ccncc1]

To a solution of methyl 2-(diethoxyphosphoryl)acetate (2.033 mL, 11.20 mmol) dissolved in dry THF (10 mL) was added potassium 2-methylpropan-2-olate (1.257 g, 11.20 mmol) dissolved in dry THF (10 mL) at 0° C. and the mixture was stirred under nitrogen atmosphere for 25 min. Then, isonicotinaldehyde (0.880 mL, 9.34 mmol) dissolved in dry THF (10 mL) was added to the mixture stirred at RT for 1 h. saturated NH$_4$Cl solution (60 mL) was added to the solution and then EtOAc; the layers were separated. The aqueous layer was extracted with EtOAc twice and then the combined organic layer was dried with MgSO$_4$, filtered, and the solvent was removed to give 1.511 g of (E)-methyl 3-(pyridin-4-yl)acrylate (99%). LC-MS m/z 163.9 (M+H)$^+$, 0.41 (ret. time).

143

Methyl 3-(3-(hydroxymethyl)-4-methylphenyl)-3-(pyridin-4-yl)propanoate

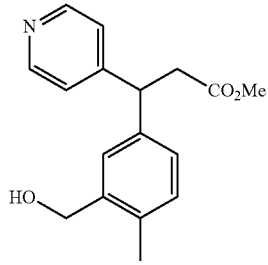 [SMILES: COC(=O)CC(c1ccncc1)c1ccc(C)c(CO)c1]

To a solution of (E)-methyl 3-(pyridin-4-yl)acrylate (511 mg, 3.13 mmol) dissolved in 1,4-dioxane (6 mL) and water (6 mL) was added (3-(hydroxymethyl)-4-methylphenyl)boronic acid (780 mg, 4.70 mmol), [RhCl(cod)]$_2$ (173 mg, 0.313 mmol) and TEA (0.873 mL, 6.26 mmol) and the mixture was heated in microwave at 100° C. for 1 h. water was added (10 mL) to quench the reaction and EtOAc was added; the layers were separated. The aqueous layer was extracted with EtOAc twice; then the combined organic layer was dried with MgSO$_4$, filtered, concentrated and purified by silica gel chromatography to give 360 mg of methyl 3-(3-(hydroxymethyl)-4-methylphenyl)-3-(pyridin-4-yl)propanoate (13%) LC-MS m/z 286.1 (M+H)$^+$, 0.54 (ret. time).

Methyl 3-(3-((1,1-dioxido-3,4-dihydro-2H-benzo[b][1,4,5]oxathiazepin-2-yl)methyl)-4-methylphenyl)-3-(pyridin-4-yl)propanoate

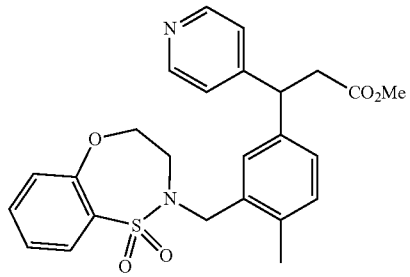 [SMILES: COC(=O)CC(c1ccncc1)c1ccc(C)c(CN2CCOc3ccccc3S2(=O)=O)c1]

To a stirred solution of methyl 3-(3-(hydroxymethyl)-4-methylphenyl)-3-(pyridin-4-yl)propanoate (360 mg, 1.262 mmol) dissolved in dry THF (7 mL) cooled at 0° C. was added 3,4-dihydro-2H-benzo[b][1,4,5]oxathiazepine 1,1-dioxide (264 mg, 1.325 mmol), DIAD (0.491 mL, 2.52 mmol) and PS—PPh$_3$ (1.15 g, 2.52 mmol). The ice bath was removed once the addition is over, and the mixture was stirred at RT for 1 h. The mixture was filtered, concentrated and purified by silica gel chromatography to give 430 mg of methyl 3-(3-((1,1-dioxido-3,4-dihydro-2H-benzo[b][1,4,5]oxathiazepin-2-yl)methyl)-4-methylphenyl)-3-(pyridin-4-yl)propanoate (73% yield). LC-MS m/z 467.2 (M+H)$^+$, 0.79 (ret. time).

144

4-(1-(3-((1,1-dioxido-3,4-dihydro-2H-benzo[b][1,4,5]oxathiazepin-2-yl)methyl)-4-methylphenyl)-3-methoxy-3-oxopropyl)pyridine 1-oxide

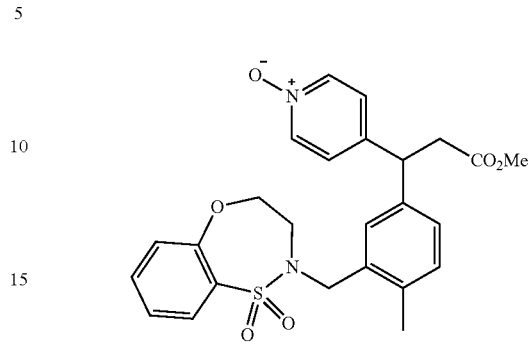

To a solution of methyl 3-(3-((1,1-dioxido-3,4-dihydro-2H-benzo[b][1,4,5]oxathiazepin-2-yl)methyl)-4-methylphenyl)-3-(pyridin-4-yl)propanoate (430 mg, 0.922 mmol) dissolved in MeOH (10 mL) was added magnesium monoperoxyphthalate hexahydrate (456 mg, 0.922 mmol) and the mixture was stirred at RT for 4 h. The solvent was removed, the mixture was dissolved in MeOH and purified through reverse-phase chromatography to give 180 mg of 4-(1-(3-((1,1-dioxido-3,4-dihydro-2H-benzo[b][1,4,5]oxathiazepin-2-yl)methyl)-4-methylphenyl)-3-methoxy-3-oxopropyl)pyridine 1-oxide (40.5%). LC-MS m/z 483.1 (M+H)$^+$, 0.87 (ret. time).

Methyl 3-(3-((1,1-dioxido-3,4-dihydro-2H-benzo[b][1,4,5]oxathiazepin-2-yl)methyl)-4-methylphenyl)-3-(tetrazolo[1,5-a]pyridin-7-yl)propanoate

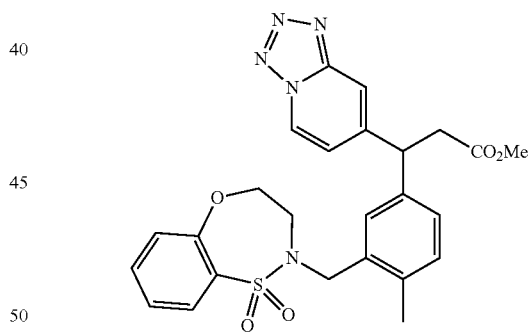

To 4-(1-(3-((1,1-dioxido-3,4-dihydro-2H-benzo[b][1,4,5]oxathiazepin-2-yl)methyl)-4-methylphenyl)-3-methoxy-3-oxopropyl)pyridine 1-oxide (180 mg, 0.373 mmol) was added diphenyl phosphorazidate (482 µl, 2.238 mmol) and pyridine (75 µl, 0.933 mmol), then the mixture was purged with nitrogen and heated stirring at 120° C. for 30 h. Water was added (5 mL), then EtOAc was added and the layers were separated. The aqueous layer was extracted with EtOAc twice; then the combined organic layer was dried with MgSO$_4$, filtered, concentrated and purified by silica gel chromatography to give 96.1 mg of methyl 3-(3-((1,1-dioxido-3,4-dihydro-2H-benzo[b][1,4,5]oxathiazepin-2-yl)methyl)-4-methylphenyl)-3-(tetrazolo[1,5-a]pyridin-7-yl)propanoate (28%). LC-MS m/z 508.2 (M+H)$^+$, 0.98 (ret. time).

145

3-(3-((1,1-dioxido-3,4-dihydro-2H-benzo[b][1,4,5]oxathiazepin-2-yl)methyl)-4-methylphenyl)-3-(tetrazolo[1,5-a]pyridin-7-yl)propanoic acid

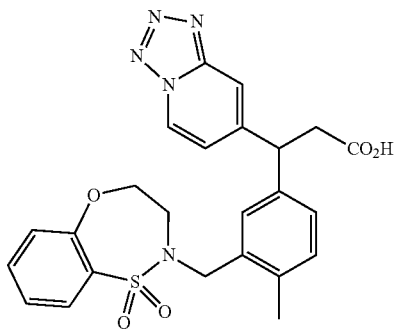 [SMILES: Cc1ccc(C(CC(=O)O)c2ccn3nnnc3c2)cc1CN1CCOc2ccccc2S1(=O)=O]

To a solution of methyl 3-(3-((1,1-dioxido-3,4-dihydro-2H-benzo[b][1,4,5]oxathiazepin-2-yl)methyl)-4-methylphenyl)-3-(tetrazolo[1,5-a]pyridin-7-yl)propanoate (96.1 mg, 0.189 mmol) dissolved in MeOH (6 mL) was added NaOH 1N (0.379 mL, 0.379 mmol) and the mixture was heated in microwave at 100° C. for 3 h. The mixture was acidified with HCL 1N until pH=2, concentrated under reduced pressure, and purified on reverse-phase HPLC (Sunfire C18, 19×100 mm, 5 u column), eluting at 18 mL/min with a linear gradient running from 35% $CH_3CN/H_2O$ (0.1% formic acid) to 65% $CH_3CN/H_2O$ (0.1% formic acid) over 10 min. The desired fractions were collected and dried by V10 solvent evaporator. Dried fractions were transferred to a vial with MeCN, and dried under $N_2$ stream at 45° C. to afford 13 mg of 3-(3-((1,1-dioxido-3,4-dihydro-2H-benzo[b][1,4,5]oxathiazepin-2-yl)methyl)-4-methylphenyl)-3-(tetrazolo[1,5-a]pyridin-7-yl)propanoic acid (14%). LC-MS m/z 508.2 (M+H)+, 0.98 (ret. time).

Example 59

3-(3-((4,4-dioxido-1,4,5-oxathiazepan-5-yl)methyl)-4-methylphenyl)-3-(7-methoxy-1-methyl-1H-benzo[d][1,2,3]triazol-5-yl)propanoic acid

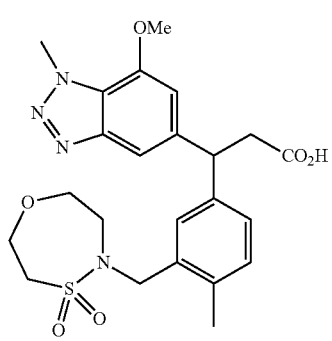 [SMILES: COc1cc(C(CC(=O)O)c2ccc(C)c(CN3CCOCCS3(=O)=O)c2)cc2nnn(C)c12]

146

Ethyl 3-(3-(hydroxymethyl)-4-methylphenyl)-3-(7-methoxy-1-methyl-1H-benzo[d][1,2,3]triazol-5-yl)propanoate

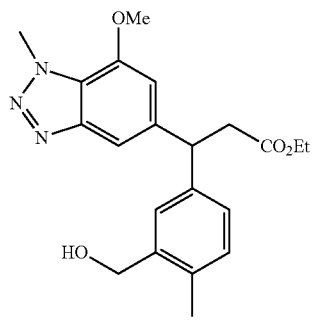 [SMILES: CCOC(=O)CC(c1ccc(C)c(CO)c1)c1cc(OC)c2c(c1)nnn2C]

To a solution of (E)-ethyl 3-(7-methoxy-1-methyl-1H-benzo[d][1,2,3]triazol-5-yl)acrylate (2 g, 7.65 mmol) and (3-(hydroxymethyl)-4-methylphenyl)boronic acid (3.177 g, 19.13 mmol) dissolved in 1,4-dioxane (6 mL) and water (6.00 mL) was added [RhCl(cod)]$_2$ (0.863 g, 1.56 mmol) and TEA (4.13 mL, 31.8 mmol) and the mixture was put in microwave at 100° C. for 9 h. The mixture was filtered, and washed with EtOAc; then the filtrate was washed with water twice and brine once. The organic layer was dried over $MgSO_4$, concentrated and purified by silica gel chromatography to get 885 mg of ethyl 3-(3-(hydroxymethyl)-4-methylphenyl)-3-(7-methoxy-1-methyl-1H-benzo[d][1,2,3]triazol-5-yl)propanoate (30.2%). LC-MS m/z 384.1 (M+H)+, 0.92 (ret. time).

Ethyl 3-(3-(chloromethyl)-4-methylphenyl)-3-(7-methoxy-1-methyl-1H-benzo[d][1,2,3]triazol-5-yl)propanoate

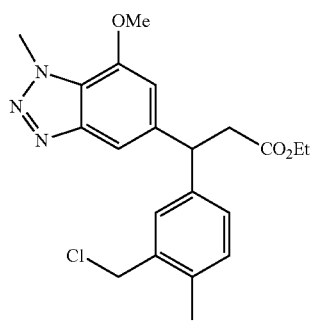 [SMILES: CCOC(=O)CC(c1ccc(C)c(CCl)c1)c1cc(OC)c2c(c1)nnn2C]

To a solution of ethyl 3-(3-(hydroxymethyl)-4-methylphenyl)-3-(7-methoxy-1-methyl-1H-benzo[d][1,2,3]triazol-5-yl)propanoate (416 mg, 1.085 mmol) dissolved in DCM (6 mL) was added thionyl chloride (0.119 mL, 1.627 mmol) and the mixture was stirred at RT for. The solvent was removed to get 466 mg of ethyl 3-(3-(chloromethyl)-4-methylphenyl)-3-(7-methoxy-1-methyl-1H-benzo[d][1,2,3]triazol-5-yl)propanoate (466 mg, 1.160 mmol, 107% yield). LC-MS m/z 402.1 (M+H)+, 1.13 (ret. time).

147

Ethyl 3-(3-(((2-hydroxyethyl)amino)methyl)-4-methylphenyl)-3-(7-methoxy-1-methyl-1H-benzo[d][1,2,3]triazol-5-yl)propanoate

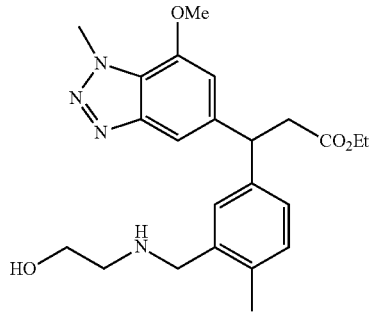 [SMILES: CCOC(=O)CC(c1ccc(C)c(CNCCO)c1)c1cc(OC)c2c(c1)nnn2C]

To a solution of ethyl 3-(3-(chloromethyl)-4-methylphenyl)-3-(7-methoxy-1-methyl-1H-benzo[d][1,2,3]triazol-5-yl)propanoate (156.5 mg, 0.389 mmol) dissolved in THF (4 mL) was added Et$_3$N (0.133 mL, 0.974 mmol) and ethanolamine (0.177 mL, 2.92 mmol) and the mixture was stirred at RT for 65 h. The solvent was removed, the mixture was dissolved in MeOH and purified through reverse-phase chromatography to get 50.8 mg of ethyl 3-(3-(((2-hydroxyethyl)amino)methyl)-4-methylphenyl)-3-(7-methoxy-1-methyl-1H-benzo[d][1,2,3]triazol-5-yl)propanoate (30.6%). LC-MS m/z 427.2 (M+H)$^+$, 0.70 (ret. time).

Ethyl 3-(3-((4,4-dioxido-1,4,5-oxathiazepan-5-yl)methyl)-4-methylphenyl)-3-(7-methoxy-1-methyl-1H-benzo[d][1,2,3]triazol-5-yl)propanoate

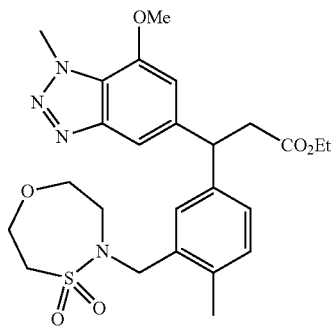 [SMILES: CCOC(=O)CC(c1ccc(C)c(CN2CCOCCS2(=O)=O)c1)c1cc(OC)c2c(c1)nnn2C]

To a solution of ethyl 3-(3-(((2-hydroxyethyl)amino)methyl)-4-methylphenyl)-3-(7-methoxy-1-methyl-1H-benzo[d][1,2,3]triazol-5-yl)propanoate (50.8 mg, 0.119 mmol) dissolved in DCM (1.5 mL) was added Et$_3$N (0.081 mL, 0.596 mmol) and 2-chloroethanesulfonyl chloride (0.019 mL, 0.179 mmol) and the mixture was stirred at RT for 90 min. The solvent was removed; the mixture was dissolved with MeOH (1.5 mL) and purified through reverse-phase chromatography to afford 57.5 mg of ethyl 3-(3-((4,4-dioxido-1,4,5-oxathiazepan-5-yl)methyl)-4-methylphenyl)-3-(7-methoxy-1-methyl-1H-benzo[d][1,2,3]triazol-5-yl)propanoate (94%). LC-MS m/z 517.2 (M+H)$^+$, 1.01 (ret. time).

148

3-(3-((4,4-dioxido-1,4,5-oxathiazepan-5-yl)methyl)-4-methylphenyl)-3-(7-methoxy-1-methyl-1H-benzo[d][1,2,3]triazol-5-yl)propanoic acid

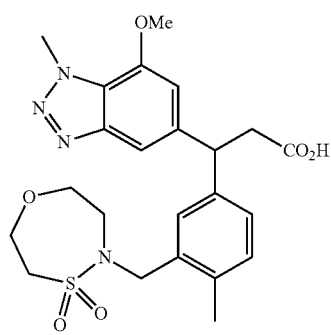 [SMILES: COc1cc(C(CC(=O)O)c2ccc(C)c(CN3CCOCCS3(=O)=O)c2)cc2nnn(C)c12]

To a solution of ethyl 3-(3-((4,4-dioxido-1,4,5-oxathiazepan-5-yl)methyl)-4-methylphenyl)-3-(7-methoxy-1-methyl-1H-benzo[d][1,2,3]triazol-5-yl)propanoate (57.7 mg, 0.112 mmol) dissolved in THF (2 mL) was added a solution of LiOH 50 mg/mL (1.336 mL, 2.79 mmol) and the mixture was stirred at RT for 40 h. The mixture was acidified with HCl 1N until pH=2-3; concentrated under reduced pressure, and purified on reverse-phase HPLC (Sunfire C18, 19×100 mm, 5 u column), eluting at 18 mL/min with a linear gradient running from 25% CH$_3$CN/H$_2$O (0.1% formic acid) to 55% CH$_3$CN/H$_2$O (0.1% formic acid) over 10 min. The desired fractions were collected and dried by V10 solvent evaporator. Dried fractions were transferred to a vial with MeCN, and dried under N$_2$ stream at 45° C. to get 11.7 mg of 3-(3-((4,4-dioxido-1,4,5-oxathiazepan-5-yl)methyl)-4-methylphenyl)-3-(7-methoxy-1-methyl-1H-benzo[d][1,2,3]triazol-5-yl)propanoic acid (21%). LC-MS m/z 489.2 (M+H)$^+$, 0.85 (ret. time).

Example 60

3-(3-((1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoic acid

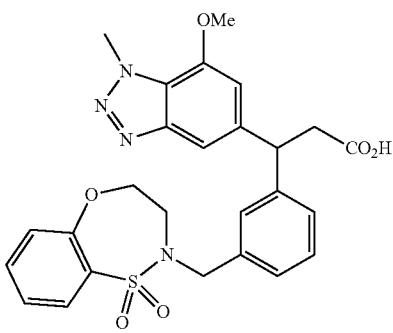 [SMILES: COc1cc(C(CC(=O)O)c2cccc(CN3CCOc4ccccc4S3(=O)=O)c2)cc2nnn(C)c12]

149

Ethyl 3-(3-(hydroxymethyl)phenyl)-3-(7-methoxy-1-methyl-1H-benzo[d][1,2,3]triazol-5-yl)propanoate

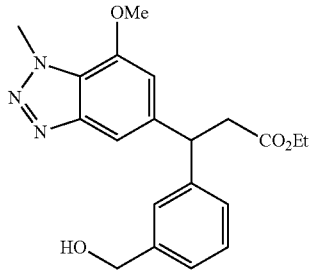 [SMILES: CCOC(=O)CC(c1cccc(CO)c1)c1cc(OC)c2c(c1)nnn2C]

To a solution of (E)-ethyl 3-(7-methoxy-1-methyl-1H-benzo[d][1,2,3]triazol-5-yl)acrylate (1 g, 3.83 mmol) dissolved in 1,4-dioxane (10 mL) and water (10 mL) was added (3-(hydroxymethyl)phenyl)boronic acid (1.90 g, 12.50 mmol), [RhCl(cod)]$_2$ (0.423 g, 0.765 mmol) and TEA (1.227 mL, 8.80 mmol) and the mixture was heated in microwave at 150° C. for 1 h. water (35 mL) was added to the mixture which was extracted with EtOAc thrice; the combined organic layer was dried with MgSO$_4$, concentrated and purified by silica gel chromatography to get 779 mg of ethyl 3-(3-(hydroxymethyl)phenyl)-3-(7-methoxy-1-methyl-1H-benzo[d][1,2,3]triazol-5-yl)propanoate (55.1%). LC-MS m/z 370.0 (M+H)$^+$, 0.87 (ret. time).

Ethyl 3-(3-((1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoate

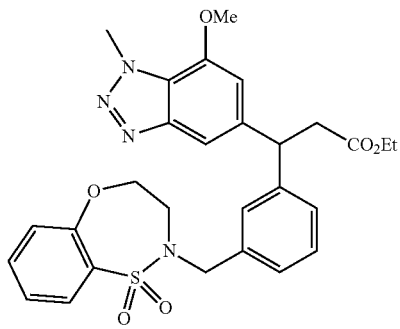 [SMILES: CCOC(=O)CC(c1cccc(CN2CCOc3ccccc3S2(=O)=O)c1)c1cc(OC)c2c(c1)nnn2C]

To a 0° C. cooled solution of ethyl 3-(3-(hydroxymethyl)phenyl)-3-(7-methoxy-1-methyl-1H-benzo[d][1,2,3]triazol-5-yl)propanoate (55.5 mg, 0.150 mmol) dissolved in dry THF (2 mL) was added 3,4-dihydro-2H-benzo[b][1,4,5]oxathiazepine 1,1-dioxide (30.8 mg, 0.155 mmol), DIAD (53 μl, 0.273 mmol) and PS—PPh$_3$ (169 mg, 0.270 mmol) and the mixture was stirred at 0° C. for 90 min. The mixture was filtered, concentrated and purified by silica gel chromatography to get 60 mg of ethyl 3-(3-((1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoate (72.5%). LC-MS m/z 551.3 (M+H)$^+$, 1.10 (ret. time).

150

3-(3-((1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoic acid

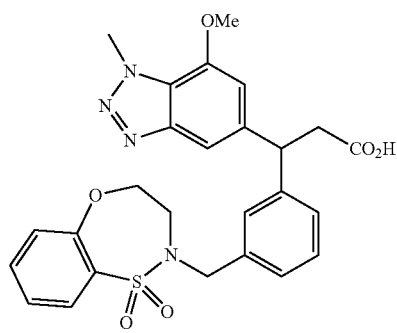 [SMILES: COc1cc(C(CC(=O)O)c2cccc(CN3CCOc4ccccc4S3(=O)=O)c2)cc2nnn(C)c12]

To a solution of ethyl 3-(3-((1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoate (60 mg, 0.109 mmol) dissolved in MeOH (2 mL) was added a solution of NaOH 1N (0.272 mL, 0.272 mmol) and the mixture was heated in microwave at 100° C. for 45 min. The mixture was acidified with HCl 1N until pH=2-3, concentrated under reduced pressure, and purified on reverse-phase HPLC (Sunfire C18, 19×100 mm, 5 u column), eluting at 18 mL/min with a linear gradient running from 35% CH$_3$CN/H$_2$O (0.1% formic acid) to 60% CH$_3$CN/H$_2$O (0.1% formic acid) over 10 min. The desired fractions were collected and dried by V10 solvent evaporator. Dried fractions were transferred to a vial with MeCN, and dried under N$_2$ stream at 45° C. to afford 10 mg of 3-(3-((1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoic acid (17.56%). LC-MS m/z 523.2 (M+H)$^+$, 0.95 (ret. time).

Example 61

3-(7-methoxy-1-methyl-1H-benzo[d][1,2,3]triazol-5-yl)-3-(3-(((R)-4-methyl-1,1-dioxido-3,4-dihydro-2H-pyrido[2,3-b][1,4,5]oxathiazepin-2-yl)methyl)phenyl)propanoic acid

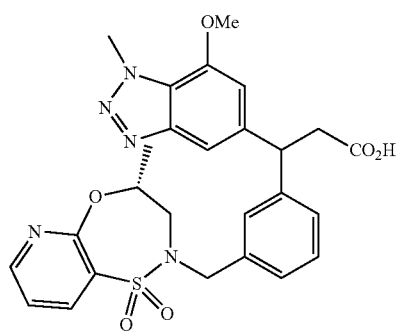 [SMILES: COc1cc(C(CC(=O)O)c2cccc(CN3C[C@@H](C)Oc4ncccc4S3(=O)=O)c2)cc2nnn(C)c12]

Ethyl 3-(3-(hydroxymethyl)phenyl)-3-(7-methoxy-1-methyl-1H-benzo[d][1,2,3]triazol-5-yl)propanoate

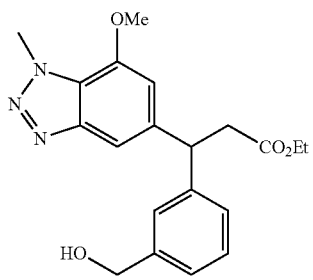 [SMILES: CCOC(=O)CC(c1cccc(CO)c1)c1cc(OC)c2c(c1)nnn2C]

To a solution of (E)-ethyl 3-(7-methoxy-1-methyl-1H-benzo[d][1,2,3]triazol-5-yl)acrylate (1 g, 3.83 mmol) dissolved in 1,4-dioxane (10 mL) and water (10 mL) was added (3-(hydroxymethyl)phenyl)boronic acid (1.90 g, 12.50 mmol), [RhCl(cod)]$_2$ (0.423 g, 0.765 mmol) and TEA (1.227 mL, 8.80 mmol) and the mixture was heated in microwave at 150° C. for 1 h. water (35 mL) was added to the mixture which was extracted with EtOAc thrice; the combined organic layer was dried with MgSO$_4$, concentrated and purified by silica gel chromatography to get 779 mg of ethyl 3-(3-(hydroxymethyl)phenyl)-3-(7-methoxy-1-methyl-1H-benzo[d][1,2,3]triazol-5-yl)propanoate (55.1%). LC-MS m/z 370.0 (M+H)$^+$, 0.87 (ret. time).

3-(7-methoxy-1-methyl-1H-benzo[d][1,2,3]triazol-5-yl)-3-(3-(((R)-4-methyl-1,1-dioxido-3,4-dihydro-2H-pyrido[2,3-b][1,4,5]oxathiazepin-2-yl)methyl)phenyl)propanoic acid

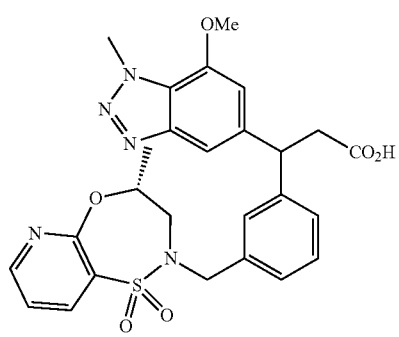 [SMILES: COc1cc(C(CC(=O)O)c2cccc(CN3C[C@@H](C)Oc4ncccc4S3(=O)=O)c2)cc2nnn(C)c12]

To a stirred solution of ethyl 3-(3-(hydroxymethyl)phenyl)-3-(7-methoxy-1-methyl-1H-benzo[d][1,2,3]triazol-5-yl)propanoate (50 mg, 0.135 mmol) dissolved in dry THF (2 mL) was added (R)-4-methyl-3,4-dihydro-2H-pyrido[2,3-b][1,4,5]oxathiazepine 1,1-dioxide (31.3 mg, 0.146 mmol), DIAD (0.078 mL, 0.400 mmol) and PS—PPh$_3$ (253 mg, 0.405 mmol) at 0° C. The ice bath was removed once the addition was over, and the mixture was stirred at RT for 96 h. The mixture was filtered and the solvent was removed; then the mixture was dissolved in MeOH (2 mL) and NaOH 1N (0.406 mL, 0.406 mmol) was added and the mixture was heated in microwave for 1 h at 100° C. The result mixture was acidified with HCl 1N was added until pH=3, concentrated under reduced pressure, and purified on reverse-phase HPLC (Sunfire C18, 19×100 mm, 5 u column), eluting at 18 mL/min with a linear gradient running from 25% CH$_3$CN/H$_2$O (0.1% formic acid) to 50% CH$_3$CN/H$_2$O (0.1% formic acid) over 10 min. The desired fractions were collected and dried by V10 solvent evaporator. Dried fractions were transferred to a vial with MeCN, and dried under N$_2$ stream at 45° C. to afford 24.3 mg of the desired product 3-(7-methoxy-1-methyl-1H-benzo[d][1,2,3]triazol-5-yl)-3-(3-(((R)-4-methyl-1,1-dioxido-3,4-dihydro-2H-pyrido[2,3-b][1,4,5]oxathiazepin-2-yl)methyl)phenyl)propanoic acid (33.4%). LC-MS m/z 538.3 (M+H)$^+$, 0.88 (ret. time).

Example 62

3-(7-methoxy-1-methyl-1H-benzo[d][1,2,3]triazol-5-yl)-3-(3-((4-methyl-1,1-dioxido-3,4-dihydro-2H-benzo[b][1,4,5]oxathiazepin-2-yl)methyl)phenyl)propanoic acid

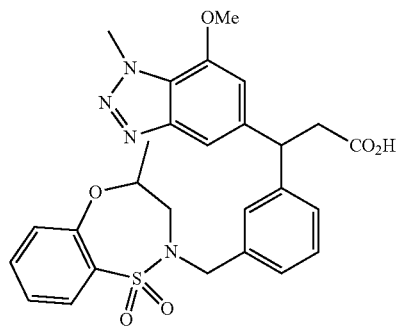 [SMILES: COc1cc(C(CC(=O)O)c2cccc(CN3CC(C)Oc4ccccc4S3(=O)=O)c2)cc2nnn(C)c12]

Ethyl 3-(3-(hydroxymethyl)phenyl)-3-(7-methoxy-1-methyl-1H-benzo[d][1,2,3]triazol-5-yl)propanoate

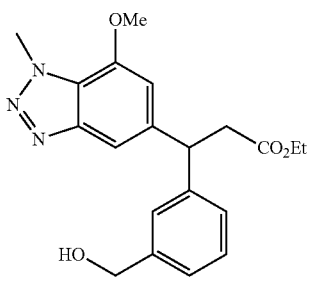 [SMILES: CCOC(=O)CC(c1cccc(CO)c1)c1cc(OC)c2c(c1)nnn2C]

To a solution of (E)-ethyl 3-(7-methoxy-1-methyl-1H-benzo[d][1,2,3]triazol-5-yl)acrylate (1 g, 3.83 mmol) dissolved in 1,4-dioxane (10 mL) and water (10 mL) was added (3-(hydroxymethyl)phenyl)boronic acid (1.90 g, 12.50 mmol), [RhCl(cod)]$_2$ (0.423 g, 0.765 mmol) and TEA (1.227 mL, 8.80 mmol) and the mixture was heated in microwave at 150° C. for 1 h. water (35 mL) was added to the mixture which was extracted with EtOAc thrice; the combined organic layer was dried with MgSO$_4$, concentrated and purified by silica gel chromatography to get 779 mg of ethyl 3-(3-(hydroxymethyl)phenyl)-3-(7-methoxy-1-methyl-1H-benzo[d][1,2,3]triazol-5-yl)propanoate (55.1%). LC-MS m/z 370.0 (M+H)$^+$, 0.87 (ret. time).

3-(7-methoxy-1-methyl-1H-benzo[d][1,2,3]triazol-5-yl)-3-(3-((4-methyl-1,1-dioxido-3,4-dihydro-2H-benzo[b][1,4,5]oxathiazepin-2-yl)methyl)phenyl)propanoic acid

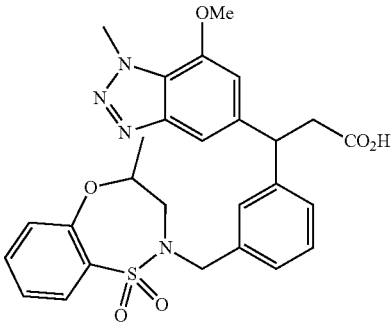 [SMILES: COc1cc(C(CC(=O)O)c2cccc(CN3CC(C)Oc4ccccc4S3(=O)=O)c2)cc2nnn(C)c12]

To a stirred solution of ethyl 3-(3-(hydroxymethyl)phenyl)-3-(7-methoxy-1-methyl-1H-benzo[d][1,2,3]triazol-5-yl)propanoate (50 mg, 0.135 mmol) dissolved in dry THF (2 mL) was added 4-methyl-3,4-dihydro-2H-benzo[b][1,4,5]oxathiazepine 1,1-dioxide (53.3 mg, 0.249 mmol), DIAD (0.088 mL, 0.400 mmol) and PS—PPh$_3$ (169 mg, 0.271 mmol) at 0° C. The ice bath was removed after 20 min, and the mixture was stirred at RT for 50 h. The mixture was filtered, concentrated, dissolved in MeOH (2 mL); then NaOH 1N (1.088 mL, 1.088 mmol) was added and the mixture was heated in microwave for 2 h at 100° C. (after 1 h 34-10).

The result mixture was acidified with HCl 6N (182 mL) then HCl 1N were added until pH=2. The result mixture was concentrated under reduced pressure, and purified on reverse-phase HPLC (Sunfire C18, 19×100 mm, 5 u column), eluting at 18 mL/min with a linear gradient running from 35% CH$_3$CN/H$_2$O (0.1% formic acid) to 65% CH$_3$CN/H$_2$O (0.1% formic acid) over 10 min. The desired fractions were collected and dried by V10 solvent evaporator. Dried fractions were transferred to a vial with MeCN, and dried under N$_2$ stream at 45° C. then evaporated down and given to the purification team to get 27.7 mg of 3-(7-methoxy-1-methyl-1H-benzo[d][1,2,3]triazol-5-yl)-3-(3-((4-methyl-1,1-dioxido-3,4-dihydro-2H-benzo[b][1,4,5]oxathiazepin-2-yl)methyl)phenyl)propanoic acid (38.1%). LC-MS m/z 537.2 (M+H)$^+$, 0.98 (ret. time).

Example 63

3-(7-methoxy-1-methyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)phenyl)propanoic acid

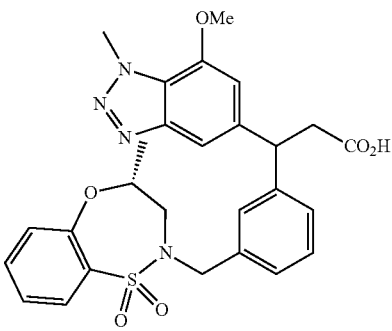 [SMILES: COc1cc(C(CC(=O)O)c2cccc(CN3C[C@@H](C)Oc4ccccc4S3(=O)=O)c2)cc2nnn(C)c12]

Ethyl 3-(3-(hydroxymethyl)phenyl)-3-(7-methoxy-1-methyl-1H-benzo[d][1,2,3]triazol-5-yl)propanoate

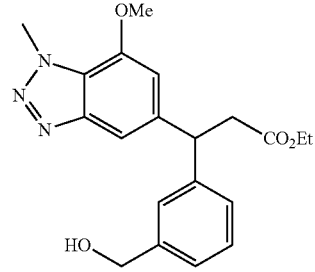 [SMILES: CCOC(=O)CC(c1cccc(CO)c1)c1cc(OC)c2c(c1)nnn2C]

To a solution of (E)-ethyl 3-(7-methoxy-1-methyl-1H-benzo[d][1,2,3]triazol-5-yl)acrylate (1 g, 3.83 mmol) dissolved in 1,4-dioxane (10 mL) and water (10 mL) was added (3-(hydroxymethyl)phenyl)boronic acid (1.90 g, 12.50 mmol), [RhCl(cod)]$_2$ (0.423 g, 0.765 mmol) and TEA (1.227 mL, 8.80 mmol) and the mixture was heated in microwave at 150° C. for 1 h. water (35 mL) was added to the mixture which was extracted with EtOAc thrice; the combined organic layer was dried with MgSO$_4$, concentrated and purified by silica gel chromatography to get 779 mg of ethyl 3-(3-(hydroxymethyl)phenyl)-3-(7-methoxy-1-methyl-1H-benzo[d][1,2,3]triazol-5-yl)propanoate (55.1%).

LC-MS m/z 370.0 (M+H)$^+$, 0.87 (ret. time).

3-(7-methoxy-1-methyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)phenyl)propanoic acid

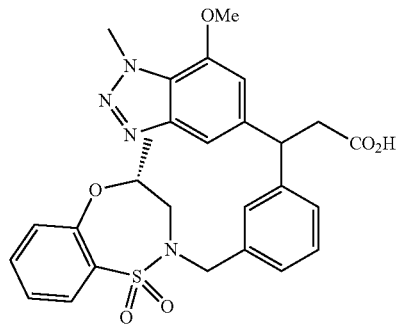 [SMILES: COc1cc(C(CC(=O)O)c2cccc(CN3C[C@@H](C)Oc4ccccc4S3(=O)=O)c2)cc2nnn(C)c12]

To a solution of ethyl 3-(3-(hydroxymethyl)phenyl)-3-(7-methoxy-1-methyl-1H-benzo[d][1,2,3]triazol-5-yl)propanoate (40 mg, 0.108 mmol) dissolved in dry THF (2 mL) was added (R)-4-methyl-3,4-dihydro-2H-benzo[b][1,4,5]oxathiazepine 1,1-dioxide (23.09 mg, 0.108 mmol), DIAD (0.040 mL, 0.206 mmol) and PS—PPh$_3$ (135 mg, 0.217 mmol) at 0° C. The ice bath was removed once the addition was over, and the mixture was stirred at RT for 1 h. The mixture was filtered, concentrated, dissolved in MeOH (2 mL), then NaOH 1N (0.434 mL, 0.434 mmol) was added and the mixture was heated in microwave at 100° C. for 2 h. The result mixture was acidified with HCl 1N until pH=2, concentrated under reduced pressure, and purified on reverse-phase HPLC (Sunfire C18, 19×100 mm, 5 u column), eluting at 18 mL/min with a linear gradient running from 35% CH$_3$CN/H$_2$O (0.1% formic acid) to 65% CH$_3$CN/H$_2$O (0.1% formic acid) over 10 min. The desired fractions were collected and dried by V10 solvent evaporator. Dried fractions were transferred to a vial with MeCN, and dried under N$_2$ stream at 45° C. to get 21.9 mg of 3-(7-methoxy-1-methyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)phenyl)propanoic acid (37.7%). LC-MS m/z 537.2 (M+H)$^+$, 1.01 (ret. time).

Example 64

3-(3-((4-ethyl-1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoic acid

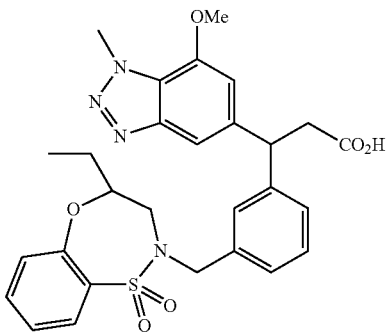 [SMILES: CCC1CN(Cc2cccc(C(CC(=O)O)c3cc(OC)c4c(c3)nnn4C)c2)S(=O)(=O)c2ccccc2O1]

Ethyl 3-(3-(hydroxymethyl)phenyl)-3-(7-methoxy-1-methyl-1H-benzo[d][1,2,3]triazol-5-yl)propanoate

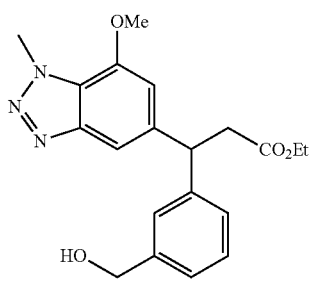 [SMILES: CCOC(=O)CC(c1cccc(CO)c1)c1cc(OC)c2c(c1)nnn2C]

To a solution of (E)-ethyl 3-(7-methoxy-1-methyl-1H-benzo[d][1,2,3]triazol-5-yl)acrylate (1 g, 3.83 mmol) dissolved in 1,4-dioxane (10 mL) and water (10 mL) was added (3-(hydroxymethyl)phenyl)boronic acid (1.90 g, 12.50 mmol), [RhCl(cod)]$_2$ (0.423 g, 0.765 mmol) and TEA (1.227 mL, 8.80 mmol) and the mixture was heated in microwave at 150° C. for 1 h. water (35 mL) was added to the mixture which was extracted with EtOAc thrice; the combined organic layer was dried with MgSO$_4$, concentrated and purified by silica gel chromatography to get 779 mg of ethyl 3-(3-(hydroxymethyl)phenyl)-3-(7-methoxy-1-methyl-1H-benzo[d][1,2,3]triazol-5-yl)propanoate (55.1%). LC-MS m/z 370.0 (M+H)$^+$, 0.87 (ret. time).

3-(3-((4-ethyl-1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoic acid

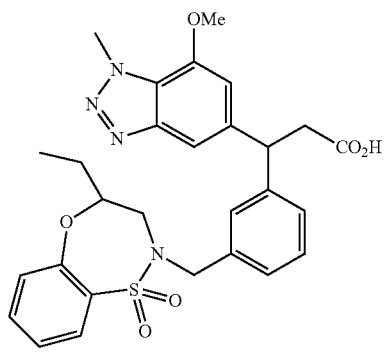 [SMILES: CCC1CN(Cc2cccc(C(CC(=O)O)c3cc(OC)c4c(c3)nnn4C)c2)S(=O)(=O)c2ccccc2O1]

To a stirred solution of ethyl 3-(3-(hydroxymethyl)phenyl)-3-(7-methoxy-1-methyl-1H-benzo[d][1,2,3]triazol-5-yl)propanoate (40 mg, 0.108 mmol) dissolved in dry THF (2 mL) was added 4-ethyl-3,4-dihydro-2H-benzo[b][1,4,5]oxathiazepine 1,1-dioxide (25.8 mg, 0.114 mmol), DIAD (0.042 mL, 0.217 mmol) and PS—PPh$_3$ (135 mg, 0.217 mmol) at 0° C. The ice bath was removed once the addition was over and the mixture was stirred at RT for 1 h. The mixture was filtered, concentrated, dissolved in MeOH (2.000 mL) then NaOH 1N (0.541 mL, 0.541 mmol) was added and the mixture was put in microwave at 100° C. for 1 h. The mixture was acidified with HCl 1N until pH=2-3, concentrated under reduced pressure, and purified on reverse-phase HPLC (Sunfire C18, 19×100 mm, 5 u column), eluting at 18 mL/min with a linear gradient running from 40% CH$_3$CN/H$_2$O (0.1% formic acid) to 65% CH$_3$CN/H$_2$O (0.1% formic acid) over 10 min. The desired fractions were collected and dried by V10 solvent evaporator. Dried fractions were transferred to a vial with MeCN, and dried under N$_2$ stream at 45° C. to get 21.3 mg of 3-(3-((4-ethyl-1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoic acid (35.7%). LC-MS m/z 551.2 (M+H)$^+$, 1.01 (ret. time).

Example 65

3-(3-((4-ethyl-1,1-dioxido-3,4-dihydro-2H-pyrido[2,3-b][1,4,5]oxathiazepin-2-yl)methyl)phenyl)-3-(7-methoxy-1-methyl-1H-benzo[d][1,2,3]triazol-5-yl)propanoic acid

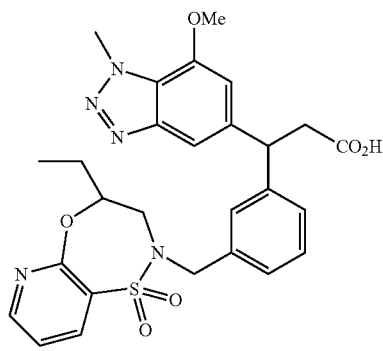 [SMILES: CCC1CN(Cc2cccc(C(CC(=O)O)c3cc(OC)c4c(c3)nnn4C)c2)S(=O)(=O)c2cccnc2O1]

Ethyl 3-(3-(hydroxymethyl)phenyl)-3-(7-methoxy-1-methyl-1H-benzo[d][1,2,3]triazol-5-yl)propanoate

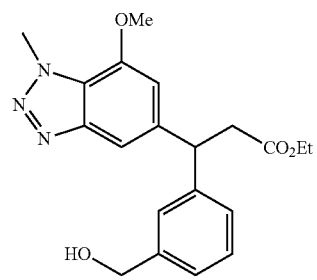 [SMILES: CCOC(=O)CC(c1cccc(CO)c1)c1cc(OC)c2c(c1)nnn2C]

To a solution of (E)-ethyl 3-(7-methoxy-1-methyl-1H-benzo[d][1,2,3]triazol-5-yl)acrylate (1 g, 3.83 mmol) dissolved in 1,4-dioxane (10 mL) and water (10 mL) was added (3-(hydroxymethyl)phenyl)boronic acid (1.90 g, 12.50 mmol), [RhCl(cod)]$_2$ (0.423 g, 0.765 mmol) and TEA (1.227 mL, 8.80 mmol) and the mixture was heated in microwave at 150° C. for 1 h. water (35 mL) was added to the mixture which was extracted with EtOAc thrice; the combined organic layer was dried with MgSO₄, concentrated and purified by silica gel chromatography to get 779 mg of ethyl 3-(3-(hydroxymethyl)phenyl)-3-(7-methoxy-1-methyl-1H-benzo[d][1,2,3]triazol-5-yl)propanoate (55.1%). LC-MS m/z 370.0 (M+H)⁺, 0.87 (ret. time).

3-(3-((4-ethyl-1,1-dioxido-3,4-dihydro-2H-pyrido[2,3-b][1,4,5]oxathiazepin-2-yl)methyl)phenyl)-3-(7-methoxy-1-methyl-1H-benzo[d][1,2,3]triazol-5-yl)propanoic acid

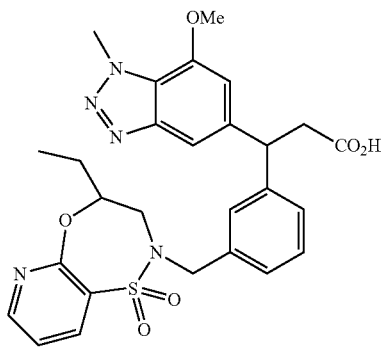 [SMILES: CCC1CN(Cc2cccc(C(CC(=O)O)c3cc(OC)c4c(c3)nnn4C)c2)S(=O)(=O)c2cccnc2O1]

To a stirred solution of ethyl 3-(3-(hydroxymethyl)phenyl)-3-(7-methoxy-1-methyl-1H-benzo[d][1,2,3]triazol-5-yl)propanoate (40 mg, 0.108 mmol) dissolved in dry THF (2 mL) was added 4-ethyl-3,4-dihydro-2H-pyrido[2,3-b][1,4,5]oxathiazepine 1,1-dioxide (26.0 mg, 0.114 mmol), DIAD (0.042 mL, 0.217 mmol) and PS—PPh₃ (135 mg, 0.217 mmol) at 0° C. The ice bath was removed once the addition was over, and the solution was stirred at RT for 1 h. The mixture was filtered, concentrated, dissolved in MeOH (2.000 mL) then NaOH 1N (0.541 mL, 0.541 mmol) was added and the mixture was heated in microwave at 100° C. for 1 h. The mixture was acidified with HCl 1N was added until pH=2-3, concentrated under reduced pressure, and purified on reverse-phase HPLC (Sunfire C18, 19×100 mm, 5 u column), eluting at 18 mL/min with a linear gradient running from 30% CH₃CN/H₂O (0.1% formic acid) to 55% CH₃CN/H₂O (0.1% formic acid) over 10 min. The desired fractions were collected and dried by V10 solvent evaporator. Dried fractions were transferred to a vial with MeCN, and dried under N₂ stream at 45° C. to get 18.3 mg of 3-(3-((4-ethyl-1,1-dioxido-3,4-dihydro-2H-pyrido[2,3-b][1,4,5]oxathiazepin-2-yl)methyl)phenyl)-3-(7-methoxy-1-methyl-1H-benzo[d][1,2,3]triazol-5-yl)propanoic acid (30.6%). LC-MS m/z 552.2 (M+H)⁺, 0.89 (ret. time).

Example 66

3-(1,4-dimethyl-1H-benzo[d][1,2,3]triazol-5-yl)-3-(3-((1,1-dioxido-3,4-dihydro-2H-benzo[b][1,4,5]oxathiazepin-2-yl)methyl)-4-fluorophenyl)propanoic acid

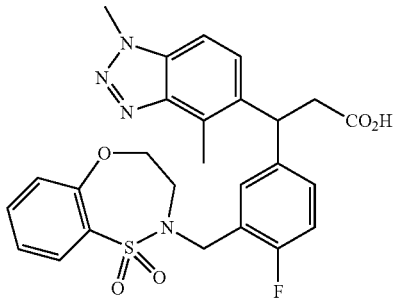 [SMILES: Cc1c(C(CC(=O)O)c2ccc(F)c(CN3CCOc4ccccc4S3(=O)=O)c2)ccc2c1nnn2C]

(2-fluoro-5-(4,4,5,5-tetramethyl-1,3,2-dioxaborolan-2-yl)phenyl)methanol

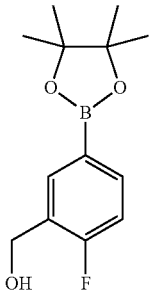 [SMILES: CC1(C)OB(c2ccc(F)c(CO)c2)OC1(C)C]

A suspension of (5-bromo-2-fluorophenyl)methanol (1046 mg, 5.10 mmol) dissolved in 1,4-dioxane (15 mL) was treated with potassium acetate (1903 mg, 19.39 mmol) and 4,4,4',4',5,5,5',5'-octamethyl-2,2'-bi(1,3,2-dioxaborolane) (1555 mg, 6.12 mmol) and put under nitrogen atmosphere for 10 min before adding (PPh₃)₂PdCl₂ (215 mg, 0.306 mmol) then the mixture (which was split in 2 20 mL microwave vials because of the volume) was put in microwave at 120° C. for 30 min. The combined solution was filtered through celite and washed with EtOAc; then the dark colored mixture was washed with water thrice and brine once, dried over MgSO₄, filtered, concentrated and purified by silica gel chromatography to get 762 mg of (2-fluoro-5-(4,4,5,5-tetramethyl-1,3,2-dioxaborolan-2-yl)phenyl)methanol (59.2%). LC-MS m/z 235.0 (M-18)⁺, 0.94 (ret. time).

(E)-ethyl 3-(1,4-dimethyl-1H-benzo[d][1,2,3]triazol-5-yl)acrylate

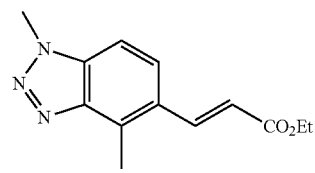

To a solution of 5-bromo-1,4-dimethyl-1H-benzo[d][1,2,3]triazole (1000 mg, 4.42 mmol) dissolved in DMF (14 mL) were added ethyl acrylate (4.24 mL, 39.8 mmol), DIPEA (2.70 mL, 15.48 mmol), tri-o-tolylphosphine (539 mg, 1.769 mmol) and Pd(OAc)₂ (199 mg, 0.885 mmol) and the solution was heated in microwave at 100° C. for 3 h. The result mixture was filtered through celite and washed with EtOAc, then washed with water twice and brine once. The combined organic layer was dried over MgSO₄, filtered, concentrated and purified by silica gel chromatography to get 627.3 mg of (E)-ethyl 3-(1,4-dimethyl-1H-benzo[d][1,2,3]triazol-5-yl)acrylate (57.8%). LC-MS m/z 246.0 (M+1)⁺, 0.85 (ret. time).

Ethyl 3-(1,4-dimethyl-1H-benzo[d][1,2,3]triazol-5-yl)-3-(4-fluoro-3-(hydroxymethyl)phenyl)propanoate

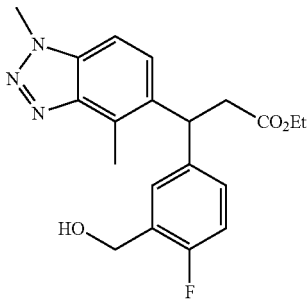 [SMILES: CCOC(=O)CC(c1ccc(F)c(CO)c1)c1ccc2c(nnn2C)c1C]

To a solution of (E)-ethyl 3-(1,4-dimethyl-1H-benzo[d][1,2,3]triazol-5-yl)acrylate (490 mg, 1.998 mmol) and (2-fluoro-5-(4,4,5,5-tetramethyl-1,3,2-dioxaborolan-2-yl)phenyl)methanol (762 mg, 3.02 mmol) dissolved in 1,4-dioxane (9 mL) and water (6 mL) was added [RhCl(cod)]$_2$ (65 mg, 0.132 mmol) and TEA (0.557 mL, 4.00 mmol) and the mixture was heated in microwave at 100° C. for 1 h. The result mixture was filtrated, dissolved in water (10 mL) and EtOAc and the layers were separated. then the mixture was extracted with EtOAc twice. The combined organic layer was dried over MgSO$_4$, filtrated, concentrated and purified by silica gel chromatography to get 400 mg of ethyl 3-(1,4-dimethyl-1H-benzo[d][1,2,3]triazol-5-yl)-3-(4-fluoro-3-(hydroxymethyl)phenyl) propanoate (53.9%). LC-MS m/z 372.2 (M+1)$^+$, 0.84 (ret. time).

3-(1,4-dimethyl-1H-benzo[d][1,2,3]triazol-5-yl)-3-(3-((1,1-dioxido-3,4-dihydro-2H-benzo[b][1,4,5]oxathiazepin-2-yl)methyl)-4-fluorophenyl)propanoic acid

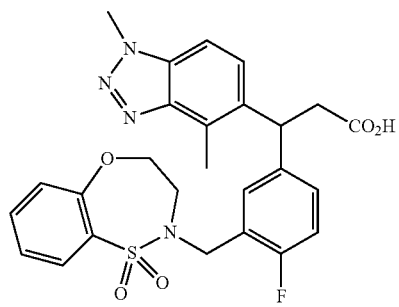 [SMILES: Cc1c(C(CC(=O)O)c2ccc(F)c(CN3CCOc4ccccc4S3(=O)=O)c2)ccc2c1nnn2C]

To a stirred solution of ethyl 3-(1,4-dimethyl-1H-benzo[d][1,2,3]triazol-5-yl)-3-(4-fluoro-3-(hydroxymethyl)phenyl)propanoate (40 mg, 0.108 mmol) dissolved in dry THF (3 mL) were added 3,4-dihydro-2H-benzo[b][1,4,5]oxathiazepine 1,1-dioxide (22.53 mg, 0.113 mmol), DIAD (0.042 mL, 0.215 mmol) and PS—PPh$_3$ (135 mg, 0.215 mmol) at 0° C. The ice bath was removed once the addition was over and the mixture was stirred at RT for 1 h 45 min. The mixture was filtered, concentrated, dissolved in MeOH (2 mL) and NaOH 1N (0.538 mL, 0.538 mmol) was added and then the mixture was heated in microwave at 100° C. for 1 h. The result mixture was acidified with HCl 1N until pH=2-3, concentrated under reduced pressure, and purified on reverse-phase HPLC (Sunfire C18, 19×100 mm, 5 u column), eluting at 18 mL/min with a linear gradient running from 35% CH$_3$CN/H$_2$O (0.1% formic acid) to 60% CH$_3$CN/H$_2$O (0.1% formic acid) over 10 min. The desired fractions were collected and dried by V10 solvent evaporator. Dried fractions were transferred to a vial with MeCN, and dried under N$_2$ stream at 45° C. to get 17.9 mg of 3-(1,4-dimethyl-1H-benzo[d][1,2,3]triazol-5-yl)-3-(3-((1,1-dioxido-3,4-dihydro-2H-benzo[b][1,4,5]oxathiazepin-2-yl)methyl)-4-fluorophenyl)propanoic acid (31.7%). LC-MS m/z 525.3 (M+1)$^+$, 0.94 (ret. time).

Example 67

3-(1,4-dimethyl-1H-benzo[d][1,2,3]triazol-5-yl)-3-(4-fluoro-3-(((R)-4-methyl-1,1-dioxido-3,4-dihydro-2H-benzo[b][1,4,5]oxathiazepin-2-yl)methyl)phenyl)propanoic acid

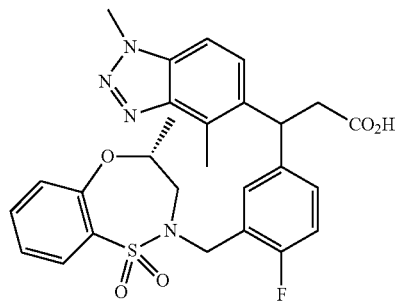 [SMILES: Cc1c(C(CC(=O)O)c2ccc(F)c(CN3C[C@@H](C)Oc4ccccc4S3(=O)=O)c2)ccc2c1nnn2C]

(2-fluoro-5-(4,4,5,5-tetramethyl-1,3,2-dioxaborolan-2-yl)phenyl)methanol

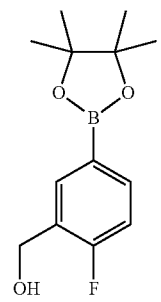

A suspension of (5-bromo-2-fluorophenyl)methanol (1046 mg, 5.10 mmol) dissolved in 1,4-dioxane (15 mL) was treated with potassium acetate (1903 mg, 19.39 mmol) and 4,4,4',4',5,5,5',5'-octamethyl-2,2'-bi(1,3,2-dioxaborolane) (1555 mg, 6.12 mmol) and put under nitrogen atmosphere for 10 min before adding (PPh$_3$)$_2$PdCl$_2$ (215 mg, 0.306 mmol) then the mixture (which was split in 2 20 mL microwave vials because of the volume) was put in microwave at 120° C. for 30 min. The combined solution was filtered through celite and washed with EtOAc; then the dark colored mixture was washed with water thrice and brine once, dried over MgSO$_4$, filtered, concentrated and purified by silica gel chromatography to get 762 mg of (2-fluoro-5-

(4,4,5,5-tetramethyl-1,3,2-dioxaborolan-2-yl)phenyl) methanol (59.2%). LC-MS m/z 235.0 (M-18)⁺, 0.94 (ret. time).

(E)-ethyl 3-(1,4-dimethyl-1H-benzo[d][1,2,3]triazol-5-yl)acrylate

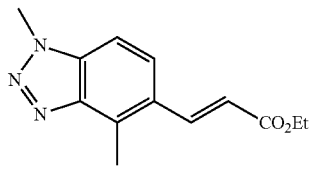 [SMILES: CCOC(=O)/C=C/c1ccc2c(nnn2C)c1C]

To a solution of 5-bromo-1,4-dimethyl-1H-benzo[d][1,2,3]triazole (1000 mg, 4.42 mmol) dissolved in DMF (14 mL) were added ethyl acrylate (4.24 mL, 39.8 mmol), DIPEA (2.70 mL, 15.48 mmol), tri-o-tolylphosphine (539 mg, 1.769 mmol) and Pd(OAc)₂ (199 mg, 0.885 mmol) and the solution was heated in microwave at 100° C. for 3 h. The result mixture was filtered through celite and washed with EtOAc, then washed with water twice and brine once. The combined organic layer was dried over MgSO₄, filtered, concentrated and purified by silica gel chromatography to get 627.3 mg of (E)-ethyl 3-(1,4-dimethyl-1H-benzo[d][1,2,3]triazol-5-yl) acrylate (57.8%). LC-MS m/z 246.0 (M+1)⁺, 0.85 (ret. time).

Ethyl 3-(1,4-dimethyl-1H-benzo[d][1,2,3]triazol-5-yl)-3-(4-fluoro-3-(hydroxymethyl)phenyl)propanoate

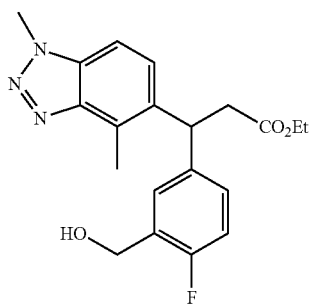 [SMILES: CCOC(=O)CC(c1ccc(F)c(CO)c1)c1ccc2c(nnn2C)c1C]

To a solution of (E)-ethyl 3-(1,4-dimethyl-1H-benzo[d][1,2,3]triazol-5-yl)acrylate (490 mg, 1.998 mmol) and (2-fluoro-5-(4,4,5,5-tetramethyl-1,3,2-dioxaborolan-2-yl)phenyl)methanol (762 mg, 3.02 mmol) dissolved in 1,4-dioxane (9 mL) and water (6 mL) was added [RhCl(cod)]₂ (65 mg, 0.132 mmol) and TEA (0.557 mL, 4.00 mmol) and the mixture was heated in microwave at 100° C. for 1 h. The result mixture was filtrated, dissolved in water (10 mL) and EtOAc and the layers were separated. then the mixture was extracted with EtOAc twice. The combined organic layer was dried over MgSO₄, filtrated, concentrated and purified by silica gel chromatography to get 400 mg of ethyl 3-(1,4-dimethyl-1H-benzo[d][1,2,3]triazol-5-yl)-3-(4-fluoro-3-(hydroxymethyl)phenyl) propanoate (53.9%). LC-MS m/z 372.2 (M+1)⁺, 0.84 (ret. time).

3-(1,4-dimethyl-1H-benzo[d][1,2,3]triazol-5-yl)-3-(4-fluoro-3-(((R)-4-methyl-1,1-dioxido-3,4-dihydro-2H-benzo[b][1,4,5]oxathiazepin-2-yl)methyl)phenyl)propanoic acid

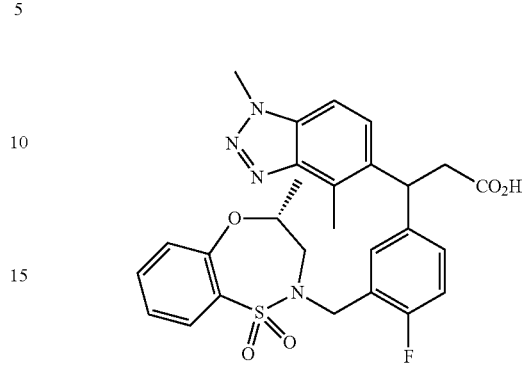

To a stirred solution of ethyl 3-(1,4-dimethyl-1H-benzo[d][1,2,3]triazol-5-yl)-3-(4-fluoro-3-(hydroxymethyl)phenyl)propanoate (40.9 mg, 0.110 mmol) dissolved in dry THF (2 mL) were added (R)-4-methyl-3,4-dihydro-2H-benzo[b][1,4,5]oxathiazepine 1,1-dioxide (24.66 mg, 0.116 mmol), (E)-diisopropyl diazene-1,2-dicarboxylate (0.043 mL, 0.220 mmol) and PS—PPh₃ (138 mg, 0.220 mmol) at 0° C. The ice bath was removed after 20 min, and the mixture was stirred at RT for 18 h. The mixture was filtered, concentrated, dissolved in MeOH (2.000 mL) then NaOH 1N (0.551 mL, 0.551 mmol) was added and the mixture was heated in microwave for 1 h at 100° C. The mixture was acidified with HCl 1N was added to the mixture until pH=2-3, concentrated under reduced pressure, and purified on reverse-phase HPLC (Sunfire C18, 19×100 mm, 5 u column), eluting at 18 mL/min with a linear gradient running from 35% CH₃CN/H₂O (0.1% formic acid) to 65% CH₃CN/H₂O (0.1% formic acid) over 10 min. The desired fractions were collected and dried by V10 solvent evaporator. Dried fractions were transferred to a vial with MeCN, and dried under N₂ stream at 45° C. to get 7.4 mg of 3-(1,4-dimethyl-1H-benzo[d][1,2,3]triazol-5-yl)-3-(4-fluoro-3-(((R)-4-methyl-1,1-dioxido-3,4-dihydro-2H-benzo[b][1,4,5]oxathiazepin-2-yl)methyl)phenyl)propanoic acid (12.48%). LC-MS m/z 532.2 (M+1)⁺, 0.99 (ret. time).

Example 68

3-(1,4-dimethyl-1H-benzo[d][1,2,3]triazol-5-yl)-3-(3-((4-ethyl-1,1-dioxido-3,4-dihydro-2H-benzo[b][1,4,5]oxathiazepin-2-yl)methyl)-4-fluorophenyl)propanoic acid

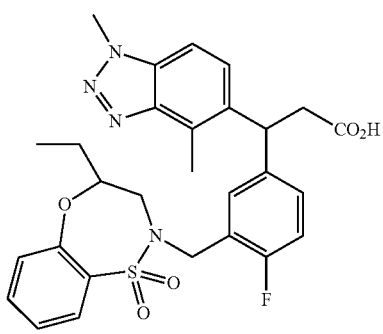 [SMILES: CCC1CN(Cc2cc(C(CC(=O)O)c3ccc4c(nnn4C)c3C)ccc2F)S(=O)(=O)c2ccccc2O1]

163

(2-fluoro-5-(4,4,5,5-tetramethyl-1,3,2-dioxaborolan-2-yl)phenyl)methanol

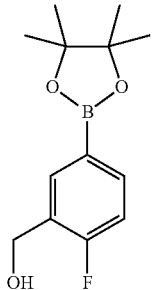 [SMILES: CC1(C)OB(c2ccc(F)c(CO)c2)OC1(C)C]

A suspension of (5-bromo-2-fluorophenyl)methanol (1046 mg, 5.10 mmol) dissolved in 1,4-dioxane (15 mL) was treated with potassium acetate (1903 mg, 19.39 mmol) and 4,4,4',4',5,5,5',5'-octamethyl-2,2'-bi(1,3,2-dioxaborolane) (1555 mg, 6.12 mmol) and put under nitrogen atmosphere for 10 min before adding (PPh$_3$)$_2$PdCl$_2$ (215 mg, 0.306 mmol) then the mixture (which was split in 2 20 mL microwave vials because of the volume) was put in microwave at 120° C. for 30 min. The combined solution was filtered through celite and washed with EtOAc; then the dark colored mixture was washed with water thrice and brine once, dried over MgSO$_4$, filtered, concentrated and purified by silica gel chromatography to get 762 mg of (2-fluoro-5-(4,4,5,5-tetramethyl-1,3,2-dioxaborolan-2-yl)phenyl) methanol (59.2%). LC-MS m/z 235.0 (M-18)$^+$, 0.94 (ret. time).

(E)-ethyl 3-(1,4-dimethyl-1H-benzo[d][1,2,3]triazol-5-yl)acrylate

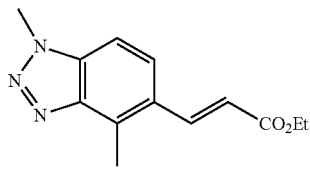 [SMILES: CCOC(=O)/C=C/c1ccc2c(nnn2C)c1C]

To a solution of 5-bromo-1,4-dimethyl-1H-benzo[d][1,2,3]triazole (1000 mg, 4.42 mmol) dissolved in DMF (14 mL) were added ethyl acrylate (4.24 mL, 39.8 mmol), DIPEA (2.70 mL, 15.48 mmol), tri-o-tolylphosphine (539 mg, 1.769 mmol) and Pd(OAc)$_2$ (199 mg, 0.885 mmol) and the solution was heated in microwave at 100° C. for 3 h. The result mixture was filtered through celite and washed with EtOAc, then washed with water twice and brine once. The combined organic layer was dried over MgSO$_4$, filtered, concentrated and purified by silica gel chromatography to get 627.3 mg of (E)-ethyl 3-(1,4-dimethyl-1H-benzo[d][1,2,3]triazol-5-yl)acrylate (57.8%). LC-MS m/z 246.0 (M+1)$^+$, 0.85 (ret. time).

164

Ethyl 3-(1,4-dimethyl-1H-benzo[d][1,2,3]triazol-5-yl)-3-(4-fluoro-3-(hydroxymethyl)phenyl)propanoate

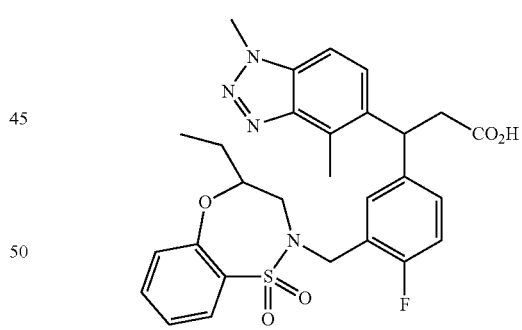

To a solution of (E)-ethyl 3-(1,4-dimethyl-1H-benzo[d][1,2,3]triazol-5-yl)acrylate (490 mg, 1.998 mmol) and (2-fluoro-5-(4,4,5,5-tetramethyl-1,3,2-dioxaborolan-2-yl)phenyl)methanol (762 mg, 3.02 mmol) dissolved in 1,4-dioxane (9 mL) and water (6 mL) was added [RhCl(cod)]$_2$ (65 mg, 0.132 mmol) and TEA (0.557 mL, 4.00 mmol) and the mixture was heated in microwave at 100° C. for 1 h. The result mixture was filtrated, dissolved in water (10 mL) and EtOAc and the layers were separated. then the mixture was extracted with EtOAc twice. The combined organic layer was dried over MgSO$_4$, filtrated, concentrated and purified by silica gel chromatography to get 400 mg of ethyl 3-(1,4-dimethyl-1H-benzo[d][1,2,3]triazol-5-yl)-3-(4-fluoro-3-(hydroxymethyl)phenyl) propanoate (53.9%). LC-MS m/z 372.2 (M+1)$^+$, 0.84 (ret. time).

3-(1,4-dimethyl-1H-benzo[d][1,2,3]triazol-5-yl)-3-(3-((4-ethyl-1,1-dioxido-3,4-dihydro-2H-benzo[b][1,4,5]oxathiazepin-2-yl)methyl)-4-fluorophenyl)propanoic acid To a stirred solution of ethyl 3-(1,4-dimethyl-1H-benzo[d][1,2,3]triazol-5-yl)-3-(4-fluoro-3-(hydroxymethyl)phenyl)propanoate (40 mg, 0.108 mmol) dissolved in dry THF (2 mL) were added 4-ethyl-3,4-dihydro-2H-benzo[b][1,4,5]oxathiazepine 1,1-dioxide (25.7 mg, 0.113 mmol), DIAD (0.042 mL, 0.215 mmol) and PS—PPh$_3$ (135 mg, 0.215 mmol) at 0° C. The ice bath was removed after 10 min and the mixture was stirred at RT for 4 h. The mixture was filtered, concentrated, dissolved in MeOH (2.000 mL), then NaOH 1N (0.538 mL, 0.538 mmol) was added and the mixture was heated in microwave at 100° C. for 45 min. The result mixture was acidified with HCl 1N was added until pH=2-3, concentrated under reduced pressure, and purified on reverse-phase HPLC (Sunfire C18, 19×100 mm, 5 u column), eluting at 18 mL/min with a linear gradient running from 25% CH₃CN/H₂O (0.1% formic acid) to 50% CH₃CN/H₂O (0.1% formic acid) over 10 min. The desired fractions were collected and dried by V10 solvent evaporator. Dried fractions were transferred to a vial with MeCN, and dried under N$_2$ stream at 45° C. to get 27.1 mg of 3-(1,4-dimethyl-1H-benzo[d][1,2,3]triazol-5-yl)-3-(3-((4-ethyl-1,1-dioxido-3,4-dihydro-2H-benzo[b][1,4,5]oxathiazepin-2-yl)methyl)-4-fluorophenyl)propanoic acid (45.5%). LC-MS m/z 553.2 (M+1)$^+$, 1.05 (ret. time).

Example 69

3-(1,4-dimethyl-1H-benzo[d][1,2,3]triazol-5-yl)-3-(4-fluoro-3-(((R)-4-methyl-1,1-dioxido-3,4-dihydro-2H-pyrido[2,3-b][1,4,5]oxathiazepin-2-yl)methyl)phenyl)propanoic acid

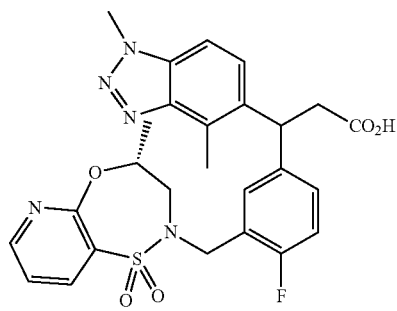 [SMILES: Cc1c(C(CC(=O)O)c2ccc(F)c(CN3C[C@@H](C)Oc4ncccc4S3(=O)=O)c2)ccc2c1nnn2C]

(2-fluoro-5-(4,4,5,5-tetramethyl-1,3,2-dioxaborolan-2-yl)phenyl)methanol

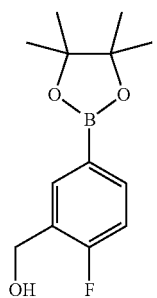 [SMILES: CC1(C)OB(c2ccc(F)c(CO)c2)OC1(C)C]

A suspension of (5-bromo-2-fluorophenyl)methanol (1046 mg, 5.10 mmol) dissolved in 1,4-dioxane (15 mL) was treated with potassium acetate (1903 mg, 19.39 mmol) and 4,4,4',4',5,5,5',5'-octamethyl-2,2'-bi(1,3,2-dioxaborolane) (1555 mg, 6.12 mmol) and put under nitrogen atmosphere for 10 min before adding (PPh₃)₂PdCl₂ (215 mg, 0.306 mmol) then the mixture (which was split in 2 20 mL microwave vials because of the volume) was put in microwave at 120° C. for 30 min. The combined solution was filtered through celite and washed with EtOAc; then the dark colored mixture was washed with water thrice and brine once, dried over MgSO₄, filtered, concentrated and purified by silica gel chromatography to get 762 mg of (2-fluoro-5-(4,4,5,5-tetramethyl-1,3,2-dioxaborolan-2-yl)phenyl)methanol (59.2%). LC-MS m/z 235.0 (M-18)$^+$, 0.94 (ret. time).

(E)-ethyl 3-(1,4-dimethyl-1H-benzo[d][1,2,3]triazol-5-yl)acrylate

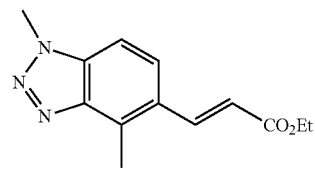

To a solution of 5-bromo-1,4-dimethyl-1H-benzo[d][1,2,3]triazole (1000 mg, 4.42 mmol) dissolved in DMF (14 mL) were added ethyl acrylate (4.24 mL, 39.8 mmol), DIPEA (2.70 mL, 15.48 mmol), tri-o-tolylphosphine (539 mg, 1.769 mmol) and Pd(OAc)₂ (199 mg, 0.885 mmol) and the solution was heated in microwave at 100° C. for 3 h. The result mixture was filtered through celite and washed with EtOAc, then washed with water twice and brine once. The combined organic layer was dried over MgSO₄, filtered, concentrated and purified by silica gel chromatography to get 627.3 mg of (E)-ethyl 3-(1,4-dimethyl-1H-benzo[d][1,2,3]triazol-5-yl)acrylate (57.8%). LC-MS m/z 246.0 (M+1)$^+$, 0.85 (ret. time).

Ethyl 3-(1,4-dimethyl-1H-benzo[d][1,2,3]triazol-5-yl)-3-(4-fluoro-3-(hydroxymethyl)phenyl)propanoate

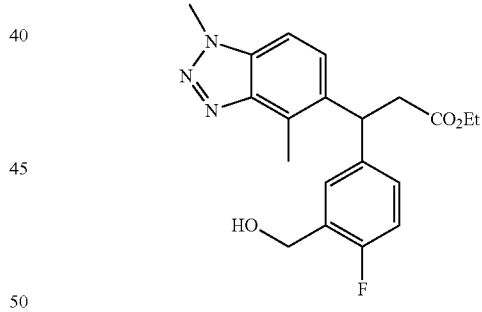

To a solution of (E)-ethyl 3-(1,4-dimethyl-1H-benzo[d][1,2,3]triazol-5-yl)acrylate (490 mg, 1.998 mmol) and (2-fluoro-5-(4,4,5,5-tetramethyl-1,3,2-dioxaborolan-2-yl)phenyl)methanol (762 mg, 3.02 mmol) dissolved in 1,4-dioxane (9 mL) and water (6 mL) was added [RhCl(cod)]₂ (65 mg, 0.132 mmol) and TEA (0.557 mL, 4.00 mmol) and the mixture was heated in microwave at 100° C. for 1 h. The result mixture was filtrated, dissolved in water (10 mL) and EtOAc and the layers were separated. then the mixture was extracted with EtOAc twice. The combined organic layer was dried over MgSO₄, filtrated, concentrated and purified by silica gel chromatography to get 400 mg of ethyl 3-(1,4-dimethyl-1H-benzo[d][1,2,3]triazol-5-yl)-3-(4-fluoro-3-(hydroxymethyl)phenyl)propanoate (53.9%). LC-MS m/z 372.2 (M+1)$^+$, 0.84 (ret. time).

167

3-(1,4-dimethyl-1H-benzo[d][1,2,3]triazol-5-yl)-3-(4-fluoro-3-(((R)-4-methyl-1,1-dioxido-3,4-dihydro-2H-pyrido[2,3-b][1,4,5]oxathiazepin-2-yl)methyl)phenyl)propanoic acid

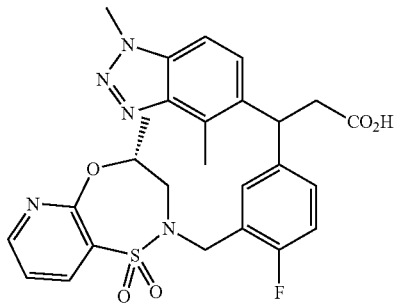 [SMILES: Cc1c(C(CC(=O)O)c2ccc(F)c(CN3C[C@@H](C)Oc4ncccc4S3(=O)=O)c2)ccc2c1nnn2C]

To a solution of ethyl 3-(1,4-dimethyl-1H-benzo[d][1,2,3]triazol-5-yl)-3-(4-fluoro-3-(hydroxymethyl)phenyl)propanoate (40 mg, 0.108 mmol) dissolved in dry THF (2 mL) was added (R)-4-methyl-3,4-dihydro-2H-pyrido[2,3-b][1,4,5]oxathiazepine 1,1-dioxide (25 mg, 0.117 mmol), DIAD (0.042 mL, 0.215 mmol) and PS—PPh$_3$ (135 mg, 0.215 mmol) at 0° C. The ice bath was removed after for 10 min and the mixture was stirred at RT for 2 h 30 min. The mixture was concentrated, dissolved in MeOH (2.000 mL) and the mixture was heated in microwave at 100° C. for 1 h. The result mixture was acidified with HCl 1N was added until pH=2-3, then the mixture was concentrated under reduced pressure, and purified on reverse-phase HPLC (Sunfire C18, 19×100 mm, 5 u column), eluting at 18 mL/min with a linear gradient running from 30% CH$_3$CN/H$_2$O (0.1% formic acid) to 55% CH$_3$CN/H$_2$O (0.1% formic acid) over 10 min. The desired fractions were collected and dried by V10 solvent evaporator. Dried fractions were transferred to a vial with MeCN, and dried under N$_2$ stream at 45° C. to get 28.5 mg of the desired product 3-(1,4-dimethyl-1H-benzo[d][1,2,3]triazol-5-yl)-3-(4-fluoro-3-(((R)-4-methyl-1,1-dioxido-3,4-dihydro-2H-pyrido[2,3-b][1,4,5]oxathiazepin-2-yl)methyl)phenyl)propanoic acid (49.0%). LC-MS m/z 540.2 (M+1)$^+$, 0.84 (ret. time).

Example 70

3-(1,4-dimethyl-1H-benzo[d][1,2,3]triazol-5-yl)-3-(3-((1,1-dioxido-3,4-dihydro-2H-pyrido[4,3-b][1,4,5]oxathiazepin-2-yl)methyl)-4-methylphenyl)propanoic acid

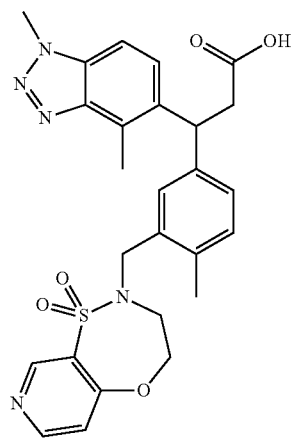

168

Ethyl 3-(1,4-dimethyl-1H-benzo[d][1,2,3]triazol-5-yl)-3-(3-(hydroxymethyl)-4-methylphenyl)propanoate

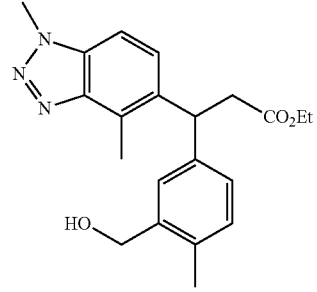 [SMILES: CCOC(=O)CC(c1ccc(C)c(CO)c1)c1ccc2c(nnn2C)c1C]

(E)-ethyl 3-(1,4-dimethyl-1H-benzo[d][1,2,3]triazol-5-yl)acrylate (400 mg, 1.631 mmol) in 1,4-dioxane (10 mL) and water (5 mL) was treated with (3-(hydroxymethyl)-4-methylphenyl)boronic acid (406 mg, 2.446 mmol), Et$_3$N (0.341 mL, 2.446 mmol) and [RhCl(cod)]$_2$ (45.1 mg, 0.082 mmol). The result reaction mixture was stirred at 95° C. for 90 min. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min to give 410 mg (68.4%) of the title compound.

LC-MS m/z 368.2 (M+H)$^+$, 0.87 (ret. time).

(R)-4-methyl-3,4-dihydro-2H-benzo[b][1,4,5]oxathiazepine 1,1-dioxide

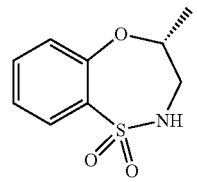

(R)-1-aminopropan-2-ol (0.198 mL, 2.57 mmol) in THF (5 mL) and water (1.250 mL) was treated with K$_2$CO$_3$ (355 mg, 2.57 mmol) and then 2-fluorobenzene-1-sulfonyl chloride (0.340 mL, 2.57 mmol) slowly. The result reaction mixture was stirred at RT for 1 h. The reaction mixture was diluted with H$_2$O (10 mL), extracted with EtOAc (20+2*10 mL). The combined organic layer was washed with brine (15 mL), dried over MgSO$_4$, and concentrated to give 690 mg of crude (R)-2-amino-N-(2-hydroxypropyl)benzene sulfonamide. (R)-2-fluoro-N-(2-hydroxypropyl)benzenesulfonamide (690 mg, 2.96 mmol) in DMSO (4 mL) was added KOt-Bu (996 mg, 8.87 mmol) then heated at 80° C. for 2 h. The reaction mixture was diluted with H$_2$O (10 mL), acidified with HCl (1 N) to pH 7, extracted with EtOAc (3×20 mL). The combined organic layer was washed with brine (20 mL), dried over MgSO$_4$, filtered, and concentrated to give 525 mg (83%) of the title compound. LC-MS m/z 214.0 (M+H)$^+$, 0.58 (ret. time).

Ethyl 3-(1,4-dimethyl-1H-benzo[d][1,2,3]triazol-5-yl)-3-(3-((1,1-dioxido-3,4-dihydro-2H-pyrido[4,3-b][1,4,5]oxathiazepin-2-yl)methyl)-4-methylphenyl)propanoate

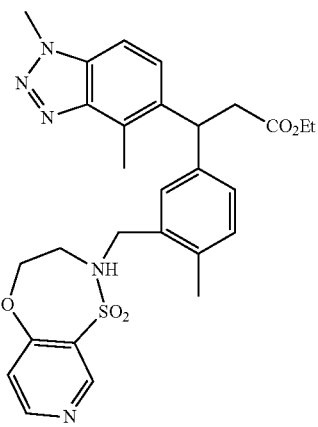 [SMILES: CCOC(=O)CC(c1ccc(C)c(CN2CCOc3ccncc3S2(=O)=O)c1)c1ccc2c(nnn2C)c1C]

To a solution of ethyl 3-(1,4-dimethyl-1H-benzo[d][1,2,3]triazol-5-yl)-3-(3-(hydroxymethyl)-4-methylphenyl)propanoate (160 mg, 0.435 mmol), 3,4-dihydro-2H-pyrido[4,3-b][1,4,5]oxathiazepine 1,1-dioxide (92 mg, 0.457 mmol), and ADDP (220 mg, 0.871 mmol) in THF (5 mL) at 0° C. was added tributylphosphine (176 mg, 0.871 mmol). The ice-bath was removed after 20 min and stirring continued at RT for 1 h. ADDP (220 mg, 0.871 mmol) and tributylphosphine (176 mg, 0.871 mmol) was added and the reaction was stirred for 48 h. The reaction mixture was concentrated and purified by reverse-phase HPLC neutral condition to give 110 mg (46%) of the title compound. LC-MS m/z 550.3 (M+H)$^+$, 1.01 (ret. time).

3-(1,4-dimethyl-1H-benzo[d][1,2,3]triazol-5-yl)-3-(3-((1,1-dioxido-3,4-dihydro-2H-pyrido[4,3-b][1,4,5]oxathiazepin-2-yl)methyl)-4-methylphenyl)propanoic acid

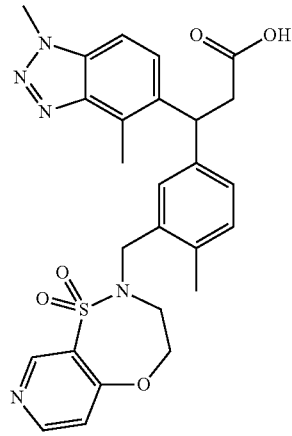

Ethyl 3-(1,4-dimethyl-1H-benzo[d][1,2,3]triazol-5-yl)-3-(3-((1,1-dioxido-3,4-dihydro-2H-pyrido[4,3-b][1,4,5]oxathiazepin-2-yl)methyl)-4-methylphenyl)propanoate (110 mg, 0.200 mmol) was dissolved in THF (2 mL) and water (0.400 mL) then was added LiOH (47.9 mg, 2.001 mmol). The reaction mixture was stirred at RT for 20 h. The reaction mixture was acidified with HCl (1 N) and concentrated. The crude product was dissolved in DMSO (1 mL), filtered through a 0.45 μm acrodisc, and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 101 mg (97%) of the title compound. LC-MS m/z 550.3 (M+H)$^+$, 1.01 (ret. time).

Example 71

3-(1,4-dimethyl-1H-benzo[d][1,2,3]triazol-5-yl)-3-(4-methyl-3-((5-methyl-1,1-dioxido-4,5-dihydropyrido[4,3-f][1,2,5]thiadiazepin-2(3H)-yl)methyl)phenyl)propanoic acid

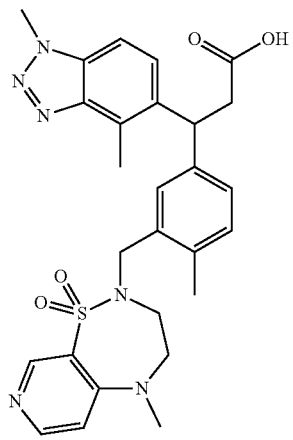 [SMILES: Cc1ccc(C(CC(=O)O)c2ccc3c(nnn3C)c2C)cc1CN1CCN(C)c2ccncc2S1(=O)=O]

Ethyl 3-(1,4-dimethyl-1H-benzo[d][1,2,3]triazol-5-yl)-3-(3-(hydroxymethyl)-4-methylphenyl)propanoate

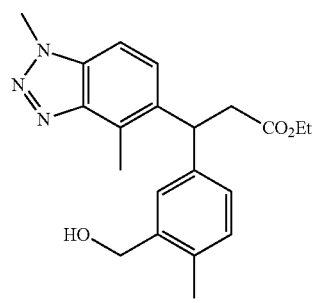 [SMILES: CCOC(=O)CC(c1ccc(C)c(CO)c1)c1ccc2c(nnn2C)c1C]

(E)-ethyl 3-(1,4-dimethyl-1H-benzo[d][1,2,3]triazol-5-yl)acrylate (400 mg, 1.631 mmol) in 1,4-dioxane (10 mL) and water (5 mL) was added (3-(hydroxymethyl)-4-methylphenyl)boronic acid (406 mg, 2.446 mmol), Et$_3$N (0.341 mL, 2.446 mmol) and [RhCl(cod)]$_2$ (45.1 mg, 0.082 mmol). The result reaction mixture was stirred at 95° C. for 90 min. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min to give 410 mg (68.4%) of the title compound. LC-MS m/z 368.2 (M+H)$^+$, 0.87 (ret. time).

Ethyl 3-(1,4-dimethyl-1H-benzo[d][1,2,3]triazol-5-yl)-3-(4-methyl-3-((5-methyl-1,1-dioxido-4,5-dihydropyrido[4,3-f][1,2,5]thiadiazepin-2(3H)-yl)methyl)phenyl)propanoate

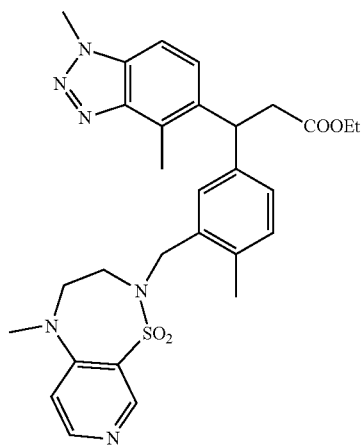 [SMILES: CCOC(=O)CC(c1ccc(C)c(CN2CCN(C)c3ccncc3S2(=O)=O)c1)c1ccc2c(nnn2C)c1C]

To a solution of ethyl 3-(1,4-dimethyl-1H-benzo[d][1,2,3]triazol-5-yl)-3-(3-(hydroxymethyl)-4-methylphenyl)propanoate (145 mg, 0.394 mmol), 5-methyl-2,3,4,5-tetrahydropyrido[4,3-f][1,2,5]thiadiazepine 1,1-dioxide (80 mg, 0.375 mmol), and ADDP (189 mg, 0.750 mmol) in THF (5 mL) at 0° C. was added tributylphosphine (152 mg, 0.750 mmol). The ice-bath was removed after 20 min and stirring continued at RT for 1 h. Added tributylphosphine (152 mg, 0.750 mmol) and ADDP (189 mg, 0.750 mmol) more, and stirred at RT for 18 h. The reaction mixture was concentrated and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 60 mg (28.4%) of the title compound. LC-MS m/z 566.3 (M+H)$^+$, 0.82 (ret. time).

3-(1,4-dimethyl-1H-benzo[d][1,2,3]triazol-5-yl)-3-(4-methyl-3-((5-methyl-1,1-dioxido-4,5-dihydropyrido[4,3-f][1,2,5]thiadiazepin-2(3H)-yl)methyl)phenyl)propanoic acid

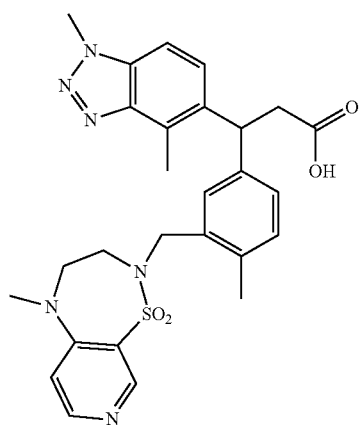 [SMILES: Cc1ccc(C(CC(=O)O)c2ccc3c(nnn3C)c2C)cc1CN1CCN(C)c2ccncc2S1(=O)=O]

Ethyl 3-(1,4-dimethyl-1H-benzo[d][1,2,3]triazol-5-yl)-3-(4-methyl-3-((5-methyl-1,1-dioxido-4,5-dihydropyrido[4,3-f][1,2,5]thiadiazepin-2(3H)-yl)methyl)phenyl)propanoate (60 mg, 0.107 mmol) was dissolved in THF (1 mL) and water (0.200 mL) then was added LiOH (25.5 mg, 1.066 mmol). The result reaction mixture was stirred at RT for 20 h. The reaction mixture was acidified with HCl (1 N) and concentrated. The crude product was dissolved in DMSO (1 mL), filtered through a 0.45 μm acrodisc, and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 20 mg (35%) of the title compound. LC-MS m/z 534.9 (M+H)$^+$, 0.68 (ret. time).

Example 72

3-(4-chloro-3-(((R)-4-methyl-1,1-dioxido-3,4-dihydro-2H-benzo[b][1,4,5]oxathiazepin-2-yl)methyl)phenyl)-3-(1,4-dimethyl-1H-benzo[d][1,2,3]triazol-5-yl)propanoic acid

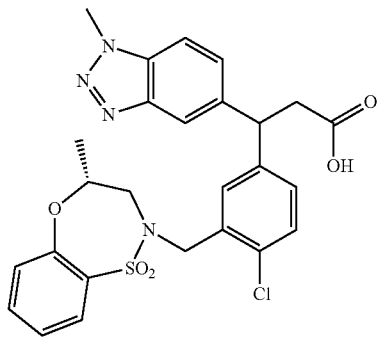 [SMILES: C[C@@H]1CN(Cc2cc(C(CC(=O)O)c3ccc4c(c3)nnn4C)ccc2Cl)S(=O)(=O)c2ccccc2O1]

Ethyl 3-(4-chloro-3-(hydroxymethyl)phenyl)-3-(1,4-dimethyl-1H-benzo[d][1,2,3]triazol-5-yl)propanoate

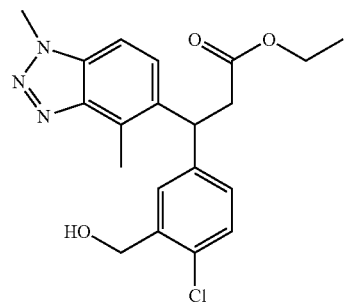 [SMILES: CCOC(=O)CC(c1ccc(Cl)c(CO)c1)c1ccc2c(nnn2C)c1C]

To a suspension of (E)-ethyl 3-(1,4-dimethyl-1H-benzo[d][1,2,3]triazol-5-yl)acrylate (300 mg, 1.223 mmol), (2-chloro-5-(4,4,5,5-tetramethyl-1,3,2-dioxaborolan-2-yl)phenyl)methanol (657 mg, 2.446 mmol) Et$_3$N (0.707 mL, 5.10 mmol) in 1,4-dioxane (20 mL) and water (10 mL) at RT was added [RhCl(cod)]$_2$ (33.8 mg, 0.061 mmol). The resulting suspension was heated at 95° C. for 1 h. The reaction mixture was diluted with water and extracted with EtOAc (3×). The combined organic phases were washed with water (3×), brine (1×), dried over MgSO$_4$ and the solvent removed under reduced pressure. The crude product was purified on a silica cartridge (40 g) with a Combiflash Companion, eluting at 35 mL/min with a gradient running from 0% EtOAc/hexanes to 70% over 35 min. LC-MS m/z 388.0 (M+H)+, 0.92 (ret. time).

Ethyl 3-(4-chloro-3-(((R)-4-methyl-1,1-dioxido-3,4-dihydro-2H-benzo[b][1,4,5]oxathiazepin-2-yl)methyl)phenyl)-3-(1,4-dimethyl-1H-benzo[d][1,2,3]triazol-5-yl)propanoate

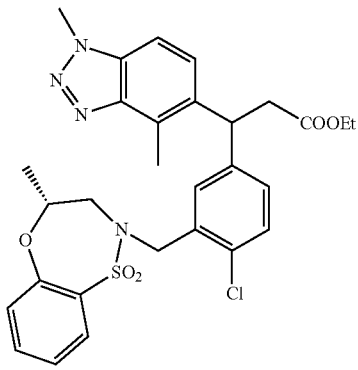 [SMILES: CCOC(=O)CC(c1ccc(Cl)c(CN2C[C@@H](C)Oc3ccccc3S2(=O)=O)c1)c1ccc2c(nnn2C)c1C]

To a solution of ethyl 3-(4-chloro-3-(hydroxymethyl)phenyl)-3-(1,4-dimethyl-1H-benzo[d][1,2,3]triazol-5-yl)propanoate (80 mg, 0.206 mmol), (R)-4-methyl-3,4-dihydro-2H-benzo[b][1,4,5]oxathiazepine 1,1-dioxide (66.0 mg, 0.309 mmol), and ADDP (156 mg, 0.619 mmol) in THF (3 mL) at 0° C. was added tributylphosphine (125 mg, 0.619 mmol). The ice-bath was removed after 20 min and stirring continued at RT for 1 h. Additional tributylphosphine (125 mg, 0.619 mmol) and ADDP (156 mg, 0.619 mmol) was added, and the reaction stirred at RT for 3 h. The reaction mixture was concentrated and purified by reverse-phase HPLC (YMC C18 S-5 µm/12 nm 50×20 mm preparatory column), eluting at 20 mL/min with a linear gradient running from 20% CH3CN/H2O to 90% CH3CN/H2O over 10 min to give 55 mg (45.7%) of the title compound. LC-MS m/z 583.3 (M+H)+, 1.21 (ret. time).

3-(4-chloro-3-(((R)-4-methyl-1,1-dioxido-3,4-dihydro-2H-benzo[b][1,4,5]oxathiazepin-2-yl)methyl)phenyl)-3-(1,4-dimethyl-1H-benzo[d][1,2,3]triazol-5-yl)propanoic acid

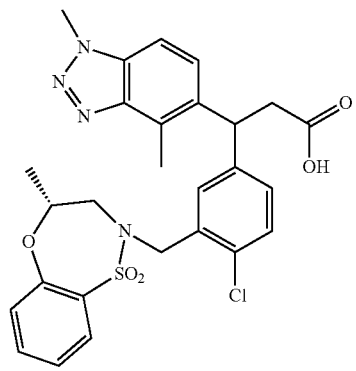 [SMILES: Cc1c(C(CC(=O)O)c2ccc(Cl)c(CN3C[C@@H](C)Oc4ccccc4S3(=O)=O)c2)ccc2c1nnn2C]

Ethyl 3-(4-chloro-3-(((R)-4-methyl-1,1-dioxido-3,4-dihydro-2H-benzo[b][1,4,5]oxathiazepin-2-yl)methyl)phenyl)-3-(1,4-dimethyl-1H-benzo[d][1,2,3]triazol-5-yl)propanoate (55 mg, 0.094 mmol) was dissolved in THF (2 mL) and water (0.400 mL) then was added LiOH (22.59 mg, 0.943 mmol). The result reaction mixture was stirred at RT for 20 h. The reaction mixture was acidified with HCl (1 N) and concentrated. The crude product was dissolved in DMSO (1 mL), filtered through a 0.45 µm acrodisc, and purified by reverse-phase HPLC (YMC C18 S-5 µm/12 nm 50×20 mm preparatory column), eluting at 20 mL/min with a linear gradient running from 20% CH3CN/H2O to 90% CH3CN/H2O over 10 min to give 32 mg (61.1%) of the title compound. LC-MS m/z 555.0 (M+H)+, 0.98 (ret. time).

Example 73

3-(4-chloro-3-(((R)-4-methyl-1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoic acid

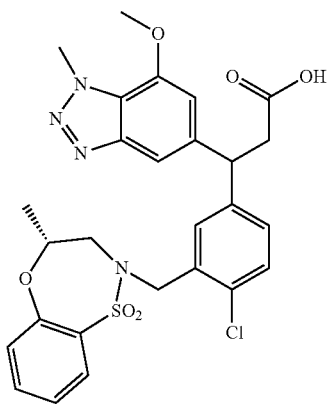 [SMILES: COc1cc(C(CC(=O)O)c2ccc(Cl)c(CN3C[C@@H](C)Oc4ccccc4S3(=O)=O)c2)cc2nnn(C)c12]

Ethyl 3-(4-chloro-3-(hydroxymethyl)phenyl)-3-(7-methoxy-1-methyl-1H-benzo[d][1,2,3]triazol-5-yl)propanoate

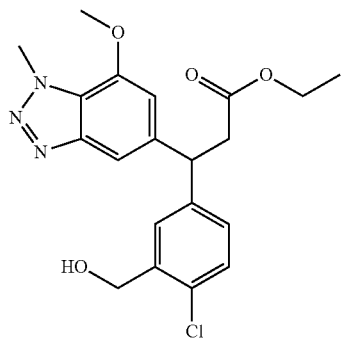 [SMILES: CCOC(=O)CC(c1ccc(Cl)c(CO)c1)c1cc(OC)c2c(c1)nnn2C]

(E)-ethyl 3-(7-methoxy-1-methyl-1H-benzo[d][1,2,3]triazol-5-yl)acrylate (200 mg, 0.765 mmol) in 1,4-dioxane (10 mL) and water (5.00 mL) was added (2-chloro-5-(4,4,5,5-tetramethyl-1,3,2-dioxaborolan-2-yl)phenyl)methanol (370 mg, 1.378 mmol), Et3N (116 mg, 1.148 mmol) and [RhCl(cod)]2 (21.17 mg, 0.038 mmol). The resulting reaction mixture was stirred at 95° C. for 1 h. The reaction mixture was extracted with EtOAc (3×10 mL). The combined organic layer was dried over MgSO4, filtered and concentrated. Then, product was purified over a silica cartridge (40 g) using Combiflash Companion eluting at 18 mL/min running a gradient of 0-30% EtOAc/hexane over 30 min then 30% to 100% over 20 min to give 120 mg (38.8%) of the title compound. LC-MS m/z 404.1 (M+H)+, 0.95 (ret. time).

ethyl 3-(4-chloro-3-(((R)-4-methyl-1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoate

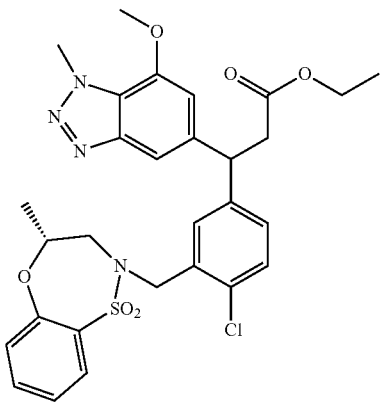 [SMILES: CCOC(=O)CC(c1ccc(Cl)c(CN2C[C@@H](C)Oc3ccccc3S2(=O)=O)c1)c1cc(OC)c2c(c1)nnn2C]

To a solution of ethyl 3-(4-chloro-3-(hydroxymethyl)phenyl)-3-(7-methoxy-1-methyl-1H-benzo[d][1,2,3]triazol-5-yl)propanoate (120 mg, 0.297 mmol), (R)-4-methyl-3,4-dihydro-2H-benzo[b][1,4,5]oxathiazepine 1,1-dioxide (63.4 mg, 0.297 mmol) and ADDP (75.0 mg, 0.297 mmol) in THF (5 mL) at 0° C. was added tributylphosphine (0.073 mL, 0.297 mmol). The ice-bath was removed after 20 min and stirring continued at RT for 1 h. Added tributylphosphine (0.073 mL, 0.297 mmol) and ADDP (75.0 mg, 0.297 mmol) more, and stirred at RT for 3 h. The reaction mixture was concentrated and purified by reverse-phase HPLC (YMC C18 S-5 μm/12 nm 50×20 mm preparatory column), eluting at 20 mL/min with a linear gradient running from 20% CH₃CN/H₂O to 90% CH₃CN/H₂O over 10 min to give 45 mg (25.3%) of the title compound. LC-MS m/z 599.4 (M+H)+, 1.24 (ret. time).

3-(4-chloro-3-(((R)-4-methyl-1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoic acid

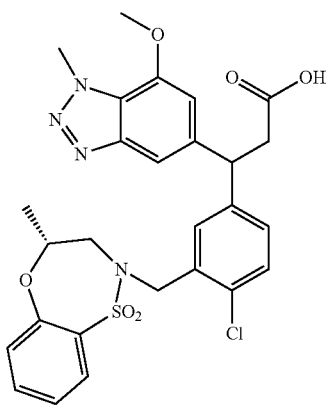 [SMILES: COc1cc(C(CC(=O)O)c2ccc(Cl)c(CN3C[C@@H](C)Oc4ccccc4S3(=O)=O)c2)cc2nnn(C)c12]

Ethyl 3-(4-chloro-3-(((R)-4-methyl-1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoate (45 mg, 0.075 mmol) was dissolved in THF (2 mL) and water (0.400 mL) then was added LiOH (17.99 mg, 0.751 mmol). The resulting reaction mixture was stirred at RT for 20 h. The reaction mixture was acidified with HCl (1 N) and concentrated. The crude product was dissolved in DMSO (1 mL), filtered through a 0.45 μm acrodisc, and purified by reverse-phase HPLC (YMC C18 S-5 μm/12 nm 50×20 mm preparatory column), eluting at 20 mL/min with a linear gradient running from 20% CH₃CN/H₂O to 90% CH₃CN/H₂O over 10 min to give 28 mg (65.3%) of the title compound. LC-MS m/z 571.2 (M+H)+, 1.07 (ret. time).

Example 74

3-(3-methoxyphenyl)-3-(4-methyl-3-(((R)-4-methyl-1,1-dioxido-3,4-dihydro-2H-benzo[b][1,4,5]oxathiazepin-2-yl)methyl)phenyl)propanoic acid

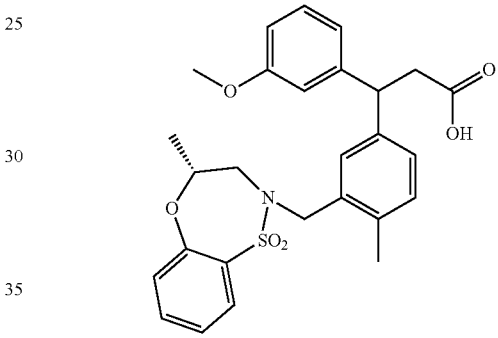

Ethyl 3-(3-(hydroxymethyl)-4-methylphenyl)-3-(3-methoxyphenyl)propanoate

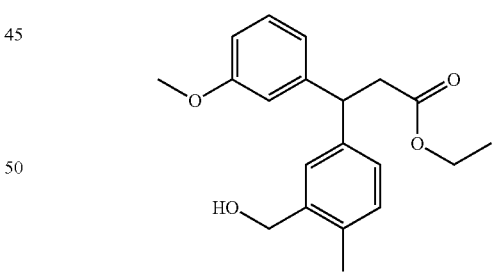

(E)-ethyl 3-(3-methoxyphenyl)acrylate (300 mg, 1.455 mmol) in 1,4-dioxane (10 mL) and water (5.00 mL) was added (3-(hydroxymethyl)-4-methylphenyl)boronic acid (362 mg, 2.182 mmol), Et₃N (221 mg, 2.182 mmol) and [RhCl(cod)]₂ (40.2 mg, 0.073 mmol). The result reaction mixture was stirred at 95° C. for 30 min. The reaction mixture was extracted with EtOAc (3×10 mL). The combined organic layer was dried over MgSO₄, filtered, and concentrated then, the product was purified over a silica cartridge (40 g) using Combiflash Companion eluting at 18 mL/min running a gradient of 0-30% EtOAc/hexane over 30 min then, 30% to 100% over 20 min. The solvent was removed under reduced pressure to give 350 mg (73.3%) of the title compound. LC-MS m/z 311.1 (M+H)+, 1.03 (ret. time).

ethyl 3-(3-methoxyphenyl)-3-(4-methyl-3-(((R)-4-methyl-1,1-dioxido-3,4-dihydro-2H-benzo[b][1,4,5]oxathiazepin-2-yl)methyl)phenyl)propanoate

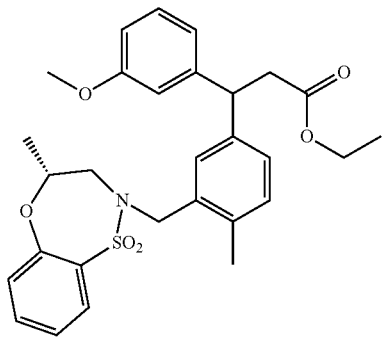 [SMILES: CCOC(=O)CC(c1cccc(OC)c1)c1ccc(C)c(CN2C[C@@H](C)Oc3ccccc3S2(=O)=O)c1]

To a solution of ethyl 3-(3-(hydroxymethyl)-4-methylphenyl)-3-(3-methoxyphenyl)propanoate (100 mg, 0.305 mmol), (R)-4-methyl-3,4-dihydro-2H-benzo[b][1,4,5]oxathiazepine 1,1-dioxide (78 mg, 0.365 mmol) and ADDP (154 mg, 0.609 mmol) in THF (5 mL) at 0° C. was added tributylphosphine (0.150 mL, 0.609 mmol). The ice-bath was removed after 20 min and stirring continued at RT for 1 h. The reaction mixture was concentrated and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 130 mg (82%) of the title compound. LC-MS m/z 524.3 (M+H)+, 1.27 (ret. time).

3-(3-methoxyphenyl)-3-(4-methyl-3-(((R)-4-methyl-1,1-dioxido-3,4-dihydro-2H-benzo[b][1,4,5]oxathiazepin-2-yl)methyl)phenyl)propanoic acid

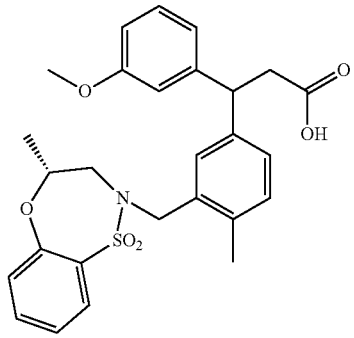 [SMILES: COc1cccc(C(CC(=O)O)c2ccc(C)c(CN3C[C@@H](C)Oc4ccccc4S3(=O)=O)c2)c1]

Ethyl 3-(3-methoxyphenyl)-3-(4-methyl-3-(((R)-4-methyl-1,1-dioxido-3,4-dihydro-2H-benzo[b][1,4,5]oxathiazepin-2-yl)methyl)phenyl)propanoate (130 mg, 0.248 mmol) was dissolved in THF (2 mL) and water (0.400 mL) then was added LiOH (49.5 mg, 2.069 mmol). The result reaction mixture was stirred at RT for 20 h. The reaction mixture was acidified with HCl (1 N) and concentrated. The crude product was dissolved in DMSO (2 mL), filtered through a 0.45 μm acrodisc, and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 70 mg (68.3%) of the title compound. LC-MS m/z 496.0 (M+H)+, 1.12 (ret. time).

Example 75

3-(4-chloro-3-(((R)-4-methyl-1,1-dioxido-3,4-dihydro-2H-benzo[b][1,4,5]oxathiazepin-2-yl)methyl)phenyl)-3-(1-methyl-1H-benzo[d][1,2,3]triazol-5-yl)propanoic acid

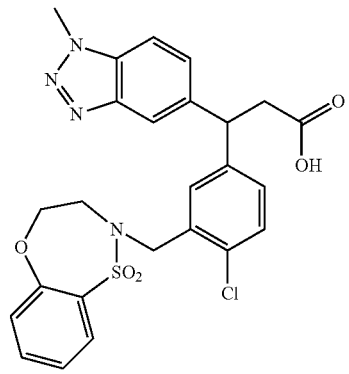 [SMILES: Cn1nnc2cc(C(CC(=O)O)c3ccc(Cl)c(CN4CCOc5ccccc5S4(=O)=O)c3)ccc21]

Methyl 3-(4-chloro-3-(hydroxymethyl)phenyl)-3-(1-methyl-1H-benzo[d][1,2,3]triazol-5-yl)propanoate

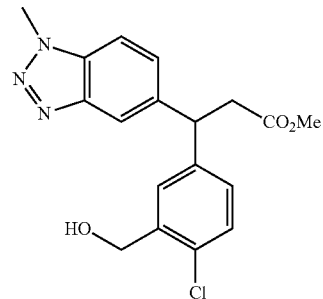 [SMILES: COC(=O)CC(c1ccc(Cl)c(CO)c1)c1ccc2c(c1)nnn2C]

Methyl diethylphosphonoacetate (0.125 mL, 0.683 mmol) in THF (2.500 mL) was added KOtBu (77 mg, 0.683 mmol) and stirred at RT for 10 min before adding 1-methyl-1H-benzo[d][1,2,3]triazole-5-carbaldehyde (100 mg, 0.620 mmol) in THF (0.5 mL). The reaction mixture was stirred at RT for 30 min. The reaction mixture was added water (15 mL), extracted with EtOAc (3×20 mL). The combined organic layer was washed with brine (15 mL), dried over MgSO$_4$, filtered, and concentrated to afford desired intermediate (E)-methyl 3-(1-methyl-1H-benzo[d][1,2,3]triazol-5-yl)acrylate as a white slightly orange solid. To this intermediate was added 1,4-dioxane (4.50 mL) and water (1.5 mL) then (2-chloro-5-(4,4,5,5-tetramethyl-1,3,2-dioxaborolan-2-yl)phenyl)methanol (333 mg, 1.241 mmol), TEA (0.259 mL, 1.861 mmol) and [RhCl(cod)]$_2$ (17.16 mg, 0.031 mmol). The resulting reaction mixture was stirred at 90° C. for 45 min. The reaction mixture was extracted with brine (50 mL), dried over MgSO$_4$, filtered, and concentrated then, product was purified over a silica cartridge (40 g) using Combiflash Companion eluting at 18 mL/min running a gradient of 0-30% EtOAc/hexane over 30 min then 30% to 100% over 20 min. The solvent was removed under reduced pressure to give 88 mg (39.4%) of the title compound. LC-MS m/z 360.0 (M+H)$^+$, 0.83 (ret. time).

Methyl 3-(4-chloro-3-(((R)-4-methyl-1,1-dioxido-3,4-dihydro-2H-benzo[b][1,4,5]oxathiazepin-2-yl)methyl)phenyl)-3-(1-methyl-1H-benzo[d][1,2,3]triazol-5-yl)propanoate

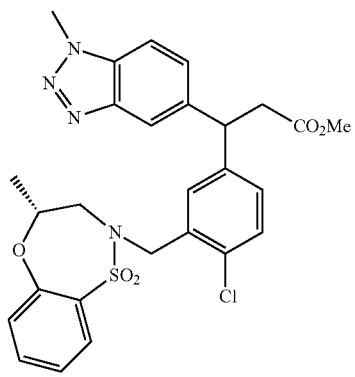 [SMILES: COC(=O)CC(c1ccc(Cl)c(CN2C[C@@H](C)Oc3ccccc3S2(=O)=O)c1)c1ccc2c(c1)nnn2C]

To a solution of methyl 3-(4-chloro-3-(hydroxymethyl)phenyl)-3-(1-methyl-1H-benzo[d][1,2,3]triazol-5-yl)propanoate (88 mg, 0.245 mmol), (R)-4-methyl-3,4-dihydro-2H-benzo[b][1,4,5]oxathiazepine 1,1-dioxide (62.6 mg, 0.293 mmol) and ADDP (123 mg, 0.489 mmol) in THF at 0° C. was added tributylphosphine (99 mg, 0.489 mmol). The ice-bath was removed after 20 min and stirring continued at RT for 1 h. The reaction mixture was concentrated and purified by reverse-phase HPLC (YMC C18 S-5 µm/12 nm 50×20 mm preparatory column), eluting at 20 mL/min with a linear gradient running from 20% CH$_3$CN/H$_2$O to 90% CH$_3$CN/H$_2$O over 10 min to give 55 mg (40.5%) of the title compound. LC-MS m/z 555.2 (M+H)$^+$, 1.13 (ret. time).

3-(4-chloro-3-(((R)-4-methyl-1,1-dioxido-3,4-dihydro-2H-benzo[b][1,4,5]oxathiazepin-2-yl)methyl)phenyl)-3-(1-methyl-1H-benzo[d][1,2,3]triazol-5-yl)propanoic acid\

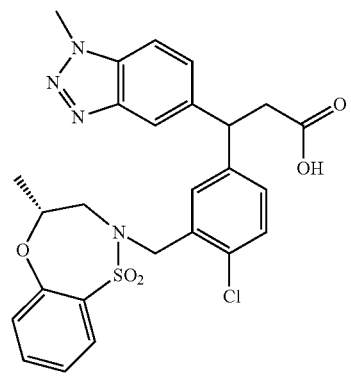 [SMILES: C[C@@H]1CN(Cc2cc(C(CC(=O)O)c3ccc4c(c3)nnn4C)ccc2Cl)S(=O)(=O)c2ccccc2O1]

Methyl 3-(4-chloro-3-(((R)-4-methyl-1,1-dioxido-3,4-dihydro-2H-benzo[b][1,4,5]oxathiazepin-2-yl)methyl)phenyl)-3-(1-methyl-1H-benzo[d][1,2,3]triazol-5-yl)propanoate (55 mg, 0.099 mmol) was dissolved in THF (2 mL) and water (0.4 mL) then was added LiOH (19.78 mg, 0.826 mmol). The result reaction mixture was stirred at RT for 20 h. The reaction mixture was acidified with HCl (1 N) and concentrated. The crude product was dissolved in DMSO (2 mL), filtered through a 0.45 µm acrodisc, and purified by reverse-phase HPLC (YMC C18 S-5 µm/12 nm 50×20 mm preparatory column), eluting at 20 mL/min with a linear gradient running from 20% CH$_3$CN/H$_2$O to 90% CH$_3$CN/H$_2$O over 10 min to give 38 mg (85%) of the title compound. LC-MS m/z 541.2 (M+H)$^+$, 1.02 (ret. time).

Example 76

3-(3-methoxy-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid

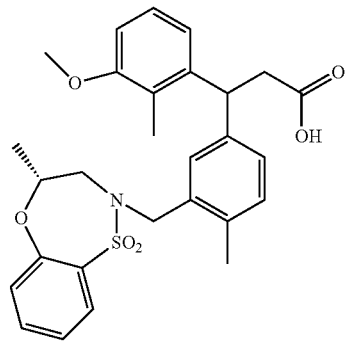 [SMILES: COc1cccc(C(CC(=O)O)c2ccc(C)c(CN3C[C@@H](C)Oc4ccccc4S3(=O)=O)c2)c1C]

1-bromo-3-methoxy-2-methylbenzene

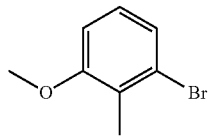

To 3-bromo-2-methylphenol (500 mg, 2.67 mmol) in DMF (10 mL) was added potassium carbonate (1108 mg, 8.02 mmol) and the mixture was stirred for 5 min before was added MeI (0.836 mL, 13.37 mmol) and let the reaction was stirred at 50° C. for 2 h. The reaction was washed with waster (30 mL), extracted with EtOAc (20 mL+3×20 mL) and concentrated to give 450 mg (80%) of the title compound. LC-MS m/z 305.9 (M+H)$^+$, 1.09 (ret. time).

(E)-ethyl 3-(3-methoxy-2-methylphenyl)acrylate

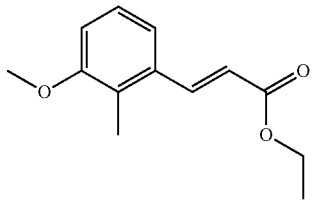 [SMILES: CCOC(=O)/C=C/c1cccc(OC)c1C]

To a solution of 1-bromo-3-methoxy-2-methylbenzene (515 mg, 2.56 mmol) in DMF (10 mL) at RT was added ethyl acrylate (2564 mg, 25.6 mmol) and N-ethyl-N-isopropylpropan-2-amine (2.68 mL, 15.37 mmol), tri-o-tolylphosphine (312 mg, 1.025 mmol), Pd(OAc)$_2$ (115 mg, 0.512 mmol). The reaction mixture was heated in microwave under high absorption at 150° C. for 2 h. The reaction mixture was passed through celite and washed with EtOAc. The filtrate was washed with water twice, brine (1×). The organic layer was collected and concentrated to give the crude product. The crude product was purified on a silica cartridge (40 g) with a Combiflash Companion, eluting at 35 mL/min with a gradient running from 0% EtOAc/hexanes to 50% over 35 min. The desired fractions were concentrated under reduced pressure to give 450 mg (80%) of the title compound. LC-MS m/z 220.9 (M+H)$^+$, 1.11 (ret. time).

Ethyl 3-(3-(hydroxymethyl)-4-methylphenyl)-3-(3-methoxy-2-methylphenyl)propanoate

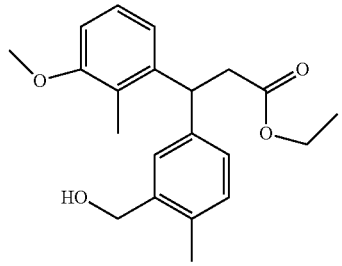 [SMILES: CCOC(=O)CC(c1ccc(C)c(CO)c1)c1cccc(OC)c1C]

(E)-ethyl 3-(3-methoxy-2-methylphenyl)acrylate (200 mg, 0.908 mmol) in 1,4-dioxane (10 mL) and water (5.00 mL) was added (3-(hydroxymethyl)-4-methylphenyl)boronic acid (226 mg, 1.362 mmol), Et$_3$N (138 mg, 1.362 mmol) and [RhCl(cod)]$_2$ (22.39 mg, 0.045 mmol). The resulting reaction mixture was stirred at 95° C. for 30 min. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min. The solvent was removed under reduced pressure to give 190 mg (61.1%) of the title compound. LC-MS m/z 321.0 (M+H)$^+$, 1.08 (ret. time).

ethyl 3-(3-methoxy-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoate

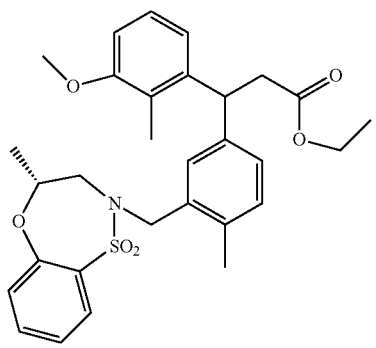 [SMILES: CCOC(=O)CC(c1ccc(C)c(CN2C[C@@H](C)Oc3ccccc3S2(=O)=O)c1)c1cccc(OC)c1C]

To a solution of ethyl 3-(3-(hydroxymethyl)-4-methylphenyl)-3-(3-methoxy-2-methylphenyl)propanoate (60 mg, 0.175 mmol), (R)-4-methyl-3,4-dihydro-2H-benzo[b][1,4,5] oxathiazepine 1,1-dioxide (44.8 mg, 0.210 mmol) and ADDP (88 mg, 0.350 mmol) in THF (5 mL) at 0° C. was added tributylphosphine (0.086 mL, 0.350 mmol). The ice-bath was removed after 20 min and stirring continued at RT for 2 h. The reaction mixture was concentrated and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 45 mg (47.8%) of the title compound. LC-MS m/z 538.3 (M+H)$^+$, 1.40 (ret. time).

3-(3-methoxy-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid

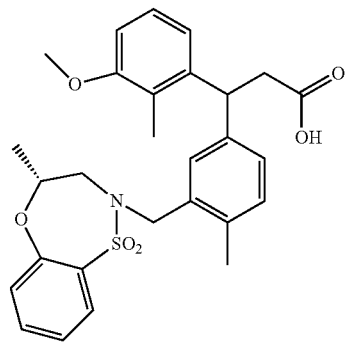 [SMILES: COc1cccc(C(CC(=O)O)c2ccc(C)c(CN3C[C@@H](C)Oc4ccccc4S3(=O)=O)c2)c1C]

Ethyl 3-(3-methoxy-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoate (45 mg, 0.084 mmol) was dissolved in THF (2 mL) and water (0.4 mL) then was added LiOH (1.670 mg, 0.070 mmol). The result reaction mixture was stirred at RT for 20 h. The reaction mixture was acidified with HCl (1 N) and concentrated. The crude product was dissolved in DMSO (2 mL), filtered through a 0.45 μm acrodisc, and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 22 mg (61%) of the title compound. LC-MS m/z 510.0 (M+H)$^+$, 1.19 (ret. time).

Example 77

3-(4-methyl-3-(((R)-4-methyl-1,1-dioxido-3,4-dihydro-2H-benzo[b][1,4,5]oxathiazepin-2-yl)methyl)phenyl)-3-(3-methyl-3H-[1,2,3]triazolo[4,5-b]pyridin-6-yl)propanoic acid

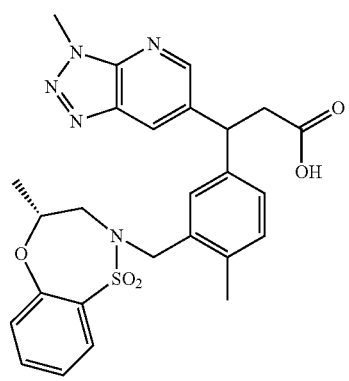 [SMILES: Cc1ccc(C(CC(=O)O)c2cnc3c(c2)nnn3C)cc1CN1C[C@@H](C)Oc2ccccc2S1(=O)=O]

5-Bromo-N-methyl-3-nitropyridin-2-amine

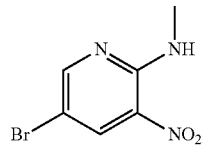

To a solution of 5-bromo-3-nitropyridin-2-amine (3 g, 13.76 mmol) in DMF (20 mL) at 0° C., NaH (0.605 g, 15.14 mmol) was added. After 30 min, MeI (0.946 mL, 15.14 mmol) was added, and the reaction stirred for 30 min after which time water was added to quench the reaction. EtOAc was added, and the layers were separated. The aqueous layer was extracted once with EtOAc, and the combined organic layers were washed once with brine. The organic layer was concentrated. The crude product was then purified on a silica cartridge (40 g) with a Combiflash Companion, eluting at 30 mL/min with a gradient running from 100% Hexane s to 80% EtOAc over 35 min) to give 1.5 g (47%) of the title compound. LC-MS m/z 231.8, 233.8 (M+H)$^+$, 0.89 (ret. time).

5-Bromo-N2-methylpyridine-2,3-diamine

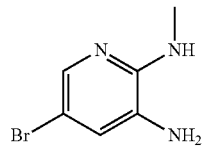

To a solution of 5-bromo-N-methyl-3-nitropyridin-2-amine (800 mg, 3.45 mmol) in EtOH (20 mL) at RT, SnCl$_2$.2H$_2$O (3112 mg, 13.79 mmol) was added. The reaction mixture was stirred for the 4 h at 80° C. The solvent was evaporated under reduce pressure and saturated NaHCO$_3$ solution was added to pH=7 then was extracted with EtOAc (2×), and the combined organic layers were washed once with brine. The organic layer was concentrated to give 720 mg (103%) of the title compound. LC-MS m/z 202.1, 203.9 (M+H)$^+$, 0.33 (ret. time).

6-Bromo-3-methyl-3H-[1,2,3]triazolo[4,5-b]pyridine

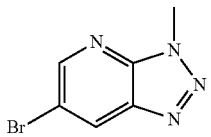

To a solution of 5-bromo-N2-methylpyridine-2,3-diamine (720 mg, 3.56 mmol) in H$_2$SO$_4$ (1.90 µL, 35.6 mmol) at RT, NaNO$_2$ (246 mg, 3.56 mmol) was added. The reaction mixture was stirred for 1 h after which time water was added to quench the reaction. EtOAc was added, and the layers were separated. The aqueous layer was extracted once with EtOAc, and the combined organic layers were washed once with brine. The organic layer was concentrated to give 694 mg (91%) of the title compound. LC-MS m/z 212.8, 214.8 (M+H)$^+$, 0.66 (ret. time).

(E)-ethyl 3-(3-methyl-3H-[1,2,3]triazolo[4,5-b]pyridin-6-yl)acrylate

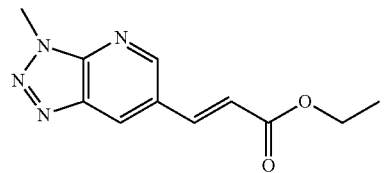 [SMILES: CCOC(=O)/C=C/c1cnc2c(c1)nnn2C]

To a solution of 6-bromo-3-methyl-3H-[1,2,3]triazolo[4,5-b]pyridine (200 mg, 0.939 mmol) in DMF (8 mL) at RT was added ethyl acrylate (940 mg, 9.39 mmol) and N-ethyl-N-isopropylpropan-2-amine (728 mg, 5.63 mmol),tri-o-tolylphosphine (114 mg, 0.376 mmol), Pd(OAc)$_2$ (42.2 mg, 0.188 mmol). The reaction mixture was heated in microwave under high absorption at 150° C. for 2 h. The reaction mixture was passed through celite and washed with EtOAc. The filtrate was washed with water twice, brine (1×). The organic layer was collected and concentrated to give the crude product. The crude product was purified on a silica cartridge (40 g) with a Combiflash Companion, eluting at 35 mL/min with a gradient running from 0% EtOAc/hexanes to 50% over 35 min. The desired fractions were concentrated under reduced pressure to give 195 mg (89%) of the title compound. LC-MS m/z 233.0 (M+H)$^+$, 0.78 (ret. time).

Ethyl 3-(3-(hydroxymethyl)-4-methylphenyl)-3-(3-methyl-3H-[1,2,3]triazolo[4,5-b]pyridin-6-yl)propanoate

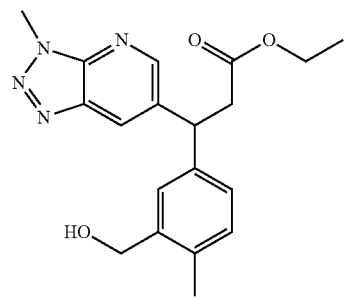 [SMILES: CCOC(=O)CC(c1ccc(C)c(CO)c1)c1cnc2c(c1)nnn2C]

(E)-ethyl 3-(3-methyl-3H-[1,2,3]triazolo[4,5-b]pyridin-6-yl)acrylate (200 mg, 0.861 mmol) in 1,4-dioxane (10 mL) and water (5.00 mL) was added (3-(hydroxymethyl)-4-methylphenyl)boronic acid (257 mg, 1.550 mmol), Et$_3$N (131 mg, 1.292 mmol) and [RhCl(cod)]$_2$ (21.23 mg, 0.043 mmol). The resulting reaction mixture was stirred at 95° C. for 1 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min. The solvent was removed under reduced pressure to give 137 mg (44.9%) of the title compound. LC-MS m/z 355.1 (M+H)+, 0.82 (ret. time).

Ethyl 3-(4-methyl-3-(((R)-4-methyl-1,1-dioxido-3,4-dihydro-2H-benzo[b][1,4,5]oxathiazepin-2-yl)methyl)phenyl)-3-(3-methyl-3H-[1,2,3]triazolo[4,5-b]pyridin-6-yl)propanoate

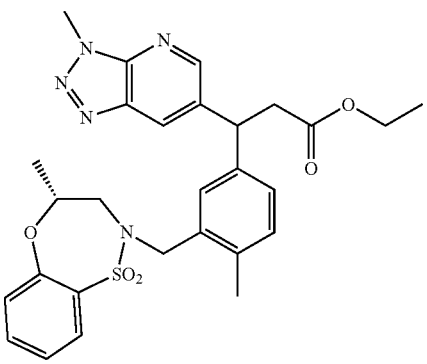 [SMILES: CCOC(=O)CC(c1ccc(C)c(CN2C[C@@H](C)Oc3ccccc3S2(=O)=O)c1)c1cnc2c(c1)nnn2C]

To a solution of ethyl 3-(3-(hydroxymethyl)-4-methylphenyl)-3-(3-methyl-3H-[1,2,3]triazolo[4,5-b]pyridin-6-yl)propanoate (80 mg, 0.226 mmol), (R)-4-methyl-3,4-dihydro-2H-benzo[b][1,4,5]oxathiazepine 1,1-dioxide (57.8 mg, 0.271 mmol) and ADDP (114 mg, 0.451 mmol) in THF (5 mL) at 0° C. was added tributylphosphine (0.111 mL, 0.451 mmol). The ice-bath was removed after 20 min and stirring continued at RT for 1 h. The reaction mixture was concentrated and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 90 mg (72%) of the title compound. LC-MS m/z 550.3 (M+H)+, 1.11 (ret. time).

3-(4-methyl-3-(((R)-4-methyl-1,1-dioxido-3,4-dihydro-2H-benzo[b][1,4,5]oxathiazepin-2-yl)methyl)phenyl)-3-(3-methyl-3H-[1,2,3]triazolo[4,5-b]pyridin-6-yl)propanoic acid

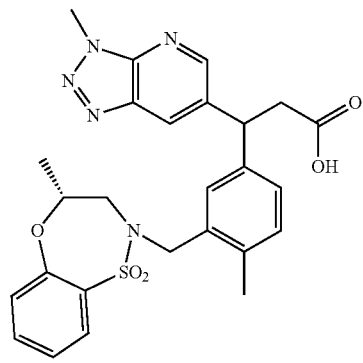 [SMILES: Cc1ccc(C(CC(=O)O)c2cnc3c(c2)nnn3C)cc1CN1C[C@@H](C)Oc2ccccc2S1(=O)=O]

Ethyl 3-(4-methyl-3-(((R)-4-methyl-1,1-dioxido-3,4-dihydro-2H-benzo[b][1,4,5]oxathiazepin-2-yl)methyl)phenyl)-3-(3-methyl-3H-[1,2,3]triazolo[4,5-b]pyridin-6-yl)propanoate (90 mg, 0.164 mmol) was dissolved in THF (2 mL) and water (0.4 mL) then was added LiOH (3.27 mg, 0.136 mmol). The resulting reaction mixture was stirred at RT for 20 h. The reaction mixture was acidified with HCl (1 N) and concentrated. The crude product was dissolved in DMSO (2 mL), filtered through a 0.45 μm acrodisc, and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 50 mg (70%) of the title compound. LC-MS m/z 522.1 (M+H)+, 0.96 (ret. time).

Example 78

3-(1-methyl-2-oxo-1,2-dihydropyridin-4-yl)-3-(4-methyl-3-(((R)-4-methyl-1,1-dioxido-3,4-dihydro-2H-benzo[b][1,4,5]oxathiazepin-2-yl)methyl)phenyl)propanoic acid

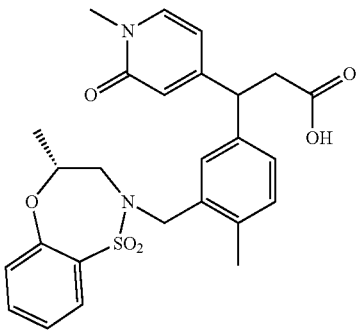 [SMILES: Cc1ccc(C(CC(=O)O)c2ccn(C)c(=O)c2)cc1CN1C[C@@H](C)Oc2ccccc2S1(=O)=O]

(E)-Ethyl 3-(1-methyl-2-oxo-1,2-dihydropyridin-4-yl)acrylate

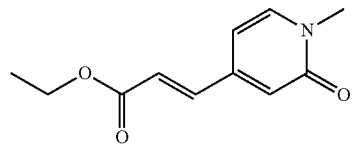

To a solution of 4-bromo-1-methylpyridin-2(1H)-one (370 mg, 1.968 mmol) in DMF (20 mL), ethyl acrylate (1182 mg, 11.81 mmol), tri-o-tolylphosphine (180 mg, 0.590 mmol), N-ethyl-N-isopropylpropan-2-amine (1017 mg, 7.87 mmol) and Pd(OAc)$_2$ (66.3 mg, 0.295 mmol) were added. The reaction mixture was heated in a microwave at 120° C. for 2 h. Water was added to quench the reaction. EtOAc was added, and the layers were separated. The aqueous layer was extracted once with EtOAc, and the combined organic layers were washed once with brine. The organic layer was concentrated. The crude product was then purified on a silica cartridge (40 g) with a Combiflash Companion, eluting at 30 mL/min with a gradient running from 100% CH$_2$Cl$_2$ s to 80% MeOH/CH$_2$Cl$_2$ over 35 min) to give 334 mg (82%) of the title compound. LC-MS m/z 207.9 (M+H)+, 0.67 (ret. time).

187

Ethyl 3-(3-(hydroxymethyl)-4-methylphenyl)-3-(1-methyl-2-oxo-1,2-dihydropyridin-4-yl)propanoate

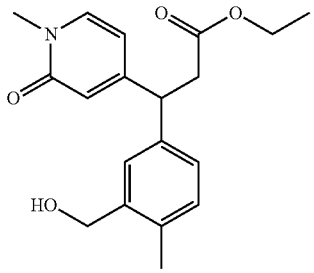 [SMILES: CCOC(=O)CC(c1ccc(C)c(CO)c1)c1ccn(C)c(=O)c1]

To (E)-ethyl 3-(1-methyl-2-oxo-1,2-dihydropyridin-4-yl)acrylate (140 mg, 0.676 mmol) in 1,4-dioxane (10 mL) and water (5.00 mL) was added (3-(hydroxymethyl)-4-methylphenyl)boronic acid (202 mg, 1.216 mmol), Et$_3$N (103 mg, 1.013 mmol) and [RhCl(cod)]$_2$ (16.66 mg, 0.034 mmol). The resulting reaction mixture was stirred at 95° C. for 72 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% (MeOH (7%): NH4OH (3%) in DCM (90%))/DCM over 30 min then, 30% to 100% over 20 min. The solvent was removed under reduced pressure to give 120 mg (53.9%) of the title compound. LC-MS m/z 330.1 (M+H)$^+$, 0.73 (ret. time).

Ethyl 3-(1-methyl-2-oxo-1,2-dihydropyridin-4-yl)-3-(4-methyl-3-(((R)-4-methyl-1,1-dioxido-3,4-dihydro-2H-benzo[b][1,4,5]oxathiazepin-2-yl)methyl)phenyl)propanoate

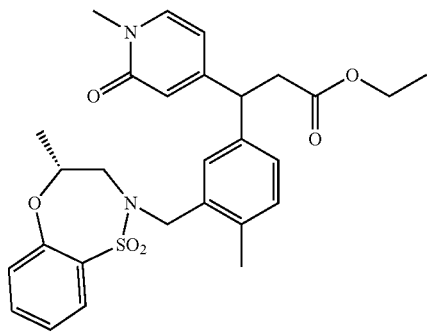 [SMILES: CCOC(=O)CC(c1ccc(C)c(CN2C[C@@H](C)Oc3ccccc3S2(=O)=O)c1)c1ccn(C)c(=O)c1]

To a solution of ethyl 3-(3-(hydroxymethyl)-4-methylphenyl)-3-(1-methyl-2-oxo-1,2-dihydropyridin-4-yl)propanoate (60 mg, 0.182 mmol), (R)-4-methyl-3,4-dihydro-2H-benzo[b][1,4,5]oxathiazepine 1,1-dioxide (46.6 mg, 0.219 mmol) and ADDP (92 mg, 0.364 mmol) in THF (5 mL) at 0° C. was added tributylphosphine (73.7 mg, 0.364 mmol). The ice-bath was removed after 20 min and stirring continued at RT for 1 h. The reaction mixture was concentrated and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 15 mg (15%) of the title compound. LC-MS m/z 525.4 (M+H)$^+$, 1.01 (ret. time).

188

3-(1-methyl-2-oxo-1,2-dihydropyridin-4-yl)-3-(4-methyl-3-(((R)-4-methyl-1,1-dioxido-3,4-dihydro-2H-benzo[b][1,4,5]oxathiazepin-2-yl)methyl)phenyl)propanoic acid

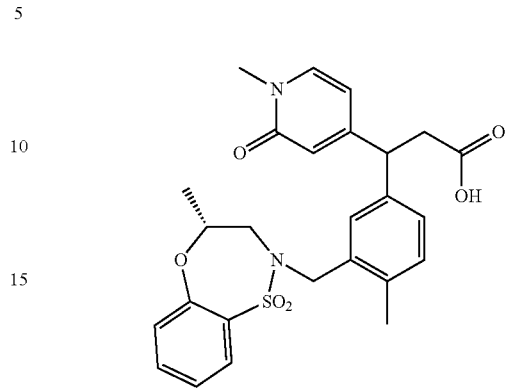

Ethyl 3-(1-methyl-2-oxo-1,2-dihydropyridin-4-yl)-3-(4-methyl-3-(((R)-4-methyl-1,1, dioxido-3,4-dihydro-2H-benzo[b][1,4,5]oxathiazepin-2-yl)methyl)phenyl)propanoate (80 mg, 0.152 mmol) was dissolved in THF (2 mL) and water (0.4 mL) then was added LiOH (36.5 mg, 1.525 mmol). The result reaction mixture was stirred at RT for 20 h. The reaction mixture was acidified with HCl (1 N) and concentrated. The crude product was dissolved in DMSO (2 mL), filtered through a 0.45 μm acrodisc, and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 5 mg (7%) of the title compound. LC-MS m/z 497.3 (M+H)$^+$, 0.89 (ret. time).

Example 79

3-(3,7-dimethyl-3H-[1,2,3]triazolo[4,5-b]pyridin-6-yl)-3-(4-methyl-3-(((R)-4-methyl-1,1-dioxido-3,4-dihydro-2H-benzo[b][1,4,5]oxathiazepin-2-yl)methyl)phenyl)propanoic acid

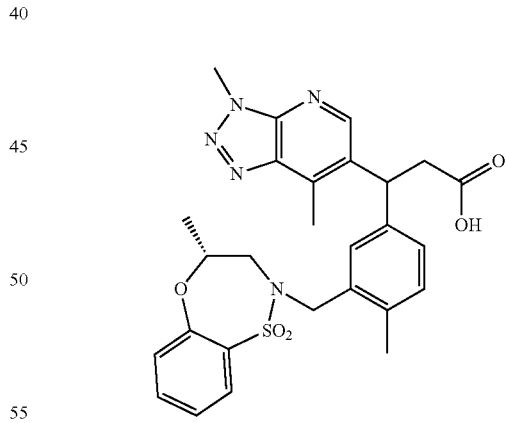

5-Bromo-N2,4-dimethylpyridine-2,3-diamine

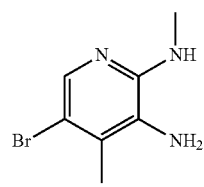

To a solution of 5-bromo-N,4-dimethyl-3-nitropyridin-2-amine (1000 mg, 4.06 mmol) in EtOH (20 mL) at RT, SnCl₂.2H₂O (3668 mg, 16.26 mmol) was added. The reaction mixture was stirred for 1 h. The solvent was evaporated under reduce pressure and saturated NaHCO₃ solution was added to pH=7 then it was extracted with EtOAc (3×40 mL), and the combined organic layers were washed once with brine. The organic layer was concentrated to give 720 mg (82%) of the title compound. LC-MS m/z 216.0, 218.0 (M+H)⁺, 0.54 (ret. time).

6-Bromo-3,7-dimethyl-3H-[1,2,3]triazolo[4,5-b]pyridine

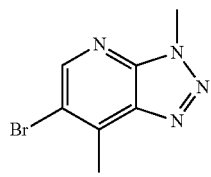

To a solution of 5-bromo-N2,4-dimethylpyridine-2,3-diamine (720 mg, 3.33 mmol) in H₂SO₄ (1.78 µL, 33.3 mmol) at RT, NaNO₂ (230 mg, 3.33 mmol) was added in 10 min. The reaction mixture was stirred for 1 h after which time water was added to quench the reaction. EtOAc was added, and the layers were separated. The aqueous layer was extracted once with EtOAc, and the combined organic layers were washed once with brine. The organic layer was concentrated to give 750 mg (99%) of the title compound. LC-MS m/z 227.0, 229.0 (M+H)⁺, 0.75 (ret. time).

(E)-ethyl 3-(3,7-dimethyl-3H-[1,2,3]triazolo[4,5-b]pyridin-6-yl)acrylate

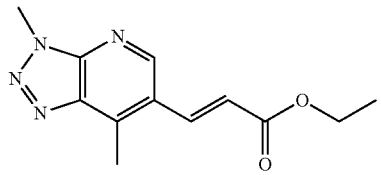

To a solution of 6-bromo-3,7-dimethyl-3H-[1,2,3]triazolo[4,5-b]pyridine (200 mg, 0.881 mmol) in DMF (8 mL) at RT was added ethyl acrylate (882 mg, 8.81 mmol) and N-ethyl-N-isopropylpropan-2-amine (683 mg, 5.28 mmol), tri-o-tolylphosphine (107 mg, 0.352 mmol), Pd(OAc)₂ (39.6 mg, 0.176 mmol). The reaction mixture was heated in microwave under high absorption at 150° C. for 2 h. The reaction mixture was passed through celite and washed with EtOAc. The filtrate was washed with water twice, brine (1×). The organic layer was collected and concentrated to give the crude product. The crude product was purified on a silica cartridge (40 g) with a Combiflash Companion, eluting at 35 mL/min with a gradient running from 0% EtOAc/hexanes to 50% over 35 min. The desired fractions were concentrated under reduced pressure to give 140 mg (65%) of the title compound. LC-MS m/z 247.0 (M+H)⁺, 0.79 (ret. time).

Ethyl 3-(3,7-dimethyl-3H-[1,2,3]triazolo[4,5-b]pyridin-6-yl)-3-(3-(hydroxymethyl)-4-methylphenyl)propanoate

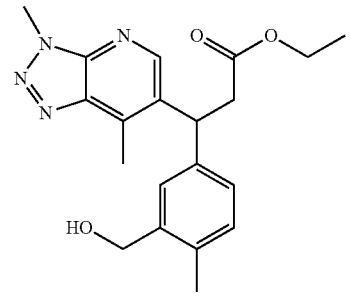 [SMILES: CCOC(=O)CC(c1ccc(C)c(CO)c1)c1cnc2c(nnn2C)c1C]

To (E)-ethyl 3-(3,7-dimethyl-3H-[1,2,3]triazolo[4,5-b]pyridin-6-yl)acrylate (140 mg, 0.568 mmol) in 1,4-dioxane (10 mL) and water (5.00 mL) was added (3-(hydroxymethyl)-4-methylphenyl)boronic acid (170 mg, 1.023 mmol), Et₃N (86 mg, 0.853 mmol) and. [RhCl(cod)]₂ (14.02 mg, 0.028 mmol). The resulting reaction mixture was stirred at 95° C. for 1 h. The reaction mixture was extracted with EtOAc (3×10 mL). The combined organic layer was dried over MgSO₄, filtered, and concentrated then, the product was purified over a silica cartridge (40 g) using Combiflash Companion eluting at 18 mL/min running a gradient of 0-30% (MeOH (7%): NH4OH (3%) in DCM (90%))/DCM over 30 min then, 30% to 100% over 20 min. The solvent was removed under reduced pressure to give 70 mg (33%) of the title compound.

LC-MS m/z 369.1 (M+H)⁺, 0.85 (ret. time).

Ethyl 3-(3,7-dimethyl-3H-[1,2,3]triazolo[4,5-b]pyridin-6-yl)-3-(4-methyl-3-(((R)-4-methyl-1,1-dioxido-3,4-dihydro-2H-benzo[b][1,4,5]oxathiazepin-2-yl)methyl)phenyl)propanoate

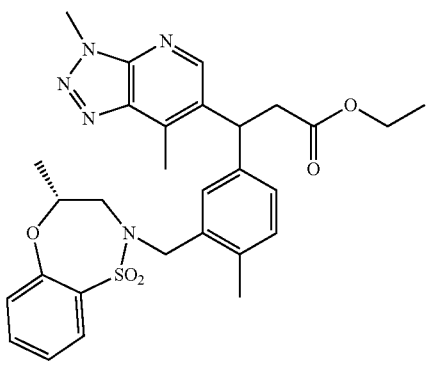 [SMILES: CCOC(=O)CC(c1ccc(C)c(CN2C[C@@H](C)Oc3ccccc3S2(=O)=O)c1)c1cnc2c(nnn2C)c1C]

To a solution of ethyl 3-(3,7-dimethyl-3H-[1,2,3]triazolo[4,5-b]pyridin-6-yl)-3-(3-(hydroxymethyl)-4-methylphenyl)propanoate (70 mg, 0.190 mmol), (R)-4-methyl-3,4-dihydro-2H-benzo[b][1,4,5]oxathiazepine 1,1-dioxide (48.6 mg, 0.228 mmol) and ADDP (96 mg, 0.380 mmol) in THF (5 mL) at 0° C. was added tributylphosphine (0.094 mL, 0.380 mmol). The ice-bath was removed after 20 min and stirring continued at RT for 1 h. The reaction mixture was extracted with EtOAc (3×10 mL). The combined organic layer was dried over MgSO₄, filtered, and concentrated then, the product was purified over a silica cartridge (40 g) using Combiflash Companion eluting at 18 mL/min running a gradient of 0-30% EtOAc/hexane over 30 min then, 30% to 100% over 20 min. The solvent was removed under reduced pressure to give 80 mg (74%) of the title compound. LC-MS m/z 564.3 (M+H)⁺, 1.13 (ret. time).

3-(3,7-dimethyl-3H-[1,2,3]triazolo[4,5-b]pyridin-6-yl)-3-(4-methyl-3-(((R)-4-methyl-1,1-dioxido-3,4-dihydro-2H-benzo[b][1,4,5]oxathiazepin-2-yl)methyl)phenyl)propanoic acid

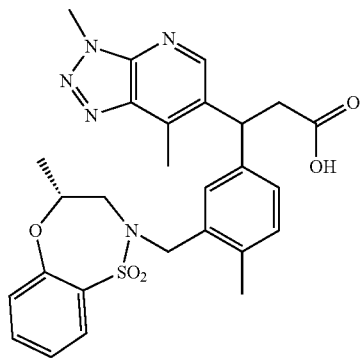 [SMILES: Cc1ccc(C(CC(=O)O)c2cnc3c(nnn3C)c2C)cc1CN1C[C@@H](C)Oc2ccccc2S1(=O)=O]

Ethyl 3-(3,7-dimethyl-3H-[1,2,3]triazolo[4,5-b]pyridin-6-yl)-3-(4-methyl-3-(((R)-4-methyl-1,1-dioxido-3,4-dihydro-2H-benzo[b][1,4,5]oxathiazepin-2-yl)methyl)phenyl)propanoate (80 mg, 0.142 mmol) was dissolved in THF (2 mL) and water (0.4 mL) then was added LiOH (34.0 mg, 1.419 mmol). The resulting reaction mixture was stirred at RT for 20 h. The reaction mixture was acidified with HCl (1 N) and concentrated. The crude product was dissolved in DMSO (2 mL), filtered through a 0.45 μm acrodisc, and purified by reverse-phase HPLC (YMC C18 S-5 μm/12 nm 50×20 mm preparatory column), eluting at 20 mL/min with a linear gradient running from 20% CH₃CN/H₂O to 90% CH₃CN/H₂O over 10 min to give 7 mg (10%) of the title compound. LC-MS m/z 535.9.3 (M+H)⁺, 0.98 (ret. time).

Example 80

3-(3,5-dimethoxyphenyl)-3-(4-methyl-3-(((R)-4-methyl-1,1-dioxido-3,4-dihydro-2H-benzo[b][1,4,5]oxathiazepin-2-yl)methyl)phenyl)propanoic acid

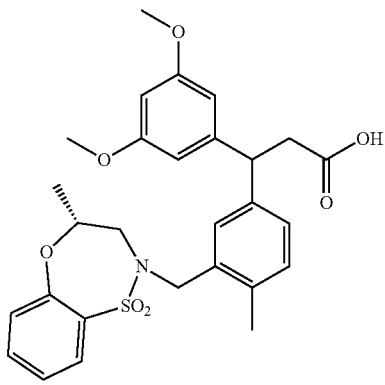 [SMILES: COc1cc(OC)cc(C(CC(=O)O)c2ccc(C)c(CN3C[C@@H](C)Oc4ccccc4S3(=O)=O)c2)c1]

(E)-ethyl 3-(3,5-dimethoxyphenyl)acrylate

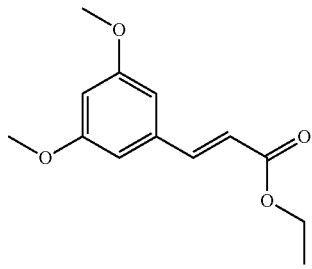 [SMILES: CCOC(=O)/C=C/c1cc(OC)cc(OC)c1]

To a solution of 1-bromo-3,5-dimethoxybenzene (400 mg, 1.843 mmol) in DMF (10 mL) at RT was added ethyl acrylate (1845 mg, 18.43 mmol) and N-ethyl-N-isopropyl-propan-2-amine (1.926 mL, 11.06 mmol), tri-o-tolylphosphine (224 mg, 0.737 mmol), Pd(OAc)₂ (83 mg, 0.369 mmol). The reaction mixture was heated in microwave under high absorption at 150° C. for 2 h. The reaction mixture was passed through celite and washed with EtOAc. The filtrate was washed with water twice, brine (1×). The organic layer was collected and concentrated to give the crude product. The crude product was purified on a silica cartridge (40 g) with a Combiflash Companion, eluting at 35 mL/min with a gradient running from 0% EtOAc/hexanes to 50% over 35 min. The desired fractions were concentrated under reduced pressure to give 390 mg (90%) of the title compound. LC-MS m/z 237.0 (M+H)⁺, 1.04 (ret. time).

Ethyl 3-(3,5-dimethoxyphenyl)-3-(3-(hydroxymethyl)-4-methylphenyl)propanoate

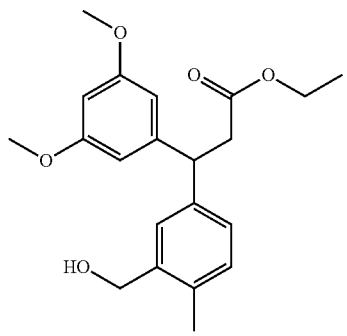 [SMILES: CCOC(=O)CC(c1cc(OC)cc(OC)c1)c1ccc(C)c(CO)c1]

To (E)-ethyl 3-(3,5-dimethoxyphenyl)acrylate (200 mg, 0.847 mmol) in 1,4-dioxane (10 mL) and water (5.00 mL) was added (3-(hydroxymethyl)-4-methylphenyl)boronic acid (253 mg, 1.524 mmol), Et₃N (128 mg, 1.270 mmol) and [RhCl(cod)]₂ (20.87 mg, 0.042 mmol). The resulting reaction mixture was stirred at 95° C. for 1 h. The reaction mixture was extracted with EtOAc (3×10 mL). The combined organic layer was dried over MgSO₄, filtered, and concentrated then, the product was purified over a silica cartridge (40 g) using Combiflash Companion eluting at 18 mL/min running a gradient of 0-30% (MeOH (7%): NH4OH (3%) in DCM (90%))/DCM over 30 min then, 30% to 100% over 20 min. The solvent was removed under reduced pressure to give 90 mg (30%) of the title compound. LC-MS m/z 341.1 (M+H)⁺, 1.01 (ret. time).

Ethyl 3-(3,5-dimethoxyphenyl)-3-(4-methyl-3-(((R)-4-methyl-1,1-dioxido-3,4-dihydro-2H-benzo[b][1,4,5]oxathiazepin-2-yl)methyl)phenyl)propanoate

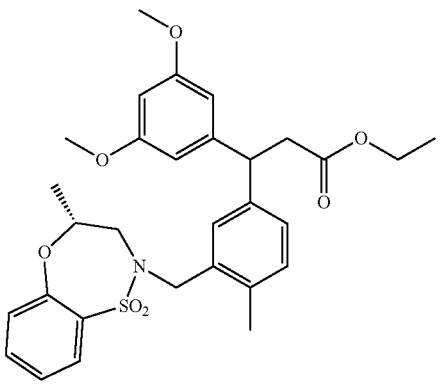 [SMILES: CCOC(=O)CC(c1cc(OC)cc(OC)c1)c1ccc(C)c(CN2C[C@@H](C)Oc3ccccc3S2(=O)=O)c1]

To a solution of ethyl 3-(3,5-dimethoxyphenyl)-3-(3-(hydroxymethyl)-4-methylphenyl)propanoate (90 mg, 0.251 mmol), (R)-4-methyl-3,4-dihydro-2H-benzo[b][1,4,5]oxathiazepine 1,1-dioxide (80 mg, 0.377 mmol) and ADDP (127 mg, 0.502 mmol) in THF (5 mL) at 0° C. was added tributylphosphine (0.124 mL, 0.502 mmol). The ice-bath was removed after 20 min and stirring continued at RT for 1 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min. The solvent was removed under reduced pressure to give 109 mg (78%) of the title compound. LC-MS m/z 554.3 (M+H)$^+$, 1.30 (ret. time).

3-(3,5-dimethoxyphenyl)-3-(4-methyl-3-(((R)-4-methyl-1,1-dioxido-3,4-dihydro-2H-benzo[b][1,4,5]oxathiazepin-2-yl)methyl)phenyl)propanoic acid

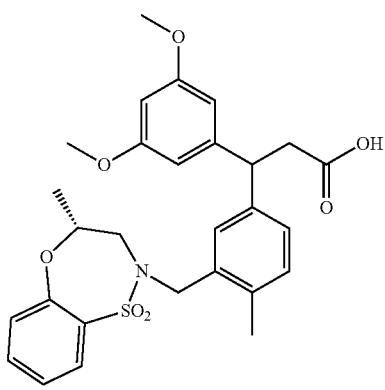 [SMILES: COc1cc(OC)cc(C(CC(=O)O)c2ccc(C)c(CN3C[C@@H](C)Oc4ccccc4S3(=O)=O)c2)c1]

Ethyl 3-(3,5-dimethoxyphenyl)-3-(4-methyl-3-(((R)-4-methyl-1,1-dioxido-3,4-dihydro-2H-benzo[b][1,4,5]oxathiazepin-2-yl)methyl)phenyl)propanoate (109 mg, 0.197 mmol) was dissolved in THF (2 mL) and water (0.4 mL) then treated with LiOH (47.1 mg, 1.969 mmol). The resulting reaction mixture was stirred at RT for 20 h. The reaction mixture was acidified with HCl (1 N) and concentrated. The crude product was dissolved in DMSO (2 mL), filtered through a 0.45 μm acrodisc, and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 53 mg (52%) of the title compound. LC-MS m/z 526.3 (M+H)$^+$, 1.11 (ret. time).

Example 81

3-(5-methoxypyridin-3-yl)-3-(4-methyl-3-(((R)-4-methyl-1,1-dioxido-3,4-dihydro-2H-benzo[b][1,4,5]oxathiazepin-2-yl)methyl)phenyl)propanoic acid

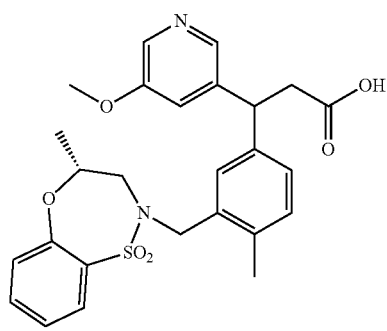 [SMILES: COc1cncc(C(CC(=O)O)c2ccc(C)c(CN3C[C@@H](C)Oc4ccccc4S3(=O)=O)c2)c1]

(E)-Ethyl 3-(5-methoxypyridin-3-yl)acrylate

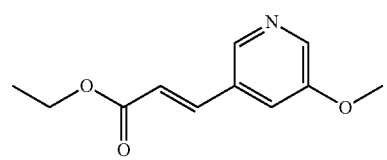

To a solution of 3-bromo-5-methoxypyridine (500 mg, 2.66 mmol) in DMF (20 mL), N-ethyl-N-isopropylpropan-2-amine (1375 mg, 10.64 mmol), tri-o-tolylphosphine (243 mg, 0.798 mmol), and Pd(OAc)$_2$ (90 mg, 0.399 mmol) were added. The reaction mixture was heated in a microwave at 120° C. for 2 h. water was added to quench the reaction. EtOAc was added, and the layers were separated. The aqueous layer was extracted once with EtOAc, and the combined organic layers were washed once with brine. The organic layer was concentrated. The crude product was then purified on a silica cartridge (40 g) with a Combiflash Companion, eluting at 30 mL/min with a gradient running from 100% CH$_2$Cl$_2$ s to 80% MeOH/CH$_2$Cl$_2$ over 35 min) to give 450 mg (82%) of the title compound. LC-MS m/z 207.9 (M+H)$^+$, 0.64 (ret. time).

Ethyl 3-(3-(hydroxymethyl)-4-methylphenyl)-3-(5-methoxypyridin-3-yl)propanoate

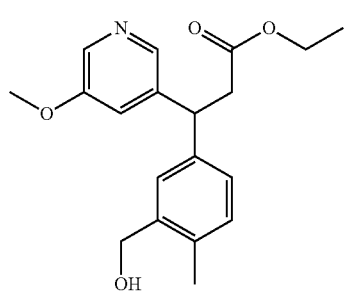 [SMILES: CCOC(=O)CC(c1cncc(OC)c1)c1ccc(C)c(CO)c1]

To a suspension of (E)-ethyl 3-(5-methoxypyridin-3-yl)acrylate (150 mg, 0.724 mmol), (3-(hydroxymethyl)-4-methylphenyl)boronic acid (144 mg, 0.869 mmol), Et$_3$N (220 mg, 2.172 mmol) and [RhCl(cod)]$_2$ (35.7 mg, 0.072 mmol) were added at RT in 1,4-dioxane (1 mL) and water (1.000 mL). The resulting suspension was heated to 95° C. for 1 h. The solvent was evaporated under reduce pressure and then purified on a silica cartridge (40 g) with a Combiflash Companion, eluting at 30 mL/min with a gradient running from 100% Hexane s to 80% EtOAc over 35 min) to give 130 mg (54.5%) of the title compound. LC-MS m/z 330.1 (M+H)$^+$, 0.67 (ret. time).

Ethyl 3-(5-methoxypyridin-3-yl)-3-(4-methyl-3-(((R)-4-methyl-1,1-dioxido-3,4-dihydro-2H-benzo[b][1,4,5]oxathiazepin-2-yl)methyl)phenyl)propanoate

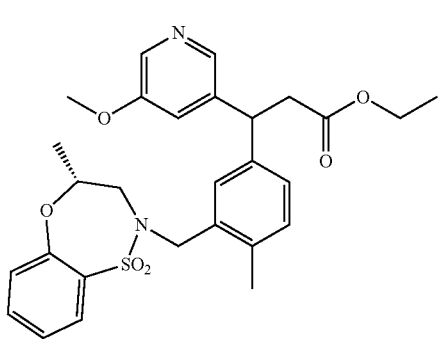 [SMILES: CCOC(=O)CC(c1cncc(OC)c1)c1ccc(C)c(CN2C[C@@H](C)Oc3ccccc3S2(=O)=O)c1]

To a solution of ethyl 3-(3-(hydroxymethyl)-4-methylphenyl)-3-(5-methoxypyridin-3-yl)propanoate (70 mg, 0.213 mmol), (R)-4-methyl-3,4-dihydro-2H-benzo[b][1,4,5]oxathiazepine 1,1-dioxide (68.0 mg, 0.319 mmol) and ADDP (107 mg, 0.425 mmol) in THF (5 mL) at 0° C. was added tributylphosphine (0.105 mL, 0.425 mmol). The icebath was removed after 20 min and stirring continued at RT for 1 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min. The solvent was removed under reduced pressure to give 80 mg (72%) of the title compound. LC-MS m/z 525.3 (M+H)$^+$, 1.01 (ret. time).

3-(5-methoxypyridin-3-yl)-3-(4-methyl-3-(((R)-4-methyl-1,1-dioxido-3,4-dihydro-2H-benzo[b][1,4,5]oxathiazepin-2-yl)methyl)phenyl)propanoic acid

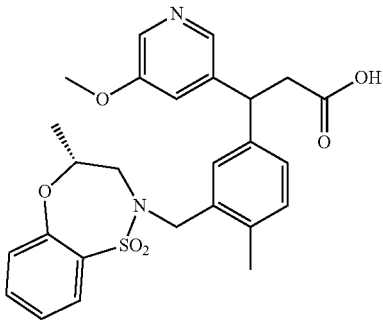 [SMILES: COc1cncc(C(CC(=O)O)c2ccc(C)c(CN3C[C@@H](C)Oc4ccccc4S3(=O)=O)c2)c1]

Ethyl 3-(5-methoxypyridin-3-yl)-3-(4-methyl-3-(((R)-4-methyl-1,1-dioxido-3,4-dihydro-2H-benzo[b][1,4,5]oxathiazepin-2-yl)methyl)phenyl)propanoate (109 mg, 0.208 mmol) was dissolved in THF (2 mL) and water (0.4 mL) then was added LiOH (49.8 mg, 2.078 mmol). The resulting reaction mixture was stirred at RT for 20 h. The reaction mixture was acidified with HCl (1 N) and concentrated. The crude product was dissolved in DMSO (2 mL), filtered through a 0.45 μm acrodisc, and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 37 mg (40%) of the title compound. LC-MS m/z 497.2 (M+H)$^+$, 0.87 (ret. time).

Example 82

3-(3-methoxy-5-(trifluoromethoxy)phenyl)-3-(4-methyl-3-(((R)-4-methyl-1,1-dioxido-3,4-dihydro-2H-benzo[b][1,4,5]oxathiazepin-2-yl)methyl)phenyl)propanoic acid

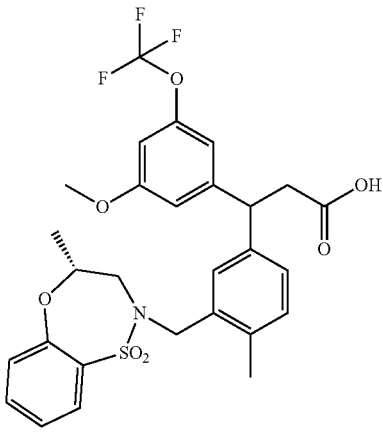 [SMILES: COc1cc(OC(F)(F)F)cc(C(CC(=O)O)c2ccc(C)c(CN3C[C@@H](C)Oc4ccccc4S3(=O)=O)c2)c1]

(E)-ethyl-3-(3-methoxy-5-(trifluoromethoxy)phenyl)acrylate

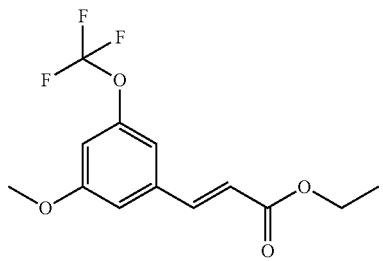 [SMILES: CCOC(=O)/C=C/c1cc(OC)cc(OC(F)(F)F)c1]

To a solution of 1-bromo-3-methoxy-5-(trifluoromethoxy)benzene (300 mg, 1.107 mmol) in DMF (5 mL) at RT was added ethyl acrylate (1108 mg, 11.07 mmol) and N-ethyl-N-isopropylpropan-2-amine (858 mg, 6.64 mmol), tri-o-tolylphosphine (135 mg, 0.443 mmol), Pd(OAc)$_2$ (49.7 mg, 0.221 mmol). The reaction mixture was heated in microwave under high absorption at 150° C. for 2 h. The reaction mixture was passed through celite and washed with EtOAc. The filtrate was washed with water twice, brine (1×). The organic layer was collected and concentrated to give the crude product. The crude product was purified on a silica cartridge (40 g) with a Combiflash Companion, eluting at 35 mL/min with a gradient running from 0% EtOAc/hexanes to 50% over 35 min. The desired fractions were concentrated under reduced pressure to give 215 mg (67%) of the title compound. LC-MS m/z 291.1 (M+H)$^+$, 1.20 (ret. time).

Ethyl 3-(3-(hydroxymethyl)-4-methylphenyl)-3-(3-methoxy-5-(trifluoromethoxy)phenyl)propanoate

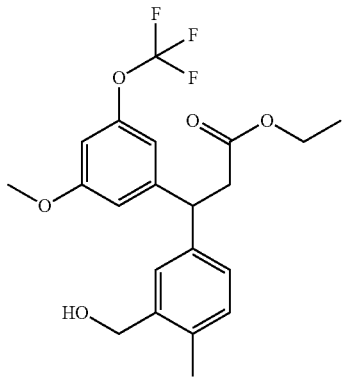 [SMILES: CCOC(=O)CC(c1cc(OC)cc(OC(F)(F)F)c1)c1ccc(C)c(CO)c1]

To (E)-ethyl 3-(3-methoxy-5-(trifluoromethoxy)phenyl) acrylate (115 mg, 0.396 mmol) in 1,4-dioxane (10 mL) and water (5.00 mL) was added (3-(hydroxymethyl)-4-methylphenyl)boronic acid (118 mg, 0.713 mmol), Et$_3$N (60.1 mg, 0.594 mmol) and. [RhCl(cod)]$_2$ (9.77 mg, 0.020 mmol). The result reaction mixture was stirred at 95° C. for 1 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min to give 120 mg (73%) of the title compound. LC-MS m/z 395.1 (M+H)$^+$, 1.16 (ret. time).

Ethyl 3-(3-methoxy-5-(trifluoromethoxy)phenyl)-3-(4-methyl-3-(((R)-4-methyl-1,1-dioxido-3,4-dihydro-2H-benzo[b][1,4,5]oxathiazepin-2-yl)methyl) phenyl)propanoate

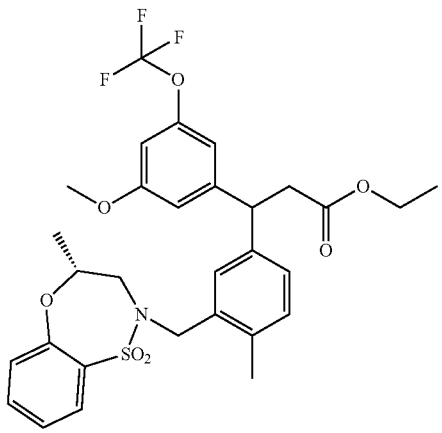 [SMILES: CCOC(=O)CC(c1cc(OC)cc(OC(F)(F)F)c1)c1ccc(C)c(CN2C[C@@H](C)Oc3ccccc3S2(=O)=O)c1]

To a solution of ethyl 3-(3-(hydroxymethyl)-4-methylphenyl)-3-(3-methoxy-5-(trifluoromethoxy)phenyl)propanoate (50 mg, 0.121 mmol), (R)-4-methyl-3,4-dihydro-2H-benzo[b][1,4,5]oxathiazepine 1,1-dioxide (31.0 mg, 0.145 mmol) and ADDP (61.2 mg, 0.242 mmol) in THF (5 mL) at 0° C. was added tributylphosphine (0.060 mL, 0.242 mmol). The ice-bath was removed after 20 min and stirring continued at RT for 1 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min. The solvent was removed under reduced pressure to give 40 mg (55%) of the title compound. LC-MS m/z 608.3 (M+H)$^+$, 1.42 (ret. time).

3-(3-methoxy-5-(trifluoromethoxy)phenyl)-3-(4-methyl-3-(((R)-4-methyl-1,1-dioxido-3,4-dihydro-2H-benzo[b][1,4,5]oxathiazepin-2-yl)methyl)phenyl) propanoic acid

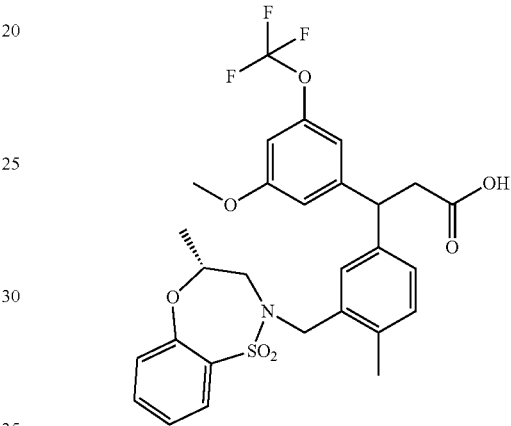

Ethyl 3-(3-methoxy-5-(trifluoromethoxy)phenyl)-3-(4-methyl-3-(((R)-4-methyl-1,1-dioxido-3,4-dihydro-2H-benzo[b][1,4,5]oxathiazepin-2-yl)methyl)phenyl)propanoate (40 mg, 0.066 mmol) was dissolved in THF (2 mL) and water (0.4 mL) then was added LiOH (15.76 mg, 0.658 mmol). The result reaction mixture was stirred at RT for 20 h. The reaction mixture was acidified with HCl (1 N) and concentrated. The crude product was dissolved in DMSO (2 mL), filtered through a 0.45 µm acrodisc, and purified by reverse-phase HPLC (YMC C18 S-5 µm/12 nm 50×20 mm preparatory column), eluting at 20 mL/min with a linear gradient running from 20% CH$_3$CN/H$_2$O to 90% CH$_3$CN/H$_2$O over 10 min to give 17 mg (44%) of the title compound. LC-MS m/z 580.2 (M+H)$^+$, 1.25 (ret. time).

Example 83

3-(3-((4-ethyl-1,1-dioxido-3,4-dihydro-2H-benzo[b][1,4,5]oxathiazepin-2-yl)methyl)-4-methylphenyl)-3-(1-methyl-2-oxo-1,2-dihydropyridin-4-yl)propanoic acid

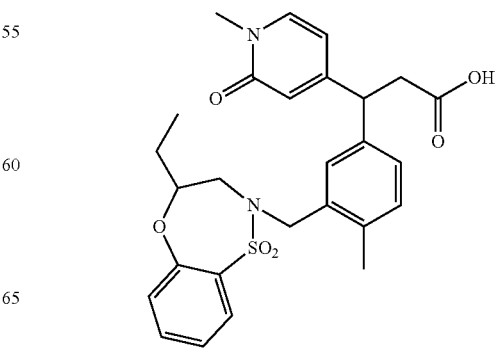

199

(E)-Ethyl 3-(1-methyl-2-oxo-1,2-dihydropyridin-4-yl)acrylate

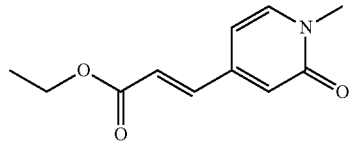

To a solution of 4-bromo-1-methylpyridin-2(1H)-one (1000 mg, 5.32 mmol) in DMF (20 mL), ethyl acrylate (3195 mg, 31.9 mmol), tri-o-tolylphosphine (486 mg, 1.596 mmol), N-ethyl-N-isopropylpropan-2-amine (2750 mg, 21.27 mmol) and Pd(OAc)$_2$ (179 mg, 0.798 mmol) were added. The reaction mixture was heated in a microwave at 120° C. for 2 h. Water was added to quench the reaction. EtOAc was added, and the layers were separated. The aqueous layer was extracted once with EtOAc, and the combined organic layers were washed once with brine. The organic layer was concentrated. The crude product was then purified on a silica cartridge (40 g) with a silica cartridge (40 g) with a Combiflash Companion, eluting at 30 mL/min with a gradient running from 100% CH$_2$Cl$_2$ s to 80% MeOH/CH$_2$Cl$_2$ over 35 min) to give 334 mg (77%) of the title compound. LC-MS m/z 207.9 (M+H)$^+$, 0.67 (ret. time).

Ethyl 3-(3-(hydroxymethyl)-4-methylphenyl)-3-(1-methyl-2-oxo-1,2-dihydropyridin-4-yl)propanoate

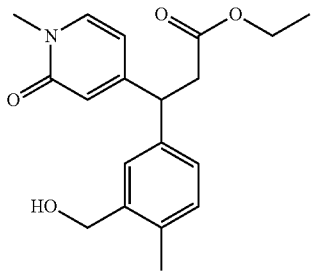 [SMILES: CCOC(=O)CC(c1ccc(C)c(CO)c1)c1ccn(C)c(=O)c1]

To (E)-ethyl 3-(1-methyl-2-oxo-1,2-dihydropyridin-4-yl)acrylate (580 mg, 2.80 mmol) in 1,4-dioxane (10 mL) and water (5.00 mL) was added (3-(hydroxymethyl)-4-methylphenyl)boronic acid (836 mg, 5.04 mmol), Et$_3$N (425 mg, 4.20 mmol) and [RhCl(cod)]$_2$ (69.0 mg, 0.140 mmol). The resulting reaction mixture was stirred at 95° C. for 1 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min to give 500 mg (54%) of the title compound. LC-MS m/z 330.1.1 (M+H)$^+$, 0.71 (ret. time).

200

Ethyl 3-(3-((4-ethyl-1,1-dioxido-3,4-dihydro-2H-benzo[b][1,4,5]oxathiazepin-2-yl)methyl)-4-methylphenyl)-3-(1-methyl-2-oxo-1,2-dihydropyridin-4-yl)propanoate

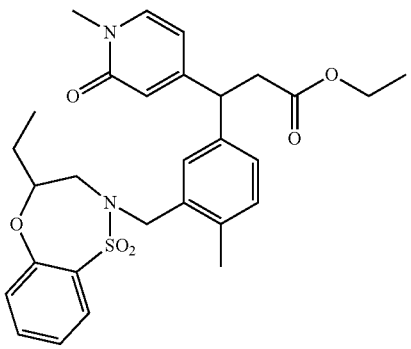 [SMILES: CCOC(=O)CC(c1ccc(C)c(CN2CC(CC)Oc3ccccc3S2(=O)=O)c1)c1ccn(C)c(=O)c1]

To a solution of ethyl 3-(3-(hydroxymethyl)-4-methylphenyl)-3-(1-methyl-2-oxo-1,2-dihydropyridin-4-yl)propanoate (80 mg, 0.243 mmol), 4-ethyl-3,4-dihydro-2H-benzo[b][1,4,5]oxathiazepine 1,1-dioxide (66.2 mg, 0.291 mmol) and ADDP (123 mg, 0.486 mmol) in THF (5 mL) at 0° C. was added tributylphosphine (98 mg, 0.486 mmol). The ice-bath was removed after 20 min and stirring continued at RT for 1 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min. The solvent was removed under reduced pressure to give 90 mg (69%) of the title compound. LC-MS m/z 539.3 (M+H)$^+$, 1.05 (ret. time).

3-(3-((4-ethyl-1,1-dioxido-3,4-dihydro-2H-benzo[b][1,4,5]oxathiazepin-2-yl)methyl)-4-methylphenyl)-3-(1-methyl-2-oxo-1,2-dihydropyridin-4-yl)propanoic acid

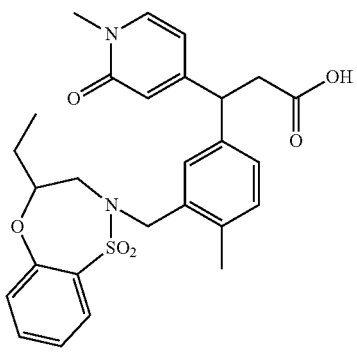 [SMILES: CCC1CN(Cc2cc(C(CC(=O)O)c3ccn(C)c(=O)c3)ccc2C)S(=O)(=O)c2ccccc2O1]

Ethyl 3-(3-((4-ethyl-1,1-dioxido-3,4-dihydro-2H-benzo[b][1,4,5]oxathiazepin-2-yl)methyl)-4-methylphenyl)-3-(1- methyl-2-oxo-1,2-dihydropyridin-4-yl)propanoate (150 mg, 0.278 mmol) was dissolved in THF (2 mL) and water (0.4 mL) then was added LiOH (66.7 mg, 2.78 mmol). The result reaction mixture was stirred at RT for 20 h. The reaction mixture was acidified with HCl (1 N) and concentrated. The crude product was dissolved in DMSO (2 mL), filtered through a 0.45 μm acrodisc, and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 45 mg (32%) of the title compound. LC-MS m/z 511.2 (M+H)$^+$, 0.89 (ret. time).

Example 84

3-(1-methyl-2-oxo-1,2-dihydropyridin-4-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid

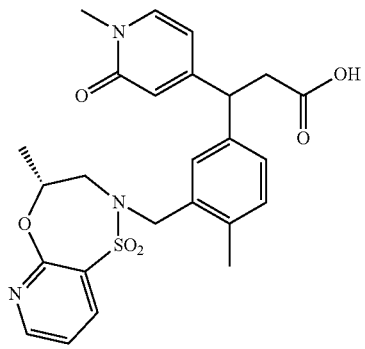 [SMILES: Cc1ccc(C(CC(=O)O)c2ccn(C)c(=O)c2)cc1CN1C[C@@H](C)Oc2ncccc2S1(=O)=O]

Ethyl 3-(3-(hydroxymethyl)-4-methylphenyl)-3-(1-methyl-2-oxo-1,2-dihydropyridin-4-yl)propanoate

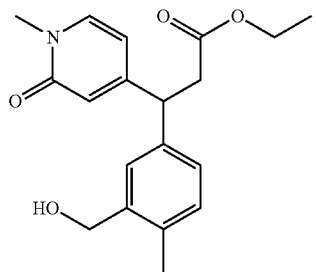 [SMILES: CCOC(=O)CC(c1ccc(C)c(CO)c1)c1ccn(C)c(=O)c1]

To (E)-ethyl 3-(1-methyl-2-oxo-1,2-dihydropyridin-4-yl)acrylate (580 mg, 2.80 mmol) in 1,4-dioxane (10 mL) and water (5.00 mL) was added (3-(hydroxymethyl)-4-methylphenyl)boronic acid (836 mg, 5.04 mmol), Et$_3$N (425 mg, 4.20 mmol) and. [RhCl(cod)]$_2$ (69.0 mg, 0.140 mmol). The resulting reaction mixture was stirred at 95° C. for 1 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min to give 500 mg (54%) of the title compound. LC-MS m/z 330.1.1 (M+H)$^+$, 0.71 (ret. time).

3-(1-methyl-2-oxo-1,2-dihydropyridin-4-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoic acid

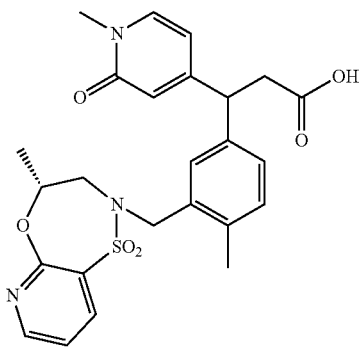 [SMILES: Cc1ccc(C(CC(=O)O)c2ccn(C)c(=O)c2)cc1CN1C[C@@H](C)Oc2ncccc2S1(=O)=O]

To a solution of ethyl 3-(3-(hydroxymethyl)-4-methylphenyl)-3-(1-methyl-2-oxo-1,2-dihydropyridin-4-yl)propanoate (80 mg, 0.243 mmol), (R)-4-methyl-3,4-dihydro-2H-pyrido[2,3-b][1,4,5]oxathiazepine 1,1-dioxide (62.4 mg, 0.291 mmol) and ADDP (123 mg, 0.486 mmol) in THF (5 mL) at 0° C. was added tributylphosphine (98 mg, 0.486 mmol). The ice-bath was removed after 20 min and stirring continued at RT for 1 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min. The solvent was removed under reduced pressure to give 190 mg of crude ethyl 3-(1-methyl-2-oxo-1,2-dihydropyridin-4-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoate. Ethyl 3-(1-methyl-2-oxo-1,2-dihydropyridin-4-yl)-3-(4-methyl-3-(((R)-4-methyl-1,1-dioxido-3,4-dihydro-2H-pyrido[2,3-b][1,4,5]oxathiazepin-2-yl)methyl)phenyl)propanoate (150 mg, 0.285 mmol) was dissolved in THF (2 mL) and water (0.4 mL) then was added LiOH (68.3 mg, 2.85 mmol). The result reaction mixture was stirred at RT for 20 h. The reaction mixture was acidified with HCl (1 N) and concentrated. The crude product was dissolved in DMSO (2 mL), filtered through a 0.45 μm acrodisc, and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 42 mg (30%) of the title compound. LC-MS m/z 498.2 (M+H)$^+$, 0.73 (ret. time).

Example 85

3-(4-chloro-3-(((R)-4-methyl-1,1-dioxido-3,4-dihydro-2H-benzo[b][1,4,5]oxathiazepin-2-yl)methyl)phenyl)-3-(1-methyl-2-oxo-1,2-dihydropyridin-4-yl)propanoic acid

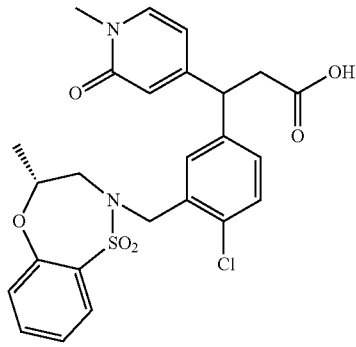 [SMILES: C[C@@H]1CN(Cc2cc(C(CC(=O)O)c3ccn(C)c(=O)c3)ccc2Cl)S(=O)(=O)c2ccccc2O1]

(2-chloro-5-(4,4,5,5-tetramethyl-1,3,2-dioxaborolan-2-yl)phenyl)methanol

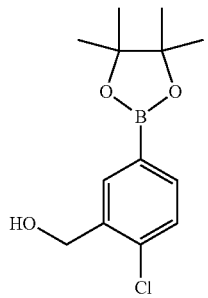 [SMILES: CC1(C)OB(c2ccc(Cl)c(CO)c2)OC1(C)C]

A suspension of (5-bromo-2-chlorophenyl)methanol (700 mg, 3.16 mmol), potassium acetate (1179 mg, 12.01 mmol)) and 4,4,4',4',5,5,5',5'-octamethyl-2,2'-bi(1,3,2-dioxaborolane) (963 mg, 3.79 mmol) degassed with a stream of nitrogen for ~10 min after which time was added (PPh$_3$)$_2$PdCl$_2$ (133 mg, 0.190 mmol) and the mixture was heated to 120° C. for 30 min in a microwave at high power. After this time, the suspension was cooled and filtered through celite using EtOAc to wash the celite. The dark colored solution was washed with water (4× gently), brine (1×), dried over MgSO$_4$, filtered and concentrated under reduced pressure. The crude product was purified over a silica cartridge (12 g, solid load) using Combiflash Companion eluting at 30 mL/min running a gradient of 0-30% EtOAC/hexane over 40 min nm. The solvent was removed under reduced pressure to give 350 mg (41%) of the title compound. LC-MS m/z 251.0 (M+H)$^+$, 1.01 (ret. time).

Ethyl 3-(4-chloro-3-(hydroxymethyl)phenyl)-3-(1-methyl-2-oxo-1,2-dihydropyridin-4-yl)propanoate To (E)-ethyl 3-(1-methyl-2-oxo-1,2-dihydropyridin-4-yl)acrylate (150 mg, 0.724 mmol) in 1,4-dioxane (10 mL) and water (5.00 mL) was added (2-chloro-5-(4,4,5,5-tetramethyl-1,3,2-dioxaborolan-2-yl)phenyl)methanol (350 mg, 1.303 mmol), Et$_3$N (110 mg, 1.086 mmol) and [RhCl(cod)]$_2$ (17.85 mg, 0.036 mmol). The result reaction mixture was stirred at 95° C. for 1 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min to give 162 mg (64%) of the title compound. LC-MS m/z 350.1 (M+H)$^+$, 0.74 (ret. time).

Ethyl 3-(4-chloro-3-(((R)-4-methyl-1,1-dioxido-3,4-dihydro-2H-benzo[b][1,4,5]oxathiazepin-2-yl)methyl)phenyl)-3-(1-methyl-2-oxo-1,2-dihydropyridin-4-yl)propanoate To a solution of ethyl 3-(4-chloro-3-(hydroxymethyl)phenyl)-3-(1-methyl-2-oxo-1,2-dihydropyridin-4-yl)propanoate (162 mg, 0.463 mmol), (R)-4-methyl-3,4-dihydro-2H-benzo[b][1,4,5]oxathiazepine 1,1-dioxide (178 mg, 0.834 mmol) and ADDP (117 mg, 0.463 mmol) in THF (5 mL) at 0° C. was added tributylphosphine (0.114 mL, 0.463 mmol). The ice-bath was removed after 20 min and stirring continued at RT for 1 h. Added 2 eq more tributylphosphine and ADDP and let running over the weekend. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min. The solvent was removed under reduced pressure to give 150 mg (60%) of the title compound. LC-MS m/z 545.2 (M+H)⁺, 1.05 (ret. time).

3-(4-chloro-3-(((R)-4-methyl-1,1-dioxido-3,4-di-hydro-2H-benzo[b][1,4,5]oxathiazepin-2-yl)methyl)phenyl)-3-(1-methyl-2-oxo-1,2-dihydropyridin-4-yl)propanoic acid

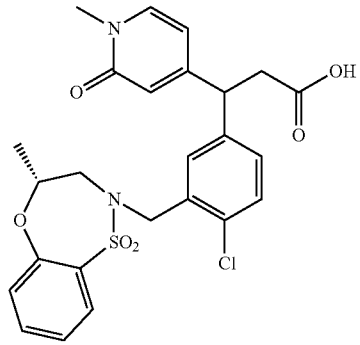 [SMILES: C[C@@H]1CN(Cc2cc(C(CC(=O)O)c3ccn(C)c(=O)c3)ccc2Cl)S(=O)(=O)c2ccccc2O1]

Ethyl 3-(4-chloro-3-(((R)-4-methyl-1,1-dioxido-3,4-di-hydro-2H-benzo[b][1,4,5]oxathiazepin-2-yl)methyl)phenyl)-3-(1-methyl-2-oxo-1,2-dihydropyridin-4-yl)propanoate (150 mg, 0.275 mmol) was dissolved in THF (2 mL) and water (0.4 mL) then was added LiOH (65.9 mg, 2.75 mmol). The resulting reaction mixture was stirred at RT for 20 h. The reaction mixture was acidified with HCl (1 N) and concentrated. The crude product was dissolved in DMSO (2 mL), filtered through a 0.45 μm acrodisc, and purified by reverse-phase HPLC (YMC C18 S-5 μm/12 nm 50×20 mm preparatory column), eluting at 20 mL/min with a linear gradient running from 20% CH₃CN/H₂O to 90% CH₃CN/H₂O over 10 min to give 74 mg (52%) of the title compound. LC-MS m/z 517.1 (M+H)⁺, 0.90 (ret. time).

Example 86

3-(1-methyl-2-oxo-1,2-dihydropyridin-4-yl)-3-(4-methyl-3-((5-methyl-1,1-dioxido-4,5-dihydrobenzo[f][1,2,5]thiadiazepin-2(3H)-yl)methyl)phenyl)propanoic acid

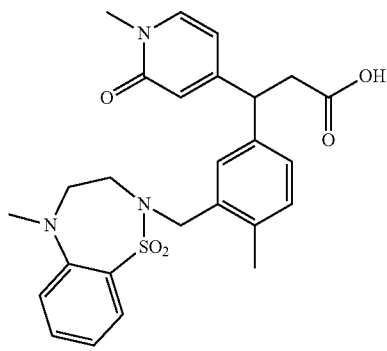 [SMILES: Cc1ccc(C(CC(=O)O)c2ccn(C)c(=O)c2)cc1CN1CCN(C)c2ccccc2S1(=O)=O]

5-methyl-2,3,4,5-tetrahydrobenzo[f][1,2,5]thiadiazepine 1,1-dioxide

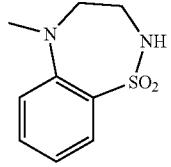

To (E)-ethyl 3-(1-methyl-2-oxo-1,2-dihydropyridin-4-yl)acrylate (580 mg, 2.80 mmol) in 1,4-dioxane (10 mL) and water (5.00 mL) was added (3-(hydroxymethyl)-4-methylphenyl)boronic acid (836 mg, 5.04 mmol), Et₃N (425 mg, 4.20 mmol) and. [RhCl(cod)]₂ (69.0 mg, 0.140 mmol). The resulting reaction mixture was stirred at 95° C. for 1 h. The reaction mixture was extracted with EtOAc (3×10 mL). The combined organic layer was dried over MgSO₄, filtered, concentrated. The product was purified over a silica cartridge (40 g) using Combiflash Companion eluting at 18 mL/min running a gradient of 0-30% EtOAc/hexane over 30 min then 30% to 100% over 20 min. The solvent was removed under reduced pressure to give 500 mg (54%) of the title compound. LC-MS m/z 330.1 (M+H)⁺, 0.71 (ret. time).

Ethyl 3-(3-(hydroxymethyl)-4-methylphenyl)-3-(1-methyl-2-oxo-1,2-dihydropyridin-4-yl)propanoate

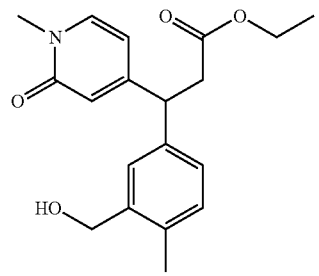 [SMILES: CCOC(=O)CC(c1ccc(C)c(CO)c1)c1ccn(C)c(=O)c1]

(E)-ethyl 3-(1-methyl-2-oxo-1,2-dihydropyridin-4-yl)acrylate (580 mg, 2.80 mmol) in 1,4-dioxane (10 mL) and water (5.00 mL) was added (3-(hydroxymethyl)-4-methylphenyl)boronic acid (836 mg, 5.04 mmol), Et₃N (425 mg, 4.20 mmol) and. [RhCl(cod)]₂ (69.0 mg, 0.140 mmol). The resulting reaction mixture was stirred at 95° C. for 1 h. The reaction mixture was extracted with EtOAc (3×10 mL). The combined organic layer was dried over MgSO₄, filtered, and concentrated then, the product was purified over a silica cartridge (40 g) using Combiflash Companion eluting at 18 mL/min running a gradient of 0-30% EtOAc/hexane over 30 min then, 30% to 100% over 20 min to give 500 mg (54%) of the title compound. LC-MS m/z 330.1.1 (M+H)⁺, 0.71 (ret. time).

Ethyl 3-(1-methyl-2-oxo-1,2-dihydropyridin-4-yl)-3-(4-methyl-3-((5-methyl-1,1-dioxido-4,5-dihydrobenzo[f][1,2,5]thiadiazepin-2(3H)-yl)methyl)phenyl)propanoate

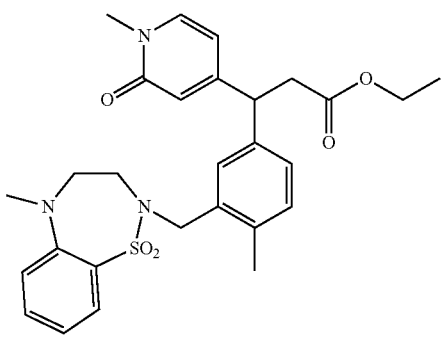 [SMILES: CCOC(=O)CC(c1ccc(C)c(CN2CCN(C)c3ccccc3S2(=O)=O)c1)c1ccn(C)c(=O)c1]

To a solution of ethyl 3-(3-(hydroxymethyl)-4-methylphenyl)-3-(1-methyl-2-oxo-1,2-dihydropyridin-4-yl)propanoate (80 mg, 0.243 mmol), 5-methyl-2,3,4,5-tetrahydrobenzo[f][1,2,5]thiadiazepine 1,1-dioxide (61.9 mg, 0.291 mmol) and ADDP (123 mg, 0.486 mmol) in THF (5 mL) at 0° C. was added tributylphosphine (98 mg, 0.486 mmol). The ice-bath was removed after 20 min and stirring continued at RT for 1 h. Added 2 eq more tributylphosphine and ADDP and let running over week end. The reaction mixture was extracted with EtOAc (3×10 mL). The combined organic layer was dried over MgSO₄, filtered, and concentrated then, the product was purified over a silica cartridge (40 g) using Combiflash Companion eluting at 18 mL/min running a gradient of 0-30% EtOAc/hexane over 30 min then, 30% to 100% over 20 min. The solvent was removed under reduced pressure to give 80 mg (63%) of the title compound. LC-MS m/z 524.3 (M+H)⁺, 0.98 (ret. time).

3-(1-methyl-2-oxo-1,2-dihydropyridin-4-yl)-3-(4-methyl-3-((5-methyl-1,1-dioxido-4,5-dihydrobenzo[f][1,2,5]thiadiazepin-2(3H)-yl)methyl)phenyl)propanoic acid

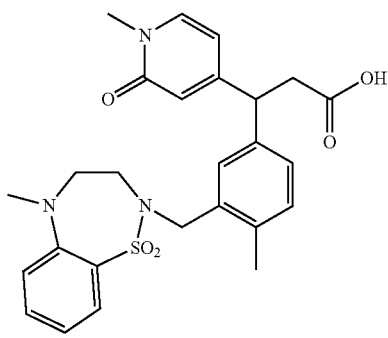 [SMILES: Cc1ccc(C(CC(=O)O)c2ccn(C)c(=O)c2)cc1CN1CCN(C)c2ccccc2S1(=O)=O]

Ethyl 3-(1-methyl-2-oxo-1,2-dihydropyridin-4-yl)-3-(4-methyl-3-((5-methyl-1,1-dioxido-4,5-dihydrobenzo[f][1,2,5]thiadiazepin-2(3H)-yl)methyl)phenyl)propanoate (80 mg, 0.153 mmol) was dissolved in THF (2 mL) and water (0.4 mL) then was added LiOH (36.6 mg, 1.528 mmol). The result reaction mixture was stirred at RT for 20 h. The reaction mixture was acidified with HCl (1 N) and concentrated. The crude product was dissolved in DMSO (2 mL), filtered through a 0.45 µm acrodisc, and purified by reverse-phase HPLC (YMC C18 S-5 µm/12 nm 50×20 mm preparatory column), eluting at 20 mL/min with a linear gradient running from 20% CH₃CN/H₂O to 90% CH₃CN/H₂O over 10 min to give 37 mg (49%) of the title compound. LC-MS m/z 496.3 (M+H)⁺, 0.85 (ret. time).

Example 87

3-(4-fluoro-1,7-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

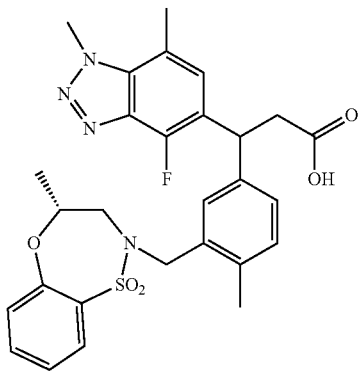 [SMILES: Cc1ccc(C(CC(=O)O)c2cc(C)c3c(nnn3C)c2F)cc1CN1C[C@@H](C)Oc2ccccc2S1(=O)=O]

(R)-4-methyl-3,4-dihydro-2H-benzo[b][1,4,5]oxathiazepine 1,1-dioxide

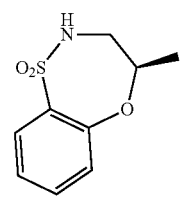

To (R)-1-aminopropan-2-ol (2.023 mL, 25.7 mmol) in THF (40 mL) and water (10.00 mL) was added K₂CO₃ (3551 mg, 25.7 mmol) and then 2-fluorobenzene-1-sulfonyl chloride (3.40 mL, 25.7 mmol) slowly. The resulting reaction mixture was stirred at RT for 1 h. The reaction mixture was diluted with H₂O (10 mL), extracted with EtOAc (20+2*10 mL). The combined organic layer was washed with brine (15 mL), dried over MgSO₄, and concentrated to give 6750 mg of crude (R)-2-fluoro-N-(2-hydroxypropyl)benzenesulfonamide. (R)-2-fluoro-N-(2-hydroxypropyl)benzenesulfonamide (4.56 mL, 28.7 mmol) in DMSO (16 mL) was added KOt-Bu (3223 mg, 28.7 mmol) then heated at 80° C. for 2 h. The reaction mixture was diluted with H₂O (50 mL), acidified with HCl (1 N) to pH ~7, extracted with EtOAc (3×60 mL). The combined organic layer was washed with brine (80 mL), dried over MgSO₄, filtered, and concentrated to give 4700 mg (60%) of the title compound. LC-MS m/z 216.0 (M+H)⁺, 0.57 (ret. time).

Ethyl 3-(4-fluoro-1,7-dimethyl-1H-benzo[d][1,2,3]triazol-5-yl)-3-(3-(hydroxymethyl)-4-methylphenyl)propanoate

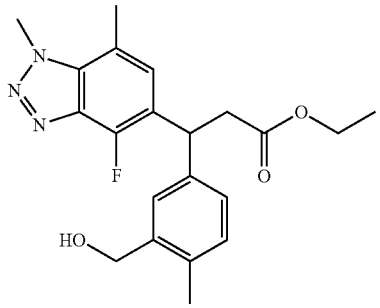 [SMILES: CCOC(=O)CC(c1ccc(C)c(CO)c1)c1cc(C)c2c(nnn2C)c1F]

To (E)-ethyl 3-(4-fluoro-1,7-dimethyl-1H-benzo[d][1,2,3]triazol-5-yl)acrylate (200 mg, 0.760 mmol) in 1,4-dioxane (10 mL) and water (5.00 mL) was added (3-(hydroxymethyl)-4-methylphenyl)boronic acid (227 mg, 1.367 mmol), Et$_3$N (0.159 mL, 1.140 mmol) and [RhCl(cod)]$_2$ (18.73 mg, 0.038 mmol). The resulting reaction mixture was stirred at 95° C. for 1 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min to give 146 mg (50%) of the title compound. LC-MS m/z 386.3 (M+H)$^+$, 0.96 (ret. time).

Ethyl 3-(4-fluoro-1,7-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate

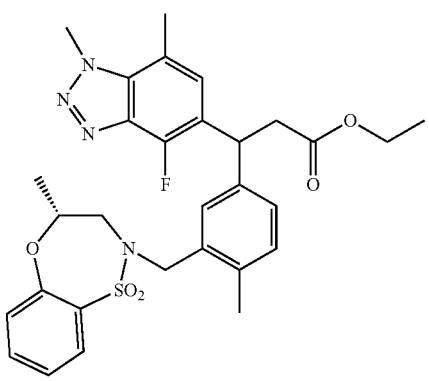 [SMILES: CCOC(=O)CC(c1ccc(C)c(CN2C[C@@H](C)Oc3ccccc3S2(=O)=O)c1)c1cc(C)c2c(nnn2C)c1F]

To a solution of ethyl 3-(4-fluoro-1,7-dimethyl-1H-benzo[d][1,2,3]triazol-5-yl)-3-(3-(hydroxymethyl)-4-methylphenyl)propanoate (146 mg, 0.379 mmol), (R)-4-methyl-3,4-dihydro-2H-benzo[b][1,4,5]oxathiazepine 1,1-dioxide (242 mg, 1.136 mmol) and ADDP (191 mg, 0.758 mmol) in THF (5 mL) at 0° C. was added tributylphosphine (0.187 mL, 0.758 mmol). The ice-bath was removed after 20 min and stirring continued at RT for 1 h. Added 2 eq more tributylphosphine and ADDP and let running over week end. Checked LCMS after 50 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min. The solvent was removed under reduced pressure to give 139 mg (63%) of the title compound. LC-MS m/z 581.4 (M+H)$^+$, 1.21 (ret. time).

3-(4-fluoro-1,7-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

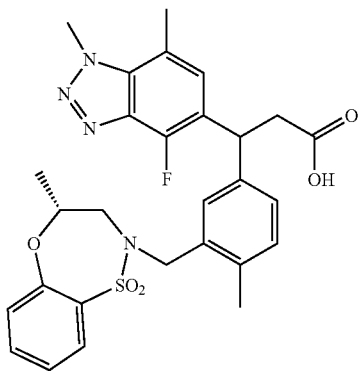 [SMILES: Cc1ccc(C(CC(=O)O)c2cc(C)c3c(nnn3C)c2F)cc1CN1C[C@@H](C)Oc2ccccc2S1(=O)=O]

Ethyl 3-(4-fluoro-1,7-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate (139 mg, 0.239 mmol) was dissolved in THF (2 mL) and water (0.4 mL) then was added LiOH (57.3 mg, 2.394 mmol). The resulting reaction mixture was stirred at RT for 20 h. The reaction mixture was acidified with HCl (1 N) and concentrated. The crude product was dissolved in DMSO (2 mL), filtered through a 0.45 µm acrodisc, and purified by reverse-phase HPLC (YMC C18 S-5 µm/12 nm 50×20 mm preparatory column), eluting at 20 mL/min with a linear gradient running from 20% CH$_3$CN/H$_2$O to 90% CH$_3$CN/H$_2$O over 10 min to give 37 mg (49%) of the title compound. LC-MS m/z 553.3 (M+H)$^+$, 1.05 (ret. time).

Example 88

3-(4-fluoro-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

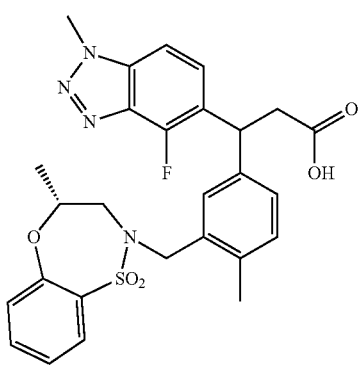 [SMILES: Cc1ccc(C(CC(=O)O)c2ccc3c(nnn3C)c2F)cc1CN1C[C@@H](C)Oc2ccccc2S1(=O)=O]

211

(E)-Ethyl 3-(4-fluoro-1-methyl-1H-benzo[d][1,2,3]triazol-5-yl)acrylate

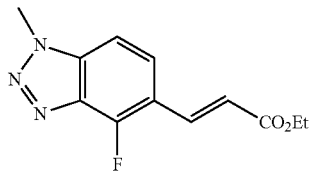 [SMILES: CCOC(=O)/C=C/c1ccc2c(nnn2C)c1F]

To a solution of 5-bromo-4-fluoro-1-methyl-1H-benzo[d][1,2,3]triazole (780 mg, 3.39 mmol), 3-ethoxy-3-oxoprop-1-en-1-ylium (672 mg, 6.78 mmol) in N-Methyl-2-pyrrolidone (NMP) (20 mL), triphenylphosphine (178 mg, 0.678 mmol) and Et$_3$N (0.945 mL, 6.78 mmol) were added then Pd(OAc)$_2$ (152 mg, 0.678 mmol). The resulting reaction mixture was stirred at 120° C. for 3 h. Water was added to quench the reaction. EtOAc was added, and the layers were separated. The aqueous layer was extracted once with EtOAc, and the combined organic layers were washed once with brine. The organic layer was concentrated. The crude product was purified by silica gel chromatograph (petroleum ether:EtOAc=3:1) to give 400 mg (46.4%) of the title compound. LC-MS m/z 250.0 (M+H)$^+$, 1.63 (ret. time).

Ethyl 3-(4-fluoro-1-methyl-1H-benzo[d][1,2,3]triazol-5-yl)-3-(3-(hydroxymethyl)-4-methylphenyl)propanoate

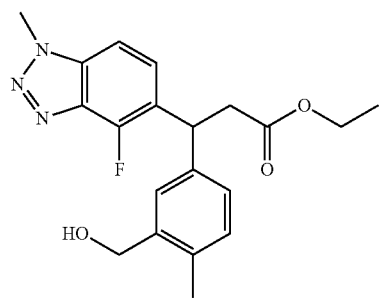 [SMILES: CCOC(=O)CC(c1ccc(C)c(CO)c1)c1ccc2c(nnn2C)c1F]

To (E)-ethyl 3-(4-fluoro-1-methyl-1H-benzo[d][1,2,3]triazol-5-yl)acrylate (200 mg, 0.802 mmol) in 1,4-dioxane (10 mL) and water (5.00 mL) was added (3-(hydroxymethyl)-4-methylphenyl)boronic acid (240 mg, 1.444 mmol), Et$_3$N (0.168 mL, 1.204 mmol) and [RhCl(cod)]$_2$ (19.78 mg, 0.040 mmol). The resulting reaction mixture was stirred at 95° C. for 1 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min to give 173 mg (58%) of the title compound. LC-MS m/z 372.2 (M+H)$^+$, 0.86 (ret. time).

212

Ethyl 3-(4-fluoro-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate

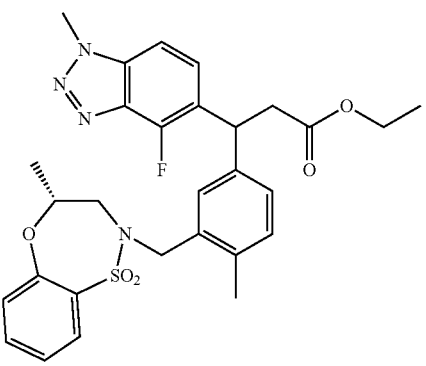 [SMILES: CCOC(=O)CC(c1ccc(C)c(CN2C[C@@H](C)Oc3ccccc3S2(=O)=O)c1)c1ccc2c(nnn2C)c1F]

To a solution of ethyl 3-(4-fluoro-1-methyl-1H-benzo[d][1,2,3]triazol-5-yl)-3-(3-(hydroxymethyl)-4-methylphenyl)propanoate (173 mg, 0.466 mmol), (R)-4-methyl-3,4-dihydro-2H-benzo[b][1,4,5]oxathiazepine 1,1-dioxide (298 mg, 1.397 mmol) and ADDP (235 mg, 0.932 mmol) in THF (5 mL) at 0° C. was added tributylphosphine (0.230 mL, 0.932 mmol). The ice-bath was removed after 20 min and stirring continued at RT for 1 h. The reaction mixture was extracted with EtOAc (3×10 mL). The combined organic layer was dried over MgSO$_4$, filtered, and concentrated then, the product was purified over a silica cartridge (40 g) using Combiflash Companion eluting at 18 mL/min running a gradient of 0-30% EtOAc/hexane over 30 min then, 30% to 100% over 20 min. The solvent was removed under reduced pressure to give 110 mg (42%) of the title compound. LC-MS m/z 537.3 (M+H)$^+$, 1.15 (ret. time).

3-(4-fluoro-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

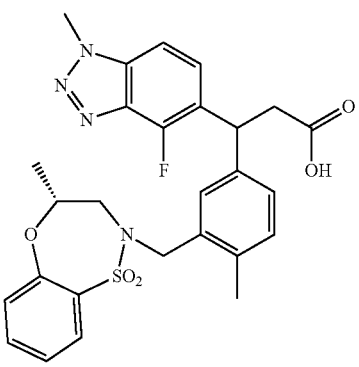 [SMILES: Cc1ccc(C(CC(=O)O)c2ccc3c(nnn3C)c2F)cc1CN1C[C@@H](C)Oc2ccccc2S1(=O)=O]

Ethyl 3-(4-fluoro-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate (110 mg, 0.194 mmol) was dissolved in THF (2 mL) and water (0.4 mL) then was added LiOH (46.5 mg, 1.941 mmol). The resulting reaction mixture was stirred at RT for 20 h. The reaction mixture was acidified with HCl (1 N) and concentrated. The crude product was dissolved in DMSO (2 mL), filtered through a 0.45 µm acrodisc, and purified by reverse-phase HPLC (YMC C18 S-5 µm/12 nm 50×20 mm preparatory column), eluting at 20 mL/min with a linear gradient running from 20% CH₃CN/H₂O to 90% CH₃CN/H₂O over 10 min to give 37 mg (49%) of the title compound. LC-MS m/z 553.3 (M+H)⁺, 1.05 (ret. time).

Example 89

3-(3-(((((cyclopentyloxy)carbonyl)(methyl)amino)methyl)-4-methylphenyl)-3-(7-methoxy-1,4-dimethyl-1H-benzo[d][1,2,3]triazol-5-yl)propanoic acid

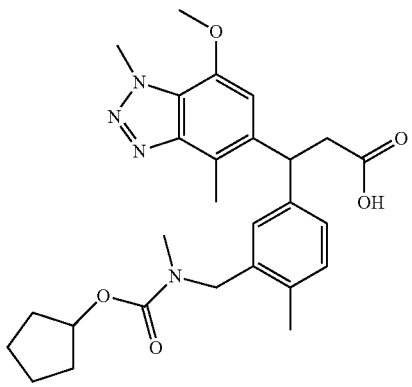 [SMILES: COc1cc(C(CC(=O)O)c2ccc(C)c(CN(C)C(=O)OC3CCCC3)c2)c(C)c2nnn(C)c12]

(E)-Ethyl 3-(7-methoxy-1,4-dimethyl-1H-benzo[d][1,2,3]triazol-5-yl)acrylate

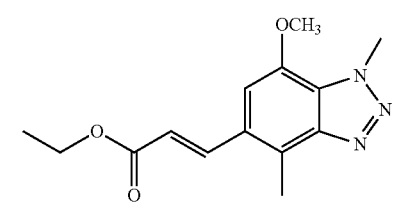 [SMILES: CCOC(=O)/C=C/c1cc(OC)c2c(nnn2C)c1C]

To a solution of 5-bromo-7-methoxy-1,4-dimethyl-1H-benzo[d][1,2,3]triazole (1000 mg, 3.90 mmol) in DMF (20 mL), ethyl acrylate (2346 mg, 23.43 mmol), tri-o-tolylphosphine (357 mg, 1.171 mmol), N-ethyl-N-isopropylpropan-2-amine (2019 mg, 15.62 mmol) and Pd(OAc)₂ (131 mg, 0.586 mmol) were added. The reaction mixture was heated in a microwave at 110° C. for 1 h. Water was added to quench the reaction. EtOAc was added, and the layers were separated. The aqueous layer was extracted once with EtOAc, and the combined organic layers were washed once with brine. The organic layer was concentrated. The crude product was then purified on a silica cartridge (40 g) with a Combiflash Companion, eluting at 30 mL/min with a gradient running from 100% Hexanes to 80% EtOAc/Hexanes over 35 min) to give 950 mg (88%) of the title compound. LC-MS m/z 276.0 (M+H)⁺, 0.97 (ret. time).

Ethyl 3-(3-(hydroxymethyl)-4-methylphenyl)-3-(7-methoxy-1,4-dimethyl-1H-benzo[d][1,2,3]triazol-5-yl)propanoate

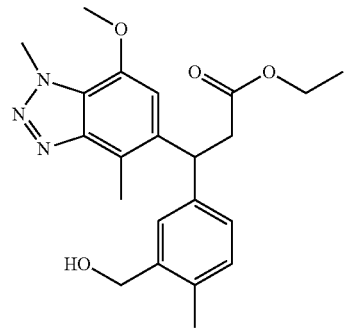 [SMILES: CCOC(=O)CC(c1ccc(C)c(CO)c1)c1cc(OC)c2c(nnn2C)c1C]

To (E)-ethyl 3-(7-methoxy-1,4-dimethyl-1H-benzo[d][1,2,3]triazol-5-yl)acrylate (150 mg, 0.545 mmol) in 1,4-dioxane (10 mL) and water (5.00 mL) was added (3-(hydroxymethyl)-4-methylphenyl)boronic acid (163 mg, 0.981 mmol), Et₃N (83 mg, 0.817 mmol) and [RhCl(cod)]₂ (13.43 mg, 0.027 mmol). The result reaction mixture was stirred at 95° C. for 1 h. The reaction mixture was extracted with EtOAc (3×10 mL). The combined organic layer was dried over MgSO₄, filtered, and concentrated then, the product was purified over a silica cartridge (40 g) using Combiflash Companion eluting at 18 mL/min running a gradient of 0-30% EtOAc/hexane over 30 min then, 30% to 100% over 20 min to give 170 mg (70%) of the title compound. LC-MS m/z 398.2 (M+H)⁺, 0.93 (ret. time).

Ethyl 3-(3-(chloromethyl)-4-methylphenyl)-3-(7-methoxy-1,4-dimethyl-1H-benzo[d][1,2,3]triazol-5-yl)propanoate

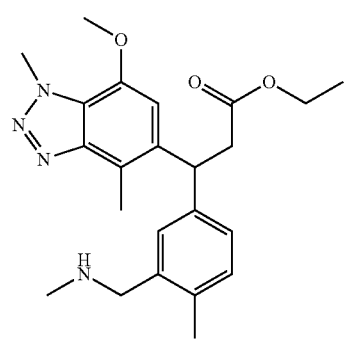 [SMILES: CCOC(=O)CC(c1ccc(C)c(CNC)c1)c1cc(OC)c2c(nnn2C)c1C]

To a solution of ethyl 3-(3-(hydroxymethyl)-4-methylphenyl)-3-(7-methoxy-1,4-dimethyl-1H-benzo[d][1,2,3]triazol-5-yl)propanoate (350 mg, 0.881 mmol) dissolved in DCM (6 mL) was added thionyl chloride (0.096 mL, 1.321 mmol) and the mixture was stirred at RT for 48 h. After checking LC-MS, the mixture was evaporated down with V10 evaporator under vacuum to get 326 mg crude of ethyl 3-(3-(chloromethyl)-4-methylphenyl)-3-(7-methoxy-1,4-dimethyl-1H-benzo[d][1,2,3]triazol-5-yl)propanoate. 1). To the crude ethyl 3-(3-(chloromethyl)-4-methylphenyl)-3-(7-methoxy-1,4-dimethyl-1H-benzo[d][1,2,3]triazol-5-yl)propanoate (200 mg, 0.481 mmol) dissolved in THF (2 mL) was added methanamine (14.93 mg, 0.481 mmol) and N-ethyl-N-isopropylpropan-2-amine (249 mg, 1.923 mmol) and the mixture was heated under Microwave conditions (120° C., 1 h, high) then, the mixture was evaporated down with a rotavap evaporator under vacuum, dissolved in DCM and purified through Combi flash to give 170 mg (70%) of the title compound. LC-MS m/z 411.2 (M+H)$^+$, 0.70 (ret. time).

Ethyl 3-(3-(((((cyclopentyloxy)carbonyl)(methyl)amino)methyl)-4-methylphenyl)-3-(7-methoxy-1,4-dimethyl-1H-benzo[d][1,2,3]triazol-5-yl)propanoate

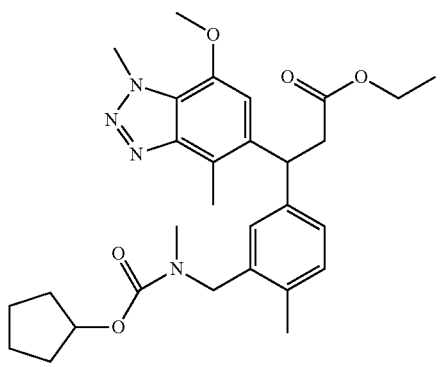 [SMILES: CCOC(=O)CC(c1ccc(C)c(CN(C)C(=O)OC2CCCC2)c1)c1cc(OC)c2c(nnn2C)c1C]

To a solution of ethyl 3-(7-methoxy-1,4-dimethyl-1H-benzo[d][1,2,3]triazol-5-yl)-3-(4-methyl-3-((methylamino)methyl)phenyl)propanoate (90 mg, 0.219 mmol) and Et$_3$N (33.3 mg, 0.329 mmol) in DCM (4 mL), in an ice bath, was added drop wise a solution of cyclopentyl chloroformate (0.055 mL, 0.438 mmol) in DCM (1 mL). The resulting solution was taken out of the ice bath and left to stir for 18 h. The reaction mixture was further diluted with DCM and washed with water (3×) and brine (1×). The organic layer was dried over MgSO$_4$, filtered and concentrated under reduced pressure give 52 mg (60%) of the title compound. LC-MS m/z 523.4 (M+H)$^+$, 1.26 (ret. time).

3-(3-(((((cyclopentyloxy)carbonyl)(methyl)amino)methyl)-4-methylphenyl)-3-(7-methoxy-1,4-dimethyl-1H-benzo[d][1,2,3]triazol-5-yl)propanoic acid

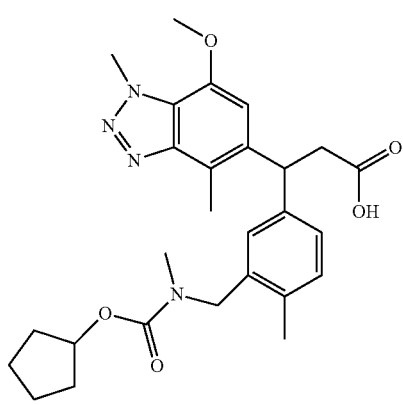 [SMILES: COc1cc(C(CC(=O)O)c2ccc(C)c(CN(C)C(=O)OC3CCCC3)c2)c(C)c2nnn(C)c12]

Ethyl 3-(3-(((((cyclopentyloxy)carbonyl)(methyl)amino)methyl)-4-methylphenyl)-3-(7-methoxy-1,4-dimethyl-1H-benzo[d][1,2,3]triazol-5-yl)propanoate (60 mg, 0.115 mmol) was dissolved in THF (2 mL) and water (0.4 mL) then was added LiOH (27.5 mg, 1.148 mmol). The result reaction mixture was stirred at RT for 20 h. The reaction mixture was acidified with HCl (1 N) and concentrated. The crude product was dissolved in DMSO (2 mL), filtered through a 0.45 μm acrodisc, and purified by reverse-phase HPLC (YMC C18 S-5 μm/12 nm 50×20 mm preparatory column), eluting at 20 mL/min with a linear gradient running from 20% CH$_3$CN/H$_2$O to 90% CH$_3$CN/H$_2$O over 10 min to give 10 mg (17%) of the title compound. LC-MS m/z 495.3 (M+H)$^+$, 1.08 (ret. time).

Example 90

3-(1,4-Dimethyl-1H-benzo[d][1,2,3]triazol-5-yl)-3-(4-methyl-3-((N-methylcyclopentanesulfonamido)methyl)phenyl)propanoic acid

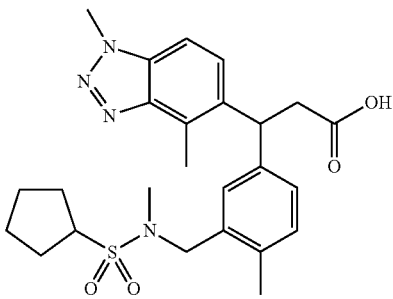 [SMILES: Cc1ccc(C(CC(=O)O)c2ccc3c(nnn3C)c2C)cc1CN(C)S(=O)(=O)C1CCCC1]

(E)-Ethyl 3-(1,4-dimethyl-1H-benzo[d][1,2,3]triazol-5-yl)acrylate

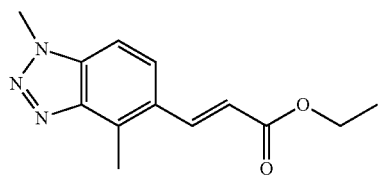 [SMILES: CCOC(=O)/C=C/c1ccc2c(nnn2C)c1C]

To a solution of 5-bromo-1,4-dimethyl-1H-benzo[d][1,2,3]triazole (1100 mg, 4.87 mmol) in DMF (5 mL) at RT was added ethyl acrylate (3.11 mL, 29.2 mmol) and N-ethyl-N-isopropylpropan-2-amine (3.40 mL, 19.46 mmol), tri-o-tolylphosphine (444 mg, 1.460 mmol), followed by Pd(OAc)$_2$ (164 mg, 0.730 mmol). The reaction mixture was heated in microwave under high absorption at 150° C. for 2 h. The reaction mixture was passed through celite and washed with EtOAc. The filtrate was washed with water twice, brine (1×). The organic layer was collected and concentrated to give the crude product. The crude product was purified by flash chromatography to give the title compound (662 mg, 2.70 mmol, 55.5% yield) and a less pure batch (481 mg, 1.961 mmol, 40.3% yield). LC-MS m/z 246.1 (M+H)$^+$, 0.85 min (ret. time)

217

Ethyl 3-(1,4-dimethyl-1H-benzo[d][1,2,3]triazol-5-yl)-3-(3-(hydroxymethyl)-4-methylphenyl)propanoate

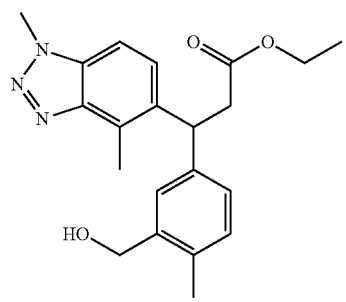 [SMILES: CCOC(=O)CC(c1ccc(C)c(CO)c1)c1ccc2c(nnn2C)c1C]

To a suspension of (E)-ethyl 3-(1,4-dimethyl-1H-benzo[d][1,2,3]triazol-5-yl)acrylate (1200 mg, 4.89 mmol), (3-(hydroxymethyl)-4-methylphenyl)boronic acid (974 mg, 5.87 mmol), and [RhCl(cod)]$_2$ (271 mg, 0.489 mmol) in 1,4-dioxane (10 mL) and water (10 mL) at RT was added Et$_3$N (2.046 mL, 14.68 mmol). The resulting suspension was heated in a Biotage microwave at high absorption for 60 min at 150° C. The reaction mixture was passed through celite and washed with EtOAc. The filtrate was washed with water twice, brine (1×). The organic layer was collected and concentrated to give the crude product. The crude product was purified by flash chromatography to give the title compound (1290 mg, 3.51 mmol, 71.8% yield) and a less pure batch (453 mg). LC-MS m/z 367.8 (M+H)$^+$, 0.86 min (ret. time)

N-Methylcyclopentanesulfonamide

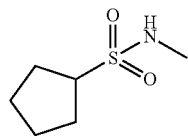

Methylamine-2.0 M THF (2.5 mL, 5 mmol) was added to a solution of cyclopentanesulfonyl chloride (0.3 mL, 2.275 mmol) in DCM (5 mL) at 0° C. The solution was stirred for 20 h. DCM (2 mL) was added and washed with saturated NaHCO$_3$ and brine. The organic layer was dried over Na$_2$SO$_4$, filtered and the filtrate was concentrated under reduced pressure to give the crude product. It was re-dissolved in DCM (4 mL) and 0.5 mL of Et$_3$N was added and stirred for 1 h. Water (2 mL) was added and the mixture extracted twice with DCM. The organic layer was washed with brine, dried over Na$_2$SO$_4$, filtered and concentrated to give the title compound (212 mg, 1.299 mmol, 57.1% yield). LC-MS m/z 163.9 (M+H)$^+$, 0.48 min (ret. time)

218

Ethyl 3-(1,4-dimethyl-1H-benzo[d][1,2,3]triazol-5-yl)-3-(4-methyl-3-((N-methylcyclo-pentanesulfonamido)methyl)phenyl)propanoate

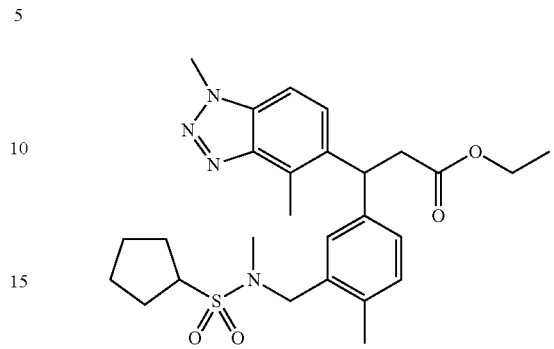

To a solution of ethyl 3-(1,4-dimethyl-1H-benzo[d][1,2,3]triazol-5-yl)-3-(3-(hydroxymethyl)-4-methylphenyl)propanoate (70 mg, 0.191 mmol), N-methylcyclopentanesulfonamide (31.1 mg, 0.191 mmol) and 1,1'-(Azodicarbonyl)dipiperidine (96 mg, 0.381 mmol) under nitrogen in THF (3 mL) stirred at 0° C. was added tri-n-butylphosphine (0.094 mL, 0.381 mmol). The reaction mixture was stirred at 25° C. for 40 min, during which a precipitate generated. The mixture was stirred at RT for 18 h. The solvent was removed and the crude product purified by preparatory HPLC under neutral conditions to give the title compound (34 mg, 0.066 mmol, 34.8% yield). LC-MS m/z 513.3 (M+H)$^+$, 1.15 min (ret. time)

3-(1,4-Dimethyl-1H-benzo[d][1,2,3]triazol-5-yl)-3-(4-methyl-3-((N-methylcyclopentanesulfonamido)methyl)phenyl)propanoic acid

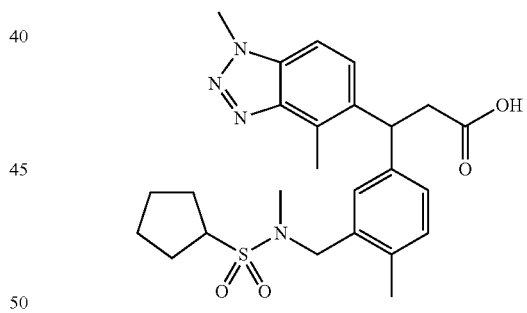

To a solution of ethyl 3-(1,4-dimethyl-1H-benzo[d][1,2,3]triazol-5-yl)-3-(4-methyl-3-((N-methylcyclopentanesulfonamido)methyl)phenyl)propanoate (34 mg, 0.066 mmol) in MeOH (2 mL) at RT was added 2M solution of LiOH (0.332 mL, 0.663 mmol). The mixture was heated in a Biotage microwave at normal absorption for 30 min at 85° C. It was acidified with 1N HCl to pH ~1 and then extracted with EtOAc twice. The organic layer was dried over Na$_2$SO$_4$, filtered and concentrated. The crude product was purified by preparatory HPLC under acidic conditions. To the resulting product was added 0.1 mL of 2M solution of LiOH and 1 mL of MeOH. The mixture was stirred for 6 h. EtOAc was added and extracted to obtain organic layer 1. The aqueous layer was adjusted to pH to 1 with 1N HCl and then extracted with EtOAc to obtain the organic layer 2. The combined organic layers were concentrated and then purified by preparatory HPLC under acidic conditions to give the title compound (13 mg, 0.027 mmol, 40.4% yield) as solid. LC-MS m/z 485.3 (M+H)⁺, 0.91 min (ret. time).

Example 91

2-(Dimethylamino)-2-oxoethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

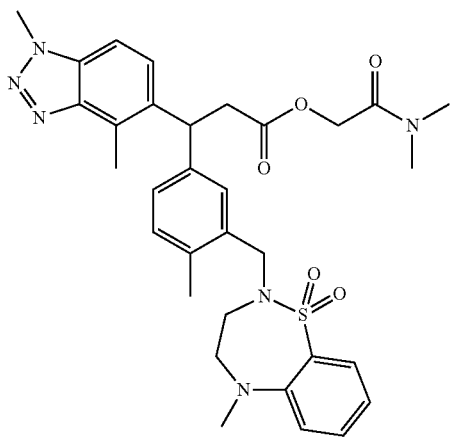 [SMILES: Cc1ccc(C(CC(=O)OCC(=O)N(C)C)c2ccc3c(nnn3C)c2C)cc1CN1CCN(C)c2ccccc2S1(=O)=O]

2-((2-Hydroxyethyl)(methyl)amino)benzenesulfonamide

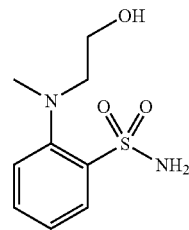

2-Fluorobenzenesulfonamide (1.80 g, 10.28 mmol) in 2-(methylamino)ethanol (8.25 mL, 103 mmol) was heated with microwave irradiation at 130° C. for 1 h. The reaction mixture was diluted with H₂O (10 mL), adjusted pH to ~5 with 6 N HCl, extracted with EtOAc (3×50 mL). The organic layer was washed with brine (25 mL), dried over Na₂SO₄, filtered, concentrated to give the title compound (1.975 g, 8.58 mmol, 83% yield) as white solid. LC-MS m/z 231.1 (M+H)⁺, 0.55 min (ret. time).

5-Methyl-2,3,4,5-tetrahydrobenzo[f][1,2,5]thiadiazepine 1,1-dioxide

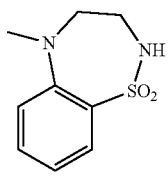

To 2-((2-Hydroxyethyl)(methyl)amino)benzenesulfonamide (1.975 g, 8.58 mmol) in THF (100 mL) was added DIAD (2.001 mL, 10.29 mmol), PS-PpH₃ (4.29 g, 12.86 mmol). The result reaction mixture was stirred at RT for 1 h. The reaction mixture was filtered, concentrated and was purified by flash chromatography to give the title compound. This material was triturated with ether twice to give the title compound (1.04 g, 4.90 mmol, 57.1% yield) (27-A3) as white solid. LC-MS m/z 213.0 (M+H)⁺, 0.56 min (ret. time).

Ethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

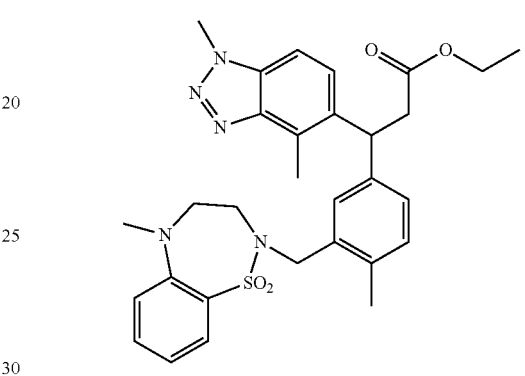

To a solution of ethyl 3-(1,4-dimethyl-1H-benzo[d][1,2,3]triazol-5-yl)-3-(3-(hydroxymethyl)-4-methylphenyl)propanoate (580 mg, 1.578 mmol), 5-methyl-2,3,4,5-tetrahydrobenzo[f][1,2,5]thiadiazepine 1,1-dioxide (352 mg, 1.657 mmol), and 1,1'-(Azodicarbonyl)dipiperidine (797 mg, 3.16 mmol) in THF (15 mL) at 0° C. was added tri-n-butylphosphine (0.779 mL, 3.16 mmol). The ice-bath was removed after 20 min and stirring continued at RT for 20 h. The reaction mixture was purified by flash chromatography to give the title compound (659 mg, 1.173 mmol, 74.3% yield) as oil. LC-MS m/z 561.9 (M+H)⁺, 1.13 min (ret. time)

3-(1,4-Dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid

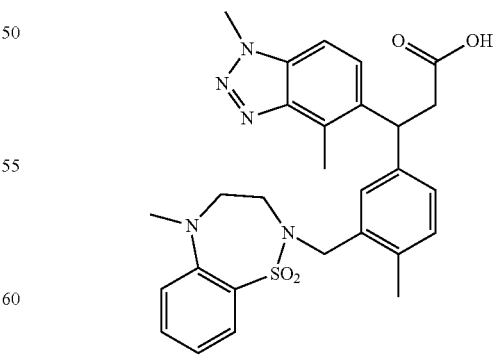

To a solution of ethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate (659 mg, 1.173 mmol) in MeOH (5 mL) was added several drops of THF. The mixture was stirred at RT was added 2M solution of LiOH (5.87 mL, 11.73 mmol). The mixture was stirred at RT for 17 h. The pH was adjusted to 1 with 1N HCl. No solid precipitated out from the solution. It was extracted with EtOAc twice. The organic layer was dried over Na$_2$SO$_4$, filtered and concentrated to give the title compound (652 mg, 1.222 mmol, 104% yield) as solid. LC-MS m/z 533.9 (M+H)$^+$, 0.99 min (ret. time).

2-(Dimethylamino)-2-oxoethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

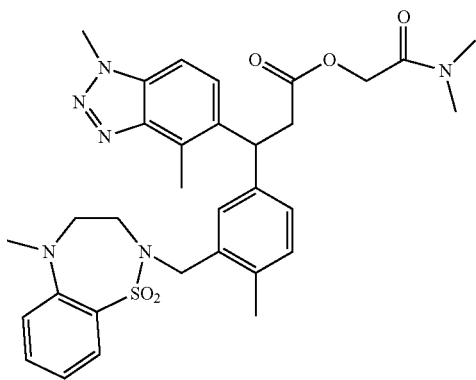

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (50 mg, 0.094 mmol) in acetone (1 mL) was added 2-bromo-N,N-dimethylacetamide (31.1 mg, 0.187 mmol). The mixture was heated in a Biotage microwave at high absorption for 50 min at 100° C. The solvent was removed and the crude product purified with preparative HPLC under neutral conditions to give the title compound (35.35 mg, 0.057 mmol, 61.0% yield). LC-MS m/z 619.3 (M+H)$^+$, 1.03 min (ret. time). $^1$H NMR (400 MHz, DMSO-d$_6$) δ=7.79 (d, J=7.8 Hz, 1H), 7.62-7.48 (m, 3H), 7.30 (s, 1H), 7.21 (d, J=8.3 Hz, 1H), 7.18-7.05 (m, 3H), 4.86 (t, J=7.7 Hz, 1H), 4.74-4.62 (m, 2H), 4.25 (s, 3H), 4.10 (s, 2H), 3.30-3.16 (m, 6H), 2.99 (s, 3H), 2.84 (s, 3H), 2.76 (d, J=4.0 Hz, 6H), 2.24 (s, 3H).

Example 92

(5-Methyl-2-oxo-1,3-dioxol-4-yl)methyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

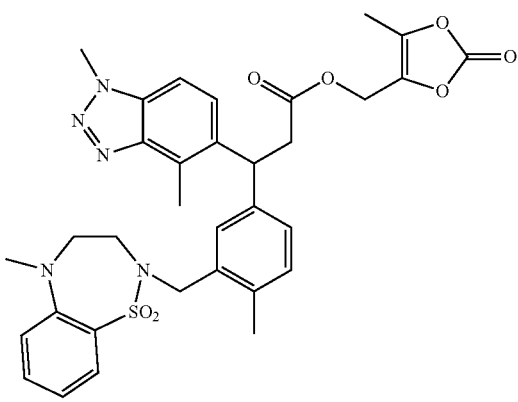 [SMILES: Cc1ccc(C(CC(=O)OCc2oc(=O)oc2C)c2ccc3c(nnn3C)c2C)cc1CN1CCN(C)c2ccccc2S1(=O)=O]

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (60 mg, 0.112 mmol) in acetone (1 mL) was added 4-(chloromethyl)-5-methyl-1,3-dioxol-2-one (33.4 mg, 0.225 mmol). The mixture was heated in a Biotage microwave at high absorption for 50 min at 100° C., another 50 min at 100° C. The solvent was removed and the crude product purified with preparative HPLC under neutral conditions to give the title compound (31 mg, 0.048 mmol, 42.7% yield) as white solid. LC-MS m/z 646.4 (M+H)$^+$, 1.10 min (ret. time)$^1$H NMR (400 MHz, DMSO-d$_6$) δ=7.78 (d, J=7.8 Hz, 1H), 7.64-7.46 (m, 3H), 7.34-7.03 (m, 5H), 4.94-4.75 (m, 3H), 4.23 (s, 3H), 4.08 (s, 2H), 3.29-3.16 (m, 2H), 2.99 (s, 3H), 2.75 (s, 3H), 2.23 (s, 3H), 1.96 (s, 3H).

Example 93

2-Hydroxyethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

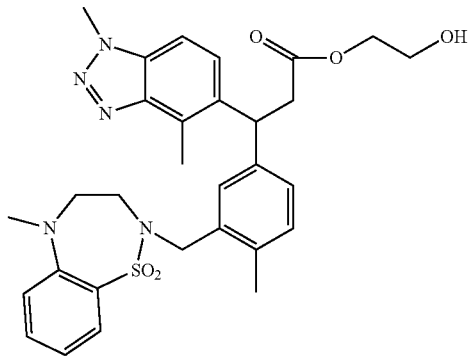 [SMILES: Cc1ccc(C(CC(=O)OCCO)c2ccc3c(nnn3C)c2C)cc1CN1CCN(C)c2ccccc2S1(=O)=O]

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (55 mg, 0.103 mmol) in DCM (2 mL) was added oxalyl dichloride (0.059 mL, 0.412 mmol) followed by a drop of DMF. The mixture was stirred at RT for 20 h. Ethane-1,2-diol (64.0 mg, 1.031 mmol) was added and stirred for 2 h. The solvent was removed and the crude product purified with preparative HPLC under neutral conditions to give the title compound (36 mg, 0.062 mmol, 60.5% yield). LC-MS m/z 578.4 (M+H)$^+$, 0.96 min (ret. time)$^1$H NMR (400 MHz, DMSO-d$_6$) δ=7.78 (d, J=7.8 Hz, 1H), 7.62-7.46 (m, 3H), 7.31-7.02 (m, 5H), 4.85 (t, J=7.9 Hz, 1H), 4.75 (t, J=5.4 Hz, 1H), 4.25 (s, 3H), 4.09 (s, 2H), 3.91 (t, J=5.0 Hz, 2H), 3.46 (q, J=5.1 Hz, 2H), 3.30-3.25 (m, 2H), 3.18 (d, J=7.8 Hz, 4H), 2.99 (s, 3H), 2.76 (s, 3H), 2.23 (s, 3H).

Example 94

Ethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

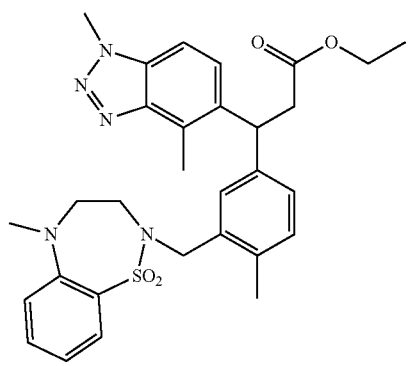 [SMILES: CCOC(=O)CC(c1ccc(C)c(CN2CCN(C)c3ccccc3S2(=O)=O)c1)c1ccc2c(nnn2C)c1C]

To a solution of ethyl 3-(1,4-dimethyl-1H-benzo[d][1,2,3]triazol-5-yl)-3-(3-(hydroxymethyl)-4-methylphenyl)propanoate (50 mg, 0.136 mmol), 5-methyl-2,3,4,5-tetrahydrobenzo[f][1,2,5]thiadiazepine 1,1-dioxide (43.3 mg, 0.204 mmol) and ADDP (68.7 mg, 0.272 mmol) in THF (3 mL) at 0° C. was added tri-n-butylphosphine (0.067 mL, 0.272 mmol). After the addition, the ice-bath was removed and stirred at RT for 20 h. The crude product was purified by preparatory HPLC under neutral conditions to give the title compound (31 mg, 0.055 mmol, 40.6% yield). LC-MS m/z 562.3 (M+H)$^+$, 1.18 min (ret. time) $^1$H NMR (400 MHz, DMSO-d$_6$) δ=7.79 (d, J=7.8 Hz, 1H), 7.63-7.45 (m, 3H), 7.33-7.04 (m, 5H), 4.83 (t, J=7.9 Hz, 1H), 4.25 (s, 3H), 4.09 (s, 2H), 3.94 (q, J=7.0 Hz, 2H), 3.30-3.12 (m, 6H), 2.99 (s, 3H), 2.76 (s, 3H), 2.23 (s, 3H), 1.03 (t, 3H).

Example 95

2-(Dimethylamino)ethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

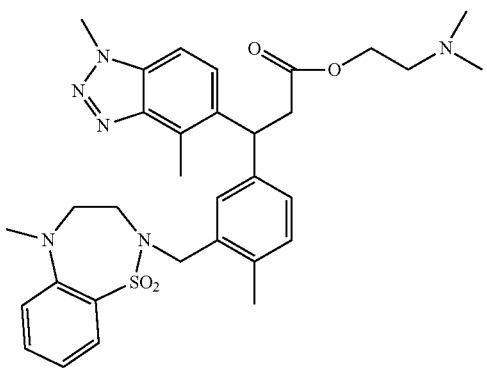

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (55 mg, 0.103 mmol) in DCM (2 mL) was added oxalyl chloride (0.036 mL, 0.412 mmol) followed by a drop of DMF. The mixture was stirred at RT for 20 h. 2-(dimethylamino)ethanol (0.104 mL, 1.031 mmol) was added and stirred for 2 h. The solvent was removed and the crude product purified by preparatory HPLC under neutral conditions to give the title compound (31 mg, 0.051 mmol, 49.7% yield) as solid. LC-MS m/z 605.3 (M+H)$^+$, 0.88 min (ret. time) $^1$H NMR (400 MHz, DMSO-d$_6$) δ=7.79 (d, J=7.8 Hz, 1H), 7.62-7.46 (m, 3H), 7.31-7.04 (m, 5H), 4.83 (t, J=7.9 Hz, 1H), 4.25 (s, 3H), 4.09 (s, 2H), 3.96 (t, J=5.8 Hz, 2H), 3.28 (br. s., 2H), 3.17 (t, J=8.5 Hz, 4H), 2.99 (s, 3H), 2.75 (s, 3H), 2.32-2.19 (m, 5H), 2.03 (s, 6H).

Example 96

2-Morpholinoethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

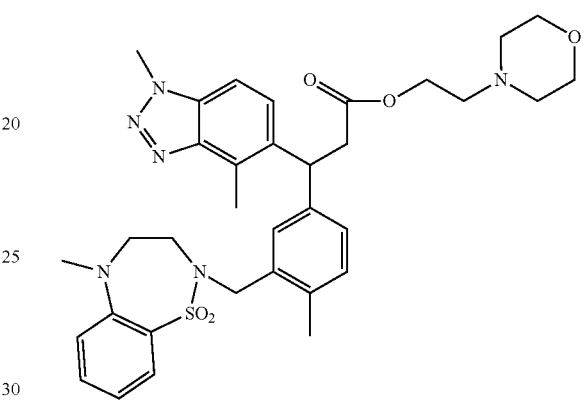

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (55 mg, 0.103 mmol) in DCM (2 mL) was added oxalyl chloride (0.036 mL, 0.412 mmol) followed by a drop of DMF. The mixture was stirred at RT for 20 h. 2-Morpholinoethanol (13.52 mg, 0.103 mmol) was added and stirred for 2 h. The solvent was removed and the crude product purified with preparative HPLC under neutral conditions to give the title compound (32.9 mg, 0.051 mmol, 49.4% yield) as white solid. LC-MS m/z 647.4 (M+H)$^+$, 0.86 min (ret. time).

Example 97

3-(Dimethylamino)propyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

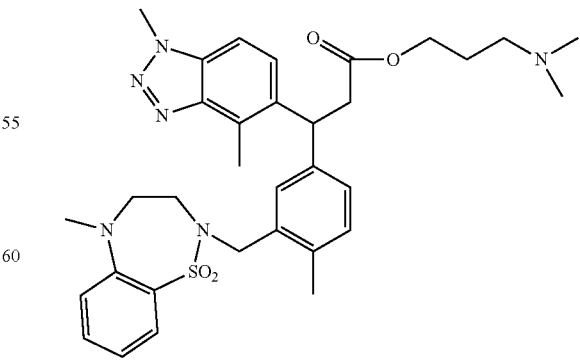

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (55 mg, 0.103 mmol) in DCM (2 mL) was added oxalyl chloride (0.036 mL, 0.412 mmol) followed by a drop of DMF. The mixture was stirred at RT for 20 h. 3-(Dimethylamino)propan-1-ol (106 mg, 1.031 mmol) was added and stirred for 2 h. The solvent was removed and the crude product purified with preparative HPLC under neutral conditions to give the title compound (50.8 mg, 0.082 mmol, 80% yield) as white solid. LC-MS m/z 619.5 (M+H)$^+$, 0.89 min (ret. time).

Example 98

2-Oxotetrahydrofuran-3-yl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

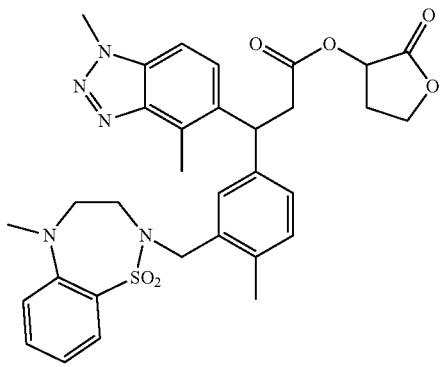 [SMILES: Cc1ccc(C(CC(=O)OC2CCOC2=O)c2ccc3c(nnn3C)c2C)cc1CN1CCN(C)c2ccccc2S1(=O)=O]

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (60 mg, 0.112 mmol) in acetone (1 mL) was added 3-bromodihydrofuran-2(3H)-one (0.026 mL, 0.281 mmol). The mixture was heated in a Biotage microwave at high absorption for 50 min at 100° C. The solvent was removed and the crude product purified with preparative HPLC under neutral conditions to give the title compound (50 mg, 0.081 mmol, 72.0% yield) as white solid. LC-MS m/z 618.2 (M+H)$^+$, 1.03 min (ret. time)$^1$H NMR (400 MHz, DMSO-d$_6$) δ=7.71 (d, J=7.5 Hz, 1H), 7.56-7.41 (m, 3H), 7.21 (s, 1H), 7.17-7.06 (m, 2H), 7.05-6.95 (m, 2H), 5.32 (t, J=9.2 Hz, 1H), 4.78 (br. s., 1H), 4.29-4.07 (m, 5H), 4.02 (s, 2H), 3.23-3.18 (m, 4H), 3.15-3.08 (m, 2H), 2.92 (s, 3H), 2.68 (s, 3H), 2.39-2.27 (m, 1H), 2.16 (s, 3H), 1.94-1.78 (m, 1H).

Example 99

((3-(1,4-Dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoyl)oxy)methyl pivalate

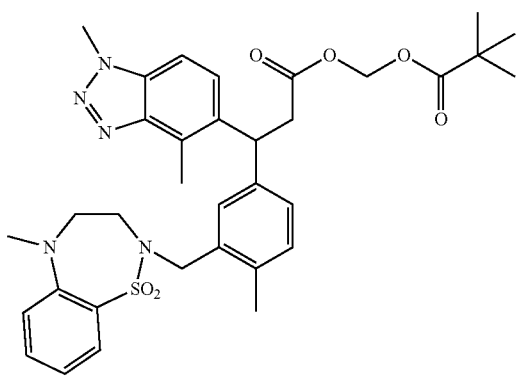 [SMILES: Cc1ccc(C(CC(=O)OCOC(=O)C(C)(C)C)c2ccc3c(nnn3C)c2C)cc1CN1CCN(C)c2ccccc2S1(=O)=O]

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (60 mg, 0.112 mmol) in acetone (1 mL) was added chloromethyl pivalate (33.9 mg, 0.225 mmol). The mixture was heated in a Biotage microwave at high absorption for 50 min at 100° C. Chloromethyl pivalate (33.9 mg, 0.225 mmol) and Et$_3$N (0.047 mL, 0.337 mmol) were added and heated in microwave for 50 min at 100° C. The solvent was removed and the crude product purified with preparative HPLC under neutral conditions to give the title compound (35 mg, 0.054 mmol, 48.1% yield) as white solid. LC-MS m/z 648.4 (M+H)$^+$, 1.24 min (ret. time)$^1$H NMR (400 MHz, DMSO-d$_6$) δ=7.79 (d, J=7.5 Hz, 1H), 7.62-7.49 (m, 3H), 7.27 (s, 1H), 7.24-7.13 (m, 2H), 7.13-7.04 (m, 2H), 5.60 (s, 2H), 4.84 (t, J=7.9 Hz, 1H), 4.24 (s, 3H), 4.08 (s, 2H), 3.30-3.22 (m, 4H), 3.19 (br. s., 2H), 2.99 (s, 3H), 2.76 (s, 3H), 2.23 (s, 3H), 0.92 (s, 9H).

Example 100

3-Aminopropyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

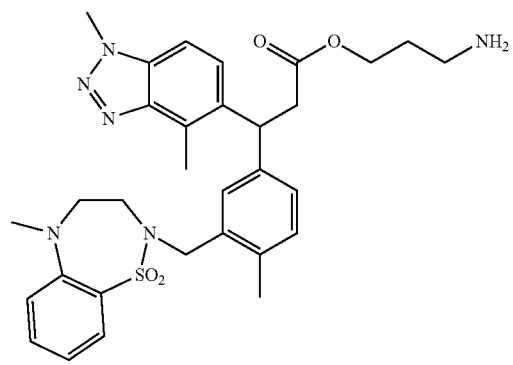 [SMILES: Cc1ccc(C(CC(=O)OCCCN)c2ccc3c(nnn3C)c2C)cc1CN1CCN(C)c2ccccc2S1(=O)=O]

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (55 mg, 0.103 mmol) in DCM (2 mL) was added oxalyl dichloride (0.059 mL, 0.412 mmol) followed by a drop of DMF. The mixture was stirred at RT for 20 h. Tert-butyl (3-hydroxypropyl)carbamate (0.040 mL, 0.412 mmol) was added and stirred for 2 h. 4M HCl in dioxane (0.129 mL, 0.515 mmol) was added and stirred for 2 h. The solvent was removed and the crude product purified by preparative HPLC under acidic conditions to provide the title compound (28 mg, 0.040 mmol, 38.5% yield) as light pink solid. LC-MS m/z 591.3 (M+H)$^+$, 0.86 min (ret. time)$^1$H NMR (400 MHz, DMSO-d$_6$) δ=7.79 (d, J=7.8 Hz, 1H), 7.71-7.47 (m, 5H), 7.28 (s, 1H), 7.21 (d, J=8.3 Hz, 1H), 7.18-7.05 (m, 3H), 4.84 (s, 1H), 4.25 (s, 3H), 4.09 (s, 2H), 3.98 (t, J=6.0 Hz, 2H), 3.20 (d, J=7.5 Hz, 6H), 2.99 (s, 3H), 2.77 (s, 6H), 2.22 (s, 3H), 1.76 (d, 2H).

Example 101

2-Amino-3-methylbutyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

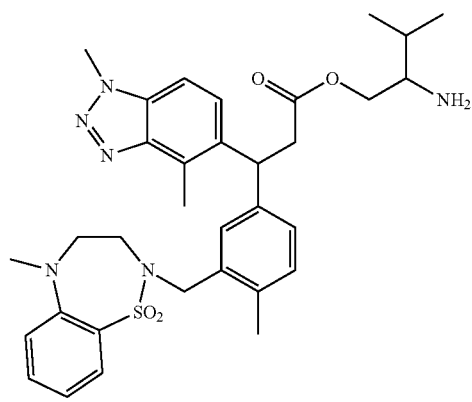 [SMILES: Cc1ccc(C(CC(=O)OCC(N)C(C)C)c2ccc3c(nnn3C)c2C)cc1CN1CCN(C)c2ccccc2S1(=O)=O]

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (60 mg, 0.112 mmol) in DCM (2 mL) was added oxalyl dichloride (0.064 mL, 0.450 mmol) and a drop of DMF. The mixture was stirred at RT for 20 h. Tert-butyl (1-hydroxy-3-methylbutan-2-yl)carbamate (68.6 mg, 0.337 mmol) was added and stirred for 2 h. 30 mg of tert-Butyl (1-hydroxy-3-methylbutan-2-yl)carbamate was added and stirred at for 18 h. The solvent was removed and the crude product purified with preparative HPLC under neutral conditions to give the title compound (50 mg, 0.068 mmol, 60.7% yield) as pink solid. LC-MS m/z 619.4 (M+H)$^+$, 0.89 min (ret. time).

Example 102

2-(1H-Imidazol-1-yl)ethyl 3-(1,4-dimethyl-1H-benzo[d][1,2,3]triazol-5-yl)-3-(4-methyl-34(5-methyl-1,1-dioxido-4,5-dihydrobenzo[f][1,2,5]thiadiazepin-2(3H)-yl)methyl)phenyl)propanoate

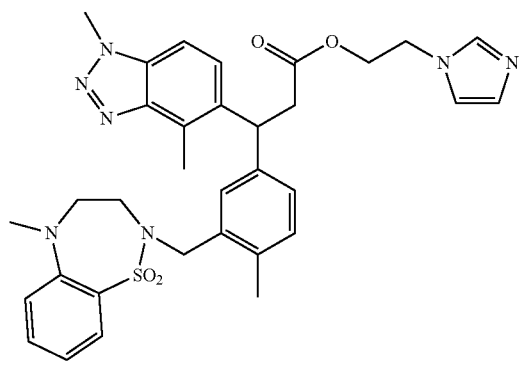 [SMILES: Cc1ccc(C(CC(=O)OCCn2ccnc2)c2ccc3c(nnn3C)c2C)cc1CN1CCN(C)c2ccccc2S1(=O)=O]

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (50 mg, 0.094 mmol) in acetone (1 mL) was added 1-(2-chloroethyl)-1H-imidazole hydrochloride (31.3 mg, 0.187 mmol) and Et$_3$N (0.065 mL, 0.468 mmol). The mixture was heated in a Biotage microwave at high absorption for 2 h at 100° C. Salt was filtered and the filtrate was re-dissolved in DMF (1 mL). 1-(2-Chloroethyl)-1H-imidazole hydrochloride (31.3 mg, 0.187 mmol) and Et$_3$N (0.065 mL, 0.468 mmol) were added. The mixture was heated in a Biotage microwave at high absorption for 1 h at 120° C. Solid was filtered and the filtrate was concentrated. The crude product was purified with preparative HPLC under neutral conditions to give the title (31 mg, 0.049 mmol, 52.7% yield) as white solid. LC-MS m/z 628.3 (M+H)$^+$, 0.89 min (ret. time)$^1$H NMR (400 MHz, DMSO-d$_6$) δ=7.78 (d, J=7.3 Hz, 1H), 7.64-7.44 (m, 4H), 7.28-7.17 (m, 2H), 7.16-7.01 (m, 4H), 6.83 (s, 1H), 4.79 (t, J=7.8 Hz, 1H), 4.25 (s, 3H), 4.21-4.05 (m, 6H), 3.29-3.14 (m, 6H), 2.98 (s, 3H), 2.72 (s, 3H), 2.22 (s, 3H).

Example 103

3-(Diethylamino)propyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

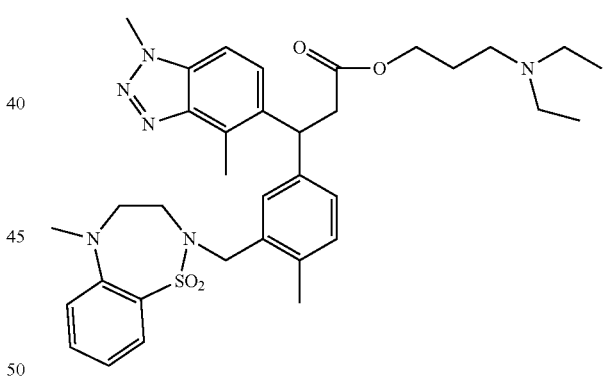

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (55 mg, 0.103 mmol) in DCM (2 mL) was added oxalyl chloride (0.036 mL, 0.412 mmol) followed by a drop of DMF. The mixture was stirred at RT for 2 h. 3-(diethylamino)propan-1-ol (135 mg, 1.031 mmol) was added and stirred for 18 h. 1 mL of THF was added and was heated in a Biotage microwave at high absorption for 40 min at 100° C. The solvent was removed and the crude product purified with preparative HPLC under neutral conditions to give the title compound (31.6 mg, 0.049 mmol, 47.4% yield) as solid. LC-MS m/z 647.4 (M+H)$^+$, 0.92 Min (ret. time).

Example 104

4-(Dimethylamino)butyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

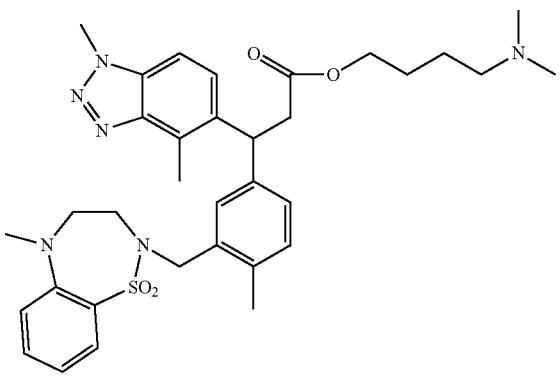

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (55 mg, 0.103 mmol) in DCM (2 mL) was added oxalyl chloride (0.036 mL, 0.412 mmol) followed by a drop of DMF. The mixture was stirred at RT for 2 h. 4-(dimethylamino)butan-1-ol (121 mg, 1.031 mmol) was added and stirred for 18 h. 1 mL of THF was added and was heated in a Biotage microwave at high absorption for 40 min at 100° C. The solvent was removed and the crude product purified with preparative HPLC under neutral conditions to give the title compound (38.6 mg, 0.061 mmol, 59.2% yield) as solid. LC-MS m/z 633.5 (M+H)$^+$, 0.93 min (ret. time).

Example 105

3-(Dimethylamino)-2,2-dimethylpropyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

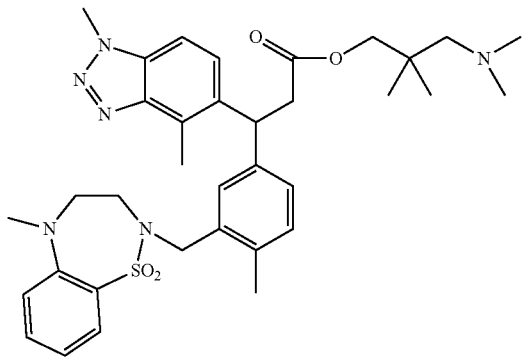

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (50 mg, 0.094 mmol) in DCM (2 mL) was added oxalyl chloride (0.033 mL, 0.375 mmol) followed by a drop of DMF. The mixture was stirred at RT for 2 h. 3-(Dimethylamino)-2,2-dimethylpropan-1-ol (123 mg, 0.937 mmol) was added and stirred for 20 h. It was heated at 50° C. for 17 h. 1 mL of THF was added and was heated in a Biotage microwave at high absorption for 40 min at 100° C. The solvent was removed and the crude product purified with preparative HPLC under neutral conditions to give the title compound (11.8 mg, 0.018 mmol, 19.47% yield) as solid. LC-MS m/z 647.5 (M+H)$^+$, 0.94 min (ret. time).

Example 106

3-(Pyrrolidin-1-yl)propyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

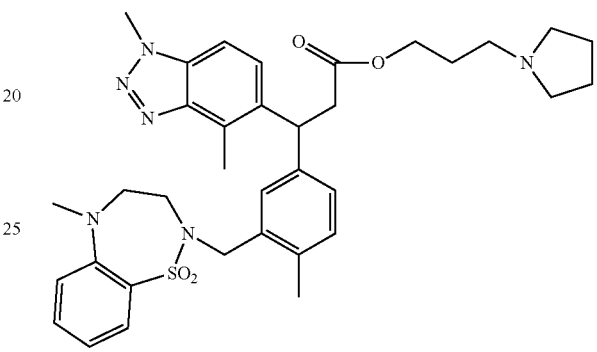

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (55 mg, 0.103 mmol) in DCM (2 mL) was added oxalyl chloride (0.036 mL, 0.412 mmol) followed by a drop of DMF. The mixture was stirred at RT for 2 h. 3-(Pyrrolidin-1-yl)propan-1-ol (12.11 mg, 0.094 mmol) and THF (1 mL) were added and heated in a Biotage microwave at high absorption for 40 min at 100° C. The solvent was removed and the crude product purified with preparative HPLC under neutral conditions to give the title compound (11.2 mg, 0.017 mmol, 18.54% yield) as solid. LC-MS m/z 645.3 (M+H)$^+$, 0.93 min (ret. time).

Example 107

1-(Dimethylamino)propan-2-yl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

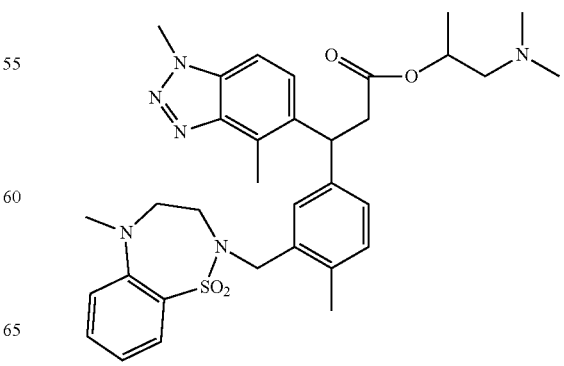

231

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (50 mg, 0.094 mmol) in DCM (2 mL) was added oxalyl chloride (0.033 mL, 0.375 mmol) followed by a drop of DMF. The mixture was stirred at RT for 3 h. 1-(Dimethylamino)propan-2-ol (97 mg, 0.937 mmol) was added and stirred for 17 h. 1 mL of THF was added and heated in a Biotage microwave at normal absorption for 40 min at 100° C. The solvent was removed and the crude product purified with preparative HPLC under neutral conditions to give the title compound (14.9 mg, 0.024 mmol, 25.7% yield) as solid. LC-MS m/z 619.4 (M+H)$^+$, 0.91 min (ret. time).

Example 108

3-morpholinopropyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

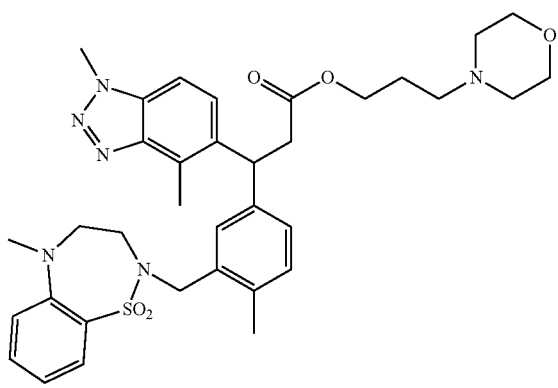 [SMILES: Cc1ccc(C(CC(=O)OCCCN2CCOCC2)c2ccc3c(nnn3C)c2C)cc1CN1CCN(C)c2ccccc2S1(=O)=O]

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (50 mg, 0.094 mmol) in DMF (1 mL) was added 4-(3-chloropropyl)morpholine hydrochloride (37.5 mg, 0.187 mmol) and Et$_3$N (0.065 mL, 0.468 mmol). The mixture was heated in a Biotage microwave at high absorption for 1 h at 120° C., 1 h at. 150° C. The reaction was filtered and the filtrate concentrated and purified with preparative HPLC under neutral conditions to give the title compound (27.5 mg, 0.042 mmol, 44.4% yield) as white solid. LC-MS m/z 661.3 (M+H)$^+$, 0.92 min (ret. time).

Example 109

Methyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl) phenyl)propanoate

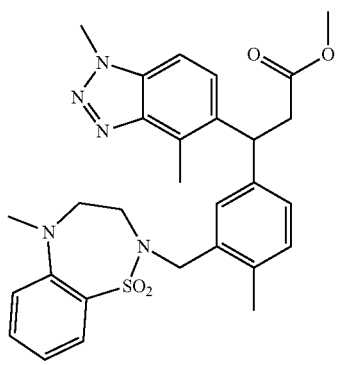

232

The title compound was obtained (7.8 mg, 0.014 mmol) from the purification procedure for 2-(5-(1-(1,4-dimethyl-1H-benzo[d][1,2,3]triazol-5-yl)-3-hydroxypropyl)-2-methylbenzyl)-5-methyl-2,3,4,5-tetrahydrobenzo[f][1,2,5]thiadiazepine 1,1-dioxide. LC-MS: m/z 548.2 (M+H)$^+$, 1.11 min. (ret. time)

Example 110

Methylpyrrolidin-3-yl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

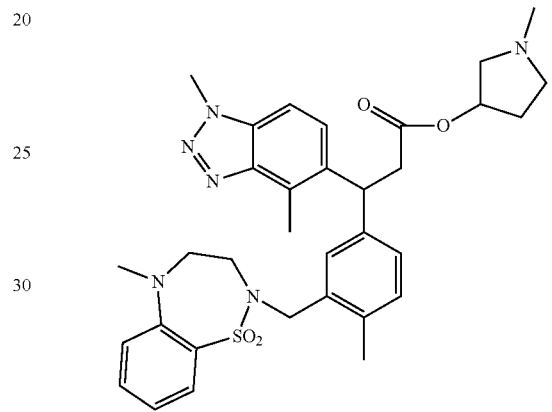

(E)-Ethyl 3-(1,4-dimethyl-1H-benzo[d][1,2,3]triazol-5-yl)acrylate

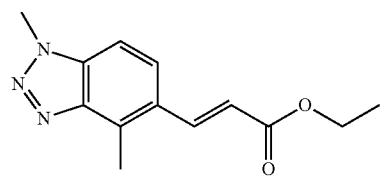 [SMILES: CCOC(=O)/C=C/c1ccc2c(nnn2C)c1C]

To a solution of 5-bromo-1,4-dimethyl-1H-benzo[d][1,2,3]triazole (1100 mg, 4.87 mmol) in DMF (5 mL) at RT was added ethyl acrylate (3.11 mL, 29.2 mmol) and N-ethyl-N-isopropylpropan-2-amine (3.40 mL, 19.46 mmol), tri-o-tolylphosphine (444 mg, 1.460 mmol), followed by Pd(OAc)$_2$ (164 mg, 0.730 mmol). The reaction mixture was heated in microwave under high absorption at 150° C. for 2 h. The reaction mixture was passed through celite and washed with EtOAc. The filtrate was washed with water (1×), and brine (1×). The organic layer was collected and concentrated. The crude product was purified by flash chromatography to give the title compound (450 mg, 1.835 mmol, 37.7% yield) and an impure batch. The impure batch was triturated with ether to give the title compound (740 mg, 3.02 mmol, 62.0% yield) as yellow solid. LC-MS m/z 246.0 (M+H)$^+$, 0.88 min (ret. time).

233

Ethyl 3-(1,4-dimethyl-1H-benzo[d][1,2,3]triazol-5-yl)-3-(3-(hydroxymethyl)-4-methylphenyl)propanoate

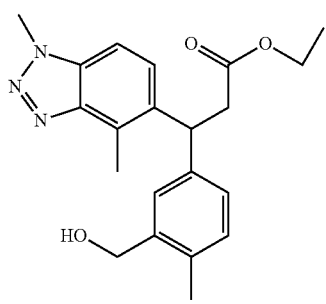 [SMILES: CCOC(=O)CC(c1ccc(C)c(CO)c1)c1ccc2c(nnn2C)c1C]

To a suspension of (E)-ethyl 3-(1,4-dimethyl-1H-benzo[d][1,2,3]triazol-5-yl)acrylate (1200 mg, 4.89 mmol), (3-(hydroxymethyl)-4-methylphenyl)boronic acid (974 mg, 5.87 mmol), and [RhCl(cod)]$_2$ (241 mg, 0.489 mmol) in 1,4-dioxane (10 mL) and water (10 mL) at RT was added Et$_3$N (2.046 mL, 14.68 mmol). The resulting suspension was heated in a Biotage microwave at high absorption for 60 min at 150° C. The reaction mixture was passed through celite and washed with EtOAc. The filtrate was washed with water twice, brine (1×). The organic layer was collected and concentrated. The crude product was purified by flash chromatography to give the title compound (1.04 g, 2.83 mmol, 57.9% yield) as oil. LC-MS m/z 367.9 (M+H)$^+$, 0.89 min (ret. time).

3-(1,4-Dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid

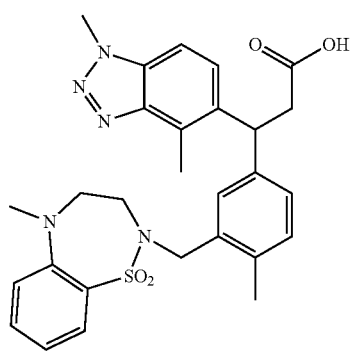 [SMILES: Cc1ccc(C(CC(=O)O)c2ccc3c(nnn3C)c2C)cc1CN1CCN(C)c2ccccc2S1(=O)=O]

To a solution of ethyl 3-(1,4-dimethyl-1H-benzo[d][1,2,3]triazol-5-yl)-3-(3-(hydroxymethyl)-4-methylphenyl)propanoate (1040 mg, 2.83 mmol), 5-methyl-2,3,4,5-tetrahydrobenzo[f][1,2,5]thiadiazepine 1,1-dioxide (631 mg, 2.97 mmol), and 1,1'-(Azodicarbonyl)dipiperidine (1428 mg, 5.66 mmol) in THF (10 mL) at 0° C. was added tri-n-butylphosphine (1.397 mL, 5.66 mmol). The ice-bath was removed after 20 min and stirring continued at RT for 20 h. A 2M solution of LiOH (9.91 mL, 19.81 mmol) was added and the reaction mixture was stirred at for 18 h. The reaction mixture was acidified with 1N HCl, diluted and extracted with EtOAc twice. The organic layer was combined and concentrated. It was purified by flash chromatography to give the title compound (818 mg, 1.533 mmol, 54.2% yield) as oil and a less pure bath (401 mg, 0.751 mmol, 26.5% yield). LC-MS m/z 534.1 (M+H)$^+$, 0.98 min (ret. time).

234

1-Methylpyrrolidin-3-yl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

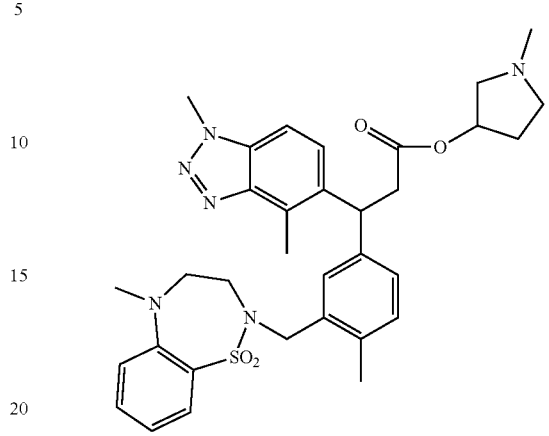

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (50 mg, 0.094 mmol) (N26428-95-A1) in DCM (2 mL) was added oxalyl chloride (0.033 mL, 0.375 mmol) followed by a drop of DMF. The mixture was stirred at RT for 2 h. 1-Methylpyrrolidin-3-ol (95 mg, 0.937 mmol) was added and stirred for 20 h. One mL of DMF was added and the reaction was heated in a Biotage microwave at high absorption for 40 min at 100° C. The solvent was removed and the crude product purified with preparative HPLC under neutral conditions to give the title compound (12 mg, 0.019 mmol, 20.77% yield) as solid. LC-MS m/z 617.2 (M+H)$^+$, 0.91 min (ret. time).

Example 111

1-Methylpiperidin-3-yl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

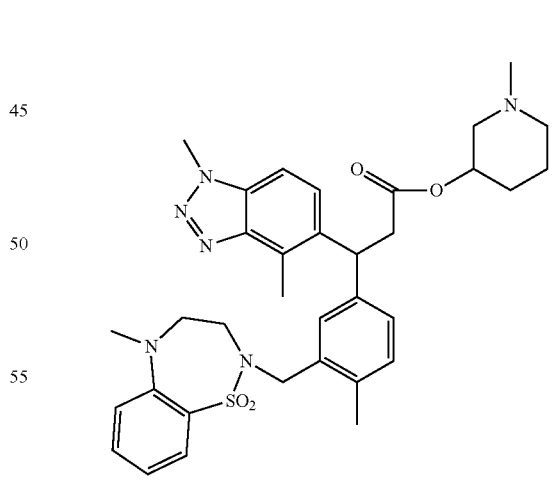

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (50 mg, 0.094 mmol) in DCM (2 mL) was added oxalyl chloride (0.033 mL, 0.375 mmol) followed by a drop of DMF. The mixture was stirred at RT for 2 h. 1-Methylpiperidin-3-ol (108 mg, 0.937 mmol) was added and stirred for 20 h.

1 mL of DMF was added and was heated in a Biotage microwave at high absorption for 40 min at 100° C. The solvent was removed and the crude product purified with preparative HPLC under neutral conditions to give the title compound (14 mg, 0.022 mmol, 23.69% yield). LC-MS m/z 631.5 (M+H)+, 0.92 Min (ret. time).

Example 112

((S)-1-Methylpyrrolidin-2-yl)methyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

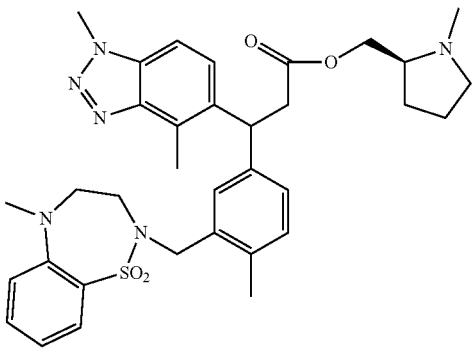 [SMILES: Cc1ccc(C(CC(=O)OC[C@@H]2CCCN2C)c2ccc3c(nnn3C)c2C)cc1CN1CCN(C)c2ccccc2S1(=O)=O]

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (40 mg, 0.075 mmol) in DCM (2 mL) was added oxalyl chloride (0.026 mL, 0.300 mmol) followed by a drop of DMF. The mixture was stirred at RT for 2 h. (S)-(1-Methylpyrrolidin-2-yl)methanol (86 mg, 0.750 mmol) was added and stirred for 20 h. It was heated at 50° C. for 17 h. 1 mL of THF was added and was heated in a Biotage microwave at high absorption for 40 min at 100° C. The solvent was removed and the crude product purified with preparative HPLC under neutral conditions to give the title compound (14.2 mg, 0.023 mmol, 30.0% yield) as solid. LC-MS m/z 647.5 (M+H)+, 0.94 min (ret. time)

Example 113

Pyrrolidin-3-ylmethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

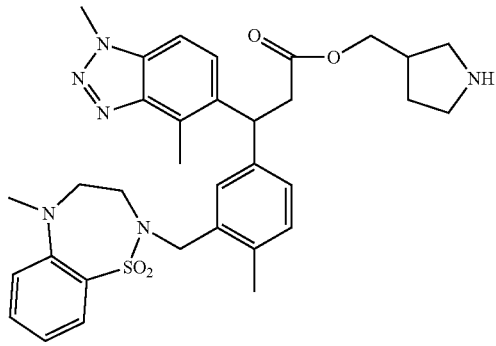 [SMILES: Cc1ccc(C(CC(=O)OCC2CCNC2)c2ccc3c(nnn3C)c2C)cc1CN1CCN(C)c2ccccc2S1(=O)=O]

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (40 mg, 0.075 mmol) in DCM (2 mL) was added oxalyl chloride (0.026 mL, 0.300 mmol) followed by a drop of DMF. The mixture was heated in a Biotage microwave at high absorption for 40 min at 100° C., 30 min at 100° C. 4M HCl in dioxane (0.094 mL, 0.375 mmol) was added and stirred for 20 h. Solvent was dried and the crude product was purified with preparative HPLC under neutral conditions to give the title compound (12 mg, 0.019 mmol, 26.0% yield). LC-MS m/z 617.4 (M+H)+, 0.89 min (ret. time).

Example 114

1-Methylpiperidin-4-yl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

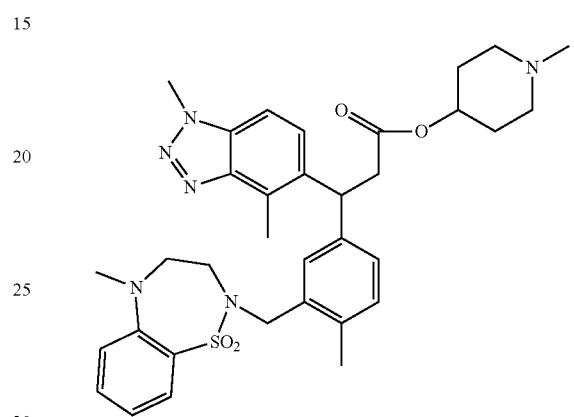

To a solution of 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid (50 mg, 0.094 mmol) in DCM (2 mL) was added oxalyl chloride (0.033 mL, 0.375 mmol) followed by a drop of DMF. The mixture was stirred at RT for 2 h. 1-Methylpiperidin-4-ol (108 mg, 0.937 mmol) was added and stirred for 1 h. 1 mL of DMF was added and was heated in a Biotage microwave at high absorption for 40 min at 100° C. The solvent was removed and the crude product purified with preparative HPLC under neutral conditions to give the title compound (24.7 mg, 0.039 mmol, 41.8% yield) was obtained as solid. LC-MS m/z 631.6 (M+H)+, 0.91 min (ret. time).

Example 115

3-(4-Methyl-3-(((R)-4-methyl-1,1-dioxido-3,4-dihydro-2H-benzo[b][1,4,5]oxathiazepin-2-yl)methyl)phenyl)-3-(3-methyl-[1,2,3]triazolo[1,5-a]pyridin-6-yl)propanoic acid

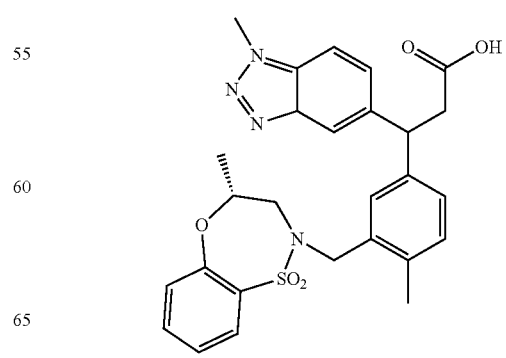

6-Bromo-3-methyl-[1,2,3]triazolo[1,5-a]pyridine

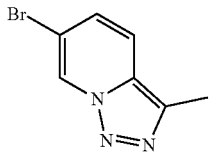

A mixture of 1-(5-bromopyridin-2-yl)ethanone (1 g, 5.00 mmol), hydrazine hydrate (2.67 mL, 55.0 mmol) in MeOH (15 mL) was heated to reflux for 3 h. 1N NaOH (5 mL) was added and extracted with DCM twice. The organic layer was dried over $Na_2SO_4$, filtered and concentrated. The residue was dissolved in 8 mL $CHCl_3$, manganese dioxide (1.043 g, 12.00 mmol) was added and the mixture was heated at 70° C. for 19 h and then for a further 4 h. It was cooled, filtered through celite and concentrated to give the title compound (960 mg, 4.53 mmol, 91% yield) as yellow solid. LC-MS m/z 213.9 (M+H)⁺, 0.67 min (ret. time).

(E)-Ethyl 3-(3-methyl-[1,2,3]triazolo[1,5-a]pyridin-6-yl)acrylate

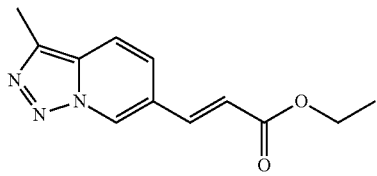 [SMILES: CCOC(=O)/C=C/c1ccc2c(C)nnn2c1]

To a solution of 6-bromo-3-methyl-[1,2,3]triazolo[1,5-a]pyridine (200 mg, 0.943 mmol) in DMF (3 mL) at RT was added ethyl acrylate (0.602 mL, 5.66 mmol) and N-ethyl-N-isopropylpropan-2-amine (0.659 mL, 3.77 mmol), tri-o-tolylphosphine (86 mg, 0.283 mmol), followed by $Pd(OAc)_2$ (31.8 mg, 0.141 mmol). The reaction mixture was heated in microwave under high absorption at 150° C. for 1.5 h. The crude reaction mixture was passed through celite and washed with EtOAc. The filtrate was washed with brine (1×). The organic layer was collected and concentrated. The crude product was purified by flash chromatography to give the title compound (70 mg, 0.303 mmol, 32.1% yield) as solid. LC-MS m/z 246.0 (M+H)⁺, 0.88 min (ret. time).

Ethyl 3-(3-(hydroxymethyl)-4-methylphenyl)-3-(3-methyl-[1,2,3]triazolo[1,5-a]pyridin-6-yl)propanoate

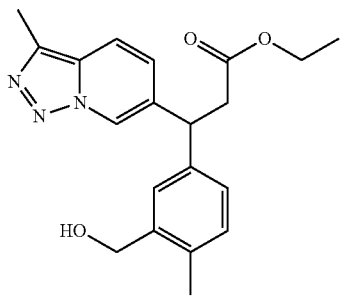 [SMILES: CCOC(=O)CC(c1ccc(C)c(CO)c1)c1ccc2c(C)nnn2c1]

To a suspension of (E)-ethyl 3-(3-methyl-[1,2,3]triazolo[1,5-a]pyridin-6-yl)acrylate (220 mg, 0.951 mmol), (3-(hydroxymethyl)-4-methylphenyl)boronic acid (189 mg, 1.142 mmol), $Et_3N$ (0.396 mL, 2.85 mmol) in 1,4-dioxane (2 mL) and water (2.000 mL) was added $[RhCl(cod)]_2$ (46.9 mg, 0.095 mmol). The resulting suspension was heated in a Biotage microwave at high absorption for 60 min at 130° C. It was passed through celite and washed with EtOAc. The solvent was removed and the crude product purified by flash chromatography to give the title compound (194 mg, 0.549 mmol, 57.7% yield) as yellow oil. LC-MS m/z 354.2 (M+H)⁺, 0.85 min (ret. time).

3-(4-Methyl-3-(((R)-4-methyl-1,1-dioxido-3,4-dihydro-2H-benzo[b][1,4,5]oxathiazepin-2-yl)methyl)phenyl)-3-(3-methyl-[1,2,3]triazolo[1,5-a]pyridin-6-yl)propanoic acid

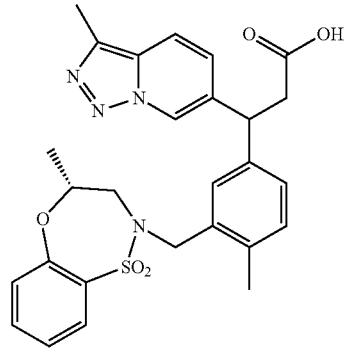 [SMILES: Cc1ccc(C(CC(=O)O)c2ccc3c(C)nnn3c2)cc1CN1C[C@@H](C)Oc2ccccc2S1(=O)=O]

To a solution of ethyl 3-(3-(hydroxymethyl)-4-methylphenyl)-3-(3-methyl-[1,2,3]triazolo[1,5-a]pyridin-6-yl)propanoate (90 mg, 0.255 mmol), (R)-4-methyl-3,4-dihydro-2H-benzo[b][1,4,5]oxathiazepine 1,1-dioxide (57.0 mg, 0.267 mmol), and 1,1'-(Azodicarbonyl)dipiperidine (129 mg, 0.509 mmol) in THF (10 mL) at 0° C. was added tri-n-butylphosphine (0.126 mL, 0.509 mmol). The ice-bath was removed after 20 min and stirring continued at RT for 20 h. The solvent was removed and the crude product purified with preparative HPLC under neutral conditions to give the intermediate ethyl 3-(4-methyl-3-(((R)-4-methyl-1,1-dioxido-3,4-dihydro-2H-benzo[b][1,4,5]oxathiazepin-2-yl)methyl)phenyl)-3-(3-methyl-[1,2,3]triazolo[1,5-a]pyridin-6-yl)propanoate. This was dissolved in MeOH (2 mL). A 2M solution of LiOH (0.891 mL, 1.783 mmol) was added and the mixture was heated in a Biotage microwave at high absorption for 30 min at 80° C. 1N HCl was added to adjust pH to 2. It was purified with preparative HPLC under acidic conditions give the title compound (64.4 mg, 0.124 mmol, 48.6% yield) as white solid. LC-MS m/z 521.2 (M+H)⁺, 0.97 min (ret. time)

Example 116

Ethyl 3-(3-((N-isopropylphenylsulfonamido)methyl)-4-methylphenyl)-3-(7-methoxy-1-methyl-1H-benzo[d][1,2,3]triazol-5-yl)propanoate

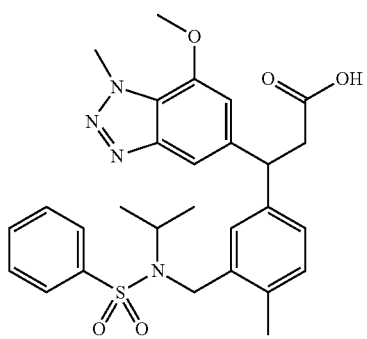 [SMILES: COc1cc(C(CC(=O)O)c2ccc(C)c(CN(C(C)C)S(=O)(=O)c3ccccc3)c2)cc2nnn(C)c12]

Ethyl 3-(3-((isopropylamino)methyl)-4-methylphenyl)-3-(7-methoxy-1-methyl-1H-benzo[d][1,2,3]triazol-5-yl)propanoate

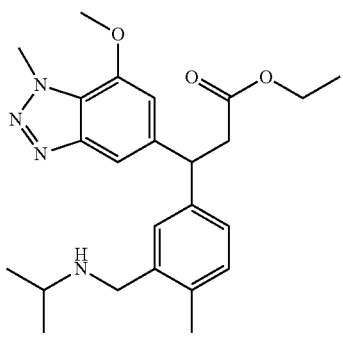 [SMILES: CCOC(=O)CC(c1ccc(C)c(CNC(C)C)c1)c1cc(OC)c2c(c1)nnn2C]

To a solution of ethyl 3-(3-(hydroxymethyl)-4-methylphenyl)-3-(7-methoxy-1-methyl-1H-benzo[d][1,2,3]triazol-5-yl)propanoate (150 mg, 0.391 mmol) and Et₃N (0.271 mL, 1.956 mmol) in DCM (4 mL) at −78° C. was added gradually methanesulfonyl chloride (0.076 mL, 0.978 mmol). The mixture was then stirred for 2.5 at this temperature under a nitrogen atmosphere. After this time methanesulfonyl chloride (0.076 mL, 0.978 mmol) was added then stirred for 2 h more. Propan-2-amine (0.333 mL, 3.91 mmol) was then added and the mixture is left to return to RT while stirring for a further 18 h. The mixture was then taken up in DCM and washed with a solution of NaCl (4×) and NaHCO₃ (1×). The organic phase was dried over Na₂SO₄, filtered and concentrated down under reduced pressure to give a yellow solid (231 mg, 83%). LC-MS m/z 425 (M+H)⁺, 0.78 min. (ret time).

Ethyl 3-(3-((N-isopropylphenylsulfonamido)methyl)-4-methylphenyl)-3-(7-methoxy-1-methyl-1H-benzo[d][1,2,3]triazol-5-yl)propanoate

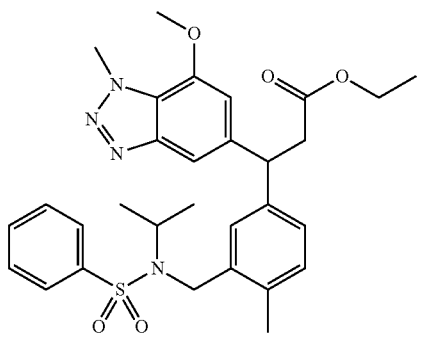 [SMILES: CCOC(=O)CC(c1ccc(C)c(CN(C(C)C)S(=O)(=O)c2ccccc2)c1)c1cc(OC)c2c(c1)nnn2C]

To a solution of ethyl 3-(3-((isopropylamino)methyl)-4-methylphenyl)-3-(7-methoxy-1-methyl-1H-benzo[d][1,2,3]triazol-5-yl)propanoate (231 mg, 0.544 mmol) and Et₃N (0.379 mL, 2.72 mmol) in DCM (6 mL) in an ice bath was added benzenesulfonyl chloride (0.105 mL, 0.816 mmol). This mixture was then warmed to RT and stirred for 18 h. After this time was added benzenesulfonyl chloride (0.035 mL, 0.272 mmol) and stirred for 1 h, then Et₃N (0.152 mL, 1.088 mmol) was added. The reaction stirred for 3 h further. After this time the solution was further diluted with DCM, washed with water (3×) and brine (1×). The organic phase was dried over MgSO₄, filtered and concentrated under reduced pressure. The resulting residue was then purified by silica gel chromatography using an Isco Combiflash Rf and eluting, 0-60% EtOAc/Hex to give the title compound (70 mg, 22.78%). LC-MS m/z 565 (M+H)⁺, 1.25 min. (ret time).

3-(3-((N-isopropylphenylsulfonamido)methyl)-4-methylphenyl)-3-(7-methoxy-1-methyl-1H-benzo[d][1,2,3]triazol-5-yl)propanoic acid

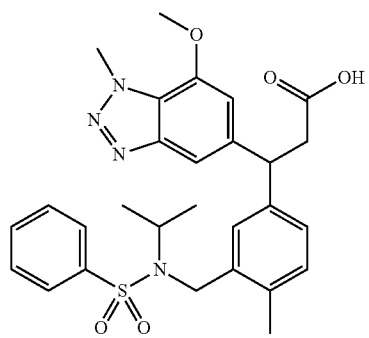 [SMILES: COc1cc(C(CC(=O)O)c2ccc(C)c(CN(C(C)C)S(=O)(=O)c3ccccc3)c2)cc2nnn(C)c12]

To a solution of ethyl 3-(3-((N-isopropylphenylsulfonamido)methyl)-4-methylphenyl)-3-(7-methoxy-1-methyl-1H-benzo[d][1,2,3]triazol-5-yl)propanoate (70 mg, 0.110 mmol) in THF (1 mL) and water (1 mL) was added LiOH (13.21 mg, 0.552 mmol). This was left to stir for 17 h. After this time, 1 N HCl was added to the reaction mixture drop wise until the mixture was at pH 1. The acidic solution was diluted with EtOAc, washed with water (3×), dried over MgSO₄, filtered and the solvents removed under reduced pressure to afford a solid. The resulting residue was purified by reverse-phase HPLC (Sunfire 19×100 mm 5 u preparatory column) eluting at 18 mL/min at a gradient of 0-80% CH₃CN/water for 10 min to give the title compound (51 mg, 86%). LC-MS m/z 537 (M+H)⁺, 1.06 min. (ret time).

Example 117

3-(1,4-dimethyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl)propanoic acid

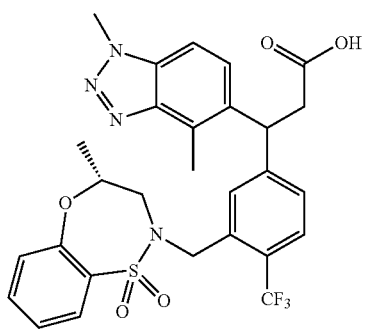 [SMILES: Cc1c(C(CC(=O)O)c2ccc(C(F)(F)F)c(CN3C[C@@H](C)Oc4ccccc4S3(=O)=O)c2)ccc2c1nnn2C]

(E)-ethyl 3-(1,4-dimethyl-1H-benzo[d][1,2,3]triazol-5-yl)acrylate

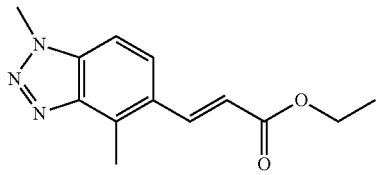 [SMILES: CCOC(=O)/C=C/c1ccc2c(nnn2C)c1C]

To a solution of 5-bromo-1,4-dimethyl-1H-benzo[d][1,2,3]triazole (2 g, 8.85 mmol) in DMF (60 mL) was added ethyl acrylate (5.78 mL, 53.1 mmol), N-ethyl-N-isopropylpropan-2-amine (6.16 mL, 35.4 mmol), tri-o-tolylphosphine (0.808 g, 2.65 mmol), and Pd(OAc)$_2$ (0.298 g, 1.327 mmol). The mixtures were split evenly to 4 20 mL microwave vials then submitted to the microwave at 120° C. at high absorption for 2 h. After this time, the separate reaction mixtures were combined and filtered through celite which was washed through with EtOAc. The filtrate was then washed with water (3×) and brine (1×), dried over MgSO$_4$, filtered and the solvent removed under reduced pressure. The resulting residue was then purified by silica gel chromatography using an Isco Combiflash Rf and eluting, 0-40% EtOAc/Hex to give the title compound (1.719 g, 71.3%). LC-MS m/z 246 (M+H)$^+$, 0.86 min. (ret time).

Ethyl 3-(1,4-dimethyl-1H-benzo[d][1,2,3]triazol-5-yl)-3-(3-(hydroxymethyl)-4-(trifluoromethyl)phenyl)propanoate

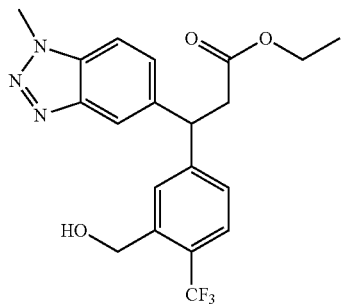 [SMILES: CCOC(=O)CC(c1ccc(C(F)(F)F)c(CO)c1)c1ccc2c(c1)nnn2C]

To a suspension of (5-(4,4,5,5-tetramethyl-1,3,2-dioxaborolan-2-yl)-2-(trifluoromethyl)phenyl)methanol (369 mg, 1.223 mmol), (E)-ethyl 3-(1,4-dimethyl-1H-benzo[d][1,2,3]triazol-5-yl)acrylate (200 mg, 0.815 mmol) and Et$_3$N (0.170 mL, 1.223 mmol) in 1,4-dioxane (10 mL) and water (6 mL) was added [RhCl(cod)]$_2$ (20.10 mg, 0.041 mmol) and was left to stir at 95° C. for 1 h. The 1,4-dioxane was removed under reduced pressure and the mixture filtered through celite which was washed with EtOAc. The filtrate was diluted with water and extracted with EtOAc (3×). The combined organic phases were washed with water (3×), brine (1×), dried over MgSO$_4$ and the solvent removed under reduced pressure to afford a yellow oil. The resulting residue was then purified by silica gel chromatography using an Isco Combiflash Rf and eluting, 0-60% EtOAc/Hex to give the title compound (238 mg, 69.3%). LC-MS m/z 422 (M+H)$^+$, 0.96 min. (ret time).

Ethyl 3-(1,4-dimethyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl)propanoate

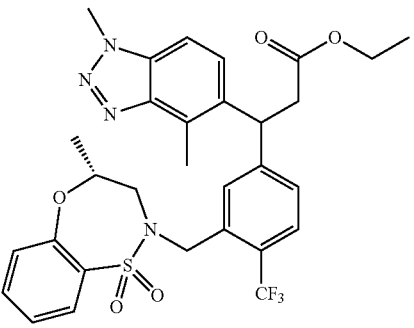 [SMILES: CCOC(=O)CC(c1ccc(C(F)(F)F)c(CN2C[C@@H](C)Oc3ccccc3S2(=O)=O)c1)c1ccc2c(nnn2C)c1C]

Under Argon and in an ice bath, ethyl 3-(1,4-dimethyl-1H-benzo[d][1,2,3]triazol-5-yl)-3-(3-(hydroxymethyl)-4-(trifluoromethyl)phenyl)propanoate (238 mg, 0.565 mmol)), (R)-4-methyl-3,4-dihydro-2H-benzo[b][1,4,5]oxathiazepine 1,1-dioxide (516 mg, 1.694 mmol), were dissolved in THF (5 mL), and then tributylphosphine (0.282 mL, 1.130 mmol)). The reaction mixture was stirred 5 min and then ADDP (285 mg, 1.130 mmol) was added. This was then stirred for 10 min and then warmed to 23 C and stirred for 64 h. The solution was then cooled to 0° C. in an ice bath and further tributylphosphine (0.282 mL, 1.130 mmol) and ADDP (285 mg, 1.130 mmol) and left to stir for 3 h further. After this time the solvent was removed under reduced pressure. The resulting residue was then purified by silica gel chromatography using an Isco Combiflash Rf and eluting, 0-50% EtOAc/Hex to give the title compound (344 mg, 95%). LC-MS m/z 617 (M+H)$^+$, 1.23 min. (ret time).

3-(1,4-dimethyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl)propanoic acid

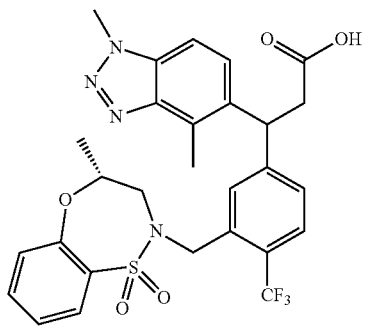 [SMILES: Cc1c(C(CC(=O)O)c2ccc(C(F)(F)F)c(CN3C[C@@H](C)Oc4ccccc4S3(=O)=O)c2)ccc2c1nnn2C]

To a solution of ethyl 3-(1,4-dimethyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl) propanoate (344 mg, 0.558 mmol) in THF (4 mL) and water (2 mL) was added LiOH (66.8 mg, 2.79 mmol). This was left to stir for 18 h. After this time, 1 N HCl was added to the reaction mixture drop wise until the mixture was at pH 1. The acidic solution was diluted with EtOAc, washed with water (3×), dried over MgSO₄, filtered and the solvents removed under reduced pressure to afford a white solid. The resulting residue was purified by reverse-phase HPLC (Atlantics T3, 19×100 mm, 5 u prep column) eluting at 18 mL/min at a gradient of 40-70% CH₃CN/water for 10 min to give the title compound (169 mg, 51.5%). LC-MS m/z 589 (M+H)⁺, 1.1 min. (ret time).

Example 118

3-(4-Chloro-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

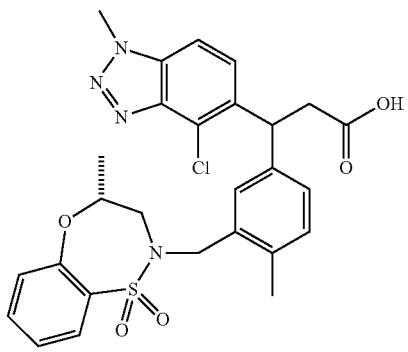 [SMILES: Cc1ccc(C(CC(=O)O)c2ccc3c(nnn3C)c2Cl)cc1CN1C[C@@H](C)Oc2ccccc2S1(=O)=O]

3-Chloro-2-nitroaniline

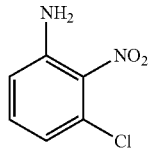

A solution of 3-chloro-2-nitrobenzoic acid (20 g, 99 mmol) and Et₃N (20.74 mL, 149 mmol) in DMF (100 mL) was treated with diphenyl phosphorazidate (32.8 g, 119 mmol) followed by stirring at RT for 3 h. The reaction mixture was then treated with water (200 mL) followed by warming at 100° C. for 1 h. The solution was cooled and the flask fitted with a short-path distillation head and the DMF removed by distillation under high vacuum. The solid residue was dissolved in EtOAc and washed with saturated NaHCO₃ solution. Filtered through celite and the filtrate was washed with water (3×), brine and dried over Na₂SO₄, filtered and concentrated under reduce pressure to give 10 g (53.4%) of the title compound. LC-MS m/z 173.1 (M+H)⁺, 1.67 (ret. time).

4-Bromo-3-chloro-2-nitroaniline

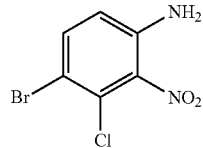 [SMILES: Nc1ccc(Br)c(Cl)c1[N+](=O)[O-]]

3-Chloro-2-nitroaniline (10 g, 57.9 mmol) and NBS (10.31 g, 57.9 mmol) were dissolved in AcOH (500 mL). The reaction mixture was stirred at reflux temperature for 45 min. After cooling, the reaction mixture was added to 1.5 L of water. The resultant precipitate was filtered off and dried under high vacuum to give 10 g (68.6%) of the title compound.

4-Bromo-3-chloro-N-methyl-2-nitroaniline

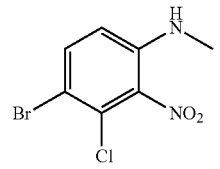

To a solution of the 4-bromo-3-chloro-2-nitroaniline (10 g, 39.8 mmol) in DMF (300 mL) at 0° C., NaH (1.145 g, 47.7 mmol) was added. After stirring for 30 min, MeI (2.98 mL, 47.7 mmol) was added and the reaction mixture was stirred 30 min further. Water (10 mL) was added. The red precipitate was collected by filtration, washed with water and dried to give 6 g (56.8%) of the title compound.

4-Bromo-3-chloro-N1-methylbenzene-1,2-diamine

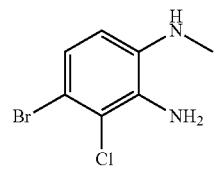

To 4-bromo-3-chloro-N-methyl-2-nitroaniline (6 g, 22.60 mmol) in AcOH (200 mL), zinc (4.43 g, 67.8 mmol) was added in small portions. Then the reaction mixture was stirred at RT for 10 h. The reaction mixture was filtered through celite and the solid was washed copiously with EtOAc. The combined solutions were concentrated to give 5 g (80%) of the title compound. LC-MS m/z 235.0 (M+H)⁺, 1.76 (ret. time).

5-Bromo-4-chloro-1-methyl-1H-benzo[d][1,2,3]triazole

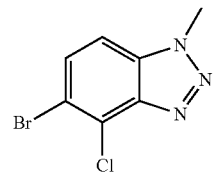

To 4-bromo-3-chloro-N1-methylbenzene-1,2-diamine (5 g, 21.23 mmol) in H₂SO₄ (10 mL, 188 mmol) at 0° C., NaNO₂ (2.051 g, 29.7 mmol) was added in small portions over 20 minute. After stirring 30 min further, 200 mL of water was added. The resulting precipitate was collected by filtration, washed with water and dried. The mother liquors were left to stand for 16 h and a second batch of precipitate formed, which was collected as before. The combined solids were columned in EtOAc to remove inorganic salts to give 3.73 g (71.3%) of the title compound. LC-MS m/z 245.9 (M+H)+, 1.69 (ret. time).

(E)-ethyl 3-(4-chloro-1-methyl-1H-benzo[d][1,2,3]triazol-5-yl)acrylate

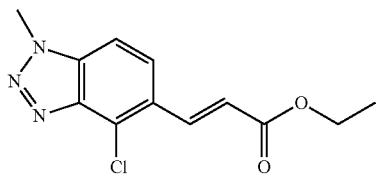 [SMILES: CCOC(=O)/C=C/c1ccc2c(nnn2C)c1Cl]

A solution of 5-bromo-4-chloro-1-methyl-1H-benzo[d][1,2,3]triazole (739 mg, 3.0 mmol), Pd(OAc)₂ (135 mg, 0.600 mmol), tri-o-tolylphosphine (365 mg, 1.200 mmol), DMF (3 mL), ethyl acrylate (3.93 mL, 36.0 mmol), and Hunig's base (4.19 mL, 24.00 mmol) were combined in a microwave vial and a stream of Ar was bubbled through the mixture for 1 min and then the vial was sealed and heated on the microwave at 130° C. under high absorption for 3 h. Cooled, more Pd(OAc)₂ (0.067 g, 0.30 mmol) and tri-tolyphosphine (183 mg, 0.6 mmol) was added and the mixture was again degassed with a stream of Ar and the resulting mixture was sealed and heated in the microwave for 2 h at 130° C. The reaction was diluted with EtOAc (75 mL), filtered through a glass fiber filter and the filtrate was washed with water (3×50 mL) and saturated aqueous NaCl (50 mL), dried (Na₂SO₄) and concentrated to a dark brown solid. The crude product was pre-adsorbed on an inert support and purified on a silica cartridge (40 g) with a Combiflash Companion, eluting at 40 mL/min with a gradient running from hexanes to 60% EtOAc/hexanes over 35 min. The desired fractions were pooled and concentrated to afford 535 mg (67%) of the title compound. LC-MS m/z 266.0 (M+H)+, 0.84 (ret. time).

Ethyl 3-(4-chloro-1-methyl-1H-benzo[d][1,2,3]triazol-5-yl)-3-(3-(hydroxymethyl)-4-methylphenyl)propanoate

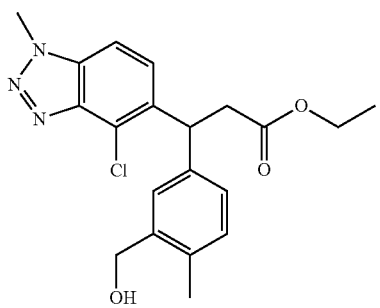 [SMILES: CCOC(=O)CC(c1ccc(C)c(CO)c1)c1ccc2c(nnn2C)c1Cl]

To (E)-ethyl 3-(4-chloro-1-methyl-1H-benzo[d][1,2,3]triazol-5-yl)acrylate (0.8 g, 3.01 mmol) in 1,4-Dioxane (20.00 mL) and Water (10 mL) was added (3-(hydroxymethyl)-4-methylphenyl)boronic acid (0.750 g, 4.52 mmol), Et₃N (0.420 mL, 3.01 mmol), and [RhCl(cod)]₂ (0.074 g, 0.151 mmol). Argon was bubbled through the reaction for 3 min and then the mixture was heated to 95° C. internal temp for 1.5 h. The reaction was cooled, diluted with EtOAc (50 mL), washed with water (2×50 mL), and saturated aqueous NaCl (50 mL), dried (Na₂SO₄), concentrated, pre-adsorbed on an inert support and the crude product was purified on a silica cartridge (40 g) with a Combiflash Companion, eluting at 40 mL/min with a gradient running from hexanes to 100% EtOAc over 30 min. The desired fractions were pooled and concentrated to afford 953 mg (82%) of the title compound. LC-MS m/z 388.0 390.3 (M+H)+, 0.85 (ret. time).

Ethyl 3-(4-chloro-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate

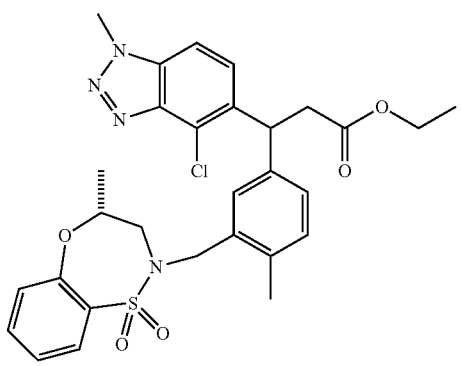

Under Argon, ethyl 3-(4-chloro-1-methyl-1H-benzo[d][1,2,3]triazol-5-yl)-3-(3-(hydroxymethyl)-4-methylphenyl)propanoate (125 mg, 0.322 mmol), and (R)-4-methyl-3,4-dihydro-2H-benzo[b][1,4,5]oxathiazepine 1,1-dioxide (84 mg, 0.394 mmol), were dissolved in THF (2.5 mL), and cooled to 4° C. on an ice-bath and then tributylphosphine (0.161 mL, 0.645 mmol) was added. Stirred 5 min and then ADDP (163 mg, 0.645 mmol) was added. Stirred 10 min and then warmed to 23° C. and stirred for 3 h to afford a brown suspension. The volatiles were removed in vacuo and the crude reaction was pre-adsorbed onto an inert support and the crude product was purified on a silica cartridge (12 g) with a Combiflash Companion, eluting at 30 mL/min with a gradient running from hexanes to 70% EtOAc/hexanes over 25 min. The desired fractions were pooled to afford 180 mg (96%) of the title compound. LC-MS m/z 582.9 585.0 (M+H)+, 1.14 (ret. time).

3-(4-Chloro-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

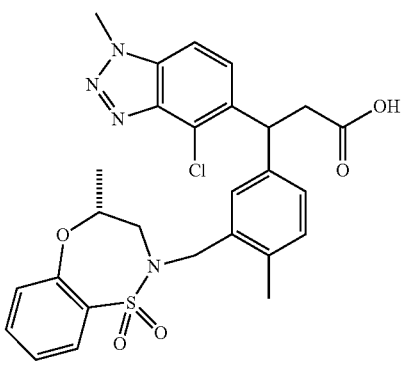

Ethyl 3-(4-chloro-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate (178 mg, 0.305 mmol) was dissolved in THF (3 mL) and a solution of LiOH (146 mg, 6.11 mmol) dissolved in water (3 mL) was added. The resulting 2 phase mixture was diluted with MeOH (1 mL) and a homogeneous though cloudy suspension was obtained. Stirred 1.5 h and the reaction was concentrated in vacuo and the residual mixture was combined with 1M HCl (20 mL) and EtOAc (75 mL) and the EtOAc was washed with H2O (20 mL) and saturated aqueous NaCl (20 mL), dried (Na$_2$SO$_4$) and concentrated. The crude product was dissolved in DMSO (4 mL), filtered through a 0.45 μm acrodisc, and purified by reverse-phase HPLC (YMC C18 S-5 μm/12 nm 50×20 mm preparatory column), eluting at 20 mL/min with a linear gradient running from 10% CH$_3$CN/H$_2$O (0.1% TFA) to 90% CH$_3$CN/H$_2$O (0.1% TFA) over 10 min. The desired fractions were pooled and concentrated in vacuo to afford 153 mg of 3-(4-Chloro-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid (90%). LC-MS m/z 555.0 556.9 (M+H)$^+$, 0.99 (ret. time).

Example 119

2-Methyl-3-(1-methyl-1H-benzo[d][1,2,3]triazol-5-yl)-3-(4-methyl-3-((N-methylphenylsulfonamido)methyl)phenyl)propanoic acid

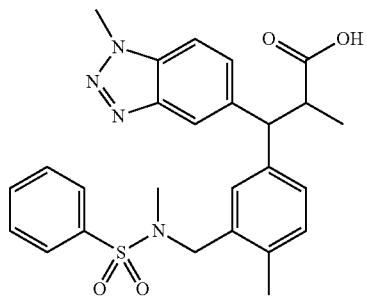

(E)-methyl 3-(1-methyl-1H-benzo[d][1,2,3]triazol-5-yl)acrylate

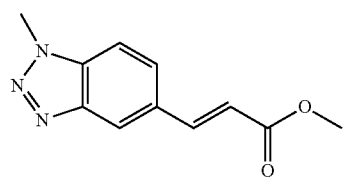 [SMILES: COC(=O)/C=C/c1ccc2c(c1)nnn2C]

To a suspension of KOt-Bu (2.61 g, 23.27 mmol) in THF (115 mL) at 0° C., was added methyl 2-(dimethoxyphosphoryl)acetate (4.50 mL, 27.9 mmol). After 1 h and 15 mins was added 1-methyl-1H-benzo[d][1,2,3]triazole-5-carbaldehyde (3 g, 18.61 mmol) in small portions over 15 min. The resulting solution was stirred for a further 1 h and 15 mins. Saturated NH$_4$Cl and water were added to quench the reaction. The mixture was extracted with EtOAc (3×), washed with water (3×) and brine (1×), dried over MgSO$_4$, filtered and the solvent removed under reduced pressure to give a orange powder (3.678 g, 91%). LC-MS m/z 218 (M+H)$^+$, 0.67 min (ret time), 100% purity.

Methyl 3-(3-(hydroxymethyl)-4-methylphenyl)-3-(1-methyl-1H-benzo[d][1,2,3]triazol-5-yl)propanoate

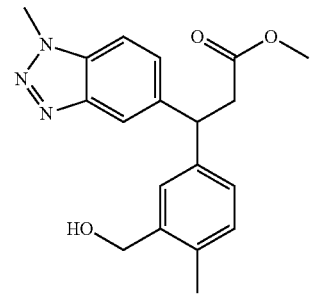

To a suspension of (3-(hydroxymethyl)-4-methylphenyl)boronic acid (1.142 g, 6.88 mmol), (E)-methyl 3-(1-methyl-1H-benzo[d][1,2,3]triazol-5-yl)acrylate (1 g, 4.60 mmol), and [RhCl(cod)]$_2$ (0.255 g, 0.517 mmol) in Water (20.00 mL) and 1,4-Dioxane (50 mL), in a 100 mL round bottom flask equipped with stirrer bar and reflux condeser, was added Et$_3$N (1.276 mL, 9.21 mmol). The resulting suspension was heated to 95° C. and allowed to stir for 3 h. The reaction mixture was cooled, diluted with water and extracted with EtOAc (3×). The organic phase washed with water (3×) and brine (1×), dried over MgSO$_4$, filtered and concentrated to give a brown oil. The resulting residue was then purified by silica gel chromatography using an Isco Combiflash Rf and eluting, 0-40% EtOAc/DCM to give the title compound (583 mg, 33.6%). LC-MS m/z 340 (M+H)$^+$, 0.77 min (ret time), 90% purity.

Methyl 3-(3-(chloromethyl)-4-methylphenyl)-3-(1-methyl-1H-benzo[d][1,2,3]triazol-5-yl)propanoate

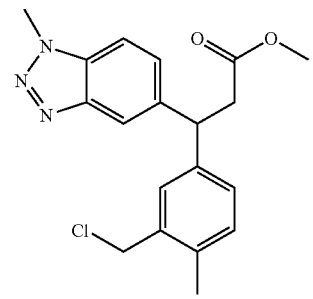

To a solution of methyl 3-(3-(hydroxymethyl)-4-methylphenyl)-3-(1-methyl-1H-benzo[d][1,2,3]triazol-5-yl)propanoate (580 mg, 1.538 mmol) and Et$_3$N (2 mL, 14.35 mmol) in DCM (26 mL) at −78° C. was added gradually mesyl chloride (0.300 mL, 3.85 mmol). The mixture was then warmed to 23° C. over 1 h and stirred for 22 h under an argon atmosphere. The mixture was then diluted with water, and extracted with EtOAc (3×). The combined organic layers were washed with water (3×) and with brine (1×), dried over Na$_2$SO$_4$, filtered and concentrated under reduced pressure to give Methyl 3-(3-(chloromethyl)-4-methylphenyl)-3-(1-methyl-1H-benzo[d][1,2,3]triazol-5-yl)propanoate as a brown solid (1.323 g, 240%). LC-MS m/z 358.2, 360.2 (M+H)$^+$, 1.09 min (ret time), 79 purity.

249

Methyl 3-(1-methyl-1H-benzo[d][1,2,3]triazol-5-yl)-3-(4-methyl-3-((N-methylphenylsulfonamido)methyl)phenyl)propanoate

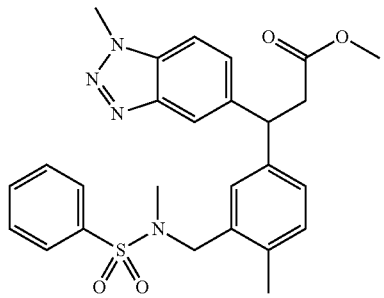

To a solution of methyl 3-(3-(chloromethyl)-4-methylphenyl)-3-(1-methyl-1H-benzo[d][1,2,3]triazol-5-yl)propanoate (1.3 g, 2.87 mmol) in CH$_3$CN (20 mL) was added potassium iodide (0.238 g, 1.435 mmol), potassium carbonate (0.754 g, 5.45 mmol) and N-methylbenzenesulfonamide (0.483 mL, 3.44 mmol) and the resulting solution left to stir at 23° C. for further 19.5 h. The temperature was then raised to 50° C. for a further 20 h and the reaction mixture was cooled to 4° C. for ~60 h (over the weekend). The reaction was then diluted with water and extracted with EtOAc (3×). The combined organic layers were then combined and washed with water (3×) brine (1×), dried over MgSO$_4$ and the solvent removed under reduced pressure. The resulting residue was then purified by silica gel chromatography using an Isco Combiflash Rf and eluting, 0-20% EtOAc/DCM to give the title compound (323 mg, 22.85%). LC-MS m/z 494 (M+H)$^+$, 1.08 min (ret time), 100% purity.

3-(1-methyl-1H-benzo[d][1,2,3]triazol-5-yl)-3-(4-methyl-3-((N-methylphenylsulfonamido)methyl)phenyl)propanoic acid

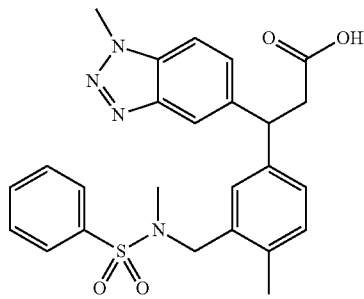

To a solution of methyl 3-(1-methyl-1H-benzo[d][1,2,3]triazol-5-yl)-3-(4-methyl-3-((N-methylphenylsulfonamido)methyl)phenyl)propanoate (0.32 g, 0.650 mmol) in THF (10 mL), MeOH (5.00 mL) and Water (5.00 mL) was added LiOH (78 mg, 3.26 mmol) and this was left to stir at room temp for 23 h. After this time, 1 N HCl was added to the reaction mixture dropwise until the mixture was at pH 1. The acidic solution was diluted with EtOAc, washed with water (3×), dried over MgSO$_4$, filtered and the solvents removed under reduced pressure to afford a white solid (310 mg, 100%). LC-MS m/z 479 (M+H)$^+$, 0.94 min (ret time), 100% purity.

250

Methyl 3-(1-methyl-1H-benzo[d][1,2,3]triazol-5-yl)-3-(4-methyl-3-((N-methylphenylsulfonamido)methyl)phenyl)propanoate

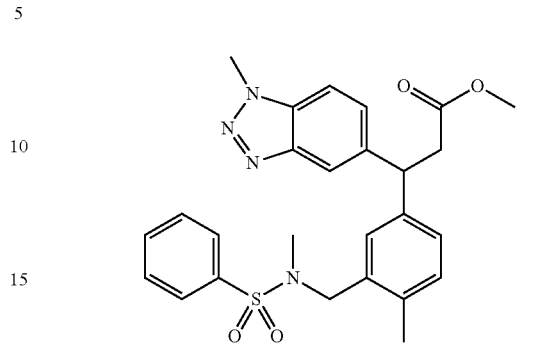

To a solution of 3-(1-methyl-1H-benzo[d][1,2,3]triazol-5-yl)-3-(4-methyl-3-((N-methylphenylsulfonamido)methyl)phenyl)propanoic acid (100 mg, 0.209 mmol) in DMF (5 mL) was added potassium carbonate (116 mg, 0.836 mmol) and methyl 4-methylbenzenesulfonate (117 mg, 0.627 mmol) and this was left to stir at 23° C. for 1 h 20 mins. After this time, the reaction mixture was quenched with water, partitioned between EtOAc and sat. NaHCO$_3$. The organic phase was then washed with sat. NaHCO$_3$ and brine, dried over Na$_2$SO$_4$, filtered and the solvent removed under reduced pressure to afford a white solid. The residue was then combined with a second reaction described just below for further purification. In a second reaction a solution of 3-(1-methyl-1H-benzo[d][1,2,3]triazol-5-yl)-3-(4-methyl-3-((N-methylphenylsulfonamido)methyl)phenyl)propanoic acid (201 mg, 0.420 mmol) in DMF (11 mL) was treated with potassium carbonate (232 mg, 1.680 mmol) and methyl 4-methylbenzenesulfonate (235 mg, 1.260 mmol) and this was left to stir at 23° C. for 40 mins. After this time, the reaction mixture was quenched with water, partitioned between EtOAc and sat. NaHCO$_3$. The organic phase was then washed with sat. NaHCO$_3$ and brine, dried over Na$_2$SO$_4$, filtered and the solvent removed under reduced pressure to afford a white solid. At this time the residue was combined with that of the first experiment for purification. The resulting residues were then purified by silica gel chromatography using an Isco Combiflash Rf and eluting, 0-20% EtOAc/DCM to give the title compound (143 mg, 46% combined yield). LC-MS m/z 493 (M+H)$^+$, 1.08 min (ret time), 100% purity.

Methyl 2-methyl-3-(1-methyl-1H-benzo[d][1,2,3]triazol-5-yl)-3-(4-methyl-3-((N-methylphenylsulfonamido)methyl)phenyl)propanoate

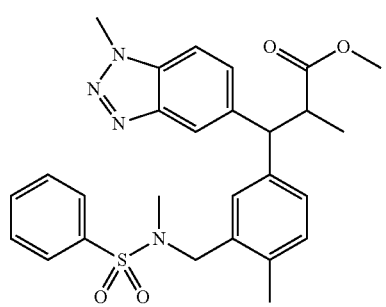

2M n-BuLi in hexane (0.780 mL, 1.559 mmol) was added dropwise to a dry-ice-acetone bath (~−70° C.) cooled solution of diisopropylamine (0.273 mL, 1.949 mmol) in THF (2 mL). Stirred 10 min and then the dry-ice-acetone bath was replaced with an ice bath and stirred for another 10 min to afford 0.52 M LDA in THF.

A portion of the 0.52M LDA in THF (0.325 mL, 0.169 mmol) was added to THF (1 mL) and cooled on dry-ice acetone to near −70° C. To this, methyl 3-(1-methyl-1H-benzo[d][1,2,3]triazol-5-yl)-3-(4-methyl-3-((N-methylphenylsulfonamido)methyl)phenyl)propanoate (64 mg, 0.130 mmol) in THF (2 mL) was added dropwise with dry-ice acetone bath cooling (internal T=<−65° C.) and the light yellow solution was stirred at <−65° C. for 30 min, the bath was replaced with a dry-ice CH$_3$CN bath (~−40° C.) and stirred 15 min. Then MeI (0.162 mL, 2.60 mmol) was added in one portion and the mixture was warmed to 23° C. and stirred 30 min. The reaction was quenched with water (10 mL), diluted with EtOAc (75 mL), further diluted with 1N HCl (20 mL) and the resulting organic phase was washed again with saturated aqueous NaCl, dried (Na$_2$SO$_4$), filtered and the solvent removed under reduced pressure to afford 61 mg of a brown gum which was a 78:22 mixture of isomers based on the LCMS. The diastereoisomers were separated by preparative HPLC. (Sunfire C18, 19×100 mm, 5 u; A=Water+0.1% TFA: B=MeCN+0.1% TFA; 18 mL/min; 35% B to 65% B in 12 min) to afford 20 mg (34%) of the major diastereomer of the title compound as a mixture of enantiomers of the same, undefined relative stereochemistry at the parent C-2 and C-3 (20 mg) LC-MS m/z 506.9 (M+H)$^+$, 1.08 (ret. time), and 7 mg (10%) of the minor diastereomer of the title compound as a mixture of enantiomers of the same, undefined relative stereochemistry at the parent C-2 and C-3 LC-MS m/z 507.0 (M+H)$^+$, 1.08 (ret. time).

2-Methyl-3-(1-methyl-1H-benzo[d][1,2,3]triazol-5-yl)-3-(4-methyl-3-((N-methylphenylsulfonamido)methyl)phenyl)propanoic acid

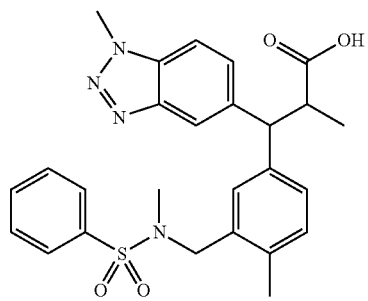

2-Methyl-3-(1-methyl-1H-benzo[d][1,2,3]triazol-5-yl)-3-(4-methyl-3-((N-methylphenylsulfonamido)methyl)phenyl) propanoate (20 mg, 0.039 mmol) (a single diastereomer as a mixture of enantiomers of the same, undefined relative stereochemistry at the parent C-2 and C-3) (the major product from the preceding step), was dissolved in THF (1 mL) and 1M aqueous LiOH (0.790 mL, 0.790 mmol) was added to afford a 2 phase system. MeOH (1 mL) was added forming a cloudy, single phase and the suspension was stirred 3 days. The volatile solvent was removed and the residue was diluted with EtOAc (75 mL) and 1M aqueous HCl (25 mL). The EtOAc was washed with water and saturated aqueous NaCl and dried (Na$_2$SO$_4$) and concentrated to afford 16 mg which was purified by preparative HPLC (Atlantics T3, 19×100 mm, 5 u; A=Water+0.1% TFA: B=MeCN+0.1% TFA; 18 mL/min; 20% B to 65% B in 15 min) to afford 11 mg of the title compound as a single diastereomer which is a mixture of enantiomers of the same, undefined relative stereochemistry at the parent C-2 and C-3. LC-MS m/z 493.1 (M+H)$^+$, 1.00 (ret. time).

Example 120

2-methyl-3-(1-methyl-1H-benzo[d][1,2,3]triazol-5-yl)-3-(4-methyl-3-((N-methylphenylsulfonamido)methyl)phenyl)propanoic acid

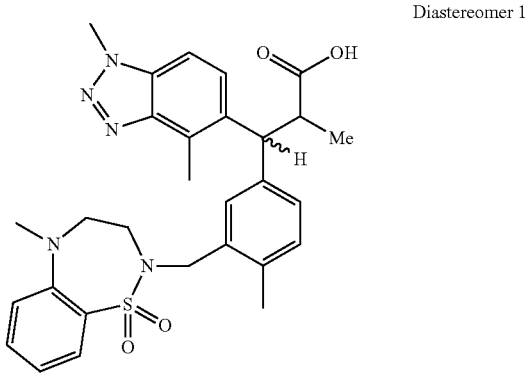

Example 121

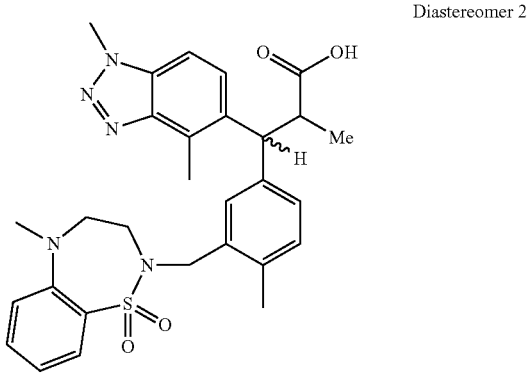

Example 122

Ethyl 3-(1,4-dimethyl-1H-benzo[d][1,2,3]triazol-5-yl)-2-methyl-3-(4-methyl-3-((5-methyl-1,1-dioxido-4,5-dihydrobenzo[f][1,2,5]thiadiazepin-2(3H)-yl)methyl)phenyl)propanoate

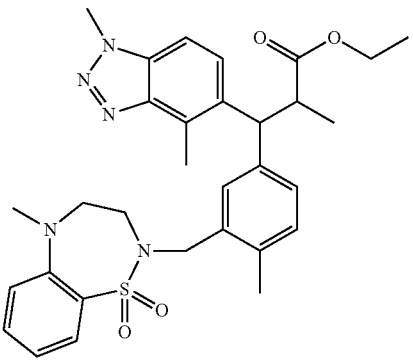

A 2M n-BuLi in hexanes solution (1.100 mL, 2.200 mmol) is added to a dry-ice acetone bath cooled solution (~−70° C.) of diisopropylamine (0.381 mL, 2.67 mmol) in THF (2 mL). The clear solution was stirred at dry-ice acetone bath temp for 10 min and then was warmed on an ice-water bath and stirred for 10 min to afford 0.63 M LDA.

A portion of the 0.63M LDA (0.367 mL, 0.231 mmol) diluted with THF (1 mL) was cooled on a dry-ice acetone bath and ethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate (100 mg, 0.178 mmol) dissolved in THF (2 mL) was added dropwise (T<−65° C.). The red solution was stirred with dry-ice acetone cooling for 30 min and then the dry-ice acetone bath was replaced with a dry-ice CH₃CN bath (~−40° C.) and the red solution was stirred for 15 min, MeI (0.223 mL, 3.56 mmol) was added in one portion and the yellow solution was warmed to 23° C. and stirred 15 min. The volatiles were removed in vacuo and the residue was diluted with EtOAc (75 mL) and washed with 0.5 M aqueous HCl (25 mL) and saturated aq NaCl (25 mL), dried Na₂SO₄ and concentrated to afford 103 mg of a brown foam. The crude product was dissolved in CH₃CN (4 mL), filtered through a 0.45 mm acrodisc, and purified by reverse-phase HPLC (YMC C18 S-5 mm/12 nm 50×20 mm preparatory column), eluting at 20 mL/min with a linear gradient running from 20% CH₃CN/H₂O (0.1% TFA) to 90% CH₃CN/H₂O (0.1% TFA) over 10 min. The desired fractions were concentrated in vacuo to afford 99 mg (97%) of the title compound as a mixture of isomers. LC-MS m/z 576.3 (M+H)⁺, 1.20 (ret. time).

Diastereomer 1

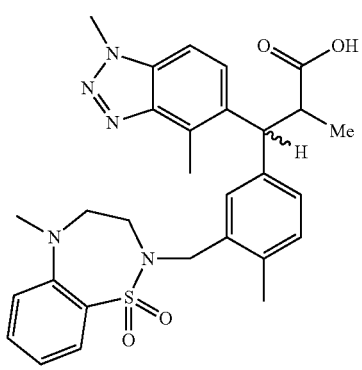

Example 121

Diastereomer 2

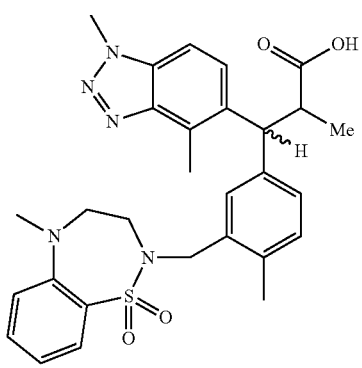

Example 122

2-methyl-3-(1-methyl-1H-benzo[d][1,2,3]triazol-5-yl)-3-(4-methyl-3-((N-methylphenylsulfonamido)methyl)phenyl)propanoic acid Ethyl 3-(1,4-dimethyl-1H-benzo[d][1,2,3]triazol-5-yl)-2-methyl-3-(4-methyl-3-((5-methyl-1,1-dioxido-4,5-dihydrobenzo[f][1,2,5]thiadiazepin-2(3H)-yl)methyl)phenyl)propanoate (99 mg, 0.172 mmol) was dissolved in THF (3 mL) and then LiOH (82 mg, 3.44 mmol) dissolved in water (3 mL) and MeOH (1 mL) was added and a clear solution was obtained. Stirred 20 h at 23° C. and then was heated to 50° C. for 6 h and cooled to 23° C. and stirred in a sealed vial for 3 days. Then the reaction was reheated to 50° C. for 6 h. The solvent was evaporated in vacuo and the residue was combined with EtOAc (75 mL) and 1M aqueous HCl (25 mL). Phases separated and the aqueous phase was extracted with EtOAc (25 mL) and the combined EtOAc was washed with water (25 mL) and saturated aqueous NaCl (25 mL) dried (Na₂SO₄), concentrated to afford 69 mg. The crude product was dissolved in DMSO (3.5 mL), filtered through a 0.45 mm acrodisc, and purified by reverse-phase HPLC (YMC C18 S-5 mm/12 nm 50×20 mm preparatory column), eluting at 20 mL/min with a linear gradient running from 20% CH₃CN/H₂O (0.1% TFA) to 85% CH₃CN/H₂O (0.1% TFA) over 10 min (0.5 mL/injection).

Example 121

The first fraction to elute: 16 mg ((17%) LC-MS m/z 548.2 (M+H)⁺, 0.99 (ret. time).

Example 122

The second fraction to elute: 26 mg (28%) LC-MS m/z 548.2 (M+H)⁺, 1.04 (ret. time).

Example 123

3-(4-Methyl-3-(((R)-4-methyl-1,1-dioxido-3,4-dihydro-2H-benzo[b][1,4,5]oxathiazepin-2-yl)methyl)phenyl)-5-(1H-1,2,3-triazol-4-yl)pentanoic acid

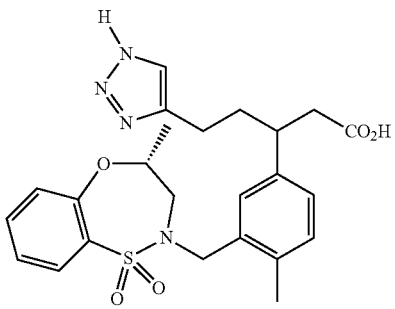

3-(1-Benzyl-1H-1,2,3-triazol-4-yl)propan-1-ol

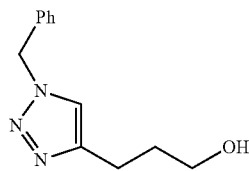 [SMILES: OCCCc1cn(Cc2ccccc2)nn1]

CuSO₄ (0.60 g, 15 mol %), sodium ascorbate (1.0 g, 20 mol %) and pent-4-yn-1-ol (2.32 mL, 24.97 mmol) were added to a solution of (azidomethyl)benzene (3.12 mL, 24.97 mmol) in MeOH (100 mL). The solution was stirred at 23° C. for 2 days. MeOH was evaporated and the mixture left was diluted with EtOAc and filtered through silica. The mixture was concentrated, giving 4.8 g (88%) of the title compound. LC-MS m/z 218.1 (M+H)⁺, 0.59 (ret. time).

3-(1-Benzyl-1H-1,2,3-triazol-4-yl)propanal

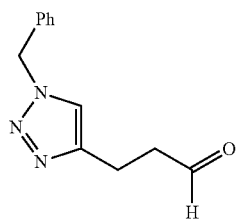 [SMILES: O=CCCc1cn(Cc2ccccc2)nn1]

DMSO (2.61 mL, 36.8 mmol) was added dropwise to a solution of oxalyl chloride (1.61 mL, 18.41 mmol) in CH₂Cl₂ (15 mL) at −78° C. After 2 min, a solution of 3-(1-benzyl-1H-1,2,3-triazol-4-yl)propan-1-ol (1.0 g, 4.6 mmol) in CH₂Cl₂ (5 mL) was added slowly over 5 min. After an additional 15 min, Et₃N (5.14 mL, 36.8 mmol) was added, and the mixture was stirred at −78° C. for 5 min and then the mixture was warmed to 23° C. The mixture was diluted with EtOAc, washed with water and brine. The combined extracts were dried over MgSO₄, filtered, concentrated and purified over Silica gel (40 g) with Combiflash Companion eluting at 40 mL/min with a gradient running from 0-100% EtOAc/Hexane over 25 min. The product containing fractions were combined and the solvent removed under reduced pressure giving 0.48 g (48%) of the title compound. LC-MS m/z 216.0 (M+H)⁺, 0.72 (ret. time).

(E)-Ethyl 5-(1-benzyl-1H-1,2,3-triazol-4-yl)pent-2-enoate

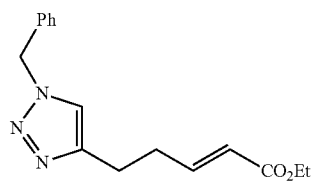 [SMILES: CCOC(=O)/C=C/CCc1cn(Cc2ccccc2)nn1]

NaH (106 mg, 2.66 mmol) was added to a solution of ethyl 2-(diethoxyphosphoryl)acetate (325 mg, 1.45 mmol) in DCM (6 mL) in small portions at 0° C., the mixture was stirred at 23° C. for 10 min. Then 3-(1-benzyl-1H-1,2,3-triazol-4-yl)propanal (260 mg, 1.21 mmol) was added at 23° C. The mixture was stirred for 1 h. NH₄Cl (saturated aqueous) was added and the solution was extracted with DCM. The combined extracts were dried over MgSO₄, filtered, concentrated and purified over Silica gel (12 g) with Combiflash Companion eluting at 30 mL/min with a gradient running from 0-100% EtOAc/Hexane over 20 min. The product containing fractions were combined and the solvent removed under reduced pressure giving 0.63 g (52%) of the title compound. LC-MS m/z 286.1 (M+H)⁺, 0.91 (ret. time).

Ethyl 5-(1-benzyl-1H-1,2,3-triazol-4-yl)-3-(3-(hydroxymethyl)-4-methylphenyl)pentanoate

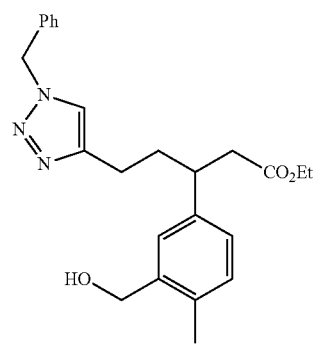

(3-(Hydroxymethyl)-4-methylphenyl)boronic acid (0.24 g, 1.47 mmol), Et₃N (0.21 mL, 1.47 mmol) and [RhCl(cod)]₂ (24 mg, 49 µmol) was added to a solution of (E)-ethyl 5-(1-benzyl-1H-1,2,3-triazol-4-yl)pent-2-enoate (0.28 g, 0.98 mmol) in 1,4-Dioxane (5 mL) and Water (2.5 mL). The reaction was heated in a microwave at 120° C. (high absorption) for 1 h, and then heated in a microwave at 140° C. (high absorption) for another 2 h. The reaction mixture was concentrated to get rid of most 1,4-dioxane and diluted in EtOAc, washed with water and brine. The combined extracts were dried over MgSO₄, filtered, concentrated and purified over Silica gel (12 g) with Combiflash Companion eluting at 30 mL/min with a gradient running from 0-100% EtOAc/Hexane over 20 min. The product containing fractions were combined and the solvent removed under reduced pressure giving 0.28 g (70%) of the title compound. LC-MS m/z 408.3 (M+H)⁺, 0.97 (ret. time).

Ethyl 5-(1-benzyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate

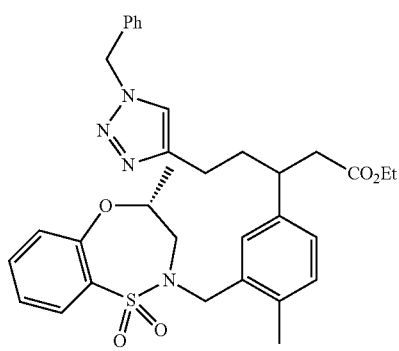

Tri-n-butylphosphine (0.121 mL, 0.491 mmol) was added to a solution of ethyl 5-(1-benzyl-1H-1,2,3-triazol-4-yl)-3-(3-(hydroxymethyl)-4-methylphenyl)pentanoate (100 mg, 0.26 mmol), (R)-4-methyl-3,4-dihydro-2H-benzo[b][1,4,5]oxathiazepine 1,1-dioxide (54.9 mg, 0.26 mmol), and ADDP (124 mg, 0.49 mmol) in THF (3 mL) at 0° C. The ice-bath was removed after 20 min and stirred at 23° C. for 1 h. The reaction mixture was concentrated and purified over Silica gel (12 g) with Combiflash Companion eluting at 30 mL/min with a gradient running from 0-100% EtOAc/Hexane over 25 min. Product containing fractions were combined and the solvent removed under reduced pressure giving 0.11 g (77%) of the title compound. LC-MS m/z 603.5 (M+H)$^+$, 1.26 (ret. time).

Ethyl 3-(4-methyl-3-(((R)-4-methyl-1,1-dioxido-3,4-dihydro-2H-benzo[b][1,4,5]oxathiazepin-2-yl)methyl)phenyl)-5-(1H-1,2,3-triazol-4-yl)pentanoate

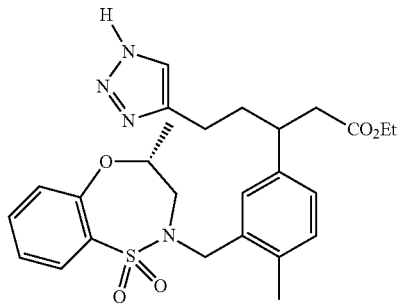

Pd/C (30 mg, 0.028 mmol, 10% Wt) was added to a solution of ethyl 5-(1-benzyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate (113.6 mg, 0.19 mmol) in MeOH (2 mL) at 23° C., under 1 atm H$_2$ for 3 days, filtered and concentrated giving 47.8 mg (50%) of the title compound. LC-MS m/z 513.3 (M+H)$^+$, 1.04 (ret. time).

3-(4-Methyl-3-(((R)-4-methyl-1,1-dioxido-3,4-dihydro-2H-benzo[b][1,4,5]oxathiazepin-2-yl)methyl)phenyl)-5-(1H-1,2,3-triazol-4-yl)pentanoic acid

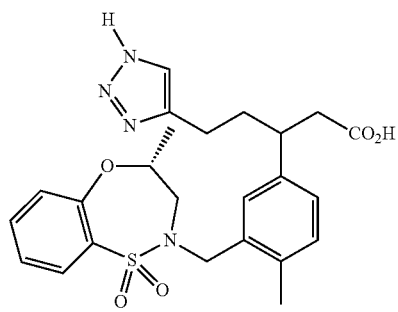

LiOH (26 mg, 1.09 mmol) was added to a solution of ethyl 3-(4-methyl-3-(((R)-4-methyl-1,1-dioxido-3,4-dihydro-2H-benzo[b][1,4,5]oxathiazepin-2-yl)methyl)phenyl)-5-(1H-1,2,3-triazol-4-yl)pentanoate (27.8 mg, 0.054 mmol) in THF (2.5 mL) and H$_2$O (0.5 mL). The reaction mixture was stirred at 23° C. for 30 h. The reaction mixture was acidified with HCl (1 N, 1 mL), concentrated and purified by a Gilson HPLC (YMC C18 5 mm/12 nm 50×20 mm preparatory column), eluting at 20 mL/min with a linear gradient running from 10% CH$_3$CN/H$_2$O to 90% CH$_3$CN/H$_2$O over 10 min giving 9 mg (34%) of the title compound. LC-MS m/z 485.1 (M+H)$^+$, 0.90 (ret. time).

Example 124

5-(1-Benzyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid

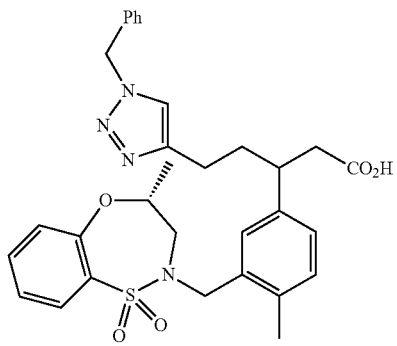

5-(1-Benzyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid

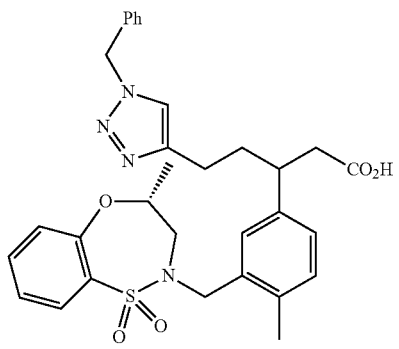

LiOH (63.6 mg, 2.65 mmol) was added to a solution of ethyl 5-(1-benzyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate (80 mg, 0.13 mmol) in THF (5 mL) and H$_2$O (1 mL). The reaction mixture was stirred at 23° C. 18 h and heated at 50° C. for additional 12 h. The reaction mixture was acidified with HCl (1 N, 2.65 mL), concentrated and purified by a Gilson HPLC (YMC C18 5 mm/12 nm 50×20 mm preparatory column), eluting at 20 mL/min with a linear gradient running from 10% CH$_3$CN/H$_2$O to 90% CH$_3$CN/H$_2$O over 10 min giving 42 mg (55%) of the title compound. LC-MS m/z 575.3 (M+H)$^+$, 1.09 (ret. time).

Example 125

5-(2-Methyl-2H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid

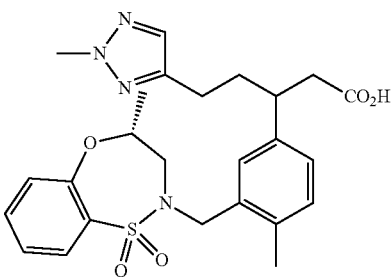 [SMILES: Cc1ccc(C(CCc2cnn(C)n2)CC(=O)O)cc1CN1C[C@@H](C)Oc2ccccc2S1(=O)=O]

Ethyl 5-(2-methyl-2H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate (A)

$K_2CO_3$ (13.35 mg, 0.097 mmol) and methyl iodide (6.0 μL, 0.097 mmol) were added to ethyl 3-(4-methyl-3-(((R)-4-methyl-1,1-dioxido-3,4-dihydro-2H-benzo[b][1,4,5]oxathiazepin-2-yl)methyl)phenyl)-5-(1H-1,2,3-triazol-4-yl)pentanoate (45 mg, 0.088 mmol) in DMF (1 mL) at 0° C. under nitrogen. The mixture was stirred at 0° C. for 1 h, allowed to warm to 23° C. and stirred for 16 h. The solvent was evaporated, diluted in EtOAc, washed with water and brine. The combined extracts were dried over $MgSO_4$, filtered, concentrated and purified over Silica gel (4 g) with Combiflash Companion eluting at 18 mL/min with a gradient running from 0-100% EtOAc/hexane over 25 min The product containing fractions eluted first, were combined and the solvent removed under reduced pressure giving 11 mg (24%) of the title compound (A) LC-MS m/z 527.2 (M+H)$^+$, 1.19 (ret. time), Later fractions were then obtained containing an unseparated mixture of ethyl 5-(2-methyl-2H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl) pentanoate (B) and ethyl 5-(1-methyl-1H-1,2,3-triazol-5-yl)-3-(4-methyl-3-(((R)-4-methyl-1,1-dioxido-3,4-dihydro-2H-benzo[b][1,4,5]oxathiazepin-2-yl)methyl)phenyl) pentanoate (C) LC-MS m/z 527.2 (M+H)$^+$, 1.11 (ret. time);

The chromatography on the same column was continued eluting at 18 mL/min with a gradient running from 0-20% MeOH/DCM over 10 min. The fractions from the more polar solvent system were combined and the solvent removed under reduced pressure giving ethyl 5-(1,3-dimethyl-2,3-dihydro-1H-1,2,3-triazol-4-yl)-3-(4-methyl-3-

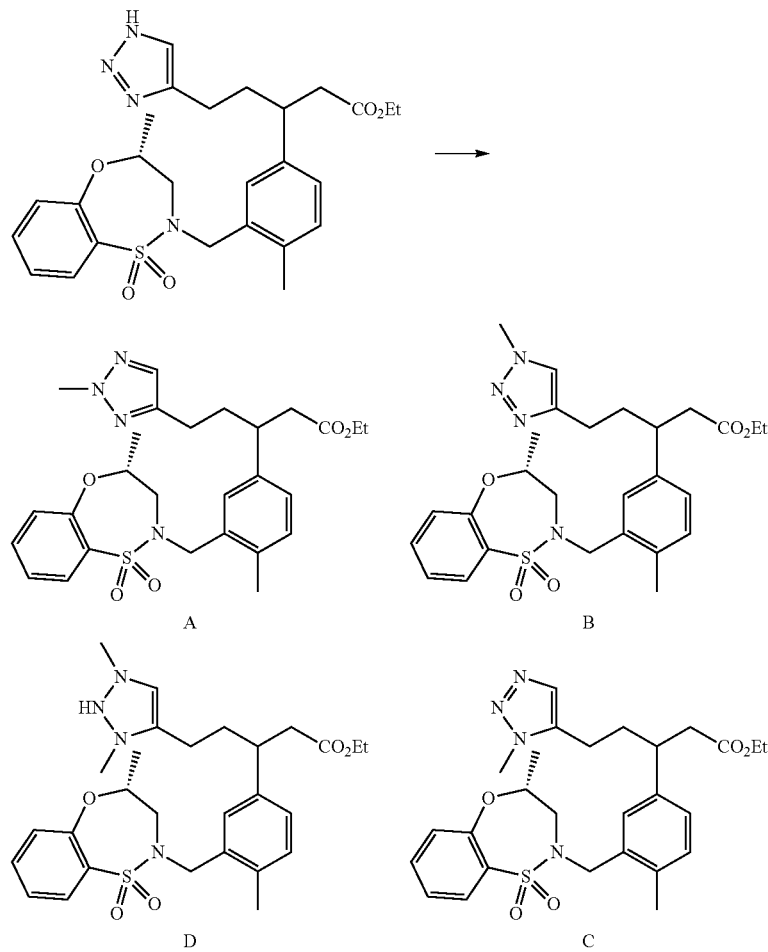

(((R)-4-methyl-1,1-dioxido-3,4-dihydro-2H-benzo[b][1,4,5]oxathiazepin-2-yl)methyl)phenyl)pentanoate (D) LC-MS m/z 541.2 (M+H)+, 0.94 (ret. time).

5-(2-Methyl-2H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid

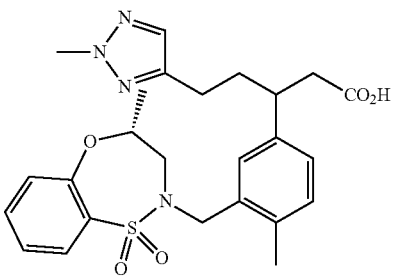 [SMILES: Cc1ccc(C(CCc2cnn(C)n2)CC(=O)O)cc1CN1C[C@@H](C)Oc2ccccc2S1(=O)=O]

LiOH (9.09 mg, 0.38 mmol) was added to a solution of ethyl 5-(2-methyl-2H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate (10 mg, 0.019 mmol) in THF (1 mL) and H₂O (0.2 mL). The result reaction mixture was stirred at 23° C. for 30 h. The reaction mixture was acidified with HCl (1 N, 0.38 mL), concentrated and purified by a Gilson HPLC (YMC C18 5 mm/12 nm 50×20 mm preparatory column), eluting at 20 mL/min with a linear gradient running from 10% CH₃CN/H₂O to 90% CH₃CN/H₂O over 10 min giving 5.9 mg (63%) of the title compound. LC-MS m/z 499.3 (M+H)+, 1.01 (ret. time)

Example 126

5-(1-Methyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid

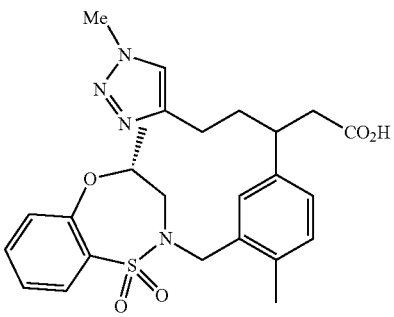 [SMILES: Cc1ccc(C(CCc2cn(C)nn2)CC(=O)O)cc1CN1C[C@@H](C)Oc2ccccc2S1(=O)=O]

Pent-4-ynal

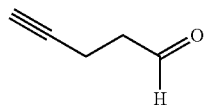

DMSO (5.58 g, 71.4 mmol) was added dropwise to a solution of oxalyl chloride (4.53 g, 35.7 mmol) in CH₂Cl₂ (80 mL) at −78° C. The mixture was stirred at −78° C. for 15 min, 3-pentyn-1-ol (2.0 g, 23.8 mmol) in CH₂Cl₂ (20 mL) was added dropwise to the reaction mixture and the mixture was stirred 15 min. Et₃N (10.84 g, 107.1 mmol) was added and the reaction mixture was stirred an additional 15 min, then the reaction mixture was warmed to 0° C. and quenched with water. The aqueous layer was extracted with DCM. The combined organic phase was washed with water, brine and dried over Na₂SO₄. The organic layer was concentrated, giving 0.6 g (31%) of the title compound. ¹H NMR (400 MHz, CHLOROFORM-d) δ ppm 2.54 (td, J=7.03, 2.51 Hz, 2H); 2.68-2.76 (m, 2H); 4.72 (s, 1H); 9.83 (s, 1H).

(E)-Ethyl hept-2-en-6-ynoate

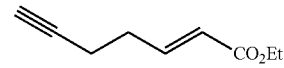

NaH (1.056 g, 26.4 mmol) was added in small portions to a solution of ethyl 2-(diethoxyphosphoryl)acetate (3.03 mL, 14.4 mmol) in DCM (15 mL). The mixture was stirred at 23° C. for 5 min, crude pent-4-ynal (~1 mL, 12 mmol) in DCM (10 mL) was added slowly, and the mixture was stirred at 23° C. for 30 min. NH₄Cl (saturated aqueous) was added and the solution was extracted with DCM. The crude product was then purified on a silica cartridge (12 g) with a Combiflash Companion, eluting at 30 mL/min with a gradient running from 0-60% EtOAc/hexane over 20 min. The product containing fractions were combined and the solvent removed under reduced pressure giving 1.32 g (72%) of the title compound. LC-MS m/z 153.0 (M+H)+, 0.82 (ret. time).

(E)-Ethyl 5-(1-methyl-1H-1,2,3-triazol-4-yl)pent-2-enoate

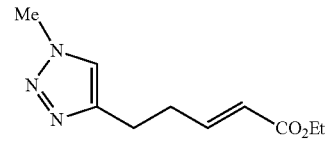

NaN₃ (0.077 g, 1.183 mmol), CuI (0.2 mg, 1.183 umol) and methyl iodide (0.074 mL, 1.18 mmol) were added to a solution of (E)-ethyl hept-2-en-6-ynoate (0.2 mL, 1.18 mmol) in water (5 mL), the mixture was stirred at 70° C. for 14 h. The mixture was concentrated and purified over Silica gel (12 g) with Combiflash Companion eluting at 30 mL/min with a gradient running from 0-20% MeOH/DCM over 16 min giving 80 mg (32%) of the title compound. LC-MS m/z 210.0 (M+H)+, 0.63 (ret. time).

Ethyl 3-(3-(hydroxymethyl)-4-methylphenyl)-5-(1-methyl-1H-1,2,3-triazol-4-yl)pentanoate

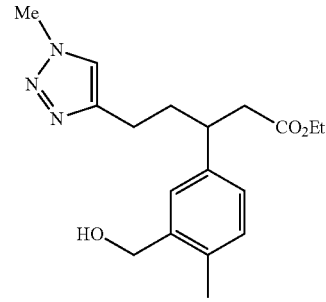 [SMILES: CCOC(=O)CC(CCc1cn(C)nn1)c1ccc(C)c(CO)c1]

(3-(Hydroxymethyl)-4-methylphenyl)boronic acid (0.095 g, 0.57 mmol), Et<sub>3</sub>N (0.08 mL, 0.57 mmol) and [RhCl(cod)]<sub>2</sub> (9.43 mg, 0.019 mmol) were added to a solution of (E)-ethyl 5-(1-methyl-1H-1,2,3-triazol-4-yl)pent-2-enoate (0.08 g, 0.38 mmol) in 1,4-Dioxane (1 mL) and Water (0.5 mL). The reaction was heated in a microwave at 140° C. (high absorption) for 4 h. The mixture was concentrated and purified over Silica gel (12 g) with Combiflash Companion eluting at 30 mL/min with a gradient running from 0-20% MeOH/DCM over 16 min giving 0.12 g (95%) of the title compound. LC-MS m/z 332.2 (M+H)$^+$, 0.77 (ret. time).

Ethyl 5-(1-methyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate

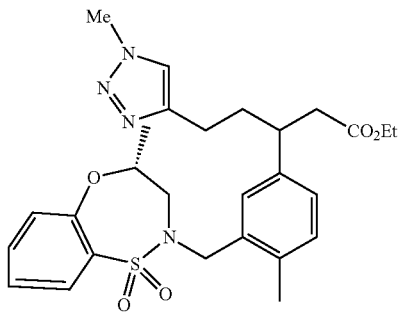 [SMILES: CCOC(=O)CC(CCc1cn(C)nn1)c1ccc(C)c(CN2C[C@@H](C)Oc3ccccc3S2(=O)=O)c1]

Tri-n-butylphosphine (0.089 mL, 0.36 mmol) was added slowly to a solution of ethyl 3-(3-(hydroxymethyl)-4-methylphenyl)-5-(1-methyl-1H-1,2,3-triazol-4-yl)pentanoate (60 mg, 0.18 mmol), (R)-4-methyl-3,4-dihydro-2H-benzo[b][1,4,5]oxathiazepine 1,1-dioxide (41 mg, 0.19 mmol), and ADDP (91 mg, 0.36 mmol) in THF (2 mL) at 0° C. The ice-bath was removed after 20 min and stirring continued at 23° C. for 2 h. The reaction mixture was concentrated and purified with Combiflash chromatograph over Silica gel (12 g) with Combiflash Companion eluting at 30 mL/min with a gradient running from 0-70% EtOAc/Hexane over 25 min giving 87 mg (91%) of the title compound. LC-MS m/z 527.3 (M+H)$^+$, 1.06 (ret. time).

5-(1-Methyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid

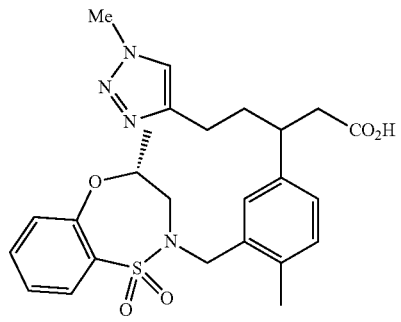 [SMILES: Cc1ccc(C(CCc2cn(C)nn2)CC(=O)O)cc1CN1C[C@@H](C)Oc2ccccc2S1(=O)=O]

LiOH (79 mg, 3.3 mmol) was added to a solution of ethyl 5-(1-methyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate (87 mg, 0.17 mmol) in THF (1.5 mL) and H<sub>2</sub>O (1.5 mL). The reaction mixture was stirred at 23° C. 16 h. The mixture was washed with EtOAc and the aqueous layer was acidified with 1N HCl and extracted with EtOAc. The acid phase extract was concentrated giving 44 mg (53%) of the title compound. LC-MS m/z 499.2 (M+H)$^+$, 0.91 (ret. time).

Example 127

5-(1-Ethyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid

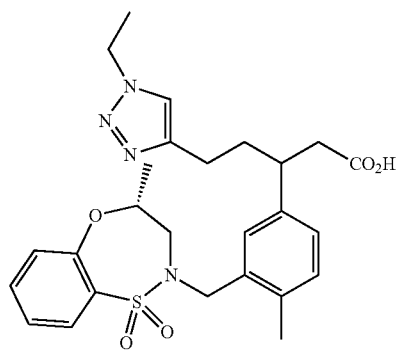 [SMILES: CCn1cc(CCC(CC(=O)O)c2ccc(C)c(CN3C[C@@H](C)Oc4ccccc4S3(=O)=O)c2)nn1]

(E)-Ethyl 5-(1-ethyl-1H-1,2,3-triazol-4-yl)pent-2-enoate

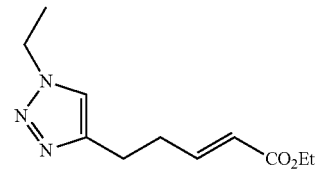 [SMILES: CCOC(=O)/C=C/CCc1cn(CC)nn1]

NaN<sub>3</sub> (0.085 g, 1.31 mmol), CuI (0.25 mg, 1.31 umol) and iodoethane (0.090 mL, 1.31 mmol) was added to a solution of (E)-ethyl hept-2-en-6-ynoate (0.2 g, 1.31 mmol) in water (5 mL), the mixture was stirred at 70° C. for 14 h. The mixture was concentrated and purified over Silica gel (12 g) with Combiflash Companion eluting at 30 mL/min with a gradient running from 0-30% MeOH/DCM over 20 min giving 100 mg (34%) of the title compound. LC-MS m/z 224.1 (M+H)$^+$, 0.65 (ret. time).

Ethyl 5-(1-ethyl-1H-1,2,3-triazol-4-yl)-3-(3-(hydroxymethyl)-4-methylphenyl)pentanoate

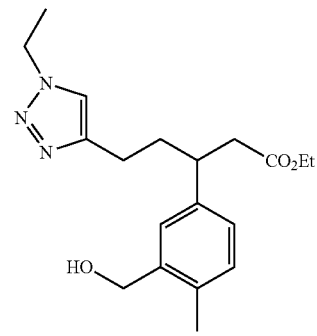 [SMILES: CCOC(=O)CC(CCc1cn(CC)nn1)c1ccc(C)c(CO)c1]

(3-(Hydroxymethyl)-4-methylphenyl)boronic acid (0.11 g, 0.67 mmol), Et₃N (0.094 mL, 0.67 mmol) and [RhCl(cod)]₂ (11 mg, 0.022 mmol) were added to a solution of (E)-ethyl 5-(1-ethyl-1H-1,2,3-triazol-4-yl)pent-2-enoate (0.1 g, 0.45 mmol) in 1,4-Dioxane (1 mL) and Water (0.5 mL). The reaction was heated in a microwave at 140° C. (high absorption) for 4 h. The mixture was concentrated and purified over Silica gel (12 g) with Combiflash Companion eluting at 30 mL/min with a gradient running from 0-10% MeOH/DCM over 20 min giving 64 mg (41%) of the title compound and 50 mg recovered (E)-ethyl 5-(1-ethyl-1H-1,2,3-triazol-4-yl)pent-2-enoate. LC-MS m/z 346.2 (M+H)⁺, 0.81 (ret. time).

Ethyl 5-(1-ethyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate

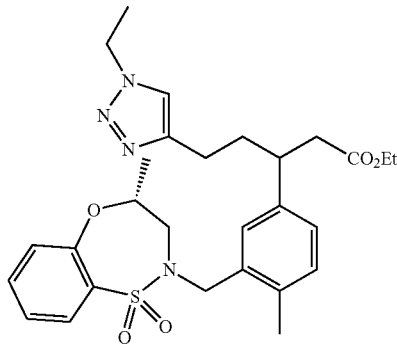 [SMILES: CCOC(=O)CC(CCc1cn(CC)nn1)c1ccc(C)c(CN2C[C@@H](C)Oc3ccccc3S2(=O)=O)c1]

Tri-n-butylphosphine (0.091 mL, 0.37 mmol) was added slowly to a solution of ethyl 5-(1-ethyl-1H-1,2,3-triazol-4-yl)-3-(3-(hydroxymethyl)-4-methylphenyl)pentanoate (64 mg, 0.19 mmol), (R)-4-methyl-3,4-dihydro-2H-benzo[b][1,4,5]oxathiazepine 1,1-dioxide (41 mg, 0.2 mmol) and ADDP (93 mg, 0.37 mmol) in THF (2 mL) at 0° C. The ice-bath was removed after 20 min and stirring continued at 23° C. for 2 h. The reaction mixture was concentrated and purified over Silica gel (12 g) with Combiflash Companion eluting at 30 mL/min with a gradient running from 0-100% EtOAc/Hexane over 25 min giving 100 mg (100%) of the title compound. LC-MS m/z 541.2 (M+H)⁺, 1.09 (ret. time).

5-(1-Ethyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid

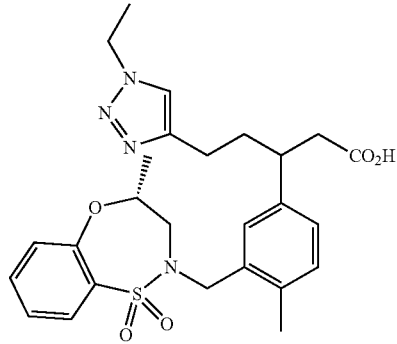 [SMILES: CCn1cc(CCC(CC(=O)O)c2ccc(C)c(CN3C[C@@H](C)Oc4ccccc4S3(=O)=O)c2)nn1]

LiOH (79 mg, 3.3 mmol) was added to a solution of ethyl 5-(1-methyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate (105 mg, 0.2 mmol) in THF (2 mL) and H₂O (2 mL). The reaction mixture was stirred at 23° C. overnight. The mixture was washed with EtOAc and the aqueous layer was acidified with 1N HCl, extracted with EtOAc. After concentration the crude product was dissolved in DMSO (1 mL), filtered through a 0.45 mm acrodisc, and purified on a Gilson HPLC (YMC C18 5 mm/12 nm 50×20 mm preparatory column), eluting at 20 mL/min with a linear gradient running from 10% CH₃CN/H₂O to 90% CH₃CN/H₂O over 10 min giving 92 mg (92%) of the title compound. LC-MS m/z 513.4 (M+H)⁺, 0.97 (ret. time).

Example 128

3-(7-Methoxy-1-methyl-1H-benzo[d][1,2,3]triazol-5-yl)-3-(4-methyl-3-(((R)-4-methyl-1,1-dioxido-3,4-dihydro-2H-pyrido[4,3-b][1,4,5]oxathiazepin-2-yl)methyl)phenyl)propanoic acid

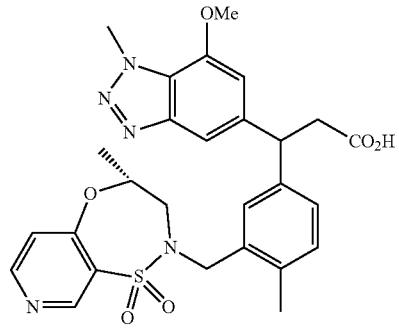 [SMILES: COc1cc(C(CC(=O)O)c2ccc(C)c(CN3C[C@@H](C)Oc4ccncc4S3(=O)=O)c2)cc2nnn(C)c12]

4-Chloropyridine-3-sulfonyl chloride

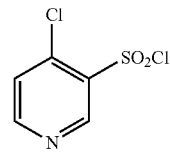 [SMILES: O=S(=O)(Cl)c1cnccc1Cl]

Pentachlorophosphorane (7.29 g, 35 mmol), phosphoryl trichloride (1.86 mL, 20 mmol) were added to 4-hydroxypyridine-3-sulfonic acid (1.75 g, 10 mmol). The mixture was stirred at 125° C. for 1 h. The solution was allowed to cool to 23° C. and then concentrated to remove excess POCl₃, diluted with Et₂O and poured onto ice. The residue was stirred for 5 min and then was neutralized with solid NaHCO₃, the mixture was extracted with EtOAc and combined extracts were dried (Na₂SO₄) and concentrated giving 2.02 g (95%) of the title compound. LC-MS m/z 211.8 (M+H)⁺, 0.74 (ret. time).

3-(1-Benzyl-1H-1,2,3-triazol-4-yl)propanal

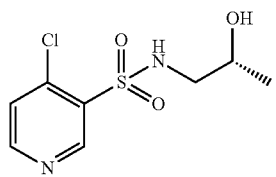

K$_2$CO$_3$ (0.36 g, 2.59 mmol) and 2-chloropyridine-3-sulfonyl chloride (0.5 g, 2.36 mmol) were added slowly to a solution of (R)-1-aminopropan-2-ol (0.2 g, 2.59 mmol) in THF (5 mL) and Water (2 mL). The reaction mixture was stirred at 23° C. for 1 h. The reaction mixture was diluted with H$_2$O, extracted with EtOAc. The combined extracts were washed with brine, dried over MgSO$_4$, filtered and concentrated giving 0.55 g (93%) of the title compound. LC-MS m/z 251.0 (M+H)$^+$, 0.45 (ret. time).

(R)-4-Methyl-3,4-dihydro-2H-pyrido[4,3-b][1,4,5]oxathiazepine 1,1-dioxide

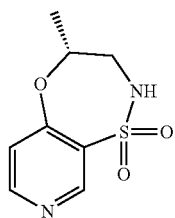

KOt-Bu (0.74 g, 6.57 mmol) was added in small portions to a solution of (R)-4-chloro-N-(2-hydroxypropyl)pyridine-3-sulfonamide (0.55 g, 2.19 mmol) in DMSO (10 mL) then heated at 80° C. for 2 h. The reaction mixture was diluted with H$_2$O, acidified with HCl (1 N) to pH ~7 and extracted with EtOAc. The combined extracts were washed with brine, dried over MgSO$_4$, filtered, concentrated and purified over Silica gel (12 g) with Combiflash Companion eluting at 30 mL/min with a gradient running from 0-100% EtOAc/Hexane over 30 min. The product containing fractions were combined and the solvent removed under reduced pressure giving 0.19 g (41%) of the title compound. LC-MS m/z 215.0 (M+H)$^+$, 0.29 (ret. time).

Ethyl 3-(3-(hydroxymethyl)-4-methylphenyl)-3-(7-methoxy-1-methyl-1H-benzo[d][1,2,3]triazol-5-yl)propanoate

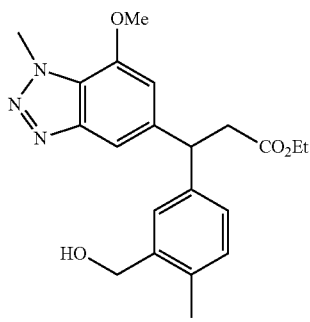 [SMILES: CCOC(=O)CC(c1ccc(C)c(CO)c1)c1cc(OC)c2c(c1)nnn2C]

(3-(Hydroxymethyl)-4-methylphenyl)boronic acid (0.95 g, 5.74 mmol), Et$_3$N (0.8 mL, 5.74 mmol) and [RhCl(cod)]$_2$ (0.094 g, 0.19 mmol) were added to a solution of (E)-ethyl 3-(7-methoxy-1-methyl-1H-benzo[d][1,2,3]triazol-5-yl)acrylate (1.0 g, 3.83 mmol) in 1,4-Dioxane (20 mL) and Water (10 mL). The reaction was stirred at 95° C. for 1 h. The reaction mixture was evaporated to get rid of most 1,4-dioxane, diluted with EtOAc and washed with water. The combined extracts were washed with brine, dried over MgSO$_4$, filtered, concentrated and purified over Silica gel (40 g) with Combiflash Companion eluting at 40 mL/min with a gradient running from 0-100% EtOAc/Hexane over 35 min giving 1.07 g (73%) of the title compound. LC-MS m/z 384.2 (M+H)$^+$, 0.89 (ret. time).

Ethyl 3-(7-methoxy-1-methyl-1H-benzo[d][1,2,3]triazol-5-yl)-3-(4-methyl-3-(((R)-4-methyl-1,1-dioxido-3,4-dihydro-2H-pyrido[4,3-b][1,4,5]oxathiazepin-2-yl)methyl)phenyl)propanoate

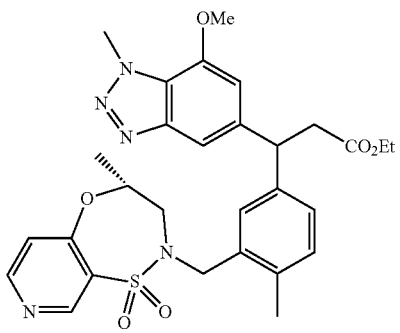 [SMILES: CCOC(=O)CC(c1ccc(C)c(CN2C[C@@H](C)Oc3ccncc3S2(=O)=O)c1)c1cc(OC)c2c(c1)nnn2C]

Tri-n-butylphosphine (0.13 mL, 0.52 mmol) was added to a solution of ethyl 3-(3-(hydroxymethyl)-4-methylphenyl)-3-(7-methoxy-1-methyl-1H-benzo[d][1,2,3]triazol-5-yl)propanoate (100 mg, 0.26 mmol), (R)-4-methyl-3,4-dihydro-2H-pyrido[4,3-b][1,4,5]oxathiazepine 1,1-dioxide (58.7 mg, 0.27 mmol) and ADDP (132 mg, 0.52 mmol) in THF (3 mL) at 0° C. The ice-bath was removed after 20 min and stirring continued at 23° C. for 2 h. The reaction mixture was filtered, concentrated giving the title compound. The crude product was used for next step without any further purification. LC-MS m/z 580.4 (M+H)$^+$, 1.08 (ret. time).

3-(7-Methoxy-1-methyl-1H-benzo[d][1,2,3]triazol-5-yl)-3-(4-methyl-3-(((R)-4-methyl-1,1-dioxido-3,4-dihydro-2H-pyrido[4,3-b][1,4,5]oxathiazepin-2-yl)methyl)phenyl)propanoic acid

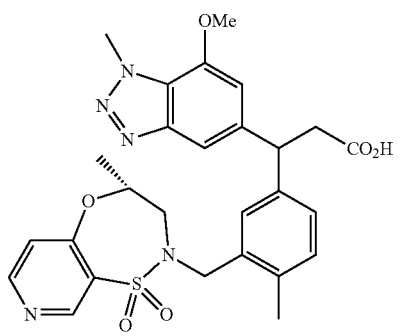 [SMILES: COc1cc(C(CC(=O)O)c2ccc(C)c(CN3C[C@@H](C)Oc4ccncc4S3(=O)=O)c2)cc2nnn(C)c12]

LiOH (125 mg, 5.22 mmol) was added to a solution of ethyl 3-(7-methoxy-1-methyl-1H-benzo[d][1,2,3]triazol-5-yl)-3-(4-methyl-3-(((R)-4-methyl-1,1-dioxido-3,4-dihydro-2H-pyrido[4,3-b][1,4,5]oxathiazepin-2-yl)methyl)phenyl)propanoate (151 mg, 0.26 mmol) in THF (12.5 mL) and H$_2$O (2.5 mL). The reaction mixture was stirred at 23° C. for 30 h. The mixture was washed with EtOAc and the aqueous layer was acidified with 1N HCl, extracted with EtOAc. After concentration the crude product was dissolved in DMSO (1 mL), filtered through a 0.45 mm acrodisc, and purified on a neutral Gilson HPLC (YMC C18 5 mm/12 nm 50×20 mm preparatory column), eluting at 20 mL/min with a linear gradient running from 10% CH$_3$CN/H$_2$O to 90% CH$_3$CN/H$_2$O over 10 min giving 36.8 mg (26%, 2 steps) of the title compound. LC-MS m/z 552.3 (M+H)$^+$, 0.92 (ret. time).

Example 129

3-(1,4-Dimethyl-1H-benzo[d][1,2,3]triazol-5-yl)-3-(4-methyl-3-(((R)-4-methyl-1,1-dioxido-3,4-dihydro-2H-pyrido[4,3-b][1,4,5]oxathiazepin-2-yl)methyl)phenyl)propanoic acid

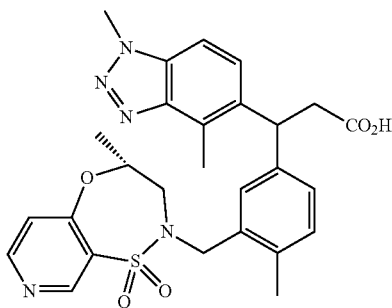 [SMILES: Cc1ccc(C(CC(=O)O)c2ccc3c(nnn3C)c2C)cc1CN1C[C@@H](C)Oc2ccncc2S1(=O)=O]

Ethyl 3-(1,4-dimethyl-1H-benzo[d][1,2,3]triazol-5-yl)-3-(3-(hydroxymethyl)-4-methylphenyl)propanoate

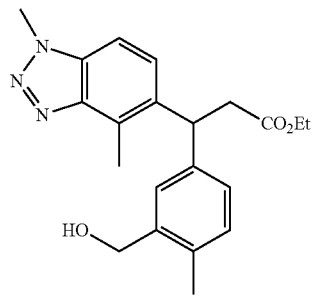 [SMILES: CCOC(=O)CC(c1ccc(C)c(CO)c1)c1ccc2c(nnn2C)c1C]

3-(Hydroxymethyl)-4-methylphenyl)boronic acid (0.51 g, 3.06 mmol), Et$_3$N (0.43 mL, 3.06 mmol) and [RhCl(cod)]$_2$ (0.05 g, 0.1 mmol) were added to (E)-ethyl 3-(1,4-dimethyl-1H-benzo[d][1,2,3]triazol-5-yl)acrylate (0.50 g, 2.04 mmol) in 1,4-Dioxane (10 mL) and Water (5 mL). The resulting reaction mixture was stirred at 95° C. for 1 h. The reaction mixture was evaporated to get rid of most 1,4-dioxane, diluted with EtOAc and washed with water. The combined extracts were washed with brine, dried over MgSO$_4$, filtered, concentrated and purified over Silica gel (12 g) with Combiflash Companion eluting at 30 mL/min with a gradient running from 0-100% EtOAc/Hexane over 25 min giving 550 mg (73%) of the title compound. LC-MS m/z 368.2 (M+H)$^+$, 0.87 (ret. time).

Ethyl 3-(1,4-dimethyl-1H-benzo[d][1,2,3]triazol-5-yl)-3-(4-methyl-3-(((R)-4-methyl-1,1-dioxido-3,4-dihydro-2H-pyrido[4,3-b][1,4,5]oxathiazepin-2-yl)methyl)phenyl)propanoate

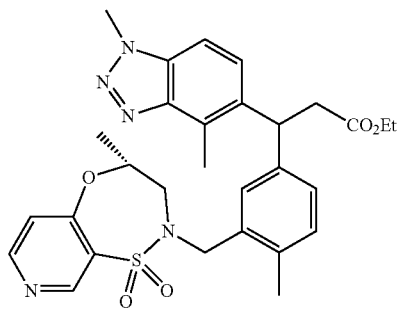 [SMILES: CCOC(=O)CC(c1ccc(C)c(CN2C[C@@H](C)Oc3ccncc3S2(=O)=O)c1)c1ccc2c(nnn2C)c1C]

Tri-n-butylphosphine (0.13 mL, 0.54 mmol) was added to a solution of ethyl 3-(1,4-dimethyl-1H-benzo[d][1,2,3]triazol-5-yl)-3-(3-(hydroxymethyl)-4-methylphenyl)propanoate (100 mg, 0.27 mmol), (R)-4-methyl-3,4-dihydro-2H-pyrido[4,3-b][1,4,5]oxathiazepine 1,1-dioxide (61.2 mg, 0.29 mmol) and ADDP (137 mg, 0.54 mmol) in THF (3 mL) at 0° C. The ice-bath was removed after 20 min and stirring continued at 23° C. for 2 h. The reaction mixture was filtered, concentrated giving the title compound. The crude product was used for next step without any further purification. LC-MS m/z 564.4 (M+H)$^+$, 1.06 (ret. time).

3-(1,4-Dimethyl-1H-benzo[d][1,2,3]triazol-5-yl)-3-(4-methyl-3-(((R)-4-methyl-1,1-dioxido-3,4-dihydro-2H-pyrido[4,3-b][1,4,5]oxathiazepin-2-yl)methyl)phenyl)propanoic acid

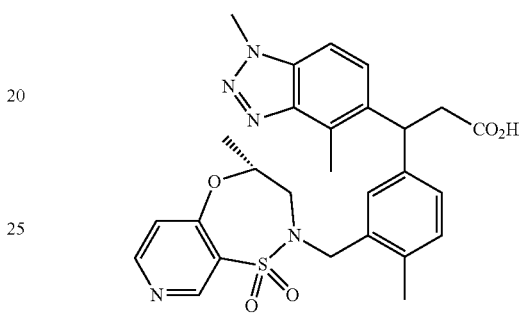

LiOH (8.47 mg, 0.35 mmol) was added to a solution of ethyl 3-(1,4-dimethyl-1H-benzo[d][1,2,3]triazol-5-yl)-3-(4-methyl-3-(((R)-4-methyl-1,1-dioxido-3,4-dihydro-2H-pyrido[4,3-b][1,4,5]oxathiazepin-2-yl)methyl)phenyl)propanoate (153 mg, 0.27 mmol) in THF (1 mL) and H$_2$O (0.2 mL). The reaction mixture was stirred at 23° C. for 30 h. The mixture was washed with EtOAc and the aqueous layer was acidified with 1N HCl, extracted with EtOAc. After concentration of the acid phase extract the crude product was dissolved in DMSO (1 mL), filtered through a 0.45 microm acrodisc, and purified on a Gilson HPLC (YMC C18 5 mm/12 nm 50×20 mm preparatory column), eluting at 20 mL/min with a linear gradient running from 10% CH$_3$CN/H$_2$O to 90% CH$_3$CN/H$_2$O over 10 min giving 32 mg (22%, 2 steps) of the title compound. LC-MS m/z 536.1 (M+H)$^+$, 0.89 (ret. time).

Example 130

3-(4-methyl-3-(((R)-4-methyl-1,1-dioxido-3,4-dihydro-2H-benzo[b][1,4,5]oxathiazepin-2-yl)methyl)phenyl)-3-(1-methyl-4-(trifluoromethyl)-1H-benzo[d][1,2,3]triazol-5-yl)propanoic acid

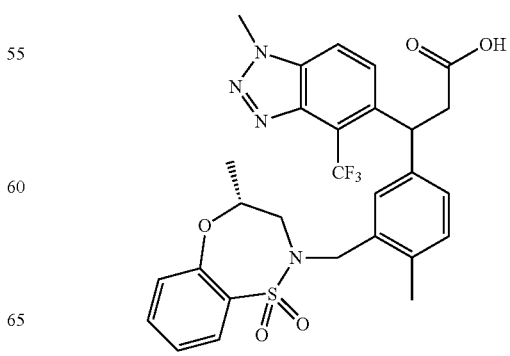

271

N-(3-(trifluoromethyl)phenyl)acetamide

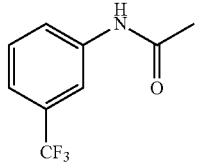

A solution of 3-(trifluoromethyl)aniline (20 g, 124 mmol) in acetic anhydride (70 mL, 741 mmol) was stirred at RT for 16 h. Water was added and extracted with EtOAc. The organic layer was washed with water and brine, dried and concentrated to give 20 g (79%). of title compound.

N-(2-nitro-3-(trifluoromethyl)phenyl)acetamide

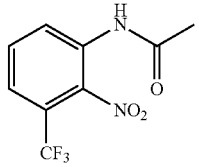 [SMILES: CC(=O)Nc1cccc(C(F)(F)F)c1[N+](=O)[O-]]

N-(3-(trifluoromethyl)phenyl)acetamide (5.0 g, 24.61 mmol) was added in small portions to the cold fuming nitric acid (10 mL, 224 mmol) taken in a dry round bottom flask at −30° C. The reaction mixture was stirred for another 10 min at the same temperature then was quenched with water (50 mL) and extracted with EtOAc. The combined organic layers were dried over $MgSO_4$ and concentrated. The residue was purified by silica gel chromatography (Hexane:EtOAc: 4:1) to give 1.0 g (6.37%) of title compound.

N-Methyl-N-(2-nitro-3-(trifluoromethyl)phenyl) acetamide

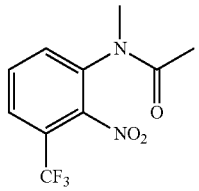 [SMILES: CC(=O)N(C)c1cccc(C(F)(F)F)c1[N+](=O)[O-]]

NaH (0.484 g, 20.15 mmol) was added to a solution of N-(2-nitro-3-(trifluoromethyl)phenyl)acetamide (5.0 g, 20.15 mmol) in DMF (3 mL), NaH (0.484 g, 20.15 mmol). After 30 min, MeI (1.254 mL, 20.15 mmol) was added. The reaction mixture was stirred at RT for 1 h. A solution of aqueous $NaHCO_3$ was added, and then it was extracted with EtOAc. The organic layer was washed with water and brine, dried over $MgSO_4$, and was filtered. The filtrate was concentrated under the reduced pressure. The crude product was purified by silica gel chromatography (hexane:EtOAc=2:1) to give 4.6 g (87%) of title compound. LC-MS m/z 263.0 $(M+H)^+$, 1.65 (ret. time).

272

N-Methyl-2-nitro-3-(trifluoromethyl)aniline

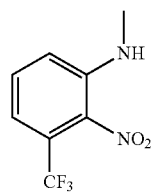

To a solution of N-methyl-N-(2-nitro-3-(trifluoromethyl) phenyl)acetamide (100 mg, 0.381 mmol) in EtOH (5 mL), solution of NaOH (100 mg, 2.500 mmol) in 2 mL of water was added. Then the reaction mixture was stirred at reflux temperature for 1 h. Then the reaction mixture was cooled to RT and the solvent was evaporated under reduced pressure. The crude product was diluted with water (50 mL), extracted with EtOAc (2×). The combined organic layers were dried over $MgSO_4$ and concentrated to give 40 mg, (47.6%) of title compound.

4-Bromo-N-methyl-2-nitro-3-(trifluoromethyl)aniline

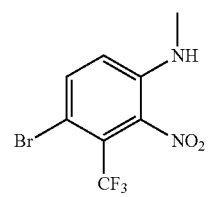 [SMILES: CNc1ccc(Br)c(C(F)(F)F)c1[N+](=O)[O-]]

To a solution of N-methyl-2-nitro-3-(trifluoromethyl)aniline (3.9 g, 17.72 mmol) in DMF (2 mL), 1-bromopyrrolidine-2,5-dione (3.15 g, 17.72 mmol) was added. The reaction mixture was stirred at RT for 16 h. Water was added and extracted with EtOAc. The organic layer was washed with water and brine, dried and concentrated to give 4.2 g, (79%) of crude title compound. LC-MS m/z 299.0 $(M+H)^+$, 1.22 (ret. time).

4-Bromo-N1-methyl-3-(trifluoromethyl)benzene-1,2-diamine

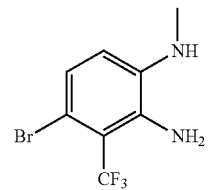

To a solution of 4-bromo-N-methyl-2-nitro-3-(trifluoromethyl)aniline (14.4 g, 48.2 mmol) in AcOH (5 mL) at 0° C., zinc (3.15 g, 48.2 mmol) was added. Then the reaction mixture was stirred at 50° C. for 2 h. The reaction mixture was filtered. The filtrate was concentrated under the reduced pressure to give 8.6 g, (66.4%) of crude title compound. LC-MS m/z 271.0 $(M+H)^+$, 1.77 (ret. time).

5-Bromo-1-methyl-4-(trifluoromethyl)-1H-benzo[d][1,2,3]triazole

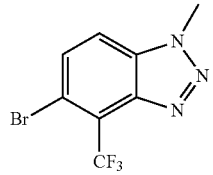

To 4-bromo-N1-methyl-3-(trifluoromethyl)benzene-1,2-diamine (8.6 g, 32.0 mmol) in $H_2SO_4$ (350 mL, 1400 mmol) at 0° C., $NaNO_2$ (2.205 g, 32.0 mmol) in water (20 mL) was added dropwise and the resultant reaction mixture was stirred for 2 h at 0° C. The mixture was alkalized with concentrated ammonia, and then extracted with $CH_2Cl_2$. The separated organic layer was washed with water, dried with MgSO4, filtered and the solvent was evaporated under reduced pressure. The crude product was purified by silica gel chromatography (hexane:EtOAc=4:1) to give 4.2 g (42.7%) of the title compound. LC-MS m/z 281 $(M+H)^+$, 1.71 (ret. time).

(E)-ethyl 3-(1-methyl-4-(trifluoromethyl)-1H-benzo[d][1,2,3]triazol-5-yl)acrylate

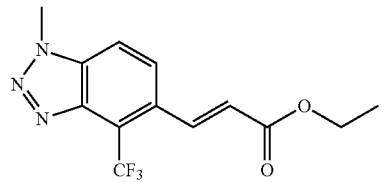 [SMILES: CCOC(=O)/C=C/c1ccc2c(nnn2C)c1C(F)(F)F]

To a solution of 5-bromo-1-methyl-4-(trifluoromethyl)-1H-benzo[d][1,2,3]triazole (1.00 g, 3.57 mmol) in DMF (10 mL) in a 20 mL microwave reaction vessel was added ethyl acrylate (1.425 mL, 13.06 mmol), tri-o-tolylphosphine (0.199 g, 0.654 mmol), and DIPEA (1.524 mL, 8.73 mmol). The solution was flushed with nitrogen for 3 min after which time $Pd(OAc)_2$ (0.073 g, 0.325 mmol) was added. The reaction was heated in a microwave reactor at 150° C. for 30 min. The reaction was then filtered through Celite and washed with EtOAc. The organics were washed with water (3×). The aqueous layer was back extracted with EtOAc and the combined organics were washed with water, brine and dried with $MgSO_4$. The solvent was concentrated and the residue was purified by silica gel chromatography using an Isco Combiflash Rf and eluting, 0 to 40% EtOAc/Hexane and then 5% MeOH/DCM to give the title compound (0.680 g, 52%) LC-MS m/z 300 $(M+H)^+$, 0.95 min (ret time).

Ethyl 3-(3-(hydroxymethyl)-4-methylphenyl)-3-(1-methyl-4-(trifluoromethyl)-1H-benzo[d][1,2,3]triazol-5-yl)propanoate

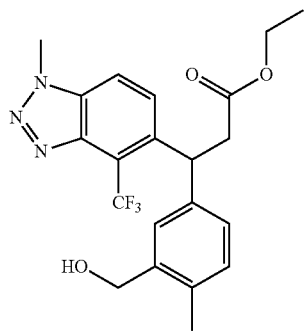 [SMILES: CCOC(=O)CC(c1ccc(C)c(CO)c1)c1ccc2c(nnn2C)c1C(F)(F)F]

To a solution of (E)-ethyl 3-(1-methyl-4-(trifluoromethyl)-1H-benzo[d][1,2,3]triazol-5-yl)acrylate (0.680 g, 1.886 mmol) and (3-(hydroxymethyl)-4-methylphenyl)boronic acid (0.509 g, 3.07 mmol) in 1,4-dioxane (25 mL) and water (15 mL) was added $Et_3N$ (0.394 mL, 2.83 mmol) and $[RhCl(cod)]_2$ (0.052 g, 0.105 mmol). The reaction was heated at 95° C. for 1.5 h. Afterwards, the reaction was cooled and most of the solvent removed. The residue was diluted with water and extracted EtOAc (3×), combined organics were washed with water, brine, and dried with $MgSO_4$. The solvent was concentrated and the residue was purified by silica gel chromatography using an Isco Combiflash Rf and eluting, 0 to 40% EtOAc/DCM to give the title compound (0.649 g, 80%) LC-MS m/z 422 $(M+H)^+$, 0.95 min (ret time).

Ethyl 3-(4-methyl-3-(((R)-4-methyl-1,1-dioxido-3,4-dihydro-2H-benzo[b][1,4,5]oxathiazepin-2-yl)methyl)phenyl)-3-(1-methyl-4-(trifluoromethyl)-1H-benzo[d][1,2,3]triazol-5-yl)propanoate

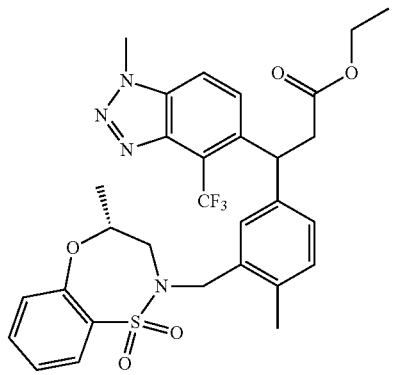 [SMILES: CCOC(=O)CC(c1ccc(C)c(CN2C[C@@H](C)Oc3ccccc3S2(=O)=O)c1)c1ccc2c(nnn2C)c1C(F)(F)F]

To a solution of ethyl 3-(3-(hydroxymethyl)-4-methylphenyl)-3-(1-methyl-4-(trifluoromethyl)-1H-benzo[d][1,2,3]triazol-5-yl)propanoate (0.100 g, 0.237 mmol) and (R)-4-methyl-3,4-dihydro-2H-benzo[b][1,4,5]oxathiazepine 1,1-dioxide (0.061 g, 0.285 mmol) in dry THF (10 mL), at 0° C., was added tributylphosphine (0.119 mL, 0.475 mmol). Reaction stirred for 5 min and then ADDP (0.120 g, 0.475 mmol) was added and stirred at 0° C. for 10 min and then at RT for 19 h. The solvent was concentrated and the residue was purified by silica gel chromatography using an Isco Combiflash Rf and eluting, 0 to 50% EtOAc/Hexane to give the title compound (0.132, 90%) LC-MS m/z 422 $(M+H)^+$, 1.22 min (ret time).

3-(4-methyl-3-(((R)-4-methyl-1,1-dioxido-3,4-dihydro-2H-benzo[b][1,4,5]oxathiazepin-2-yl)methyl)phenyl)-3-(1-methyl-4-(trifluoromethyl)-1H-benzo[d][1,2,3]triazol-5-yl)propanoic acid

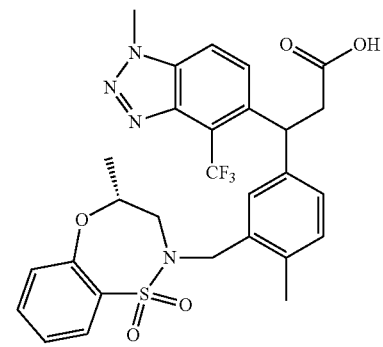 [SMILES: Cc1ccc(C(CC(=O)O)c2ccc3c(nnn3C)c2C(F)(F)F)cc1CN1C[C@@H](C)Oc2ccccc2S1(=O)=O]

To a solution of ethyl 3-(4-methyl-3-(((R)-4-methyl-1,1-dioxido-3,4-dihydro-2H-benzo[b][1,4,5]oxathiazepin-2-yl)methyl)phenyl)-3-(1-methyl-4-(trifluoromethyl)-1H-benzo[d][1,2,3]triazol-5-yl)propanoate (0.132 g, 0.214 mmol) in THF (1 mL), MeOH (1.000 mL), and water (1.000 mL) was added LiOH (0.015 g, 0.642 mmol) and stirred at RT for 18 h. The solvent was concentrated and the residue was diluted with EtOAc and acidified with 1N HCl. The aqueous layer was extracted with EtOAc (3×). The combined organics were washed with water (2×), brine, dried with MgSO₄, and the solvent was concentrated. The resulting residue was purified by reverse-phase HPLC (Atlantics T3 19×150 mm 5 u preparatory column), eluting at 18 mL/min with a linear gradient running from 40% to 65% with CH₃CN and water over 10 min to give the title compound (81 mg, 64%), LC-MS m/z 589 (M+H)⁺, 1.03 min (ret time).

Example 131

3-(7-methoxy-1-methyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl)propanoic acid

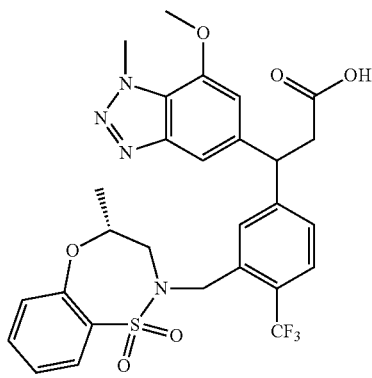 [SMILES: COc1cc(C(CC(=O)O)c2ccc(C(F)(F)F)c(CN3C[C@@H](C)Oc4ccccc4S3(=O)=O)c2)cc2nnn(C)c12]

(5-bromo-2-(trifluoromethyl)phenyl)methanol

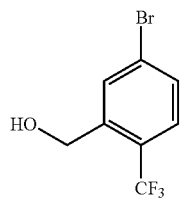 [SMILES: OCc1cc(Br)ccc1C(F)(F)F]

To a solution of 5-bromo-2-(trifluoromethyl)benzoic acid (2.50 g, 9.29 mmol) in THF (25 mL) in ice bath was added 1.7M BH₃.THF (24.78 mL, 37.2 mmol). The reaction was stirred at RT for 18 h. The reaction was then cooled in ice bath and additional 1.0M BH₃.THF (27.9 mL, 27.9 mmol) and stirred for 9 h. Afterwards, the reaction was quenched with MeOH and all solvents were concentrated. The residue was dissolved in a mixture of EtOAc/sat NaHCO3 and extracted water with EtOAc (3×), brine, dried with MgSO₄. The solvent was concentrated and the residue was purified by silica gel chromatography using an Isco Combiflash Rf and eluting, 0 to 3% EtOAc/DCM to give the title compound (1.20 g, 81%) LC-MS m/z 254 (M+H)⁺, 0.99 min (ret time).

(5-(4,4,5,5-tetramethyl-1,3,2-dioxaborolan-2-yl)-2-(trifluoromethyl)phenyl)methanol

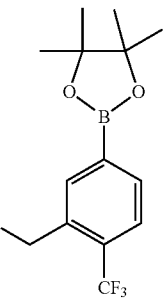

This reaction was divided into 3 equal reactions in 3 microwave reaction vessels. To a solution of (5-bromo-2-(trifluoromethyl)phenyl)methanol (1.918 g, 7.52 mmol) in 1,4-Dioxane (34.2 mL) in a 20 mL microwave reaction vessel was added bis(pinacolato)diboron (2.292 g, 9.02 mmol), and potassium acetate (2.214 g, 22.56 mmol). The solution was degassed with nitrogen for 5 min and then (PPh₃)₂PdCl₂ (0.317 g, 0.451 mmol) was added. The reaction was heated in a microwave reactor at 150° C. for 20 min. Combined samples were filtered through column of Celite and washed with EtOAc. All solvents were concentrated. The residue was dissolved in EtOAc, washed with water (4×), brine, and dried with MgSO₄. The solvent was concentrated and the residue was purified by silica gel chromatography using an Isco Combiflash Rf and eluting, 0 to 20% EtOAc/DCM. Product was re-purified using 0 to 20% Acetone/Hexane to give the title compound (0.722 g, 31%) Product was unstable to LCMS conditions so structure was confirmed by NMR. ¹H NMR (400 MHz CDCl3) δ ppm 1.39 (s, 12H) 1.82 (t, J=6.40 Hz, 1H) 4.91 (d, J=6.02 Hz, 2H) 7.67 (d, J=7.53 Hz, 1H) 7.85 (d, J=7.78 Hz, 1H) 8.14 (s, 1H).

Ethyl 3-(3-(hydroxymethyl)-4-(trifluoromethyl)phenyl)-3-(7-methoxy-1-methyl-1H-benzo[d][1,2,3]triazol-5-yl)propanoate

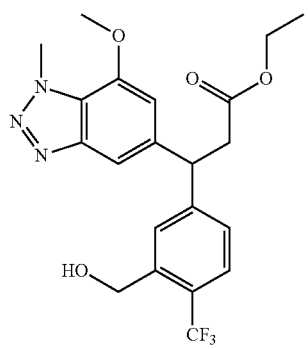 [SMILES: CCOC(=O)CC(c1ccc(C(F)(F)F)c(CO)c1)c1cc(OC)c2c(c1)nnn2C]

To a solution of (E)-ethyl 3-(7-methoxy-1-methyl-1H-benzo[d][1,2,3]triazol-5-yl)acrylate (0.200 g, 0.765 mmol) and (5-(4,4,5,5-tetramethyl-1,3,2-dioxaborolan-2-yl)-2-(trifluoromethyl)phenyl)methanol (0.168 g, 0.556 mmol) in 1,4-dioxane (10 mL) and water (6.25 mL) was added Et₃N (0.160 mL, 1.148 mmol) and [RhCl(cod)]₂ (0.019 g, 0.038 mmol). The reaction was heated at 95° C. for 2 h. Additional (5-(4,4,5,5-tetramethyl-1,3,2-dioxaborolan-2-yl)-2-(trifluoromethyl)phenyl)methanol (0.062 g, 0.205 mmol) was added at this point and heated for an additional 2 h. The solvent was concentrated and the residue was diluted with water and extracted with EtOAc (3×). The combined organics were washed with water, brine, and dried with MgSO₄. The solvent was concentrated and the residue was purified by silica gel chromatography using an Isco Combiflash Rf and eluting, 0 to 40% EtOAc/DCM to give the title compound (1.23 g, 28%) LC-MS m/z 438 (M+H)⁺, 1.02 min (ret time).

Ethyl 3-(7-methoxy-1-methyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl)propanoate

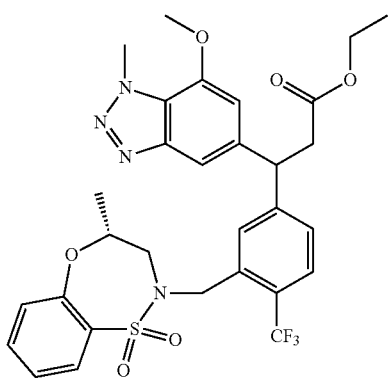 [SMILES: CCOC(=O)CC(c1ccc(C(F)(F)F)c(CN2C[C@@H](C)Oc3ccccc3S2(=O)=O)c1)c1cc(OC)c2c(c1)nnn2C]

To a solution of ethyl 3-(3-(hydroxymethyl)-4-(trifluoromethyl)phenyl)-3-(7-methoxy-1-methyl-1H-benzo[d][1,2,3]triazol-5-yl)propanoate (0.123 g, 0.217 mmol) and (R)-4-methyl-3,4-dihydro-2H-benzo[b][1,4,5]oxathiazepine 1,1-dioxide (0.055 g, 0.260 mmol) in dry THF (10 mL), at 0° C., was added tributylphosphine (0.108 mL, 0.433 mmol). The reaction was stirred for 5 min and then ADDP (0.109 g, 0.433 mmol) was added and stirred at 0° C. for 10 min and then at RT for 2 h. It was then heated to 50° C. for 2 h. Afterwards, the reaction was cooled to 0° C. and an additional portion of tributylphosphine (0.108 mL, 0.433 mmol) was added and stirred RT for 18 h. The reaction was cooled to 0° C. and an additional portion of tributylphosphine (0.054 mL, 0.217 mmol) was added and stirred for 10 min. (R)-4-methyl-3,4-dihydro-2H-benzo[b][1,4,5]oxathiazepine 1,1-dioxide (9.23 mg, 0.043 mmol) and ADDP (0.055 g, 0.217 mmol) were added and stirred for 5 h. The solvent was concentrated and the residue was purified by silica gel chromatography using an Isco Combiflash Rf and eluting, 0 to 50% EtOAc/Hexane and repurified eluting, 0 to 10% EtOAc/DCM to give the title compound (0.080 g, 47%) LC-MS m/z 633 (M+H)⁺, 1.22 min (ret time).

3-(7-methoxy-1-methyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl)propanoic acid

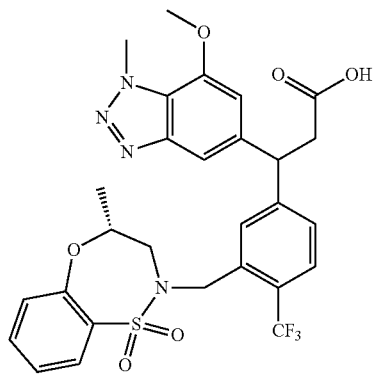 [SMILES: COc1cc(C(CC(=O)O)c2ccc(C(F)(F)F)c(CN3C[C@@H](C)Oc4ccccc4S3(=O)=O)c2)cc2nnn(C)c12]

To a solution of ethyl 3-(7-methoxy-1-methyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl)propanoate (0.080 g, 0.102 mmol) in THF (1 mL), MeOH (1.000 mL), and water (1.000 mL) was added LiOH (7.36 mg, 0.307 mmol) and stirred at RT for 5 h. The solvent was concentrated and the residue was diluted with EtOAc and acidified with 1N HCl. The aqueous layer was extracted with EtOAc (3×) and the combined organics were washed with water (2×), brine, dried with MgSO₄, and the solvent was concentrated. The resulting residue was purified by reverse-phase HPLC (Atlantics T3 19×150 mm 5 u preparatory column), eluting at 18 mL/min with a linear gradient running from 40% to 70% with CH₃CN and water over 10 min to give the title compound (41 mg, 62%), LC-MS m/z 605 (M+H)⁺, 1.11 min (ret time).

Example 132

3-(7-Methoxy-1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

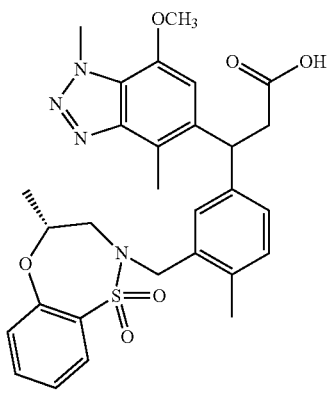 [SMILES: COc1cc(C(CC(=O)O)c2ccc(C)c(CN3C[C@@H](C)Oc4ccccc4S3(=O)=O)c2)c(C)c2nnn(C)c12]

5-Bromo-7-iodo-1,4-dimethyl-1H-benzo[d][1,2,3]triazole

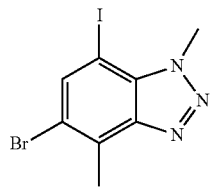

NaIO₄ (0.378 g, 1.769 mmol) was suspended in a stirred mixture of AcOH (2 mL) with Ac₂O (2.98 mL, 31.5 mmol) cooled to 5-10° C. Concentrated H₂SO₄ (1.792 mL, 33.6 mmol) was very slowly added dropwise. Then 5-bromo-1,4-dimethyl-1H-benzo[d][1,2,3]triazole (1 g, 4.42 mmol) was added, and the stirring was continued for 16 h at RT. The reaction mixture was poured into ice-water containing the previously dissolved Na₂SO₃. After 15 min, the collected precipitate was worked up with EtOAc and Na₂SO₃ solution. The crude product was then purified on a silica cartridge (40 g) with a Combiflash Companion, eluting at 40 mL/min with a gradient running from 100% hexanes to 80% EtOAc/hexanes over 35 min) to give 286 mg (18.34%) of the title compound. LC-MS m/z 351.9, 353.9 (M+H)⁺, 1.03 (ret. time).

5-Bromo-7-methoxy-1,4-dimethyl-1H-benzo[d][1,2,3]triazole

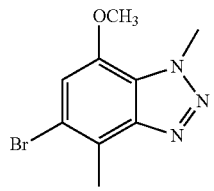

To a solution of 5-bromo-7-iodo-1,4-dimethyl-1H-benzo[d][1,2,3]triazole (286 mg, 0.813 mmol) in MeOH (5 mL) at RT, copper(I) iodide (77 mg, 0.406 mmol) and Cs₂CO₃ (530 mg, 1.625 mmol) were added. Then the reaction mixture was stirred at 110° C. for 40 min. The solvent was evaporated under reduced pressure. The crude product was then purified on a silica cartridge (12 g) with a Combiflash Companion, eluting at 20 mL/min with a gradient running from 100% hexanes to 80% EtOAc/hexanes over 35 min) to give 68 mg (32.7%) of the title compound. LC-MS m/z 256.1, 258.0 (M+H)⁺, 0.91 (ret. time).

(E)-ethyl 3-(7-methoxy-1,4-dimethyl-1H-benzo[d][1,2,3]triazol-5-yl)acrylate

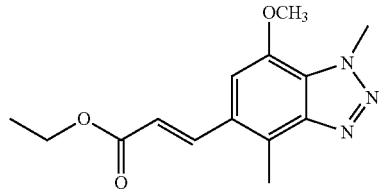 [SMILES: CCOC(=O)/C=C/c1cc(OC)c2c(nnn2C)c1C]

To a solution of 5-bromo-7-methoxy-1,4-dimethyl-1H-benzo[d][1,2,3]triazole (88 mg, 0.344 mmol) in DMF (1 mL), ethyl acrylate (206 mg, 2.062 mmol), DIPEA (0.240 mL, 1.374 mmol) and Pd(OAc)₂ (11.57 mg, 0.052 mmol) were added. The reaction mixture was heated in a microwave at 110° C. for 1 h. Water was added to quench the reaction. EtOAc was added, and the layers were separated. The aqueous layer was extracted once with EtOAc, and the combined organic layers were washed once with brine. The organic layer was concentrated. The crude product was then purified on a silica cartridge (40 g) with a Combiflash Companion, eluting at 40 mL/min with a gradient running from 100% hexanes to 80% EtOAc/hexanes over 35 min) to give 90 mg (95%) of the title compound. LC-MS m/z 276.1 (M+H)⁺, 0.93 (ret. time).

Ethyl 3-(3-(hydroxymethyl)-4-methylphenyl)-3-(7-methoxy-1,4-dimethyl-1H-benzo[d][1,2,3]triazol-5-yl)propanoate

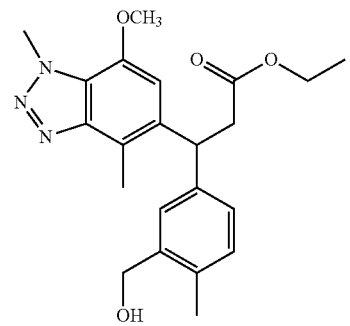 [SMILES: CCOC(=O)CC(c1ccc(C)c(CO)c1)c1cc(OC)c2c(nnn2C)c1C]

To a suspension of (E)-ethyl 3-(7-methoxy-1,4-dimethyl-1H-benzo[d][1,2,3]triazol-5-yl)acrylate (90 mg, 0.327 mmol), (3-(hydroxymethyl)-4-methylphenyl)boronic acid (65.1 mg, 0.392 mmol) and [RhCl(cod)]₂ (16.12 mg, 0.033 mmol) at RT in 1,4-dioxane (1 mL) and water (1.000 mL), was added Et₃N (0.137 mL, 0.981 mmol). The resulting suspension was heated to 95° C. for 4 h. The solvent was evaporated under reduce pressure. The crude product was then purified on a silica cartridge (12 g) with a Combiflash Companion, eluting at 20 mL/min with a gradient running from 100% hexanes to 80% EtOAc/hexanes over 35 min) to give 90 mg (69.3%) of the title compound. LC-MS m/z 398.0 (M+H)⁺, 0.94 (ret. time).

Ethyl 3-(7-methoxy-1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate

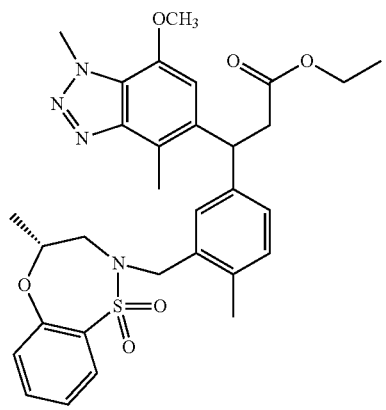 [SMILES: CCOC(=O)CC(c1ccc(C)c(CN2C[C@@H](C)Oc3ccccc3S2(=O)=O)c1)c1cc(OC)c2c(nnn2C)c1C]

To a solution of methyl 3-(3-(hydroxymethyl)-4-methylphenyl)-3-(7-methoxy-1,4-dimethyl-1H-benzo[d][1,2,3]triazol-5-yl)propanoate (43 mg, 0.112 mmol), (R)-4-methyl- 3,4-dihydro-2H-benzo[b][1,4,5]oxathiazepine 1,1-dioxide (26.3 mg, 0.123 mmol), ADDP (56.6 mg, 0.224 mmol) in THF (1 mL) at 0° C., tributylphosphine (0.056 mL, 0.224 mmol) was added. After the addition the ice-bath was removed and stirring continued at RT for 2 h. The solvent was evaporated under reduce pressure. The crude product was then purified on a silica cartridge (12 g) with a Combiflash Companion, eluting at 20 mL/min with a gradient running from 100% hexanes to 80% EtOAc/hexanes over 35 min) to give 53 mg (71.8%) of the title compound. LC-MS m/z 593.3 (M+H)$^+$, 1.14 (ret. time).

3-(7-Methoxy-1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

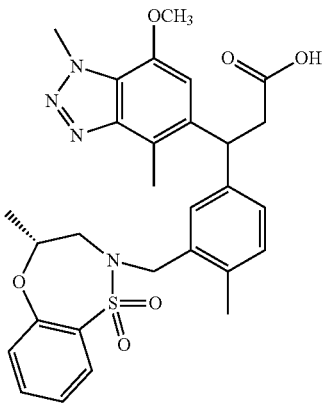 [SMILES: COc1cc(C(CC(=O)O)c2ccc(C)c(CN3C[C@@H](C)Oc4ccccc4S3(=O)=O)c2)c(C)c2nnn(C)c12]

To a solution of ethyl 3-(7-methoxy-1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl) propanoate (53 mg, 0.089 mmol) in MeOH (1 mL), NaOH (35.8 mg, 0.894 mmol) was added. The reaction mixture was stirred at 60° C. for 2 h. Then the crude was cooled down to RT. HCl (1N) was added until pH=1. The solid was filtered and purified by reverse-phase HPLC under neutral condition to get 23.4 mg (45.5%) of the title compound. LC-MS m/z 565.2 (M+H)$^+$, 1.02 (ret. time).

Example 133

3-(1-Ethyl-2-oxo-1,2-dihydropyridin-4-yl)-3-(4-methyl-3-(((R)-4-methyl-1,1-dioxido-3,4-dihydro-2H-benzo[b][1,4,5]oxathiazepin-2-yl)methyl)phenyl)propanoic acid

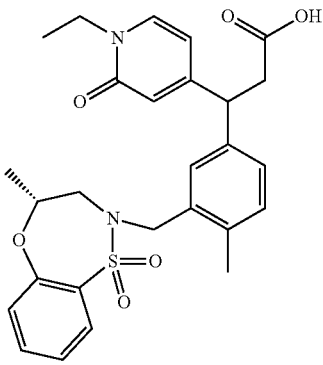 [SMILES: CCn1ccc(C(CC(=O)O)c2ccc(C)c(CN3C[C@@H](C)Oc4ccccc4S3(=O)=O)c2)cc1=O]

5-Bromo-1-ethylpyridin-2(1H)-one

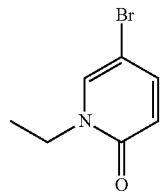

To a solution of 5-bromo-2-methoxypyridine (600 mg, 3.19 mmol) in DMF (10 mL), iodoethane (747 mg, 4.79 mmol) and K$_2$CO$_3$ (1323 mg, 9.57 mmol) were added. The reaction was stirred at 70° C. for 4 h. Then the solvent was evaporated. 20 mL of water was added to the residue, then it was adjusted to pH=8. EtOAc (3×30 mL) was extracted the water layer. The combined organic layer, dried with Mg$_2$SO$_4$ and conc. to get crude product. The crude product was then purified on a silica cartridge (40 g) with a Combiflash Companion, eluting at 40 mL/min with a gradient running from 100% CH$_2$Cl$_2$ to 80% MeOH/CH$_2$CH$_2$ over 35 min) to give 300 mg (46.5%) of the title compound. LC-MS m/z 202.1 (M+H)$^+$, 0.61 (ret. time).

(E)-Ethyl 3-(1-ethyl-2-oxo-1,2-dihydropyridin-4-yl)acrylate

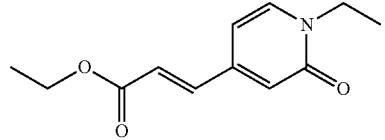 [SMILES: CCOC(=O)/C=C/c1ccn(CC)c(=O)c1]

To a solution of 4-bromo-1-ethylpyridin-2(1H)-one (285 mg, 1.411 mmol) in DMF (20 mL), ethyl acrylate (847 mg, 8.46 mmol), tri-o-tolylphosphine (129 mg, 0.423 mmol), N-ethyl-N-isopropylpropan-2-amine (729 mg, 5.64 mmol) and Pd(OAc)$_2$ (47.5 mg, 0.212 mmol) were added. The reaction mixture was heated in a microwave at 120° C. for 2 h. Water was added to quench the reaction. EtOAc was added and the layers were separated. The aqueous layer was extracted once with EtOAc, and the combined organic layers were washed once with brine. The organic layer was concentrated. The crude product was then purified on a silica cartridge (40 g) with a Combiflash Companion, eluting at 40 mL/min with a gradient running from 100% CH$_2$Cl$_2$ s to 80% MeOH/CH$_2$Cl$_2$ over 35 min) to give 208 mg (66.6%) of the title compound. LC-MS m/z 221.9 (M+H)$^+$, 0.71 (ret. time).

Ethyl 3-(1-ethyl-2-oxo-1,2-dihydropyridin-4-yl)-3-(3-(hydroxymethyl)-4-methylphenyl)propanoate

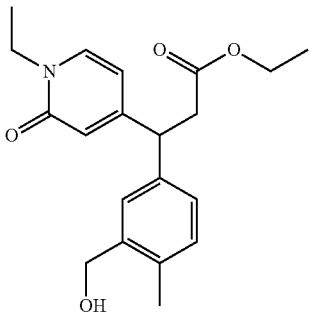 [SMILES: CCOC(=O)CC(c1ccc(C)c(CO)c1)c1ccn(CC)c(=O)c1]

To a solution of (E)-ethyl 3-(1-ethyl-2-oxo-1,2-dihydropyridin-4-yl)acrylate (100 mg, 0.452 mmol) in a mixture of 1,4-dioxane (4.5 mL) and water (1.5 mL), (3-(hydroxymethyl)-4-methylphenyl)boronic acid (90 mg, 0.542 mmol),) was added Et3N (0.189 mL, 1.356 mmol) and [RhCl(cod)]₂ (22.29 mg, 0.045 mmol). Then it was heated in a microwave at 150° C. for 1 h. The solvent was evaporated under reduce pressure. The crude product was then purified on a silica cartridge (12 g) with a Combiflash Companion, eluting at 20 mL/min with a gradient running from 100% CH₂Cl₂ s to 80% MeOH/CH₂Cl₂ over 35 min) to give 88.5 mg (57%) of the title compound. LC-MS m/z 344.3 (M+H)⁺, 0.78 (ret. time).

Ethyl 3-(1-ethyl-2-oxo-1,2-dihydropyridin-4-yl)-3-(4-methyl-3-(((R)-4-methyl-1,1-dioxido-3,4-dihydro-2H-benzo[b][1,4,5]oxathiazepin-2-yl)methyl)phenyl)propanoate

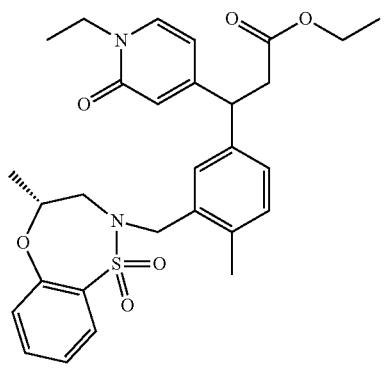 [SMILES: CCOC(=O)CC(c1ccc(C)c(CN2C[C@@H](C)Oc3ccccc3S2(=O)=O)c1)c1ccn(CC)c(=O)c1]

To a solution of methyl 3-(1-ethyl-2-oxo-1,2-dihydropyridin-4-yl)-3-(3-(hydroxymethyl)-4-methylphenyl)propanoate (86.5 mg, 0.263 mmol) in THF (2 mL) at 0° C., (R)-4-methyl-3,4-dihydro-2H-benzo[b][1,4,5]oxathiazepine 1,1-dioxide (88 mg, 0.289 mmol) and ADDP (133 mg, 0.525 mmol) were added. Then tributylphosphine (106 mg, 0.525 mmol) was added. The reaction mixture was warmed to RT and stirred for 2 h. The solvent was evaporated under reduce pressure. The crude product was then purified on a silica cartridge (12 g) with a Combiflash Companion, eluting at 20 mL/min with a gradient running from 100% CH₂Cl₂ s to 80% MeOH/CH₂Cl₂ over 35 min) to give 56 mg (39.6%) of the title compound. LC-MS m/z 539.3 (M+H)⁺, 1.05 (ret. time).

3-(1-Ethyl-2-oxo-1,2-dihydropyridin-4-yl)-3-(4-methyl-3-(((R)-4-methyl-1,1-dioxido-3,4-dihydro-2H-benzo[b][1,4,5]oxathiazepin-2-yl)methyl)phenyl)propanoic acid

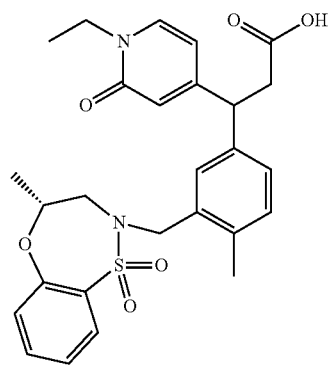 [SMILES: CCn1ccc(C(CC(=O)O)c2ccc(C)c(CN3C[C@@H](C)Oc4ccccc4S3(=O)=O)c2)cc1=O]

To a solution of ethyl 3-(1-ethyl-2-oxo-1,2-dihydropyridin-4-yl)-3-(4-methyl-3-(((R)-4-methyl-1,1-dioxido-3,4-dihydro-2H-benzo[b][1,4,5]oxathiazepin-2-yl)methyl)phenyl)propanoate (56 mg, 0.104 mmol) in MeOH (1 mL) and water (0.1 mL), LiOH (24.90 mg, 1.040 mmol) was added. Then the reaction mixture was stirred at RT for 4 h. HCl (1N) was added until pH=1. The solid was filtered and purified by reverse-phase HPLC under neutral condition to get 40 mg (75%) of the title compound. LC-MS m/z 511.3 (M+H)⁺, 0.91 (ret. time).

Example 134

3-(4-Methyl-3-(((R)-4-methyl-1,1-dioxido-3,4-dihydro-2H-benzo[b][1,4,5]oxathiazepin-2-yl)methyl)phenyl)-3-(2-oxo-1-propyl-1,2-dihydropyridin-4-yl)propanoic acid

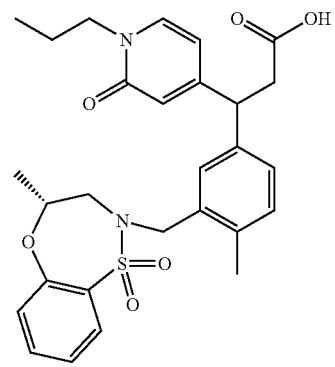 [SMILES: CCCn1ccc(C(CC(=O)O)c2ccc(C)c(CN3C[C@@H](C)Oc4ccccc4S3(=O)=O)c2)cc1=O]

5-Bromo-1-propylpyridin-2(1H)-one

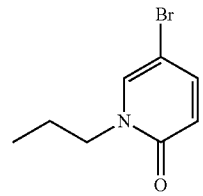

To a solution of 5-bromopyridin-2(1H)-one (600 mg, 3.45 mmol) in DMF (10 mL), K₂CO₃ (1906 mg, 13.79 mmol) and 1-iodopropane (879 mg, 5.17 mmol) were added. Then the reaction was stirred at 70° C. for 4 h. Water was added to quench the reaction. EtOAc was added, and the layers were separated. The aqueous layer was extracted once with EtOAc, and the combined organic layers were washed once with brine. The organic layer was concentrated. The crude product was then purified on a silica cartridge (40 g) with a Combiflash Companion, eluting at 40 mL/min with a gradient running from 100% CH₂Cl₂ s to 80% MeOH/CH₂Cl₂ over 35 min) to give 600 mg (83%) of the title compound. LC-MS m/z 216.2 (M+H)⁺, 0.68 (ret. time).

(E)-Ethyl 3-(2-oxo-1-propyl-1,2-dihydropyridin-4-yl)acrylate

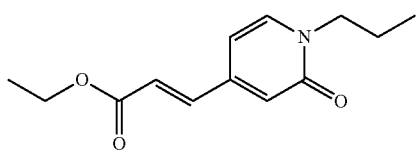 [SMILES: CCCn1ccc(/C=C/C(=O)OCC)cc1=O]

285

To a solution of 4-bromo-1-propylpyridin-2(1H)-one (620 mg, 2.87 mmol) in DMF (20 mL), ethyl acrylate (1724 mg, 17.22 mmol), tri-o-tolylphosphine (262 mg, 0.861 mmol), N-ethyl-N-isopropylpropan-2-amine (1483 mg, 11.48 mmol) and Pd(OAc)$_2$ (97 mg, 0.430 mmol) were added. The reaction mixture was heated in a microwave at 120° C. for 2 h. Water was added to quench the reaction. EtOAc was added, and the layers were separated. The aqueous layer was extracted once with EtOAc, and the combined organic layers were washed once with brine. The organic layer was concentrated. The crude product was then purified on a silica cartridge (40 g) with a Combiflash Companion, eluting at 40 mL/min with a gradient running from 100% CH$_2$Cl$_2$ to 80% MeOH/CH$_2$Cl$_2$ over 35 min) to give 532 mg (79%) of the title compound. LC-MS m/z 235.9 (M+H)$^+$, 0.77 (ret. time).

Ethyl 3-(3-(hydroxymethyl)-4-methylphenyl)-3-(2-oxo-1-propyl-1,2-dihydropyridin-4-yl)propanoate

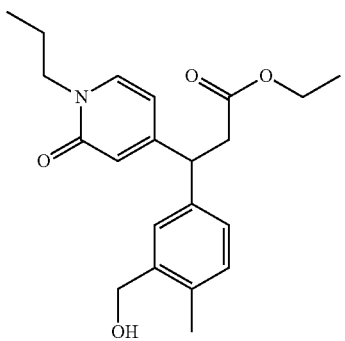 [SMILES: CCCn1ccc(C(CC(=O)OCC)c2ccc(C)c(CO)c2)cc1=O]

To a solution of (E)-ethyl 3-(2-oxo-1-propyl-1,2-dihydropyridin-4-yl)acrylate (150 mg, 0.638 mmol) in a mixture of 1,4-dioxane (4.5 mL) and water (1.5 mL), (3-(hydroxymethyl)-4-methylphenyl)boronic acid (127 mg, 0.765 mmol), Et$_3$N (194 mg, 1.913 mmol) and [RhCl(cod)]$_2$ (31.4 mg, 0.064 mmol) were added. Then it was heated in a microwave at 150° C. for 1 hr. The solvent was evaporated under reduce pressure. The crude product was then purified on a silica cartridge (12 g) with a Combiflash Companion, eluting at 20 mL/min with a gradient running from 100% CH$_2$Cl$_2$ s to 80% MeOH/CH$_2$Cl$_2$ over 35 min) to give 107 mg (47%) of the title compound. LC-MS m/z 358.1 (M+H)$^+$, 0.82 (ret. time).

Ethyl 3-(4-methyl-3-(((R)-4-methyl-1,1-dioxido-3,4-dihydro-2H-benzo[b][1,4,5]oxathiazepin-2-yl)methyl)phenyl)-3-(2-oxo-1-propyl-1,2-dihydropyridin-4-yl)propanoate

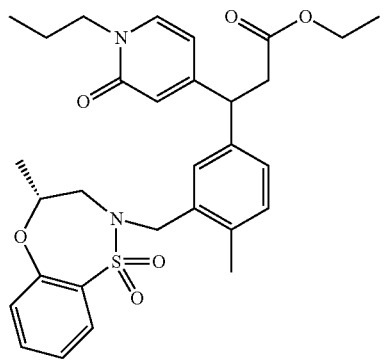 [SMILES: CCCn1ccc(C(CC(=O)OCC)c2ccc(C)c(CN3C[C@@H](C)Oc4ccccc4S3(=O)=O)c2)cc1=O]

286

To a solution of methyl 3-(3-(hydroxymethyl)-4-methylphenyl)-3-(2-oxo-1-propyl-1,2-dihydropyridin-4-yl)propanoate (107 mg, 0.312 mmol) in THF (2 mL) at 0° C., (R)-4-methyl-3,4-dihydro-2H-benzo[b][1,4,5]oxathiazepine 1,1-dioxide (104 mg, 0.343 mmol) and ADDP (157 mg, 0.623 mmol) were added. Then tributylphosphine (126 mg, 0.623 mmol) was added. The reaction mixture was warmed to RT and stirred for 2 h. The solvent was evaporated under reduce pressure. The crude product was then purified on a silica cartridge (12 g) with a Combiflash Companion, eluting at 20 mL/min with a gradient running from 100% CH$_2$Cl$_2$ s to 80% MeOH/CH$_2$Cl$_2$ over 35 min) to give 160 mg (93%) of the title compound. LC-MS m/z 553.5 (M+H)$^+$, 1.10 (ret. time).

3-(4-Methyl-3-(((R)-4-methyl-1,1-dioxido-3,4-dihydro-2H-benzo[b][1,4,5]oxathiazepin-2-yl)methyl)phenyl)-3-(2-oxo-1-propyl-1,2-dihydropyridin-4-yl)propanoic acid

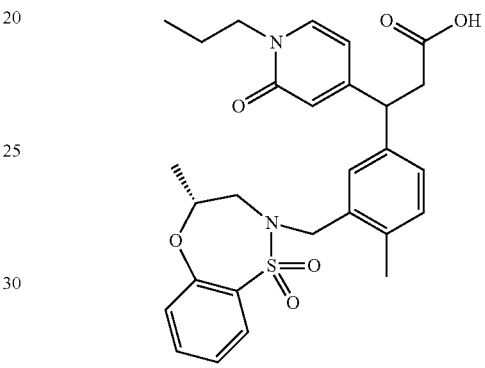

To a solution of ethyl 3-(4-methyl-3-(((R)-4-methyl-1,1-dioxido-3,4-dihydro-2H-benzo[b][1,4,5]oxathiazepin-2-yl)methyl)phenyl)-3-(2-oxo-1-propyl-1,2-dihydropyridin-4-yl)propanoate (160 mg, 0.289 mmol) in MeOH (1 mL) and water (0.1 mL), LiOH (69.3 mg, 2.89 mmol) was added. Then the reaction mixture was stirred at RT for 4 h. HCl (1 N) was added until pH=1. The solid was filtered and purified by reverse-phase HPLC under neutral condition to get 31.8 mg (20.94%) of the title compound. LC-MS m/z 525.4 (M+H)$^+$, 0.95 (ret. time).

Example 135

3-(4-Methyl-3-(((R)-4-methyl-1,1-dioxido-3,4-dihydro-2H-benzo[b][1,4,5]oxathiazepin-2-yl)methyl)phenyl)-3-(1-methyl-6-oxo-1,6-dihydropyridin-2-yl)propanoic acid

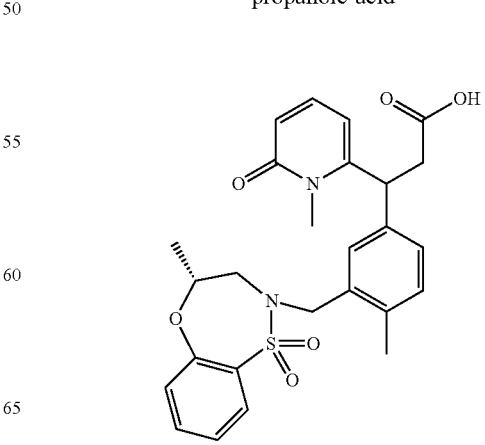

6-Bromo-1-methylpyridin-2(1H)-one

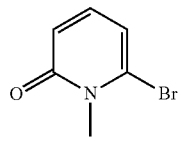

To a solution of 6-bromopyridin-2(1H)-one (500 mg, 2.87 mmol) in DMF (10 mL), K₂CO₃ (1191 mg, 8.62 mmol) and MeI (612 mg, 4.31 mmol) were added. The reaction mixture was stirred at 80° C. for 2 h. Water was added to quench the reaction. EtOAc was added, and the layers were separated. The aqueous layer was extracted once with EtOAc, and the combined organic layers were washed once with brine. The organic layer was concentrated. The crude product was then purified on a silica cartridge (40 g) with a Combiflash Companion, eluting at 40 mL/min with a gradient running from 100% $CH_2Cl_2$ s to 80% MeOH/$CH_2Cl_2$ over 35 min) to give 280 mg (51.8%) of the title compound. LC-MS m/z 188.0 (M+H)⁺, 0.54 (ret. time).

(E)-Ethyl 3-(1-methyl-6-oxo-1,6-dihydropyridin-2-yl)acrylate

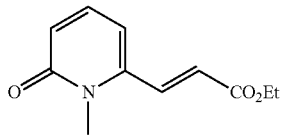

To a solution of 6-bromo-1-methylpyridin-2(1H)-one (280 mg, 1.489 mmol) in DMF (10 mL), tri-o-tolylphosphine (136 mg, 0.447 mmol), ethyl acrylate (895 mg, 8.94 mmol) and N-ethyl-N-isopropylpropan-2-amine (770 mg, 5.96 mmol) were added. Then Pd(OAc)₂ (50.2 mg, 0.223 mmol) was added. The reaction mixture was heated in a microwave at 120° C. for 4 h. Water was added to quench the reaction. EtOAc was added, and the layers were separated. The aqueous layer was extracted once with EtOAc, and the combined organic layers were washed once with brine. The organic layer was concentrated. The crude product was then purified on a silica cartridge (40 g) with a Combiflash Companion, eluting at 40 mL/min with a gradient running from 100% $CH_2Cl_2$ to 80% MeOH/$CH_2Cl_2$ over 35 min) to give 96 mg (31.1%) of the title compound. LC-MS m/z 208.1 (M+H)⁺, 0.62 (ret. time).

Ethyl 3-(3-(hydroxymethyl)-4-methylphenyl)-3-(1-methyl-6-oxo-1,6-dihydropyridin-2-yl)propanoate

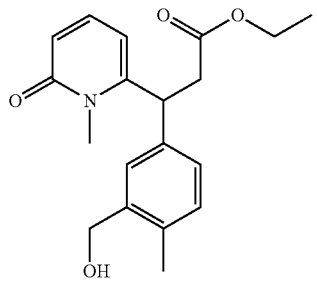 [SMILES: CCOC(=O)CC(c1ccc(C)c(CO)c1)c1cccc(=O)n1C]

To a solution of (E)-ethyl 3-(1-methyl-6-oxo-1,6-dihydropyridin-2-yl)acrylate (95 mg, 0.458 mmol) in 1,4-dioxane (4.5 mL) and water (1.5 mL), (3-(hydroxymethyl)-4-methylphenyl)boronic acid (91 mg, 0.550 mmol) and [RhCl(cod)]₂ (22.60 mg, 0.046 mmol) were added. Then the reaction mixture was heated in a microwave at 120° C. for 1 h. The solvent was evaporated under reduce pressure. The crude product was then purified on a silica cartridge (12 g) with a Combiflash Companion, eluting at 20 mL/min with a gradient running from 100% $CH_2Cl_2$ s to 80% MeOH/$CH_2Cl_2$ over 35 min) to give 130 mg (86%) of the title compound. LC-MS m/z 330.2 (M+H)⁺, 0.75 (ret. time).

Ethyl 3-(4-methyl-3-(((R)-4-methyl-1,1-dioxido-3,4-dihydro-2H-benzo[b][1,4,5]oxathiazepin-2-yl)methyl)phenyl)-3-(1-methyl-6-oxo-1,6-dihydropyridin-2-yl)propanoate

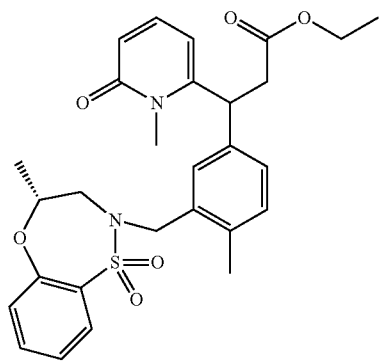 [SMILES: CCOC(=O)CC(c1ccc(C)c(CN2C[C@@H](C)Oc3ccccc3S2(=O)=O)c1)c1cccc(=O)n1C]

To a solution of methyl 3-(3-(hydroxymethyl)-4-methylphenyl)-3-(1-methyl-6-oxo-1,6-dihydropyridin-2-yl)propanoate (95 mg, 0.301 mmol) in THF (2 mL) at 0° C., (R)-4-methyl-3,4-dihydro-2H-benzo[b][1,4,5]oxathiazepine 1,1-dioxide (101 mg, 0.331 mmol) and ADDP (152 mg, 0.602 mmol) were added. Then tributylphosphine (122 mg, 0.602 mmol) was added. The reaction mixture was warmed to RT and stirred for 2 h. The solvent was evaporated under reduce pressure. The crude product was then purified on a silica cartridge (12 g) with a Combiflash Companion, eluting at 20 mL/min with a gradient running from 100% $CH_2Cl_2$ s to 80% MeOH/$CH_2Cl_2$ over 35 min) to give 150 mg (95%) of the title compound. LC-MS m/z 525.4 (M+H)⁺, 1.02 (ret. time).

3-(4-Methyl-3-(((R)-4-methyl-1,1-dioxido-3,4-dihydro-2H-benzo[b][1,4,5]oxathiazepin-2-yl)methyl)phenyl)-3-(1-methyl-6-oxo-1,6-dihydropyridin-2-yl)propanoic acid

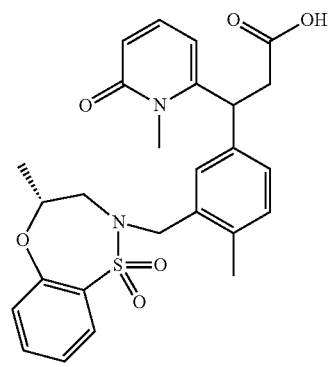 [SMILES: Cc1ccc(C(CC(=O)O)c2cccc(=O)n2C)cc1CN1C[C@@H](C)Oc2ccccc2S1(=O)=O]

To a solution of ethyl 3-(4-methyl-3-(((R)-4-methyl-1,1-dioxido-3,4-dihydro-2H-benzo[b][1,4,5]oxathiazepin-2-yl)

methyl)phenyl)-3-(1-methyl-6-oxo-1,6-dihydropyridin-2-yl)propanoate (95 mg, 0.181 mmol) in MeOH (2 mL) at 0° C., LiOH (4.34 mg, 0.181 mmol) was added. Then the reaction mixture was warmed to RT and stirred for 1.5 h. HCl (1 N) was added until pH=1. The solid was filtered and purified by reverse-phase HPLC under neutral condition to get 31.8 mg (20.94%) of the title compound. LC-MS m/z 497.3 (M+H)+, 0.87 (ret. time).

Example 136

3-{4-chloro-3-[(N-methylmethanesulfonamido)methyl]phenyl}-3-(1-methyl-1H-1,2,3-benzotriazol-5-yl)propanoic acid

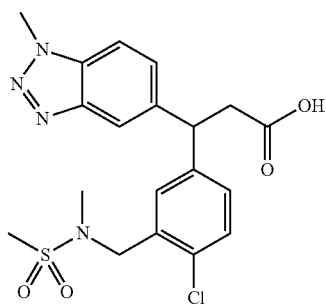 [SMILES: CN(Cc1cc(C(CC(=O)O)c2ccc3c(c2)nnn3C)ccc1Cl)S(C)(=O)=O]

N-(2-Chloro-5-formyl-benzyl)-N-methyl-methanesulfonamide

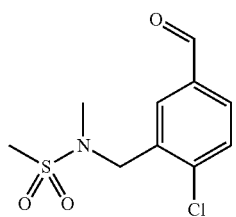 [SMILES: CN(Cc1cc(C=O)ccc1Cl)S(C)(=O)=O]

A mixture of 4-chloro-3-(bromomethyl)benzaldehyde (0.25 g, 1.07 mmol), N-methyl methanesulfonamide (0.129 g, 1.18 mmol) and K₂CO₃ (0.163 g, 1.18 mmol) in MeCN was stirred at RT under N₂ overnight. The mixture was diluted with water and extracted with DCM (×3). The combined organic layers were washed with brine and dried over MgSO₄. Filtration and concentration to dryness afforded the product as a yellow oil (0.247 g, 88%), used without further purification. LCMS (M+18)+279, RT 1.15 min.

(E)-3-{4-Chloro-3-[(methanesulfonyl-methyl-amino)-methyl]-phenyl}-acrylic acid methyl ester

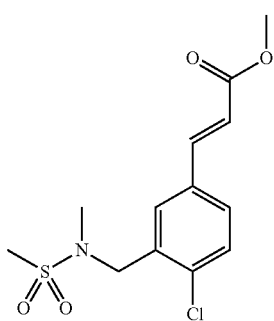

A stirred solution of t-BuOK (0.212 g, 1.89 mmol) in THF (10 mL) at 0° C. under N₂ was treated with trimethyl phosphonoacetate (0.403 g, 2.17 mmol). After 30 mins, a solution of N-(2-Chloro-5-formyl-benzyl)-N-methyl-methanesulfonamide (0.247 g, 0.94 mmol) in THF (2 mL) was added. The mixture was stirred for 3 h, then treated with NH₄Cl (aq., sat.), diluted with water and extracted with DCM (×3). The combined organic layers were washed with water and brine and dried over MgSO₄. Filtration and concentration to dryness followed by purification by silica gel chromatography (100% DCM) gave the product as a colourless solid (0.277 g, 92%). LCMS (M+18)+335/3371 (01), RT 1.30 min.

1-Methyl-5-(4,4,5,5-tetramethyl-[1,3,2]dioxaborolan-2-yl)-1H-benzotriazole

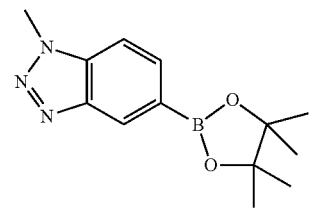 [SMILES: Cn1nnc2cc(B3OC(C)(C)C(C)(C)O3)ccc21]

A stirred mixture of 5-bromo-1-methylbenzotriazole (prepared according to PCT Int. Appl., 2012119046; 1.28 g, 6.04 mmol), bis(pinacolato)diboron (1.69 g, 6.04 mmol), KOAc (1.18 g, 12.08 mmol) and PdCl₂(dppf) (0.221 g, 0.30 mmol) in dioxane was degassed with N₂ for 10 mins and then heated at 90° C. for 5 h. After cooling the mixture was partitioned between water and EtOAc. The organic phase was dried (MgSO4), filtered and concentrated to dryness. The residue was purified by flash chromatography (EtOAc/petrol gradient 0-40%) to give the product (1.21 g, 72%). LCMS (M+H)+ 260, RT 1.30 min.

3-{4-chloro-3-[(N-methylmethanesulfonamido)methyl]phenyl}-3-(1-methyl-1H-1,2,3-benzotriazol-5-yl)propanoic acid

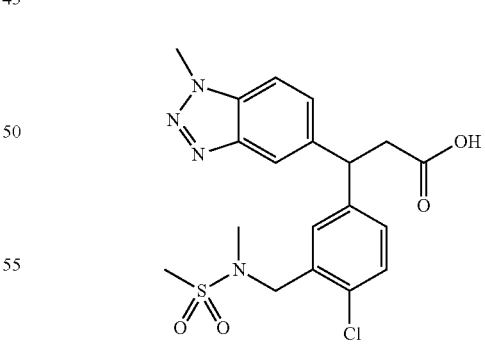

A stirred mixture of (E)-3-{4-Chloro-3-[(methanesulfonyl-methyl-amino)-methyl]-phenyl}-acrylic acid methyl ester (0.117 g, 0.37 mmol), 1-Methyl-5-(4,4,5,5-tetramethyl-[1,3,2]dioxaborolan-2-yl)-1H-benzotriazole (0.191 g, 0.74 mmol), [RhCl(cod)]₂ (0.009 g, 0.02 mmol), Et₃N (0.056 g, 0.55 mmol), 1,4-dioxane (0.18 mL) and water (1.23 mL) was heated in a reacti vial at 95° C. for 18 h. LiOH (1M, 2 mL) was added and the mixture stirred at RT for 2 h. The mixture was treated with citric acid (5%, aq.) and extracted with CHCl₃:IPA (3:1, ×2). The combined organic layers were washed successively with water and brine, dried over MgSO4, filtered and concentrated to dryness. Purification by preparative HPLC (Agilent, formic acid method and Agilent TFA) gave the product as a colorless oil (0.028 g, 17%). LCMS (M+H)⁺ 437/439 (Cl), RT 0.99 min.

¹H NMR (400 MHz, Me-d3-OD): 7.92 (1H, s), 7.69 (1H, d), 7.56-7.46 (2H, m), 7.37 (1H, d), 7.29 (1H, dd), 4.75 (1H, t), 4.44 (2H, s), 4.31 (3H, s), 3.18 (2H, d), 2.92 (3H, s), 2.76 (3H, s).

Example 137

Methyl 3-{4-chloro-3-[(N-propylpyridine-3-sulfonamido)methyl]phenyl}-3-(1-methyl-1H-1,2,3-benzotriazol-5-yl)propanoate

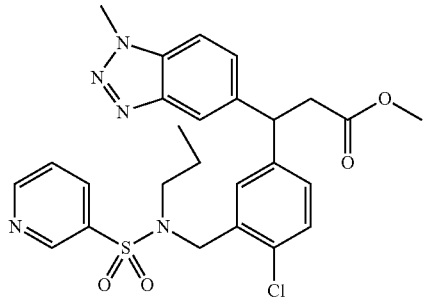 [SMILES: CCCN(Cc1cc(C(CC(=O)OC)c2ccc3c(c2)nnn3C)ccc1Cl)S(=O)(=O)c1cccnc1]

[2-Chloro-5-(3,3,4,4-tetramethyl-borolan-1-yl)-phenyl]-methanol

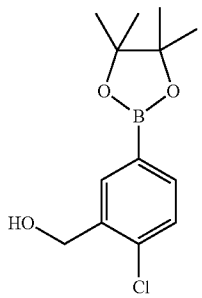 [SMILES: CC1(C)OB(c2ccc(Cl)c(CO)c2)OC1(C)C]

A stirred mixture of 5-bromo-2-chlorobenzyl alcohol (4.10 g, 18.0 mmol), bis(pinacolato)diboron (5.53 g, 21.6 mmol) and KOAc (7.05 g, 71.8 mmol) in dioxane was degassed with N₂, treated with (PPh₃)₂PdCl₂ (0.756 g, 1.08 mmol), and heated under reflux for 2.5 h. The reaction was diluted with water and extracted with EtOAc (×2). The combined organic layers were washed with brine, dried over MgSO₄ and concentrated to dryness. The residue was purified by silica gel chromatography (50% DCM/petrol) to yield a colourless solid (3.5 g, 73%). A further fraction of slightly less pure material was isolated as a yellow oil (1.0 g, 12%). LCMS (M+18)+286/288(Cl), RT 1.38 min.

(E)-3-(1-Methyl-1H-benzotriazol-5-yl)-acrylic acid methyl ester

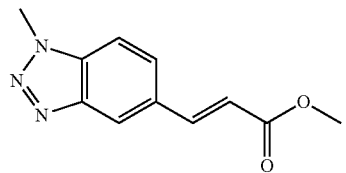 [SMILES: COC(=O)/C=C/c1ccc2c(c1)nnn2C]

A stirred solution of t-BuOK (2.10 g, 18.6 mmol) in THF (100 mL) at 0° C. under N₂ was treated with trimethyl phosphonoacetate (4.30 g, 23.3 mmol). After 30 mins, 1-methyl-1H-1,2,3-benzotriazole-5-carbaldehyde (2.50 g, 15.5 mmol) was added slowly in portions. After 1 h, the mixture was treated with NH₄Cl (aq., sat.), diluted with water and then extracted with n-heptane (×3), resulting in a precipitate which was isolated by filtration. The combined organic layers were washed with water and brine, dried over MgSO₄, filtered and concentrated to dryness, giving a beige solid which was washed with toluene and dried under vacuum. This material was combined with the precipitate above to give the product as a beige solid (3.1 g, 92%). LCMS (M+H)⁺ 218, RT 1.12 min.

3-(4-Chloro-3-hydroxymethyl-phenyl)-3-(1-methyl-1H-benzotriazol-5-yl)-propionic acid methyl ester A stirred mixture of [2-Chloro-5-(3,3,4,4-tetramethyl-borolan-1-yl)-phenyl]-methanol (0.927 g, 3.45 mmol), (E)-3-(1-Methyl-1H-benzotriazol-5-yl)-acrylic acid methyl ester (0.500 g, 2.30 mmol), [RhCl(cod)]₂ (0.057 g, 0.12 mmol), Et₃N (0.349 g, 3.45 mmol), 1,4-dioxane (1.2 mL) and water (7.7 mL) was heated at 95° C. for 6 h. Additional [2-Chloro-5-(3,3,4,4-tetramethyl-borolan-1-yl)-phenyl]-methanol (0.5 eq) and [RhCl(cod)]₂ (0.050 g, 0.10 mmol) were added and the mixture heated again for 16 h. The mixture was diluted with water and extracted with CHCl₃:IPA (3:1, ×3). The combined organic layers were washed successively with water and brine, dried over MgSO₄, filtered and concentrated to dryness. The residue was taken up into MeOH and the solution treated with 2 drops conc. HCl, then stirred under reflux for 4 h. Concentration to dryness followed by purification by silica gel chromatography (100% DCM) gave the product as a white solid (0.560 g, 68%). LCMS (M+H)⁺ 360/362 (Cl), RT 1.18 min.

Pyridine-3-sulfonic acid propylamide

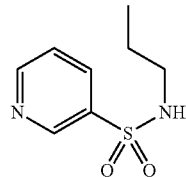

A stirred solution of 3-pyridylsulfonyl chloride hydrochloride (0.240 g, 1.12 mmol) and iPr$_2$NEt (0.217 g, 1.68 mmol) in DCM (4 mL) at 4° C. was treated with n-propylamine (0.166 g, 2.80 mmol). After 3 h the reaction was diluted with NaHCO$_3$ (aq., sat.) and extracted with EtOAc (×2). The combined organic layers were washed successively with water and brine, dried over MgSO$_4$, filtered and concentrated to dryness giving a yellow oil (0.217 g, 97%). LCMS MH+ 201, (M−H)− 199, RT 0.95 min.

Methyl 3-{4-chloro-3-[(N-propylpyridine-3-sulfonamido)methyl]phenyl}-3-(1-methyl-1H-1,2,3-benzotriazol-5-yl)propanoate

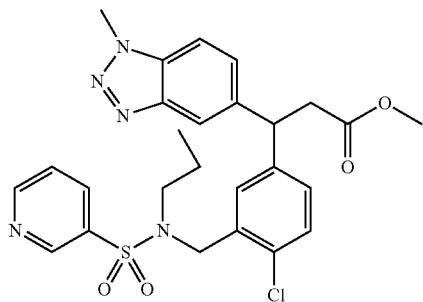 [SMILES: CCCN(Cc1cc(C(CC(=O)OC)c2ccc3c(c2)nnn3C)ccc1Cl)S(=O)(=O)c1cccnc1]

A stirred solution of 3-(4-Chloro-3-hydroxymethyl-phenyl)-3-(1-methyl-1H-benzotriazol-5-yl)-propionic acid methyl ester (0.250 g, 0.69 mmol), pyridine-3-sulfonic acid propylamide (0.139 g, 0.69 mmol) and 1,1'-(azodicarbonyl)dipiperidine (0.354 g, 1.39 mmol) in THF (2 mL) at 4° C. under N$_2$ was treated with tri-n-butylphosphine (0.284 g, 1.39 mmol). A thick suspension formed and the mixture diluted with THF (4 mL), then warmed to RT. After 16 h the mixture was cooled to 4° C. and treated with further 1,1'-(azodicarbonyl)dipiperidine (0.354 g, 1.39 mmol) and tri-n-butylphosphine (0.284 g, 1.39 mmol). After a further 6 h at RT the mixture was treated with water and extracted with EtOAc (×3). The combined organic layers were washed with water and brine, dried over MgSO$_4$, filtered and concentrated to dryness. The residue was purified by silica gel chromatography by gradient elution (100% DCM to 40% EtOAc in DCM) followed by preparative HPLC giving the product as a colourless solid (0.040 g, 11%). LCMS MH+ 542/544 (Cl), RT 1.38 min.

$^1$H NMR (400 MHz, Me-d3-OD): 8.94 (1H, s), 8.78 (1H, d), 8.19 (1H, d), 7.89 (1H, s), 7.70 (1H, d), 7.59 (1H, dd), 7.47 (1H, d), 7.43 (1H, s), 7.32-7.25 (2H, m), 4.73 (1H, t), 4.51 (2H, s), 4.32 (3H, s), 3.61 (3H, s), 3.20 (2H, dd), 3.17-3.08 (2H, m), 1.35-1.27 (2H, m), 0.66 (3H, t).

Example 138

3-{4-chloro-3-[(N-propylpyridine-3-sulfonamido)methyl]phenyl}-3-(1-methyl-1H-1,2,3-benzotriazol-5-yl)propanoic acid

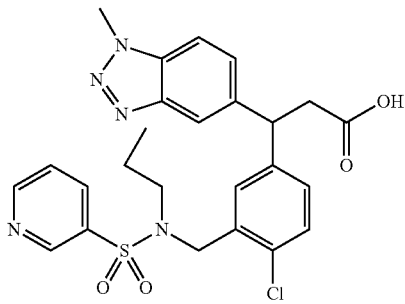 [SMILES: CCCN(Cc1cc(C(CC(=O)O)c2ccc3c(c2)nnn3C)ccc1Cl)S(=O)(=O)c1cccnc1]

A solution of methyl 3-{4-chloro-3-[(N-propylpyridine-3-sulfonamido)methyl]phenyl}-3-(1-methyl-1H-1,2,3-benzotriazol-5-yl)propanoate (0.10 g, 0.18 mmol) in MeOH (6 mL) was treated with LiOH (1M, aq., 4 mL) and stirred over night at RT. The solution was diluted with water, adjusted to pH 4-5 and extracted with EtOAc (×3). The combined organic layers were washed with water and brine, dried over MgSO$_4$, filtered and concentrated to dryness. The residue was purified by phenomenix silica cartridge. LC/MS showed insufficient purity: the residue was taken up in EtOAc and extracted into NaOH (×2, 2M). The combined aqueous layers were washed with EtOAc, then acidified with citric acid (pH ~4-5). The aqueous layers were extracted with EtOAc (×3), and these combined organic layers were washed with water and brine, dried over MgSO$_4$, filtered and concentrated to dryness to give the product as a colourless solid (0.019 g, 20%). LCMS (M+H)$^+$ 528/530 (Cl), RT 1.09 min.

$^1$H NMR (400 MHz, Me-d3-OD): 8.93 (1H, s), 8.77 (1H, d), 8.20-8.15 (1H, m), 7.90 (1H, s), 7.69 (1H, d), 7.58 (1H, dd), 7.48 (1H, d), 7.44-7.39 (1H, m), 7.29 (2H, s), 4.70 (1H, t), 4.51 (2H, s), 4.32 (3H, s), 3.18-3.09 (4H, m), 1.35-1.28 (2H, m), 0.65 (3H, t).

Example 139

3-{4-chloro-3-[(N-ethylpyridine-3-sulfonamido)methyl]phenyl}-3-(1-methyl-1H-1,2,3-benzotriazol-5-yl)propanoic acid

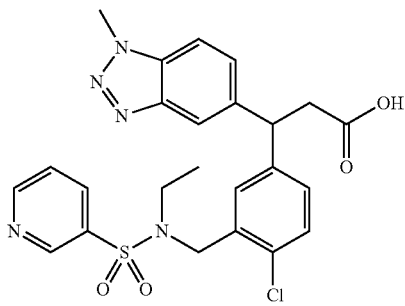 [SMILES: CCN(Cc1cc(C(CC(=O)O)c2ccc3c(c2)nnn3C)ccc1Cl)S(=O)(=O)c1cccnc1]

Pyridine-3-sulfonic acid ethylamide

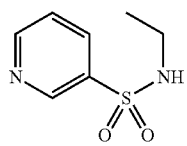

Prepared using an analogous procedure to pyridine-3-sulfonic acid propylamide, using 3-pyridylsulfonyl chloride hydrochloride (0.300 g, 1.40 mmol), iPr₂NEt (0.217 g, 1.68 mmol), ethylamine (2M in THF, 1.40 mL, 2.8 mmol) and DCM (4 mL), to give a yellow oil (0.161 g, 62%). LCMS M−H 185, RT 0.58 min.

3-{4-chloro-3-[(N-ethylpyridine-3-sulfonamido)methyl]phenyl}-3-(1-methyl-1H-1,2,3-benzotriazol-5-yl)propanoic acid

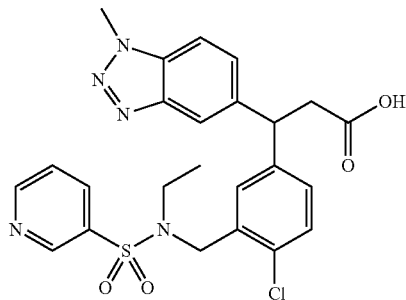 [SMILES: CCN(Cc1cc(C(CC(=O)O)c2ccc3c(c2)nnn3C)ccc1Cl)S(=O)(=O)c1cccnc1]

Prepared from 3-(4-Chloro-3-hydroxymethyl-phenyl)-3-(1-methyl-1H-benzotriazol-5-yl)-propionic acid methyl ester (0.250 g, 0.69 mmol) and pyridine-3-sulfonic acid ethylamide (0.129 g, 0.69 mmol), using an analogous procedure to 3-{4-chloro-3-[(N-propylpyridine-3-sulfonamido)methyl]phenyl}-3-(1-methyl-1H-1,2,3-benzotriazol-5-yl) propanoic acid, to give a colourless oil (0.043 g, 12%). LCMS (M−H)− 514.00, RT 1.04 min. ¹H NMR (400 MHz, Me-d3-OD): 8.94 (1H, d), 8.76 (1H, dd), 8.18 (1H, dt), 7.89 (1H, s), 7.69 (1H, d), 7.58 (1H, dd), 7.48 (1H, dd), 7.43 (1H, s), 7.29 (2H, s), 4.70 (1H, t), 4.54 (2H, s), 4.32 (3H, s), 3.30-3.24 (2H, m), 3.21-3.09 (2H, m), 0.95 (3H, t).

Example 140

3-{4-chloro-3-[(N-methylpyridine-3-sulfonamido)methyl]phenyl}-3-(1-methyl-1H-1,2,3-benzotriazol-5-yl)propanoic acid

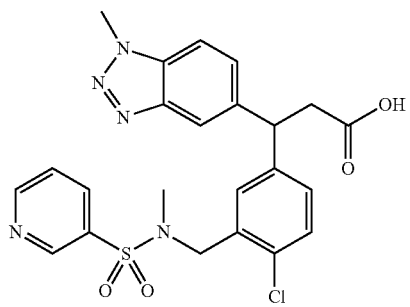 [SMILES: CN(Cc1cc(C(CC(=O)O)c2ccc3c(c2)nnn3C)ccc1Cl)S(=O)(=O)c1cccnc1]

Pyridine-3-sulfonic acid methylamide

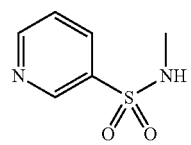

Prepared using an analogous procedure to pyridine-3-sulfonic acid propylamide, using 3-pyridylsulfonyl chloride hydrochloride (0.355 g, 1.40 mmol), methylamine (33% in MeOH, 3 mL, excess) and DCM (3 mL), to give a white solid (0.357 g, quant.). LCMS M−H 173, RT 0.54 min.

3-{4-chloro-3-[(N-methylpyridine-3-sulfonamido)methyl]phenyl}-3-(1-methyl-1H-1,2,3-benzotriazol-5-yl)propanoic acid

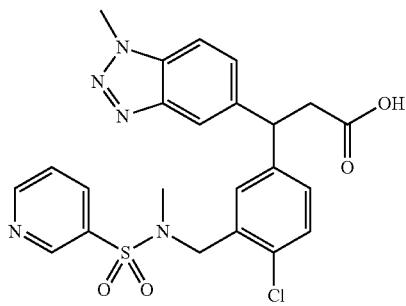 [SMILES: CN(Cc1cc(C(CC(=O)O)c2ccc3c(c2)nnn3C)ccc1Cl)S(=O)(=O)c1cccnc1]

A stirred solution of 3-(4-Chloro-3-hydroxymethyl-phenyl)-3-(1-methyl-1H-benzotriazol-5-yl)-propionic acid methyl ester (0.120 g, 0.33 mmol), pyridine-3-sulfonic acid methylamide (0.057 g, 0.33 mmol) and 1,1'-(azodicarbonyl)dipiperidine (0.168 g, 0.67 mmol) in THF (4 mL) under N2 was treated with tri-n-butylphosphine (0.135 g, 0.67 mmol). After 16 h the mixture was treated with further 1,1'-(azodicarbonyl)dipiperidine (0.168 g, 0.67 mmol) and tri-n-butylphosphine (0.135 g, 0.67 mmol). After a further 4 h the mixture was treated with LiOH (1M, aq., 3 mL) and stirred for a further 3 h. The mixture was diluted with water and washed with EtOAc (×3). The aqueous phase was acidified with 1M HCl and extracted with iPrOH/CHCl3 (1/3). The combined organic layers were washed with water and brine, dried over MgSO4, filtered and concentrated to dryness. The residue was purified by preparative HPLC giving the product as an off-white solid (0.022 g, 13%). LCMS M−H 500/502, RT 1.00 min. ¹H NMR (400 MHz, Me-d3-OD): 8.98 (1H, d), 8.88-8.76 (1H, m), 8.30-8.18 (1H, m), 7.89 (1H, s), 7.76-7.60 (2H, m), 7.60-7.44 (1H, m), 7.41 (1H, s), 7.36-7.25 (2H, m), 4.75 (1H, t), 4.53-4.34 (2H, m), 4.34-4.25 (3H, m), 3.08-2.88 (2H, m), 2.82-2.64 (3H, m).

Example 141

3-{4-chloro-3-[(N-methyl-1,5-dimethyl-1H-pyrazole-4-sulfonamido)methyl]phenyl}-3-(1-methyl-1H-1,2,3-benzotriazol-5-yl)propanoic acid

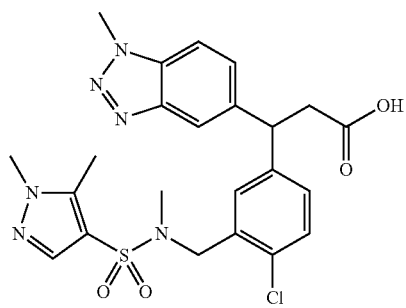 [SMILES: Cc1c(S(=O)(=O)N(C)Cc2cc(C(CC(=O)O)c3ccc4c(c3)nnn4C)ccc2Cl)cnn1C]

1,5-Dimethyl-1H-pyrazole-4-sulfonic acid methylamide

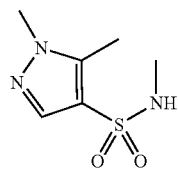

Prepared by an analogous procedure to pyridine-3-sulfonic acid propylamide, using 1,4-dimethylpyrazol-4-ylsulfonyl chloride (0.389 g, 2.00 mmol), methylamine (33% in MeOH, 3 mL, excess) and DCM (2 mL), to give a white solid (0.312 g, 83%). LCMS M−H 190, RT 0.59 min.

3-{4-chloro-3-[(N-methyl-1,5-dimethyl-1H-pyrazole-4-sulfonamido)methyl]phenyl}-3-(1-methyl-1H-1,2,3-benzotriazol-5-yl)propanoic acid

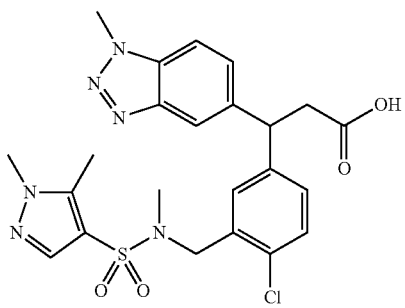 [SMILES: Cc1c(S(=O)(=O)N(C)Cc2cc(C(CC(=O)O)c3ccc4c(c3)nnn4C)ccc2Cl)cnn1C]

A stirred solution of 3-(4-Chloro-3-hydroxymethyl-phenyl)-3-(1-methyl-1H-benzotriazol-5-yl)-propionic acid methyl ester (0.125 g, 0.35 mmol), 1,5-Dimethyl-1H-pyrazole-4-sulfonic acid methylamide (0.066 g, 0.35 mmol) and 1,1'-(azodicarbonyl)dipiperidine (0.177 g, 0.69 mmol) in THF (2 mL) under $N_2$ was treated with tri-n-butylphosphine (0.139 g, 0.69 mmol). After 16 h the mixture was treated with further 1,1'-(azodicarbonyl)dipiperidine (0.177 g, 0.69 mmol) and tri-n-butylphosphine (0.139 g, 0.69 mmol). After a further 6 h at RT the mixture was treated with water and extracted with EtOAc (×3). The combined organic layers were washed with water and brine, dried over $MgSO_4$, filtered and concentrated to dryness. The residue was purified by silica chromatography (MeOH/DCM gradient 0-10%) to give a solid which was taken up in MeOH (0.5 mL), treated with LiOH (1M, aq., 3 mL) and stirred for 2 h. The mixture was diluted with water and washed with DCM. The aqueous phase was acidified with 1M HCl and extracted with iPrOH/CHCl3 (2×, 1/3). The combined organic layers were washed with water and brine, dried over $MgSO_4$, filtered and concentrated to dryness. The residue was purified by preparative HPLC giving the product as a colourless solid (0.009 g, 5%). LCMS (M−H)− 515, RT 1.03 min. $^1$H NMR (400 MHz, Me-d3-OD): 7.93-7.85 (1H, m), 7.73 (1H, s), 7.66 (1H, d), 7.50 (1H, d), 7.45-7.36 (1H, m), 7.36-7.25 (2H, m), 4.79-4.70 (1H, m), 4.31 (3H, s), 4.25 (2H, s), 3.86 (3H, s), 3.00 (2H, d), 2.58 (3H, s), 2.52 (3H, s).

Example 142

3-(4-chloro-3-((5-methyl-1,1-dioxido-4,5-dihydrobenzo[f][1,2,5]thiadiazepin-2(3H)-yl)methyl)phenyl)-3-(1-methyl-1H-benzo[d][1,2,3]triazol-5-yl)propanoic acid

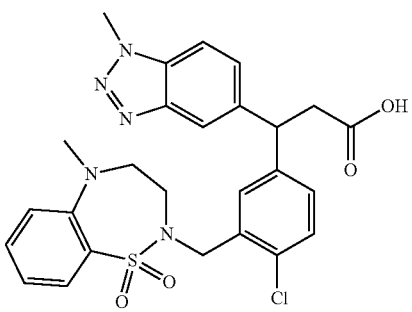 [SMILES: CN1CCN(Cc2cc(C(CC(=O)O)c3ccc4c(c3)nnn4C)ccc2Cl)S(=O)(=O)c2ccccc21]

2-[(2-Hydroxy-ethyl)-methyl-amino]-benzenesulfonamide

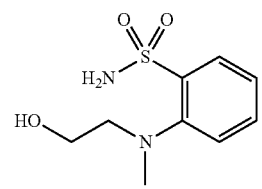

A stirred mixture of 2-fluorobenzenesulfonamide (3.00 g, 17.1 mmol), 2-(methylamino)ethanol (2.57 g, 34.3 mmol), $Cs_2CO_3$ (11.2 g, 34.3 mmol) and DMSO (11 mL) was heated at 120° C. for 48 h. The mixture was cooled to RT, treated with additional 2-(methylamino)ethanol (2.57 g, 34.3 mmol) and $Cs_2CO_3$ (11.2 g, 34.3 mmol), and heated at 120° C. for a further 16 h. After cooling the mixture was diluted with water and extracted with DCM (×3). The combined organic layers were washed with brine, dried over $MgSO_4$, filtered and concentrated to dryness giving a colourless oil (1.8 g, 46%). LCMS MH+ 231, RT 0.93 min.

5-Methyl-2,3,4,5-tetrahydro-benzo[f][1,2,5]thiadiazepine 1,1-dioxide

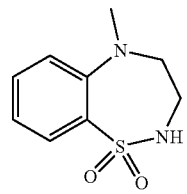

A stirred solution of 2-[(2-Hydroxy-ethyl)-methyl-amino]-benzenesulfonamide (1.20 g, 5.21 mmol) and 1,1'-(azodicarbonyl)dipiperidine (2.66 g, 10.4 mmol) in THF (260 mL) at 4° C. was treated with tri-n-butylphosphine (2.13 g, 10.4 mmol). The mixture was warmed to RT and stirred overnight and then concentrated to dryness. The residue was subjected to silica chromatography (eluting with 50% DCM/petrol followed by 100% DCM). A precipitate formed in one fraction, which was isolated by filtration and dried under vacuum, giving the product as a yellow solid (0.383 g, 76%). A further 0.080 g was obtained by preparative HPLC from impure fractions. LCMS MH+ 213, RT 0.98 min.

3-(4-chloro-3-((5-methyl-1,1-dioxido-4,5-dihydrobenzo[f][1,2,5]thiadiazepin-2(3H)-yl)methyl)phenyl)-3-(1-methyl-1H-benzo[d][1,2,3]triazol-5-yl)propanoic acid

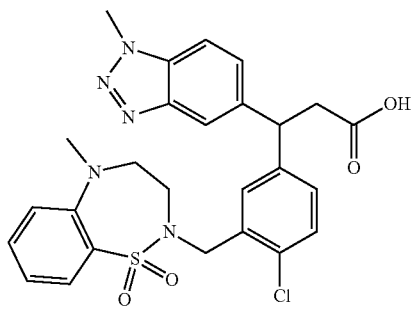 [SMILES: CN1CCN(Cc2cc(C(CC(=O)O)c3ccc4c(c3)nnn4C)ccc2Cl)S(=O)(=O)c2ccccc21]

A stirred solution of 3-(4-Chloro-3-hydroxymethyl-phenyl)-3-(1-methyl-1H-benzotriazol-5-yl)-propionic acid methyl ester (0.254 g, 0.71 mmol), 5-Methyl-2,3,4,5-tetrahydrobenzo[f][1,2,5]thiadiazepine 1,1-dioxide (0.100 g, 0.47 mmol), and 1,1'-(azodicarbonyl)dipiperidine (0.240 g, 0.94 mmol) in THF (2 mL) at 4° C. was treated with tri-n-butylphosphine (0.193 g, 0.94 mmol). Further THF (4 mL) was added due to a thick suspension forming, and the mixture warmed to RT. After 4 h the mixture was cooled to 4° C., and treated with further 1,1'-(azodicarbonyl)dipiperidine (0.240 g, 0.94 mmol) and tri-n-butylphosphine (0.193 g, 0.94 mmol). The mixture was warmed to RT and stirred for 16 h at RT, then treated with NaOH (2M, 2 mL) and stirred for a further 3 h. The mixture was acidified using citric acid and extracted with EtOAc (×3). The combined organic layers were washed with water and brine, dried over MgSO$_4$, filtered and concentrated to dryness. Purification by repeated HPLC gave the product as a colourless oil (0.004 g, 2%). LCMS MH+ 540, RT 1.12 min. $^1$H NMR (400 MHz, Me-d3-OD): 7.88 (1H, s), 7.85 (1H, dd), 7.66 (1H, d), 7.50 (3H, d), 7.34-7.25 (2H, m), 7.18 (1H, d), 7.06 (1H, t), 4.75 (1H, t), 4.31 (5H, s), 3.41 (2H, s), 3.03 (3H, s), 2.99 (2H, dd).

Example 143

3-(1-methyl-1H-1,2,3-benzotriazol-5-yl)-3-{4-methyl-3-[(N-methylbenzenesulfonamido)methyl]phenyl}propanoic acid

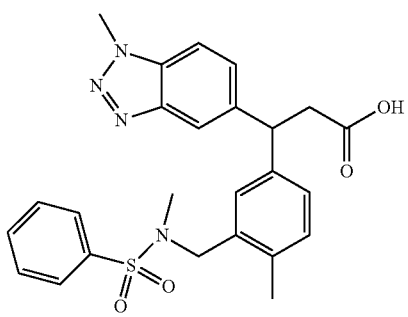 [SMILES: Cc1ccc(C(CC(=O)O)c2ccc3c(c2)nnn3C)cc1CN(C)S(=O)(=O)c1ccccc1]

3-(3-Hydroxymethyl-4-methyl-phenyl)-3-(1-methyl-1H-benzotriazol-5-yl)-propionic acid methyl ester

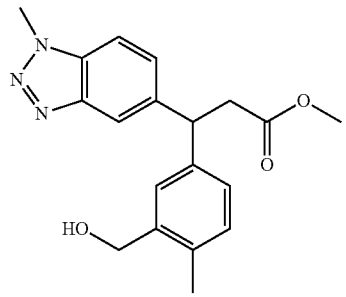 [SMILES: COC(=O)CC(c1ccc(C)c(CO)c1)c1ccc2c(c1)nnn2C]

A stirred mixture of (E)-3-(1-Methyl-1H-benzotriazol-5-yl)-acrylic acid methyl ester (0.325 g, 1.50 mmol), 3-hydroxymethyl-4-methylbenzeneboronic acid (0.498 g, 3.0 mmol), [RhCl(cod)]$_2$ (0.037 g, 0.08 mmol), Et$_3$N (0.3 mL, 2.25 mmol), 1,4-dioxane (5 mL) and water (0.5 mL) was heated at 95° C. for 3 h. After cooling to RT the mixture was diluted with water and extracted with EtOAc (×3). The combined organic layers were washed successively with water and brine, dried over MgSO$_4$, filtered and concentrated to dryness. Purification using silica gel chromatography (EtOAc/petrol gradient 30-80%) gave the product as a white solid (0.406 g, 80%). LCMS (M+H)$^+$ 340, RT 1.16 min.

3-(1-methyl-1H-1,2,3-benzotriazol-5-yl)-3-{4-methyl-3-[(N-methylbenzenesulfonamido) methyl]phenyl}propanoic acid

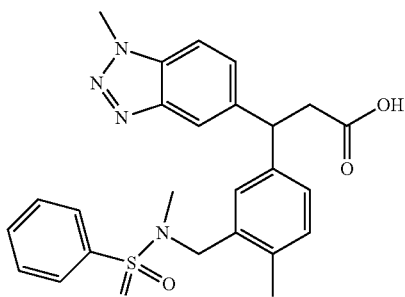

Prepared by a similar procedure to 3-(4-chloro-3-((5-methyl-1,1-dioxido-4,5-dihydrobenzo[f][1,2,5]thiadiazepin-2(3H)-yl)methyl)phenyl)-3-(1-methyl-1H-benzo[d][1,2,3]triazol-5-yl)propanoic acid, using 3-(3-Hydroxymethyl-4-methyl-phenyl)-3-(1-methyl-1H-benzotriazol-5-yl)-propionic acid methyl ester (0.123 mg, 0.36 mmol) and N-methyl benzenesulfonamide (0.062 g, 0.36 mmol), with purification by HPLC (Agilent formic acid) to give the product as a colourless oil (0.040 g, 23%). LCMS (M+H)$^+$ 479, RT 1.06 min.

$^1$H NMR (400 MHz, Me-d3-OD): 7.91-7.82 (3H, m), 7.74-7.60 (4H, m), 7.46 (1H, d), 7.21-7.10 (3H, m), 4.67 (1H, t), 4.29 (3H, s), 4.13 (2H, s), 3.01 (2H, d), 2.46 (3H, s), 2.40-2.30 (3H, m).

Example 144

3-(1-methyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoic acid

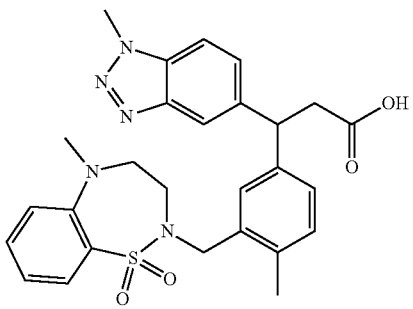 [SMILES: Cc1ccc(C(CC(=O)O)c2ccc3c(c2)nnn3C)cc1CN1CCN(C)c2ccccc2S1(=O)=O]

Prepared using a similar procedure to 3-{4-chloro-3-[(N-methylpyridine-3-sulfonamido)methyl]phenyl}-3-(1-methyl-1H-1,2,3-benzotriazol-5-yl)propanoic acid, using 5-Methyl-2,3,4,5-tetrahydro-benzo[f][1,2,5]thiadiazepine 1,1-dioxide (0.080 g, 0.38 mmol) and 3-(3-Hydroxymethyl-4-methyl-phenyl)-3-(1-methyl-1H-benzotriazol-5-yl)-propionic acid methyl ester (0.192 g, 0.57 mmol), with purification by HPLC (Agilent, formic acid) to give a colourless solid (0.038 g, 19%). LCMS (M+H)⁺ 520, RT 1.10 min.
¹H NMR (400 MHz, Me-d3-OD): 7.90-7.85 (2H, m), 7.66 (1H, d), 7.58-7.50 (1H, m), 7.48 (1H, dd), 7.27-7.13 (4H, m), 7.08 (1H, t), 4.68 (1H, t), 4.31 (3H, s), 4.20 (2H, s), 3.26 (4H, s), 3.14 (2H, d), 3.02 (3H, s), 2.33 (3H, s).

Example 145

3-(7-methoxy-1-methyl-1H-1,2,3-benzotriazol-5-yl)-3-{4-methyl-3-[(N-methylbenzenesulfonamido)methyl]phenyl}propanoic acid

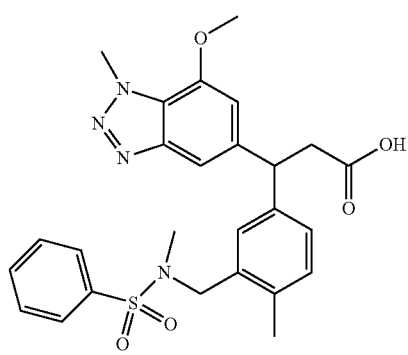 [SMILES: COc1cc(C(CC(=O)O)c2ccc(C)c(CN(C)S(=O)(=O)c3ccccc3)c2)cc2nnn(C)c12]

4-Bromo-2-methoxy-6-nitro-N-methylaniline

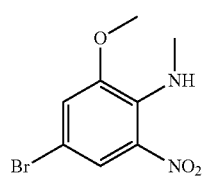

A stirred solution of 2-methoxy-4-bromo-6-nitroaniline (0.525 g, 2.13 mmol) in DMF (3 mL) at 4° C. was treated with NaH (0.051 g, 2.13 mmol). After 30 min the mixture was treated with MeI. After a further 30 min the mixture was diluted with water and filtered. The filtrate was dried to give the product as a red solid, used without further purification (0.486 g, 87%). LCMS MH+ 261/263, RT 1.42 min.

5-Bromo-7-methoxy-1-methyl-1H-benzotriazole

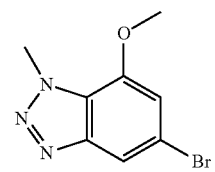

A mixture of 4-Bromo-2-methoxy-6-nitro-N-methylaniline (0.527 g, 2.02 mmol) and zinc powder (0.65 g, 10 mmol) in AcOH (glacial, 15 mL) was stirred at RT for 20 mins. The mixture was filtered through celite, washing with EtOAc. The combined filtrates were concentrated to dryness, and the residue dissolved in H2SO4 (10% aq., 20 mL). After cooling to 4° C., the stirred solution was treated with NaNO₂ (0.167 g, 2.42 mmol) in three portions. After 30 mins, the solution was diluted with water and extracted with EtOAc (3×). The combined organic phases were dried (MgSO4), filtered and concentrated to dryness to give the product, used without further purification (0.515 g, quant.). LCMS (M+H)⁺ 242/244, RT 1.23 min.

(E)-3-(7-Methoxy-1-methyl-1H-benzotriazol-5-yl)-acrylic acid ethyl ester

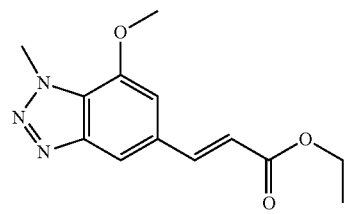 [SMILES: CCOC(=O)/C=C/c1cc(OC)c2c(c1)nnn2C]

A stirred solution of 5-Bromo-7-methoxy-1-methyl-1H-benzotriazole (564 mg, 2.33 mmol) in DMF (15 mL) was treated with ethyl acrylate (0.43 mL, 4.66 mmol) and DIPEA (1.03 mL, 5.81 mmol) and degassed with N2 for 10 min, then treated with Pd(OAc)₂ (0.052 g, 0.23 mmol) and tri-2-tolylphosphine (0.143 g, 0.47 mmol). The mixture was stirred at 140° C. for 90 min, then cooled and diluted with water. Extraction with DCM (3×), drying over MgSO₄, filtration, concentration to dryness and silica chromatography (EtOAc/petrol, gradient 20-70%) gave the product as a white solid (0.582 g, 96%). LCMS (M+H)⁺ 262, RT 1.28 min.

3-(3-Hydroxymethyl-4-methyl-phenyl)-3-(7-methoxy-1-methyl-1H-benzotriazol-5-yl)-propionic acid ethyl ester

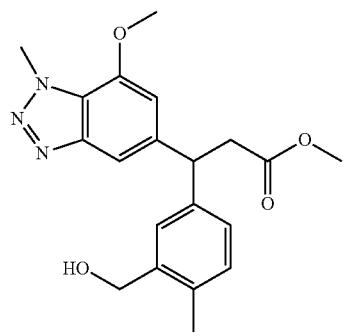 [SMILES: COC(=O)CC(c1ccc(C)c(CO)c1)c1cc(OC)c2c(c1)nnn2C]

Prepared by a similar procedure to 3-(3-Hydroxymethyl-4-methyl-phenyl)-3-(1-methyl-1H-benzotriazol-5-yl)-propionic acid methyl ester, using (E)-3-(7-Methoxy-1-methyl-1H-benzotriazol-5-yl)-acrylic acid ethyl ester (0.261 g, 1 mmol), 3-hydroxymethyl-4-methylbenzeneboronic acid (0.249 g, 1.5 mmol), [RhCl(cod)]$_2$ (0.025 g, 0.05 mmol), Et$_3$N (0.20 mL, 1.5 mmol), 1,4-dioxane (2 mL) and water (0.2 mL), followed by silica chromatography (EtOAc/petrol gradient 0-60%) to give a white solid (0.143 g, 37%). LCMS (M+H)$^+$ 384, RT 1.26 min.

3-(7-methoxy-1-methyl-1H-1,2,3-benzotriazol-5-yl)-3-{4-methyl-3-[(N-methylbenzenesulfonamido)methyl]phenyl}propanoic acid

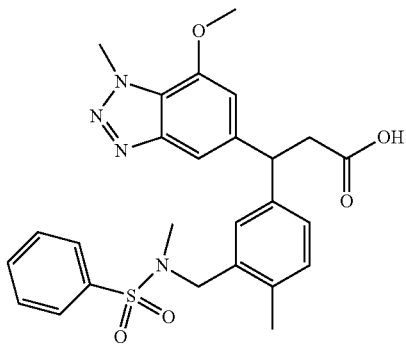 [SMILES: COc1cc(C(CC(=O)O)c2ccc(C)c(CN(C)S(=O)(=O)c3ccccc3)c2)cc2nnn(C)c12]

Prepared by a similar procedure to 3-(4-chloro-3-((5-methyl-1,1-dioxido-4,5-dihydrobenzo[f][1,2,5]thiadiazepin-2(3H)-yl)methyl)phenyl)-3-(1-methyl-1H-benzo[d][1,2,3]triazol-5-yl)propanoic acid, using 3-(3-Hydroxymethyl-4-methyl-phenyl)-3-(7-methoxy-1-methyl-1H-benzotriazol-5-yl)-propionic acid ethyl ester (0.116 mg, 0.30 mmol) and N-methyl benzenesulfonamide (0.052 g, 0.30 mmol), with purification by HPLC to give the product as a colourless glass (0.039 g, 26%). LCMS (M+H)$^+$ 509, RT 1.10 min. $^1$H NMR (400 MHz, Me-d3-OD): 7.84 (2H, d), 7.73-7.55 (3H, m), 7.36 (1H, s), 7.27-7.15 (2H, m), 7.12 (1H, d), 6.83 (1H, s), 4.64 (1H, t), 4.37 (3H, s), 4.11 (2H, s), 3.93 (3H, s), 3.01-2.84 (2H, m), 2.48 (3H, s), 2.33 (3H, s).

Example 146

3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid

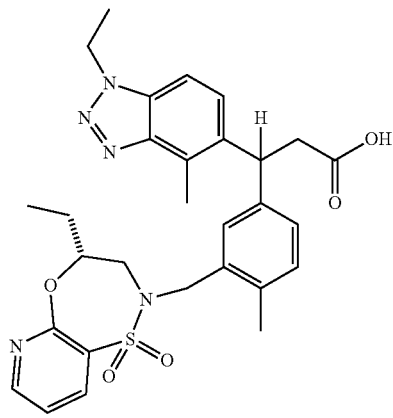 [SMILES: CC[C@@H]1CN(Cc2cc(C(CC(=O)O)c3ccc4c(nnn4CC)c3C)ccc2C)S(=O)(=O)c2cccnc2O1]

Ethyl 3-(1-ethyl-4-methyl-1H-benzo[d][1,2,3]triazol-5-yl)-3-(3-(hydroxymethyl)-4-methylphenyl)propanoate

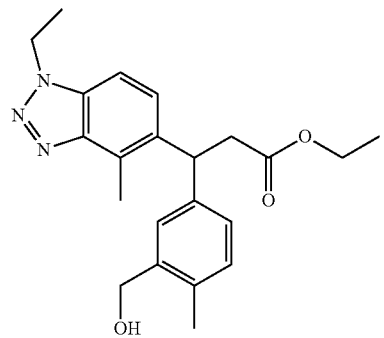 [SMILES: CCOC(=O)CC(c1ccc(C)c(CO)c1)c1ccc2c(nnn2CC)c1C]

(E)-ethyl 3-(1-ethyl-4-methyl-1H-benzo[d][1,2,3]triazol-5-yl)acrylate (1.037 g, 4.0 mmol), (3-(hydroxymethyl)-4-methylphenyl)boronic acid (0.996 g, 6.00 mmol), [RhCl(cod)]$_2$ (0.099 g, 0.200 mmol), and Et$_3$N (0.558 mL, 4.00 mmol) were added to 1,4-dioxane (28 mL), and water (14 mL) and a stream of Ar was bubbled through the mixture for ~2 min. The reaction was stirred under Ar for 3 h at 23° C. The solvent was removed in vacuo and the residue was diluted with DCM (15 mL) and the crude product was purified via silica gel chromatography with a gradient running from DCM to 60% EtOAc in DCM over 30 min. The desired fractions were pooled and concentrated to afford ethyl 3-(1-ethyl-4-methyl-1H-benzo[d][1,2,3]triazol-5-yl)-3-(3-(hydroxymethyl)-4-methylphenyl) propanoate (1.50 g, 3.93 mmol, 98% yield) as a gummy yellow foam. $^1$H NMR (400 MHz, CHLOROFORM-d) δ ppm 0.90-1.09 (m, 3H) 1.46-1.68 (m, 3H) 2.13-2.33 (m, 3H) 2.68-2.87 (m, 3H) 2.88-3.19 (m, 2H) 3.80-4.04 (m, 2H) 4.43-4.65 (m, 4H) 4.84-4.99 (m, 1H) 6.87-7.06 (m, 2H) 7.09-7.17 (m, 1H) 7.17-7.25 (m, 3H) 7.25-7.34 (m, 1H). LC-MS m/z 382.3 (M+H)$^+$, 0.92 (ret. time).

Ethyl 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoate

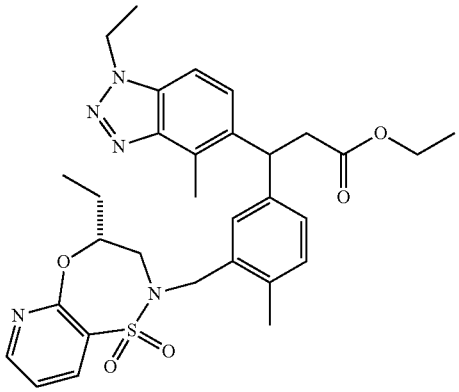 [SMILES: CCOC(=O)CC(c1ccc(C)c(CN2C[C@@H](CC)Oc3ncccc3S2(=O)=O)c1)c1ccc2c(nnn2CC)c1C]

Ethyl 3-(1-ethyl-4-methyl-1H-benzo[d][1,2,3]triazol-5-yl)-3-(3-(hydroxymethyl)-4-methylphenyl)propanoate (1.5 g, 3.93 mmol), (R)-4-ethyl-3,4-dihydro-2H-pyrido[2,3-b][1,4,5]oxathiazepine 1,1-dioxide (0.942 g, 4.13 mmol), and ADDP (1.984 g, 7.86 mmol) were dissolved in THF (42 mL) and tributylphosphine (1.964 mL, 7.86 mmol) was added and the reaction was stirred for 3 h. The solvent was removed in vacuo and the crude product re-dissolved in DCM. and purified via silica gel chromatography. The desired fractions were pooled and concentrated to afford ethyl 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoate (2.3 g, 3.89 mmol, 99% yield). $^1$H NMR (400 MHz, CHLOROFORM-d) δ ppm 0.78-0.97 (m, 3H) 0.98-1.13 (m, 3H) 1.43-1.56 (m, 3H) 2.24 (s, 3H) 2.68-2.82 (m, 3H) 2.86-3.18 (m, 3H) 3.34-3.61 (m, 1H) 3.86-4.00 (m, 2H) 4.16-4.42 (m, 1H) 4.46-4.70 (m, 2H) 4.79-4.98 (m, 1H) 6.87-7.00 (m, 1H) 7.00-7.10 (m, 2H) 7.19 (s, 5H) 8.01-8.25 (m, 1H) 8.11-8.22 (m, 1H) 8.23-8.48 (m, 1H) 8.29-8.50 (m, 1H) 8.30-8.54 (m, 1H).). LC-MS m/z 592.4 (M+H)$^+$, 1.12 (ret. time).

3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid

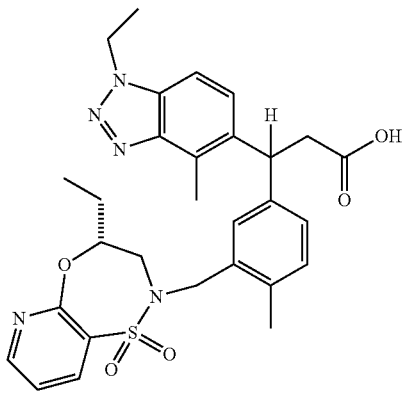 [SMILES: CC[C@@H]1CN(Cc2cc(C(CC(=O)O)c3ccc4c(nnn4CC)c3C)ccc2C)S(=O)(=O)c2cccnc2O1]

Ethyl 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoate (2.3 g, 3.89 mmol) was dissolved in THF (30 mL) and a solution of LiOH (1.862 g, 78 mmol) dissolved in H$_2$O (30.0 mL) was added. Sufficient MeOH (50 mL) was added to form a cloudy solution and the mixture was stirred 2 h. The solvent was removed in vacuo and the residue was diluted with EtOAc (100 mL) and water (40 mL) and the phases were separated. The aqueous phase was combined with 6M HCl (20 mL, 120 mmol) extracted again with EtOAc (75 mL) and the combined organics dried (MgSO$_4$) and concentrated to afford 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (1.84 g, 3.26 mmol, 84% yield). LC-MS m/z 564.2 (M+H)$^+$, 0.95 (ret. time).

The resulting sample was separated into the pure isomers by chiral SFC (supercritical fluid chromatography) Column: Chiralpak AD, 20×250 mm, 5 u; Co-solvent: 30% MeOH; Flow rate: 50 g/min; Back Pressure: 100 bar Desired fractions were collected and dried in vacuo. The dried samples were transferred to pre-weight 20 mL vial with MeOH, and dried under nitrogen stream at 45° C. to afford two isomers.

(S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid

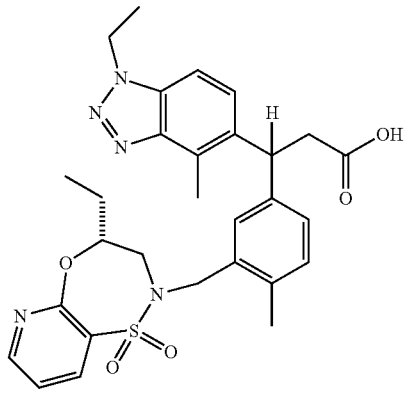 [SMILES: CC[C@@H]1CN(Cc2cc(C(CC(=O)O)c3ccc4c(nnn4CC)c3C)ccc2C)S(=O)(=O)c2cccnc2O1]

The first isomer to elute: $^1$H NMR (400 MHz, CHLOROFORM-d) ppm 0.70-0.94 (m, 3H) 1.46-1.65 (m, 4H) 2.10-2.31 (m, 3H) 2.64-2.80 (m, 3H) 2.84-3.16 (m, 3H) 3.32-3.58 (m, 1H) 3.86-4.04 (m, 1H) 4.15-4.40 (m, 2H) 4.49-4.63 (m, 2H) 4.80-4.95 (m, 1H) 6.91-7.01 (m, 1H) 7.01-7.10 (m, 2H) 7.13-7.33 (m, 4H) 8.08-8.22 (m, 1H) 8.33-8.50 (m, 1H).). LC-MS m/z 564.2 (M+H)$^+$, 0.99 (ret. time).

(R)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid

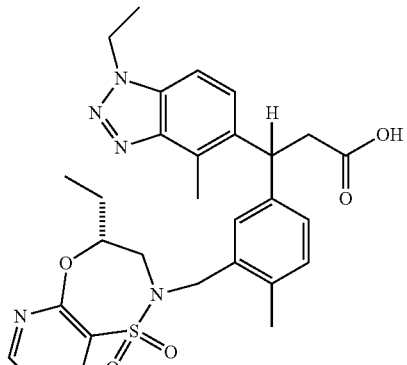

The second isomer to elute: $^1$H NMR (400 MHz, CHLOROFORM-d) δ ppm 0.59-0.86 (m, 3H) 1.32-1.53 (m, 4H) 2.17 (s, 3H) 2.55-2.77 (m, 3H) 2.79-3.09 (m, 3H) 3.23-3.50 (m, 3H) 3.75-3.94 (m, 1H) 4.12-4.37 (m, 1H) 4.42-4.59 (m, 2H) 4.74-4.90 (m, 1H) 6.83-6.93 (m, 1H) 6.94-7.04 (m, 2H) 7.12 (s, 3H) 7.14-7.29 (m, 2H) 8.00-8.19 (m, 1H) 8.25-8.39 (m, 1H). LC-MS m/z 564.2 (M+H)$^+$, 0.97 (ret. time).

(S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid

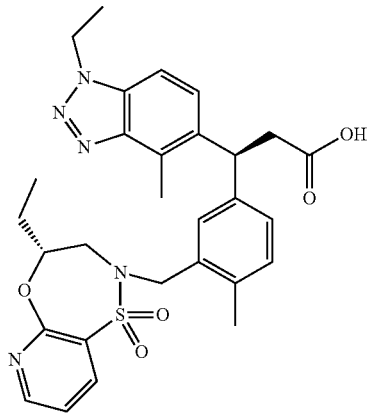 [SMILES: CC[C@@H]1CN(Cc2cc([C@H](CC(=O)O)c3ccc4c(nnn4CC)c3C)ccc2C)S(=O)(=O)c2cccnc2O1]

Tert-butyl (3-methyl-2-nitrophenyl)carbamate

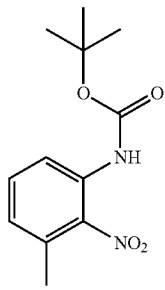

To the mixture of 3-methyl-2-nitrobenzoic acid (30 g, 166 mmol) in tert-butanol (250 mL) was added diphenyl phosphorazidate (50.1 g, 182 mmol) and TEA (25.4 mL, 182 mmol). The reaction mixture was stirred at 82° C. for 10 h after which time 2000 mL of water was added. The resulting precipitate was filtered to afford the title compound tert-butyl (3-methyl-2-nitrophenyl)carbamate (41 g, 135 mmol, 82% yield). LC-MS m/z 153.1 (M-Boc)$^+$, 1.78 (ret. time).

Tert-butyl ethyl(3-methyl-2-nitrophenyl)carbamate

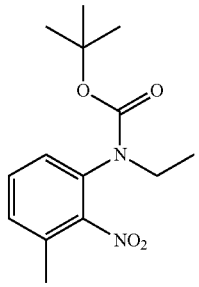 [SMILES: CCN(C(=O)OC(C)(C)C)c1cccc(C)c1[N+](=O)[O-]]

To a solution of tert-butyl (3-methyl-2-nitrophenyl)carbamate (36 g, 143 mmol) in DMF (300 mL) was added NaH (6.28 g, 157 mmol) at 0° C. After the reaction mixture was stirred at 0° C. for 1 h, iodoethane (12.69 mL, 157 mmol) was added. The reaction mixture was stirred at RT for 1 h after which time it was quenched with NH$_4$Cl, extracted with EtOAc (3×30 mL), washed with saturated NaCl, dried with Na$_2$SO$_4$ and concentrated to give the title compound tert-butyl ethyl(3-methyl-2-nitrophenyl)carbamate (39 g, 90%). LC-MS m/z 303.1 (M+Na)$^+$, 1.39 (ret. time).

N-ethyl-3-methyl-2-nitroaniline

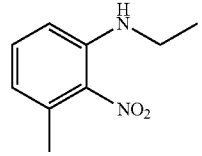

To a solution of tert-butyl methyl (3-methyl-2-nitrophenyl)carbamate (39 g, 146 mmol) in DCM (300 mL), TFA (110 mL, 1428 mmol) was added. The reaction mixture was stirred at 80° C. for 2 h after which time the solvent was removed and the pH adjusted to pH=9, extracted with EtOAc (3×30 mL) and concentrated to give title compound N-ethyl-3-methyl-2-nitroaniline (22 g, 113 mmol, 84% yield). LC-MS m/z 181 (M+H)$^+$, 1.34 (ret. time).

4-Bromo-N-ethyl-3-methyl-2-nitroaniline

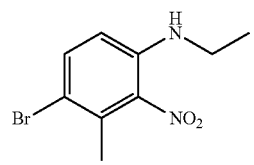

To a solution of N-ethyl-3-methyl-2-nitroaniline (22 g, 113 mmol) in DMF (150 mL), the mixture of NBS (18.11 g, 102 mmol) in DMF (150 mL) was added slowly at 0° C. The resulting reaction mixture was stirred at RT for 16 h after which time it was extracted with EtOAc (3×30 mL), washed with brine, dried with Mg$_2$SO$_4$ and concentrated to afford the title compound 4-bromo-N-ethyl-3-methyl-2-nitroaniline (28 g, 106 mmol, 94% yield). LC-MS m/z 261.0, 262.0 (M+H)$^+$, 1.89 (ret. time).

4-Bromo-N1-ethyl-3-methylbenzene-1,2-diamine

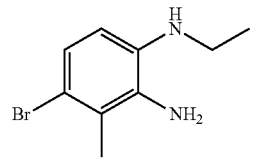

To a solution of 4-bromo-N-ethyl-3-methyl-2-nitroaniline (28 g, 108 mmol) in EtOH (100 mL) was added SnCl$_2$.2H$_2$O (98 g, 432 mmol) in EtOH (100 mL). The reaction mixture was stirred at 95° C. for 2 h. NaOH solution was added until the pH was greater than 14. The solid was filtered to afford the title compound 4-bromo-N1-ethyl-3-methylbenzene-1,2-diamine (17 g, 68.7% yield). LC-MS m/z 230.9 [(M+H)$^+$, 1.58 (ret. time).

5-Bromo-1-ethyl-4-methyl-1H-benzo[d][1,2,3]triazole

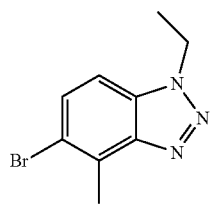

A stirred suspension of 4-bromo-N1-ethyl-3-methylbenzene-1,2-diamine (8 g, 34.9 mmol) in $H_2SO_4$ (7.44 mL, 140 mmol) was treated with a solution of $NaNO_2$ (3.61 g, 52.4 mmol) in water (150 mL). The mixture was stirred at 0° C. for 2 h after which time it was filtered to afford the title compound 5-bromo-1-ethyl-4-methyl-1H-benzo[d][1,2,3]triazole (6.7 g, 26.5 mmol, 76% yield). LC-MS m/z 240.1, 243.1 [(M+H)$^+$, 1.92 (ret. time).

(E)-ethyl 3-(1-ethyl-4-methyl-1H-benzo[d][1,2,3]triazol-5-yl)acrylate

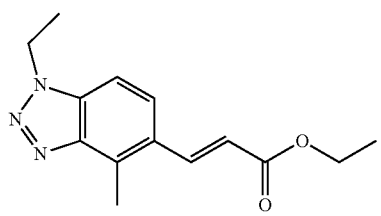 [SMILES: CCOC(=O)/C=C/c1ccc2c(nnn2CC)c1C]

A mixture of tri-o-tolylphosphine (0.849 g, 2.79 mmol), ethyl acrylate (5.59 g, 55.8 mmol), 5-bromo-1-ethyl-4-methyl-1H-benzo[d][1,2,3]triazole (6.7 g, 27.9 mmol), Pd(OAc)$_2$ (0.313 g, 1.395 mmol), and $K_2CO_3$ (7.71 g, 55.8 mmol) in DMF (50 mL) was stirred at 120° C. for 12 h. The reaction mixture was poured into water and extracted with EtOAc (3×30 mL). The organic layer was dried and concentrated. The product was purified over a silica gel column and eluted with hexane:EtOAc (4:1) to give the title compound (E)-ethyl 3-(1-ethyl-4-methyl-1H-benzo[d][1,2,3]triazol-5-yl)acrylate (5 g, 18.50 mmol, 66.3% yield). LC-MS m/z 260.2 [(M+H)$^+$, 1.63 (ret. time).

(R)-1-aminobutan-2-ol

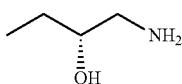

To a solution of NH$_4$OH (~28% solution in H$_2$O) (21.60 mL, 555 mmol) was added (R)-2-ethyloxirane (4 g, 55.5 mmol). The resulting reaction mixture was stirred at RT for 20 h. The reaction mixture was concentrated under reduced pressure to afford the desired product (R)-1-aminobutan-2-ol (4.5 g, 50.5 mmol, 91% yield). $^1$H NMR (400 MHz, CHLOROFORM-d) δ ppm 0.97 (t, J=7.53 Hz, 3H) 1.42-1.53 (m, 2H) 1.71 (br. s., 3H) 2.47-2.59 (m, 1H) 2.85 (dd, J=12.80, 3.26 Hz, 1H) 3.39-3.49 (m, 1H).

(R)-2-chloro-N-(2-hydroxypropyl)pyridine-3-sulfonamide

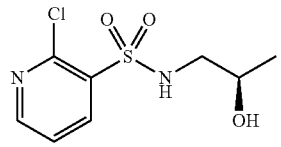

To a solution of (R)-1-amino-2-butanol (2.5 g, 28.0 mmol) in THF (80 mL) and water (16 mL) was added $K_2CO_3$ (2.477 g, 17.92 mmol) followed by 2-chloropyridine-3-sulfonyl chloride (3.8 g, 17.92 mmol). The resulting reaction mixture was stirred at RT for 5 h. The reaction mixture was diluted with H$_2$O (100 mL) and extracted with EtOAc (2×100 mL). The combined organic layer was washed with brine (15 mL), dried over MgSO$_4$ and concentrated under reduced pressure to afford the title compound 2-chloro-N-(2-hydroxybutyl)pyridine-3-sulfonamide (5.1 g, 17.56 mmol, 98% yield). LC-MS m/z 265.1 (M+H)$^+$, 1.29 (ret. time).

(R)-4-ethyl-3,4-dihydro-2H-pyrido[2,3-b][1,4,5]oxathiazepine 1,1-dioxide

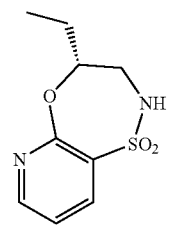

To a solution of (R)-2-chloro-N-(2-hydroxybutyl)pyridine-3-sulfonamide (3 g, 11.33 mmol) in dimethyl sulfoxide (10 mL) was added KOtBu (3.81 g, 34.0 mmol). The resulting reaction was stirred at 80° C. for 2 h. The reaction mixture was diluted with ice H$_2$O (30 mL) and extracted with EtOAc (2×30 mL). The combined organic layer was washed with brine (20 mL), dried over MgSO$_4$ and concentrated under reduced pressure, purified by silica gel chromatography (Hexane:EtOAc) to afford the title compound (R)-4-ethyl-3,4-dihydro-2H-pyrido[2,3-b][1,4,5]oxathiazepine 1,1-dioxide (2.0 g, 8.76 mmol, 77% yield). LC-MS m/z 228.9 (M+H)$^+$, 1.18 (ret. time).

Methyl 5-bromo-2-methylbenzoate

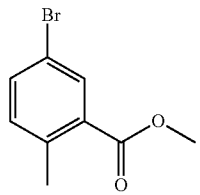

311

To a solution of 5-bromo-2-methylbenzoic acid (15 g, 69.8 mmol) in MeOH (100 mL) was added $H_2SO_4$ (1 mL, 18.76 mmol) slowly under nitrogen at RT. The resulting reaction mixture was stirred at 65° C. for 16 h. Water (50 mL) was added to the reaction mixture and extracted with EtOAc (3×60 mL). The combined organic layer was concentrated to afford the title compound methyl 5-bromo-2-methylbenzoate (15 g, 65.5 mmol, 94% yield). LC-MS MS m/z 231.1 $(M+H)^+$, 1.98 (ret. time)

5-Bromo-2-methylphenyl)methanol

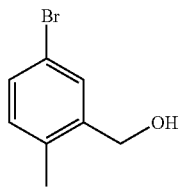

To a solution of methyl 5-bromo-2-methylbenzoate (108 g, 471 mmol) in THF (1600 mL) was added $LiAlH_4$ (21.47 g, 566 mmol) slowly under nitrogen at 0° C. The resulting mixture was stirred at 0° C. for 1 hr. Then 3.73 mL of water was added to the reaction mixture, followed by 3.75 mL of 10% NaOH, and 11.19 mL of water, filtered and concentrated to afford the title compound (5-bromo-2-methylphenyl)methanol (88 g, 416 mmol, 88% yield). LC-MS MS m/z 185.1 (M–OH)+, 1.59 (ret. time)

(2-Methyl-5-(4,4,5,5-tetramethyl-1,3,2-dioxaborolan-2-yl)phenyl)methanol

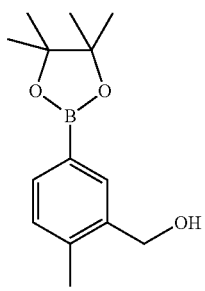 [SMILES: Cc1ccc(B2OC(C)(C)C(C)(C)O2)cc1CO]

To a solution of (5-bromo-2-methylphenyl)methanol (55 g, 274 mmol) in 1,4-dioxane (1000 mL) was added potassium acetate (81 g, 821 mmol) and bis(pinacolato)diboron (104 g, 410 mmol). The reaction mixture was degassed with Argon for 30 min, and then $PdCl_2(dppf)\text{-}CH_2Cl_2$ adduct (13.40 g, 16.41 mmol) was added and the reaction mixture stirred at 100° C. for 16 h after which time it was filtered through a pad of celite. The filtrate was concentrated under reduced pressure. The crude residue was purified via silica gel chromatography using EtOAc:Hexane (3:7) to afford the title compound (2-methyl-5-(4,4,5,5-tetramethyl-1,3,2-dioxaborolan-2-yl)phenyl)methanol (60 g, 230 mmol, 84% yield). LC-MS m/z 271.3 $(M+H)^+$, 1.17 (ret. time).

312

(S)-ethyl 3-(1-ethyl-4-methyl-1H-benzo[d][1,2,3]triazol-5-yl)-3-(3-(hydroxymethyl)-4-methylphenyl)propanoate

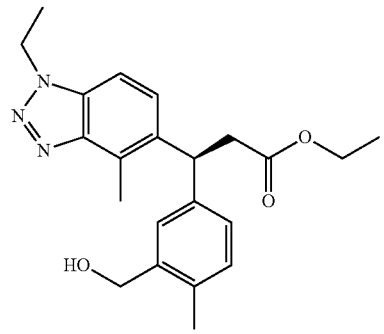 [SMILES: CCOC(=O)C[C@@H](c1ccc(C)c(CO)c1)c1ccc2c(nnn2CC)c1C]

To a solution of (2-methyl-5-(4,4,5,5-tetramethyl-1,3,2-dioxaborolan-2-yl)phenyl)methanol (11.48 g, 46.3 mmol), (E)-ethyl 3-(1-ethyl-4-methyl-1H-benzo[d][1,2,3]triazol-5-yl)acrylate (4 g, 15.43 mmol), Bis(norbornadiene)rhodium (I)tetrafluoroborate (0.577 g, 1.543 mmol), (R)-(+)-2,2'-Bis(di-p-tolylphosphino)-1,1'-binaphthyl (1.131 g, 1.666 mmol) in 1,4-dioxane (100 mL), was added a solution of potassium hydroxide (0.865 g, 15.43 mmol) in water (15.43 mL). The reaction mixture was stirred at 25° C. for 20 h under nitrogen after which time 800 mL of water was added and the reaction extracted with EtOAc (3×80 mL). The organic phase was dried over $Mg_2SO_4$ and concentrated. The crude product was purified by silica gel chromatography (Hexane/EtoAc) to afford ethyl 3-(1-ethyl-4-methyl-1H-benzo[d][1,2,3]triazol-5-yl)-3-(3-(hydroxymethyl)-4-methylphenyl)propanoate (4.0 g, 9.25 mmol, 97.7% yield). LC-MS m/z 382.2 $(M+H)^+$, 1.58 (ret. time).

Ethyl 3-(1-ethyl-4-methyl-1H-benzo[d][1,2,3]triazol-5-yl)-3-(3-(hydroxymethyl)-4-methylphenyl)propanoate (5.2 g) was separated into the pure isomers by chiral SFC (supercritical fluid chromatography)

Instrument: SFC-200 (Thar, Waters); Column: Chiralpak AD-H 50*250 mm 5 um (Daicel); column temperature: 35° C.

Mobile phase: $CO_2$/MeOH (0.5% DEA)=60/40; Flow: 160 g/min; Back pressure: 100 Bar; Cycle time of stack injection: 10.0 min; Load per injection: 208 mg; Dissolve sample in MeOH (41.6 mg/mL); Wavelength: 214 nm Desired fractions were collected and dried in vacuo. The dried sample was and dried under a nitrogen stream at 45° C. to afford 3.8 g of (S)-ethyl 3-(1-ethyl-4-methyl-1H-benzo[d][1,2,3]triazol-5-yl)-3-(3-(hydroxymethyl)-4-methylphenyl)propanoate.

(S)-ethyl 3-(3-(chloromethyl)-4-methylphenyl)-3-(1-ethyl-4-methyl-1H-benzo[d][1,2,3]triazol-5-yl)propanoate

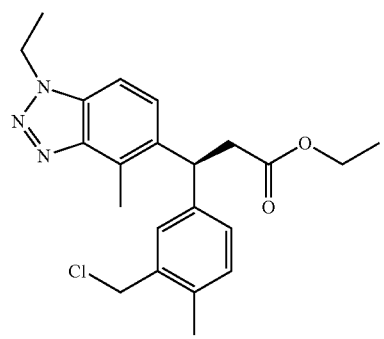 [SMILES: CCOC(=O)C[C@@H](c1ccc(C)c(CCl)c1)c1ccc2c(nnn2CC)c1C]

To a solution of (S)-ethyl 3-(1-ethyl-4-methyl-1H-benzo[d][1,2,3]triazol-5-yl)-3-(3-(hydroxymethyl)-4-methylphenyl)propanoate (3 g, 7.86 mmol) in DCM (30 mL) was added thionyl chloride (0.689 mL, 9.44 mmol) and one drop of DMF. The reaction mixture was stirred at RT for 1 hr. The solvent was removed by reduced pressure to afford the title compound (S)-ethyl 3-(3-(chloromethyl)-4-methylphenyl)-3-(1-ethyl-4-methyl-1H-benzo[d][1,2,3]triazol-5-yl)propanoate (3.1 g, 7.54 mmol, 96% yield). LC-MS m/z 400.2 (M+H)$^+$, 1.77 (ret. time).

(S)-ethyl 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoate

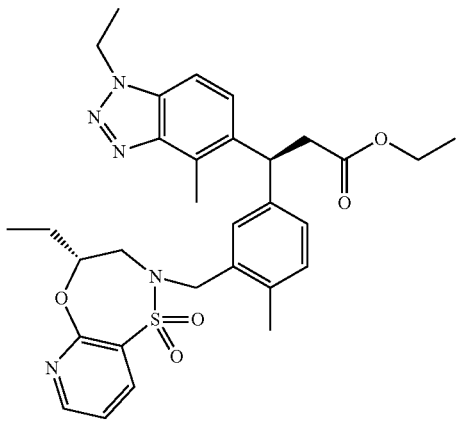 [SMILES: CCOC(=O)C[C@@H](c1ccc(C)c(CN2C[C@@H](CC)Oc3ncccc3S2(=O)=O)c1)c1ccc2c(nnn2CC)c1C]

To a solution of (R)-4-ethyl-3,4-dihydro-2H-pyrido[2,3-b][1,4,5]oxathiazepine 1,1-dioxide (1.946 g, 8.53 mmol) in DMF (50 mL) was added NaH (0.465 g, 11.63 mmol) under nitrogen at 0° C. The reaction mixture was stirred for 10 min, then (S)-ethyl 3-(3-(chloromethyl)-4-methylphenyl)-3-(1-ethyl-4-methyl-1H-benzo[d][1,2,3]triazol-5-yl)propanoate (3.1 g, 7.75 mmol) was added to the reaction mixture. The reaction mixture was stirred at 10° C. for 2 h. Water (50 mL) was added to the reaction mixture and extracted with EtOAc (3×50 mL). The combined organic layer was washed with brine, dried over MgSO$_4$ and concentrated to afford the title compound (S)-ethyl 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoate (4.5 g, 6.90 mmol, 89% yield). LC-MS m/z 592.3 (M+H)$^+$, 2.07 (ret. time).

(S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid

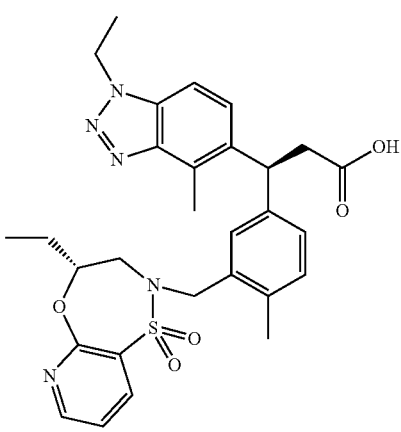 [SMILES: CC[C@@H]1CN(Cc2cc([C@H](CC(=O)O)c3ccc4c(nnn4CC)c3C)ccc2C)S(=O)(=O)c2cccnc2O1]

To a solution of (S)-ethyl 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoate (4.5 g, 6.90 mmol) in MeOH (36 mL) and THF (30.0 mL) was added a solution of NaOH (1.657 g, 41.4 mmol) in water (30.0 mL). The reaction mixture was stirred at 10° C. for 24 h. 2 N HCl was added until pH=1 and the mixture filtered. The solid was washed with ether to afford the title compound (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (3.6 g, 6.39 mmol, 93% yield). LC-MS m/z 564.2 (M+H)$^+$, 1.88 (ret. time).

$^1$H NMR (400 MHz, DMSO-d$_6$) δ ppm 0.95 (t, J=7.15 Hz, 3H) 1.27-1.57 (m, 4H) 1.77 (br. s., 1H) 2.25 (s, 3H) 2.76 (s, 3H) 2.84 (d, J=15.31 Hz, 1H) 3.04 (d, J=8.03 Hz, 2H) 3.57-3.74 (m, 2H) 3.94 (d, J=14.05 Hz, 1H) 4.35 (br. s., 1H) 4.44 (d, J=14.05 Hz, 1H) 4.68 (q, J=7.45 Hz, 2H) 4.81 (t, J=7.91 Hz, 1H) 7.13 (d, J=7.53 Hz, 1H) 7.19-7.28 (m, 2H) 7.47 (d, J=7.78 Hz, 2H) 7.60 (d, J=8.53 Hz, 1H) 8.24 (d, J=7.53 Hz, 1H) 8.56 (d, J=4.77 Hz, 1H) 12.13 (s, 1H).

Example 147

3-(1-Ethyl-4-methyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl)propanoic acid

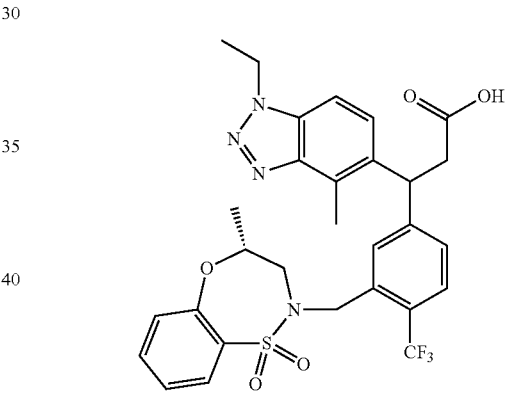

(5-Bromo-2-(trifluoromethyl)phenyl)methanol

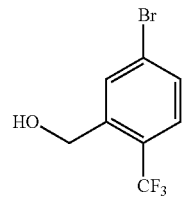

To a solution of 5-bromo-2-(trifluoromethyl)benzoic acid (2.44 g, 9.07 mmol) in THF (25 mL) in ice bath was added 1.0M BH$_3$.THF (27.2 mL, 27.2 mmol). Stirred at RT for 18 h. Afterwards, the reaction was cooled in an ice bath and added 1.0M BH$_3$.THF (27.2 mL, 27.2 mmol). The reaction was stirred at RT for 3 h and quenched with MeOH and dissolved in EtOAc/sat. NaHCO$_3$. The aqueous layer was extracted EtOAc (3×), washed with water, (2×), brine, dried with MgSO$_4$, and concentrated the solvents. The residue was purified by flash chromatography to provide the title compound. (1.95 g, 7.28 mmol, 80%) LC-MS m/z 236.0 (M+H)$^+$, 0.93 min (ret. time).

(5-(4,4,5,5-Tetramethyl-1,3,2-dioxaborolan-2-yl)-2-(trifluoromethyl)phenyl)methanol

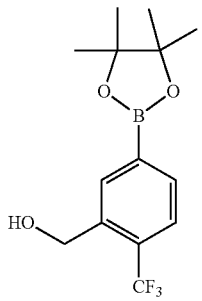 [SMILES: CC1(C)OB(c2ccc(C(F)(F)F)c(CO)c2)OC1(C)C]

To a solution of (5-bromo-2-(trifluoromethyl)phenyl)methanol (1.00 g, 3.92 mmol) in 1,4-dioxane (15 mL) in a 20 mL microwave reaction vessel was added bis(pinacolato)diboron (1.195 g, 4.71 mmol), and potassium acetate (1.154 g, 11.76 mmol). The solution was degassed with nitrogen for 5 min and then (PPh$_3$)$_2$PdCl$_2$ (0.165 g, 0.235 mmol) was added. The reaction was heated on microwave at 150° C. for 20 min. The reaction was filtered through column of Celite and washed with EtOAc. The solvent was concentrated and the residue was dissolved in EtOAc, washed with water (4×), brine, dried with MgSO$_4$ and concentrated. The residue was purified by flash chromatography, eluting with 0-20% acetone/hexane to provide the title compound. (0.727 g, 2.40 mmol, 61%) $^1$H NMR (400 MHz, CHLOROFORM-d) δ ppm 1.38 (s, 12H) 4.91 (s, 2H) 7.67 (d, J=7.53 Hz, 1H) 7.85 (d, J=7.53 Hz, 1H) 8.14 (s, 1H)

Ethyl 3-(1-ethyl-4-methyl-1H-benzo[d][1,2,3]triazol-5-yl)-3-(3-(hydroxymethyl)-4-(trifluoromethyl)phenyl)propanoate

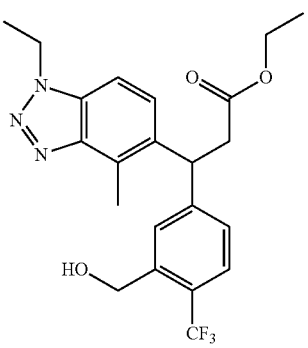 [SMILES: CCOC(=O)CC(c1ccc(C(F)(F)F)c(CO)c1)c1ccc2c(nnn2CC)c1C]

To a solution of (E)-ethyl 3-(1-ethyl-4-methyl-1H-benzo[d][1,2,3]triazol-5-yl)acrylate (0.286 g, 1.103 mmol) and (5-(4,4,5,5-tetramethyl-1,3,2-dioxaborolan-2-yl)-2-(trifluoromethyl)phenyl)methanol (0.350 g, 1.158 mmol) in 1,4-dioxane (15 mL) and water (9.0 mL) was added Et$_3$N (0.231 mL, 1.654 mmol) and [RhCl(cod)]$_2$ (0.030 g, 0.062 mmol). The reaction was heated at 95° C. for 1.5 h. Afterwards, additional (5-(4,4,5,5-tetramethyl-1,3,2-dioxaborolan-2-yl)-2-(trifluoromethyl)phenyl)methanol (0.067 g, 0.221 mmol) was added and heated for 2 h. The reaction was filtered through Celite cartridge and the solvents were concentrated. The residue was purified by flash chromatography, eluting with 0-20% EtOAc/DCM to provide the title compound. (0.280 g, 0.559 mmol, 50%) LC-MS m/z 435.0 (M+H)$^+$, 1.03 min (ret. time).

Ethyl 3-(1-ethyl-4-methyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl)propanoate

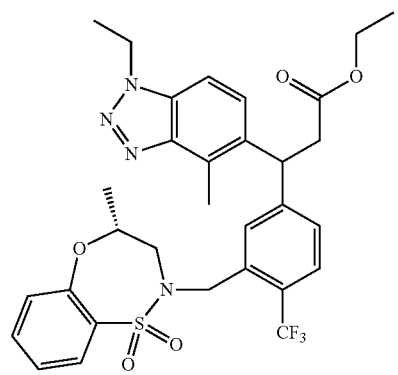 [SMILES: CCOC(=O)CC(c1ccc(C(F)(F)F)c(CN2C[C@@H](C)Oc3ccccc3S2(=O)=O)c1)c1ccc2c(nnn2CC)c1C]

To a solution of ethyl 3-(1-ethyl-4-methyl-1H-benzo[d][1,2,3]triazol-5-yl)-3-(3-(hydroxymethyl)-4-(trifluoromethyl)phenyl)propanoate (0.140 g, 0.280 mmol) and (R)-4-methyl-3,4-dihydro-2H-benzo[b][1,4,5]oxathiazepine 1,1-dioxide (0.072 g, 0.336 mmol) in dry THF (10 mL), at 0° C., was added tributylphosphine (0.140 mL, 0.559 mmol). Reaction stirred for 5 min and then ADDP (0.141 g, 0.559 mmol) was added and stirred at 0° C. for 10 min and then at RT for 6 h. The reaction was cooled in ice bath and tributylphosphine (0.070 mL, 0.280 mmol) was added and stirred for 20 min. ADDP (0.071 g, 0.280 mmol) was then added and stirring was continued at 0° C. and slowly warmed to RT for 18 h. The residue was purified by flash chromatography, eluting with 0-10% EtOAc/DCM to provide the title compound. (0.135 g, 0.214 mmol, 50%) LC-MS m/z 630.0 (M+H)$^+$, 1.25 min (ret. time).

3-(1-Ethyl-4-methyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl)propanoic acid

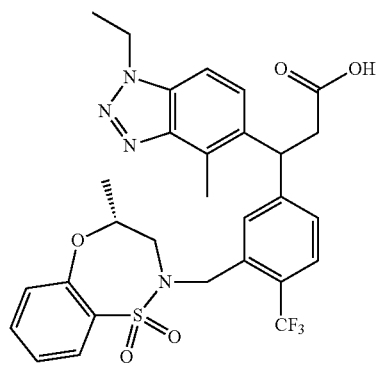 [SMILES: CCn1nnc2c(C)c(C(CC(=O)O)c3ccc(C(F)(F)F)c(CN4C[C@@H](C)Oc5ccccc5S4(=O)=O)c3)ccc21]

To a solution of ethyl 3-(1-ethyl-4-methyl-1H-benzo[d][1,2,3]triazol-5-yl)-3-(3-(((R)-4-methyl-1,1-dioxido-3,4-dihydro-2H-benzo[b][1,4,5]oxathiazepin-2-yl)methyl)-4-(trifluoromethyl)phenyl)propanoate (0.135 g, 0.214 mmol) in THF (1 mL), MeOH (1.000 mL), and water (1.000 mL) was added LiOH (0.015 g, 0.642 mmol) and stirred at RT for 4 h. The solvent was concentrated and the residue was diluted with EtOAc and acidified with 1N HCl. The aqueous layer was extracted with EtOAc (3×). The combined organics were washed with water (2×), brine, dried with MgSO$_4$ and concentrated. The residue was purified by reverse phase preparative HPLC under neutral conditions to provide the title compound (0.102 g, 0.169 mmol, 79%) LC-MS m/z 603.0 (M+H)$^+$, 1.11 min (ret. time).

Example 148

(4R)-2-(5-(1-(1,4-Dimethyl-1H-benzo[d][1,2,3]triazol-5-yl)-2-(1H-tetrazol-5-yl)ethyl)-2-methylbenzyl)-4-methyl-3,4-dihydro-2H-benzo[b][1,4,5]oxathiazepine 1,1-dioxide

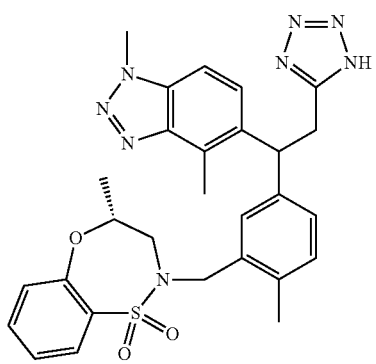 [SMILES: Cc1ccc(C(Cc2nnn[nH]2)c2ccc3c(nnn3C)c2C)cc1CN1C[C@@H](C)Oc2ccccc2S1(=O)=O]

(E)-3-(1,4-Dimethyl-1H-benzo[d][1,2,3]triazol-5-yl)acrylonitrile

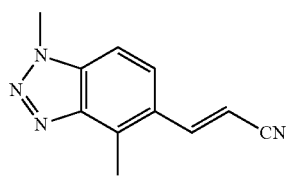

To a solution of 5-bromo-1,4-dimethyl-1H-benzo[d][1,2,3]triazole (1.00 g, 4.42 mmol) in DMF (11 mL) in a 20 mL microwave reaction vessel was added acrylonitrile (1.747 mL, 26.5 mmol), tri-o-tolylphosphine (0.404 g, 1.327 mmol), and DIPEA (3.09 mL, 17.69 mmol). The solution was flushed with nitrogen for 3 min after which Pd(OAc)$_2$ (0.149 g, 0.664 mmol) was added. The reaction was heated on microwave at 150° C. for 2 h. Additional Pd(OAc)$_2$ (0.149 g, 0.664 mmol) was added and heated on microwave at 150° C. for 1.5 h. The reaction was filtered through Celite and washed with EtOAc. The organics were washed with water (3×). Combined organics were washed with brine, dried with MgSO$_4$, and concentrated. The residue was purified by flash chromatography, eluting with 0-10% EtOAc/DCM to provide the title compound. (0.583 g, 2.94 mmol, 66%) LC-MS m/z 199.0 (M+H)$^+$, 0.70 min (ret. time).

3-(1,4-Dimethyl-1H-benzo[d][1,2,3]triazol-5-yl)-3-(3-(hydroxymethyl)-4-methylphenyl)propanenitrile

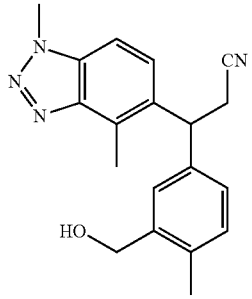 [SMILES: Cc1ccc(C(CC#N)c2ccc3c(nnn3C)c2C)cc1CO]

To a solution of (E)-3-(1,4-dimethyl-1H-benzo[d][1,2,3]triazol-5-yl)acrylonitrile (0.583 g, 2.94 mmol) and (3-(hydroxymethyl)-4-methylphenyl)boronic acid (0.586 g, 3.53 mmol) in 1,4-dioxane (25 mL) and water (15 mL) was added Et$_3$N (0.615 mL, 4.41 mmol) and [RhCl(cod)]$_2$ (0.145 g, 0.294 mmol). The reaction was heated at 95° C. for 3.5 h. The reaction was cooled and the solvents concentrated. The residue was diluted with water and extracted with EtOAc. The combined organics were washed with water (2×), and the aqueous layers were back extracted with EtOAc. The combined organics were washed with water, brine, dried with MgSO$_4$, and concentrated. The residue was purified by flash chromatography, eluting with 0-30% EtOAc/DCM to provide the title compound. (0.62 g, 1.93 mmol, 66%) LC-MS m/z 320.0 (M+H)$^+$, 0.74 min (ret. time).

3-(1,4-Dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanenitrile

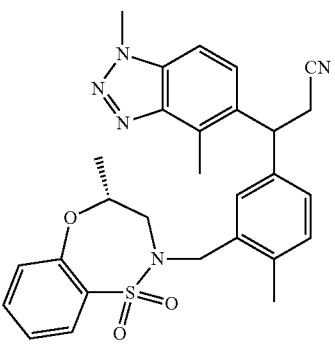 [SMILES: Cc1ccc(C(CC#N)c2ccc3c(nnn3C)c2C)cc1CN1C[C@@H](C)Oc2ccccc2S1(=O)=O]

To a solution of 3-(1,4-dimethyl-1H-benzo[d][1,2,3]triazol-5-yl)-3-(3-(hydroxymethyl)-4-methylphenyl)propanenitrile (0.183 g, 0.543 mmol), (R)-4-methyl-3,4-dihydro-2H-benzo[b][1,4,5]oxathiazepine 1,1-dioxide (0.122 g, 0.570 mmol) and ADDP (0.274 g, 1.085 mmol) in dry THF (15 mL), was added tributylphosphine (0.271 mL, 1.085 mmol) and stirred for 2.5 h. The solvent was concentrated and the residue was purified by flash chromatography, eluting with 0-20% EtOAc/DCM to provide the title compound. (0.267 g, 0.482 mmol, 89%) LC-MS m/z 516.0 (M+H)+, 1.06 min (ret. time).

(4R)-2-(5-(1-(1,4-Dimethyl-1H-benzo[d][1,2,3]triazol-5-yl)-2-(1H-tetrazol-5-yl)ethyl)-2-methylbenzyl)-4-methyl-3,4-dihydro-2H-benzo[b][1,4,5]oxathiazepine 1,1-dioxide

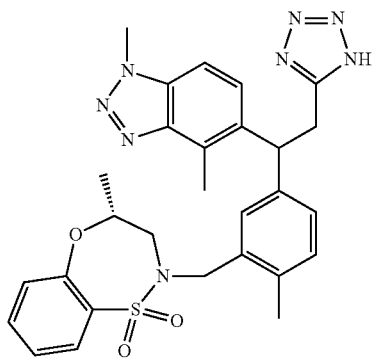 [SMILES: Cc1ccc(C(Cc2nnn[nH]2)c2ccc3c(nnn3C)c2C)cc1CN1C[C@@H](C)Oc2ccccc2S1(=O)=O]

A mixture of 3-(1,4-dimethyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl) propanenitrile (0.217 g, 0.391 mmol), TMSN3 (0.156 mL, 1.174 mmol) and TBAF (0.051 g, 0.196 mmol) in a 20 mL vial, were heated at 85° C. for 3 h. Additional THF (0.50 mL) was added and the reaction was heated for 20 h. Additional TMSN3 (0.156 mL, 1.174 mmol) was added and the reaction was heated for 3 h. Additional TBAF (0.051 g, 0.196 mmol) was added and the reaction was heated for 2.5 days. The solvent was concentrated and the residue was purified by reverse phase preparative HPLC under neutral conditions to provide the title compound (0.101 g, 0.181 mmol, 46%) LC-MS m/z 559.0 (M+H)+, 0.94 min (ret. time).

Example 149

3-(1,4-Dimethyl-1H-benzo[d][1,2,3]triazol-5-yl)-3-(4-methyl-3-(((R)-4-methyl-1,1-dioxido-3,4-dihydro-2H-pyrido[3,2-b][1,4,5]oxathiazepin-2-yl)methyl)phenyl)propanoic acid

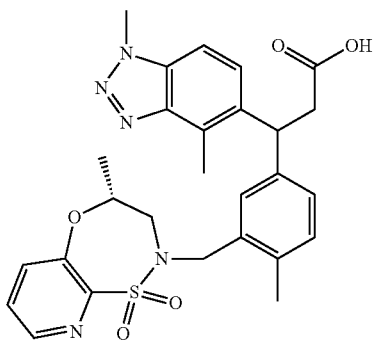 [SMILES: Cc1ccc(C(CC(=O)O)c2ccc3c(nnn3C)c2C)cc1CN1C[C@@H](C)Oc2cccnc2S1(=O)=O]

(R)-3-Fluoro-N-(2-hydroxypropyl)pyridine-2-sulfonamide

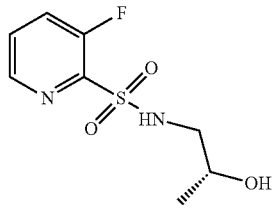

1.6 M n-BuLi in hexanes (21.31 mL, 34.1 mmol) was added, under nitrogen at RT, to a solution of 2.0 M isopropylmagnesium chloride in THF (17.05 mL, 34.1 mmol) that was diluted in additional THF (12 mL), and stirred for 15 min. The solution was then cooled to −10° C. and 2-bromo-3-fluoropyridine (5.00 g, 28.4 mmol) in THF (12.00 mL) was added dropwise via syringe pump over 30 min to this solution and stirred for 45 min. The mixture was then added via syringe pump over 20 min, to a solution of sulfuryl chloride (3.47 mL, 42.6 mmol) in toluene (12.00 mL) at −10° C. and stirred for 20 min. The reaction was warmed to 10° C. and a mixture of (R)-1-aminopropan-2-ol (3.20 g, 42.6 mmol) and DIPEA (14.89 mL, 85 mmol) in THF (5 mL) was added via syringe pump over 30 min and stirred at RT. THF (20 mL) and DCM (20 mL) were added to aid mixing. The reaction was stirred at RT for 18 h. The solvent was concentrated and the residue was purified by flash chromatography, eluting with 0-40-60% EtOAc/DCM. Column was then flushed with 5% MeOH/DCM and all combined residues were purified by flash chromatography, eluting with 0-50% EtOAc/DCM to provide the title compound. (1.29 g, 5.51 mmol, 19%) LC-MS m/z 235.0 (M+H)+, 0.47 min (ret. time).

(R)-4-Methyl-3,4-dihydro-2H-pyrido[3,2-b][1,4,5] oxathiazepine 1,1-dioxide

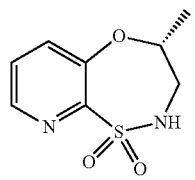

To a solution of (R)-3-fluoro-N-(2-hydroxypropyl)pyridine-2-sulfonamide (1.14 g, 4.38 mmol) in DMF (20 mL) was added KOt-Bu (0.983 g, 8.76 mmol). The reaction was then stirred at 90° C. for 3.5 h. Additional KOt-Bu (0.491 g, 4.38 mmol) was added and heated for 1.3 h. Additional KOt-Bu (0.491 g, 4.38 mmol) was added and the reaction was heated for 19 h. The reaction was cooled and was brought to neutral pH by addition of 1M HCl (8.76 mL, 8.76 mmol). All solvents were concentrated and solids were triturated with DCM and filtered. The residue was purified by flash chromatography, eluting with 0-80% EtOAc/Hexane to provide the title compound. (0.494 g, 1.84 mmol, 42%) LC-MS m/z 215.0 (M+H)+, 0.43 min (ret. time).

321

Ethyl 3-(1,4-dimethyl-1H-benzo[d][1,2,3]triazol-5-yl)-3-(4-methyl-3-(((R)-4-methyl-1,1-dioxido-3,4-dihydro-2H-pyrido[3,2-b][1,4,5]oxathiazepin-2-yl)methyl)phenyl)propanoate

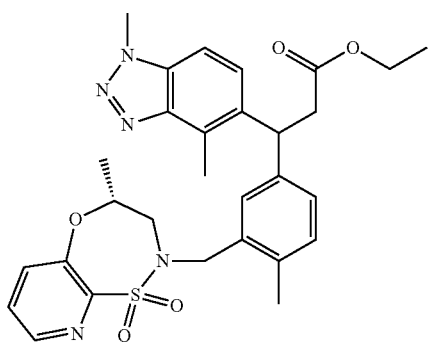 [SMILES: CCOC(=O)CC(c1ccc(C)c(CN2C[C@@H](C)Oc3cccnc3S2(=O)=O)c1)c1ccc2c(nnn2C)c1C]

To a solution of ethyl 3-(1,4-dimethyl-1H-benzo[d][1,2,3]triazol-5-yl)-3-(3-(hydroxymethyl)-4-methylphenyl)propanoate (0.078 g, 0.178 mmol), (R)-4-methyl-3,4-dihydro-2H-pyrido[3,2-b][1,4,5]oxathiazepine 1,1-dioxide (0.050 g, 0.187 mmol) and ADDP (0.090 g, 0.357 mmol) in dry THF (3 mL), was added tributylphosphine (0.089 mL, 0.357 mmol) and stirred for 3 h. Additional tributylphosphine (0.022 mL, 0.089 mmol) was added and stirred for 1 h. Additional ADDP (0.022 g, 0.089 mmol) and stirred for 3.5 h. All solvents were concentrated and the residues were purified by flash chromatography, eluting with 0-50% EtOAc/DCM. Resulting residue was re-purified by flash chromatography, eluting with 0-30% EtOAc/DCM to provide the title compound. (0.087 g, 0.120 mmol, 67%) LC-MS m/z 564.0 (M+H)$^+$, 1.04 min (ret. time).

3-(1,4-Dimethyl-1H-benzo[d][1,2,3]triazol-5-yl)-3-(4-methyl-3-(((R)-4-methyl-1,1-dioxido-3,4-dihydro-2H-pyrido[3,2-b][1,4,5]oxathiazepin-2-yl)methyl)phenyl)propanoic acid

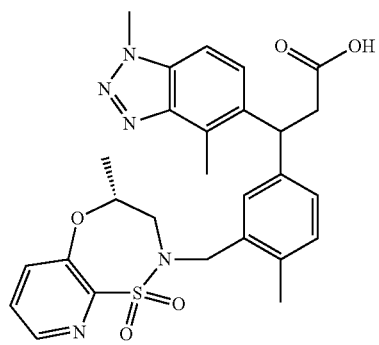 [SMILES: Cc1ccc(C(CC(=O)O)c2ccc3c(nnn3C)c2C)cc1CN1C[C@@H](C)Oc2cccnc2S1(=O)=O]

To a solution of ethyl 3-(1,4-dimethyl-1H-benzo[d][1,2,3]triazol-5-yl)-3-(4-methyl-3-(((R)-4-methyl-1,1-dioxido-3,4-dihydro-2H-pyrido[3,2-b][1,4,5]oxathiazepin-2-yl)methyl)phenyl)propanoate (0.087 g, 0.120 mmol), THF (3 mL) and water (3.00 mL) was added LiOH (0.029 g, 1.204 mmol) and stirred at RT for 20 h. Solution was acidified with 1N HCl and the solvents were concentrated and the residue was purified by reverse phase preparative HPLC under neutral conditions to provide the title compound (0.051 g, 0.095 mmol, 79%) LC-MS m/z 536.0 (M+H)$^+$, 0.86 min (ret. time).

Example 150

5-(1-Ethyl-1H-1,2,3-triazol-4-yl)-3-(4-methyl-3-(((R)-4-methyl-1,1-dioxido-3,4-dihydro-2H-pyrido[3,2-b][1,4,5]oxathiazepin-2-yl)methyl)phenyl)pentanoic acid

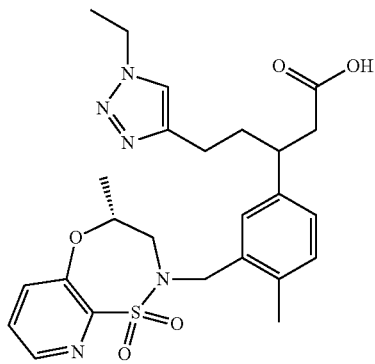 [SMILES: CCn1cc(CCC(CC(=O)O)c2ccc(C)c(CN3C[C@@H](C)Oc4cccnc4S3(=O)=O)c2)nn1]

Ethyl 5-(1-ethyl-1H-1,2,3-triazol-4-yl)-3-(3-(hydroxymethyl)-4-methylphenyl)pentanoate

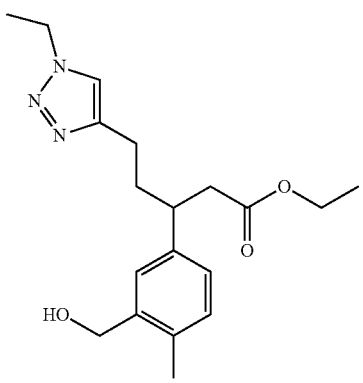 [SMILES: CCOC(=O)CC(CCc1cn(CC)nn1)c1ccc(C)c(CO)c1]

To a solution of (E)-ethyl 5-(1-ethyl-1H-1,2,3-triazol-4-yl)pent-2-enoate (700 mg, 3.14 mmol) in 1,4-dioxane (10 mL) and water (6.67 mL) was added Et$_3$N (0.655 mL, 4.70 mmol), (2-methyl-5-(4,4,5,5-tetramethyl-1,3,2-dioxaborolan-2-yl)phenyl)methanol (817 mg, 3.29 mmol) and [RhCl(cod)]$_2$ (87 mg, 0.176 mmol). The reaction was heated to 95° C. for 2 h. The reaction was cooled and filtered through a pad of celite. The filtrate was concentrated and the residue was purified by flash chromatography, eluting with 0-15% MeOH/DCM to provide the title compound. (0.720 g, 2.08 mmol, 66%) LC-MS m/z 346.0 (M+H)$^+$, 0.83 min (ret. time).

323

Ethyl 5-(1-ethyl-1H-1,2,3-triazol-4-yl)-3-(4-methyl-3-(((R)-4-methyl-1,1-dioxido-3,4-dihydro-2H-pyrido[3,2-b][1,4,5]oxathiazepin-2-yl)methyl)phenyl)pentanoate

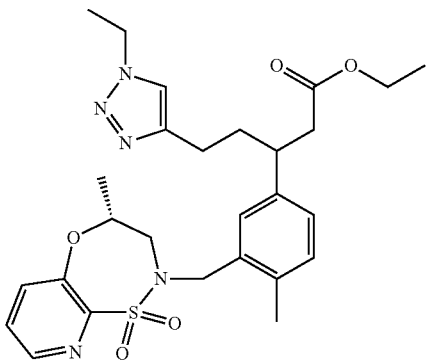 [SMILES: CCOC(=O)CC(CCc1cn(CC)nn1)c1ccc(C)c(CN2C[C@@H](C)Oc3cccnc3S2(=O)=O)c1]

To a solution of ethyl 5-(1-ethyl-1H-1,2,3-triazol-4-yl)-3-(3-(hydroxymethyl)-4-methylphenyl)pentanoate (0.050 g, 0.145 mmol), (R)-4-methyl-3,4-dihydro-2H-pyrido[3,2-b][1,4,5]oxathiazepine 1,1-dioxide (0.041 g, 0.152 mmol) and ADDP (0.073 g, 0.289 mmol) in dry THF (3 mL), was added tributylphosphine (0.072 mL, 0.289 mmol) and stirred at RT for 3.5 h. Additional tributylphosphine (0.072 mL, 0.289 mmol) was added and stirred for 18 h. Additional ADDP (0.073 g, 0.289 mmol) and tributylphosphine (0.181 mL, 0.724 mmol) was then added and stirred for 4 h. The solvent was concentrated and and the residue was purified by reverse phase preparative HPLC under neutral conditions to provide the title compound (0.056 g, 0.103 mmol, 71%) LC-MS m/z 542.0 (M+H)+, 0.99 min (ret. time).

5-(1-Ethyl-1H-1,2,3-triazol-4-yl)-3-(4-methyl-3-(((R)-4-methyl-1,1-dioxido-3,4-dihydro-2H-pyrido[3,2-b][1,4,5]oxathiazepin-2-yl)methyl)phenyl)pentanoic acid

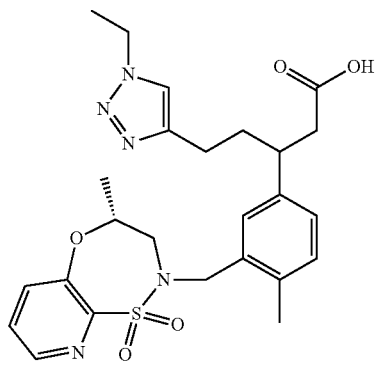 [SMILES: CCn1cc(CCC(CC(=O)O)c2ccc(C)c(CN3C[C@@H](C)Oc4cccnc4S3(=O)=O)c2)nn1]

To a solution of ethyl 5-(1-ethyl-1H-1,2,3-triazol-4-yl)-3-(4-methyl-3-(((R)-4-methyl-1,1-dioxido-3,4-dihydro-2H-pyrido[3,2-b][1,4,5]oxathiazepin-2-yl)methyl)phenyl)pentanoate (0.056 g, 0.103 mmol), in THF (3 mL) and water (3.00 mL) was added LiOH (0.012 g, 0.517 mmol). The reaction mixture was stirred for 21 h. The solvents were concentrated and and the residue was purified by reverse phase preparative HPLC under neutral conditions to provide the title compound (0.024 g, 0.047 mmol, 45%) LC-MS m/z 514.0 (M+H)+, 0.84 min (ret. time).

Example 151

5-(1-Ethyl-1H-1,2,3-triazol-4-yl)-3-(4-methyl-3-((4-methyl-1,1-dioxido-4,5-dihydropyrido[2,34][1,2]thiazepin-2(3H)-yl)methyl)phenyl)pentanoic acid

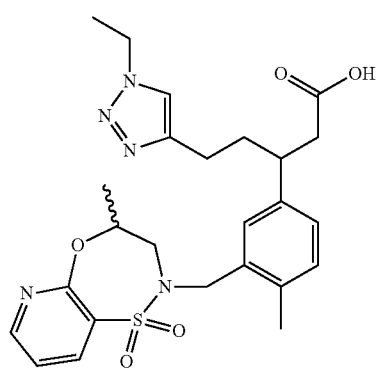 [SMILES: CCn1cc(CCC(CC(=O)O)c2ccc(C)c(CN3CC(C)Oc4ncccc4S3(=O)=O)c2)nn1]

Ethyl 5-(1-ethyl-1H-1,2,3-triazol-4-yl)-3-(4-methyl-3-((4-methyl-1,1-dioxido-4,5-dihydropyrido[2,3-f][1,2]thiazepin-2(3H)-yl)methyl)phenyl)pentanoate

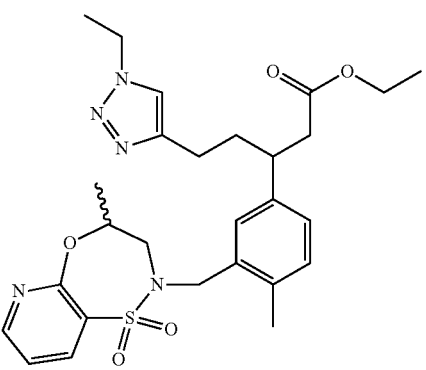 [SMILES: CCOC(=O)CC(CCc1cn(CC)nn1)c1ccc(C)c(CN2CC(C)Oc3ncccc3S2(=O)=O)c1]

To a solution of ethyl 5-(1-ethyl-1H-1,2,3-triazol-4-yl)-3-(3-(hydroxymethyl)-4-methylphenyl)pentanoate (0.050 g, 0.145 mmol), 4-methyl-2,3,4,5-tetrahydropyrido[2,3-f][1,2]thiazepine 1,1-dioxide (0.032 g, 0.152 mmol) and ADDP (0.073 g, 0.289 mmol) in dry THF (3 mL), was added tributylphosphine (0.072 mL, 0.289 mmol) and stirred for 18 h. Additional ADDP (0.073 g, 0.289 mmol) and tributylphosphine (0.145 mL, 0.579 mmol) were added and stirred for 25 h. The solvents were concentrated and the residue was purified by reverse phase preparative HPLC under neutral conditions to provide the title compound (0.040 g, 0.070 mmol, 48%) LC-MS m/z 540.0 (M+H)+, 1.05 min (ret. time).

5-(1-Ethyl-1H-1,2,3-triazol-4-yl)-3-(4-methyl-3-((4-methyl-1,1-dioxido-4,5-dihydropyrido[2,34][1,2]thiazepin-2(3H)-yl)methyl)phenyl)pentanoic acid

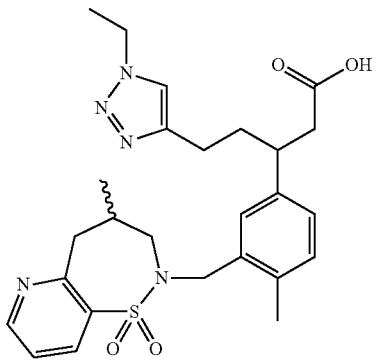 [SMILES: CCn1cc(CCC(CC(=O)O)c2ccc(C)c(CN3CC(C)Cc4ncccc4S3(=O)=O)c2)nn1]

To a solution of ethyl 5-(1-ethyl-1H-1,2,3-triazol-4-yl)-3-(4-methyl-3-((4-methyl-1,1-dioxido-4,5-dihydropyrido[2,3-f][1,2]thiazepin-2(3H)-yl)methyl)phenyl)pentanoate (0.040 g, 0.070 mmol), in THF (3 mL) and water (3.00 mL) was added LiOH (8.43 mg, 0.352 mmol). The reaction mixture was stirred for 21 h. The solvents were concentrated and the residue was purified by reverse phase preparative HPLC under neutral conditions to provide the title compound (0.009 g, 0.018 mmol, 25%) LC-MS m/z 514.0 (M+H)$^+$, 0.83 min (ret. time).

Example 152

5-(1-Ethyl-1H-1,2,3-triazol-4-yl)-3-(4-methyl-3-((4-methyl-1,1-dioxido-4,5-dihydropyrido[4,3-f][1,2]thiazepin-2(3H)-yl)methyl)phenyl)pentanoic acid

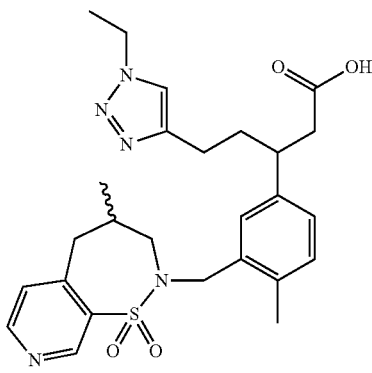 [SMILES: CCn1cc(CCC(CC(=O)O)c2ccc(C)c(CN3CC(C)Cc4ccncc4S3(=O)=O)c2)nn1]

Ethyl 5-(1-ethyl-1H-1,2,3-triazol-4-yl)-3-(4-methyl-3-((4-methyl-1,1-dioxido-4,5-dihydropyrido[4,3-f][1,2]thiazepin-2(3H)-yl)methyl)phenyl)pentanoate

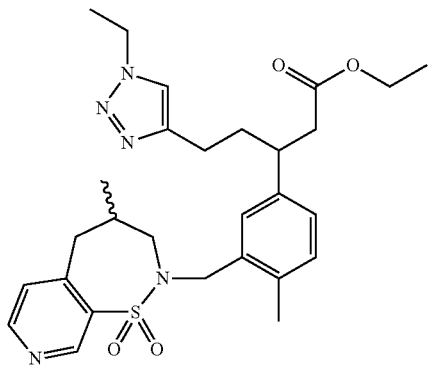 [SMILES: CCOC(=O)CC(CCc1cn(CC)nn1)c1ccc(C)c(CN2CC(C)Cc3ccncc3S2(=O)=O)c1]

To a solution of ethyl 5-(1-ethyl-1H-1,2,3-triazol-4-yl)-3-(3-(hydroxymethyl)-4-methylphenyl)pentanoate (0.050 g, 0.145 mmol), 4-methyl-2,3,4,5-tetrahydropyrido[4,3-f][1,2]thiazepine 1,1-dioxide (0.032 g, 0.152 mmol) and ADDP (0.073 g, 0.289 mmol) in dry THF (3 mL), was added tributylphosphine (0.072 mL, 0.289 mmol) and stirred for 18 h. Additional ADDP (0.073 g, 0.289 mmol) and tributylphosphine (0.145 mL, 0.579 mmol) were added and stirred for 21.5 h. The solvents were concentrated and the residue was purified by reverse phase preparative HPLC under neutral conditions to provide the title compound (0.060 g, 0.096 mmol, 66%) LC-MS m/z 540.0 (M+H)$^+$, 1.02 min (ret. time).

5-(1-Ethyl-1H-1,2,3-triazol-4-yl)-3-(4-methyl-3-((4-methyl-1,1-dioxido-4,5-dihydropyrido[4,3-f][1,2]thiazepin-2(3H)-yl)methyl)phenyl)pentanoic acid

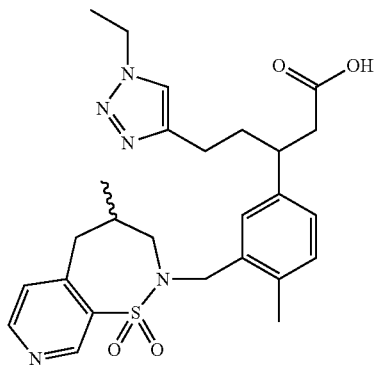 [SMILES: CCn1cc(CCC(CC(=O)O)c2ccc(C)c(CN3CC(C)Cc4ccncc4S3(=O)=O)c2)nn1]

To a solution of ethyl 5-(1-ethyl-1H-1,2,3-triazol-4-yl)-3-(4-methyl-3-((4-methyl-1,1-dioxido-4,5-dihydropyrido[4,3-f][1,2]thiazepin-2(3H)-yl)methyl)phenyl)pentanoate (0.060 g, 0.096 mmol), in THF (3 mL) and water (3.00 mL) was added LiOH (0.011 g, 0.478 mmol). The reaction mixture was stirred for 21 h. The solvents were concentrated and the residue was purified by reverse phase preparative HPLC under neutral conditions to provide the title compound (0.038 g, 0.074 mmol, 78%) LC-MS m/z 512.0 (M+H)$^+$, 0.87 min (ret. time).

Example 153

5-(1-Ethyl-1H-1,2,3-triazol-4-yl)-3-(4-methyl-3-(((R)-4-methyl-1,1-dioxido-3,4-dihydro-2H-pyrido[3,4-b][1,4,5]oxathiazepin-2-yl)methyl)phenyl)pentanoic acid

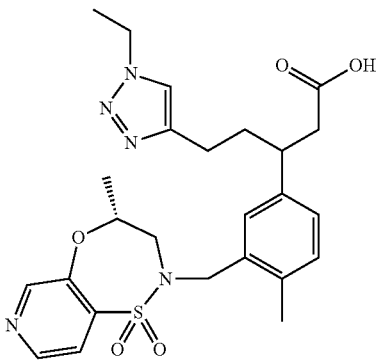 [SMILES: CCn1cc(CCC(CC(=O)O)c2ccc(C)c(CN3C[C@@H](C)Oc4cnccc4S3(=O)=O)c2)nn1]

327

(R)-3-Fluoro-N-(2-hydroxypropyl)pyridine-4-sulfonamide

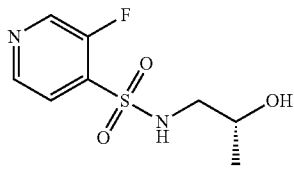

To a solution of 4-bromo-3-fluoropyridine (0.714 g, 4.06 mmol) in THF (30 mL) at −78° C. was added 1.6 M n-BuLi (2.54 mL, 4.06 mmol). After 1 h, 1,4-diazabicyclo[2.2.2]octane bis(sulfur dioxide) adduct (0.975 g, 4.06 mmol) as added at once. The bath was removed after 2 h and reaction warmed to RT over 30 min. The THF was evaporated off and dry DCM (15 mL) was added. N-chlorosuccinimide (0.542 g, 4.06 mmol) in DCM (8 mL) was then added slowly and stirred for 1 h. A solution of (R)-1-aminopropan-2-ol (0.305 g, 4.06 mmol) and DIPEA (1.417 mL, 8.11 mmol) in DCM (5 mL) was then added dropwise and stirred at RT. After completion of reaction was observed by LCMS, the solvents were concentrated and the residue was purified by flash chromatography, eluting with 0-5% MeOH/DCM to provide the title compound. (0.136 g, 0.44 mmol, 11%) LC-MS m/z 235.0 (M+H)$^+$, 0.52 min (ret. time).

(R)-4-Methyl-3,4-dihydro-2H-pyrido[3,4-b][1,4,5]oxathiazepine 1,1-dioxide

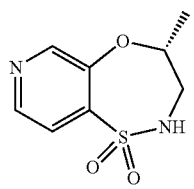

To a solution of (R)-3-fluoro-N-(2-hydroxypropyl)pyridine-4-sulfonamide (0.136 g, 0.447 mmol) in DMF (10 mL) was added KOt-Bu (0.201 g, 1.788 mmol). The reaction was then stirred at 90° C. for 2.5 h and then overnight at 45° C. Additional KOt-Bu (0.201 g, 1.788 mmol) was added and stirred at 45° C. for 2 h. The reaction was cooled and acidified with 1M HCl (0.894 mL, 0.894 mmol) to neutral pH. The solvent was concentrated and the resulting solids were triturated with DCM. The filtrate residue was purified by flash chromatography, eluting with 0-5% MeOH/DCM to provide the title compound. (0.081 g, 0.367 mmol, 82%) LC-MS m/z 215.0 (M+H)$^+$, 0.48 min (ret. time).

328

Ethyl 5-(1-ethyl-1H-1,2,3-triazol-4-yl)-3-(4-methyl-3-(((R)-4-methyl-1,1-dioxido-3,4-dihydro-2H-pyrido[3,4-b][1,4,5]oxathiazepin-2-yl)methyl)phenyl)pentanoate

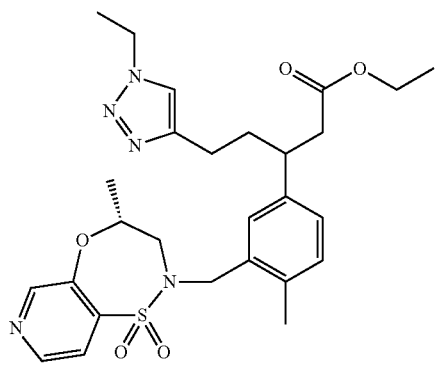 [SMILES: CCOC(=O)CC(CCc1cn(CC)nn1)c1ccc(C)c(CN2C[C@@H](C)Oc3cnccc3S2(=O)=O)c1]

To a solution of ethyl 5-(1-ethyl-1H-1,2,3-triazol-4-yl)-3-(3-(hydroxymethyl)-4-methylphenyl)pentanoate (0.062 g, 0.179 mmol), (R)-4-methyl-3,4-dihydro-2H-pyrido[3,4-b][1,4,5]oxathiazepine 1,1-dioxide (0.040 g, 0.188 mmol) and ADDP (0.091 g, 0.359 mmol) in dry THF (3 mL), was added tributylphosphine (0.179 mL, 0.718 mmol) and stirred for 20 h. The solvents were concentrated and the residue was purified by reverse phase preparative HPLC under neutral conditions to provide the title compound (0.058 g, 0.107 mmol, 59%) LC-MS m/z 542.0 (M+H)$^+$, 0.99 min (ret. time).

5-(1-Ethyl-1H-1,2,3-triazol-4-yl)-3-(4-methyl-3-(((R)-4-methyl-1,1-dioxido-3,4-dihydro-2H-pyrido[3,4-b][1,4,5]oxathiazepin-2-yl)methyl)phenyl)pentanoic acid

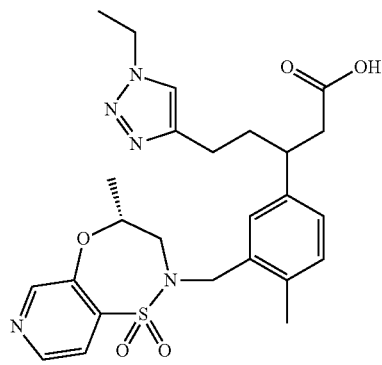

To a solution of ethyl 5-(1-ethyl-1H-1,2,3-triazol-4-yl)-3-(4-methyl-3-(((R)-4-methyl-1,1-dioxido-3,4-dihydro-2H-pyrido[3,4-b][1,4,5]oxathiazepin-2-yl)methyl)phenyl)pentanoate (0.058 g, 0.107 mmol), in THF (3 mL) and water (3.00 mL) was added LiOH (0.013 g, 0.535 mmol). The reaction mixture was stirred for 18 h. The organic solvents were concentrated, and the aqueous layer was acidified with 1N HCl, extracted EtOAc (3×), washed with brine and dried with MgSO$_4$. The solvent was concentrated and the residue was purified by reverse phase preparative HPLC under neutral conditions to provide the title compound (0.035 g, 0.069 mmol, 64%) LC-MS m/z 514.0 (M+H)$^+$, 0.86 min (ret. time).

Example 154

3-(1,4-Dimethyl-1H-benzo[d][1,2,3]triazol-5-yl)-3-(4-methyl-3-(((R)-4-methyl-1,1-dioxido-3,4-dihydro-2H-pyrido[3,4-b][1,4,5]oxathiazepin-2-yl)methyl)phenyl)propanoic acid

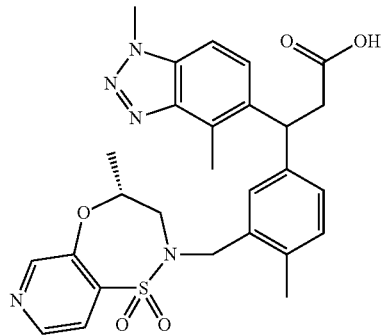 [SMILES: Cc1ccc(C(CC(=O)O)c2ccc3c(nnn3C)c2C)cc1CN1C[C@@H](C)Oc2cnccc2S1(=O)=O]

Ethyl 3-(1,4-dimethyl-1H-benzo[d][1,2,3]triazol-5-yl)-3-(4-methyl-3-(((R)-4-methyl-1,1-dioxido-3,4-dihydro-2H-pyrido[3,4-b][1,4,5]oxathiazepin-2-yl)methyl)phenyl)propanoate

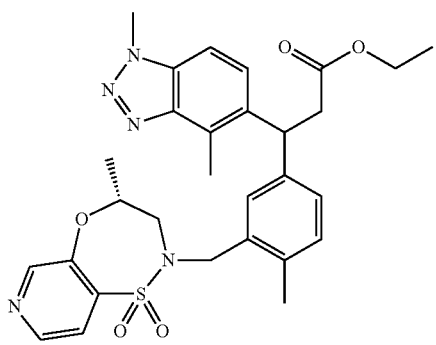 [SMILES: CCOC(=O)CC(c1ccc(C)c(CN2C[C@@H](C)Oc3cnccc3S2(=O)=O)c1)c1ccc2c(nnn2C)c1C]

To a solution of ethyl 3-(1,4-dimethyl-1H-benzo[d][1,2,3]triazol-5-yl)-3-(3-(hydroxymethyl)-4-methylphenyl)propanoate (0.071 g, 0.145 mmol), (R)-4-methyl-3,4-dihydro-2H-pyrido[3,4-b][1,4,5]oxathiazepine 1,1-dioxide (0.034 g, 0.159 mmol) and ADDP (0.076 g, 0.301 mmol) in dry THF (3 mL), was added tributylphosphine (0.151 mL, 0.603 mmol) and stirred for 2 h. The solvent was concentrated and the residue was purified by reverse phase preparative HPLC under neutral conditions to provide the title compound (0.038 g, 0.067 mmol, 46%) LC-MS m/z 542.0 (M+H)$^+$, 1.00 min (ret. time).

3-(1,4-Dimethyl-1H-benzo[d][1,2,3]triazol-5-yl)-3-(4-methyl-3-(((R)-4-methyl-1,1-dioxido-3,4-dihydro-2H-pyrido[3,4-b][1,4,5]oxathiazepin-2-yl)methyl)phenyl)propanoic acid

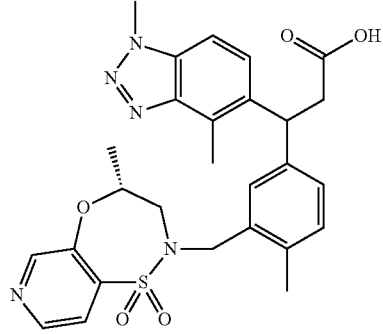 [SMILES: Cc1ccc(C(CC(=O)O)c2ccc3c(nnn3C)c2C)cc1CN1C[C@@H](C)Oc2cnccc2S1(=O)=O]

To a solution of ethyl 3-(1,4-dimethyl-1H-benzo[d][1,2,3]triazol-5-yl)-3-(4-methyl-3-(((R)-4-methyl-1,1-dioxido-3,4-dihydro-2H-pyrido[3,4-b][1,4,5]oxathiazepin-2-yl)methyl)phenyl)propanoate (0.038 g, 0.067 mmol), in THF (3 mL) and water (3.00 mL) was added LiOH (8.07 mg, 0.337 mmol). The reaction mixture was stirred for 18 h. The organic solvents were concentrated, and the aqueous layer was acidified with 1N HCl, extracted EtOAc (3×), washed with brine and dried with MgSO$_4$. The solvent was concentrated and the residue was purified by reverse phase preparative HPLC under neutral conditions to provide the title compound (0.023 g, 0.043 mmol, 63%) LC-MS m/z 514.0 (M+H)$^+$, 0.90 min (ret. time).

Example 155

3-(7-Methoxy-1-methyl-1H-benzo[d][1,2,3]triazol-5-yl)-3-(4-methyl-3-((4-methyl-1,1-dioxido-3,4-dihydro-2H-benzo[e][1,2]thiazin-2-yl)methyl)phenyl)propanoic acid

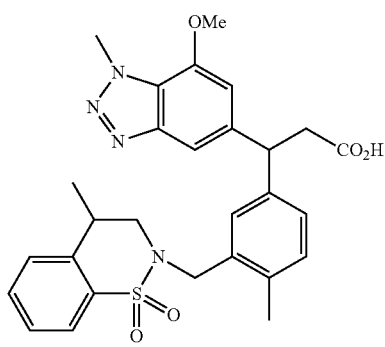 [SMILES: COc1cc(C(CC(=O)O)c2ccc(C)c(CN3CC(C)c4ccccc4S3(=O)=O)c2)cc2nnn(C)c12]

Methyl 2-(1,1-dioxido-3-oxobenzo[d]isothiazol-2(3H)-yl)acetate

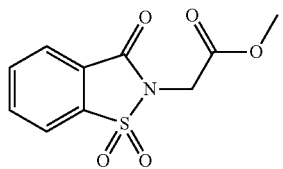 [SMILES: COC(=O)CN1C(=O)c2ccccc2S1(=O)=O]

To a solution of sodium 3-oxo-3H-benzo[d]isothiazol-2-ide 1,1-dioxide (15 g, 73.1 mmol) in DMF (30 mL) was added sodium 3-oxo-3H-benzo[d]isothiazol-2-ide 1,1-dioxide (15 g, 73.1 mmol). The mixture was stirred at 100° C. for 3 h, cooled to RT and poured into cooled water, resulting in an immediate formation of solid. The solid was filtered and washed with water, dried and recrystallized from MeOH. LC-MS: m/z 256 (M+H)⁺ 1.43 min (ret. time).

Methyl 4-hydroxy-2H-benzo[e][1,2]thiazine-3-carboxylate 1,1-dioxide

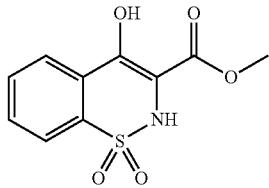 [SMILES: COC(=O)C1=C(O)c2ccccc2S(=O)(=O)N1]

NaOMe (8.25 g, 153 mmol) was suspended in dry DMF (20 mL). and then added to a solution of methyl 2-(1,1-dioxido-3-oxobenzo[d]isothiazol-2(3H)-yl)acetate (13 g, 50.9 mmol) in DMF (5 mL) at 0° C. over 7 min. Upon complete addition of the NaOMe the reaction mixture was allowed to stir for additional 30 min. The product was precipitated from the reaction mixture with the dropwise addition of 1N HCl (4.3 mL), washed with water (200 mL), and dried at 52° C. under vacuum overnight to give methyl 4-hydroxy-2H-benzo[e][1,2]thiazine-3-carboxylate 1,1-dioxide (4.8 g, 18.81 mmol, 36.9% yield). LC-MS: m/z 256 (M+H)⁺ 1.44 min (ret. time).

2H-Benzo[e][1,2]thiazin-4(3H)-one 1,1-dioxide

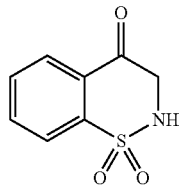 [SMILES: O=C1CNS(=O)(=O)c2ccccc21]

To a solution of methyl 4-hydroxy-2H-benzo[e][1,2]thiazine-3-carboxylate 1,1-dioxide (8.0 g, 31.3 mmol) in HCl (40 mL, 1316 mmol), The reaction mixture was stirred at 110° C. for 8 h. The reaction was cooled to RT, water was added, and extracted with EtOAc. The organic layer washed with water and brine, dried and concentrated to give crude product 2H-benzo[e][1,2]thiazin-4(3H)-one 1,1-dioxide (4.4 g, 22.31 mmol, 71.2% yield). LC-MS: m/z 198 (M+H)⁺ 1.287 min (ret. time).

4-Methylene-3,4-dihydro-2H-benzo[e][1,2]thiazine 1,1-dioxide

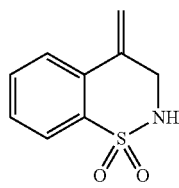

A mixture of bromo(methyl)triphenylphosphorane (8.15 g, 22.82 mmol) in toluene (2 mL) was treated with NaHMDS (22.82 mL, 22.82 mmol) at 0° C. After stirring for 1 h at RT, a solution of 2H-benzo[e][1,2]thiazin-4(3H)-one 1,1-dioxide (1.5 g, 7.61 mmol) in THF (2 mL) was added in dropwise to the above suspension, and the resulting mixture was stirred at RT for 14 h. The solution was then diluted with an aliquot amount of EtOAc and filtered through silica gel. The solvent was removed, and the crude product was purified through silica gel column chromatography (petroleum ether:EtOAc, 3:1) to obtained 4-methylene-3,4-dihydro-2H-benzo[e][1,2]thiazine 1,1-dioxide (430 mg, 2.202 mmol, 29.0% yield). LC-MS: m/z 196 (M+H)⁺, 1.36 min (ret. time).

4-Methyl-3,4-dihydro-2H-benzo[e][1,2]thiazine 1,1-dioxide

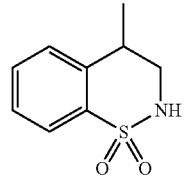

A mixture of 4-methylene-3,4-dihydro-2H-benzo[e][1,2]thiazine 1,1-dioxide (590 mg, 3.02 mmol) and Pd(OH)₂/C (10 mg, 0.071 mmol) in MeOH (20 mL) was stirred for 12 h at RT under a hydrogen atmosphere. The solid was filtered and the filtrate was concentrated under vacuum to afford 4-methyl-3,4-dihydro-2H-benzo[e][1,2]thiazine 1,1-dioxide (520 mg, 2.64 mmol, 87% yield) LC-MS: m/z 198 (M+H)⁺, 1.38 min (ret. time).

Ethyl 3-(3-(bromomethyl)-4-methylphenyl)-3-(7-methoxy-1-methyl-1H-benzo[d][1,2,3]triazol-5-yl)propanoate

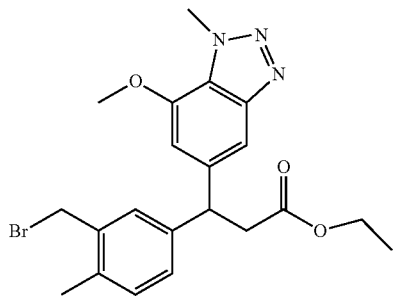 [SMILES: CCOC(=O)CC(c1ccc(C)c(CBr)c1)c1cc(OC)c2c(c1)nnn2C]

To a solution of ethyl 3-(3-(hydroxymethyl)-4-methylphenyl)-3-(7-methoxy-1-methyl-1H-benzo[d][1,2,3]triazol-5-yl)propanoate (400 mg, 1.043 mmol) in DCM (20 mL), was added PBr₃ (0.148 mL, 1.565 mmol) dropwise. The reaction mixture was stirred at 0° C. for 1 h. After which, water was added, and the aqueous layer was extracted with EtOAc, the organic layer washed with water and brine, dried and concentrated to give crude product ethyl 3-(3-(bromomethyl)-4-methylphenyl)-3-(7-methoxy-1-methyl-1H-benzo[d][1,2,3]triazol-5-yl)propanoate (340 mg, 0.762 mmol, 73.0% yield). LC-MS: m/z 446 (M+H)⁺, 1.81 min (ret. time).

333

Ethyl 3-(7-methoxy-1-methyl-1H-benzo[d][1,2,3]
triazol-5-yl)-3-(4-methyl-3-((4-methyl-1,1-dioxido-
3,4-dihydro-2H-benzo[e][1,2]thiazin-2-yl)methyl)
phenyl)propanoate

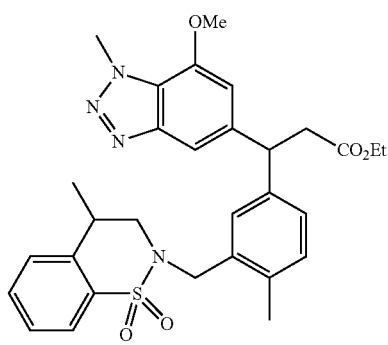 [SMILES: CCOC(=O)CC(c1ccc(C)c(CN2CC(C)c3ccccc3S2(=O)=O)c1)c1cc(OC)c2c(c1)nnn2C]

To a solution of 4-methyl-3,4-dihydro-2H-benzo[e][1,2] thiazine 1,1-dioxide (150 mg, 0.760 mmol) in DMF (20 mL), NaH (36.5 mg, 1.521 mmol) were added at 0° C. The reaction mixture was stirred at 0° C. for 1 h. The solution of ethyl 3-(3-(bromomethyl)-4-methylphenyl)-3-(7-methoxy-1-methyl-1H-benzo[d][1,2,3]triazol-5-yl)propanoate (340 mg, 0.762 mmol) in DMF (4 mL) was added dropwsie. The reaction mixture was stirred at 0° C. for 2 h. The mixture was poured into water (50 mL) and extracted with EtOAc (300 mL). The organic layer was dried and concentrated to crude product, which was purified through silica gel column chromatography (petroleum ether:EtOAc, 1:1) to provide ethyl 3-(7-methoxy-1-methyl-1H-benzo[d][1,2,3]triazol-5-yl)-3-(4-methyl-3-((4-methyl-1,1-dioxido-3,4-dihydro-2H-benzo[e][1,2]thiazin-2-yl)methyl)phenyl)propanoate (160 mg, 0.284 mmol, 37.4% yield). LC-MS: m/z 563 (M+H)+ 1.814 min (ret. time).

3-(7-Methoxy-1-methyl-1H-benzo[d][1,2,3]triazol-
5-yl)-3-(4-methyl-3-((4-methyl-1,1-dioxido-3,4-
dihydro-2H-benzo[e][1,2]thiazin-2-yl)methyl)phe-
nyl)propanoic acid

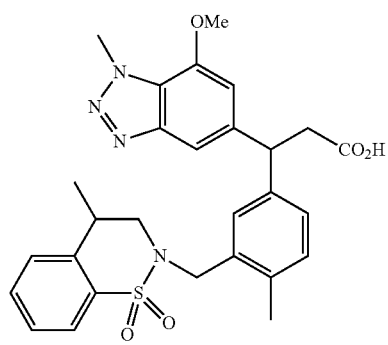 [SMILES: COc1cc(C(CC(=O)O)c2ccc(C)c(CN3CC(C)c4ccccc4S3(=O)=O)c2)cc2nnn(C)c12]

To a solution of ethyl 3-(7-methoxy-1-methyl-1H-benzo [d][1,2,3]triazol-5-yl)-3-(4-methyl-3-((4-methyl-1,1-dioxido-3,4-dihydro-2H-benzo[e][1,2]thiazin-2-yl)methyl) phenyl)propanoate (160 mg, 0.284 mmol) in THF (5 mL)

334 and water (2 mL), was added LiOH (160 mg, 6.68 mmol). The reaction mixture was stirred at 40° C. for 20 h. After which, the reaction mixture was acidified with 1N HCl and extracted with EtOAc. The organic layer was dried and concentrated to get crude product, which was purified by preparative HPLC to afford 3-(7-methoxy-1-methyl-1H-benzo[d][1,2,3]triazol-5-yl)-3-(4-methyl-3-((4-methyl-1,1-dioxido-3,4-dihydro-2H-benzo[e][1,2]thiazin-2-yl)methyl) phenyl)propanoic acid (41 mg, 0.077 mmol, 27.0% yield). LC-MS: m/z 535 (M+H)+ 1.63 min (ret. time)

Example 156

3-(3-((4-Ethyl-1,1-dioxido-3,4-dihydro-2H-benzo[e]
[1,2]thiazin-2-yl)methyl)-4-methylphenyl)-3-(7-
methoxy-1-methyl-1H-benzo[d][1,2,3]triazol-5-yl)
propanoic acid

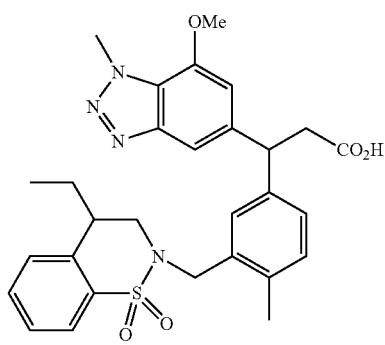 [SMILES: CCC1CN(Cc2cc(C(CC(=O)O)c3cc(OC)c4c(c3)nnn4C)ccc2C)S(=O)(=O)c2ccccc21]

(E)-4-Ethylidene-3,4-dihydro-2H-benzo[e][1,2]thi-
azine 1,1-dioxide

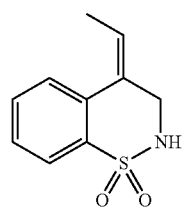

A mixture of bromo(ethyl)triphenylphosphorane (11.30 g, 30.4 mmol) in toluene (2 mL) was treated with NaHMDS (30.4 mL, 30.4 mmol) at 0° C. After stirring for 1 h at RT, a solution of 2H-benzo[e][1,2]thiazin-4(3H)-one 1,1-dioxide (2.0 g, 10.14 mmol) in THF (2 mL) was added dropwise to the above suspension, and the resulting mixture was stirred at RT for 14 h. The reaction was diluted with EtOAc and filtered through silica gel. The solvent was removed and the crude product was purified by silica gel column chromatography (petroleum ether:EtOAc, 3:1) to provide (E)-4-ethylidene-3,4-dihydro-2H-benzo[e][1,2]thiazine 1,1-dioxide (530 mg, 2.53 mmol, 24.97% yield). LC-MS: m/z 210 (M+H)+, 1.408 min (ret. time).

335

4-Ethyl-3,4-dihydro-2H-benzo[e][1,2]thiazine 1,1-dioxide

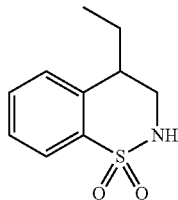

A mixture of (E)-4-ethylidene-3,4-dihydro-2H-benzo[e][1,2]thiazine 1,1-dioxide (570 mg, 2.72 mmol) and Pd(OH)$_2$/C (10 mg, 0.071 mmol) in MeOH (20 mL) was stirred for 12 h at RT under a hydrogen atmosphere. The solid was filtered, and the filtrate was concentrated under vacuum to afford 4-ethyl-3,4-dihydro-2H-benzo[e][1,2]thiazine 1,1-dioxide (510 mg, 2.414 mmol, 89% yield). LC-MS: m/z 212 (M+H)$^+$, 1.467 min (ret. time).

Ethyl 3-(3-((4-ethyl-1,1-dioxido-3,4-dihydro-2H-benzo[e][1,2]thiazin-2-yl)methyl)-4-methylphenyl)-3-(7-methoxy-1-methyl-1H-benzo[d][1,2,3]triazol-5-yl)propanoate

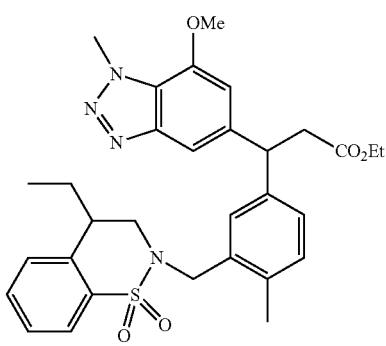 [SMILES: CCOC(=O)CC(c1ccc(C)c(CN2CC(CC)c3ccccc3S2(=O)=O)c1)c1cc(OC)c2c(c1)nnn2C]

To a solution of 4-ethyl-3,4-dihydro-2H-benzo[e][1,2]thiazine 1,1-dioxide (196 mg, 0.928 mmol) in DMF (30 mL), was added NaH (27.8 mg, 1.159 mmol) at 0° C. for 1 h. A solution of ethyl 3-(3-(bromomethyl)-4-methylphenyl)-3-(7-methoxy-1-methyl-1H-benzo[d][1,2,3]triazol-5-yl)propanoate (345 mg, 0.773 mmol) in DMF (10 mL) was added dropwsie to the reaction mixture and stirred at 0° C. for 2 h. The mixture was poured into water (50 mL) and extracted with EtOAc (300 mL). The organic layer was dried and concentrated. The crude residue was purified by silica gel column chromatography (petroleum ether:EtOAc, 1:1) to get ethyl 3-(3-((4-ethyl-1,1-dioxido-3,4-dihydro-2H-benzo[e][1,2]thiazin-2-yl)methyl)-4-methylphenyl)-3-(7-methoxy-1-methyl-1H-benzo[d][1,2,3]triazol-5-yl)propanoate (143 mg, 0.248 mmol, 32.1% yield) LC-MS: m/z 577 (M+H)$^+$ 1.904 min (ret. time).

336

3-(3-((4-Ethyl-1,1-dioxido-3,4-dihydro-2H-benzo[e][1,2]thiazin-2-yl)methyl)-4-methylphenyl)-3-(7-methoxy-1-methyl-1H-benzo[d][1,2,3]triazol-5-yl)propanoic acid

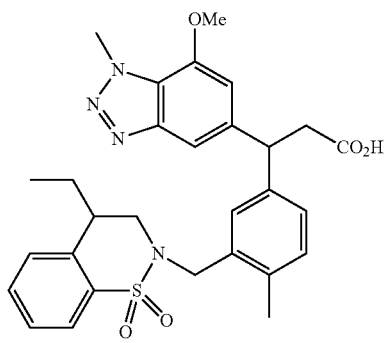 [SMILES: CCC1CN(Cc2cc(C(CC(=O)O)c3cc(OC)c4c(c3)nnn4C)ccc2C)S(=O)(=O)c2ccccc21]

To a solution of ethyl 3-(3-((4-ethyl-1,1-dioxido-3,4-dihydro-2H-benzo[e][1,2]thiazin-2-yl)methyl)-4-methylphenyl)-3-(7-methoxy-1-methyl-1H-benzo[d][1,2,3]triazol-5-yl)propanoate (133 mg, 0.231 mmol) in THF (5 mL) and water (2 mL), was added LiOH (150 mg, 6.26 mmol). The reaction mixture was stirred at 40° C. for 20 h. The reaction mixture was then acidified with HCl (1 N), and extracted with EtOAc. The organic layer was dried and concentrated to provide the crude product, which was purified by preparative HPLC to afford 3-(3-((4-ethyl-1,1-dioxido-3,4-dihydro-2H-benzo[e][1,2]thiazin-2-yl)methyl)-4-methylphenyl)-3-(7-methoxy-1-methyl-1H-benzo[d][1,2,3]triazol-5-yl)propanoic acid (53 mg, 0.097 mmol, 41.9% yield). LC/MS m/z 549 (M+H)$^+$ 1.659 min (ret. time).

Example 157

6-(Benzyl(methyl)amino)-3-(4-methyl-3-(((S)-4-methyl-1,1-dioxido-3,4-dihydro-2H-benzo[b][1,4,5]oxathiazepin-2-yl)methyl)phenyl)-6-oxohexanoic acid

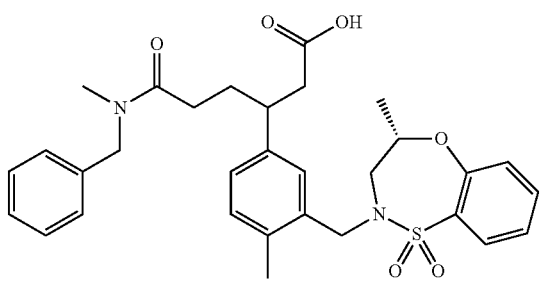 [SMILES: Cc1ccc(C(CCC(=O)N(C)Cc2ccccc2)CC(=O)O)cc1CN1C[C@H](C)Oc2ccccc2S1(=O)=O]

N-Benzyl-4-hydroxy-N-methylbutanamide

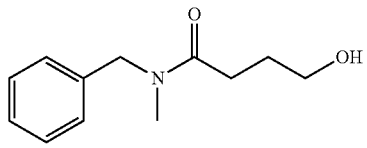

A mixture of dihydrofuran-2(3H)-one (2 g, 23.23 mmol), N-methyl-1-phenylmethanamine (2.82 g, 23.23 mmol) and Et₃N (6.48 mL, 46.5 mmol) was refluxed at 110° C. for 16 h. The reaction was cooled to RT and the solvent was concentrated. The crude residue was purified by flash column chromatography and eluted with 5% MeOH/CHCl₃ to give N-benzyl-4-hydroxy-N-methylbutanamide (1.2 g, 5.53 mmol, 23.80% yield). LC-MS m/z 208 (M+H)⁺, min (ret. time).

N-Benzyl-N-methyl-4-oxobutanamide

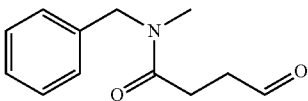

To a solution of oxalyl chloride (0.760 mL, 8.68 mmol) in DCM (20 mL) was added dropwise, a solution of dry DMSO (1.027 mL, 14.47 mmol) in DCM (20 mL) at −78° C. and stirred for 30 min. A solution of N-benzyl-4-hydroxy-N-methylbutanamide (1.2 g, 5.79 mmol) in DCM (20 mL) was then added slowly at same temperature and stirred for 30 min. Then the reaction mixture was quenched with Et₃N (4.03 mL, 28.9 mmol) at −78° C. and allowed to stir at RT. The reaction was diluted with water (50 mL) and extracted with DCM (2×50 mL). The combined organic layers were washed with brine (50 mL), dried over anhydrous Na₂SO₄, filtered and evaporated to provide N-benzyl-N-methyl-4-oxobutanamide (700 mg, 3.41 mmol, 58.9% yield). The residue was carried on to the next step without any further purification. LC-MS m/z 206 (M+H)⁺, 1.31 min (ret. time)

(E)-Ethyl 6-(benzyl(methyl)amino)-6-oxohex-2-enoate

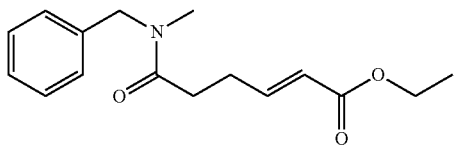 [SMILES: CCOC(=O)/C=C/CCC(=O)N(C)Cc1ccccc1]

To a suspension of NaH (164 mg, 6.82 mmol) in THF (20 mL) was added triethyl phosphonoacetate (1.024 mL, 5.12 mmol) at 0° C. and stirred for 15 min. N-benzyl-N-methyl-4-oxobutanamide (700 mg, 3.41 mmol) in THF (12 mL) was then added to the reaction mixture and stirred at RT for 2 h. The reaction mixture was quenched with cold water, extracted with EtOAc (2×). The combined organics were washed with brine, dried under anhydrous Na₂SO₄ and filtered. The filtrate was concentrated and the crude residue was purified on flash column chromotography by using EtOAc:hexane (80:20) to afford (E)-ethyl 6-(benzyl(methyl) amino)-6-oxohex-2-enoate (500 mg, 1.783 mmol, 52.3% yield). LC-MS m/z 276 (M+H)⁺, 5.06 min (ret. time).

(R)-4-Methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide

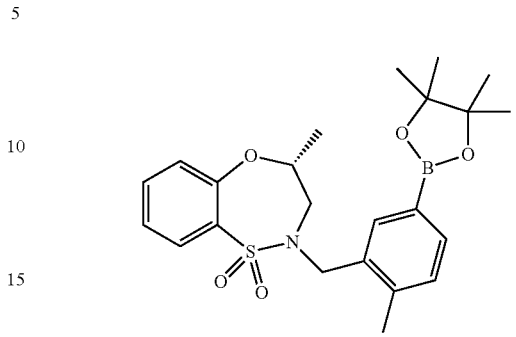

To a solution of (R)-4-methyl-3,4-dihydro-2H-benzo[b][1,4,5]oxathiazepine 1,1-dioxide (20 g, 94 mmol) and (2-methyl-5-(4,4,5,5-tetramethyl-1,3,2-dioxaborolan-2-yl) phenyl)methanol (30.3 g, 122 mmol) in THF (200 mL) was added triphenylphosphine (49.2 g, 188 mmol) and DEAD (29.7 mL, 188 mmol) at 0° C. and stirred for 3 h. The reaction was diluted with water (500 mL) and extracted with EtOAc (2×500 mL). The organic phase washed with brine (500 mL) and dried with anhydrous Na₂SO₄ and evaporated. The crude residue was purified by flash chromatography to provide (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (10.5 g, 23.14 mmol, 24.68% yield). LC-MS m/z 444.31 (M+H)⁺, 7.76 min (ret. time).

Ethyl 6-(benzyl(methyl)amino)-3-(4-methyl-3-(((S)-4-methyl-1,1-dioxido-3,4-dihydro-2H-benzo[b][1,4,5]oxathiazepin-2-yl)methyl)phenyl)-6-oxohexanoate

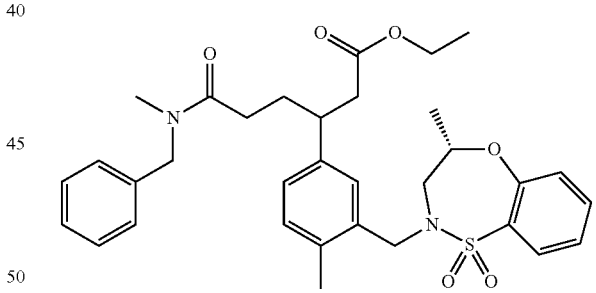

To solution of (E)-ethyl 6-(benzyl(methyl)amino)-6-oxohex-2-enoate (400 mg, 1.453 mmol) and (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (773 mg, 1.743 mmol) in mixture of 1,4-dioxane (2 mL) and water (2 mL) was added TEA (0.607 mL, 4.36 mmol) was degassed with nitrogen for 20 min, followed by the addition of [RhCl(cod)]₂ (71.6 mg, 0.145 mmol). The mixture was heated in a microwave reactor at 120° C. for 1 h. The reaction mixture was filtered through celite. The filtrate was evaporated under reduced pressure and the crude residue was purified on flash column chromatography by using EtOAc:hexane (26:74) to afford ethyl 6-(benzyl (methyl)amino)-3-(4-methyl-3-(((S)-4-methyl-1,1-dioxido-3,4-dihydro-2H-benzo[b][1,4,5]oxathiazepin-2-yl)methyl)

phenyl)-6-oxohexanoate (300 mg, 0.395 mmol, 27.2% yield). LC-MS m/z 593.38 (M+H)⁺, 2.35 min (ret. time).

6-(Benzyl(methyl)amino)-3-(4-methyl-3-(((S)-4-methyl-1,1-dioxido-3,4-dihydro-2H-benzo[b][1,4,5]oxathiazepin-2-yl)methyl)phenyl)-6-oxohexanoic acid

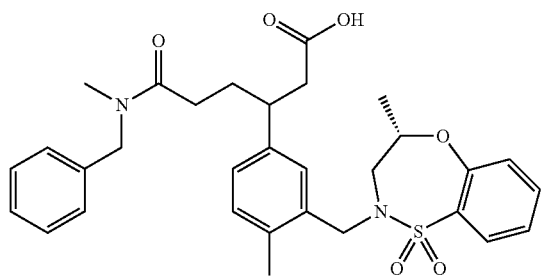 [SMILES: Cc1ccc(C(CCC(=O)N(C)Cc2ccccc2)CC(=O)O)cc1CN1C[C@H](C)Oc2ccccc2S1(=O)=O]

To a solution of ethyl 6-(benzyl(methyl)amino)-3-(4-methyl-3-(((S)-4-methyl-1,1-dioxido-3,4-dihydro-2H-benzo[b][1,4,5]oxathiazepin-2-yl)methyl)phenyl)-6-oxo-hexanoate (200 mg, 0.337 mmol) in EtOH (20 mL) was added 10% NaOH (20 mL, 0.337 mmol) at 0° C. The reaction mixture was stirred at RT for 2 h. The reaction mixture was evaporated under reduced pressure, neutralized with 1N HCl, extracted with DCM (2×), and brine. The organic layer was dried under anhydrous Na₂SO₄, filtered and evaporated under reduced pressure to get crude compound. The crude residue was purified on flash column chromatography by using MeOH:CHCl₃ (5:95) to afford 6-(benzyl(methyl)amino)-3-(4-methyl-3-(((S)-4-methyl-1,1-dioxido-3,4-dihydro-2H-benzo[b][1,4,5]oxathiazepin-2-yl)methyl)phenyl)-6-oxohexanoic acid (125 mg, 0.220 mmol, 65.3% yield). LC-MS m/z 565.43 (M+H)⁺, 1.80 min (ret. time).

Example 158

3-(3-((7-(3-(Dimethylamino)propyl)-4-methyl-1,1-dioxido-4,5-dihydrobenzo[f][1,2]thiazepin-2(3H)-yl)methyl)-4-methylphenyl)-3-(4-fluoro-2-methylphenyl)propanoic acid

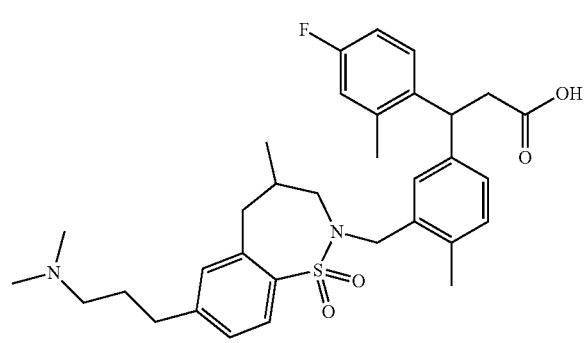 [SMILES: Cc1ccc(C(CC(=O)O)c2ccc(F)cc2C)cc1CN1CC(C)Cc2cc(CCCN(C)C)ccc2S1(=O)=O]

(E)-Ethyl 3-(4-fluoro-2-methylphenyl)acrylate

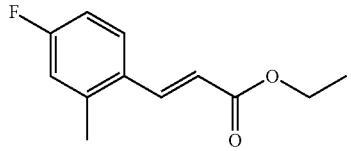

To a suspension of NaH (1.737 g, 72.4 mmol) in THF (80 mL) was added triethyl phosphonoacetate (8.69 mL, 43.4 mmol) at 0° C. The reaction was stirred for 15 min and 4-fluoro-2-methylbenzaldehyde (5 g, 36.2 mmol) in THF (12 mL) was added at 0° C. and the reaction mixture was stirred at rt for 2 h. The reaction mixture was quenched with cold water, extracted with twice EtOAc, and brine. The organic layer was dried under anhydrous Na₂SO₄ and filtered. The filtrate was concentrated and the crude residue was purified by flash column chromatography by using EtOAc:hexane (2:98) to afford (E)-ethyl 3-(4-fluoro-2-methylphenyl)acrylate (5 g, 23.23 mmol, 64.2% yield). LC-MS m/z 209.05 (M+H)⁺, 2.60 min (ret. time).

2,4-Dibromo-N-(2-methylallyl)benzenesulfonamide

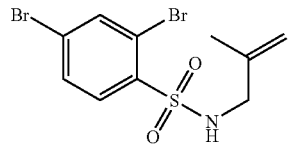 [SMILES: C=C(C)CNS(=O)(=O)c1ccc(Br)cc1Br]

To a solution of 2,4-dibromobenzene-1-sulfonyl chloride (5 g, 14.95 mmol) in DCM (30 mL) was added 2-methyl-prop-2-en-1-amine (1.170 g, 16.45 mmol) and TEA (4.17 mL, 29.9 mmol) at 0° C. The reaction mixture was stirred at RT for 16 h. The reaction mixture was quenched with cold water, extracted with EtOAc (2×), The organic layer washed with brine, dried under anhydrous Na₂SO₄ and filtered. The filtrate was evaporated to afford 2,4-dibromo-N-(2-methylallyl)benzenesulfonamide (4.5 g, 12.15 mmol, 81% yield). LC-MS m/z 367 (M+H)⁺, 2.60 min (ret. time).

7-Bromo-4-methyl-2,3,4,5-tetrahydrobenzo[f][1,2]thiazepine 1,1-dioxide

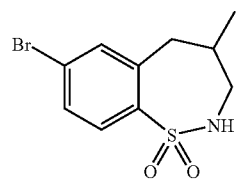

To a solution of 2,4-dibromo-N-(2-methylallyl)benzenesulfonamide (4.5 g, 12.19 mmol) in toluene (40 mL) was added AIBN (0.400 g, 2.439 mmol) and heated at up to 75° C. Tri-n-butyltin chloride (19.84 mL, 73.2 mmol) was added at 75° C. and reaction mixture was stirred at 110° C. for 16 h. The reaction mixture was cooled to RT and was evaporated. The crude residue was purified by flash column chromatography by using EtOAc:hexane (11:89) to give 7-bromo-4-methyl-2,3,4,5-tetrahydrobenzo[f][1,2]thiazepine 1,1-dioxide (2 g, 6.66 mmol, 54.6% yield). LC-MS m/z 288 (M+H)+, 3.57 min (ret. time).

Ethyl 3-(4-fluoro-2-methylphenyl)-3-(3-(hydroxymethyl)-4-methylphenyl)propanoate

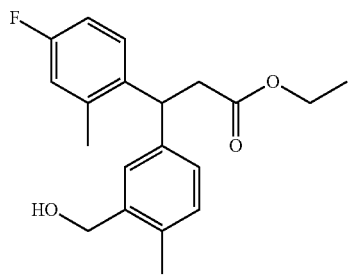 [SMILES: CCOC(=O)CC(c1ccc(C)c(CO)c1)c1ccc(F)cc1C]

To solution of (E)-ethyl 3-(4-fluoro-2-methylphenyl)acrylate (1 g, 4.80 mmol) and (2-methyl-5-(4,4,5,5-tetramethyl-1,3,2-dioxaborolan-2-yl)phenyl)methanol (1.430 g, 5.76 mmol) in mixture of 1,4-dioxane (2 mL) and water (2 mL), in a sealed tube, was added TEA (2.008 mL, 14.41 mmol) and degassed with nitrogen for 20 min. [RhCl(cod)]₂ (0.237 g, 0.480 mmol) was added and the reaction mixture was stirred at 90° C. for 2 h. The reaction mixture was filtered through celite and the filtrate was evaporated under reduced pressure. The crude residue was purified by flash column chromotography by using EtOAc:hexane (25:75) to afford ethyl 3-(4-fluoro-2-methylphenyl)-3-(3-(hydroxymethyl)-4-methylphenyl)propanoate (900 mg, 2.72 mmol, 56.7% yield). ¹H NMR (400 MHz, CDCl₃) δ ppm 7.21 (m, 1H), 7.15 (s, 1H), 7.09 (d, 1H), 7.00 (d, 1H), 6.88 (m, 2H), 4.70 (t, 1H), 4.63 (d, 2H), 4.06 (q, 2H), 2.98 (d, 2H), 2.30 (s, 6H), 1.49 (m, 1H), 1.12 (m, 3H)

Ethyl 3-(3-((7-bromo-4-methyl-1,1-dioxido-4,5-dihydrobenzo[f][1,2]thiazepin-2(3H)-yl)methyl)-4-methylphenyl)-3-(4-fluoro-2-methylphenyl)propanoate

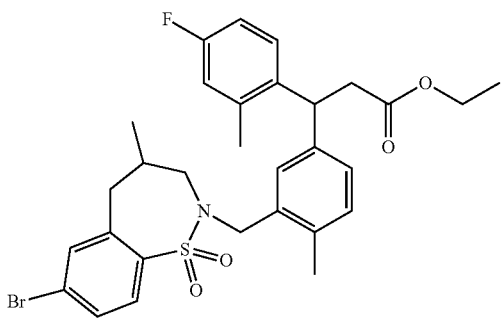 [SMILES: CCOC(=O)CC(c1ccc(C)c(CN2CC(C)Cc3cc(Br)ccc3S2(=O)=O)c1)c1ccc(F)cc1C]

To a suspension of ethyl 3-(4-fluoro-2-methylphenyl)-3-(3-(hydroxymethyl)-4-methylphenyl)propanoate (900 mg, 2.72 mmol) in THF (15 mL) was added 7-bromo-4-methyl-2,3,4,5-tetrahydrobenzo[f][1,2]thiazepine 1,1-dioxide (790 mg, 2.72 mmol) and triphenylphosphine (1429 mg, 5.45 mmol) and stirred for 10 min. Then DEAD (0.863 mL, 5.45 mmol) added at 0° C. and the reaction mixture was stirred for 1 h at RT. The reaction mixture was quenched with cold water, extracted with EtOAc (2×), brine solution, the organic layer was dried under anhydrous Na₂SO₄ and filtered. The filtrate was concentrated and the crude residue was purified by flash column chromotography by using EtOAc:hexane (20:80) to afford ethyl 3-(3-((7-bromo-4-methyl-1,1-dioxido-4,5-dihydrobenzo[f][1,2]thiazepin-2(3H)-yl)methyl)-4-methylphenyl)-3-(4-fluoro-2-methylphenyl)propanoate (1 g, 1.606 mmol, 59.0% yield). LC-MS m/z 602 (M+H)+, 1.59 min (ret. time).

(E)-Ethyl 3-(3-((7-(3-((tert-butoxycarbonyl)amino)prop-1-en-1-yl)-4-methyl-1,1-dioxido-4,5-dihydrobenzo[f][1,2]thiazepin-2(3H)-yl)methyl)-4-methylphenyl)-3-(4-fluoro-2-methylphenyl)propanoate

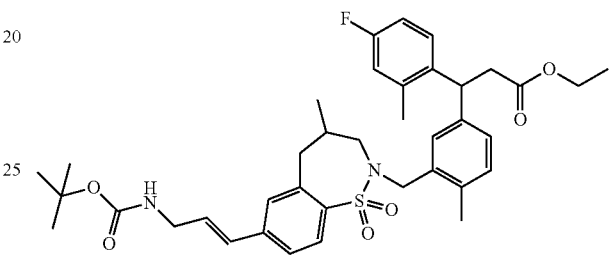

To a solution of ethyl 3-(3-((7-bromo-4-methyl-1,1-dioxido-4,5-dihydrobenzo[f][1,2]thiazepin-2(3H)-yl)methyl)-4-methylphenyl)-3-(4-fluoro-2-methylphenyl)propanoate (600 mg, 0.996 mmol) in DMF (5 mL) was added tert-butyl allylcarbamate (391 mg, 2.489 mmol), tri-O-tolylphosphine (91 mg, 0.299 mmol). The reaction was degassed for 10 min and DIPEA (0.522 mL, 2.99 mmol) and Pd(OAc)₂ (22.36 mg, 0.100 mmol) were added at RT. The reaction mixture was stirred at 90° C. in sealed tube for 2 h. The reaction was quenched with cold water, extracted with EtOAc (2×), the combined organic layers were washed with cold water, brine, dried with anhydrous Na₂SO₄ and filtered. The filtrate was evaporated and purified on flash column chromotography by using EtOAc:hexane (20:80) to afford (E)-ethyl 3-(3-((7-(3-((tert-butoxycarbonyl)amino)prop-1-en-1-yl)-4-methyl-1,1-dioxido-4,5-dihydrobenzo[f][1,2]thiazepin-2(3H)-yl)methyl)-4-methylphenyl)-3-(4-fluoro-2-methylphenyl)propanoate (500 mg, 0.737 mmol, 74.0% yield) LC-MS m/z 679 (M+H)+, 3.22 min (ret. time).

Ethyl 3-(3-((7-(3-((tert-butoxycarbonyl)amino)propyl)-4-methyl-1,1-dioxido-4,5-dihydrobenzo[f][1,2]thiazepin-2(3H)-yl)methyl)-4-methylphenyl)-3-(4-fluoro-2-methylphenyl)propanoate

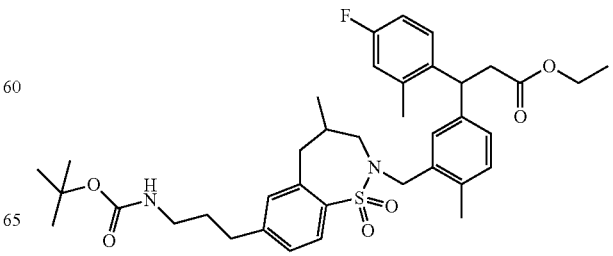

To a solution of ((E)-ethyl 3-(3-((7-(3-((tert-butoxycarbonyl)amino)prop-1-en-1-yl)-4-methyl-1,1-dioxido-4,5-dihydrobenzo[f][1,2]thiazepin-2(3H)-yl)methyl)-4-methylphenyl)-3-(4-fluoro-2-methylphenyl)propanoate (500 mg, 0.737 mmol) in EtOH (30 mL) was added 10% Pd/C (78 mg, 0.737 mmol) under nitrogen atmosphere. The reaction mixture was stirred under hydrogen atmosphere (60 psi) at RT for 6 h. The reaction mixture was filtered through a bed of celite. The filtrate was evaporated under reduced pressure and dried under vacuum to afford ethyl 3-(3-((7-(3-((tert-butoxycarbonyl)amino)propyl)-4-methyl-1,1-dioxido-4,5-dihydrobenzo[f][1,2]thiazepin-2(3H)-yl)methyl)-4-methylphenyl)-3-(4-fluoro-2-methylphenyl)propanoate (400 mg, 0.587 mmol, 80% yield). LC-MS m/z 680 (M+H)+, 3.24 min (ret. time).

Ethyl 3-(3-((7-(3-aminopropyl)-4-methyl-1,1-dioxido-4,5-dihydrobenzo[f][1,2]thiazepin-2(3H)-yl)methyl)-4-methylphenyl)-3-(4-fluoro-2-methylphenyl)propanoate

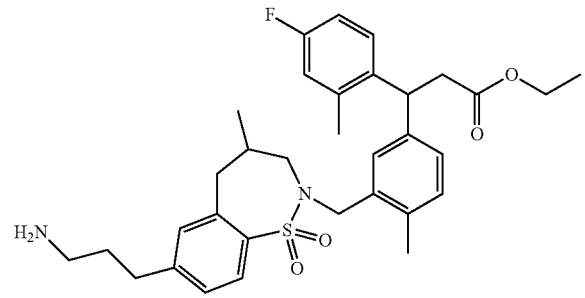 [SMILES: CCOC(=O)CC(c1ccc(C)c(CN2CC(C)Cc3cc(CCCN)ccc3S2(=O)=O)c1)c1ccc(F)cc1C]

To a solution of ethyl 3-(3-((7-(3-((tert-butoxycarbonyl)amino)propyl)-4-methyl-1,1-dioxido-4,5-dihydrobenzo[f][1,2]thiazepin-2(3H)-yl)methyl)-4-methylphenyl)-3-(4-fluoro-2-methylphenyl)propanoate (400 mg, 0.587 mmol) in 1,4-dioxane (10 mL) was added HCl in dioxane (0.018 mL, 0.587 mmol) at 0° C. The reaction was stirred at RT for 3 h. The reaction mixture was evaporated under reduced pressure, cooled to 0° C. and neutralized with saturated NaHCO3 solution. The aqueous layer was extracted with EtOAc (2x) and brine solution. The organic layer was dried with anhydrous Na2SO4 and filtered. The filtrate was evaporated to afford ethyl 3-(3-((7-(3-aminopropyl)-4-methyl-1,1-dioxido-4,5-dihydrobenzo[f][1,2]thiazepin-2(3H)-yl)methyl)-4-methylphenyl)-3-(4-fluoro-2-methylphenyl)propanoate (290 mg, 0.499 mmol, 85% yield). LC-MS m/z 581 (M+H)+, 3.7 min (ret. time).

Ethyl 3-(3-((7-(3-(dimethylamino)propyl)-4-methyl-1,1-dioxido-4,5-dihydrobenzo[f][1,2]thiazepin-2(3H)-yl)methyl)-4-methylphenyl)-3-(4-fluoro-2-methylphenyl)propanoate

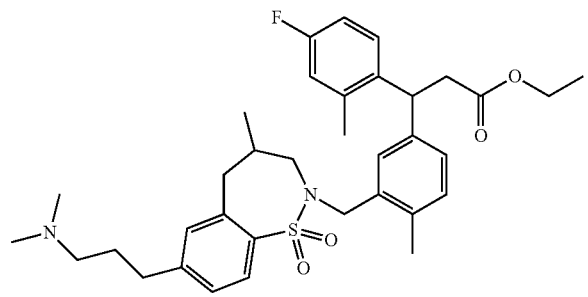 [SMILES: CCOC(=O)CC(c1ccc(C)c(CN2CC(C)Cc3cc(CCCN(C)C)ccc3S2(=O)=O)c1)c1ccc(F)cc1C]

To a solution of ethyl 3-(3-((7-(3-aminopropyl)-4-methyl-1,1-dioxido-4,5-dihydrobenzo[f][1,2]thiazepin-2(3H)-yl)methyl)-4-methylphenyl)-3-(4-fluoro-2-methylphenyl)propanoate (230 mg, 0.396 mmol) in DCM was added 37% formaldehyde (0.109 mL, 3.96 mmol). The reaction was cooled to 0° C. after which Na(OAc)3BH (126 mg, 0.594 mmol) and AcOH (0.045 mL, 0.792 mmol) were added at 0° C. to the reaction mixture and was stirred for 4 h at RT. The reaction mixture was quenched with saturated NaHCO3 solution, extracted with DCM (2x), and washed with a brine solution. The organic layer was dried under anhydrous Na2SO4 and filtered. The filtrate was concentrated to afford ethyl 3-(3-((7-(3-(dimethylamino)propyl)-4-methyl-1,1-dioxido-4,5-dihydrobenzo[f][1,2]thiazepin-2(3H)-yl)methyl)-4-methylphenyl)-3-(4-fluoro-2-methylphenyl)propanoate (200 mg, 0.280 mmol, 70.7% yield). LC-MS m/z 609 (M+H)+, 3.04 min (ret. time). This compound was used for next step without any purification.

3-(3-((7-(3-(Dimethylamino)propyl)-4-methyl-1,1-dioxido-4,5-dihydrobenzo[f][1,2]thiazepin-2(3H)-yl)methyl)-4-methylphenyl)-3-(4-fluoro-2-methylphenyl)propanoic acid

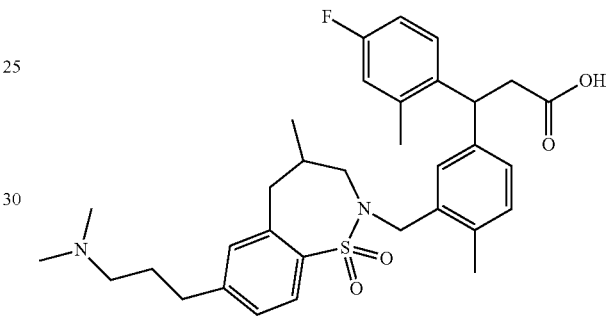

To a solution of (ethyl 3-(3-((7-(3-(dimethylamino)propyl)-4-methyl-1,1-dioxido-4,5-dihydrobenzo[f][1,2]thiazepin-2(3H)-yl)methyl)-4-methylphenyl)-3-(4-fluoro-2-methylphenyl)propanoate (200 mg, 0.329 mmol) in EtOH (10 mL) was added 10% NaOH (15 mL, 0.329 mmol) at 0° C. The reaction mixture was stirred at RT for 2 h. The reaction mixture was evaporated under reduced pressure, cooled to 0° C. and neutralized with 1N HCl. The white solid that formed was filtered and was purified by preparative HPLC to afford 3-(3-((7-(3-(dimethylamino)propyl)-4-methyl-1,1-dioxido-4,5-dihydrobenzo[f][1,2]thiazepin-2(3H)-yl)methyl)-4-methylphenyl)-3-(4-fluoro-2-Methylphenyl)propanoic acid (60 mg, 0.103 mmol, 31.2% yield). LC-MS m/z 581 (M+H)+, 2.10 min (ret. time).

Example 159

3-(4-Methyl-3-(((S)-4-methyl-1,1-dioxido-3,4-dihydro-2H-benzo[b][1,4,5]oxathiazepin-2-yl)methyl)phenyl)-6-(methylamino)-6-oxohexanoic acid

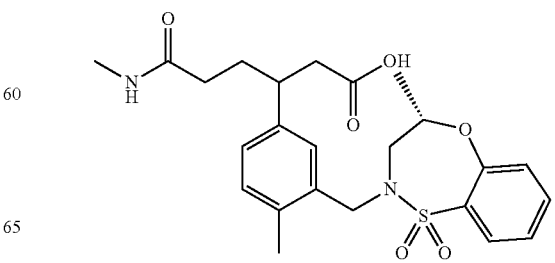

N-benzyl-4-hydroxy-N-methylbutanamide

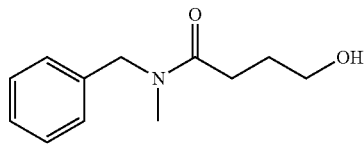

A mixture of dihydrofuran-2(3H)-one (2 g, 23.23 mmol), N-methyl-1-phenylmethanamine (2.82 g, 23.23 mmol) and Et₃N (6.48 mL, 46.5 mmol) was refluxed at 110° C. for 16 h. Afterwards, the reaction was cooled to RT and the solvent was evaporated under vacuum. The crude residue was purified by flash column chromatography eluting with 5% MeOH/CHCl3 to provide N-benzyl-4-hydroxy-N-methylbutanamide (1.2 g, 5.53 mmol, 23.80% yield). LC-MS m/z 208 (M+H)⁺, 1.23 min (ret. time).

N-Benzyl-N-methyl-4-oxobutanamide

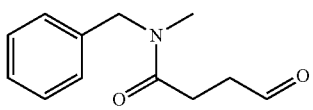

To a solution of oxalyl chloride (0.760 mL, 8.68 mmol) in DCM (20 mL) was added dropwise, a solution of dry DMSO (1.027 mL, 14.47 mmol) in DCM (20 mL) at −78° C. and stirred for 30 min. Then a solution of N-benzyl-4-hydroxy-N-methylbutanamide (1.2 g, 5.79 mmol) in DCM (20 mL) was added slowly at same temperature and stirred for 30 min. The reaction mixture was quenched with Et₃N (4.03 mL, 28.9 mmol) at −78° C. and allowed to warm to RT The solution was diluted with water (50 mL) and extracted with DCM (2×50 mL). The combined organic layers washed with brine (50 mL) and dried over anhydrous Na₂SO₄, filtered and evaporated the under vacuum to provide N-benzyl-N-methyl-4-oxobutanamide (700 mg, 3.41 mmol, 58.9% yield). Which was used to next step without any further purification. LC-MS m/z 206 (M+H)⁺, 1.31 min (ret. time).

(E)-Ethyl 6-(benzyl(methyl)amino)-6-oxohex-2-enoate

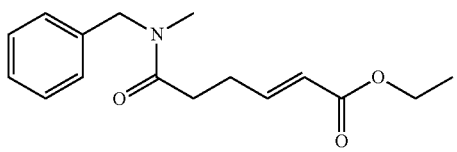 [SMILES: CCOC(=O)/C=C/CCC(=O)N(C)Cc1ccccc1]

To a suspension of NaH (164 mg, 6.82 mmol) in THF (20 mL) was added triethyl phosphonoacetate (1.024 mL, 5.12 mmol) at 0° C. and stirred for 15 min. Then N-benzyl-N-methyl-4-oxobutanamide (700 mg, 3.41 mmol) in THF (12 mL) was added to the reaction mixture and stirred at RT for 2 h. The reaction mixture was quenched with cold water, extracted with EtOAc (2×) and brine solution. The organic layer was dried under anhydrous Na₂SO₄ and filtered. The filtrate was concentrated and the crude residue was purified by flash column chromotography using EtOAc:hexane (80:20 to afford (E)-ethyl 6-(benzyl(methyl)amino)-6-oxohex-2-enoate (500 mg, 1.783 mmol, 52.3% yield) LC-MS m/z 276 (M+H)⁺, 5.96 min (ret. time).

Ethyl 6-(benzyl(methyl)amino)-3-(4-methyl-3-(((S)-4-methyl-1,1-dioxido-3,4-dihydro-2H-benzo[b][1,4,5]oxathiazepin-2-yl)methyl)phenyl)-6-oxohexanoate

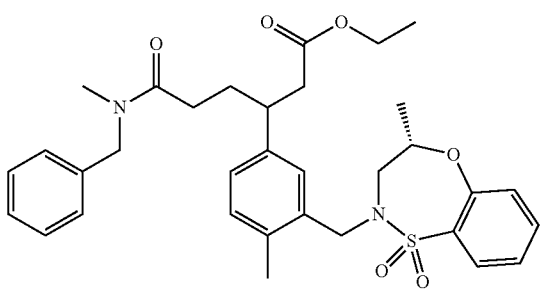 [SMILES: CCOC(=O)CC(CCC(=O)N(C)Cc1ccccc1)c1ccc(C)c(CN2C[C@H](C)Oc3ccccc3S2(=O)=O)c1]

To solution of (E)-ethyl 6-(benzyl(methyl)amino)-6-oxo-hex-2-enoate (400 mg, 1.453 mmol) and (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (773 mg, 1.743 mmol) in mixture of 1,4-dioxane (2 mL) and water (2 mL) in a microwave reaction vessel, was added TEA (0.607 mL, 4.36 mmol) and degassed with nitrogen for 20 min. [RhCl(cod)]₂ (71.6 mg, 0.145 mmol) was added and the reaction mixture was stirred at 120° C. for 1 h. The reaction mixture was filtered through a bed of celite. The filtrate was evaporated under reduced pressure and the crude residue was purified on flash column chromatography using EtOAc:hexane (26:74) to afford ethyl 6-(benzyl (methyl)amino)-3-(4-methyl-3-(((S)-4-methyl-1,1-dioxido-3,4-dihydro-2H-benzo[b][1,4,5]oxathiazepin-2-yl)methyl) phenyl)-6-oxohexanoate (300 mg, 0.395 mmol, 27.2% yield) as liquid. LC-MS m/z 593 (M+H)⁺, 2.35 min (ret. time).

Ethyl 3-(4-methyl-3-(((S)-4-methyl-1,1-dioxido-3,4-dihydro-2H-benzo[b][1,4,5]oxathiazepin-2-yl) methyl)phenyl)-6-(methylamino)-6-oxohexanoate

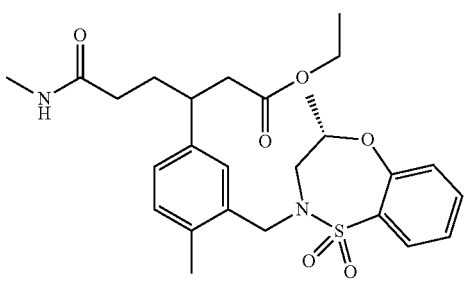 [SMILES: CCOC(=O)CC(CCC(=O)NC)c1ccc(C)c(CN2C[C@H](C)Oc3ccccc3S2(=O)=O)c1]

To solution of ethyl 6-(benzyl(methyl)amino)-3-(4-methyl-3-(((S)-4-methyl-1,1-dioxido-3,4-dihydro-2H-benzo[b][1,4,5]oxathiazepin-2-yl)methyl)phenyl)-6-oxo-hexanoate (500 mg, 0.844 mmol) in chloroform (50 mL)

was added NBS (375 mg, 2.109 mmol) and N-methylacetamide (0.065 mL, 0.844 mmol) at RT. The reaction mixture was stirred at RT for 18 h. The reaction mixture was evaporated under reduced pressure, made basic with 10% NaOH, extracted with EtOAc and dried with anhydrous $Na_2SO_4$ and filtered. The filtrate was evaporated and purified by flash column chromotography by using EtOAc:hexane (38:62) to afford ethyl 3-(4-methyl-3-(((S)-4-methyl-1,1-dioxido-3,4-dihydro-2H-benzo[b][1,4,5]oxathiazepin-2-yl)methyl)phenyl)-6-(methylamino)-6-oxohexanoate (150 mg, 0.253 mmol, 30.0% yield) as liquid. LC-MS m/z 503 $(M+H)^+$, 2.42 min (ret. time).

3-(4-Methyl-3-(((S)-4-methyl-1,1-dioxido-3,4-dihydro-2H-benzo[b][1,4,5]oxathiazepin-2-yl)methyl)phenyl)-6-(methylamino)-6-oxohexanoic acid

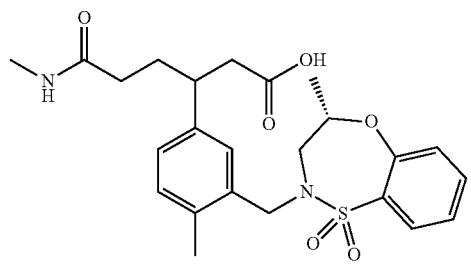 [SMILES: CNC(=O)CCC(CC(=O)O)c1ccc(C)c(CN2C[C@H](C)Oc3ccccc3S2(=O)=O)c1]

To a solution of ethyl 3-(4-methyl-3-(((S)-4-methyl-1,1-dioxido-3,4-dihydro-2H-benzo[b][1,4,5]oxathiazepin-2-yl)methyl)phenyl)-6-(methylamino)-6-oxohexanoate (150 mg, 0.298 mmol) in EtOH (15 mL) was added 10% NaOH (20 mL, 0.298 mmol) at 0° C. The reaction mixture was stirred at RT for 2 h. The reaction mixture was evaporated under reduced pressure, neutralized with 1N HCl, extracted with DCM (2×) and brine solution. The organic layer was dried under anhydrous $Na_2SO_4$ and filtered. The filtrate was evaporated under reduced pressure to get 200 mg of crude 3-(4-methyl-3-(((S)-4-methyl-1,1-dioxido-3,4-dihydro-2H-benzo[b][1,4,5]oxathiazepin-2-yl)methyl)phenyl)-6-(methylamino)-6-oxohexanoic acid.

In a separate reaction, to a solution of ethyl 3-(4-methyl-3-(((S)-4-methyl-1,1-dioxido-3,4-dihydro-2H-benzo[b][1,4,5]oxathiazepin-2-yl)methyl)phenyl)-6-(methylamino)-6-oxohexanoate (30 mg, 0.060 mmol) in EtOH (5 mL) was added 10% NaOH (5 mL, 0.060 mmol) at 0° C. The reaction mixture was stirred at RT for 2 h. The reaction mixture was evaporated under reduced pressure, neutralized with 1N HCl, extracted with DCM (2×) and brine solution. The organic layer was dried under anhydrous $Na_2SO_4$ and filtered. The filtrate was evaporated under reduced pressure to afford 30 mg of crude 3-(4-methyl-3-(((S)-4-methyl-1,1-dioxido-3,4-dihydro-2H-benzo[b][1,4,5]oxathiazepin-2-yl)methyl)phenyl)-6-(methylamino)-6-oxohexanoic acid. The products of the two reactions were combined and were purified by preparative HPLC to afford 3-(4-methyl-3-(((S)-4-methyl-1,1-dioxido-3,4-dihydro-2H-benzo[b][1,4,5]oxathiazepin-2-yl)methyl)phenyl)-6-(methylamino)-6-oxohexanoic acid (80 mg, 0.167 mmol, 56.1% yield). LC-MS m/z 475 $(M+H)^+$, 2.86 min (ret. time).

Example 160

3-(2-((Dimethylamino)methyl)-4-fluoro-6-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid

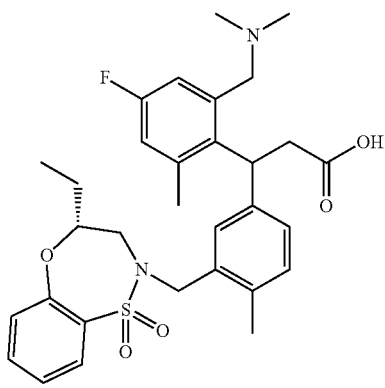 [SMILES: CC[C@@H]1CN(Cc2cc(C(CC(=O)O)c3c(C)cc(F)cc3CN(C)C)ccc2C)S(=O)(=O)c2ccccc2O1]

2-Bromo-5-fluoro-3-methylbenzaldehyde

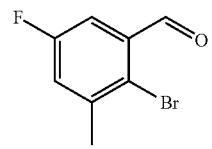

To a solution of 1,2-dibromo-5-fluoro-3-methylbenzene (200 mg, 0.746 mmol) in THF (10 mL) was added isopropylmagnesium chloride (1.5 mL, 3.00 mmol) at 0° C. The reaction was stirred at 0° C. for 1 h, after which, piperidine-1-carbaldehyde (0.1 mL, 0.746 mmol) was added at 0° C. The reaction mixture was stirred at RT for 2 h. The reaction mixture was quenched with cold water, extracted with EtOAc (2×), and brine. The organic layer was dried under anhydrous $Na_2SO_4$ and filtered. The filtrate was reduced under pressure and the crude residue was purified by flash column chromatography by using EtOAc:hexane (4:96) to afford 2-bromo-5-fluoro-3-methylbenzaldehyde (100 mg, 0.461 mmol, 61.7% yield). $^1$H NMR (400 MHz, DMSO-$d_6$) δ ppm 11.26 ppm (s, 1H), 7.64 (dd, 1H), 2.42 (dd, 1H), 2.41 (s, 3H).

1-(2-Bromo-5-fluoro-3-methylphenyl)-N,N-dimethylmethanamine

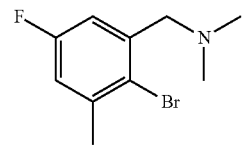

To a solution of 2-bromo-5-fluoro-3-methylbenzaldehyde (700 mg, 3.23 mmol), dimethylamine (3.23 mL, 6.45 mmol) and AcOH (0.037 mL, 0.645 mmol) in THF (10 mL) was added Na(OAc)₃BH (1367 mg, 6.45 mmol) at 5° C. and stirred at 25° C. for 5 h. The reaction was then diluted with a NaHCO₃ solution and extracted with EtOAc (2×20 mL). The combined organic layer washed with brine (20 mL), dried over Na₂SO₄, filtered and evaporated under vacuum. The crude residue was purified by flash column chromatography using EtOAc:hexane (15:85) as a solvent to give 1-(2-bromo-5-fluoro-3-methylphenyl)-N,N-dimethylmethanamine (300 mg, 1.099 mmol, 34.1% yield) as liquid. LC-MS m/z 245.99 (M+H)⁺, 1.23 min (ret. time).

(E)-Ethyl 3-(2-((dimethylamino)methyl)-4-fluoro-6-methylphenyl)acrylate

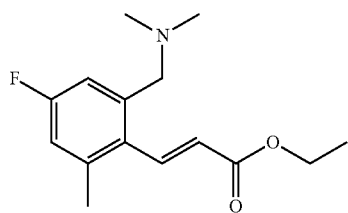 [SMILES: CCOC(=O)/C=C/c1c(C)cc(F)cc1CN(C)C]

To solution of 1-(2-bromo-5-fluoro-3-methylphenyl)-N,N-dimethylmethanamine (300 mg, 1.219 mmol) and ethyl acrylate (488 mg, 4.88 mmol) in DMF (5 mL), in a sealed tube, was added tri-o-tolylphosphine (111 mg, 0.366 mmol). The reaction was degassed with argon for 10 min then DIPEA (0.639 mL, 3.66 mmol) was added and degassing was continued for 10 min. Pd(OAc)₂ (54.7 mg, 0.244 mmol) was then added and degassed with for 20 min. The reaction mixture was stirred at 120° C. for 2 h. The reaction was quenched with cold water, extracted with EtOAc (2×), and brine. The combined organic layers were washed with cold water, dried with anhydrous Na₂SO₄ and filtered. The filtrate was evaporated under reduced pressure to yield crude (E)-ethyl 3-(2-((dimethylamino)methyl)-4-fluoro-6-methylphenyl)acrylate (250 mg) which was used for next step without purification. LC-MS m/z 266.1 (M+H)⁺, 3.89 min (ret. time).

(R)-4-Ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide

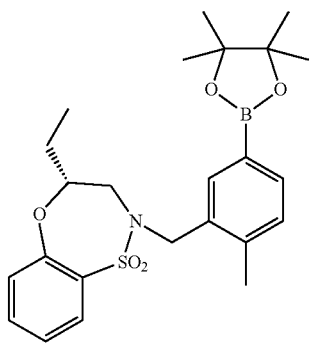 [SMILES: CC[C@@H]1CN(Cc2cc(B3OC(C)(C)C(C)(C)O3)ccc2C)S(=O)(=O)c2ccccc2O1]

To a solution of (2-methyl-5-(4,4,5,5-tetramethyl-1,3,2-dioxaborolan-2-yl)phenyl)methanol (10 g, 40.3 mmol), and (R)-4-ethyl-3,4-dihydro-2H-benzo[b][1,4,5]oxathiazepine 1,1-dioxide (9.16 g, 40.3 mmol) in THF (100 mL) was added triphenylphosphine (15.86 g, 60.5 mmol). The reaction was cooled to 0° C. and DEAD (12.76 mL, 81 mmol) was slowly added dropwise. The reaction mixture was allowed to stir at RT for 2 h. The reaction mixture was diluted with ice cold water and extracted with EtOAc (3×150 mL). The combined organic layers were washed with brine (200 mL). The organic layer was dried over anhydrous Na₂SO₄ and concentrated to afford crude residue. The crude residue was purified by flash column chromatography using 5% EtOAc/hexanes as eluent to afford (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (10.2 g, 21.74 mmol, 53.9% yield). LC-MS m/z 458 (M+H)⁺, 3.06 min (ret. time).

Ethyl 3-(2-((dimethylamino)methyl)-4-fluoro-6-methylphenyl)-3-(3-(((R)-4-ethyl-1,1-dioxido-3,4-dihydro-2H-benzo[b][1,4,5]oxathiazepin-2-yl)methyl)-4-methylphenyl)propanoate

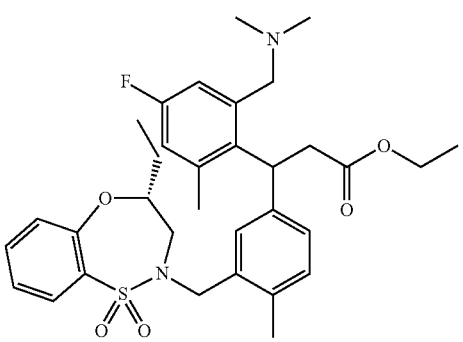 [SMILES: CCOC(=O)CC(c1ccc(C)c(CN2C[C@@H](CC)Oc3ccccc3S2(=O)=O)c1)c1c(C)cc(F)cc1CN(C)C]

A solution of (E)-ethyl 3-(2-((dimethylamino)methyl)-4-fluoro-6-methylphenyl)acrylate (150 mg, 0.565 mmol) and (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (259 mg, 0.565 mmol) in mixture of 1,4-dioxane (2 mL) and water (2 mL) was degassed with argon for 10 min. TEA (0.079 mL, 0.565 mmol) and [RhCl(cod)]₂ (250 mg, 0.565 mmol) were then added and the reaction mixture was allowed to stir at 90° C. for 1 h. The reaction mixture was filtered through a bed of celite and the filtrate was evaporated to afford crude ethyl 3-(2-((dimethylamino)methyl)-4-fluoro-6-methylphenyl)-3-(3-(((R)-4-ethyl-1,1-dioxido-3,4-dihydro-2H-benzo[b][1,4,5]oxathiazepin-2-yl)methyl)-4-methylphenyl)propanoate (180 mg, 0.126 mmol, 22.28% yield). This compound was used to next step without purification. LC-MS m/z 597.08 (M+H)⁺, 2.4 min (ret. time).

3-(2-((Dimethylamino)methyl)-4-fluoro-6-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid

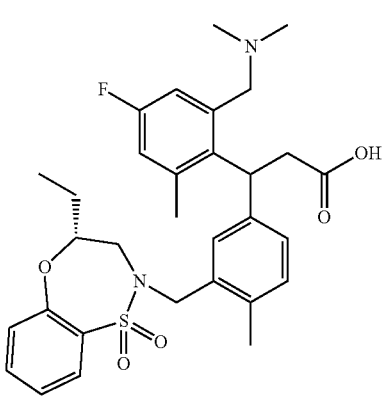 [SMILES: CC[C@@H]1CN(Cc2cc(C(CC(=O)O)c3c(C)cc(F)cc3CN(C)C)ccc2C)S(=O)(=O)c2ccccc2O1]

To a solution of ethyl 3-(2-((dimethylamino)methyl)-4-fluoro-6-methylphenyl)-3-(3-(((R)-4-ethyl-1,1-dioxido-3,4-dihydro-2H-benzo[b][1,4,5]oxathiazepin-2-yl)methyl)-4-methylphenyl)propanoate (300 mg, 0.503 mmol) in EtOH (20 mL) was added 10% NaOH (20 mL) at 0° C. Then the reaction mixture was stirred at RT for 2 h. The reaction mixture was then evaporated under reduced pressure, neutralized with 1N HCl, and extracted with DCM (2×). The organic layer was dried under anhydrous Na$_2$SO$_4$ and filtered. The filtrate was evaporated under reduced pressure to get 280 mg of crude compound. The crude compound was purified by flash column chromatography(2×) using MeOH:DCM (0.5:9.5) as solvent system, to afford 3-(2-((dimethylamino)methyl)-4-fluoro-6-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid (53 mg, 0.091 mmol). LC-MS m/z 569.28 (M+H)$^+$, 2.14 min (ret. time).

Example 161

3-(5-Methoxy-2-methylpyridin-3-yl)-3-(4-methyl-3-(((R)-4-methyl-1,1-dioxido-3,4-dihydro-2H-benzo[b][1,4,5]oxathiazepin-2-yl)methyl)phenyl)propanoic acid

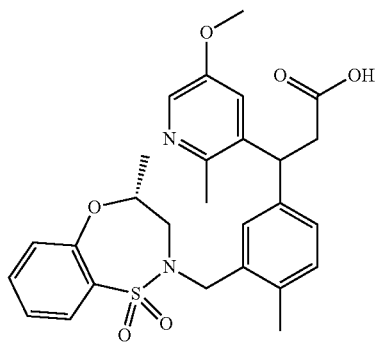 [SMILES: COc1cnc(C)c(C(CC(=O)O)c2ccc(C)c(CN3C[C@@H](C)Oc4ccccc4S3(=O)=O)c2)c1]

(Z)-Ethyl 3-(5-methoxy-2-methylpyridin-3-yl)acrylate

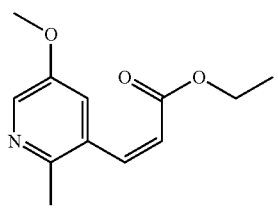 [SMILES: CCOC(=O)/C=C\c1cc(OC)cnc1C]

To a solution of 3-bromo-5-methoxy-2-methylpyridine (500 mg, 2.475 mmol) in DMF (3 mL) was added methyl acrylate ethyl acrylate (1239 mg, 12.37 mmol), tri-o-tolylphosphine (226 mg, 0.742 mmol), DIPEA (1.729 mL, 9.90 mmol) and Pd(OAc)$_2$ (5.56 mg, 0.025 mmol) at RT and stirred under microwave irradiation at 120° C. for 1.30 h. The reaction was cooled to RT, filtered through celite and washed with EtOAc (50 mL). The filtrate was washed with a brine solution (100 mL) and dried over anhydrous Na$_2$SO$_4$, filtered and the solvent was evaporated under vacuum. The residue was purified by flash column chromatography to afford (Z)-ethyl 3-(5-methoxy-2-methylpyridin-3-yl)acrylate (300 mg, 1.199 mmol, 48.5% yield). LC-MS m/z 222 (M+H)$^+$, 1.13 min (ret. time).

Ethyl 3-(5-methoxy-2-methylpyridin-3-yl)-3-(4-methyl-3-(((R)-4-methyl-1,1-dioxido-3,4-dihydro-2H-benzo[b][1,4,5]oxathiazepin-2-yl)methyl)phenyl)propanoate

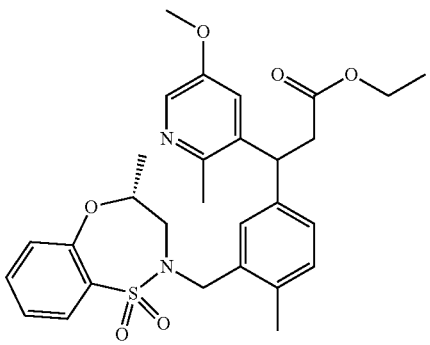 [SMILES: CCOC(=O)CC(c1ccc(C)c(CN2C[C@@H](C)Oc3ccccc3S2(=O)=O)c1)c1cc(OC)cnc1C]

To a solution of (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (1202 mg, 2.71 mmol) in 1,4-dioxane (5 mL) and water (5 mL) was added Et$_3$N (0.378 mL, 2.71 mmol). The reaction mixture was degassed with argon for 10 min and then [RhCl(cod)]$_2$ (66.9 mg, 0.136 mmol) was added again The reaction was degassed with argon for 5 min, stirred under microwave irradiation at 120° C. for 1.5 h. The reaction mixture was cooled and diluted with water (50 mL) and extracted with EtOAc (2×50 mL). The combined organic layers were washed with a brine solution (50 mL) and dried over anhydrous Na$_2$SO$_4$, filtered and evaporated. The residue was purified by flash column chromatography to afford ethyl 3-(5-methoxy-2-methylpyridin-3-yl)-3-(4-methyl-3-(((R)-4-methyl-1,1-dioxido-3,4-dihydro-2H-benzo[b][1,4,5]oxathiazepin-2-yl)methyl)phenyl)propanoate (150 mg, 0.265 mmol, 19.53% yield. $^1$H NMR (DMSO-d$_6$) δ: 7.99 (d, J=2.8 Hz, 1H), 7.80-7.74 (m, 1H), 7.68-7.61 (m, 1H), 7.39-7.28 (m, 3H), 7.26 (s, 1H), 7.19-7.08 (m, 2H), 4.50 (q, J=7.7 Hz, 1H), 4.41 (dd, J=14.9, 8.4 Hz, 2H), 3.99-3.88 (m, 2H), 3.87-3.74 (m, 4H), 3.69-3.55 (m, 1H), 3.17-2.98 (m, 2H), 2.79 (dd, J=32.2, 15.2 Hz, 1H), 2.40 (d, J=6.3 Hz, 3H), 2.23 (d, J=1.7 Hz, 3H), 1.23 (d, J=6.2 Hz, 3H), 1.10-0.99 (m, 3H).

3-(5-Methoxy-2-methylpyridin-3-yl)-3-(4-methyl-3-(((R)-4-methyl-1,1-dioxido-3,4-dihydro-2H-benzo[b][1,4,5]oxathiazepin-2-yl)methyl)phenyl)propanoic acid

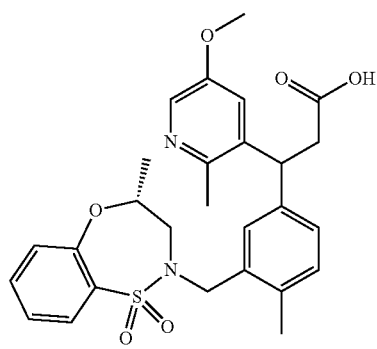 [SMILES: COc1cnc(C)c(C(CC(=O)O)c2ccc(C)c(CN3C[C@@H](C)Oc4ccccc4S3(=O)=O)c2)c1]

To a solution of ethyl 3-(5-methoxy-2-methylpyridin-3-yl)-3-(4-methyl-3-(((R)-4-methyl-1,1-dioxido-3,4-dihydro-2H-benzo[b][1,4,5]oxathiazepin-2-yl)methyl)phenyl)propanoate (150 mg, 0.278 mmol) in EtOH (3 mL) was added NaOH (0.139 mL, 0.278 mmol) and stirred at 25° C. for 2 h. The reaction mixture was concentrated under vacuum. and acidified with 1N HCl solution up to pH 4. The resultant solid was filtered, washed with water and dried well to offered 3-(5-methoxy-2-methylpyridin-3-yl)-3-(4-methyl-3-(((R)-4-methyl-1,1-dioxido-3,4-dihydro-2H-benzo[b][1,4,5]oxathiazepin-2-yl)methyl)phenyl)propanoic acid (65 mg, 0.122 mmol, 43.7% yield). LC-MS m/z 511.30 (M+H)+, 1.50 min (ret. time).

Example 162

3-(4-Methyl-3-(((R)-4-methyl-1,1-dioxido-3,4-dihydro-2H-benzo[b][1,4,5]oxathiazepin-2-yl)methyl)phenyl)-5-(o-tolyl)pentanoic acid

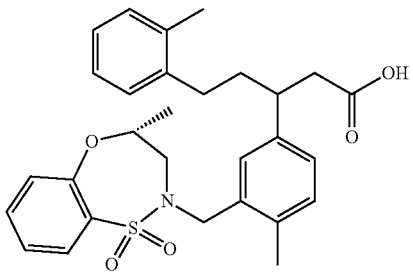 [SMILES: Cc1ccccc1CCC(CC(=O)O)c1ccc(C)c(CN2C[C@@H](C)Oc3ccccc3S2(=O)=O)c1]

3-(m-Tolyl)propan-1-ol

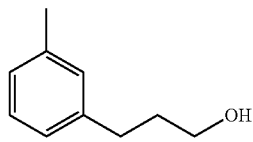

To a solution of 3-(m-tolyl)propanoic acid (2 g, 12.18 mmol) in THF (50 mL) was added 2 M LAH in THF (30 mL, 30.5 mmol) at 0° C. under nitrogen atmosphere and stirred at RT for 2 h. The reaction mixture was quenched with saturated, extracted with EtOAc (2×), the organic layer was dried under anhydrous Na₂SO₄ and filtered. The filtrate was evaporated and the crude residue was purified by flash column chromotography by using EtOAc:hexane (20:80) to afford 3-(m-tolyl)propan-1-ol (1.4 g, 9.29 mmol, 76% yield). LC-MS m/z 151 (M+H)+, 2.03 min (ret. time).

3-(m-Tolyl)propanal

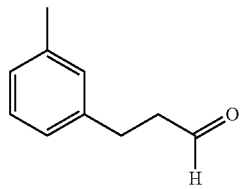

To a solution of 3-(m-tolyl)propan-1-ol (1.4 g, 9.32 mmol) in DCM (20 mL), at 0° C. was added PCC (3.01 g, 13.98 mmol) then brought RT and stirred at RT for 3 h. The crude residue was filtered through celite, and the solvent was evaporated to afford 3-(m-tolyl)propanal (1.2 g, 8.10 mmol, 87% yield). ¹H NMR (400 MHz, DMSO-d6) δ ppm 9.65 (bs, 1H), 6.85-7.20 (m, 4H), 2.90-2.20 (m, 7H).

(E)-Ethyl 5-(o-tolyl)pent-2-enoate

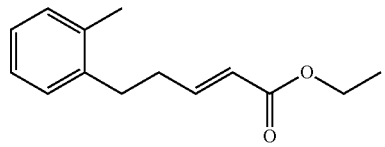 [SMILES: CCOC(=O)/C=C/CCc1ccccc1C]

To a suspension of NaH (0.486 g, 20.24 mmol) in THF (15 mL) was added triethyl phosphonoacetate (1.945 mL, 9.72 mmol) at 0° C. and stirred for 15 min. Then 3-(o-tolyl)propanal (1.2 g, 8.10 mmol) in THF (3 mL) was added to the reaction mixture and stirred at RT and stirred for 2 h. The reaction mixture was quenched with cold water, extracted with EtOAc (2×), brine, the organic layer was dried under anhydrous Na₂SO₄ and filtered. The filtrate was concentrated. the crude residue was purified on flash column chromotography by using EtOAc:hexane (80:20) to afford (E)-ethyl 5-(o-tolyl)pent-2-enoate (500 mg, 1.397 mmol, 17.25% yield) LC-MS m/z 219 (M+H)+, 2.82 min (ret. time).

Ethyl 3-(4-methyl-3-(((R)-4-methyl-1,1-dioxido-3,4-dihydro-2H-benzo[b][1,4,5]oxathiazepin-2-yl)methyl)phenyl)-5-(o-tolyl)pentanoate

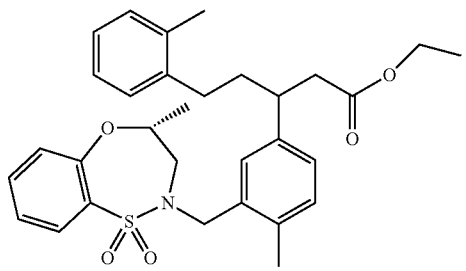 [SMILES: CCOC(=O)CC(CCc1ccccc1C)c1ccc(C)c(CN2C[C@@H](C)Oc3ccccc3S2(=O)=O)c1]

To a solution of (E)-ethyl 5-(m-tolyl)pent-2-enoate (500 mg, 2.291 mmol) in 1,4-dioxane (5 mL) and water (5 mL) was added Et₃N (0.639 mL, 4.58 mmol) and (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (2031 mg, 4.58 mmol) then reaction mixture was degassed with argon for 10 min. [RhCl(cod)]₂ (113 mg, 0.229 mmol) was added and the reaction was degassed with argon for 5 min. The reaction was then stirred at 120° C. for 16 h. Afterwards, the reaction mixture was cooled and diluted with water (50 mL) and extracted with EtOAc (2×50 mL). The combined organic layers were washed with brine (50 mL), dried over anhydrous Na₂SO₄, filtered and evaporated. The crude residue was purified by flash column chromatography and was eluted with Hex/EtOAc (4:6) to afford ethyl 3-(4-methyl-3-(((R)-4-methyl-1,1-dioxido-3,4-dihydro-2H-benzo[b][1,4,5]oxathiazepin-2-yl)methyl)phenyl)-5-(o-tolyl)pentanoate (250 mg, 0.447 mmol, 19.50% yield). LC-MS m/z 536 (M+H)$^+$, 3.20 min (ret. time).

3-(4-Methyl-3-(((R)-4-methyl-1,1-dioxido-3,4-dihydro-2H-benzo[b][1,4,5]oxathiazepin-2-yl)methyl)phenyl)-5-(o-tolyl)pentanoic acid

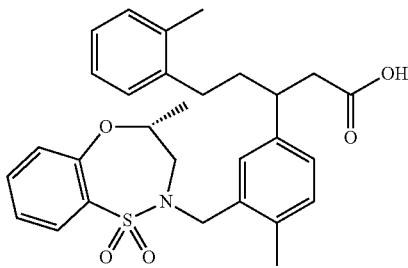 [SMILES: Cc1ccccc1CCC(CC(=O)O)c1ccc(C)c(CN2C[C@@H](C)Oc3ccccc3S2(=O)=O)c1]

To a solution of ethyl 3-(4-methyl-3-(((R)-4-methyl-1,1-dioxido-3,4-dihydro-2H-benzo[b][1,4,5]oxathiazepin-2-yl)methyl)phenyl)-5-(o-tolyl)pentanoate (150 mg, 0.280 mmol) in EtOH (3 mL) was added 2M NaOH (0.140 mL, 0.280 mmol) and stirred at 25° C. for 2 h. The reaction mixture was concentrated and the residue was cooled and acidified with 1N HCl solution up to pH 4. The resultant solid filtered, washed with water and dried to afford 3-(4-methyl-3-(((R)-4-methyl-1,1-dioxido-3,4-dihydro-2H-benzo[b][1,4,5]oxathiazepin-2-yl)methyl)phenyl)-5-(o-tolyl)pentanoic acid (55 mg, 0.107 mmol, 38.3% yield). LC-MS m/z 508.8 (M+H)$^+$, 2.86 min (ret. time).

Example 163

3-(1-Ethyl-1H-imidazol-4-yl)-3-(4-methyl-3-(((R)-4-methyl-1,1-dioxido-3,4-dihydro-2H-benzo[b][1,4,5]oxathiazepin-2-yl)methyl)phenyl)propanoic acid

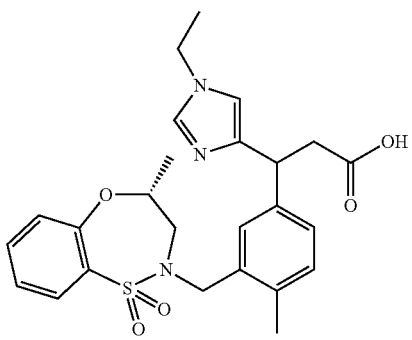 [SMILES: CCn1cnc(C(CC(=O)O)c2ccc(C)c(CN3C[C@@H](C)Oc4ccccc4S3(=O)=O)c2)c1]

(E)-Methyl 3-(1H-imidazol-4-yl)acrylate

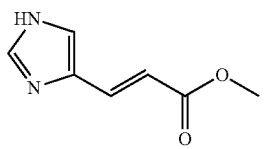

To a suspension of (E)-3-(1H-imidazol-4-yl)acrylic acid (20 g, 145 mmol) in MeOH (200 mL), stirred under nitrogen at 0° C., was added H$_2$SO$_4$ (7.72 mL, 145 mmol) dropwise over 30 min. The reaction mixture was stirred at 70° C. for 16 h. The reaction mixture was evaporated under reduced pressure. The crude compound was quenched with saturated aq. NaHCO$_3$ solution. The white solid that formed was filtered and dried under vacuum to afford (E)-methyl 3-(1H-imidazol-4-yl)acrylate (18 g, 117 mmol, 81% yield). LC-MS m/z 153 (M+H)$^+$, 2.06 min (ret. time).

(E)-Methyl 3-(1-ethyl-1H-imidazol-4-yl)acrylate

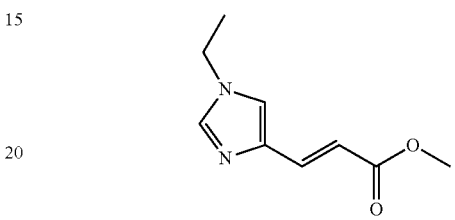

To a solution of (E)-methyl 3-(1H-imidazol-4-yl)acrylate (500 mg, 3.29 mmol) in THF (10 mL) was added NaH (263 mg, 6.57 mmol) at 0° C., under nitrogen atmosphere, and stirred for 15 min. Ethyl iodide (0.398 mL, 4.93 mmol) was then added into the reaction mixture at 0° C. and stirred at RT for 24 h. The reaction mixture was quenched with cold water, extracted with EtOAc (2×). The organic layer washed with brine, dried under anhydrous Na$_2$SO$_4$ and filtered. The filtrate was concentrated and was purified by flash column chromatography by using MeOH:DCM (2:98) to afford (E)-methyl 3-(1-ethyl-1H-imidazol-4-yl)acrylate (350 mg, 1.888 mmol, 57.4% yield). LC-MS m/z 181 (M+H)$^+$, 3.45 min (ret. time).

Methyl 3-(1-ethyl-1H-imidazol-4-yl)-3-(4-methyl-3-(((R)-4-methyl-1,1-dioxido-3,4-dihydro-2H-benzo[b][1,4,5]oxathiazepin-2-yl)methyl)phenyl)propanoate

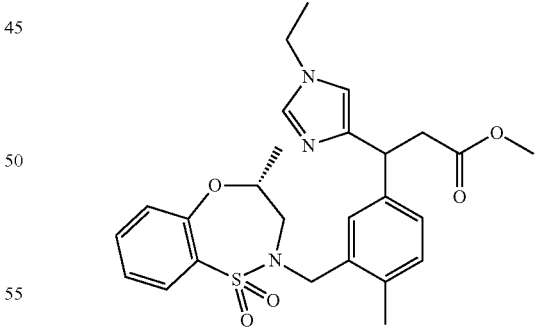

To solution of (E)-methyl 3-(1-ethyl-1H-imidazol-4-yl)acrylate (300 mg, 1.665 mmol) in mixture of 1,4-dioxane (10 mL) and water (10 mL) was added, (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (886 mg, 1.998 mmol), and TEA (0.682 mL, 4.99 mmol). The mixture was degassed with nitrogen for 20 min, followed by the addition of [RhCl(cod)]$_2$ (82 mg, 0.166 mmol) in a microwave reactor vessel. The reaction mixture was stirred at 120° C. for 1 h. The reaction mixture was quenched with cold water, and extracted with EtOAc (2×). The organic layer washed with brine, dried under anhydrous Na$_2$SO$_4$ and filtered. The filtrate was evaporated to afford methyl 3-(1-ethyl-1H-imidazol-4-20 yl)-3-(4-methyl-3-(((R)-4-methyl-1,1-dioxido-3,4-dihydro-2H-benzo[b][1,4,5]oxathiazepin-2-yl)methyl)phenyl)propanoate (400 mg, 0.388 mmol, 23.29% yield) LC-MS m/z 498 (M+H)$^+$, 1.76 min (ret. time).

3-(1-Ethyl-1H-imidazol-4-yl)-3-(4-methyl-3-(((R)-4-methyl-1,1-dioxido-3,4-dihydro-2H-benzo[b][1,4,5]oxathiazepin-2-yl)methyl)phenyl)propanoic acid

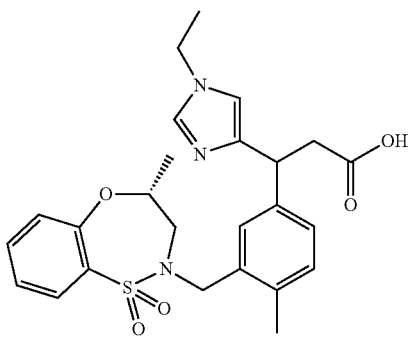 [SMILES: CCn1cnc(C(CC(=O)O)c2ccc(C)c(CN3C[C@@H](C)Oc4ccccc4S3(=O)=O)c2)c1]

To a solution of methyl 3-(1-ethyl-1H-imidazol-4-yl)-3-(4-methyl-3-(((R)-4-methyl-1,1-dioxido-3,4-dihydro-2H-benzo[b][1,4,5]oxathiazepin-2-yl)methyl)phenyl)propanoate (450 mg, 0.904 mmol) in EtOH (15 mL) was added 10% NaOH (40 mL, 0.904 mmol) at 0° C. The reaction mixture was stirred at RT for 2 h. The reaction mixture was evaporated under reduced pressure, neutralized with 1N HCl, and extracted with DCM (2×). The organic layer washed with brine, dried under anhydrous Na$_2$SO$_4$ and filtered. The filtrate was evaporated and the crude residue was purified by flash column chromatography by using MeOH:CHCl$_3$ (5:95) to afford 3-(1-ethyl-1H-imidazol-4-yl)-3-(4-methyl-3-(((R)-4-methyl-1,1-dioxido-3,4-dihydro-2H-benzo[b][1,4,5]oxathiazepin-2-yl)methyl)phenyl)propanoic acid (110 mg, 0.225 mmol, 24.93% yield) LC-MS m/z 484 (M+H)$^+$, 1.47 min (ret. time).

Example 164

5-(1-Ethyl-1H-pyrazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid

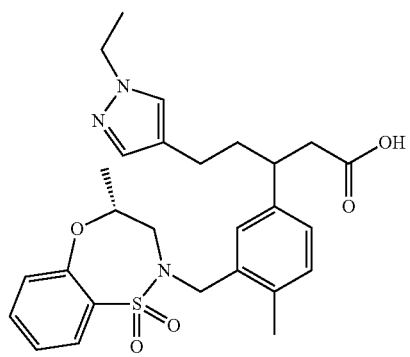 [SMILES: CCn1cc(CCC(CC(=O)O)c2ccc(C)c(CN3C[C@@H](C)Oc4ccccc4S3(=O)=O)c2)cn1]

4-Bromo-1-ethyl-1H-pyrazole

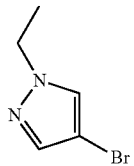

To a suspension of NaH (0.196 g, 8.16 mmol) in THF (15 mL) was added 4-bromo-1H-pyrazole (1 g, 6.80 mmol) in THF (5 mL) at 0° C., under nitrogen atmosphere, and stirred for 20 min. Ethyl iodide (0.825 mL, 10.21 mmol) was added at 0° C. and stirred at RT for 2 h. The reaction mixture was quenched with cold water, and extracted with EtOAc (2×). The organic layer washed with brine, dried under anhydrous Na$_2$SO$_4$ and filtered. The filtrate was concentrated and was purified by column chromatography to afford 4-bromo-1-ethyl-1H-pyrazole (900 mg, 5.12 mmol, 75% yield). LC-MS m/z 174 (M+H)$^+$, 1.84 min (ret. time).

(E)-Ethyl 3-(1-ethyl-1H-pyrazol-4-yl)acrylate

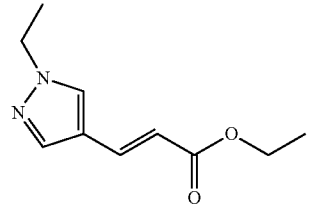

To solution of 4-bromo-1-ethyl-1H-pyrazole (900 mg, 5.14 mmol) in DMF (2 mL) in a microwave reactor vessel was added ethyl acrylate (2059 mg, 20.57 mmol), tri-o-tolylphosphine (470 mg, 1.543 mmol) and DIPEA (2.69 mL, 15.43 mmol). The mixture was degassed with nitrogen for 20 min, followed by the addition of Pd(OAc)$_2$ (115 mg, 0.514 mmol). The reaction mixture was stirred at 150° C. for 1 h. The reaction mixture was filtered through a bed of celite. The filtrate was evaporated and the crude residue was purified on flash column chromatography by using EtOAc:hexane (13:87) to afford (E)-ethyl 3-(1-ethyl-1H-pyrazol-4-yl)acrylate (400 mg, 1.547 mmol, 30.1% yield). LC-MS m/z 195 (M+H)$^+$, 1.94 min (ret. time).

Ethyl 3-(1-ethyl-1H-pyrazol-4-yl)propanoate

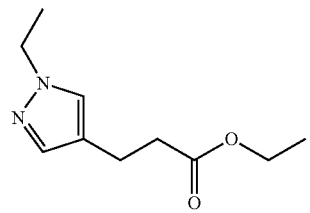

To a solution of (E)-ethyl 3-(1-ethyl-1H-pyrazol-4-yl)acrylate (400 mg, 2.059 mmol) in EtOH (20 mL) was added 10% Pd/C (110 mg, 1.030 mmol) under nitrogen atmosphere. The reaction mixture was stirred under hydrogen atmosphere (60 psi) at RT for 16 h. The reaction mixture was filtered through a bed of celite. The filtrate was evaporated to afford ethyl 3-(1-ethyl-1H-pyrazol-4-yl)propanoate (300 mg, 1.010 mmol, 49.1% yield). LC-MS m/z 197 (M+H)+, 1.72 min (ret. time).

3-(1-Ethyl-1H-pyrazol-4-yl)propan-1-ol

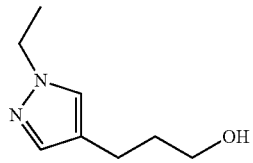

To a solution of ethyl 3-(1-ethyl-1H-pyrazol-4-yl)propanoate (300 mg, 1.529 mmol) in THF (10 mL) was added 2M LAH (3 mL, 6.00 mmol) at 0° C. under nitrogen atmosphere and stirred at RT for 2 h. The reaction mixture was cooled to 0° C., quenched with saturated Na₂SO₄, extracted with EtOAc (2×). The organic layer washed with brine, dried under anhydrous Na₂SO₄ and filtered. The filtrate was concentrated and the crude residue was purified by column chromatography using EtOAc:hexane (60:40) to afford 3-(1-ethyl-1H-pyrazol-4-yl)propan-1-ol (100 mg, 0.592 mmol, 38.8% yield). LC-MS m/z 155 (M+H)+, 1.17 min (ret. time).

3-(1-Ethyl-1H-pyrazol-4-yl)propanal

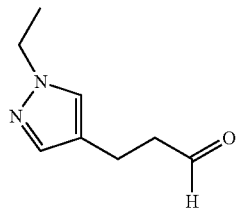

To a solution of oxalyl chloride (0.511 mL, 5.84 mmol) in DCM (20 mL) was added DMSO (0.690 mL, 9.73 mmol) at −78° C. and stirred for 20 min. 3-(1-ethyl-1H-pyrazol-4-yl)propan-1-ol (600 mg, 3.89 mmol) was added to the reaction mixture and stirred for 30 min followed by the addition of TEA (2.71 mL, 19.45 mmol) at −78° C. The reaction was warmed to RT and stirred for 3 h. The reaction mixture was quenched with cold water, extracted with DCM (2×). The organic layer washed with brine, dried under anhydrous Na₂SO₄ and filtered. The filtrate was concentrated and the crude residue was purified by column chromatography using to afford 3-(1-ethyl-1H-pyrazol-4-yl)propanal (500 mg, 3.29 mmol, 84% yield) ¹H NMR (400 MHz, DMSO-d6) δ ppm 9.75 (s, 1H), 7.50 (s, 1H), 7.27 (s, 1H), 4.08 (q, 2H), 3.90 (bs, 4H) 2.65 (s, 3H), 1.35 (t, 2H).

(E)-Ethyl 5-(1-ethyl-1H-pyrazol-4-yl)pent-2-enoate

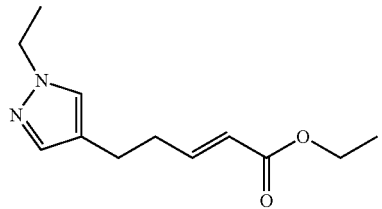 [SMILES: CCOC(=O)/C=C/CCc1cnn(CC)c1]

To a suspension of NaH (158 mg, 6.57 mmol) in THF (20 mL) was added triethyl phosphonoacetate (0.789 mL, 3.94 mmol) at 25° C. and stirred for 15 min. 3-(1-ethyl-1H-pyrazol-4-yl)propanal (500 mg, 3.29 mmol) in THF (12 mL) was then added to the reaction mixture and stirred at RT for 2 h. The reaction mixture was quenched with cold water (100 mL) and extracted with EtOAc (2×100 mL). The combined organic layers were washed with brine solution (100 mL) and dried over anhydrous Na₂SO₄, filtered and evaporated. The crude residue was purified by flash column chromatography with 20% EtOAc/hexane as the solvent system to afford ((E)-ethyl 5-(1-ethyl-1H-pyrazol-4-yl)pent-2-enoate (550 mg, 2.351 mmol, 71.6% yield). LC-MS m/z 223 (M+H)+, 2.01 min (ret. time).

Ethyl 5-(1-ethyl-1H-pyrazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate

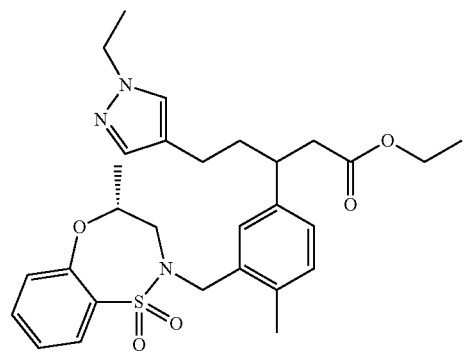 [SMILES: CCOC(=O)CC(CCc1cnn(CC)c1)c1ccc(C)c(CN2C[C@@H](C)Oc3ccccc3S2(=O)=O)c1]

To solution of (E)-ethyl 5-(1-ethyl-1H-pyrazol-4-yl)pent-2-enoate (300 mg, 1.350 mmol) in mixture of 1,4-dioxane (10 mL) and water (10 mL) was added, TEA (0.553 mL, 4.05 mmol). The reaction was degassed with nitrogen for 20 min, followed by the addition of [RhCl(cod)]₂ (66.5 mg, 0.135 mmol). The reaction mixture was stirred at 100° C. for 2 h. The reaction mixture was quenched with cold water, extracted with EtOAc (2×). The organic layer washed with brine, dried under anhydrous Na₂SO₄ and filtered. The filtrate was evaporated to afford ethyl 5-(1-ethyl-1H-pyrazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate (300 mg, 0.532 mmol, 39.4% yield). LC-MS m/z 540 (M+H)+, 2.71 min (ret. time).

5-(1-Ethyl-1H-pyrazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid

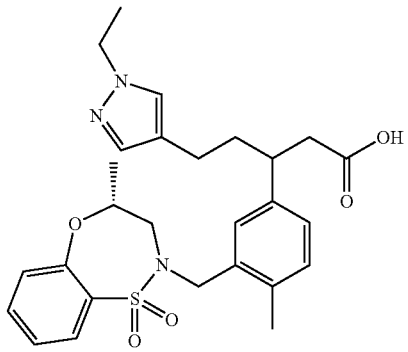 [SMILES: CCn1cc(CCC(CC(=O)O)c2ccc(C)c(CN3C[C@@H](C)Oc4ccccc4S3(=O)=O)c2)cn1]

To a solution of ethyl 5-(1-ethyl-1H-pyrazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate (350 mg, 0.649 mmol) in EtOH (15 mL) was added 10% NaOH (20 mL, 0.649 mmol) at 0° C. The reaction mixture was stirred at RT for 2 h. The reaction mixture was evaporated, neutralized with 1N HCl, and extracted with EtOAc (2×). The organic layer washed with brine, dried under anhydrous Na$_2$SO$_4$ and filtered. The filtrate was evaporated to afford 5-(1-ethyl-1H-pyrazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid (220 mg, 0.425 mmol, 65.5% yield) LC-MS m/z 512 (M+H)$^+$, 3.05 min (ret. time).

Example 165

6-Methoxy-3-(4-methyl-3-(((R)-4-methyl-1,1-dioxido-3,4-dihydro-2H-benzo[b][1,4,5]oxathiazepin-2-yl)methyl)phenyl)hexanoic acid

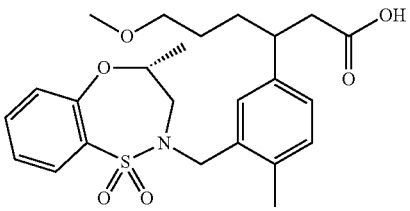 [SMILES: COCCCC(CC(=O)O)c1ccc(C)c(CN2C[C@@H](C)Oc3ccccc3S2(=O)=O)c1]

4-Methoxybutanal

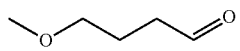

To a solution of 4-methoxybutan-1-ol (3 g, 28.8 mmol) in DCM (30 mL) was added PCC (9.31 g, 43.2 mmol) at 0° C. The reaction was stirred at RT for 1 h. The reaction mixture was filtered through celite, and washed with DCM (2×). The filtrate was concentrated to afford 4-methoxybutanal (1.5 g, 14.69 mmol, 51.0% yield). $^1$H NMR (400 MHz, DMSO-d6) δ ppm 9.65 (s, 1H), 4.00 (m, 2H), 3.30 (bs, 3H), 2.5 (m, 2H), 1.6 (m, 2H)

(E)-Ethyl 6-methoxyhex-2-enoate

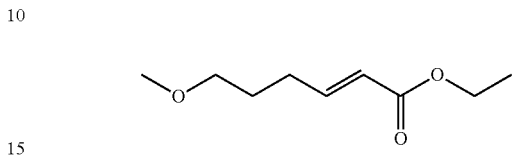

To a suspension of NaH (0.705 g, 29.4 mmol) in THF (20 mL) was added triethyl phosphonoacetate (3.53 mL, 17.62 mmol) at 0° C. and stirred for 15 min. Then 4-methoxybutanal (1.5 g, 14.69 mmol) in THF (5 mL) was added to the reaction mixture and stirred at RT for 2 h. The reaction mixture was quenched with cold water, extracted with EtOAc (2×), The organic layer washed with brine, dried under anhydrous Na$_2$SO$_4$ and filtered. The filtrate was concentrated and the crude residue was purified by flash column chromotography using EtOAc:hexane (12:78) to afford ((E)-ethyl 6-methoxyhex-2-enoate (1 g, 5.62 mmol, 38.2% yield). LC-MS m/z 173 (M+H)$^+$, 3.27 min (ret. time).

Ethyl 6-methoxy-3-(4-methyl-3-(((R)-4-methyl-1,1-dioxido-3,4-dihydro-2H-benzo[b][1,4,5]oxathiazepin-2-yl)methyl)phenyl)hexanoate

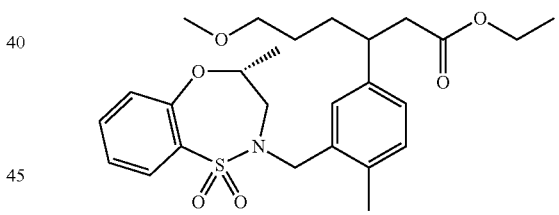

To solution of (E)-ethyl 6-methoxyhex-2-enoate (1 g, 5.81 mmol) and (R)-4-methyl-3,4-dihydro-2H-benzo[b][1,4,5]oxathiazepine 1,1-dioxide (1.857 g, 8.71 mmol) in mixture of 1,4-dioxane (10 mL) and water (10 mL) was added, TEA (2.428 mL, 17.42 mmol) and the mixture was degassed with nitrogen for 20 min. Afterwards, [RhCl(cod)]$_2$ (0.286 g, 0.581 mmol) was added in sealed tube and the reaction mixture was stirred at 90° C. for 6 h. The reaction mixture was quenched with cold water, extracted with EtOAc (2×), The organic layer washed with brine, dried under anhydrous Na$_2$SO$_4$ and filtered. The filtrate was evaporated and was purified by column chromatography using EtOAc:hexane (18:72) to afford ethyl 6-methoxy-3-(4-methyl-3-(((R)-4-methyl-1,1-dioxido-3,4-dihydro-2H-benzo[b][1,4,5]oxathiazepin-2-yl)methyl)phenyl)hexanoate (600 mg, 1.143 mmol, 19.69% yield). LC-MS m/z 489 (M+H)$^+$, 4.03 min (ret. time).

6-Methoxy-3-(4-methyl-3-(((R)-4-methyl-1,1-dioxido-3,4-dihydro-2H-benzo[b][1,4,5]oxathiazepin-2-yl)methyl)phenyl)hexanoic acid

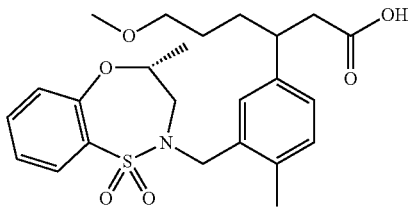 [SMILES: COCCCC(CC(=O)O)c1ccc(C)c(CN2C[C@@H](C)Oc3ccccc3S2(=O)=O)c1]

To a solution of ethyl 6-methoxy-3-(4-methyl-3-(((R)-4-methyl-1,1-dioxido-3,4-dihydro-2H-benzo[b][1,4,5]oxathiazepin-2-yl)methyl)phenyl)hexanoate (600 mg, 1.225 mmol) in EtOH (20 mL) was added 10% NaOH (30 mL, 1.225 mmol) at 0° C. The reaction mixture was stirred at RT for 6 h. The reaction mixture was evaporated under reduced pressure, neutralized with 1N HCl, extracted with EtOAc (2×), The organic layer washed with brine, dried under anhydrous $Na_2SO_4$ and filtered. The filtrate was evaporated and the crude compound was rinsed with hexane to afford 6-methoxy-3-(4-methyl-3-(((R)-4-methyl-1,1-dioxido-3,4-dihydro-2H-benzo[b][1,4,5]oxathiazepin-2-yl)methyl)phenyl)hexanoic acid (400 mg, 0.830 mmol, 67.8% yield) LC-MS m/z 462 (M+H)⁺, 2.40 min (ret. time).

Example 166

3-(3-((7-(3-((tert-Butoxycarbonyl)amino)propyl)-4-methyl-1,1-dioxido-4,5-dihydrobenzo[f][1,2]thiazepin-2(3H)-yl)methyl)-4-methylphenyl)-3-(1-methyl-1H-benzo[d][1,2,3]triazol-5-yl)propanoic acid

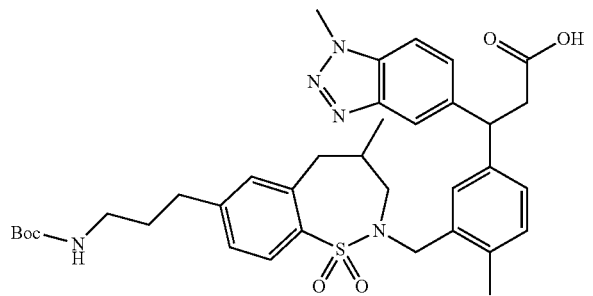 [SMILES: Cc1ccc(C(CC(=O)O)c2ccc3c(c2)nnn3C)cc1CN1CC(C)Cc2cc(CCCNC(=O)OC(C)(C)C)ccc2S1(=O)=O]

2,4-Dibromo-N-(2-methylallyl)benzenesulfonamide

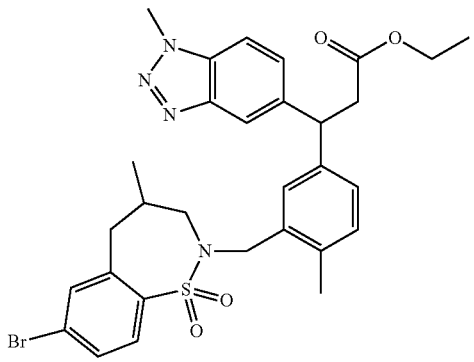 [SMILES: CCOC(=O)CC(c1ccc(C)c(CN2CC(C)Cc3cc(Br)ccc3S2(=O)=O)c1)c1ccc2c(c1)nnn2C]

To a solution of 7-bromo-4-methyl-2,3,4,5-tetrahydrobenzo[f][1,2]thiazepine 1,1-dioxide (500 mg, 1.723 mmol) in THF (20 mL) was added ethyl 3-(3-(hydroxymethyl)-4-methylphenyl)-3-(1-methyl-1H-benzo[d][1,2,3]triazol-5-yl)propanoate (609 mg, 1.723 mmol), triphenylphosphine (452 mg, 1.723 mmol) and DEAD (0.273 mL, 1.723 mmol) at 0° C. The reaction was stirred at RT for 3 h. The reaction mixture was cooled to 0° C. and quenched with water, extracted with EtOAc (2×). The organic layer washed with brine, dried under anhydrous $Na_2SO_4$ and filtered. The filtrate was evaporated and was purified by column chromatography using EtOAc:hexane (30:70) to afford ethyl 3-(3-((7-bromo-4-methyl-1,1-dioxido-4,5-dihydrobenzo[f][1,2]thiazepin-2(3H)-yl)methyl)-4-methylphenyl)-3-(1-methyl-1H-benzo[d][1,2,3]triazol-5-yl)propanoate (400 mg, 0.613 mmol, 35.6% yield). LC-MS m/z 624 (M+H)⁺, 2.83 min (ret. time).

(E)-Ethyl 3-(3-((7-(3-((tert-butoxycarbonyl)amino)prop-1-en-1-yl)-4-methyl-1,1-dioxido-4,5-dihydrobenzo[f][1,2]thiazepin-2(3H)-yl)methyl)-4-methylphenyl)-3-(1-methyl-1H-benzo[d][1,2,3]triazol-5-yl)propanoate

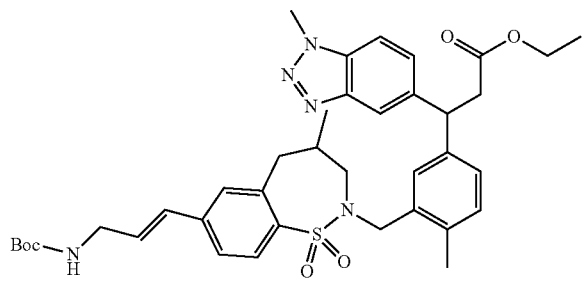 [SMILES: CCOC(=O)CC(c1ccc(C)c(CN2CC(C)Cc3cc(/C=C/CNC(=O)OC(C)(C)C)ccc3S2(=O)=O)c1)c1ccc2c(c1)nnn2C]

To solution of ethyl 3-(3-((7-bromo-4-methyl-1,1-dioxido-4,5-dihydrobenzo[f][1,2]thiazepin-2(3H)-yl)methyl)-4-methylphenyl)-3-(1-methyl-1H-benzo[d][1,2,3]triazol-5-yl) propanoate (1.5 g, 2.398 mmol) in DMF (4 mL) was added tert-butyl allylcarbamate (0.565 g, 3.60 mmol), tri-o-tolylphosphine (0.219 g, 0.719 mmol) and DIPEA (1.256 mL, 7.19 mmol) in a microwave reactor. The mixture was degassed with nitrogen for 20 min, followed by the addition of Pd(OAc)₂ (0.081 g, 0.360 mmol). The reaction mixture was stirred at 120° C. for 1 h. The reaction mixture was filtered through celite. The filtrate was evaporated under reduced pressure and the crude residue was purified by flash column chromatography by using EtOAc:hexane (38:62) to afford (E)-ethyl 3-(3-((7-(3-((tert-butoxycarbonyl)amino)prop-1-en-1-yl)-4-methyl-1,1-dioxido-4,5-dihydrobenzo[f][1,2]thiazepin-2(3H)-yl)methyl)-4-methylphenyl)-3-(1-methyl-1H-benzo[d][1,2,3]triazol-5-yl)propanoate (500 mg, 0.642 mmol, 26.8% yield) LC-MS m/z 702 (M+H)⁺, 4.08 min (ret. time).

Ethyl 3-(3-((7-(3-((tert-butoxycarbonyl)amino)propyl)-4-methyl-1,1-dioxido-4,5-dihydrobenzo[f][1,2]thiazepin-2(3H)-yl)methyl)-4-methylphenyl)-3-(1-methyl-1H-benzo[d][1,2,3]triazol-5-yl)propanoate

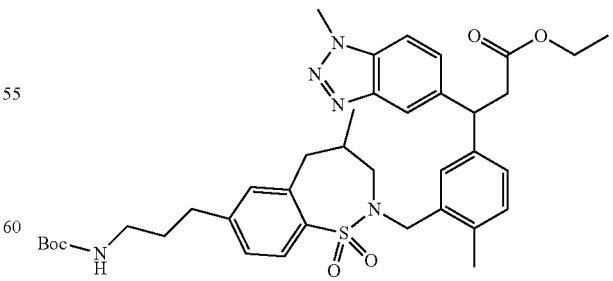

To a solution of (E)-ethyl 3-(3-((7-(3-((tert-butoxycarbonyl)amino)prop-1-en-1-yl)-4-methyl-1,1-dioxido-4,5-dihydrobenzo[f][1,2]thiazepin-2(3H)-yl)methyl)-4-methylphenyl)-3-(1-methyl-1H-benzo[d][1,2,3]triazol-5-yl) propanoate (500 mg, 0.712 mmol) in EtOH (30 mL) was added 10% Pd/C (300 mg, 0.282 mmol) under nitrogen atmosphere. The reaction mixture was stirred under hydrogen balloon at RT for 6 h. The reaction mixture was filtered through a bed of celite. The filtrate was evaporated under reduced pressure and dried under vacuum to afford ethyl 3-(3-((7-(3-((tert-butoxycarbonyl)amino)propyl)-4-methyl-1,1-dioxido-4,5-dihydrobenzo[f][1,2]thiazepin-2(3H)-yl)methyl)-4-methylphenyl)-3-(1-methyl-1H-benzo[d][1,2,3]triazol-5-yl)propanoate (400 mg, 0.316 mmol, 44.4% yield) LC-MS m/z 704 (M+H)⁺, 2.90 min (ret. time).

3-(3-((7-(3-((tert-Butoxycarbonyl)amino)propyl)-4-methyl-1,1-dioxido-4,5-dihydrobenzo[f][1,2]thiazepin-2(3H)-yl)methyl)-4-methylphenyl)-3-(1-methyl-1H-benzo[d][1,2,3]triazol-5-yl)propanoic acid

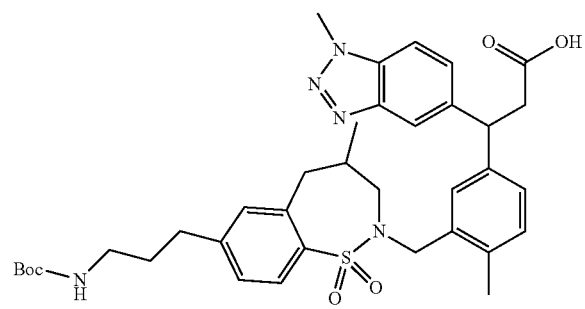 [SMILES: Cc1ccc(C(CC(=O)O)c2ccc3c(c2)nnn3C)cc1CN1CC(C)Cc2cc(CCCNC(=O)OC(C)(C)C)ccc2S1(=O)=O]

To a solution of ethyl 3-(3-((7-(3-((tert-butoxycarbonyl)amino)propyl)-4-methyl-1,1-dioxido-4,5-dihydrobenzo[f][1,2]thiazepin-2(3H)-yl)methyl)-4-methylphenyl)-3-(1-methyl-1H-benzo[d][1,2,3]triazol-5-yl)propanoate (420 mg, 0.597 mmol) in EtOH (20 mL) was added 10% NaOH (30 mL, 0.597 mmol) at 0° C. The reaction mixture was stirred at RT for 3 h. The reaction mixture was evaporated under reduced pressure, neutralized with 1N HCl, extracted with EtOAc (2×), The organic layer washed with brine, dried under anhydrous Na₂SO₄ and filtered. The filtrate was evaporated and was purified by preparative HPLC. The product washed with Et₂O to afford 3-(3-((7-(3-((tert-butoxycarbonyl)amino)propyl)-4-methyl-1,1-dioxido-4,5-dihydrobenzo[f][1,2]thiazepin-2(3H)-yl)methyl)-4-methylphenyl)-3-(1-methyl-1H-benzo[d][1,2,3]triazol-5-yl)propanoic acid (130 mg, 0.182 mmol, 30.4% yield) LC-MS m/z 676 (M+H)⁺, 2.51 min (ret. time).

Example 167

3-(3-(((R)-4-Ethyl-1,1-dioxido-3,4-dihydro-2H-benzo[b][1,4,5]oxathiazepin-2-yl)methyl)-4-methylphenyl)-3-(2-methyl-1,2,3,4-tetrahydroisoquinolin-6-yl)propanoic acid

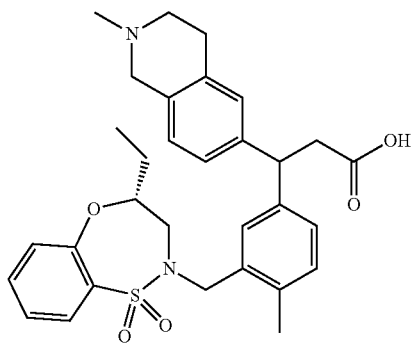 [SMILES: CC[C@@H]1CN(Cc2cc(C(CC(=O)O)c3ccc4c(c3)CCN(C)C4)ccc2C)S(=O)(=O)c2ccccc2O1]

6-Bromo-2-methyl-1,2,3,4-tetrahydroisoquinoline

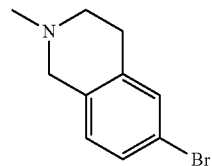

To a solution of 6-bromo-1,2,3,4-tetrahydroisoquinoline (1 g, 4.72 mmol) in formic acid (10 mL, 261 mmol) was added formaldehyde (37%) (2 mL, 72.6 mmol). The reaction was stirred at 150° C. for 15 min in a microwave reactor. The reaction mixture was concentrated under vacuum, cooled to 0° C., quenched with saturated NaHCO₃ solution, extracted with EtOAc (2×), The organic layer washed with brine, dried under anhydrous Na₂SO₄ and filtered. The filtrate was reduced under pressure to afford 6-bromo-2-methyl-1,2,3,4-tetrahydroisoquinoline (900 mg, 3.85 mmol, 82% yield). LC-MS m/z 226 (M+H)⁺, 1.29 min (ret. time). The crude compound was used for next step without further purification.

(E)-Ethyl 3-(2-methyl-1,2,3,4-tetrahydroisoquinolin-6-yl)acrylate

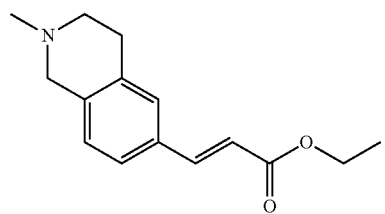 [SMILES: CCOC(=O)/C=C/c1ccc2c(c1)CCN(C)C2]

To solution of 6-bromo-2-methyl-1,2,3,4-tetrahydroisoquinoline (900 mg, 3.98 mmol) in DMF (2 mL) was added ethyl acrylate (1594 mg, 15.92 mmol), tri-o-tolylphosphine (363 mg, 1.194 mmol) and DIPEA (2.78 mL, 15.92 mmol). The mixture was degassed with nitrogen for 20 min, followed by the addition of Pd(OAc)₂ (44.7 mg, 0.199 mmol) in sealed tube. The reaction mixture was stirred at 100° C. for 3 h. The reaction mixture was then cooled to 0° C., quenched with cold water, extracted with EtOAc (2×), The organic layer washed with brine, dried under anhydrous Na₂SO₄ and filtered. The filtrate was evaporated and was purified by column chromatography using EtOAc:hexane (9:91) to afford (E)-ethyl 3-(2-methyl-1,2,3,4-tetrahydroisoquinolin-6-yl)acrylate (400 mg, 1.543 mmol, 38.8% yield) LC-MS m/z 246 (M+H)⁺, 1.40 min (ret. time).

Ethyl 3-(3-(((R)-4-ethyl-1,1-dioxido-3,4-dihydro-2H-benzo[b][1,4,5]oxathiazepin-2-yl)methyl)-4-methylphenyl)-3-(2-methyl-1,2,3,4-tetrahydroisoquinolin-6-yl)propanoate

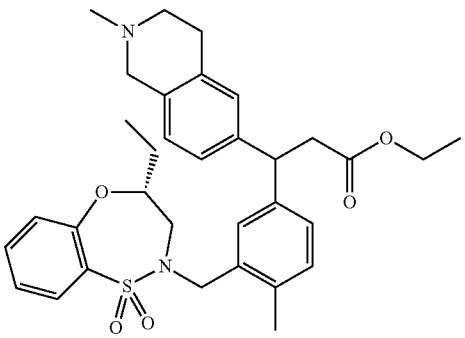 [SMILES: CCOC(=O)CC(c1ccc(C)c(CN2C[C@@H](CC)Oc3ccccc3S2(=O)=O)c1)c1ccc2c(c1)CCN(C)C2]

To solution of (E)-ethyl 3-(2-methyl-1,2,3,4-tetrahydroisoquinolin-6-yl)acrylate (400 mg, 1.631 mmol) and (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (447 mg, 0.978 mmol) in mixture of 1,4-dioxane (4 mL) and water (4 mL) was added TEA (0.682 mL, 4.89 mmol). The reaction was degassed with nitrogen for 20 min, followed by the addition of [RhCl(cod)]$_2$ (80 mg, 0.163 mmol) in a sealed tube. The reaction mixture was stirred at 90° C. for 2 h. The reaction mixture was filtered through celite. The filtrate was evaporated under reduced pressure and the crude residue was purified on flash column chromotography by using EtOAc:hexane (35:65) to afford ethyl 3-(3-(((R)-4-ethyl-1,1-dioxido-3,4-dihydro-2H-benzo[b][1,4,5]oxathiazepin-2-yl)methyl)-4-methylphenyl)-3-(2-methyl-1,2,3,4-tetrahydroisoquinolin-6-yl)propanoate (200 mg, 0.347 mmol, 21.27% yield) LC-MS m/z 576.98 (M+H)$^+$, 2.24 min (ret. time).

3-(3-(((R)-4-Ethyl-1,1-dioxido-3,4-dihydro-2H-benzo[b][1,4,5]oxathiazepin-2-yl)methyl)-4-methylphenyl)-3-(2-methyl-1,2,3,4-tetrahydroisoquinolin-6-yl)propanoic acid

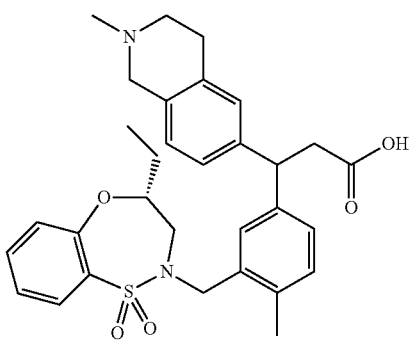 [SMILES: CC[C@@H]1CN(Cc2cc(C(CC(=O)O)c3ccc4c(c3)CCN(C)C4)ccc2C)S(=O)(=O)c2ccccc2O1]

To a solution of ethyl 3-(3-(((R)-4-ethyl-1,1-dihydro-2H-benzo[b][1,4,5]oxathiazepin-2-yl)methyl)-4-methylphenyl)-3-(2-methyl-1,2,3,4-tetrahydroisoquinolin-6-yl)propanoate (200 mg, 0.347 mmol) in EtOH 10% NaOH (15 mL, 0.347 mmol) at 0° C. The reaction mixture was stirred at RT for 2 h. The reaction mixture was evaporated under reduced pressure, cooled to 0° C. and neutralized with 1N HCl. The reaction was extracted with EtOAc (2×), The organic layer washed with brine, dried under anhydrous Na$_2$SO$_4$ and filtered. The filtrate was evaporated and was purified by column chromatography using MeOH:DCM (3:97) to afford the product as a brown solid. The solid was filtered and washed with hexane to afford 3-(3-(((R)-4-ethyl-1,1-dioxido-3,4-dihydro-2H-benzo[b][1,4,5]oxathiazepin-2-yl)methyl)-4-methylphenyl)-3-(2-methyl-1,2,3,4-tetrahydroisoquinolin-6-yl)propanoic acid (75 mg, 0.135 mmol, 38.9% yield). LC-MS m/z 549.26 (M+H)$^+$, 1.92 min (ret. time).

Example 168

5-(1-Ethyl-1H-imidazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid

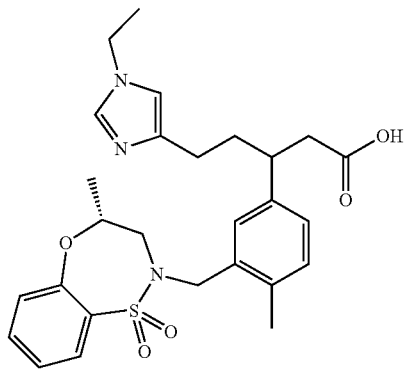 [SMILES: CCn1cnc(CCC(CC(=O)O)c2ccc(C)c(CN3C[C@@H](C)Oc4ccccc4S3(=O)=O)c2)c1]

Methyl 3-(1H-imidazol-4-yl)propanoate

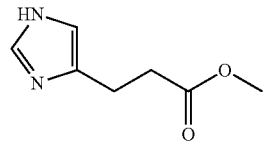

To a solution of (E)-methyl 3-(1H-imidazol-4-yl)acrylate (800 mg, 5.26 mmol) in EtOH (10 mL) was added 10% Pd/C (100 mg, 0.094 mmol) under nitrogen atmosphere. The reaction mixture was stirred under hydrogen atmosphere (60 psi) at RT for 16 h. The reaction mixture was filtered through a bed of celite. The filtrate was evaporated to afford methyl 3-(1H-imidazol-4-yl)propanoate (500 mg, 2.88 mmol, 54.8% yield). LC-MS m/z 155.1 (M+H)$^+$, 1.92 min (ret. time).

Methyl 3-(1-ethyl-1H-imidazol-4-yl)propanoate

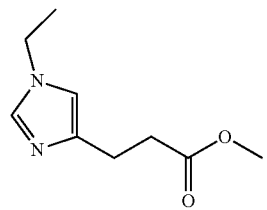

To a solution of methyl 3-(1H-imidazol-4-yl)propanoate (7 g, 45.4 mmol) in THF (50 mL) was added NaH (3.63 g, 91 mmol) at 0° C. under nitrogen atmosphere and stirred for 15 min. Then ethyl iodide (5.50 mL, 68.1 mmol) was added into the reaction mixture at 0° C. and stirred at RT 2 h. The reaction mixture was quenched with cold water, extracted with EtOAc (2×), The organic layer washed with brine, dried under anhydrous Na$_2$SO$_4$ and filtered. The filtrate was evaporated and was purified by column chromatography using EtOAc:hexane (60:40) to afford methyl 3-(1-ethyl-1H-imidazol-4-yl)propanoate (5 g, 23.89 mmol, 52.6% yield). LC-MS m/z 183.1 (M+H)$^+$, 3.18 min (ret. time).

3-(1-Ethyl-1H-imidazol-4-yl)propan-1-ol

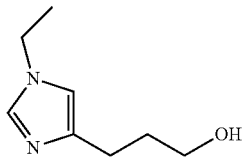

To a solution of methyl 3-(1-ethyl-1H-imidazol-4-yl)propanoate (5 g, 27.4 mmol) in THF (50 mL) was added LAH (2 mL, 2.000 mmol) at 0° C. under nitrogen atmosphere and stirred at RT for 2 h. The reaction mixture was quenched with saturated $Na_2SO_4$, extracted with EtOAc (2×), and brine. The organic layer was dried under anhydrous $Na_2SO_4$ and filtered. The filtrate was concentrated and the crude compound was purified by column chromatography to afford 3-(1-ethyl-1H-imidazol-4-yl)propan-1-ol (3.5 g, 22.70 mmol, 83% yield). $^1$H NMR (400 MHz, DMSO-d6) δ ppm 7.48 (s, 1H), 6.88 (s, 1H), 4.45 (bs, 1H), 3.90 (q, 2H), 3.43 (t, 2H), 2.47 (t, 2H), 1.70 (m, 2H), 1.20 (t, 3H).

3-(1-Ethyl-1H-imidazol-4-yl)propanal

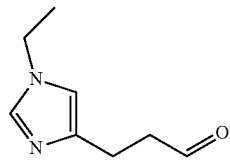

To a solution of oxalyl chloride (2.55 mL, 29.2 mmol) in DCM (30 mL) was added DMSO (3.45 mL, 48.6 mmol) at −78° C. and stirred for 20 min. Then 3-(1-ethyl-1H-imidazol-4-yl)propan-1-ol (3 g, 19.45 mmol) in DCM (8 mL) was added to the reaction mixture and stirred for 30 min. After which, TEA (13.56 mL, 97 mmol) was added at −78° C. and the reaction was warmed to RT and stirred for 3 h. The reaction mixture was quenched with cold water, extracted with DCM (2×) and brine. The organic layer was dried under anhydrous $Na_2SO_4$ and filtered. The filtrate was evaporated to afford 3-(1-ethyl-1H-imidazol-4-yl)propanal (2 g, 13.14 mmol, 67.5% yield). $^1$H NMR (400 MHz, CDCl$_3$) δ ppm 9.81 (s, 1H), 7.41 (s, 1H), 6.70 (s, 1H), 3.97 (q, 2H), 2.91 (m, 2H), 2.81 (m, 2H), 1.42 (t, 3H).

(E)-Ethyl 5-(1-ethyl-1H-imidazol-4-yl)pent-2-enoate

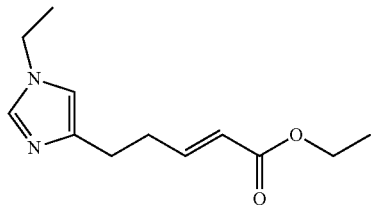 [SMILES: CCOC(=O)/C=C/CCc1cn(CC)cn1]

To a suspension of NaH (0.631 g, 26.3 mmol) in THF (20 mL) was added triethyl phosphonoacetate (3.16 mL, 15.77 mmol) at 0° C. and stirred for 15 min. Then 3-(1-ethyl-1H-imidazol-4-yl)propanal (2 g, 13.14 mmol) in THF (12 mL) was added to the reaction mixture and stirred at RT for 2 h. The reaction mixture was quenched with cold water, extracted with EtOAc (2×), The organic layer washed with brine, dried under anhydrous $Na_2SO_4$ and filtered. The filtrate was evaporated and was purified by column chromatography using EtOAc:hexane (80:20) to afford ((E)-ethyl H-imidazol-(1.6 g, 6.85 mmol, 52.1% yield). LC-MS m/z 223.20 (M+H)$^+$, 1.10 min (ret. time).

Ethyl 5-(1-ethyl-1H-imidazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate

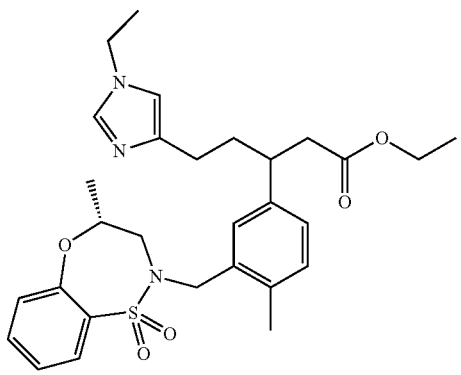 [SMILES: CCOC(=O)CC(CCc1cn(CC)cn1)c1ccc(C)c(CN2C[C@@H](C)Oc3ccccc3S2(=O)=O)c1]

To a solution of (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (598 mg, 1.350 mmol), (E)-ethyl 5-(1-ethyl-1H-imidazol-4-yl)pent-2-enoate (200 mg, 0.900 mmol) in 1,4-dioxane (5 mL) and water (1 mL) was added TEA (0.09 mL, 0.675 mmol) at RT. The reaction mixture was degassed for 10 min. Then [RhCl(cod)]$_2$ (44.4 mg, 0.090 mmol) was added under argon. The resulting suspension was heated in a microwave at high absorption for 1 h at 150° C. The reaction mixture was filtered through celite and washed with EtOAc (15 mL). The filtrate was washed with water (30 mL), brine solution (30 mL) and dried over anhydrous $Na_2SO_4$ and concentrated to afford crude compound. The crude product was purified on flash column chromatography by using MeOH:DCM (0.2:9.8) to afford ethyl 5-(1-ethyl-1H-imidazol-4-yl)-3-(4-methyl-3-(((R)-4-methyl-1,1-dioxido-3,4-dihydro-2H-benzo[b][1,4,5]oxathiazepin-2-yl)methyl)phenyl) pentanoate (320 mg, 0.043 mmol, 61.4% yield). LC-MS m/z 540.1 (M+H)$^+$, 3.65 min (ret. time).

5-(1-Ethyl-1H-imidazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid

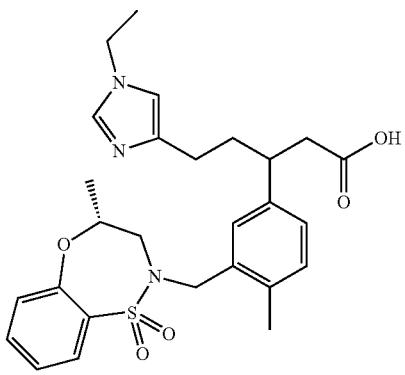 [SMILES: CCn1cnc(CCC(CC(=O)O)c2ccc(C)c(CN3C[C@@H](C)Oc4ccccc4S3(=O)=O)c2)c1]

To a solution of ethyl 5-(1-ethyl-1H-imidazol-4-yl)-3-(4-methyl-3-(((R)-4-methyl-1,1-dioxido-3,4-dihydro-2H- benzo[b][1,4,5]oxathiazepin-2-yl)methyl)phenyl)pentanoate (250 mg, 0.463 mmol) in EtOH (15 mL) was added 2N NaOH solution (10 mL) at 0° C. then allowed to stir at RT for 3 h. The reaction mixture was concentrated under reduced pressure and then acidified with 1N HCl solution and extracted with EtOAc (30 mL×4). The combined organic layers were dried over anhydrous Na₂SO₄ and concentrated to afford crude compound. The crude compound was first purified by column chromatography using MeOH:DCM (1:9) and again by preparative HPLC. The collected fractions were concentrated under reduced pressure. The aqueous layer was acidified with 1N HCl to pH 4 and extracted with ethyl acetate (25 mL×3). The organic layer was dried over anhydrous Na₂SO₄ and concentrated under reduced pressure to afford. 5-(1-ethyl-1H-imidazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid. LC-MS m/z 512.34 (M+H)⁺, 2.05 min (ret. time).

Example 169

3-(4-Methyl-3-(((R)-4-methyl-1,1-dioxido-3,4-dihydro-2H-benzo[b][1,4,5]oxathiazepin-2-yl)methyl)phenyl)-5-(pyridin-3-yl)pentanoic acid

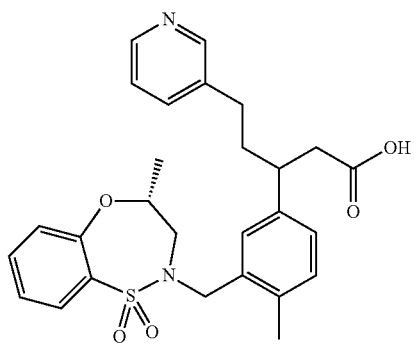 [SMILES: Cc1ccc(C(CCc2cccnc2)CC(=O)O)cc1CN1C[C@@H](C)Oc2ccccc2S1(=O)=O]

3-(Pyridin-3-yl)propanal

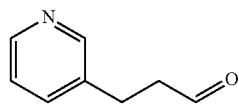

To a solution of DCM (130 mL) was added oxalyl chloride (2.87 mL, 32.8 mmol) at RT. The reaction mixture was cooled to −78° C. added a solution of DMSO (3.88 mL, 54.7 mmol) in DCM (20 mL) was added and stirred for 20 min. Then a solution of 3-(pyridin-3-yl)propan-1-ol (3 g, 21.87 mmol) in DCM (50 mL) was added at −78° C. and stirred for 30 min. After which, TEA (15.24 mL, 109 mmol) was added dropwise, and stirred for 1 h at −78° C. The reaction mixture was quenched with water and the organic layer was separated. The aqueous layer extracted with DCM (2×25 mL). The combined organic layers were washed with ice cold water (30 mL) followed by brine solution (30 mL). The organic layer was dried over anhydrous Na₂SO₄ and concentrated to afford 3-(pyridin-3-yl)propanal (2 g, 14.80 mmol, 67.7% yield). LC-MS m/z 136.17 (M+H)⁺, 0.27 min (ret. time).

(E)-Ethyl 5-(pyridin-3-yl)pent-2-enoate

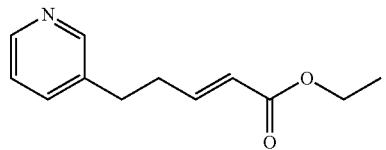

To a solution of 3-(pyridin-3-yl)propanal (2 g, 14.80 mmol) in THF (40 mL) added NaH (0.533 g, 22.20 mmol) at 0° C., stirred for 15 min, then triethyl phosphonoacetate (3.26 mL, 16.28 mmol) was added dropwise at 0° C. and stirred for 1 h. The reaction mixture was quenched with ice cold water and extracted with EtOAc (20 mL×4). The combined organic layers were dried over anhydrous Na₂SO₄ and concentrated to afford crude compound. The crude compound was purified by column chromotography using 70% EtOAc/petroleum ether as eluent. to afford (E)-ethyl 5-(pyridin-3-yl)pent-2-enoate (800 mg, 3.44 mmol, 23.22% yield). LC-MS m/z 206.23 (M+H)⁺, 1.22 min (ret. time).

Ethyl 3-(4-methyl-3-(((R)-4-methyl-1,1-dioxido-3,4-dihydro-2H-benzo[b][1,4,5]oxathiazepin-2-yl)methyl)phenyl)-5-(pyridin-3-yl)pentanoate

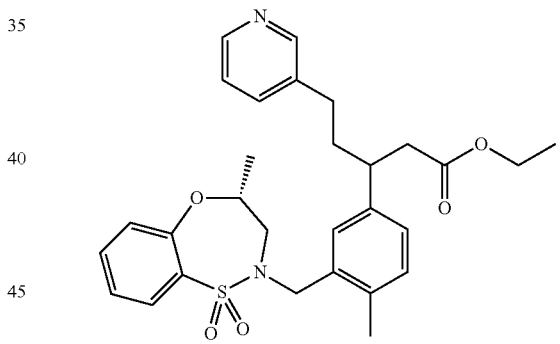

To a solution of (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (500 mg, 1.128 mmol) in 1,4-dioxane (5 mL) added (E)-ethyl 5-(pyridin-3-yl)pent-2-enoate (231 mg, 1.128 mmol), TEA (0.472 mL, 3.38 mmol) and water (5.00 mL) at RT. The reaction mixture was degassed with argon for 10 min and then [RhCl(cod)]₂ (55.6 mg, 0.113 mmol) was added under argon. The reaction mixture was heated to 90° C. for 4 h. The reaction mixture was filtered through celite and washed with ethyl acetate (50 mL). The filtrate was washed with water (30 mL) followed by a brine solution (30 mL). The combined organic layers were dried over anhydrous Na₂SO₄ and to afford crude compound. The crude compound was purified by using (1:9) MeOH:DCM as eluent to afford ethyl 3-(4-methyl-3-(((R)-4-methyl-1,1-dioxido-3,4-dihydro-2H-benzo[b][1,4,5]oxathiazepin-2-yl)methyl)phenyl)-5-(pyridin-3-yl)pentanoate (200 mg, 0.338 mmol, 29.9% yield). LC-MS m/z 523 (M+H)⁺, 2.29 min (ret. time).

3-(4-Methyl-3-(((R)-4-methyl-1,1-dioxido-3,4-dihydro-2H-benzo[b][1,4,5]oxathiazepin-2-yl)methyl)phenyl)-5-(pyridin-3-yl)pentanoic acid

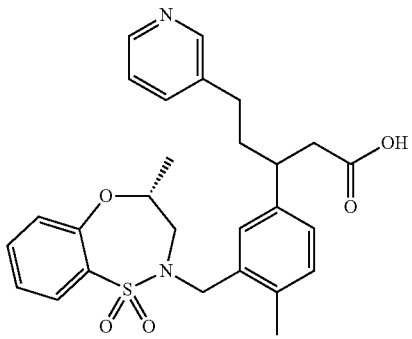 [SMILES: Cc1ccc(C(CCc2cccnc2)CC(=O)O)cc1CN1C[C@@H](C)Oc2ccccc2S1(=O)=O]

To a solution of ethyl 3-(4-methyl-3-(((R)-4-methyl-1,1-dioxido-3,4-dihydro-2H-benzo[b][1,4,5]oxathiazepin-2-yl)methyl)phenyl)-5-(pyridin-3-yl)pentanoate (200 mg, 0.383 mmol) in EtOH (10 mL) was added 10% NaOH (0.191 mL, 0.383 mmol) and stirred at RT for 3 h. The reaction mixture was concentrated under reduced pressure and acidified with 1N HCl solution to pH=4. The precipitated solid was filtered and dried under vacuum to afford crude compound. The crude compound was purified on flash column chromatography by using 2% MeOH in DCM. The collected fractions were concentrated under reduced pressure to afford 3-(4-methyl-3-(((R)-4-methyl-1,1-dioxido-3,4-dihydro-2H-benzo[b][1,4,5]oxathiazepin-2-yl)methyl)phenyl)-5-(pyridin-3-yl)pentanoic acid (55 mg, 0.109 mmol, 28.4% yield) LC-MS m/z 495.05 (M+H)$^+$, 1.78 min (ret. time).

Example 170

3-(4-Methyl-3-(((R)-4-methyl-1,1-dioxido-3,4-dihydro-2H-benzo[b][1,4,5]oxathiazepin-2-yl)methyl)phenyl)-5-(o-tolyl)pentanoic acid

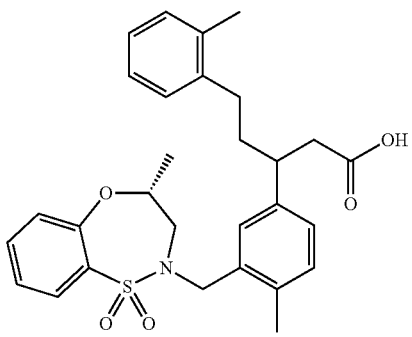 [SMILES: Cc1ccccc1CCC(CC(=O)O)c1ccc(C)c(CN2C[C@@H](C)Oc3ccccc3S2(=O)=O)c1]

3-(o-Tolyl)propan-1-ol

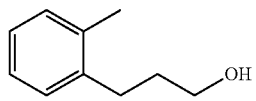

To a solution of 3-(o-tolyl)propanoic acid (2 g, 12.18 mmol) in THF (20 mL) dropwise added a 1M LAH in THF (14.62 mL, 14.62 mmol) solution at 0° C. and stirred for 1 h at 0° C. The reaction mixture was quenched with saturated Na$_2$SO$_4$ solution (15 mL) and extracted with EtOAc (2×15 mL). The combined organic layers were washed with brine solution (15 mL), dried over anhydrous Na$_2$SO$_4$ and concentrated to afford 3-(o-tolyl)propan-1-ol (1.3 g, 8.45 mmol, 69.3% yield) LC-MS m/z 150.98 (M+H)$^+$, 1.95 min (ret. time).

3-(o-Tolyl)propanal

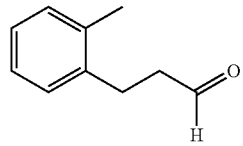

To a solution of 3-(o-tolyl)propan-1-ol (1.3 g, 8.65 mmol) in DCM (26 mL) added PCC (3.73 g, 17.31 mmol) and stirred at RT for 2 h. The reaction mixture was filtered through celite and washed with DCM. The filtrate was concentrated under reduced pressure to afford 3-(o-tolyl)propanal (700 mg, 4.72 mmol, 54.6% yield). $^1$H NMR (400 MHz, DMSO-d6) δ ppm 9.79 (s, 1H), 7.15 (m, 4H), 2.80 (m, 4H), 2.30 (s, 3H).

(E)-Ethyl 5-(o-tolyl)pent-2-enoate

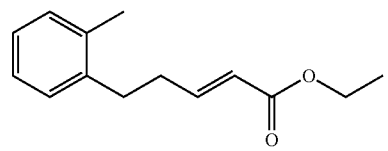 [SMILES: CCOC(=O)/C=C/CCc1ccccc1C]

To a stirred solution of NaH (227 mg, 9.45 mmol) in THF was added triethyl phosphonoacetate (1.418 mL, 7.08 mmol) dropwise at 0° C. and stirred for 20 min. Then 3-(o-tolyl)propanal (700 mg, 4.72 mmol) was added and stirred for 1 h at 0° C. The reaction mixture was quenched with ice, extracted with EtOAc (2×80 mL). The combined organic layers were washed with brine (100 mL), dried over anhydrous Na$_2$SO$_4$ and concentrated to afford (E)-ethyl 5-(o-tolyl)pent-2-enoate (600 mg, 1.986 mmol, 42.1% yield). LC-MS m/z 219.09 (M+H)$^+$, 2.76 min (ret. time).

Ethyl 3-(4-methyl-3-(((R)-4-methyl-1,1-dioxido-3,4-dihydro-2H-benzo[b][1,4,5]oxathiazepin-2-yl)methyl)phenyl)-5-(o-tolyl)pentanoate

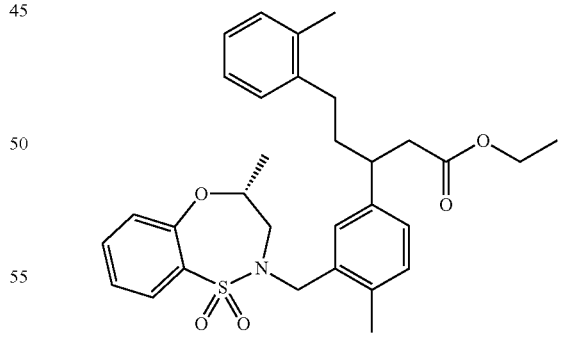

To a solution of (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (1219 mg, 2.75 mmol) in 1,4-dioxane (10 mL) added (E)-ethyl 5-(o-tolyl)pent-2-enoate (600 mg, 2.75 mmol), TEA (1.149 mL, 8.25 mmol) and water (5 mL) at RT. The reaction mixture was degassed with argon for 10 min and then [RhCl(cod)]$_2$ (136 mg, 0.275 mmol) was added under argon. The reaction mixture was heated to 90° C. for 3 h. The reaction mixture was cooled to room temperature, filtered through celite, and washed with EtOAc (50 mL). The filtrate was washed with water (30 mL). The organic layer was dried over anhydrous Na₂SO₄ and concentrated to afford crude residue. The crude residue was purified by flash column chromatography using EtOAc:hexane (1.5:8.5) to afford ethyl 3-(4-methyl-3-(((R)-4-methyl-1,1-dioxido-3,4-dihydro-2H-benzo[b][1,4,5]oxathiazepin-2-yl)methyl)phenyl)-5-(o-tolyl)pentanoate (250 mg, 0.463 mmol, 16.85% yield). LC-MS m/z 536.16 (M+H)⁺, 3.18 min (ret. time).

3-(4-Methyl-3-(((R)-4-methyl-1,1-dioxido-3,4-dihydro-2H-benzo[b][1,4,5]oxathiazepin-2-yl)methyl)phenyl)-5-(o-tolyl)pentanoic acid

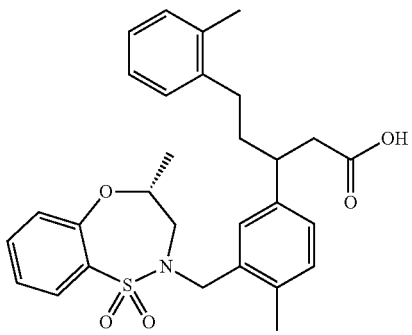 [SMILES: Cc1ccccc1CCC(CC(=O)O)c1ccc(C)c(CN2C[C@@H](C)Oc3ccccc3S2(=O)=O)c1]

To a solution of ethyl 3-(4-methyl-3-(((R)-4-methyl-1,1-dioxido-3,4-dihydro-2H-benzo[b][1,4,5]oxathiazepin-2-yl)methyl)phenyl)-5-(o-tolyl)pentanoate (310 mg, 0.579 mmol) in EtOH (10 mL) was added 10% NaOH solution (10 mL, 0.579 mmol) and the reaction mixture was stirred at RT for 2 h. The reaction mixture was concentrated under reduced pressure, acidified with 1N HCl solution upto pH=4 and extracted with EtOAc (3×30 mL). The combined organic layers were dried over anhydrous Na₂SO₄ and concentrated to afford crude compound. The crude compound washed with Et₂O and dried under vacuum to afford 3-(4-methyl-3-(((R)-4-methyl-1,1-dioxido-3,4-dihydro-2H-benzo[b][1,4,5]oxathiazepin-2-yl)methyl)phenyl)-5-(o-tolyl)pentanoic acid (110 mg, 0.214 mmol, 37.0% yield). LC-MS m/z 508.15 (M+H)⁺, 2.76 min (ret. time).

Example 171

3-(5-(2-(Dimethylamino)ethyl)-4-fluoro-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid

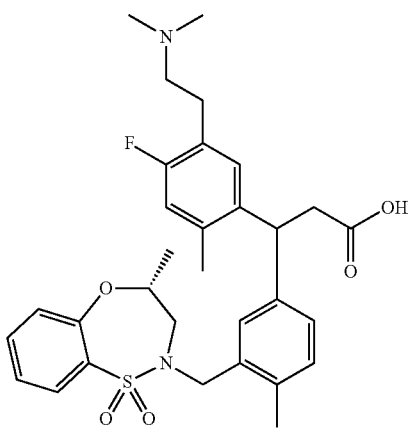 [SMILES: Cc1ccc(C(CC(=O)O)c2cc(CCN(C)C)c(F)cc2C)cc1CN1C[C@@H](C)Oc2ccccc2S1(=O)=O]

(E)-1-Bromo-4-fluoro-2-methyl-5-(2-nitrovinyl)benzene

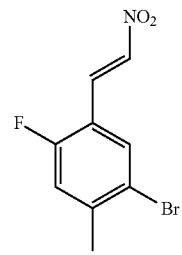

To a solution of 5-bromo-2-fluoro-4-methylbenzaldehyde (500 mg, 2.304 mmol) in nitromethane (3 mL, 55.6 mmol) was added NH₄OAc (53.3 mg, 0.691 mmol) and the reaction mixture was heated to 90° C. in microwave for 20 min. The reaction mixture was concentrated to afford crude compound. The crude compound was purified using 0.5% EtOAc in hexane. The eluted fractions were concentrated to afford (E)-1-bromo-4-fluoro-2-methyl-5-(2-nitrovinyl)benzene (150 mg, 0.510 mmol, 22.16% yield). LC-MS m/z 259 (M+H)⁺, 3.98 min (ret. time).

2-(5-Bromo-2-fluoro-4-methylphenyl)ethanamine

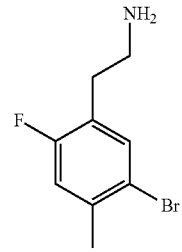

To a solution of (E)-1-bromo-4-fluoro-2-methyl-5-(2-nitrovinyl)benzene (400 mg, 1.538 mmol) in THF was added LAH (117 mg, 3.08 mmol) at 0° C. and the reaction mixture was heated to reflux for 3 h. The reaction mixture was quenched with a saturated Na₂SO₄ solution and extracted with EtOAc (3×30 mL). The combined organic layers were washed with brine solution and dried over anhydrous Na₂SO₄ and concentrated to afford crude 2-(5-bromo-2-fluoro-4-methylphenyl)ethanamine (250 mg, 0.339 mmol, 22.06% yield). LC-MS m/z 232 (M+H)⁺, 1.60 min (ret. time).

2-(5-Bromo-2-fluoro-4-methylphenyl)-N,N-dimethylethanamine

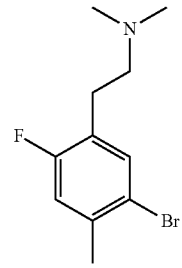

To a solution of 2-(5-bromo-2-fluoro-4-methylphenyl)-N,N-dimethylethanamine (350 mg, 1.345 mmol, 26.0% yield) in DMF (10 mL) was added NaH (0.248 g, 10.34 mmol) at 0° C. and stirred for 30 min. MeI (0.970 mL, 15.51 mmol) was then added dropwise and allowed to stir at RT for 2 h.

The reaction mixture was quenched with ice, and extracted with EtOAc (2×50 mL). The combined organic layers were washed with ice cold water (3×50 mL), brine (75 mL) and dried over anhydrous Na$_2$SO$_4$ and concentrated to afford crude compound. The crude residue was purified using 8% EtOAc in hexane to afford 2-(5-bromo-2-fluoro-4-methylphenyl)-N,N-dimethylethanamine (350 mg, 1.345 mmol, 26.0% yield). $^1$H NMR (400 MHz, CDCl$_3$) δ ppm 7.99 (d, 1H), 6.95 (d, 1H), 3.08 (m, 2H), 2.92 (m, 2H), 2.70 (s, 6H), 2.38 (s, 3H).

(E)-Ethyl 3-(5-(2-(dimethylamino)ethyl)-4-fluoro-2-methylphenyl)acrylate

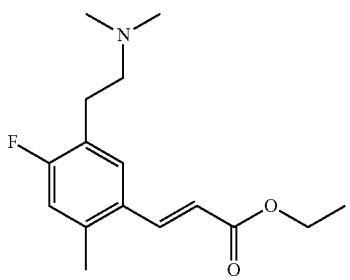 [SMILES: CCOC(=O)/C=C/c1cc(CCN(C)C)c(F)cc1C]

To a solution of 2-(5-bromo-2-fluoro-4-methylphenyl)-N,N-dimethylethanamine (350 mg, 1.345 mmol) in DMF (3 mL) was added tri-o-tolylphosphine (123 mg, 0.404 mmol), ethyl acrylate (673 mg, 6.73 mmol), and DIPEA (0.940 mL, 5.38 mmol). The reaction mixture was degassed for 15 min and then Pd(OAc)$_2$ (45.3 mg, 0.202 mmol) was added under argon. The reaction mixture was heated to 90° C. and stirred for 3 h. The reaction mixture was quenched with ice cold water and extracted with EtOAc (2×50 mL). The combined organic layers were washed with ice cold water (2×50) and brine (50 mL). The organic layer was dried over anhydrous Na$_2$SO$_4$ and to afford crude compound. The crude residue was purified using MeOH:DCM (0.2:0.8). The eluted fractions were concentrated under reduced pressure to afford (E)-ethyl 3-(5-(2-(dimethylamino)ethyl)-4-fluoro-2-methylphenyl)acrylate (190 mg, 0.579 mmol, 43.0% yield). LC-MS m/z 280 (M+H)$^+$, 1.68 min (ret. time).

Ethyl 3-(5-(2-(dimethylamino)ethyl)-4-fluoro-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoate

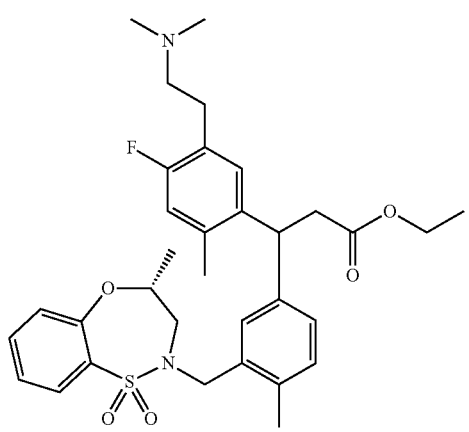 [SMILES: CCOC(=O)CC(c1ccc(C)c(CN2C[C@@H](C)Oc3ccccc3S2(=O)=O)c1)c1cc(CCN(C)C)c(F)cc1C]

To a solution of (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (190 mg, 0.429 mmol) in 1,4-dioxane (2 mL) was added (E)-ethyl 3-(5-(2-(dimethylamino)ethyl)-4-fluoro-2-methylphenyl)acrylate (120 mg, 0.429 mmol), TEA (0.179 mL, 1.286 mmol) and water (2 mL) at RT. The reaction mixture was degassed with argon for 10 min then [RhCl(cod)]$_2$ (21.13 mg, 0.043 mmol) was added under argon. The reaction mixture was heated to 90° C. and stirred for 6 h. The reaction mixture was cooled to RT, filtered through celite and washed with EtOAc (50 mL). The filtrate was washed with water (30 mL). The organic layer was dried over anhydrous Na$_2$SO$_4$ and concentrated under reduced pressure. The crude residue was purified using 5% MeOH in DCM as eluent. The eluted fractions were concentrated under reduced pressure to afford ethyl 3-(5-(2-(dimethylamino)ethyl)-4-fluoro-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoate (120 mg, 0.177 mmol, 41.2% yield). LC-MS m/z 597.05 (M+H)$^+$, 2.28 min (ret. time).

3-(5-(2-(Dimethylamino)ethyl)-4-fluoro-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid

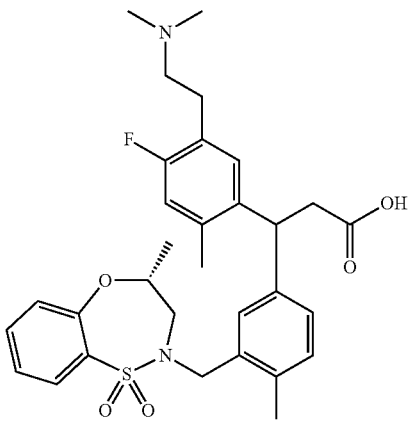 [SMILES: Cc1ccc(C(CC(=O)O)c2cc(CCN(C)C)c(F)cc2C)cc1CN1C[C@@H](C)Oc2ccccc2S1(=O)=O]

To a solution of ethyl 3-(5-(2-(dimethylamino)ethyl)-4-fluoro-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoate (120 mg, 0.201 mmol) in EtOH (5 mL) added a 10% NaOH solution (5 mL, 0.201 mmol) and the reaction mixture was stirred for 2 h at RT. The reaction mixture was concentrated under reduced pressure. The residue was added to ice cold water and acidified with 1N HCl, and extracted with EtOAc (3×20 mL). The organic layer washed with brine solution (15 mL), dried over anhydrous Na$_2$SO$_4$ and concentrated under reduced pressure. The residue was purified by preparative HPLC to afford 3-(5-(2-(dimethylamino)ethyl)-4-fluoro-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid (35 mg, 0.061 mmol, 77% yield). LC-MS m/z 568.9 (M+H)$^+$, 3.19 min (ret. time).

Example 172

3-(3-(((R)-4-Ethyl-1,1-dioxido-3,4-dihydro-2H-benzo[b][1,4,5]oxathiazepin-2-yl)methyl)-4-methylphenyl)-3-(2-methylisoindolin-5-yl)propanoic acid

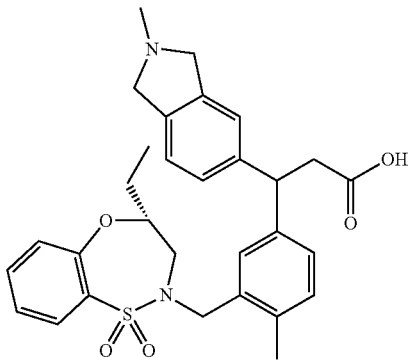 [SMILES: CC[C@@H]1CN(Cc2cc(C(CC(=O)O)c3ccc4c(c3)CN(C)C4)ccc2C)S(=O)(=O)c2ccccc2O1]

5-Bromo-2-methylisoindoline

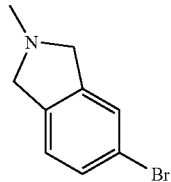

To a solution of 5-bromoisoindoline (1.5 g, 7.57 mmol) in formic acid (12 mL) was added formaldehyde (3 mL, 109 mmol) and the reaction mixture was heated to 150° C. in microwave vial for 15 min. The reaction mixture was concentrated under reduced pressure. The residue was neutralised with sat. bicarbonate solution up to pH 7 and extracted with EtOAc (3×50 mL). The combined organic layers were washed with brine and the organic layer was dried over anhydrous Na₂SO₄ and concentrated to afford crude residue. The crude residue was purified using 3% MeOH in DCM as eluent to afford 5-bromo-2-methylisoindoline (900 mg, 3.75 mmol, 49.5% yield). LC-MS m/z 211.8 (M+H)⁺, 1.15 min (ret. time).

(E)-Ethyl 3-(2-methylisoindolin-5-yl)acrylate

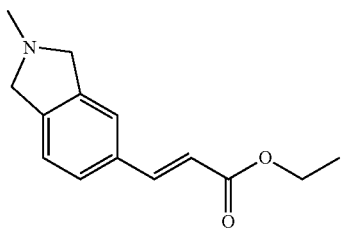 [SMILES: CCOC(=O)/C=C/c1ccc2c(c1)CN(C)C2]

To a solution of 5-bromo-2-methylisoindoline (900 mg, 4.24 mmol) in DMF (15 mL) was added tri-o-tolylphosphine (387 mg, 1.273 mmol), ethyl acrylate (2124 mg, 21.22 mmol), DIPEA (2.96 mL, 16.97 mmol). The reaction mixture was degassed for 15 min and then Pd(OAc)₂ (143 mg, 0.637 mmol) was added under argon. The reaction mixture was heated to 90° C. and stirred for 2 h. The reaction mixture was cooled to RT, filtered through celite, and washed with EtOAc (30 mL). The filtrate was diluted with ice cold water and extracted with EtOAc (3×30 mL). The combined organic layers were washed with chilled water (3×40 mL) and brine (50 mL). The organic layer was dried over anhydrous Na₂SO₄ and concentrated to afford crude residue. The crude residue was purified using 3% meOH in DCM as eluent to afford (E)-ethyl 3-(2-methylisoindolin-5-yl)acrylate (350 mg, 1.426 mmol, 33.6% yield) LC-MS m/z 232 (M+H)⁺, 1.33 min (ret. time).

Ethyl 3-(3-(((R)-4-ethyl-1,1-dioxido-3,4-dihydro-2H-benzo[b][1,4,5]oxathiazepin-2-yl)methyl)-4-methylphenyl)-3-(2-methylisoindolin-5-yl)propanoate

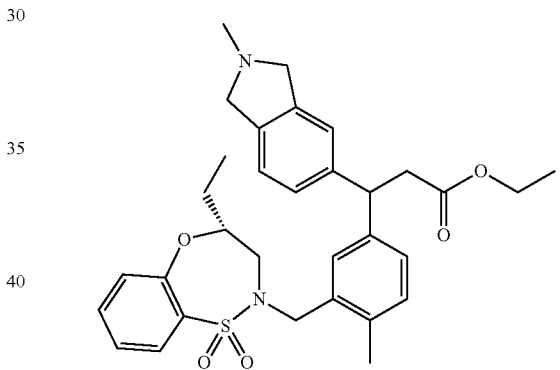

To a solution of (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (692 mg, 1.513 mmol) in 1,4-dioxane (5 mL) was added (E)-ethyl 3-(2-methylisoindolin-5-yl)acrylate (350 mg, 1.513 mmol), TEA (0.633 mL, 4.54 mmol) and water (5 mL) at RT. The reaction mixture was degassed with argon for 10 min then [RhCl(cod)]₂ (74.6 mg, 0.151 mmol) was added under argon. The reaction mixture was heated to 90° C. and stirred for 16 h. The reaction mixture was cooled to RT and filtered through celite and washed with EtOAc (50 mL). The organic layer washed with water, brine (30 mL), dried over anhydrous Na₂SO₄ and concentrated to afford crude residue. The crude residue was purified using 5% MeOH in DCM as eluent to afford ethyl 3-(3-(((R)-4-ethyl-1,1-dioxido-3,4-dihydro-2H-benzo[b][1,4,5]oxathiazepin-2-yl)methyl)-4-methylphenyl)-3-(2-methylisoindolin-5-yl)propanoate (170 mg, 0.236 mmol, 15.60% yield) LC-MS m/z 563.17 (M+H)⁺, 3.83 min (ret. time).

381

3-(3-(((R)-4-Ethyl-1,1-dioxido-3,4-dihydro-2H-benzo[b][1,4,5]oxathiazepin-2-yl)methyl)-4-methylphenyl)-3-(2-methylisoindolin-5-yl)propanoic acid

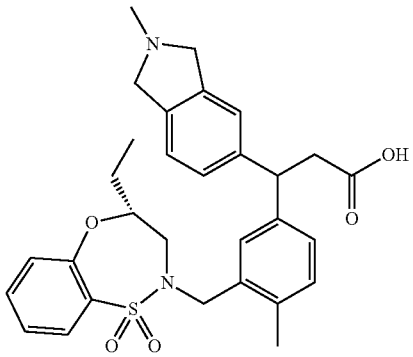 [SMILES: CC[C@@H]1CN(Cc2cc(C(CC(=O)O)c3ccc4c(c3)CN(C)C4)ccc2C)S(=O)(=O)c2ccccc2O1]

To a solution of ethyl 3-(3-(((R)-4-ethyl-1,1-dioxido-3,4-dihydro-2H-benzo[b][1,4,5]oxathiazepin-2-yl)methyl)-4-methylphenyl)-3-(2-methylisoindolin-5-yl)propanoate (170 mg, 0.302 mmol) in EtOH (10 mL) was added 10% NaOH solution (5 mL, 0.302 mmol) and stirred at RT for 2 h. The reaction mixture was concentrated under reduced pressure and the residue was diluted with ice and acidified with 1N HCl to pH 2. The aqueous layer was extracted with EtOAc (3×30 mL) and the combined organic layers were washed with brine (50 mL), dried over anhydrous $Na_2SO_4$ and concentrated to afford crude compound. The crude residue washed with $Et_2O$ followed by n-pentane and dried under vacuum to afford 3-(3-(((R)-4-ethyl-1,1-dioxido-3,4-dihydro-2H-benzo[b][1,4,5]oxathiazepin-2-yl)methyl)-4-methylphenyl)-3-(2-methylisoindolin-5-yl)propanoic acid (80 mg, 0.146 mmol, 48.3% yield). LC-MS m/z 534.8 $(M+H)^+$, 3.14 min (ret. time).

Example 173

3-(5-(3-(Dimethylamino)propyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid

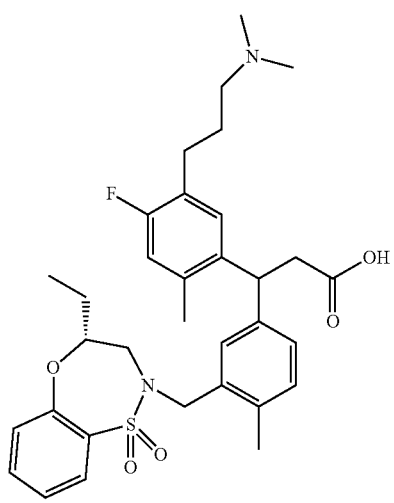 [SMILES: CC[C@@H]1CN(Cc2cc(C(CC(=O)O)c3cc(CCCN(C)C)c(F)cc3C)ccc2C)S(=O)(=O)c2ccccc2O1]

382

(E)-Ethyl 3-(5-bromo-2-fluoro-4-methylphenyl)acrylate

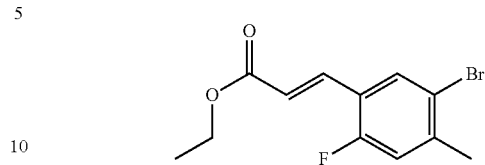

To a suspension of NaH (0.663 g, 27.6 mmol) in THF (50 mL) added triethyl phosphonoacetate (4.80 mL, 23.96 mmol) and stirred for 30 min. Then a solution of 5-bromo-2-fluoro-4-methylbenzaldehyde (4 g, 18.43 mmol) in THF was added and stirred for 2 h at RT. The reaction mixture was quenched with ice and extracted with EtOAc (3×50 mL). The combined organic layers were washed with brine (100 mL), dried over anhydrous $Na_2SO_4$ and to afford (E)-ethyl 3-(5-bromo-2-fluoro-4-methylphenyl)acrylate (3 g, 8.42 mmol, 45.7% yield). LC-MS m/z 286.88 $(M+H)^+$, 2.94 min (ret. time).

3-(5-Bromo-2-fluoro-4-methylphenyl)propan-1-ol

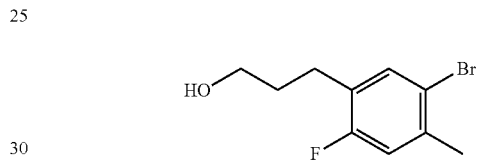

To a solution of (E)-ethyl 3-(5-bromo-2-fluoro-4-methylphenyl)acrylate (4.2 g, 14.63 mmol) in THF (40 mL) was added superhydride (43.9 mL, 43.9 mmol) at 0° C. and was allowed to warm to RT The reaction was stirred for 16 h after which the reaction mixture was quenched with ice and extracted with EtOAc (3×80 mL). The combined organic layer washed with brine (100 mL) and dried over anhydrous $Na_2SO_4$ and concentrated to afford crude compound. The crude residue was purified by column chromatography using 2% EtOAc in hexanes as eluent. The eluted fraction were concentrated to afford 3-(5-bromo-2-fluoro-4-methylphenyl)propan-1-ol (2 g, 8.09 mmol, 55.3% yield). $^1$H NMR (400 MHz, $CDCl_3$) δ ppm 7.38 (d, 1H), 6.90 (d, 1H), 3.70 (m, 2H), 2.70 (t, 2H), 2.35 (s, 3H), 1.89 (m, 2H), 1.30 (m, 1H).

3-(5-Bromo-2-fluoro-4-methylphenyl)propanal

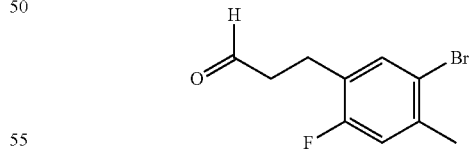

To a solution of 3-(5-bromo-2-fluoro-4-methylphenyl)propan-1-ol (2 g, 8.09 mmol) in DCM (20 mL) was added Dess-Martin periodinane (6.87 g, 16.19 mmol) at 0° C. and the reaction mixture was allowed to warm to RT and stirred for 1 h. The reaction mixture was filtered through celite, and washed with DCM. The filtrate was concentrated to afford the crude residue. The crude residue was purified by column chromatography using 5% EtOAc in hexanes as eluent. to afford 3-(5-bromo-2-fluoro-4-methylphenyl)propanal (800 mg, 3.26 mmol, 40.3% yield). $^1$H NMR (400 MHz, $CDCl_3$) δ ppm 9.80 (s, 1H), 7.35 (d, 1H), 6.90 (d, 1H), 2.94 (m, 2H), 2.77 (m, 2H), 2.35 (s, 3H).

383

3-(5-Bromo-2-fluoro-4-methylphenyl)-N,N-dimethylpropan-1-amine

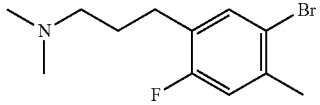

To a solution of 3-(5-bromo-2-fluoro-4-methylphenyl) propanal (800 mg, 3.26 mmol) in THF (10 mL) was added dimethylamine (3.26 mL, 6.53 mmol) and AcOH (0.037 mL, 0.653 mmol), and stirred for 30 min at RT. The reaction mixture was cooled to 0° C. and Na(OAc)$_3$BH (1384 mg, 6.53 mmol), was added and the reaction mixture was allowed to warm to RT and stirred for 5 h. The reaction mixture was quenched with a sat.bicarbonate solution and extracted with EtOAc (3×100 mL). The combined organic layer washed with brine (100 mL), dried over anhydrous Na$_2$SO$_4$ and concentrated to afford a crude residue. The crude residue was purified by column chromatography using 80% EtOAc in hexanes as eluent to afford 3-(5-bromo-2-fluoro-4-methylphenyl)-N,N-dimethylpropan-1-amine (500 mg, 1.824 mmol, 55.9% yield). $^1$H NMR (400 MHz, CDCl$_3$) δ ppm 7.37 (d, 1H), 6.90 (d, 1H), 2.61 (m, 2H), 2.41 (m, 2H), 2.32 (m, 9H), 1.72 (m, 2H).

(E)-Ethyl 3-(5-(3-(dimethylamino)propyl)-4-fluoro-2-methylphenyl)acrylate

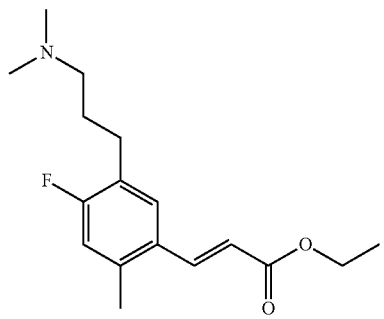 [SMILES: CCOC(=O)/C=C/c1cc(CCCN(C)C)c(F)cc1C]

To a solution of 3-(5-bromo-2-fluoro-4-methylphenyl)-N,N-dimethylpropan-1-amine (550 mg, 2.006 mmol) in DMF (15 mL) was added tri-o-tolylphosphine (183 mg, 0.602 mmol), ethyl acrylate (1004 mg, 10.03 mmol), DIPEA (1.401 mL, 8.02 mmol). The reaction mixture was degassed for 15 min and then Pd(OAc)$_2$ (67.6 mg, 0.301 mmol) was added under argon. The reaction mixture was heated to 90° C. and stirred for 2 h. The reaction mixture was cooled to RT, filtered through celite, and washed with EtOAc (30 mL). The filtrate was diluted with ice cold water and extracted with EtOAc (3×30 mL). The combined organic layers were washed with chilled water (3×40 mL) and brine (50 mL). The organic layer was dried over anhydrous Na$_2$SO$_4$ and concentrated to afford a crude residue. The crude compound was purified using 3% MeOH in DCM as eluent to afford (E)-ethyl 3-(5-(3-(dimethylamino)propyl)-4-fluoro-2-methylphenyl)acrylate (350 mg, 1.037 mmol, 51.7% yield). LC-MS m/z 294.10 (M+H)$^+$, 1.79 min (ret. time).

384

Ethyl 3-(5-(3-(dimethylamino)propyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoate

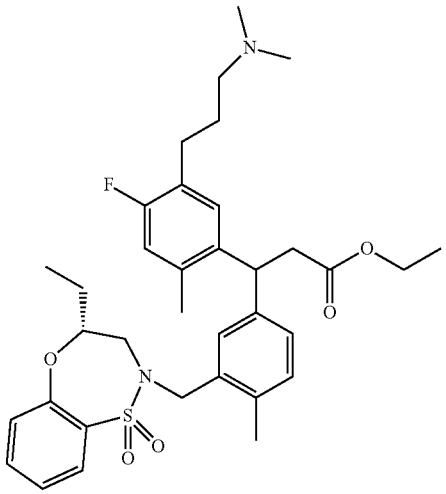 [SMILES: CCOC(=O)CC(c1ccc(C)c(CN2C[C@@H](CC)Oc3ccccc3S2(=O)=O)c1)c1cc(CCCN(C)C)c(F)cc1C]

To a solution of (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (546 mg, 1.193 mmol) in 1,4-dioxane (5 mL) was added (E)-ethyl 3-(5-(3-(dimethylamino)propyl)-4-fluoro-2-methylphenyl)acrylate (350 mg, 1.193 mmol), TEA (0.499 mL, 3.58 mmol) and water (5 mL) at RT. The reaction mixture was degassed with argon for 10 min then [RhCl(cod)]$_2$ (58.8 mg, 0.119 mmol) was added under argon. The reaction mixture was heated to 90° C. and stirred for 16 h. The reaction mixture was cooled to RT, filtered through celite, and washed with EtOAc (50 mL). The organic layer washed with water, brine (30 mL), the organic layer was dried over anhydrous Na$_2$SO$_4$ and was concentrated to afford crude residue. The crude residue was purified using 5% MeOH in DCM as eluent to afford ethyl 3-(5-(3-(dimethylamino)propyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoate (210 mg, 0.308 mmol, 25.8% yield). LC-MS m/z 625.12 (M+H)$^+$, 2.47 min (ret. time).

3-(5-(3-(Dimethylamino)propyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid

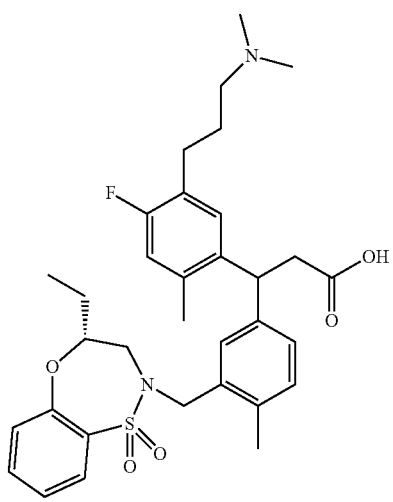 [SMILES: CC[C@@H]1CN(Cc2cc(C(CC(=O)O)c3cc(CCCN(C)C)c(F)cc3C)ccc2C)S(=O)(=O)c2ccccc2O1]

To a solution of ethyl 3-(5-(3-(dimethylamino)propyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoate (210 mg, 0.336 mmol) in EtOH (10 mL) was added 10% NaOH solution (13.44 mg, 0.336 mmol) and stirred at RT for 2 h. The reaction mixture was concentrated under reduced pressure and the residue was diluted with ice and acidified with 1N HCl solution to pH 2. The aqueous layer was extracted with EtOAc (3×30 mL). The combined organic layers were washed with brine (50 mL), dried over anhydrous Na$_2$SO$_4$ and concentrated to afford a crude residue. The crude residue washed with Et$_2$O followed by n-pentane and dried under vacuum to afford 3-(5-(3-(dimethylamino)propyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid (90 mg, 0.144 mmol, 42.9% yield). LC-MS m/z 596.90 (M+H)$^+$, 3.33 min (ret. time).

Example 174

6-Methyl-3-(4-methyl-3-(((R)-4-methyl-1,1-dioxido-3,4-dihydro-2H-benzo[b][1,4,5]oxathiazepin-2-yl)methyl)phenyl)heptanoic acid

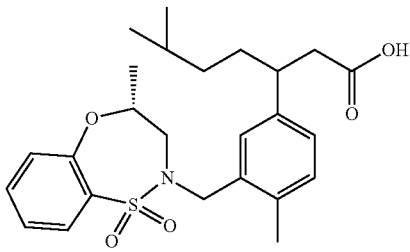 [SMILES: Cc1ccc(C(CCC(C)C)CC(=O)O)cc1CN1C[C@@H](C)Oc2ccccc2S1(=O)=O]

4-Methylpentanal

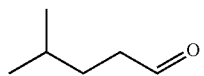

To a solution of 4-methylpentan-1-ol (2 g, 19.57 mmol) in DCM (20 mL) was added PCC (10.55 g, 48.9 mmol) portionwise and stirred at 25° C. for 3 h. The reaction mixture was filtered through celite and washed with DCM (50 mL). The filtrate was evaporated under vacuum to gave 4-methylpentanal (1.2 g, 11.98 mmol, 61.2% yield). $^1$H NMR (400 MHz, DMSO-d$_6$) δ ppm 9.70 (s, 1H), 4.00 (t, 1H), 2.42 (t, 2H), 2.30 (t, 1H), 2.20 (t, 1H), 1.52 (m, 3H), 1.45 (m, 3H).

(E)-Ethyl 6-methylhept-2-enoate

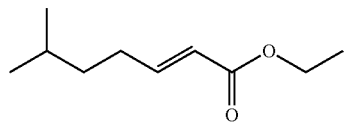

To a suspension of NaH (0.958 g, 23.96 mmol) in THF (20 mL) was added ethyl 2-(diethoxyphosphoryl)acetate (4.03 g, 17.97 mmol) at 0° C. and stirred for 30 min. Then a solution of 4-methylpentanal (1.2 g, 11.98 mmol) in THF (20 mL) was added into the reaction mixture and stirred for 2 h. The reaction mixture was diluted with ice-water (50 mL) and extracted with EtOAc (2×50 mL). The combined organic layer washed with brine (50 mL), dried over anhydrous Na$_2$SO$_4$, filtered and evaporated. The crude residue was purified on flash column chromatography using 10% EtOAc in hexane to gave (E)-ethyl 6-methylhept-2-enoate (400 mg, 2.350 mmol, 19.61% yield). $^1$H NMR (400 MHz, DMSO-d$_6$) δ ppm 6.90 (m, 2H), 5.88 (d, 1H), 4.10 (m, 3H), 2.20 (m, 3H), 1.52 (m, 3H), 1.30 (m, 3H), 1.20 (m, 3H).

Ethyl 6-methyl-3-(4-methyl-3-(((R)-4-methyl-1,1-dioxido-3,4-dihydro-2H-benzo[b][1,4,5]oxathiazepin-2-yl)methyl)phenyl)heptanoate

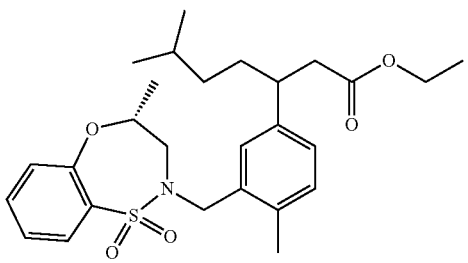 [SMILES: CCOC(=O)CC(CCC(C)C)c1ccc(C)c(CN2C[C@@H](C)Oc3ccccc3S2(=O)=O)c1]

To a solution of (E)-ethyl 6-methylhept-2-enoate (400 mg, 2.350 mmol) and (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (1563 mg, 3.52 mmol) in 1,4-dioxane (5 mL) and water (5 mL) was added Et$_3$N (0.982 mL, 7.05 mmol) and [RhCl(cod)]$_2$ (73.8 mg, 0.352 mmol). The reaction mixture was degassed with argon for 10 min and stirred under microwave irradiation at 150° C. for 1.5 h. The reaction mixture was cooled to RT and diluted with water and extracted with EtOAc. The combined organic layers were washed with brine (10 mL), dried over anhydrous Na$_2$SO$_4$, filtered and evaporated. The crude residue was purified by flash column chromatography by using 40% EtOAc in hexane as a solvent to afford ethyl 6-methyl-3-(4-methyl-3-(((R)-4-methyl-1,1-dioxido-3,4-dihydro-2H-benzo[b][1,4,5]oxathiazepin-2-yl)methyl)phenyl)heptanoate (150 mg, 0.308 mmol, 13.09% yield). $^1$H NMR (DMSO-d$_6$) δ: 7.79 (dd, J=7.7, 1.7 Hz, 1H), 7.66 (td, J=7.7, 1.7 Hz, 1H), 7.36 (td, J=7.6, 1.2 Hz, 1H), 7.30 (dd, J=8.1, 1.1 Hz, 1H), 7.17-7.08 (m, 2H), 7.08-7.02 (m, 1H), 4.52-4.39 (m, 2H), 3.93 (qdd, J=7.1, 4.5, 2.7 Hz, 2H), 3.83 (dd, J=14.1, 10.1 Hz, 1H), 3.66 (dt, J=16.0, 8.8 Hz, 1H), 2.87 (dd, J=14.8, 7.0 Hz, 2H), 2.62 (dd, J=15.1, 6.4 Hz, 1H), 2.48-2.41 (m, 1H), 2.25 (d, J=3.3 Hz, 3H), 1.64-1.36 (m, 3H), 1.28 (d, J=6.3 Hz, 3H), 1.25 (s, 1H), 1.05 (q, J=7.3 Hz, 4H), 0.80-0.72 (m, 6H)

6-Methyl-3-(4-methyl-3-(((R)-4-methyl-1,1-dioxido-3,4-dihydro-2H-benzo[b][1,4,5]oxathiazepin-2-yl)methyl)phenyl)heptanoic acid

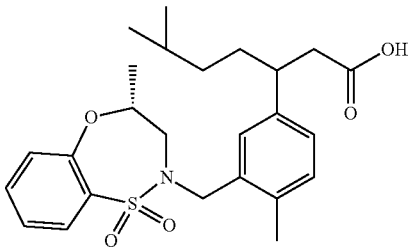 [SMILES: Cc1ccc(C(CCC(C)C)CC(=O)O)cc1CN1C[C@@H](C)Oc2ccccc2S1(=O)=O]

To a solution of ethyl 6-methyl-3-(4-methyl-3-(((R)-4-methyl-1,1-dioxido-3,4-dihydro-2H-benzo[b][1,4,5]oxathiazepin-2-yl)methyl)phenyl)heptanoate (150 mg, 0.308 mmol) in EtOH (10 mL) was added NaOH (0.154 mL, 0.308 mmol) and stirred at 25° C. for 2 h. The reaction mixture was concentrated under vacuum. The residue was cooled and acidified with 1N HCl solution to pH=3 and obtained the solid was filtered, washed with water and dried to afford 6-methyl-3-(4-methyl-3-(((R)-4-methyl-1,1-dioxido-3,4-dihydro-2H-benzo[b][1,4,5]oxathiazepin-2-yl)methyl)phenyl)heptanoic acid (65 mg, 0.138 mmol, 44.8% yield). LC-MS m/z 457.90 (M+H)$^+$, 3.26 min (ret. time).

Example 175

3-(3-(((R)-8-Chloro-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoic acid

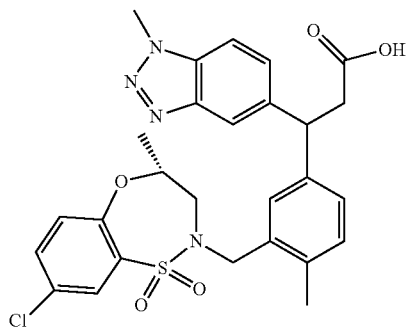 [SMILES: Cc1ccc(C(CC(=O)O)c2ccc3c(c2)nnn3C)cc1CN1C[C@@H](C)Oc2ccc(Cl)cc2S1(=O)=O]

(R)-2,5-Dichloro-N-(2-hydroxypropyl)benzenesulfonamide

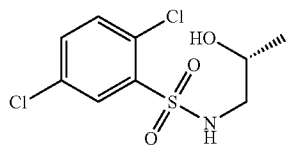 [SMILES: C[C@@H](O)CNS(=O)(=O)c1cc(Cl)ccc1Cl]

To a solution of (R)-1-aminopropan-2-ol (0.612 g, 8.15 mmol) in THF (20 mL) and water (5 mL) was added K$_2$CO$_3$ (1.126 g, 8.15 mmol) and 2,5-dichlorobenzene-1-sulfonyl chloride (2 g, 8.15 mmol) simultaneously at 25° C. and stirred for 16 h. The reaction was diluted with water (100 mL) and extracted with EtOAc (2×100 mL). The combined organic layers were washed with brine (100 mL), dried over anhydrous Na$_2$SO$_4$, filtered and evaporated. The crude product was purified by flash column chromatography and eluted with Hex/EtOAc (6:4). to provide (R)-2,5-dichloro-N-(2-hydroxypropyl)benzenesulfonamide (2 g, 7.04 mmol, 86% yield). LC-MS m/z 283 (M+H)$^+$, 3.07 min (ret. time).

(R)-8-Chloro-4-methyl-3,4-dihydro-2H-benzo[b][1,4,5]oxathiazepine 1,1-dioxide

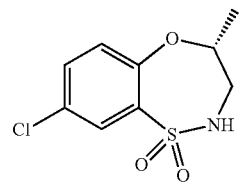

To a solution of (R)-2,5-dichloro-N-(2-hydroxypropyl)benzenesulfonamide (2 g, 7.04 mmol) in dimethyl sulfoxide (DMSO) (20 mL) was added KOt-Bu (1.580 g, 14.08 mmol) at RT and stirred at 80° C. for 4 h. The reaction mixture was cooled to 0° C., diluted with water and 1N HCl solution and extracted with EtOAc (2×50 mL). The combined organic layers were washed with brine (50 mL), dried over anhydrous Na$_2$SO$_4$, filtered and evaporated. The crude residue was purified by flash column chromatography using EtOAc:hexane (3:7). to afford (R)-8-chloro-4-methyl-3,4-dihydro-2H-benzo[b][1,4,5]oxathiazepine 1,1-dioxide (1.3 g, 5.16 mmol, 73.4% yield). LC-MS m/z 248 (M+H)$^+$, 2.02 min (ret. time).

Ethyl 3-(3-(((R)-8-chloro-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoate

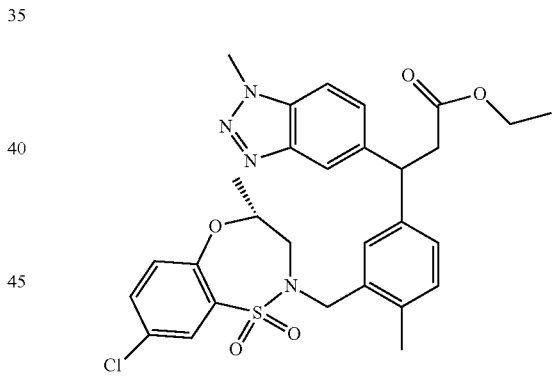

To a solution of (R)-8-chloro-4-methyl-3,4-dihydro-2H-benzo[b][1,4,5]oxathiazepine 1,1-dioxide (421 mg, 1.698 mmol) and ethyl 3-(3-(hydroxymethyl)-4-methylphenyl)-3-(1-methyl-1H-benzo[d][1,2,3]triazol-5-yl)propanoate (500 mg, 1.415 mmol) in THF (10 mL) was added triphenylphosphine (445 mg, 1.698 mmol) and DEAD (0.448 mL, 2.83 mmol) at 0° C. and stirred for 4 h. The reaction mixture was diluted with water (50 mL) and extracted with EtOAc (2×50 mL). The combined organic layers were washed with brine (50 mL), dried over anhydrous Na$_2$SO$_4$, filtered and evaporated. The crude residue was purified by flash column chromatography using EtOAc:hexane (4:6) to afford ethyl 3-(3-(((R)-8-chloro-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoate (300 mg, 0.490 mmol, 34.7% yield). LC-MS m/z 583.2 (M+H)$^+$, 2.86 min (ret. time).

389

3-(3-(((R)-8-Chloro-4-methyl-1,1-dioxido-3,4-di-
hydro-2H-benzo[b][1,4,5]oxathiazepin-2-yl)methyl)-
4-methylphenyl)-3-(1-methyl-1H-benzo[d][1,2,3]
triazol-5-yl)propanoic acid

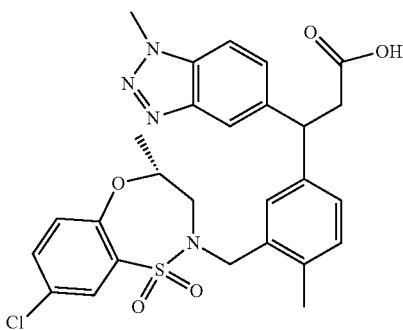 [SMILES: Cc1ccc(C(CC(=O)O)c2ccc3c(c2)nnn3C)cc1CN1C[C@@H](C)Oc2ccc(Cl)cc2S1(=O)=O]

To a solution of ethyl 3-(3-(((R)-8-chloro-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoate (150 mg, 0.257 mmol) in EtOH (10 mL) was added NaOH (0.129 mL, 0.257 mmol) and stirred at 25° C. for 2 h. The reaction mixture was concentrated under vacuum. The residue was cooled and acidified with 1N HCl solution up to pH 2 and the obtained solid was filtered, washed with water and dried to offered crude product. The crude residue was purified by flash column chromatography using MeOH:DCM (1:9) as a solvent to afford 3-(3-(((R)-8-chloro-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoic acid (70 mg, 0.122 mmol, 47.2% yield). LC-MS m/z 555.2 (M+H)$^+$, 2.55 min (ret. time).

Example 176

3-(3-(((R)-8-Cyano-4-methyl-1,1-dioxido-3,4-di-
hydro-2H-benzo[b][1,4,5]oxathiazepin-2-yl)methyl)-
4-methylphenyl)-3-(1-methyl-1H-benzo[d][1,2,3]
triazol-5-yl)propanoic acid

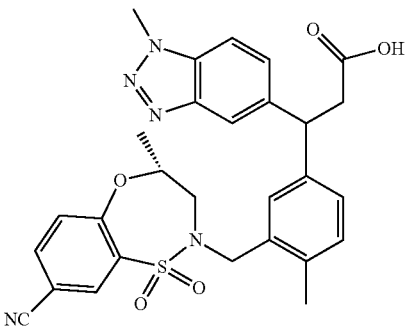 [SMILES: Cc1ccc(C(CC(=O)O)c2ccc3c(c2)nnn3C)cc1CN1C[C@@H](C)Oc2ccc(C#N)cc2S1(=O)=O]

390

Ethyl 3-(3-(((R)-8-cyano-4-methyl-1,1-dioxido-3,4-
dihydro-2H-benzo[b][1,4,5]oxathiazepin-2-yl)
methyl)-4-methylphenyl)-3-(1-methyl-1H-benzo[d]
[1,2,3]triazol-5-yl)propanoate

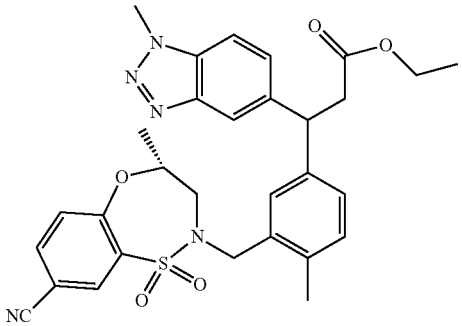 [SMILES: CCOC(=O)CC(c1ccc(C)c(CN2C[C@@H](C)Oc3ccc(C#N)cc3S2(=O)=O)c1)c1ccc2c(c1)nnn2C]

A mixture of ethyl 3-(3-(((R)-8-chloro-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoate (500 mg, 0.857 mmol), zinc cyanide (0.43 g, 0.857 mmol), N,N,N',N'-tetramethylethylenediamine (0.647 mL, 4.29 mmol) and xantphos (49.6 mg, 0.086 mmol) in DMF (10 mL) was degassed with argon for 20 min. Then Pd$_2$(dba)$_3$ (79 mg, 0.086 mmol) was added into the reaction mixture and stirred at in a microwave reactor at 140° C. for 2 h. The reaction mixture was cooled to RT and diluted with brine (20 mL) and extracted with EtOAc (3×20 mL). The combined organic layers were dried over anhydrous Na$_2$SO$_4$, filtered and evaporated. The crude residue was purified by flash column chromatography by using EtOAc:hexane (5:5) as a solvent to afford ethyl 3-(3-(((R)-8-cyano-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoate (70 mg, 0.115 mmol, 13.36% yield). LC-MS m/z 574.2 (M+H)$^+$, 2.63 min (ret. time).

3-(3-(((R)-8-Cyano-4-methyl-1,1-dioxido-3,4-di-
hydro-2H-benzo[b][1,4,5]oxathiazepin-2-yl)methyl)-
4-methylphenyl)-3-(1-methyl-1H-benzo[d][1,2,3]
triazol-5-yl)propanoic acid

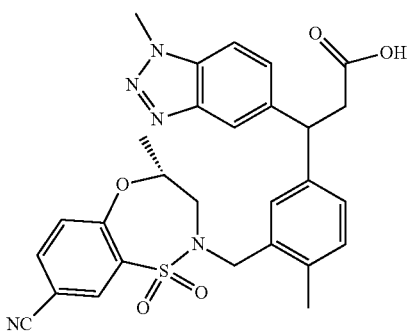 [SMILES: Cc1ccc(C(CC(=O)O)c2ccc3c(c2)nnn3C)cc1CN1C[C@@H](C)Oc2ccc(C#N)cc2S1(=O)=O]

To a solution of ethyl 3-(3-(((R)-8-cyano-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoate (150 mg, 0.261 mmol) in EtOH (3 mL) was added NaOH (0.150 mL, 0.300 mmol) at 25° C.

and stirred for 2 h. The reaction was concentrated and the residue was diluted with ice water and acidified with 2N HCl solution to pH 2, and extracted with CHCl₃ (2×50 mL). The combined organic layers were washed with brine (50 mL), dried over anhydrous Na₂SO₄, filtered and evaporated. The crude residue was purified first by flash column chromatography using MeOH:CHCl₃ (0.5:9.5) as a solvent and then by preparative HPLC to afford 3-(3-(((R)-8-cyano-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoic acid (12 mg, 0.022 mmol, 8.27% yield). LC-MS m/z 545.9 (M+H)⁺, 2.98 min (ret. time).

Example 177

3-(3-(((R)-8-carbamoyl-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoic acid

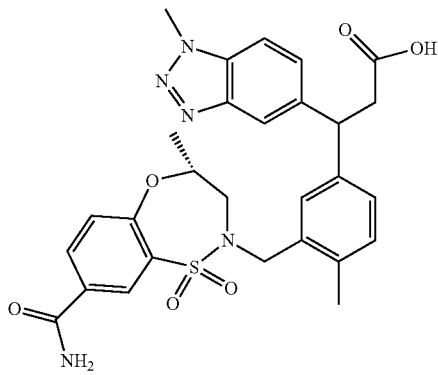 [SMILES: Cc1ccc(C(CC(=O)O)c2ccc3c(c2)nnn3C)cc1CN1C[C@@H](C)Oc2ccc(C(N)=O)cc2S1(=O)=O]

To a solution of ethyl 3-(3-(((R)-8-cyano-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoate (150 mg, 0.261 mmol) in EtOH (3 mL) was added NaOH (0.150 mL, 0.300 mmol) at 25° C. and stirred for 2 h. The reaction was concentrated and the residue was diluted with ice water and acidified with 2N HCl solution to pH 2, and extracted with CHCl₃ (2×50 mL). The combined organic layers were washed with brine (50 mL), dried over anhydrous Na₂SO₄, filtered and evaporated. The crude residue was purified by flash column chromatography using MeOH:CHCl₃ (1:9) to afford 3-(3-(((R)-8-carbamoyl-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoic acid (35 mg, 0.049 mmol, 18.87% yield) LC-MS m/z 563.9 (M+H)⁺, 2.69 min (ret. time).

The 3-(3-(((R)-8-carbamoyl-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoic acid (35 mg, 0.062 mmol) was repurified on flash column chromatography by using MeOH:CHCl₃ (1:9) as a solvent to afford 3-(3-(((R)-8-carbamoyl-4-methyl-1,1-dioxido-3,4-dihydro-2H-benzo[b][1,4,5]oxathiazepin-2-yl)methyl)-4-methylphenyl)-3-(1-methyl-1H-benzo[d][1,2,3]triazol-5-yl)propanoic acid (18 mg, 0.031 mmol, 49.8% yield). LC-MS m/z 563.9 (M+H)⁺, 2.74 min (ret. time).

Example 178

3-(5-((Dimethylamino)methyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid

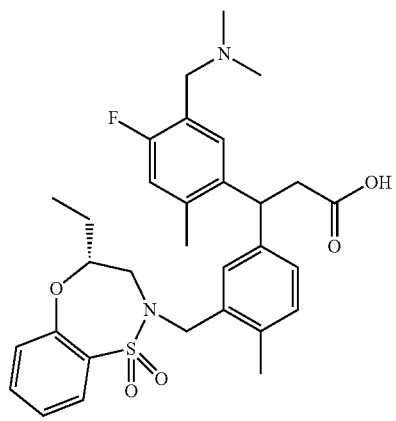 [SMILES: CC[C@@H]1CN(Cc2cc(C(CC(=O)O)c3cc(CN(C)C)c(F)cc3C)ccc2C)S(=O)(=O)c2ccccc2O1]

1-(5-Bromo-2-fluoro-4-methylphenyl)-N,N-dimethylmethanamine

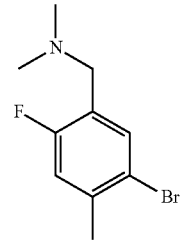

To a solution of 5-bromo-2-fluoro-4-methylbenzaldehyde (1.0 g, 4.61 mmol), dimethylamine (4.61 mL, 9.22 mmol) and AcOH (0.053 mL, 0.922 mmol) in THF (20 mL) was added Na(OAc)₃BH (1.953 g, 9.22 mmol) at 5° C. and stirred at 25° C. for 5 h. The reaction was diluted with NaHCO₃ and extracted with EtOAc (2×100 mL). The combined organic layers were washed with brine (150 mL), dried over Na₂SO₄, filtered and evaporated. The crude residue was purified by flash column chromatography using EtOAc:hexane (5:5) as a solvent to afford 1-(5-bromo-2-fluoro-4-methylphenyl)-N,N-dimethylmethanamine (800 mg, 3.09 mmol, 67.1% yield). LC-MS m/z 246.02 (M+H)⁺, 1.32 min (ret. time).

(E)-Ethyl 3-(5-((dimethylamino)methyl)-4-fluoro-2-methylphenyl)acrylate

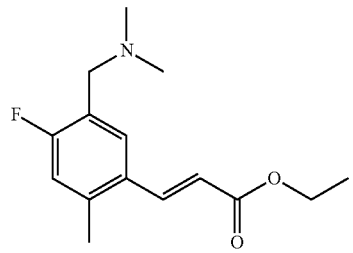 [SMILES: CCOC(=O)/C=C/c1cc(CN(C)C)c(F)cc1C]

To a solution of 1-(5-bromo-2-fluoro-4-methylphenyl)-N,N-dimethylmethanamine (800 mg, 3.25 mmol) in DMF (15 mL) was added tri-o-tolylphosphine (297 mg, 0.975 mmol), ethyl acrylate (1627 mg, 16.25 mmol) and DIPEA (2.271 mL, 13.00 mmol). The reaction mixture was degassed for 30 min $Pd(OAc)_2$ (109 mg, 0.488 mmol) was added under nitrogen atmosphere. The reaction mixture was heated to 90° C. for 2 h. The reaction was diluted with chilled water and extracted with EtOAc (3×40 mL). The combined organic layers were washed with cold water (3×100 mL), washed with brine (100 mL), dried over $Na_2SO_4$, filtered and evaporated. The crude residue was purified by flash column chromatography using EtOAc:hexane (5:5) as a solvent to afford (E)-ethyl 3-(5-((dimethylamino)methyl)-4-fluoro-2-methylphenyl)acrylate (560 mg, 2.111 mmol, 64.9% yield). $^1$H NMR (400 MHz, $CDCl_3$) δ ppm 7.90 (d, 1H), 7.55 (d, 1H), 6.90 (d, 1H), 6.32 (d, 1H), 4.27 (q, 2H), 3.47 (s, 2H), 2.41 (s, 3H), 2.27 (s, 6H), 1.35 (t, 3H).

Ethyl 3-(5-((dimethylamino)methyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoate

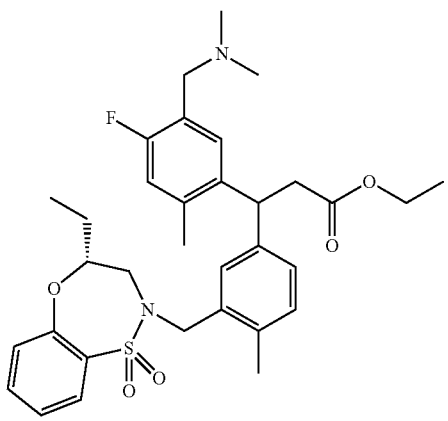 [SMILES: CCOC(=O)CC(c1ccc(C)c(CN2C[C@@H](CC)Oc3ccccc3S2(=O)=O)c1)c1cc(CN(C)C)c(F)cc1C]

To a solution of (E)-ethyl 3-(5-((dimethylamino)methyl)-4-fluoro-2-methylphenyl)acrylate (560 mg, 2.111 mmol) in 1,4-dioxane (5 mL) was added (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (965 mg, 2.111 mmol), TEA (0.883 mL, 6.33 mmol) and water (5.00 mL). The reaction mixture was degassed for 30 min and $[RhCl(cod)]_2$ (104 mg, 0.211 mmol) was added under nitrogen atmosphere. The reaction mixture was heated to 90° C. for 16 h. The reaction mixture was passed through celite and washed with EtOAc (50 mL). The filtrate was washed with water (30 mL) and brine (30 mL). The organic layers were dried over anhydrous $Na_2SO_4$ and concentrated to afford a crude residue. The crude residue was purified by flash column chromatography by using MeOH:DCM (0.3: 0.7) as solvent. The eluted fractions were concentrated to afford ethyl 3-(5-((dimethylamino)methyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoate (310 mg, 0.468 mmol, 22.18% yield). LC-MS m/z 597.1 $(M+H)^+$, 2.47 min (ret. time).

3-(5-((Dimethylamino)methyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid

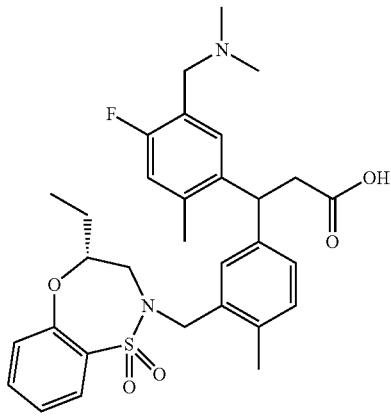 [SMILES: CC[C@@H]1CN(Cc2cc(C(CC(=O)O)c3cc(CN(C)C)c(F)cc3C)ccc2C)S(=O)(=O)c2ccccc2O1]

To a solution of ethyl 3-(5-((dimethylamino)methyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoate (310 mg, 0.519 mmol) in EtOH (5 mL) was added 10% NaOH (20.78 mg, 0.519 mmol), and the reaction mixture was stirred at RT for 2 h. The reaction mixture was concentrated under reduced pressure and diluted with ice. The reaction was acidified with 1N HCl to pH 2 and extracted with EtOAc (3×50 mL). The combined organic layers were washed with brine and concentrated to afford crude residue. The obtained residue washed with n-pentane, filtered and dried under vacuum to afford 3-(5-((dimethylamino)methyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid (150 mg, 0.255 mmol, 49.0% yield). LC-MS m/z 569.28 $(M+H)^+$, 2.03 min (ret. time).

Example 179

3-(5-(2-(Dimethylamino)ethyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid

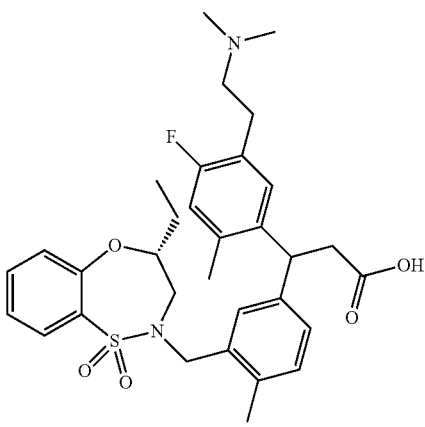 [SMILES: CC[C@@H]1CN(Cc2cc(C(CC(=O)O)c3cc(CCN(C)C)c(F)cc3C)ccc2C)S(=O)(=O)c2ccccc2O1]

Ethyl 3-(5-(2-(dimethylamino)ethyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoate

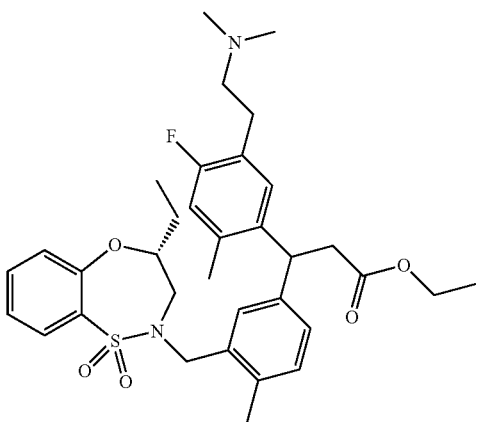 [SMILES: CCOC(=O)CC(c1ccc(C)c(CN2C[C@@H](CC)Oc3ccccc3S2(=O)=O)c1)c1cc(CCN(C)C)c(F)cc1C]

To a solution of (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (278 mg, 0.609 mmol) in 1,4-dioxane (2 mL) was added (E)-ethyl 3-(5-(2-(dimethylamino)ethyl)-4-fluoro-2-methylphenyl)acrylate (170 mg, 0.609 mmol), TEA (0.085 mL, 0.609 mmol) and water (2 mL) at RT. The reaction mixture was degassed with argon for 10 min then [RhCl(cod)]$_2$ (300 mg, 0.609 mmol) was added under argon. The reaction mixture was heated to 90° C. and stirred for 16 h. The reaction mixture was cooled to RT, passed through a bed of celite and washed with EtOAc. The organic layer washed with water and brine. The organic layer was dried over anhydrous Na$_2$SO$_4$ and concentrated to afford crude residue. The crude residue was purified using 5% MeOH in DCM as eluent to afford ethyl 3-(5-(2-(dimethylamino)ethyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoate (100 mg, 0.160 mmol, 26.4% yield). LC-MS m/z 611.15 (M+H)$^+$, 2.32 min (ret. time).

3-(5-(2-(Dimethylamino)ethyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid

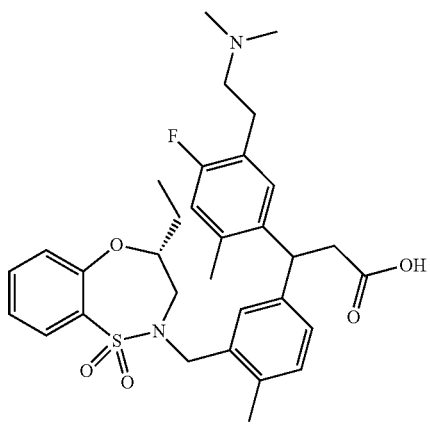 [SMILES: CC[C@@H]1CN(Cc2cc(C(CC(=O)O)c3cc(CCN(C)C)c(F)cc3C)ccc2C)S(=O)(=O)c2ccccc2O1]

To a solution of ethyl 3-(5-(2-(dimethylamino)ethyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoate (100 mg, 0.164 mmol) in EtOH (5 mL) added 10% NaOH solution (5 mL, 0.164 mmol). The reaction mixture was stirred for 2 h at RT. The reaction mixture was concentrated and the residue was diluted with ice, acidified with 1N HCl solution to pH=2 and extracted with EtOAc (3×20 mL). The combined organic layers were washed with brine (20 mL). The organic layer was dried over anhydrous Na$_2$SO$_4$ and concentrated to afford 3-(5-(2-(dimethylamino)ethyl)-4-fluoro-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid (55 mg, 0.093 mmol, 56.6% yield). LC-MS m/z 583.21 (M+H)$^+$, 2.06 min (ret. time).

Example 180

2-Amino-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid

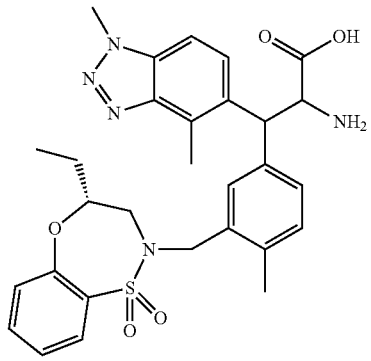 [SMILES: CC[C@@H]1CN(Cc2cc(C(c3ccc4c(nnn4C)c3C)C(N)C(=O)O)ccc2C)S(=O)(=O)c2ccccc2O1]

Ethyl 3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoate

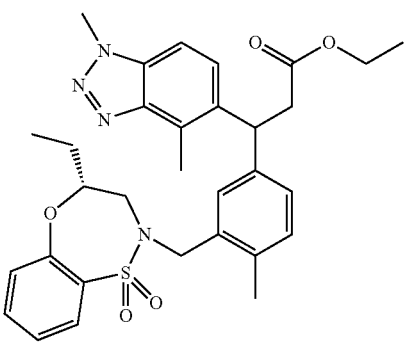 [SMILES: CCOC(=O)CC(c1ccc(C)c(CN2C[C@@H](CC)Oc3ccccc3S2(=O)=O)c1)c1ccc2c(nnn2C)c1C]

To a solution of (E)-ethyl 3-(1,4-dimethyl-1H-benzo[d][1,2,3]triazol-5-yl)acrylate (500 mg, 2.039 mmol) in 1,4- dioxane (5 mL) added (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (932 mg, 2.039 mmol), TEA (0.852 mL, 6.12 mmol) and water (5 mL) at RT. The reaction mixture was degassed with argon for 10 min then [RhCl(cod)]$_2$ (101 mg, 0.204 mmol) was added under argon. The reaction mixture was heated to 90° C. and stirred for 16 h. The reaction mixture was cooled to 30° C., diluted with water and extracted with EtOAc (3×30 mL). The combined organic layers were washed with brine (50 mL), dried over anhydrous Na$_2$SO$_4$ and concentrated under reduced pressure to afford the crude residue. The crude residue was purified by column chromatography using 50% EtOAc in hexanes as eluent. The eluted fractions were concentrated under reduced pressure to afford ethyl 3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoate (500 mg, 0.815 mmol, 40.0% yield). LC-MS m/z 577.40 (M+H)$^+$, 2.97 min (ret. time).

Ethyl 3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoate

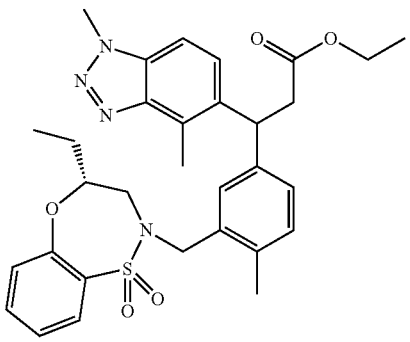 [SMILES: CCOC(=O)CC(c1ccc(C)c(CN2C[C@@H](CC)Oc3ccccc3S2(=O)=O)c1)c1ccc2c(nnn2C)c1C]

To a solution of ethyl 3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoate (500 mg, 0.867 mmol) in THF (15 mL) was added LiHMDS (2.167 mL, 2.167 mmol) at −78° C. and stirred for 1 h at same temperature. (E)-di-tert-butyl diazene-1,2-dicarboxylate (399 mg, 1.734 mmol) was then added and stirred for 1 h at −78° C. The reaction mixture was quenched with sat NH$_4$Cl solution and extracted with ethylacaetate (3×30 mL), and washed with brine solution (50 mL). The combined organic layer was dried over anhydrous Na$_2$SO$_4$ and concentrated under reduced pressure to afford the crude residue. The crude residue was purified by column chromatography using 1% MeOH in DCM as eluent to afford ethyl 3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoate (280 mg, 0.239 mmol, 27.5% yield). LC-MS m/z 577.39 (M+H)$^+$, 2.71 min (ret. time).

Di-tert-butyl 1-(1-(1,4-dimethyl-1H-benzo[d][1,2,3]triazol-5-yl)-3-ethoxy-1-(3-(((R)-4-ethyl-1,1-dioxido-3,4-dihydro-2H-benzo[b][1,4,5]oxathiazepin-2-yl)methyl)-4-methylphenyl)-3-oxopropan-2-yl)hydrazine-1,2-dicarboxylate

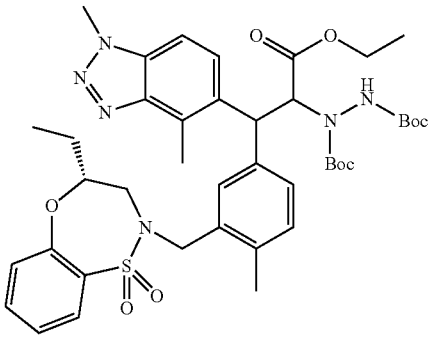 [SMILES: CCOC(=O)C(C(c1ccc(C)c(CN2C[C@@H](CC)Oc3ccccc3S2(=O)=O)c1)c1ccc2c(nnn2C)c1C)N(NC(=O)OC(C)(C)C)C(=O)OC(C)(C)C]

To a solution of ethyl 3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoate (280 mg, 0.486 mmol) in THF (15 mL) was added LiHMDS (1.457 mL, 1.457 mmol) at 25° C. and stirred for 1 h. At same temperature (E)-di-tert-butyl diazene-1,2-dicarboxylate (224 mg, 0.971 mmol) was added and stirred for 1 h at −78° C. and then allowed to warm to 25° C. The reaction was stirred for 48 h at 25° C. The reaction mixture was quenched with sat NH$_4$Cl solution and extracted with EtOAc (3×30 mL). The combined organic layers were dried over anhydrous Na$_2$SO$_4$ and concentrated under reduced pressure to afford crude residue di-tert-butyl 1-(1-(1,4-dimethyl-1H-benzo[d][1,2,3]triazol-5-yl)-3-ethoxy-1-(3-(((R)-4-ethyl-1,1-dioxido-3,4-dihydro-2H-benzo[b][1,4,5]oxathiazepin-2-yl)methyl)-4-methylphenyl)-3-oxopropan-2-yl)hydrazine-1,2-dicarboxylate (200 mg, 0.151 mmol, 31.1% yield). LC-MS m/z 807.15 (M+H)$^+$, 2.95 min (ret. time).

Ethyl 2-amino-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoate

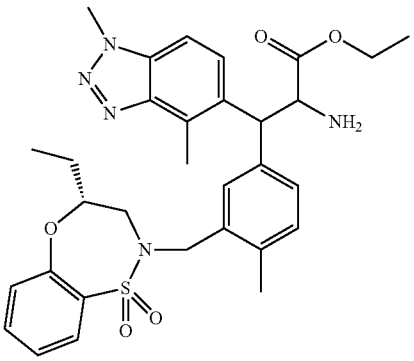 [SMILES: CCOC(=O)C(N)C(c1ccc(C)c(CN2C[C@@H](CC)Oc3ccccc3S2(=O)=O)c1)c1ccc2c(nnn2C)c1C]

To a solution of di-tert-butyl 1-(1-(1,4-dimethyl-1H-benzo[d][1,2,3]triazol-5-yl)-3-ethoxy-1-(3-(((R)-4-ethyl-1,1-dioxido-3,4-dihydro-2H-benzo[b][1,4,5]oxathiazepin-2- yl)methyl)-4-methylphenyl)-3-oxopropan-2-yl)hydrazine-1,2-dicarboxylate (200 mg, 0.248 mmol) in DCM (1 mL) was added TFA (0.5 mL, 6.49 mmol) and stirred for 2 h, after the solvent was evaporated under reduced pressure. The crude product was redissolved in MeOH (1.000 mL) and Raney Ni (10 mg, 0.248 mmol) was slowly added under a nitrogen atmosphere. The flask filled with hydrogen gas (balloon pressure) and the flask was dipped into an ultrasound sonicator bath and sonicated for 4 h at RT. The reaction mixture was then filtered through celite and washed with MeOH (5 mL). The filtrate was evaporated the solvent under vacuum. The residue was dissolved in EtOAc (20 mL) and washed with 10% aq $Na_2CO_3$ (2×10 mL), dried over anhydrous $Na_2SO_4$, filtered and evaporated the solvent under vacuum. The crude residue was purified on flash column chromatography by using 1% MeOH in DCM as eluent to afford ethyl 2-amino-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoate (130 mg, 0.174 mmol, 70.4% yield). LC-MS m/z 592.44 (M+H)$^+$, 2.05 min (ret. time).

2-Amino-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid

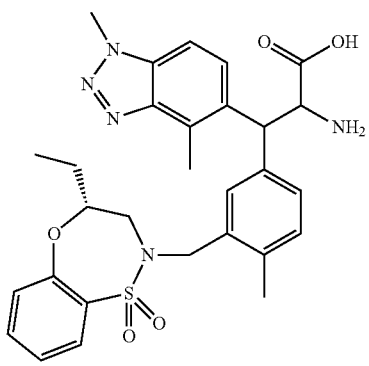 [SMILES: CC[C@@H]1CN(Cc2cc(C(c3ccc4c(nnn4C)c3C)C(N)C(=O)O)ccc2C)S(=O)(=O)c2ccccc2O1]

Experiment 1

To a solution of ethyl 2-amino-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoate (130 mg, 0.220 mmol) in EtOH (3 mL) was added NaOH (2 mL, 4.00 mmol) and stirred 25° C. for 2 h. The reaction was then diluted with 1N HCl solution (to pH 4) and the obtained solid was filtered and dried well to afford crude 2-amino-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid.

Experiment 2

To a solution of ethyl 2-amino-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoate (75 mg, 0.127 mmol) in EtOH (3 mL) was added NaOH (2 mL, 4.00 mmol) and stirred at 25° C. for 2 h. The reaction mixture was concentrated under reduced pressure and then neutralised with 1N HCl solution. The precipitated solid was filtered and the solid was dried under vacuum to afford crude 2-amino-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid.

The above crude products were combined and purified on flash column chromatography by using MeOH in DCM to afford pure 2-amino-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid (50 mg, 0.076 mmol, 34.6% yield). LC-MS m/z 564.35 (M+H)$^+$, 1.85 min (ret. time).

Final Purification

To a mixture of 2-amino-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid (50 mg, 0.089 mmol) in DCM (1 mL) was added TFA (8.20 µL, 0.106 mmol) at 25° C. and stirred for 2 h. The reaction mixture was concentrated and the residue was purified by preparative HPLC to afford 2-amino-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid trifluoro acetic acid salt (40 mg, 0.058 mmol, 65.5% yield) LC-MS m/z 564 (M+H)$^+$, 3.95 min (ret. time).

Example 181

3-(1,4-dimethyl-1H-benzo[d][1,2,3]triazol-5-yl)-3-(3-((3,3-dioxido-4,5-dihydrobenzo[d][1,2]thiazepin-2(1H)-yl)methyl)-4-methylphenyl)propanoic acid

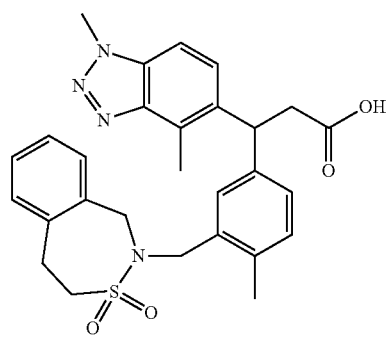 [SMILES: Cc1ccc(C(CC(=O)O)c2ccc3c(nnn3C)c2C)cc1CN1Cc2ccccc2CCS1(=O)=O]

2-Phenylethanesulfonamide

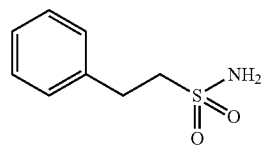 [SMILES: NS(=O)(=O)CCc1ccccc1]

A solution of 2-phenylethanesulfonyl chloride (900 mg, 4.40 mmol) in THF (30 mL) was cooled down −20° C. before it was added to a solution of $NH_4OH$ (3.42 mL, 21.99 mmol). The mixture was stirred at RT for 3 h. The reaction was extracted with EtOAc (50 mL), dried and concentrated to afford 2-phenylethanesulfonamide (670 mg, 2.63 mmol, 59.7% yield) which was used without purification. LC-MS m/z 203.1 (M+NH$_4$)$^+$, 1.41 min (ret. time).

Ethyl 3-(3-(bromomethyl)-4-methylphenyl)-3-(1,4-dimethyl-1H-benzo[d][1,2,3]triazol-5-yl)propanoate

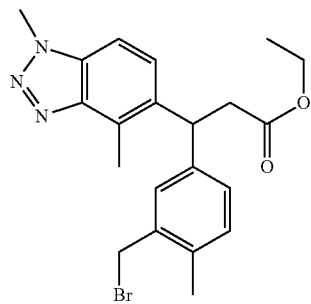 [SMILES: CCOC(=O)CC(c1ccc(C)c(CBr)c1)c1ccc2c(nnn2C)c1C]

A solution of ethyl 3-(1,4-dimethyl-1H-benzo[d][1,2,3]triazol-5-yl)-3-(3-(hydroxymethyl)-4-methylphenyl)propanoate (2.4 g, 6.53 mmol) in DCM (30 mL) was added PBr$_3$ (0.924 mL, 9.80 mmol) in DCM (30 mL) slowly under nitrogen at 0° C. The reaction mixture was stirred at 0° C. for 0.5 h. The reaction mixture was poured into 20 mL ice water. The mixture was extracted with 20 mL EtOAc (3×). The combined organic layers were washed with saturated NaHCO$_3$, brine, dried over Na$_2$SO$_4$, filtered and concentrated to afford crude ethyl 3-(3-(bromomethyl)-4-methylphenyl)-3-(1,4-dimethyl-1H-benzo[d][1,2,3]triazol-5-yl)propanoate (1.1 g, 2.388 mmol, 36.6% yield) which was obtained without further purification. LC-MS m/z 430 (M+H)$^+$, 1.80 min (ret. time).

Ethyl 3-(1,4-dimethyl-1H-benzo[d][1,2,3]triazol-5-yl)-3-(3-((3,3-dioxido-4,5-dihydrobenzo[d][1,2]thiazepin-2(1H)-yl)methyl)-4-methylphenyl)propanoate

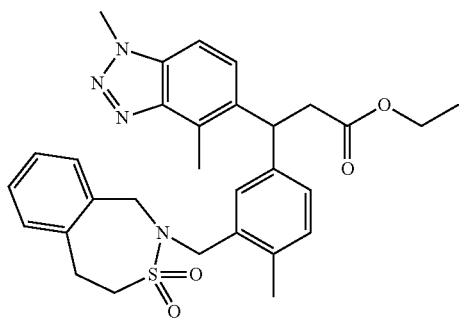 [SMILES: CCOC(=O)CC(c1ccc(C)c(CN2Cc3ccccc3CCS2(=O)=O)c1)c1ccc2c(nnn2C)c1C]

To a solution of 1,2,4,5-tetrahydrobenzo[d][1,2]thiazepine 3,3-dioxide (40 mg, 0.203 mmol) in CH$_3$CN (1 mL) was added ethyl 3-(3-(bromomethyl)-4-methylphenyl)-3-(1,4-dimethyl-1H-benzo[d][1,2,3]triazol-5-yl)propanoate (87 mg, 0.203 mmol) and K$_2$CO$_3$ (33.6 mg, 0.243 mmol). The mixture was stirred at 80° C. for 2 h. The mixture was quenched with 10 mL water and extracted with EtOAc (3×10 mL). The combined organic layers were washed with brine, dried over Na$_2$SO, filtered and concentrated to afford the crude ethyl 3-(1,4-dimethyl-1H-benzo[d][1,2,3]triazol- 5-yl)-3-(3-((3,3-dioxido-4,5-dihydrobenzo[d][1,2]thiazepin-2(1H)-yl)methyl)-4-methylphenyl)propanoate (120 mg, 0.194 mmol, 95% yield) was obtained without further purification. LC-MS m/z 547 (M+H)$^+$, 1.84 min (ret. time).

3-(1,4-dimethyl-1H-benzo[d][1,2,3]triazol-5-yl)-3-(3-((3,3-dioxido-4,5-dihydrobenzo[d][1,2]thiazepin-2(1H)-yl)methyl)-4-methylphenyl)propanoic acid

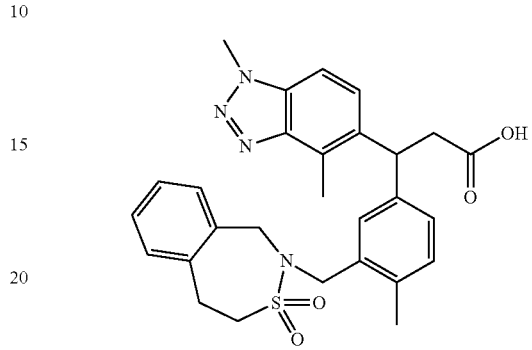

To a solution of ethyl 3-(1,4-dimethyl-1H-benzo[d][1,2,3]triazol-5-yl)-3-(3-((3,3-dioxido-4,5-dihydrobenzo[d][1,2]thiazepin-2(1H)-yl)methyl)-4-methylphenyl)propanoate (120 mg, 0.220 mmol) in THF (2 mL) was added a solution of NaOH (10.54 mg, 0.263 mmol) in water (1 mL), It was stirred at 15° C. for 24 h. The mixture was added to a solution of HCl in water till pH was less than 6. The obtained product was filtered to afford 3-(1,4-dimethyl-1H-benzo[d][1,2,3]triazol-5-yl)-3-(3-((3,3-dioxido-4,5-dihydrobenzo[d][1,2]thiazepin-2(1H)-yl)methyl)-4-methylphenyl)propanoic acid (100 mg, 0.178 mmol, 81% yield). LC-MS m/z 519 (M+H)$^+$, 1.62 min (ret. time).

Example 182

3-(1,4-Dimethyl-1H-benzo[d][1,2,3]triazol-5-yl)-3-(3-((2,2-dioxidohexahydro-1H-benzo[d][1,2]thiazin-3(4H)-yl)methyl)-4-methylphenyl)propanoic acid

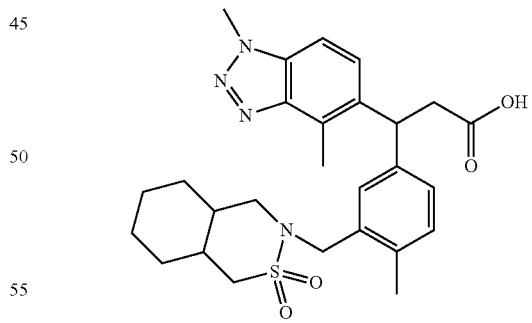

3,4-Dihydro-1H-benzo[d][1,2]thiazine 2,2-dioxide

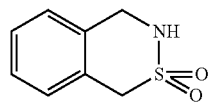 [SMILES: O=S1(=O)Cc2ccccc2CN1]

A solution of phenylethanesulfonamide (2.63 g, 15.36 mmol) in methanesulfonic acid (4 mL, 61.6 mmol) and AcOH (0.6 mL, 10.48 mmol) was added a solution of 1,3,5-trioxane (0.461 g, 5.12 mmol) in TFA (1 mL, 12.98 mmol). The mixture was stirred at 35° C. for 3 h. To the reaction mixture was added water and was extracted with chloroform. The organic layer washed with water and a saturated aqueous solution of NaHCO$_3$, dried over anhydrous Na$_2$SO$_4$ and was concentrated. The residue was purified by column chromatography on silica gel (chloroform:methanol, 100:1) to afford 3,4-dihydro-1H-benzo[d][1,2]thiazine 2,2-dioxide (2.6 g, 13.41 mmol, 87% yield). LC-MS m/z 184 (M+H)$^+$, 1.01 min (ret. time).

Octahydro-1H-benzo[d][1,2]thiazine 2,2-dioxide

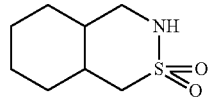 [SMILES: O=S1(=O)CC2CCCCC2CN1]

A solution of 3,4-dihydro-1H-benzo[d][1,2]thiazine 2,2-dioxide (1 g, 5.46 mmol) in AcOH (100 mL) was added 10% Pd/C (0.581 g, 0.546 mmol). The mixture was stirred at 70° C., under hydrogen at 70 MPa for 8 h. The reaction was filtered and concentrated. The crude product was purified by preparative HPLC to afford octahydro-1H-benzo[d][1,2]thiazine 2,2-dioxide (400 mg, 2.113 mmol, 38.7% yield). LC-MS m/z 190 (M+H)$^+$, 1.47 min (ret. time).

Ethyl 3-(1,4-dimethyl-1H-benzo[d][1,2,3]triazol-5-yl)-3-(3-((2,2-dioxidohexahydro-1H-benzo[d][1,2]thiazin-3(4H)-yl)methyl)-4-methylphenyl)propanoate

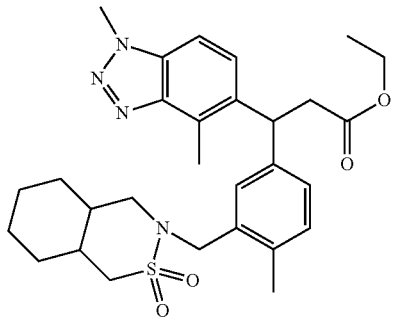 [SMILES: CCOC(=O)CC(c1ccc(C)c(CN2CC3CCCCC3CS2(=O)=O)c1)c1ccc2c(nnn2C)c1C]

A solution of octahydro-1H-benzo[d][1,2]thiazine 2,2-dioxide (100 mg, 0.528 mmol) in DMF (3 mL) was added ethyl 3-(3-(bromomethyl)-4-methylphenyl)-3-(1,4-dimethyl-1H-benzo[d][1,2,3]triazol-5-yl)propanoate (227 mg, 0.528 mmol) and 60% NaH (25.4 mg, 0.634 mmol). The mixture was stirred at 80° C. for 2 h. It was added to water and extracted with EtOAc (20 mL×3) to afford ethyl 3-(1,4-dimethyl-1H-benzo[d][1,2,3]triazol-5-yl)-3-(3-((2,2-dioxidohexahydro-1H-benzo[d][1,2]thiazin-3(4H)-yl)methyl)-4-methylphenyl)propanoate (280 mg, 0.187 mmol, 35.5% yield). LC-MS m/z 539 (M+H)$^+$, 1.94 min (ret. time).

3-(1,4-Dimethyl-1H-benzo[d][1,2,3]triazol-5-yl)-3-(3-((2,2-dioxidohexahydro-1H-benzo[d][1,2]thiazin-3(4H)-yl)methyl)-4-methylphenyl)propanoic acid

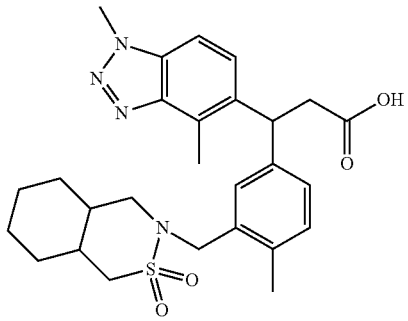 [SMILES: Cc1ccc(C(CC(=O)O)c2ccc3c(nnn3C)c2C)cc1CN1CC2CCCCC2CS1(=O)=O]

A solution of ethyl 3-(1,4-dimethyl-1H-benzo[d][1,2,3]triazol-5-yl)-3-(3-((2,2-dioxidohexahydro-1H-benzo[d][1,2]thiazin-3(4H)-yl)methyl)-4-methylphenyl)propanoate (280 mg, 0.520 mmol) in THF (2 mL) was added a solution of NaOH (24.95 mg, 0.624 mmol) in water (1 mL), It was stirred at 15° C. for 24 h. The solvents were removed by reduced pressure and the residues was adjusted pH 6 with 2N HCl. The mixture was filtered and the precipitate was collected and dried to afford. 3-(1,4-dimethyl-1H-benzo[d][1,2,3]triazol-5-yl)-3-(3-((2,2-dioxidohexahydro-1H-benzo[d][1,2]thiazin-3(4H)-yl)methyl)-4-methylphenyl)propanoic acid (70 mg, 0.134 mmol, 25.7% yield). LC-MS m/z 511 (M+H)$^+$, 1.64 min (ret. time).

Example 183

3-(1,4-Dimethyl-1H-benzo[d][1,2,3]triazol-5-yl)-3-(3-((2,2-dioxido-1H-benzo[d][1,2]thiazin-3(4H)-yl)methyl)-4-methylphenyl)propanoic acid

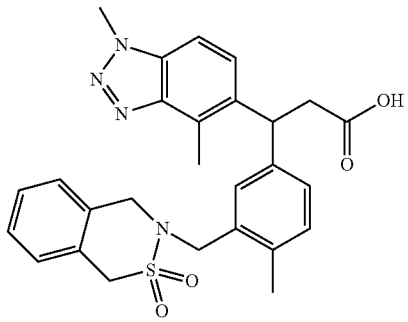 [SMILES: Cc1ccc(C(CC(=O)O)c2ccc3c(nnn3C)c2C)cc1CN1Cc2ccccc2CS1(=O)=O]

A solution of 3,4-dihydro-1H-benzo[d][1,2]thiazine 2,2-dioxide (20 mg, 0.109 mmol) in THF (2 mL) was added NaH (5.24 mg, 0.218 mmol) under nitrogen and was stirred 1 h. To the mixture was added ethyl 3-(3-(borylmethyl)-4-methylphenyl)-3-(1,4-dimethyl-1H-benzo[d][1,2,3]triazol-5-yl)propanoate (39.7 mg, 0.109 mmol) and was stirred at 15° C. for 24 h. HCl was added to the mixture until pH was less than 6. The solution was filtered and the obtained product was purified it by preparative HPLC to afford 3-(1,4-dimethyl-1H-benzo[d][1,2,3]triazol-5-yl)-3-(3-((2,2-dioxido-1H-benzo[d][1,2]thiazin-3(4H)-yl)methyl)-4-methylphenyl)propanoic acid (13 mg, 0.026 mmol, 23.60% yield). LC-MS m/z 505 (M+H)+, 1.60 min (ret. time).

Example 184

3-(1,4-Dimethyl-1H-benzo[d][1,2,3]triazol-5-yl)-3-(3-((3,3-dioxidooctahydrobenzo[d][1,2]thiazepin-2(1H)-yl)methyl)-4-methylphenyl)propanoic acid

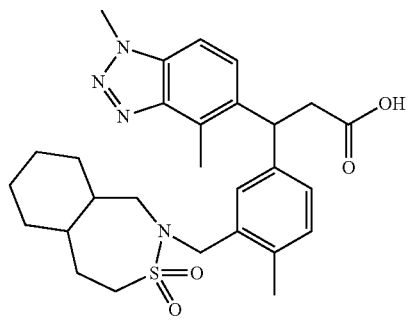 [SMILES: Cc1ccc(C(CC(=O)O)c2ccc3c(nnn3C)c2C)cc1CN1CC2CCCCC2CCS1(=O)=O]

1,2,4,5-Tetrahydrobenzo[d][1,2]thiazepine 3,3-dioxide

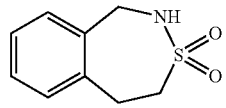

A solution of 2-phenylethanesulfonamide (540 mg, 2.92 mmol) in methanesulfonic acid (20 mL, 308 mmol) and AcOH (3 mL, 52.4 mmol) was added a solution of 1,3,5-trioxane (87 mg, 0.971 mmol) in TFA (5 mL, 64.9 mmol). The mixture was stirred at 35° C. for 3 h. To the reaction mixture was added water and the solution was extracted with chloroform. The organic layer washed with water and a saturated aqueous solution of NaHCO₃, dried over anhydrous Na₂SO₄ and was concentrated. The residue was purified by column chromatography on silica gel (chloroform: methanol 100:1) to afford 1,2,4,5-tetrahydrobenzo[d][1,2]thiazepine 3,3-dioxide (270 mg, 1.251 mmol, 42.9% yield). LC-MS m/z 198 (M+H)+, 1.43 min (ret. time).

Decahydrobenzo[d][1,2]thiazepine 3,3-dioxide

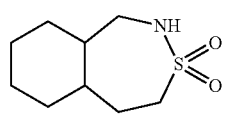

A solution of 1,2,4,5-tetrahydrobenzo[d][1,2]thiazepine 3,3-dioxide (160 mg, 0.811 mmol) in AcOH (10 mL) was added 10% Pd/C (86 mg, 0.081 mmol). The mixture was stirred at 70° C., under hydrogen at 70 MPa for 24 h. The reaction was filtered and concentrated to afford decahydrobenzo[d][1,2]thiazepine 3,3-dioxide (150 mg, 0.738 mmol, 91% yield) as solid. LC-MS m/z 204 (M+H)+, 1.57 min (ret. time).

Ethyl 3-(1,4-dimethyl-1H-benzo[d][1,2,3]triazol-5-yl)-3-(3-((3,3-dioxidooctahydrobenzo[d][1,2]thiazepin-2(1H)-yl)methyl)-4-methylphenyl)propanoate

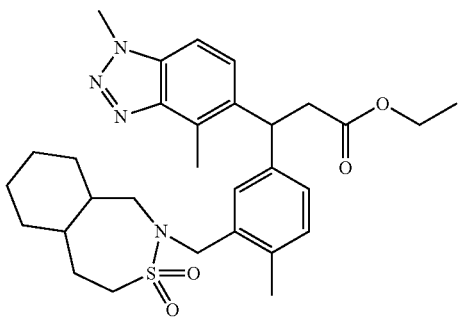 [SMILES: CCOC(=O)CC(c1ccc(C)c(CN2CC3CCCCC3CCS2(=O)=O)c1)c1ccc2c(nnn2C)c1C]

A solution of decahydrobenzo[d][1,2]thiazepine 3,3-dioxide (60 mg, 0.295 mmol) in DMF (3 mL) was added ethyl 3-(3-(bromomethyl)-4-methylphenyl)-3-(1,4-dimethyl-1H-benzo[d][1,2,3]triazol-5-yl)propanoate (127 mg, 0.295 mmol) and 60% NaH (8.50 mg, 0.354 mmol). The mixture was stirred at 80° C. for 2 h. The reaction was added to water and extracted with EtOAc (20 mL×3). to afford ethyl 3-(1,4-dimethyl-1H-benzo[d][1,2,3]triazol-5-yl)-3-(3-((3,3-dioxidooctahydrobenzo[d][1,2]thiazepin-2(1H)-yl)methyl)-4-methylphenyl)propanoate (150 mg, 0.065 mmol, 22.16% yield). LC-MS m/z 553 (M+H)+, 1.39 min (ret. time).

3-(1,4-Dimethyl-1H-benzo[d][1,2,3]triazol-5-yl)-3-(3-((3,3-dioxidooctahydrobenzo[d][1,2]thiazepin-2(1H)-yl)methyl)-4-methylphenyl)propanoic acid

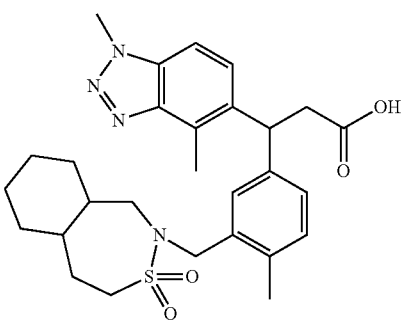 [SMILES: Cc1ccc(C(CC(=O)O)c2ccc3c(nnn3C)c2C)cc1CN1CC2CCCCC2CCS1(=O)=O]

A solution of ethyl 3-(1,4-dimethyl-1H-benzo[d][1,2,3]triazol-5-yl)-3-(3-((3,3-dioxidooctahydrobenzo[d][1,2]thiazepin-2(1H)-yl)methyl)-4-methylphenyl)propanoate (150 mg, 0.271 mmol) in THF (2 mL) was added a solution of NaOH (13.03 mg, 0.326 mmol) in water (1 mL) and was stirred at 15° C. for 24 h. The solvents were removed and the residue was adjusted pH=6 with 2N HCl. The mixture was filtered and the precipitate was collected and dried. The crude product was purified by preparative HPLC to afford 3-(1,4-dimethyl-1H-benzo[d][1,2,3]triazol-5-yl)-3-(3-((3,3-dioxidooctahydrobenzo[d][1,2]thiazepin-2(1H)-yl)methyl)-4-methylphenyl)propanoic acid (15 mg, 0.028 mmol, 10.20% yield). LC-MS m/z 525 (M+H)+, 1.67 min (ret. time).

Example 185

3-(4-Methyl-3-(((R)-4-methyl-1,1-dioxido-3,4-di-hydro-2H-benzo[b][1,4,5]oxathiazepin-2-yl)methyl)phenyl)-5-(p-tolyl)pentanoic acid

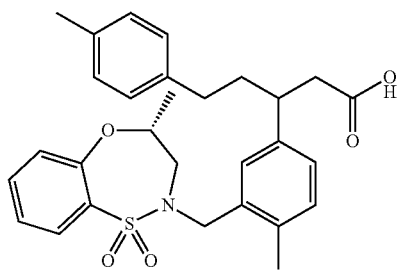 [SMILES: Cc1ccc(CCC(CC(=O)O)c2ccc(C)c(CN3C[C@@H](C)Oc4ccccc4S3(=O)=O)c2)cc1]

3-(p-Tolyl)propan-1-ol

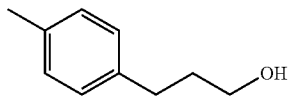

To a solution of 3-(p-tolyl)propanoic acid (5 g, 30.5 mmol) in THF (50 mL) was added 2M LAH in THF (30 mL, 30.5 mmol) at 0° C. under nitrogen atmosphere and stirred at RT for 2 h. The reaction mixture was quenched with saturated $Na_2SO_4$, extracted with EtOAc (2×). The organic layers were dried under anhydrous $Na_2SO_4$ and filtered. The filtrate was evaporated under reduced pressure and the crude residue was purified on flash column chromotography by using EtOAc:hexane (20:80) to afford 3-(p-tolyl)propan-1-ol (4.1 g, 26.1 mmol, 86% yield). $^1$H NMR (400 MHz, DMSO-$d_6$) δ ppm 7.1 (s, 4H), 4.40 (m, 1H), 3.40 (m, 2H), 2.51 (m, 2H), 2.26 (s, 3H), 1.65 (m, 2H).

3-(p-Tolyl)propanal

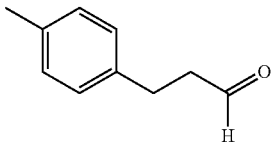

To a solution of 3-(p-tolyl)propan-1-ol (4.1 g, 27.3 mmol) in DCM (50 mL) was added PCC (8.82 g, 40.9 mmol) at 0° C. and the reaction mixture is allowed to stir at RT for 1 h. The reaction mixture was flittered through a bed of celite and the filtrate was dried over $Na_2SO_4$, filtered and evaporated under high vacuum to give 3-(p-tolyl)propanal (3.5 g, 23.62 mmol, 87% yield). $^1$H NMR (400 MHz, DMSO-$d_6$) δ ppm 9.75 (s, 1H), 7.16 (s, 4H), 2.84-2.61 (m, 4H), 2.23 (s, 3H).

(E)-Ethyl 5-(p-tolyl)pent-2-enoate

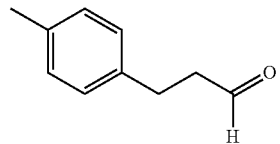

To a solution of NaH (1.133 g, 47.2 mmol) in THF (40 mL) was added triethyl phosphonoacetate (7.18 mL, 23.62 mmol) at 0° C. and reaction mixture was allowed to stir at RT for 30 min. 3-(p-tolyl)propanal (3.5 g, 23.62 mmol) was then added dropwise at 0° C. stirred at RT for 3 h. The reaction mixture was quenched with cold water and extracted with EtOAc. The combined organic layers were washed with brine and dried over $Na_2SO_4$ and concentrated under high vacuum to give crude product. The crude residue was purified by column chromatography using 3% EtOAc in hexane to afford (E)-ethyl 5-(p-tolyl)pent-2-enoate (3 g, 13.08 mmol, 55.4% yield). LC-MS m/z 219 (M+H)$^+$, 2.71 min (ret. time).

Ethyl 3-(4-methyl-3-(((R)-4-methyl-1,1-dioxido-3,4-dihydro-2H-benzo[b][1,4,5]oxathiazepin-2-yl)methyl)phenyl)-5-(p-tolyl)pentanoate

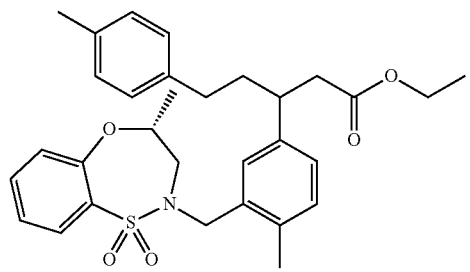 [SMILES: CCOC(=O)CC(CCc1ccc(C)cc1)c1ccc(C)c(CN2C[C@@H](C)Oc3ccccc3S2(=O)=O)c1]

To solution of (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (1 g, 2.255 mmol) and (E)-ethyl 5-(p-tolyl)pent-2-enoate (0.492 g, 2.255 mmol) in a mixture of 1,4-dioxane (10 mL) and water (8 mL) was added $Et_3N$ (0.228 g, 2.255 mmol, 0.314 mL) and degassed with nitrogen for 10 min. Afterwards, [Rh(COD)]$_2$ (1.112 g, 2.255 mmol) was added and the reaction mixture was allowed to stir at 90° C. for 1 h. The reaction mixture was quenched with water and extracted with EtOAc. The resulting organic layer washed with brine, dried over $Na_2SO_4$. The filtrate was evaporated under reduced pressure and the crude residue was purified by flash column chromotography using 80% EtOAc in hexane to give crude compound. The crude residue was purified again by column chromatography by using 30% EtOAc in hexane to afford ethyl 3-(4-methyl-3-(((R)-4-methyl-1,1-dioxido-3,4-dihydro-2H-benzo[b][1,4,5]oxathiazepin-2-yl)methyl)phenyl)-5-(p-tolyl)pentanoate (600 mg, 1.094 mmol, 48.5% yield). LC-MS m/z 536.03 (M+H)$^+$, 3.22 min (ret. time).

3-(4-Methyl-3-(((R)-4-methyl-1,1-dioxido-3,4-dihydro-2H-benzo[b][1,4,5]oxathiazepin-2-yl)methyl)phenyl)-5-(p-tolyl)pentanoic acid

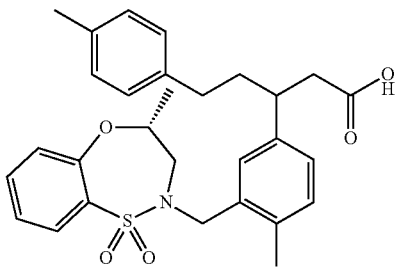 [SMILES: Cc1ccc(CCC(CC(=O)O)c2ccc(C)c(CN3C[C@@H](C)Oc4ccccc4S3(=O)=O)c2)cc1]

To a solution ethyl 3-(4-methyl-3-(((R)-4-methyl-1,1-dioxido-3,4-dihydro-2H-benzo[b][1,4,5]oxathiazepin-2-yl)methyl)phenyl)-5-(p-tolyl)pentanoate (600 mg, 1.120 mmol) in EtOH (20 mL) was added 10% NaOH (20 mL, 1.120 mmol) at 0° C. and the reaction mixture was allowed to stir at RT for 6 h. The solvent was evaporated under high vacuum, the reaction mixture was acidified with 1N HCl and extracted with EtOAc (2×30 mL). The combined organic layers were dried over Na$_2$SO$_4$ and concentrated. The crude residue washed with Et$_2$O and hexane to give 3-(4-methyl-3-(((R)-4-methyl-1,1-dioxido-3,4-dihydro-2H-benzo[b][1,4,5]oxathiazepin-2-yl)methyl)phenyl)-5-(p-tolyl)pentanoic acid (66 mg, 0.127 mmol, 11.38% yield). LC-MS m/z 508.11 (M+H)$^+$, 2.86 min (ret. time).

Example 186

3-(2,4-Difluorophenyl)-3-(3-((7-(3-(dimethylamino)propyl)-4-methyl-1,1-dioxido-4,5-dihydrobenzo[f][1,2]thiazepin-2(3H)-yl)methyl)-4-methylphenyl)propanoic acid

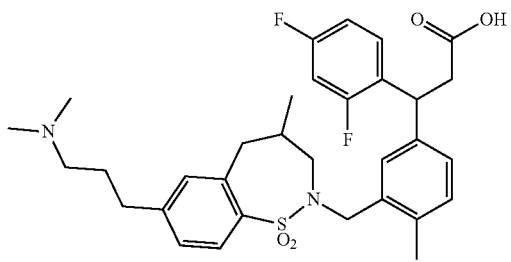 [SMILES: Cc1ccc(C(CC(=O)O)c2ccc(F)cc2F)cc1CN1CC(C)Cc2cc(CCCN(C)C)ccc2S1(=O)=O]

(E)-Ethyl 3-(2,4-difluorophenyl)acrylate

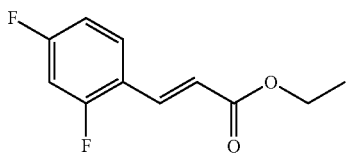

To a solution NaH (1.689 g, 70.4 mmol) in THF (100 mL) was added triethyl phosphonoacetate (10.56 mL, 52.8 mmol) at 0° C. and the reaction mixture was allowed to stir for 30 min. Afterwards, 2,4-difluorobenzaldehyde (5 g, 35.2 mmol) at 0° C. was added dropwise and the reaction mixture was allowed to stir at RT for 1 h. The reaction mixture was quenched with ice water and extracted with EtOAc (2×100 mL). The combined organic layer washed with brine solution (100 mL), dried over anhydrous Na$_2$SO$_4$, filtered and evaporated the solvent under vacuum. The crude residue was purified by flash column chromatography to afford (E)-ethyl 3-(2,4-difluorophenyl)acrylate (5 g, 23.51 mmol, 66.8% yield). LC-MS m/z 212.94 (M+H)$^+$, 2.58 min (ret. time)

Ethyl 3-(2,4-difluorophenyl)-3-(3-(hydroxymethyl)-4-methylphenyl)propanoate

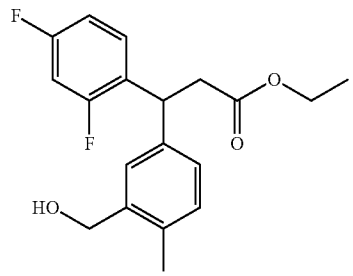

To solution of (E)-ethyl 3-(2,4-difluorophenyl)acrylate (1 g, 4.71 mmol) and (2-methyl-5-(4,4,5,5-tetramethyl-1,3,2-dioxaborolan-2-yl)phenyl)methanol (1.169 g, 4.71 mmol) in mixture of 1,4-dioxane (10 mL) and water (8 mL) was added TEA (0.477 g, 4.71 mmol, 0.657 mL) and degassed with nitrogen for 10 min. Afterwards, Rh$_2$(OAc)$_4$ (2.083 g, 4.71 mmol) was added and the reaction mixture was allowed to stir at 90° C. for 1 h. The reaction mixture was quenched with water and extracted with EtOAc. The resulting organic layer washed with brine, dried over Na$_2$SO$_4$. The filtrate was evaporated under reduced pressure and the crude residue was purified by flash column chromatography using 15% EtOAc in hexane to give ethyl 3-(2,4-difluorophenyl)-3-(3-(hydroxymethyl)-4-methylphenyl)propanoate (1 g, 2.96 mmol, 62.9% yield). LC-MS m/z 316.94 (M–OH)$^+$ 2.48 min (ret. time).

Ethyl 3-(3-((7-bromo-4-methyl-1,1-dioxido-4,5-dihydrobenzo[f][1,2]thiazepin-2(3H)-yl)methyl)-4-methylphenyl)-3-(2,4-difluorophenyl)propanoate

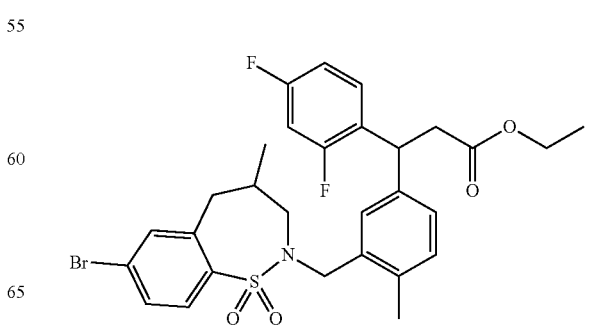

411

To a solution of ethyl 3-(2,4-difluorophenyl)-3-(3-(hydroxymethyl)-4-methylphenyl)propanoate (1 g, 2.99 mmol) and ethyl 3-(3-((7-bromo-4-methyl-1,1-dioxido-4,5-dihydrobenzo[f][1,2]thiazepin-2(3H)-yl)methyl)-4-methylphenyl)-3-(2,4-difluorophenyl)propanoate (800 mg, 1.319 mmol, 44.1% yield) was added DEAD (0.947 mL, 5.98 mmol) at 0° C. and the reaction mixture was allowed to stir at RT for 1 h. The reaction was diluted with water and extracted with EtOAc (2×10 mL). The combined organic layers were washed with brine (20 mL), dried over anhydrous Na$_2$SO$_4$, filtered and evaporated. The crude residue was purified by flash column chromatography by using EtOAc:hexane (1:9) as the solvent system to afford ethyl 3-(3-((7-bromo-4-methyl-1,1-dioxido-4,5-dihydrobenzo[f][1,2]thiazepin-2(3H)-yl)methyl)-4-methylphenyl)-3-(2,4-difluorophenyl)propanoate (800 mg, 1.319 mmol, 44.1% yield). $^1$H NMR (400 MHz, CDCl$_3$) δ ppm 7.83 (d, 1H), 7.52 (m, 2H), 7.20 (m, 1H), 7.12 (s, 2H), 7.04 (s, 1H), 6.82 (t. 1H), 6.75 (t, 1H), 4.72 (t, 1H), 4.40 (m, 1H), 4.05 (q, 2H), 3.55 (m, 3H), 3.05 (d, 2H), 2.70 (m, 1H), 2.30 (d, 3H), 2.00 (bs, 1H), 1.40 (t, 1H), 1.15 (t, 3H), 0.9 (m, 3H).

(E)-Ethyl 3-(3-((7-(3-((tert-butoxycarbonyl)amino) prop-1-en-1-yl)-4-methyl-1,1-dioxido-4,5-dihydrobenzo[f][1,2]thiazepin-2(3H)-yl)methyl)-4-methylphenyl)-3-(2,4-difluorophenyl)propanoate

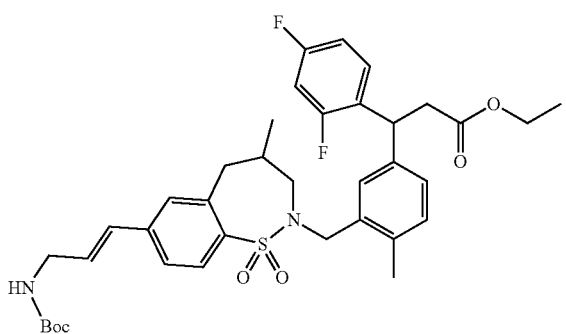 [SMILES: CCOC(=O)CC(c1ccc(C)c(CN2CC(C)Cc3cc(/C=C/CNC(=O)OC(C)(C)C)ccc3S2(=O)=O)c1)c1ccc(F)cc1F]

A solution of ethyl 3-(3-((7-bromo-4-methyl-1,1-dioxido-4,5-dihydrobenzo[f][1,2]thiazepin-2(3H)-yl)methyl)-4-methylphenyl)-3-(2,4-difluorophenyl)propanoate (100 mg, 0.165 mmol), tert-butyl allylcarbamate (78 mg, 0.495 mmol) and tri-o-tolylphosphine (15.05 mg, 0.049 mmol) and DIPEA (0.115 mL, 0.660 mmol) in DMF (2 mL) was degassed with argon for 10 min. Pd(OAc)$_2$ (7.40 mg, 0.033 mmol) was added into the reaction mixture and stirred in a microwave reactor at 100° C. for 2 h. The reaction cooled to RT, diluted with water and extracted with EtOAc (2×10 mL). The combined organic layers were washed with brine (20 mL), dried over anhydrous Na$_2$SO$_4$, filtered and evaporated. The crude residue was purified by flash column chromatography by using EtOAc:hexane (2:8) as a solvent. to afford (E)-ethyl 3-(3-((7-(3-((tert-butoxycarbonyl)amino)prop-1-en-1-yl)-4-methyl-1,1-dioxido-4,5-dihydrobenzo[f][1,2]thiazepin-2(3H)-yl)methyl)-4-methylphenyl)-3-(2,4-difluorophenyl)propanoate (50 mg, 0.065 mmol, 39.7% yield). LC-MS m/z 583 (M-100)$^+$ 4.46 min (ret. time).

412

Ethyl 3-(3-((7-(3-((tert-butoxycarbonyl)amino)propyl)-4-methyl-1,1-dioxido-4,5-dihydrobenzo[f][1,2]thiazepin-2(3H)-yl)methyl)-4-methylphenyl)-3-(2,4-difluorophenyl)propanoate

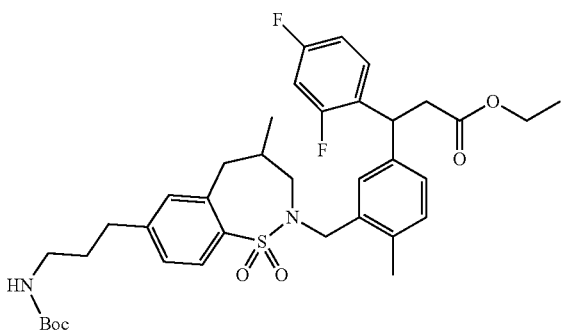 [SMILES: CCOC(=O)CC(c1ccc(C)c(CN2CC(C)Cc3cc(CCCNC(=O)OC(C)(C)C)ccc3S2(=O)=O)c1)c1ccc(F)cc1F]

To a solution of (E)-ethyl 3-(3-((7-(3-((tert-butoxycarbonyl)amino)prop-1-en-1-yl)-4-methyl-1,1-dioxido-4,5-dihydrobenzo[f][1,2]thiazepin-2(3H)-yl)methyl)-4-methylphenyl)-3-(2,4-difluorophenyl)propanoate (700 mg, 1.025 mmol) in EtOH (20 mL) was added Pd/C (30 mg, 0.282 mmol) and stirred under hydrogen atmosphere (balloon pressure) at RT for 10 h. The reaction mixture was filtered through celite and the filtrate was concentrated. The crude residue was purified by column chromatography by using 20% EtOAc in hexane to afford ethyl 3-(3-((7-(3-((tert-butoxycarbonyl)amino)propyl)-4-methyl-1,1-dioxido-4,5-dihydrobenzo[f][1,2]thiazepin-2(3H)-yl)methyl)-4-methylphenyl)-3-(2,4-difluorophenyl)propanoate (300 mg, 0.382 mmol, 74.5% yield). LC-MS m/z 584 (M-100)$^+$ 4.36 min (ret. time).

Ethyl 3-(3-((7-(3-aminopropyl)-4-methyl-1,1-dioxido-4,5-dihydrobenzo[f][1,2]thiazepin-2(3H)-yl) methyl)-4-methylphenyl)-3-(2,4-difluorophenyl) propanoate

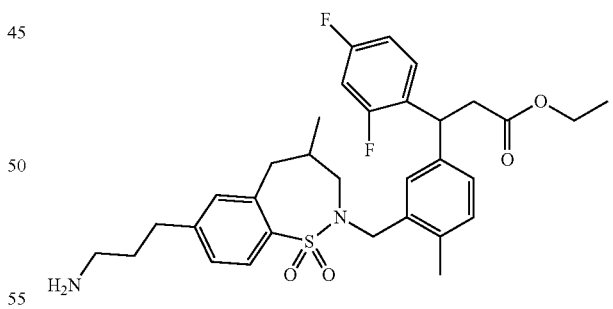

To a solution of ethyl 3-(3-((7-(3-((tert-butoxycarbonyl)amino)propyl)-4-methyl-1,1-dioxido-4,5-dihydrobenzo[f][1,2]thiazepin-2(3H)-yl)methyl)-4-methylphenyl)-3-(2,4-difluorophenyl)propanoate (550 mg, 0.803 mmol) in 1,4 dioxane (15 mL), was added HCl in 1,4 dioxane (20 mL, 0.803 mmol) dropwise under ice cold condition and the reaction mixture is allowed stir at RT for 1 h. The reaction mixture was evaporated under reduced pressure, neutralized with NaHCO$_3$ extracted with EtOAc (2×). The combined organic layers were washed with brine solution, dried under anhydrous Na$_2$SO$_4$ and filtered. The filtrate was evaporated under reduced pressure to afford crude ethyl 3-(3-((7-(3-aminopropyl)-4-methyl-1,1-dioxido-4,5-dihydrobenzo[f][1,2]thiazepin-2(3H)-yl)methyl)-4-methylphenyl)-3-(2,4-difluorophenyl)propanoate (300 mg, 0.251 mmol, 31.2%) which was carried on crude to the next step. LC-MS m/z 585.24 (M+H)+ 3.61 min (ret. time).

Ethyl 3-(2,4-difluorophenyl)-3-(3-((7-(3-(dimethylamino)propyl)-4-methyl-1,1-dioxido-4,5-dihydrobenzo[f][1,2]thiazepin-2(3H)-yl)methyl)-4-methylphenyl)propanoate

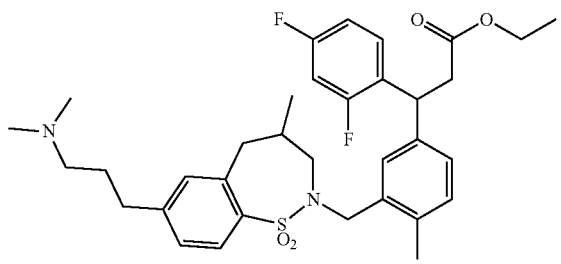 [SMILES: CCOC(=O)CC(c1ccc(C)c(CN2CC(C)Cc3cc(CCCN(C)C)ccc3S2(=O)=O)c1)c1ccc(F)cc1F]

To a solution of ethyl 3-(3-((7-(3-aminopropyl)-4-methyl-1,1-dioxido-4,5-dihydrobenzo[f][1,2]thiazepin-2(3H)-yl)methyl)-4-methylphenyl)-3-(2,4-difluorophenyl)propanoate (300 mg, 0.513 mmol) in DCM (30 mL) was added acetaldehyde (22.60 mg, 0.513 mmol) and NaBH(OAc)₃ (109 mg, 0.513 mmol) at 0° C. followed by the addition of AcOH (0.029 mL, 0.513 mmol). The reaction mixture is allowed to stir at RT for 4 h. The reaction mixture was diluted with water and extracted with EtOAc (2×). The combined organics were washed with brine, dried under anhydrous Na₂SO₄ and filtered. The filtrate was evaporated under reduced pressure to get crude ethyl 3-(2,4-difluorophenyl)-3-(3-((7-(3-(dimethylamino)propyl)-4-methyl-1,1-dioxido-4,5-dihydrobenzo[f][1,2]thiazepin-2(3H)-yl)methyl)-4-methylphenyl)propanoate (200 mg, 0.240 mmol, 46.8% yield) which was carried on without purification. LC-MS m/z 613.5 (M+H)+ 2.97 min (ret. time).

3-(2,4-Difluorophenyl)-3-(3-((7-(3-(dimethylamino)propyl)-4-methyl-1,1-dioxido-4,5-dihydrobenzo[f][1,2]thiazepin-2(3H)-yl)methyl)-4-methylphenyl)propanoic acid

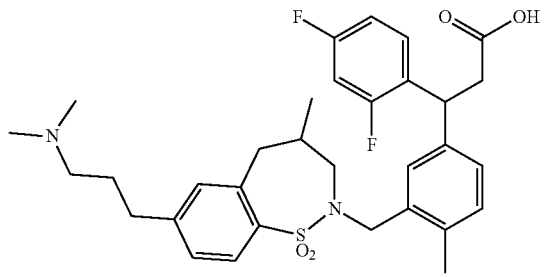 [SMILES: Cc1ccc(C(CC(=O)O)c2ccc(F)cc2F)cc1CN1CC(C)Cc2cc(CCCN(C)C)ccc2S1(=O)=O]

To a solution of ethyl 3-(2,4-difluorophenyl)-3-(3-((7-(3-(dimethylamino)propyl)-4-methyl-1,1-dioxido-4,5-dihydrobenzo[f][1,2]thiazepin-2(3H)-yl)methyl)-4-methylphenyl)propanoate (200 mg, 0.326 mmol) in EtOH (25 mL) was added 10% NaOH (25 mL, 0.326 mmol) at 0° C. and the reaction mixture was allowed to stir at RT for 2 h. The reaction mixture was evaporated under reduced pressure, neutralized with 1N HCl, and extracted with EtOAc (2×). The combined organics were washed with brine, dried under anhydrous Na₂SO₄ and filtered. The filtrate was evaporated to get crude compound. The crude compound was purified by column chromatography using MeOH:DCM (2:98). The obtained product washed with Et₂O to afford 3-(2,4-difluorophenyl)-3-(3-((7-(3-(dimethylamino)propyl)-4-methyl-1,1-dioxido-4,5-dihydrobenzo[f][1,2]thiazepin-2(3H)-yl)methyl)-4-methylphenyl)propanoic acid (56 mg, 0.095 mmol, 29.1% yield). LC-MS m/z 585.3 (M+H)+ 2.07 min (ret. time).

Example 187

3-(3-(((R)-4-Ethyl-1,1-dioxido-3,4-dihydro-2H-benzo[b][1,4,5]oxathiazepin-2-yl)methyl)-4-methylphenyl)-3-(2-methyl-1,2,3,4-tetrahydroisoquinolin-7-yl)propanoic acid

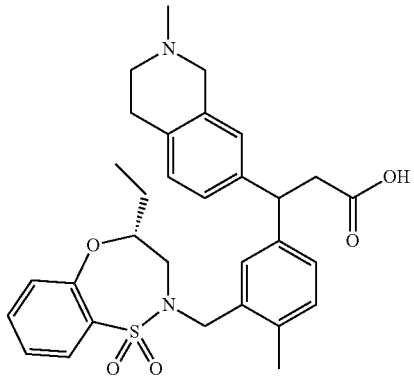 [SMILES: CC[C@@H]1CN(Cc2cc(C(CC(=O)O)c3ccc4c(c3)CN(C)CC4)ccc2C)S(=O)(=O)c2ccccc2O1]

7-Bromo-2-methyl-1,2,3,4-tetrahydroisoquinoline

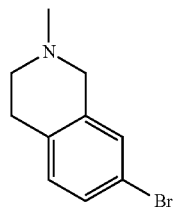

To a solution of 7-bromo-1,2,3,4-tetrahydroisoquinoline (1 g, 4.72 mmol) in formic acid (10 mL, 261 mmol) was added formaldehyde (2 mL, 72.6 mmol) (37%). The reaction was stirred at 150° C. for 15 min in a microwave reactor. The reaction mixture was evaporated under reduced pressure, neutralized with NaHCO₃ and extracted with EtOAc (2×). The combined organic layers were washed with brine, dried under anhydrous Na₂SO₄ and filtered. The filtrate was evaporated under reduced pressure to afford crude 7-bromo-2-methyl-1,2,3,4-tetrahydroisoquinoline (900 mg, 3.88 mmol, 82% yield). LC-MS m/z 227.9 (M+H)+ 3.63 min (ret. time).

415

(E)-Ethyl 3-(2-methyl-1,2,3,4-tetrahydroisoquinolin-7-yl)acrylate

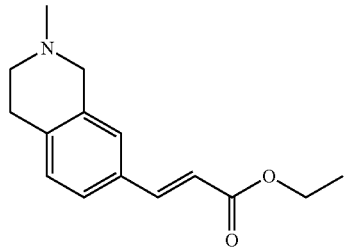 [SMILES: CCOC(=O)/C=C/c1ccc2c(c1)CN(C)CC2]

A solution of 7-bromo-2-methyl-1,2,3,4-tetrahydroisoquinoline (900 mg, 3.98 mmol), ethyl acrylate (2.365 mL, 3.98 mmol), tri-o-tolylphosphine (363 mg, 1.194 mmol) and DIPEA (2.086 mL, 11.94 mmol) in DMF (15 mL) degassed with argon for 10 min. Then Pd(OAc)$_2$ (179 mg, 0.796 mmol) was added into the reaction mixture and stirred in a microwave reactor at 100° C. for 2 h. The reaction mixture was diluted with water extracted with EtOAc (2×). The combined organics were washed with brine solution, dried under anhydrous Na$_2$SO$_4$ and filtered. The filtrate was evaporated under reduced pressure to get the crude residue. The crude residue was purified by column chromatography by using 15% EtOAc in hexane to give (E)-ethyl 3-(2-methyl-1,2,3,4-tetrahydroisoquinolin-7-yl)acrylate (400 mg, 1.489 mmol, 37.4% yield). LC-MS m/z 246 (M+H)$^+$ 3.59 min (ret. time).

Ethyl 3-(3-(((R)-4-ethyl-1,1-dioxido-3,4-dihydro-2H-benzo[b][1,4,5]oxathiazepin-2-yl)methyl)-4-methylphenyl)-3-(2-methyl-1,2,3,4-tetrahydroisoquinolin-7-yl)propanoate

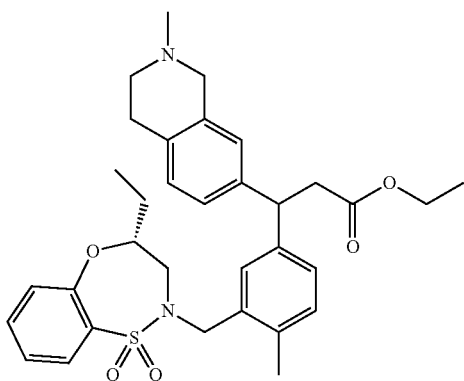 [SMILES: CCOC(=O)CC(c1ccc(C)c(CN2C[C@@H](CC)Oc3ccccc3S2(=O)=O)c1)c1ccc2c(c1)CN(C)CC2]

To solution of (E)-ethyl 3-(2-methyl-1,2,3,4-tetrahydroisoquinolin-7-yl)acrylate (400 mg, 1.631 mmol) and (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (746 mg, 1.631 mmol) in mixture of 1,4-dioxane (15 mL) and water (15.00 mL) was added TEA (165 mg, 1.631 mmol, 0.227 mL) and degassed with nitrogen for 10 min, followed by the addition of Rh$_2$(OAc)$_4$ (721 mg, 1.631 mmol). The reaction mixture was allowed to stir at 90° C. for 1 h. The reaction mixture was diluted with water extracted with EtOAc (2×). The combined organics were washed with brine solution, dried under anhydrous Na$_2$SO$_4$ and filtered. The filtrate was evaporated under reduced pressure to get the crude residue. The crude compound was purified by column chromatography using MeOH:DCM (2:98). The obtained product washed with Et$_2$O to afford ethyl 3-(3-(((R)-4-ethyl-1,1-dioxido-3,4-dihydro-2H-benzo[b][1,4,5]oxathiazepin-2-yl)methyl)-4-methylphenyl)-3-(2-methyl-1,2,3,4-tetrahydroisoquinolin-7-yl)propanoate (200 mg, 0.347 mmol, 21.27% yield). LC-MS m/z 577.8 (M+H)$^+$ 4.07 min (ret. time).

3-(3-(((R)-4-Ethyl-1,1-dioxido-3,4-dihydro-2H-benzo[b][1,4,5]oxathiazepin-2-yl)methyl)-4-methylphenyl)-3-(2-methyl-1,2,3,4-tetrahydroisoquinolin-7-yl)propanoic acid

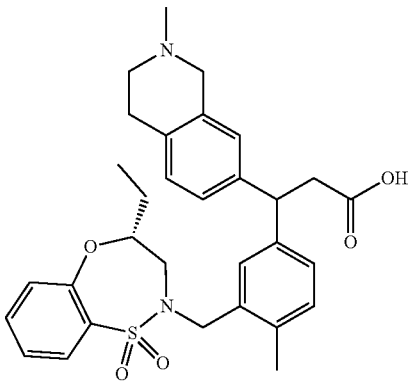 [SMILES: CC[C@@H]1CN(Cc2cc(C(CC(=O)O)c3ccc4c(c3)CN(C)CC4)ccc2C)S(=O)(=O)c2ccccc2O1]

To a solution of ethyl 3-(3-(((R)-4-ethyl-1,1-dioxido-3,4-dihydro-2H-benzo[b][1,4,5]oxathiazepin-2-yl)methyl)-4-methylphenyl)-3-(2-methyl-1,2,3,4-tetrahydroisoquinolin-7-yl)propanoate (200 mg, 0.347 mmol) in EtOH (20 mL) was added 10% NaOH (35 mL, 0.347 mmol) at 0° C. The reaction mixture was stirred at RT for 2 h. The reaction mixture was evaporated, cooled to 0° C., neutralized with 1N HCl and extracted with EtOAc. The combined organic layers were washed with brine, dried under anhydrous Na$_2$SO$_4$ and filtered. The filtrate was reduced under vacuum to afford a crude white solid. The crude compound was purified by column chromatography using MeOH: DCM (2:98). The obtained product washed with Et$_2$O to afford 3-(3-(((R)-4-ethyl-1,1-dioxido-3,4-dihydro-2H-benzo[b][1,4,5]oxathiazepin-2-yl)methyl)-4-methylphenyl)-3-(2-methyl-1,2,3,4-tetrahydroisoquinolin-7-yl)propanoic acid (69 mg, 0.123 mmol, 35.5% yield). LC-MS m/z 549.23 (M+H)$^+$ 1.90 min (ret. time).

Example 188

3-(2-(1-Methyl-1H-1,2,3-triazol-4-yl)cyclopropyl)-3-(4-methyl-3-(((R)-4-methyl-1,1-dioxido-3,4-dihydro-2H-benzo[b][1,4,5]oxathiazepin-2-yl)methyl)phenyl)propanoic acid

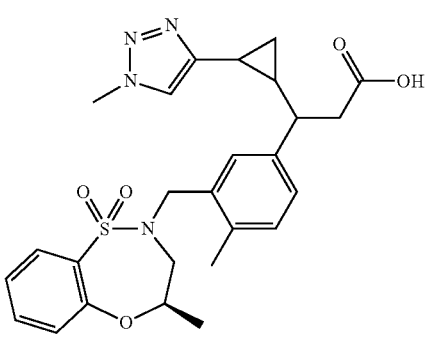 [SMILES: Cc1ccc(C(CC(=O)O)C2CC2c2cn(C)nn2)cc1CN1C[C@@H](C)Oc2ccccc2S1(=O)=O]

(E)-Ethyl pent-2-en-4-ynoate

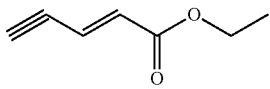

To a solution of prop-2-yn-1-ol (50 g, 892 mmol) in DCM (2 L) and dimethyl sulfoxide (DMSO) (500 mL) was added ethyl 2-(triphenylphosphoranylidene)acetate (1243 g, 3567 mmol), benzoic acid (436 g, 3567 mmol) and Dess-Martin periodinane (908 g, 2140 mmol) and stirred at 25° C. for 1 h. The crude residue was diluted with saturated bicarbonate solution and stirred for 30 min. Et$_2$O (800 mL) was added and the solution was filtered. The filtrate was extracted with Et$_2$O (1000 mL×2) washed with brine solution (500 mL), dried over anhydrous Na$_2$SO$_4$, filtered and evaporated. The crude residue was purified by flash column chromatography) using 3% EtOAc in hexane to get afford (E)-ethyl pent-2-en-4-ynoate (25 g, 201 mmol, 22.58% yield). $^1$H NMR (400 MHz, CDCl$_3$) δ ppm 6.72 (dd, 1H), 6.30 (dd, 1H), 4.22 (q, 2H), 3.32 (d, 1H), 1.30 (t, 3H).

(E)-Ethyl 3-(1-methyl-1H-1,2,3-triazol-4-yl)acrylate

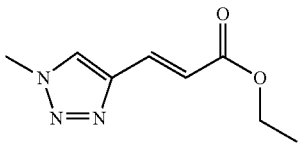

To a solution of (E)-ethyl pent-2-en-4-ynoate (25 g, 201 mmol) in water (200 mL), was added NaN$_3$ (13.09 g, 201 mmol), copper(I) iodide (0.384 g, 2.014 mmol) and MeI (12.59 mL, 201 mmol) and stirred at 70° C. for 16 h. The crude residue was diluted with saturated bicarbonate solution and stirred for 30 min, then Et$_2$O (30 mL) was added and filtered. The filtrate was extracted with Et$_2$O (2×30 mL), washed with brine solution (10 mL) and dried over anhydrous Na$_2$SO$_4$, filtered and evaporated the solvent. The crude residue was purified by flash column chromatography using 25% EtOAc in hexane to get afford (E)-ethyl 3-(1-methyl-1H-1,2,3-triazol-4-yl)acrylate (14 g, 74.9 mmol, 37.2% yield). LC-MS m/z 182.05 (M+H)$^+$ 1.50 min (ret. time).

Ethyl 2-(1-methyl-1H-1,2,3-triazol-4-yl)cyclopropanecarboxylate

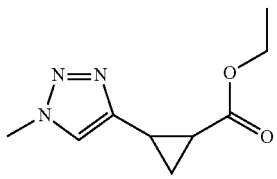

To a suspension of NaH (0.795 g, 33.1 mmol) in dimethyl sulfoxide (DMSO) (70 mL) was added portionwise trimethylsulfoxinium idodie (7.29 g, 33.1 mmol) at RT over 30 min, and maintained until a clear solution was obtained. Afterwards, (Z)-ethyl 3-(1-methyl-1H-1,2,3-triazol-4-yl)acrylate (5 g, 27.6 mmol) in dimethyl sulfoxide (DMSO) (20 mL) was added dropwise at 0° C. and stirred at 0° C. for 30 min. The crude was poured in crushed ice water and extracted with EtOAc (2×100 mL). The combined organic layers were washed with ice cold water (2×100 mL), brine (50 mL), and concentrated under reduced pressure. The crude residue was purified on flash column chromatography using 50% EtOAc in hexane. to afford ethyl 2-(1-methyl-1H-1,2,3-triazol-4-yl) cyclopropanecarboxylate (2 g, 10.24 mmol, 37.1% yield). $^1$H NMR (400 MHz, CDCl$_3$) δ ppm 7.35 (s, 1H), 4.17 (q, 2H), 4.08 (s, 3H), 2.52 (m, 1H), 2.10 (m, 1H), 1.55 (m, 2H), 1.30 (t, 3H)

(2-(1-Methyl-1H-1,2,3-triazol-4-yl)cyclopropyl)methanol

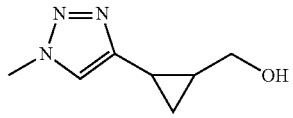

To a solution of ethyl 2-(1-methyl-1H-1,2,3-triazol-4-yl) cyclopropanecarboxylate (500 mg, 2.56 mmol) in THF (25 mL) was added LAH (146 mg, 3.84 mmol) at 0° C. and the reaction mixture was allowed to stir at RT for 3 h. The reaction mixture was quenched with saturated Na$_2$SO$_4$ and filtered through celite. The filtrate was concentrated to afford (2-(1-methyl-1H-1,2,3-triazol-4-yl)cyclopropyl) MeOH (400 mg, 2.041 mmol, 80% yield). LC-MS m/z 154 (M+H)$^+$ 1.04 min (ret. time).

2-(1-Methyl-1H-1,2,3-triazol-4-yl)cyclopropanecarbaldehyde

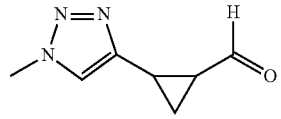

To a solution of (2-(1-methyl-1H-1,2,3-triazol-4-yl)cyclopropyl)methanol (400 mg, 2.61 mmol) in DCM (30 mL) was added manganese dioxide (681 mg, 7.83 mmol) and the reaction mixture is allowed to stir at RT for 20 h. The reaction mixture was filtered through celite and the filtrate was concentrated. The crude residue was purified by flash column chromatography using MeOH:DCM (2:98). The obtained product washed with Et$_2$O to afford 2-(1-methyl-1H-1,2,3-triazol-4-yl)cyclopropanecarbaldehyde (300 mg, 1.692 mmol, 64.8% yield). LC-MS m/z 152 (M+H)$^+$ 1.74 min (ret. time).

(E)-Ethyl 3-(2-(1-methyl-1H-1,2,3-triazol-4-yl)cyclopropyl)acrylate

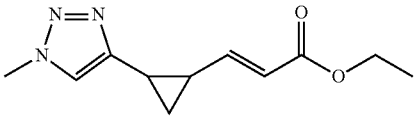 [SMILES: CCOC(=O)/C=C/C1CC1c1cn(C)nn1]

419

To a solution of NaH (95 mg, 3.97 mmol) in THF (30 mL) was added triethyl phosphonoacetate (0.596 mL, 2.98 mmol) at 0° C. and stirred for 30 min and at 0° C. Afterwards, 2-(1-methyl-1H-1,2,3-triazol-4-yl)cyclopropanecarbaldehyde (300 mg, 1.985 mmol) was added dropwise and the reaction mixture was allowed to stir at RT for 1 h. The reaction mixture was diluted with water and extracted with EtOAc (2×). The combined organic layers were washed with brine, dried under anhydrous $Na_2SO_4$ and filtered. The filtrate was evaporated under reduced pressure to get the crude product. The crude compound was purified by flash column chromatography using MeOH:DCM (2:98). The obtained product washed with $Et_2O$ to afford (E)-ethyl 3-(2-(1-methyl-1H-1,2,3-triazol-4-yl)cyclopropyl)acrylate (250 mg, 0.938 mmol, 47.2% yield). LC-MS m/z 221.9 $(M+H)^+$ 3.07 min (ret. time).

Ethyl 3-(2-(1-methyl-1H-1,2,3-triazol-4-yl)cyclopropyl)-3-(4-methyl-3-(((R)-4-methyl-1,1-dioxido-3,4-dihydro-2H-benzo[b][1,4,5]oxathiazepin-2-yl)methyl)phenyl)propanoate

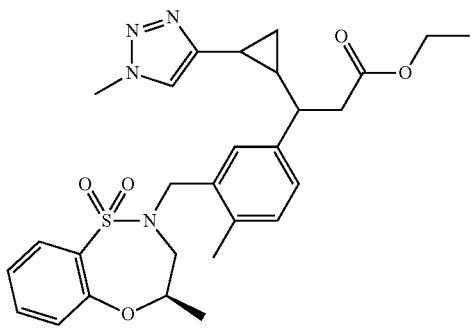 [SMILES: CCOC(=O)CC(c1ccc(C)c(CN2C[C@@H](C)Oc3ccccc3S2(=O)=O)c1)C1CC1c1cn(C)nn1]

To solution of (E)-ethyl 3-(2-(1-methyl-1H-1,2,3-triazol-4-yl)cyclopropyl)acrylate (250 mg, 1.130 mmol) and (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (501 mg, 1.130 mmol) in a mixture of 1,4-dioxane (10 mL) and water (8 mL) was added TEA (343 mg, 3.39 mmol, 0.472 mL) and degassed with nitrogen for 10 min, followed by the addition [RhCl(cod)]$_2$ (49.9 mg, 0.113 mmol). The reaction mixture was allowed to stir at 90° C. for 1 h. The reaction mixture was diluted with water extracted with EtOAc (2×), washed with brine, dried under anhydrous $Na_2SO_4$ and filtered. The filtrate was evaporated under reduced pressure to get the crude product. The crude compound was purified by column chromatography using MeOH:DCM (2:98). The obtained product washed with $Et_2O$ to afford ethyl 3-(2-(1-methyl-1H-1,2,3-triazol-4-yl)cyclopropyl)-3-(4-methyl-3-(((R)-4-methyl-1,1-dioxido-3,4-dihydro-2H-benzo[b][1,4,5]oxathiazepin-2-yl)methyl)phenyl)propanoate (400 mg, 0.674 mmol, 59.6% yield). LC-MS m/z 538.8 $(M+H)^+$ 3.76 min (ret. time).

420

3-(2-(1-Methyl-1H-1,2,3-triazol-4-yl)cyclopropyl)-3-(4-methyl-3-(((R)-4-methyl-1,1-dioxido-3,4-dihydro-2H-benzo[b][1,4,5]oxathiazepin-2-yl)methyl)phenyl)propanoic acid

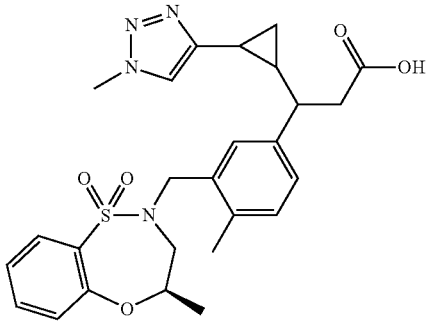 [SMILES: Cc1ccc(C(CC(=O)O)C2CC2c2cn(C)nn2)cc1CN1C[C@@H](C)Oc2ccccc2S1(=O)=O]

To a solution of ethyl 3-(2-(1-methyl-1H-1,2,3-triazol-4-yl)cyclopropyl)-3-(4-methyl-3-(((R)-4-methyl-1,1-dioxido-3,4-dihydro-2H-benzo[b][1,4,5]oxathiazepin-2-yl)methyl)phenyl)propanoate (400 mg, 0.743 mmol) in EtOH (30 mL) was added 10% NaOH (10 mL, 0.743 mmol) at 0° C. The reaction mixture was stirred at RT for 2 h. The reaction mixture was evaporated under reduced pressure, cooled to 0° C., neutralized with 1N HCl and extracted with EtOAc. The organic layer washed with brine and was dried under anhydrous $Na_2SO_4$ and filtered. The filtrate was reduced under vacuum to afford the crude product. The crude residue was purified by preparative HPLC to afford 3-(2-(1-methyl-1H-1,2,3-triazol-4-yl)cyclopropyl)-3-(4-methyl-3-(((R)-4-methyl-1,1-dioxido-3,4-dihydro-2H-benzo[b][1,4,5]oxathiazepin-2-yl)methyl)phenyl)propanoic acid (60 mg, 0.116 mmol). LC-MS m/z 511 $(M+H)^+$ 2.97 min (ret. time).

Example 189

3-(1,4-dimethyl-1H-benzo[d][1,2,3]triazol-5-yl)-2-methyl-3-(4-methyl-3-((5-methyl-1,1-dioxido-4,5-dihydrobenzo[f][1,2,5]thiadiazepin-2(3H)-yl)methyl)phenyl)propanoic acid (isomer M1) (isomer N1)

isomer M1

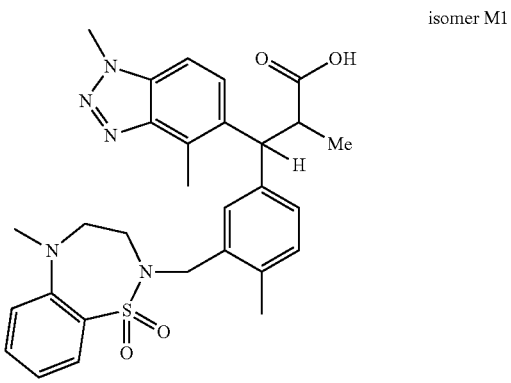

-continued isomer N1

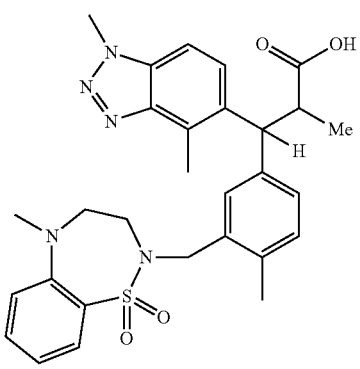

2-Ethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate

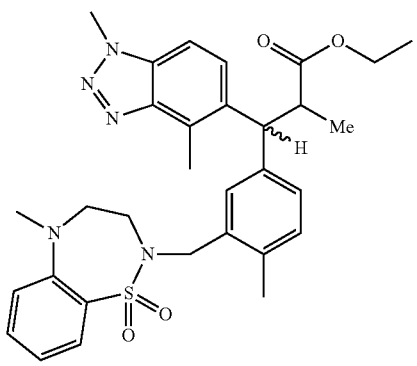 [SMILES: CCOC(=O)C(C)C(c1ccc(C)c(CN2CCN(C)c3ccccc3S2(=O)=O)c1)c1ccc2c(nnn2C)c1C]

Ethyl 3-(1,4-dimethyl-1H-benzo[d][1,2,3]triazol-5-yl)-3-(3-(hydroxymethyl)-4-methylphenyl)propanoate (1 g, 2.72 mmol), and 5-methyl-2,3,4,5-tetrahydrobenzo[f][1,2,5]thiadiazepine 1,1-dioxide (0.693 g, 3.27 mmol), were dissolved in THF (20 mL), and then tributylphosphine (1.360 mL, 5.44 mmol) was added. The reaction mixture was stirred 5 min and then ADDP (1.373 g, 5.44 mmol) was added. This was then stirred for 10 min and then warmed to 23° C. and stirred for 2 h 30 min to afford a brown suspension. The crude product was purified over a silica cartridge (120 g) using a combiflash companion, eluting at 85 mL/min running a gradient of 0-70% EtOAc/hexane for 50 mins. The fractions with product were combined and the solvent removed under reduced pressure to give an off white solid (927 mg, 60.6%). LC-MS m/z 562.2 (M+H)+, 1.17 (ret. time).

Ethyl 3-(1,4-dimethyl-1H-benzo[d][1,2,3]triazol-5-yl)-2-methyl-3-(4-methyl-3-((5-methyl-1,1-dioxido-4,5-dihydrobenzo[f][1,2,5]thiadiazepin-2(3H)-yl)methyl)phenyl)propanoate

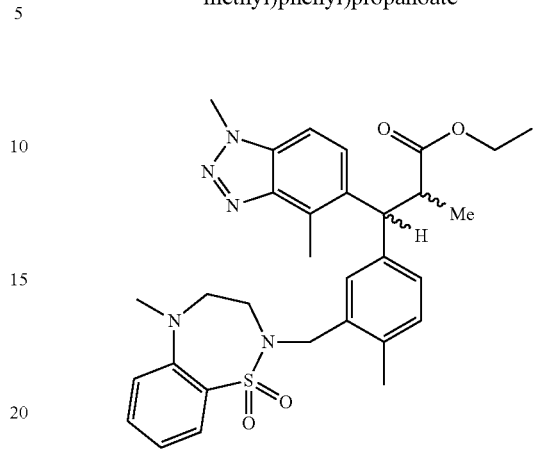

2M n-BuLi (1.100 mL, 2.200 mmol) is added to a dry-ice acetone bath cooled solution of diisopropylamine (0.381 mL, 2.67 mmol) in THF (2 mL). The clear solution was stirred at dry-ice acetone bath temp for 10 min and then was warmed on an ice-water bath and stirred for 10 min to afford 0.63 M LDA.

2-ethyl 3-(1,4-dimethyl-1H-benzo[d][1,2,3]triazol-5-yl)-3-(4-methyl-3-((5-methyl-1,1-dioxido-4,5-dihydrobenzo[f][1,2,5]thiadiazepin-2(3H)-yl)methyl)phenyl)propanoate (179 mg, 0.319 mmol dissolved in THF (2 mL) is added dropwise over a few min to a solution of dry-ice acetone bath cooled 0.63M LDA (658 µl, 0.414 mmol diluted with THF (2 mL). The wine red solution was stirred with dry-ice acetone cooling for 45 min and MeI (100 µl, 1.593 mmol was added in one portion and the red wine color turned to light yellow. The reaction was kept under Ar, stirred with dry-ice acetone cooling for 45 min and LCMS of a portion of this solution indicated no starting material, mostly product (m/e=576) and a minor amount (~10% relative to the desired product) of the dialkylated (m/z=590). The residue was diluted with EtOAc (75 mL) and water (25 mL). The aq was extracted again with EtOAc (25 mL) and the combined EtOAc washed with satd aq NaCl (25 mL), dried (Na2SO4) and concentrated to afford 182 mg ethyl 3-(1,4-dimethyl-1H-benzo[d][1,2,3]triazol-5-yl)-2-methyl-3-(4-methyl-3-((5-methyl-1,1-dioxido-4,5-dihydrobenzo[f][1,2,5]thiadiazepin-2(3H)-yl)methyl)phenyl)propanoate as a brown foam.

The crude product was dissolved in CH3CN (5 mL), filtered through a 0.45 µm acrodisc, and purified on a Gilson HPLC (YMC C18 S-5 µm/12 nm 50×20 mm preparatory column), eluting at 20 mL/min with a linear gradient running from 20% CH3CN/H2O (0.1% TFA) to 95% CH3CN/H2O (0.1% TFA) over 10 min. The major peak fractions were pooled and concentrated to afford a white foam. LC-MS m/z 576.3 (M+H)+, 1.20 (ret. time) ethyl 3-(1,4-dimethyl-1H-benzo[d][1,2,3]triazol-5-yl)-2-methyl-3-(4-methyl-3-((5-methyl-1,1-dioxido-4,5-dihydrobenzo[f][1,2,5]thiadiazepin-2(3H)-yl)methyl)phenyl)propanoate (152 mg, 0.264 mmol, 83% yield.

3-(1,4-dimethyl-1H-benzo[d][1,2,3]triazol-5-yl)-2-methyl-3-(4-methyl-3-((5-methyl-1,1-dioxido-4,5-dihydrobenzo[f][1,2,5]thiadiazepin-2(3H)-yl)methyl)phenyl)propanoic acid (isomer M1) (isomer N1)

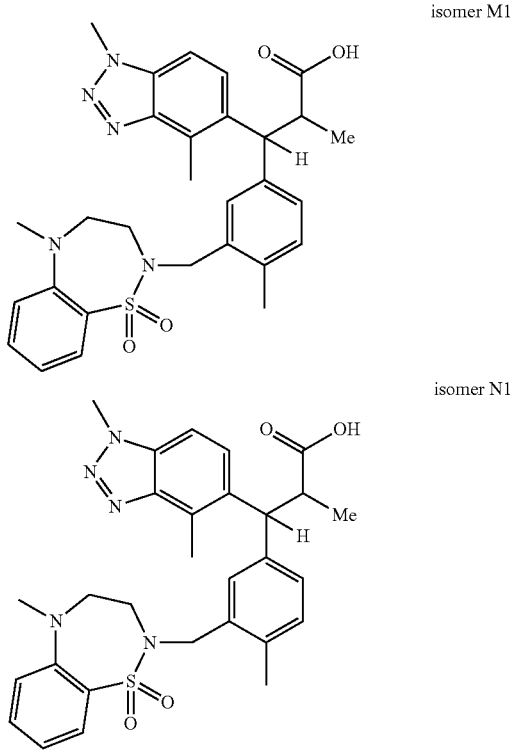

To a solution of ethyl 3-(1,4-dimethyl-1H-benzo[d][1,2,3]triazol-5-yl)-2-methyl-3-(4-methyl-3-((5-methyl-1,1-dioxido-4,5-dihydrobenzo[f][1,2,5]thiadiazepin-2(3H)-yl)methyl)phenyl)propanoate (151 mg, 0.262 mmol) in THF (3 mL) was added a solution of LiOH (126 mg, 5.25 mmol) (3 mL). MeOH (1 mL) was added and a cloudy solution was obtained. Reacted at 50° C. for 6 h and 23° C. 14 h. The reaction was diluted with EtOAc (75 mL) and 1M aq HCl (20 mL) and the aq was extracted again with EtOAc (25 mL). The combined EtOAc washed with $H_2O$ (25 mL) and saturated aqueous (aq) NaCl (25 mL) and dried ($Na_2SO_4$) and concentrated to afford the crude product as a white solid. The crude product was dissolved in DMSO (4 mL), filtered through a 0.45 mm acrodisc, and purified on a Gilson HPLC (YMC C18 S-5 μm/12 nm 50×20 mm preparatory column), eluting at 20 mL/min with a linear gradient running from 10% $CH_3CN/H_2O$ (0.1% TFA) to 90% $CH_3CN/H_2O$ (0.1% TFA) over 10 min. The first peak to elute was the minor isomer 11 mg (7.7%). LC-MS m/z 548.3 $(M+H)^+$, 1.00 min (ret. time) diastereomer B1. The second isomer 98 mg (68.2%). LC-MS m/z 548.3 $(M+H)^+$, 1.04 min (ret. time) diastereomer B2.

The major isomer was determined to be a mixture of two enantiomers by chiral sfc. Preparative enantiomer separation of the components of the major isomer (98 mg) was on chiral SFC (Chiralpak IC, 20×150 mm, 5 u, 30% MeOH, 50 g/min, 100 bar) and the resulting product was dissolved in DMSO, then diluted into MeOH (1:10). The desired fractions were collected and dried by Rotorvap to afford 23 mg each of:

isomer M1 LC-MS m/z=548.4 $(M+H)^+$, 1.05 min (ret time)

isomer N1 LC-MS m/z=548.4 $(M+H)^+$, 1.05 min (ret time)

Example 190

3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid

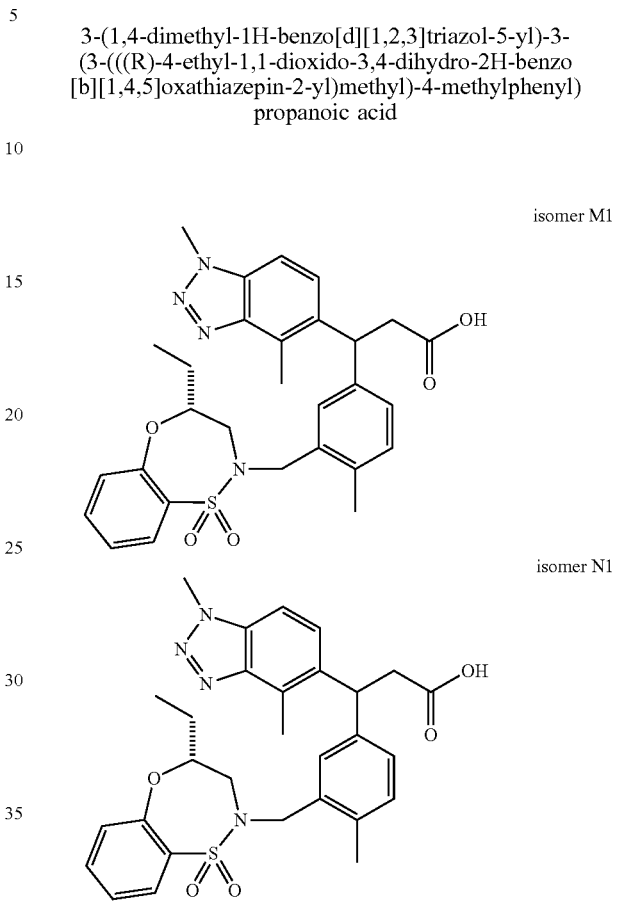

Ethyl 3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoate

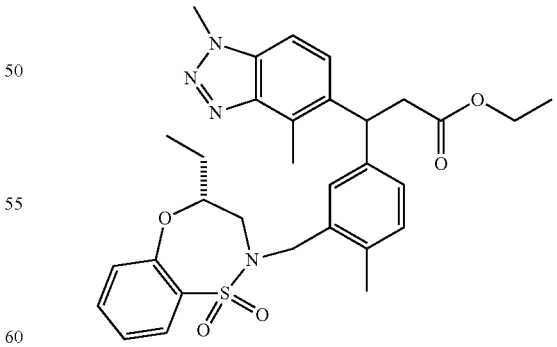

Ethyl 3-(1,4-dimethyl-1H-benzo[d][1,2,3]triazol-5-yl)-3-(3-(hydroxymethyl)-4-methylphenyl)propanoate (2.06 g, 5.61 mmol), (R)-4-ethyl-3,4-dihydro-2H-benzo[b][1,4,5]oxathiazepine 1,1-dioxide (1.338 g, 5.89 mmol, and ADDP (2.83 g, 11.21 mmol were dissolved in THF (60 mL) and tributylphosphine (2.80 mL, 11.21 mmol) was added. Stirred under Ar for 3 h. The crude product was purified on a silica cartridge (80 g) with a Combiflash Companion, eluting at 60 mL/min with a gradient running from hexanes to 80% EtOAc/hexanes over 26 min. The desired fractions were pooled and concentrated to afford ethyl 3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoate (2.59 g, 4.49 mmol, 80%) LC-MS m/z=577.5 (M+H)+, 1.19 min (ret time).

3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid

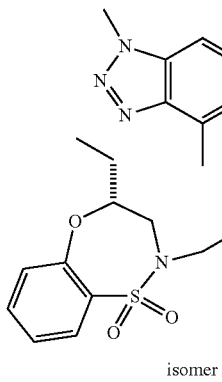

isomer M1

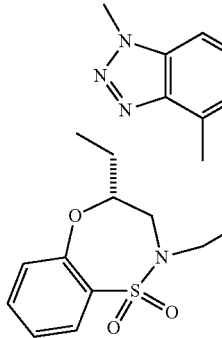

isomer N1

Ethyl 3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoate (2.8 g, 5.17 mmol) was dissolved in THF (50 mL) and a solution of LiOH (2.79 g, 116 mmol) dissolved in water (50.0 mL) was added. MeOH (50 mL) was added and the mixture was stirred 2 h. The reaction was diluted with EtOAc (200 mL) and 1M HCl (100 mL) and the phases were shaken. The aq was extracted again with EtOAc and the combined EtOAc washed with water (50 mL) and satd aq NaCl (50 mL), dried (MgSO$_4$) and concentrated to afford 3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)propanoic acid as a mixture of two isomers of unknown absolute stereochemistry. These were separated by chiral SFC (Chiralpak AD, 20×250 mm, 5 u, 30% MeOH, 50 g/min, 100 bar) Desired fractions were collected and dried by RotorVap. The dried samples were transferred to pre-weighed 20 mL vial with MeOH, and dried under a stream of nitrogen at 45° C.

Isomer M1, 1.30 g LC-MS m/z=549.3 (M+H)+, 1.02 min (ret time)

Isomer N1, 1.47 g LC-MS m/z=549.3 (M+H)+, 1.02 min (ret time).

Example 191

3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid

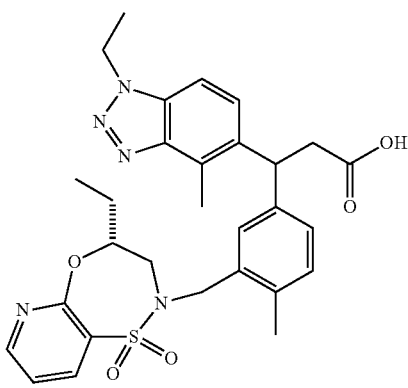

isomer M1

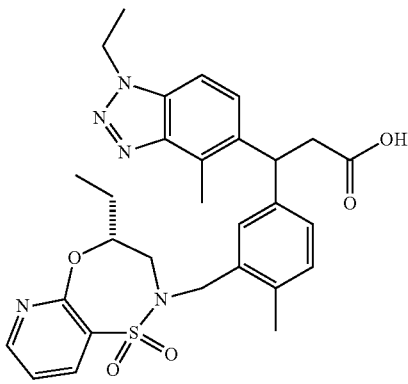

isomer N1

Ethyl 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoate

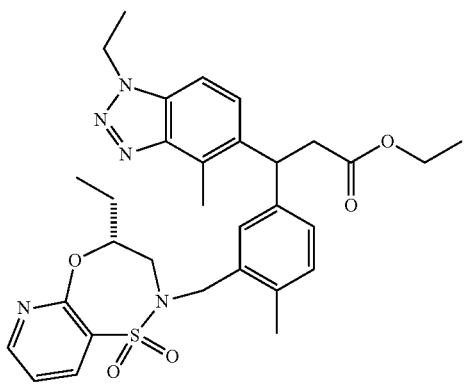 [SMILES: CCOC(=O)CC(c1ccc(C)c(CN2C[C@@H](CC)Oc3ncccc3S2(=O)=O)c1)c1ccc2c(nnn2CC)c1C]

Ethyl 3-(1-ethyl-4-methyl-1H-benzo[d][1,2,3]triazol-5-yl)-3-(3-(hydroxymethyl)-4-methylphenyl)propanoate (1.5 g, 3.93 mmol, (R)-4-ethyl-3,4-dihydro-2H-pyrido[2,3-b][1,4,5]oxathiazepine 1,1-dioxide (0.942 g, 4.13 mmol, and ADDP (1.984 g, 7.86 mmol were dissolved in THF (42 mL) and tributylphosphine (1.964 mL, 7.86 mmol) was added. The reaction mixture was stirred for 3 h, solvent was removed in vacuo and the crude product was purified on a silica cartridge (120 g) with a Combiflash Companion, eluting at 85 mL/min with a gradient running from hexanes to EtOAc over 30 min. The desired fractions were pooled and concentrated to afford ethyl 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoate (2.3 g, 3.89 mmol, 99% yield) LC-MS M/Z=592.4 (M+H)+, 1.12 min (ret time).

3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid

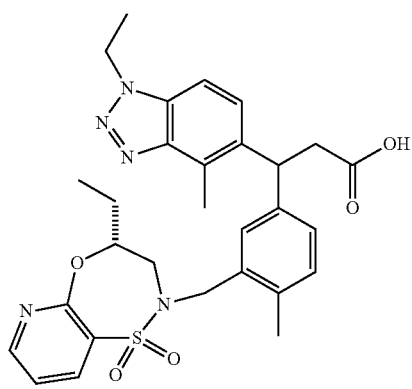

isomer M1

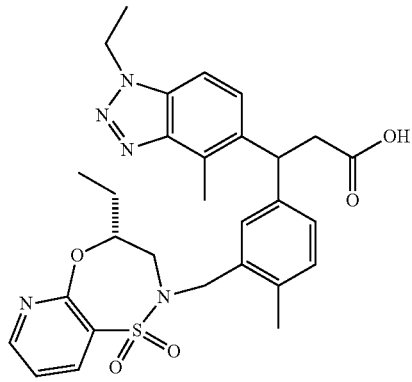

isomer N1

Ethyl 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoate (2.3 g, 3.89 mmol) was dissolved in THF (30 mL) and a solution of LiOH (1.862 g, 78 mmol) dissolved in water (30.0 mL) was added. MeOH (50 mL) was added sufficient to form a cloudy solution and the mixture was stirred 2 h. The volatile solvent was removed in vacuo and the residue was diluted with EtOAc (100 mL) and water (40 mL) and the phases were shaken. The basic phase extract was removed and the aq was combined with 6M HCl (20 mL, 120 mmol) extracted again with EtOAc (75 mL) and the acid phase EtOAc was dried (MgSO4) and concentrated to afford 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (1.84 g, 3.26 mmol, 84% yield). LC-MS m/z=564.2 (M+H)+, 0.95 min (ret time).

The sample was purified by supercritical fluid chromatography. (Chiralpak AD, 20×250 mm, 5 u; 30% MeOH; 50 g/min; 100 bar) to afford 2 pure isomers.

Isomer M1. LC-MS m/z=564.2 (M+H)+, 0.99 min (ret time).

Isomer N1 LC-MS m/z=564.2 (M+H)+, 0.97 min (ret time).

Example 192

3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoic acid

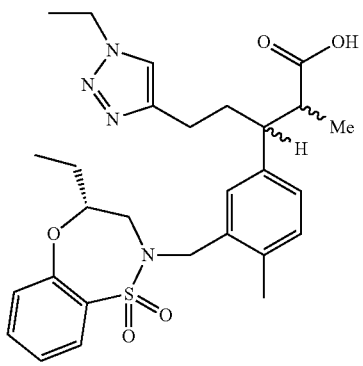 [SMILES: CC[C@@H]1CN(Cc2cc(C(CCc3cn(CC)nn3)C(C)C(=O)O)ccc2C)S(=O)(=O)c2ccccc2O1]

Isomer M1, isomer N1, isomer P1, isomer Q1

(R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide

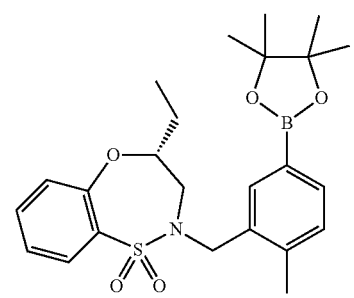 [SMILES: CC[C@@H]1CN(Cc2cc(B3OC(C)(C)C(C)(C)O3)ccc2C)S(=O)(=O)c2ccccc2O1]

429

To a solution of (R)-4-ethyl-3,4-dihydro-2H-benzo[b][1,4,5]oxathiazepine 1,1-dioxide (9 g, 39.6 mmol), (2-methyl-5-(4,4,5,5-tetramethyl-1,3,2-dioxaborolan-2-yl)phenyl)methanol (9.83 g, 39.6 mmol) and triphenylphosphine (10.39 g, 39.6 mmol) in THF (100 mL) stirred under nitrogen at 0° C. was added DEAD (6.27 mL, 39.6 mmol). The reaction mixture was stirred at 25° C. for 2 hr. and then diluted with water (200 mL) and extracted with EtOAc (200 mL×2) washed with brine solution (100 mL) and dried over anhydrous Na$_2$SO$_4$, filtered and evaporated the solvent under vacuum. The crude residue was purified on flash column chromatography (100-200 silica gel mesh) using 15% EtOAc in hexane. The collected the fractions were concentrated to afford (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (5 g, 10.39 mmol, 26.2% yield) as a white solid. $^1$H NMR: (CDCl3) δ 7.9 (d, 1), 7.7 (d, 1), 7.5 (m, 2), 7.2 (m, 3), 4.65 (d, 1), 4.05 (m, 1), 3.8 (d, 1) 3.7 (m, 1) 2.95 (d, 1), 2.4 (s, 3) 1.7 (m, 1), 1.5 (m, 1), 1.3 (s, 12), 1.05 (t, 3).

Ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)pentanoate

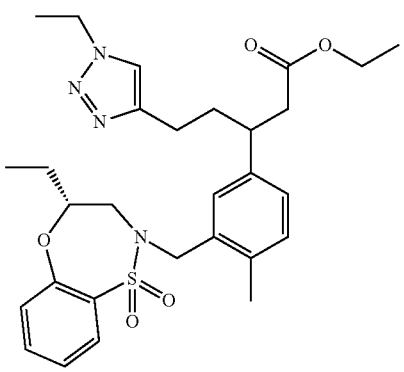 [SMILES: CCOC(=O)CC(CCc1cn(CC)nn1)c1ccc(C)c(CN2C[C@@H](CC)Oc3ccccc3S2(=O)=O)c1]

To a suspension of (E)-ethyl 5-(1-ethyl-1H-1,2,3-triazol-4-yl)pent-2-enoate (230 mg, 1.030 mmol), (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (565 mg, 1.236 mmol), and [RhCl(cod)]2 (50.8 mg, 0.103 mmol) in 1,4-dioxane (2 mL) and water (1 mL) at RT was added Et$_3$N (0.431 mL, 3.09 mmol). The resulting suspension was heated at 90° C. for 1 h. The reaction mixture was passed through celite and washed with EtOAc. The organic layer was collected and concentrated to give the crude product which was purified on a silica cartridge (40 g) with a Combiflash Companion, eluting at 35 mL/min with a gradient running from 10% EtOAc/hexanes to 100% EtOAc/hexanes over 35 min. The desired fractions were concentrated under reduced pressure to give ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)pentanoate (481 mg, 0.867 mmol, 84% yield). LC-MS m/z=555.2 (M+H)$^+$, 1.16 min (ret time).

430

Ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoate

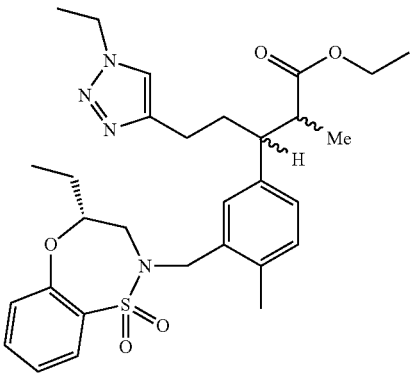 [SMILES: CCOC(=O)C(C)C(CCc1cn(CC)nn1)c1ccc(C)c(CN2C[C@@H](CC)Oc3ccccc3S2(=O)=O)c1]

2M n-BuLi (1.1 mL, 2.2 mmol) is added to a dry-ice acetone bath cooled solution of diisopropylamine (0.381 mL, 2.67 mmol) in THF (2 mL). The clear solution was stirred at dry-ice acetone bath temp for 10 min and then was warmed on an ice-water bath and stirred for 10 min to afford (1.1+0.381+2=3.48 mL 2.2/3.48=0.63 M LDA) 0.63 M LDA. 0.63M LDA (179 µl, 0.113 mmol) in THF (1 mL) was added to a dry-ice-acetone cooled solution of ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)pentanoate (50 mg, 0.090 mmol) in THF (1 mL). The yellow solution was stirred with dry-ice acetone cooling for 30 min and then the dry-ice acetone bath was replaced with a dry-ice CH$_3$CN bath (~−40 C) and the yellow solution was stirred for 20 min after which MeI (113 µl, 1.803 mmol) was added in one portion and the yellow solution was warmed to 23 C and stirred 45 min and the mixture was concentrated in vacuo. The residue was diluted with EtOAc (75 mL) and washed with water (2×25 mL) and satd aq NaCl (25 mL), dried (MgSO$_4$) and concentrated in vacuo to afford 103 mg of a brown foam. The crude product was evaluated by LCMS indicating ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoate as a mixture of diastereomers LC-MS m/z=569 (M+H)$^+$, 1.19 and 1.21 min (ret time).

3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoic acid

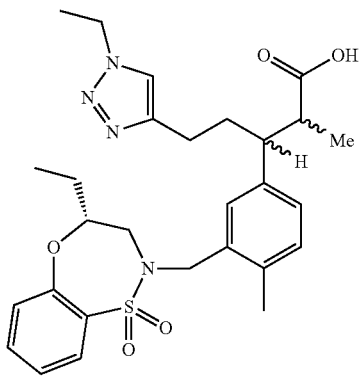 [SMILES: CC[C@@H]1CN(Cc2cc(C(CCc3cn(CC)nn3)C(C)C(=O)O)ccc2C)S(=O)(=O)c2ccccc2O1]

Ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoate (21 mg, 0.037 mmol) was dissolved in THF (0.500 mL) and LiOH (17.69 mg, 0.738 mmol) dissolved in water (0.5 mL) was added. MeOH (1.25 mL) was and the mixture was heated to 100° C. in a Biotage microwave at high setting for 30 min. The reaction was concentrated to dryness and partitioned between DCM (25 mL) and water (25 mL) (pH >12). The aq was separated and relayered with EtOAc (50 mL) and acidified to pH <2. Phases were separated. The acidified aq was extracted again with EtOAc (25 mL) and the combined acid phase extracts were concentrated to afford 8.6 mg of 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoic acid as a white foam. LCMS looks good for a mixture of the major desired diastereomer (~85%) and the minor diastereomer (~15%) LC-MS m/z=541 (M+H)$^+$, 1.01 and 1.04 min (ret time).

Example 193

3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoic acid

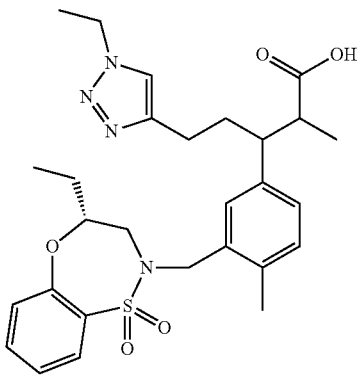 [SMILES: CC[C@@H]1CN(Cc2cc(C(CCc3cn(CC)nn3)C(C)C(=O)O)ccc2C)S(=O)(=O)c2ccccc2O1]

Ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoate

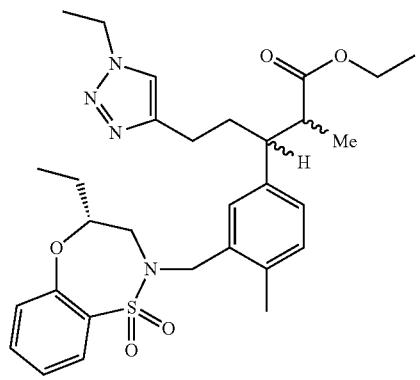 [SMILES: CCOC(=O)C(C)C(CCc1cn(CC)nn1)c1ccc(C)c(CN2C[C@@H](CC)Oc3ccccc3S2(=O)=O)c1]

2M n-BuLi (1.1 mL, 2.2 mmol) is added to a dry-ice acetone bath cooled solution of diisopropylamine (0.381 mL, 2.67 mmol) in THF (2 mL). The clear solution was stirred at dry-ice acetone bath temp for 10 min and then was warmed on an ice-water bath and stirred for 10 min to afford (1.1+0.381+2=3.48 mL 2.2/3.48=0.63 M LDA) 0.63 M LDA.

Ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)pentanoate (100 mg, 0.180 mmol) was dissolved in THF (1 mL) and cooled on a dry ice acetone bath 10 min and then 0.63 M in THF LDA (372 µl, 0.234 mmol) was added and the brown solution was stirred at −78 for 30 min warmed to ~−40 (dry ice CH$_3$CN bath) stirred 10 min and then methyl iodide (225 µl, 3.61 mmol) was added. The reaction was warmed to 23° C. and then the mixture was concentrated and the residue was diluted with EtOAc (75 mL) and washed with water (2×25 mL) and satd aq NaCl (25 mL), dried (MgSO$_4$) and concentrated to afford 103 mg of a brown foam. The crude product was evaluated by LCMS indicating monomethylated product as a mixture of isomers m/z=569, Rf=1.19 and 1.21.

The crude product was dissolved in CH$_3$CN (4 mL), filtered through a 0.45 mm acrodisc, and purified on a Gilson HPLC (YMC C18 S-5 mm/12 nm 50×20 mm preparatory column), eluting at 20 mL/min with a linear gradient running from 20% CH$_3$CN/H$_2$O (0.1% TFA) to 85% CH$_3$CN/H$_2$O (0.1% TFA) over 10 min. The desired fractions were chosen based on LCMS of the fractions and were pooled and concentrated in vacuo to afford ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoate (41 mg, 0.072 mmol, 40.0% yield). LC-MS m/z=569 (M+H)$^+$, 1.16 and 1.19 min (ret time)

3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoic acid

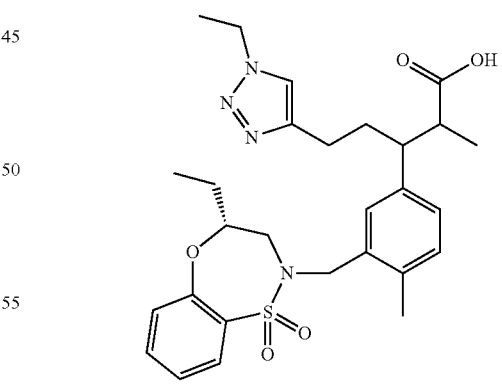

Ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoate (38.1 mg, 0.067 mmol) was dissolved in THF (1.0 mL) and a solution of LiOH (32.1 mg, 1.340 mmol) in water (1.000 mL) was added. MeOH (0.5 mL) was added and the mixture was heated in a microwave at high setting at 100° C. for 30 min. Cooled and the mixture was diluted with water (~10 mL)

and EtOAc (~20 mL) and the phases were shaken together (aqueous was ~pH 10, pH paper) and separated. The aq was acidified with 1M aq HCL (10 mL) and extracted with EtOAc (2×40 mL). The combined acid phase extracts were washed with water and then satd aq NaCl (~20 mL each), dried ($Na_2SO_4$) and concentrated to afford 38 mg of product. The crude product was dissolved in $CH_3CN$ (4 mL), filtered through a 0.45 mm acrodisc, and purified on a Gilson HPLC (YMC C18 S-5 mm/12 nm 50×20 mm preparatory column), eluting at 20 mL/min with a linear gradient running from 10% $CH_3CN/H_2O$ (0.1% TFA) to 90% $CH_3CN/H_2O$ (0.1% TFA) over 10 min. The desired fractions were pooled based on LCMS analysis of all the fractions individually and then pooling those fractions from the major peak with >90% of the m/z=541 peak. The pooled fractions were concentrated in vacuo to afford 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoic acid (12 mg, 0.022 mmol, 33.1% yield) LC-MS m/z=542.4 $(M+H)^+$, 1.02 min (ret time). Analytical sfc analysis indicates the product is a mixture of two isomers presumably with the same relative stereochemistry at the pentanoate C-2 and C-3 but with opposite absolute stereochemistry at these atoms.

Example 194

3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)pentanoic acid (isomer M1) and 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)pentanoic acid (isomer N1)

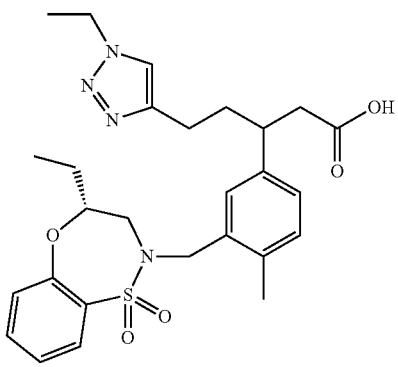

isomer M1

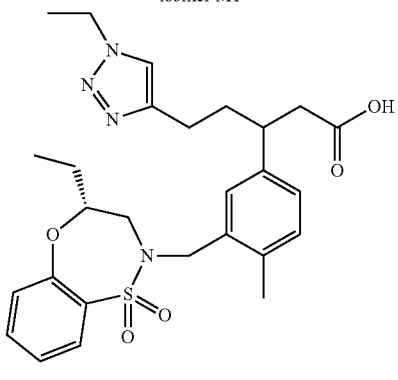

isomer N1

3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoate

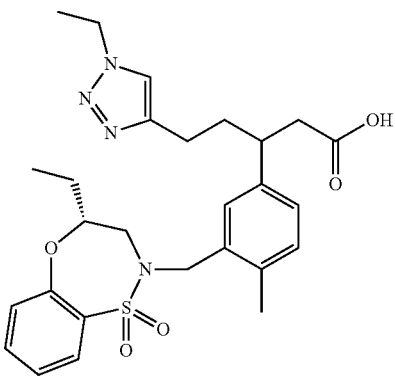 [SMILES: CC[C@@H]1CN(Cc2cc(C(CCc3cn(CC)nn3)CC(=O)O)ccc2C)S(=O)(=O)c2ccccc2O1]

60 mg of ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoate was dissolved in MeOH (2 mL). 2M LiOH (3.09 mL, 6.18 mmol) was added and the reaction mixture was heated in a Biotage microwave at high absorption for 30 min at 80° C. 0.8 mL of 1 N HCl and 1.5 mL of DMSO were added. Most of the solvent was removed at reduced pressure and the sample was purified via reverse phase chromatography (Sunfire C18, 19×100 mm, 5 u; mobile phase A=Water+0.1% TFA:Mobile phase B=MeCN+0.1% TFA; 18 mL/min; 35% B to 65% B in 10 min) to afford 62 mg of the mixture of isomers 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoate.

(R)-3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)pentanoic acid (isomer M1) and (S)-3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)pentanoic acid (isomer N1)

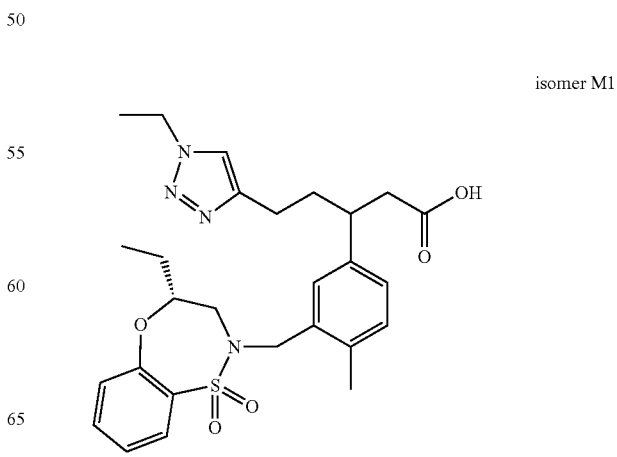

isomer M1

-continued isomer N1

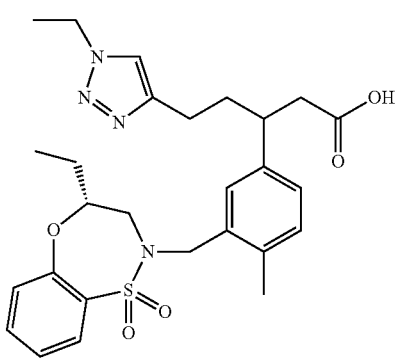

62 mg of the mixture of isomers 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)-2-methylpentanoate was separated by chiral supercritical fluid chromatography (Chiralpak AD, 20×250 mm, 5μ; 20% EtOH; 50 g/min; 100 bar) to afford:
isomer M1 (15 mg) 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)pentanoic acid LC-MS m/z 527.4 (M+H)+, 1.02 (ret. time). isomer N1 (15 mg) (S)-3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)pentanoic acid LC-MS m/z 527.4 (M+H)+, 1.02 (ret. time)

Example 195

5-Methoxy-3-(4-methyl-3-(((R)-4-methyl-1,1-dioxido-3,4-dihydro-2H-benzo[b][1,4,5]oxathiazepin-2-yl)methyl)phenyl)pentanoic acid

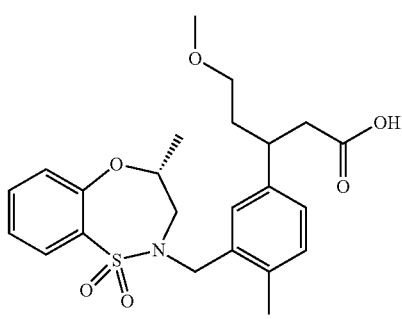 [SMILES: COCCC(CC(=O)O)c1ccc(C)c(CN2C[C@@H](C)Oc3ccccc3S2(=O)=O)c1]

3-methoxypropanal

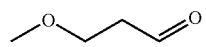

To a solution of Dess-Martin Periodinane (4.24 g, 9.99 mmol) in DCM (10 mL) was added 3-methoxypropan-1-ol (0.796 mL, 8.32 mmol) dropwise at 0° C. The reaction was allowed to warm to RT and stirred for 18 h. The mixture was then diluted with DCM (100 mL) and washed with sat. aq. NaHCO₃ containing Na₂SO₄. The phases were shaken and separated and the aqueous layer extracted again with DCM (50 mL). The combined organic layers were washed with water (50 mL) and sat. aq. NaCl (25 mL), dried (Na₂SO₄) and filtered. The solution was not concentrated due to the volatile nature of 3-methoxypropanal and carried to the next step without further manipulation.

(E)-Benzyl 5-methoxypent-2-enoate

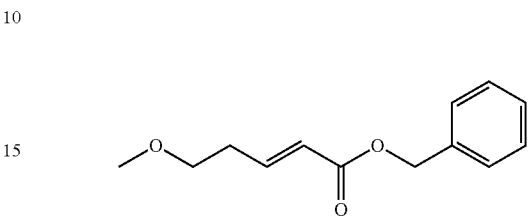

3-methoxypropanal (0.7 g, 7.95 mmol) in DCM (150 mL) was combined with benzyl 2-(triphenylphosphoranylidene)acetate (3.59 g, 8.74 mmol) and the mixture refluxed for 3 h. The reaction was cooled RT and stirred for 1 h. The reaction was diluted with DCM (20 mL) and washed with water (2×10 mL) and satd aq NaCl (15 mL), dried (Na₂SO₄) and concentrated. The residue was purified via silica gel chromatography with hexane and EtOAc to yield (E)-benzyl 5-methoxypent-2-enoate (340 mg, 1.513 mmol, 19.04% yield) as a clear oil. LC-MS m/z 221.0 (M+H)+, 0.96 min (ret. time).

Benzyl 5-methoxy-3-(4-methyl-3-(((R)-4-methyl-1,1-dioxido-3,4-dihydro-2H-benzo[b][1,4,5]oxathiazepin-2-yl)methyl)phenyl)pentanoate

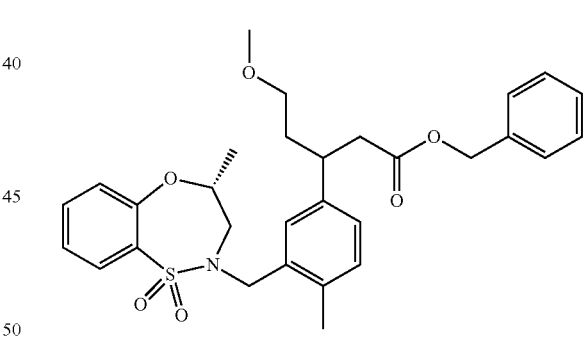

To a solution of (E)-benzyl 5-methoxypent-2-enoate (0.34 g, 1.544 mmol) and (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (0.719 g, 1.621 mmol) in 1,4-dioxane (10 mL) and water (6.67 mL) was added Et₃N (0.323 mL, 2.315 mmol) and [RhCl(cod)]₂ (0.043 g, 0.086 mmol) The reaction was heated to 95° C. and stirred for 1.5 h. The reaction was cooled and filtered through a pad of celite. The filtrate was concentrated in vacuo and purified via silica gel chromatography with hexane and EtOAc to yield benzyl 5-methoxy-3-(4-methyl-3-(((R)-4-methyl-1,1-dioxido-3,4-dihydro-2H-benzo[b][1,4,5]oxathiazepin-2-yl)methyl)phenyl)pentanoate (542 mg, 0.948 mmol, 61.4% yield) as a colorless oil. LC-MS m/z 538.3 (M+H)+, 1.30 min (ret. time).

5-Methoxy-3-(4-methyl-3-(((R)-4-methyl-1,1-di-
oxido-3,4-dihydro-2H-benzo[b][1,4,5]oxathiazepin-
2-yl)methyl)phenyl)pentanoic acid

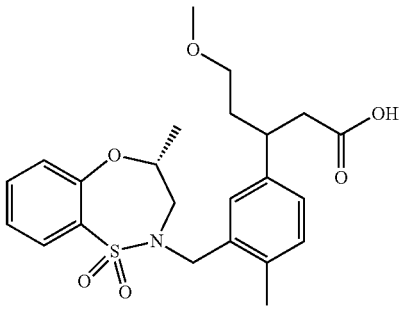 [SMILES: COCCC(CC(=O)O)c1ccc(C)c(CN2C[C@@H](C)Oc3ccccc3S2(=O)=O)c1]

To a stirred solution of benzyl 5-methoxy-3-(4-methyl-3-(((R)-4-methyl-1,1-dioxido-3,4-dihydro-2H-benzo[b][1,4,5]oxathiazepin-2-yl)methyl)phenyl)pentanoate (0.255 g, 0.474 mmol in MeOH (10 mL) was added Pd/C (0.025 g, 0.024 mmol) carefully. Then the flask was fitted with a 3-way adapter and a hydrogen balloon. The flask was purged (3×) by pulling a vacuum and releasing to hydrogen. The adapter was then equipped with a second hydrogen balloon and allowed to stir for 18 h at RT. The balloons were removed and the reaction filtered through a pad of celite. The filtrate was concentrated and purified via reverse-phase HPLC CH$_3$CN/H$_2$O (0.1% TFA) to yield title compound 5-methoxy-3-(4-methyl-3-(((R)-4-methyl-1,1-dioxido-3,4-dihydro-2H-benzo[b][1,4,5]oxathiazepin-2-yl)methyl)phenyl)pentanoic acid (152 mg, 0.340 mmol, 71.6% yield) as a white solid. LC-MS m/z 448.2 (M+H)$^+$, 0.99 min (ret. time).

Example 196

5-Cyclopentyl-3-(4-methyl-3-(((R)-4-methyl-1,1-
dioxido-3,4-dihydro-2H-benzo[b][1,4,5]oxathiaz-
epin-2-yl)methyl)phenyl)pentanoic acid

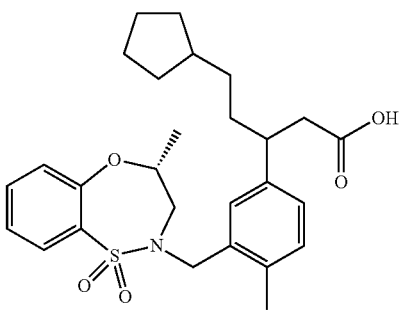 [SMILES: Cc1ccc(C(CCC2CCCC2)CC(=O)O)cc1CN1C[C@@H](C)Oc2ccccc2S1(=O)=O]

(E)-Benzyl 5-cyclopentylpent-2-enoate

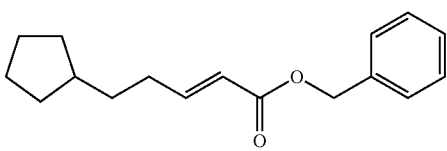 [SMILES: O=C(/C=C/CCC1CCCC1)OCc1ccccc1]

3-cyclopentylpropan-1-ol (0.5 g, 3.90 mmol) in DCM (50 mL) was combined with Dess-Martin periodinane (1.985 g, 4.68 mmol) and the mixture stirred at RT for 18 h. Once the aldehyde was formed benzyl 2-(triphenylphosphoranylidene)acetate (1.761 g, 4.29 mmol) was added and heated to reflux for 3 h. The reaction was cooled RT and stirred for 1 h. The reaction was diluted with DCM (20 mL) and washed with water (2×10 mL) and satd aq NaCl (15 mL), dried (Na$_2$SO$_4$) and concentrated. The reaction mixture was purified via silica gel chromatography with hexanes and EtOAc to yield (E)-benzyl 5-cyclopentylpent-2-enoate (444 mg, 1.358 mmol, 34.8% yield) as a colorless oil.

Benzyl 5-cyclopentyl-3-(4-methyl-3-(((R)-4-methyl-
1,1-dioxido-3,4-dihydro-2H-benzo[b][1,4,5]oxathi-
azepin-2-yl)methyl)phenyl)pentanoate

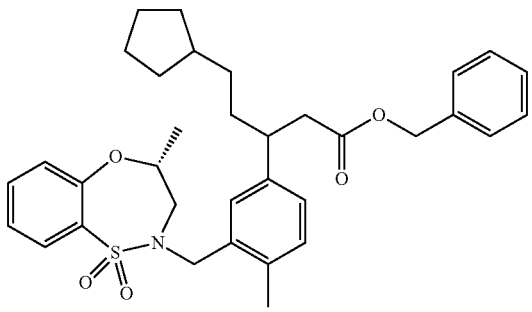 [SMILES: Cc1ccc(C(CCC2CCCC2)CC(=O)OCc2ccccc2)cc1CN1C[C@@H](C)Oc2ccccc2S1(=O)=O]

To a solution of (E)-benzyl 3-(tetrahydro-2H-pyran-4-yl) acrylate (0.40 g, 1.624 mmol) and in 1,4-dioxane (10 mL) and water (6.67 mL) was added Et$_3$N (0.340 mL, 2.436 mmol), (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (0.721 g, 1.626 mmol) and [RhCl(cod)]$_2$ (0.045 g, 0.091 mmol). The reaction was heated to 95° C. and stirred for 2 h. The reaction was cooled and filtered through a pad of celite. The filtrate was concentrated in vacuo and purified via silica gel chromatography with hexanes and EtOAc to yield benzyl 5-cyclopentyl-3-(4-methyl-3-(((R)-4-methyl-1,1-dioxido-3,4-dihydro-2H-benzo[b][1,4,5]oxathiazepin-2-yl)methyl)phenyl) pentanoate (851 mg, 0.783 mmol, 50.6% yield) as a colorless oil. LC-MS m/z 576.3 (M+H)$^+$, 1.59 min (ret. time)

5-Cyclopentyl-3-(4-methyl-3-(((R)-4-methyl-1,1-
dioxido-3,4-dihydro-2H-benzo[b][1,4,5]oxathiaz-
epin-2-yl)methyl)phenyl)pentanoic acid

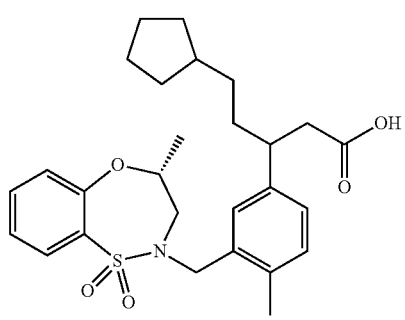 [SMILES: Cc1ccc(C(CCC2CCCC2)CC(=O)O)cc1CN1C[C@@H](C)Oc2ccccc2S1(=O)=O]

To a stirred solution of benzyl 5-cyclopentyl-3-(4-methyl-3-(((R)-4-methyl-1,1-dioxido-3,4-dihydro-2H-benzo[b][1,4,5]oxathiazepin-2-yl)methyl)phenyl)pentanoate (0.39 g, 0.677 mmol) in EtOAc (20 mL) was added Pd/C (0.036 g, 0.034 mmol) carefully. Then the flask was fitted with a 3-way adapter and a hydrogen balloon. The flask was purged (3×) by pulling a vacuum and releasing to hydrogen. The reaction was then allowed to stir for 18 h at RT. The balloon was then removed and the reaction filtered through a pad of celite. The filtrate was concentrated and purified via reverse-phase HPLC $CH_3CN/H_2O$ (0.1% TFA) to yield 5-cyclopentyl-3-(4-methyl-3-(((R)-4-methyl-1,1-dioxido-3,4-dihydro-2H-benzo[b][1,4,5]oxathiazepin-2-yl)methyl)phenyl)pentanoic acid as a white solid. LC-MS m/z 486.4 $(M+H)^+$, 1.37 min (ret. time).

Example 197

3-(3-(((R)-4-Ethyl-1,1-dioxido-3,4-dihydro-2H-pyrido[4,3-b][1,4,5]oxathiazepin-2-yl)methyl)-4-(trifluoromethyl)phenyl)-5-(1-ethyl-1H-1,2,3-triazol-4-yl)pentanoic acid

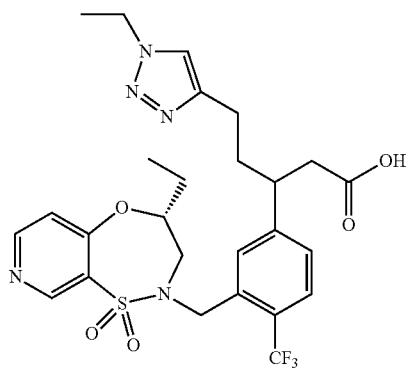 [SMILES: CC[C@@H]1CN(Cc2cc(C(CCc3cn(CC)nn3)CC(=O)O)ccc2C(F)(F)F)S(=O)(=O)c2cnccc2O1]

(5-(4,4,5,5-Tetramethyl-1,3,2-dioxaborolan-2-yl)-2-(trifluoromethyl)phenyl) MeOH

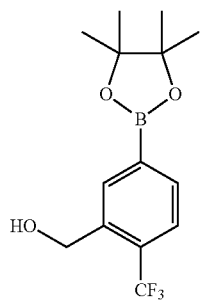 [SMILES: CC1(C)OB(c2ccc(C(F)(F)F)c(CO)c2)OC1(C)C]

To a solution of (5-bromo-2-(trifluoromethyl)phenyl)methanol (0.870 g, 3.41 mmol) in 1,4-dioxane (13 mL) in a 20 mL microwave reaction vessel was added bis(pinacolato)diboron (1.040 g, 4.09 mmol) and potassium acetate (1.004 g, 10.23 mmol) The solution was degassed with nitrogen for 5 min and then $PdCl_2$(dppf) with DCM (0.167 g, 0.205 mmol) was added. The reaction was heated on the Biotage microwave reactor at 150° C. for 20 min. After 20 min the reaction turned black. The reaction was filtered through a pad of celite, concentrated and redissolved in EtOAc (50 mL). The reaction washed with water (4×20 mL), brine (20 mL) and dried over $MgSO_4$. The residue was purified via silica gel chromatography with hexanes and EtOAc to yield (5-(4,4,5,5-tetramethyl-1,3,2-dioxaborolan-2-yl)-2-(trifluoromethyl)phenyl)methanol (800 mg, 2.383 mmol, 69.9% yield) as a clear oil. LC-MS m/z 303.1 $(M+H)^+$, 1.07 min (ret. time).

Ethyl 5-(1-ethyl-1H-1,2,3-triazol-4-yl)-3-(3-(hydroxymethyl)-4-(trifluoromethyl)phenyl)pentanoate

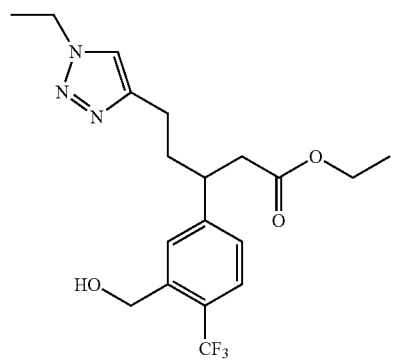 [SMILES: CCOC(=O)CC(CCc1cn(CC)nn1)c1ccc(C(F)(F)F)c(CO)c1]

To a solution of (E)-ethyl 5-(1-ethyl-1H-1,2,3-triazol-4-yl)pent-2-enoate (282 mg, 1.263 mmol) and in 1,4-dioxane (10 mL) and water (6.67 mL) was added $Et_3N$ (0.264 mL, 1.895 mmol) (5-(4,4,5,5-tetramethyl-1,3,2-dioxaborolan-2-yl)-2-(trifluoromethyl)phenyl)methanol (401 mg, 1.326 mmol) and $[RhCl(cod)]_2$ (34.9 mg, 0.071 mmol) The reaction was heated to 95° C. and stirred for 2 h. The reaction was cooled and filtered through a pad of celite. The filtrate was concentrated in vacuo and purified via silica gel chromatography with DCM and MeOH to yield ethyl 5-(1-ethyl-1H-1,2,3-triazol-4-yl)-3-(3-(hydroxymethyl)-4-(trifluoromethyl)phenyl)pentanoate (314 mg, 0.377 mmol, 29.9% yield) as a colorless oil. LC-MS m/z 400.1 $(M+H)^+$, 0.91 min (ret. time).

Ethyl 3-(3-(((R)-4-ethyl-1,1-dioxido-3,4-dihydro-2H-pyrido[4,3-b][1,4,5]oxathiazepin-2-yl)methyl)-4-(trifluoromethyl)phenyl)-5-(1-ethyl-1H-1,2,3-triazol-4-yl)pentanoate

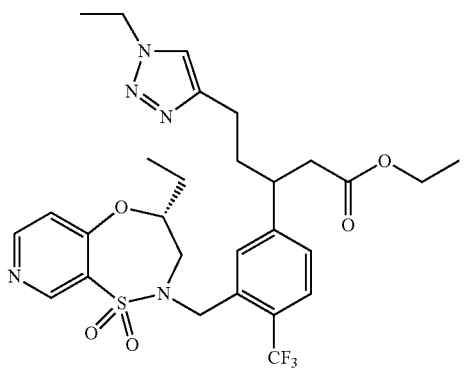 [SMILES: CCOC(=O)CC(CCc1cn(CC)nn1)c1ccc(C(F)(F)F)c(CN2C[C@@H](CC)Oc3ccncc3S2(=O)=O)c1]

To a solution of ethyl 5-(1-ethyl-1H-1,2,3-triazol-4-yl)-3-(3-(hydroxymethyl)-4-(trifluoromethyl)phenyl)pentanoate (80 mg, 0.100 mmol) (R)-4-ethyl-3,4-dihydro-2H-pyrido[4,3-b][1,4,5]oxathiazepine 1,1-dioxide (24.00 mg, 0.105 mmol) and ADDP (50.5 mg, 0.200 mmol) in dry THF (3 mL) was added tributylphosphine (40.5 mg, 0.200 mmol) After 15 min the reaction became cloudy. The reaction was stirred for an additional 20 h and the reaction mixture was concentrated. The reaction mixture was redissolved in a minimal amount of MeOH and purified via reverse-phase HPLC $CH_3CN/H_2O$ (neutral) to yield ethyl 3-(3-(((R)-4-ethyl-1,1-dioxido-3,4-dihydro-2H-pyrido[4,3-b][1,4,5]oxathiazepin-2-yl)methyl)-4-(trifluoromethyl)phenyl)-5-(1-ethyl-1H-1,2,3-triazol-4-yl)pentanoate (50 mg, 0.063 mmol, 63.1% yield) as a clear oil. LC-MS m/z 610.2 (M+H)$^+$, 1.07 min (ret. time).

3-(3-(((R)-4-Ethyl-1,1-dioxido-3,4-dihydro-2H-pyrido[4,3-b][1,4,5]oxathiazepin-2-yl)methyl)-4-(trifluoromethyl)phenyl)-5-(1-ethyl-1H-1,2,3-triazol-4-yl)pentanoic acid

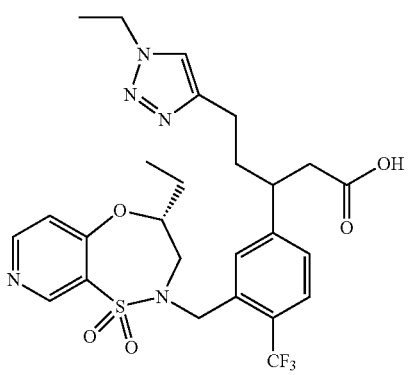 [SMILES: CC[C@@H]1CN(Cc2cc(C(CCc3cn(CC)nn3)CC(=O)O)ccc2C(F)(F)F)S(=O)(=O)c2cnccc2O1]

To a solution of ethyl 3-(3-(((R)-4-ethyl-1,1-dioxido-3,4-dihydro-2H-pyrido[4,3-b][1,4,5]oxathiazepin-2-yl)methyl)-4-(trifluoromethyl)phenyl)-5-(1-ethyl-1H-1,2,3-triazol-4-yl)pentanoate (30 mg, 0.049 mmol) in THF (3 mL) was added LiOH (11.78 mg, 0.492 mmol) and water (3.00 mL) The reaction was stirred at RT for 21 h. The reaction was almost complete after 5 h but was continued overnight to ensure completion. The reaction was concentrated and purified via reverse-phase HPLC $CH_3CN/H_2O$ (neutral) to yield 3-(3-(((R)-4-ethyl-1,1-dioxido-3,4-dihydro-2H-pyrido[4,3-b][1,4,5]oxathiazepin-2-yl)methyl)-4-(trifluoromethyl)phenyl)-5-(1-ethyl-1H-1,2,3-triazol-4-yl)pentanoic acid (26 mg, 0.045 mmol, 91% yield) as a white solid. LC-MS m/z 582.2 (M+H)$^+$, 0.94 min (ret. time).

Example 198

5-(1-Ethyl-1H-1,2,3-triazol-4-yl)-3-(3-((4-methyl-1,1-dioxido-4,5-dihydrobenzo[f][1,2]thiazepin-2(3H)-yl)methyl)-4-(trifluoromethyl)phenyl)pentanoic acid

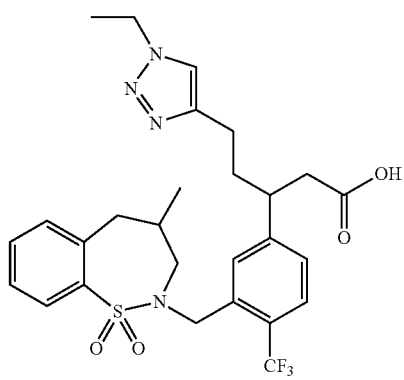 [SMILES: CCn1cc(CCC(CC(=O)O)c2ccc(C(F)(F)F)c(CN3CC(C)Cc4ccccc4S3(=O)=O)c2)nn1]

(5-(4,4,5,5-Tetramethyl-1,3,2-dioxaborolan-2-yl)-2-(trifluoromethyl)phenyl) MeOH

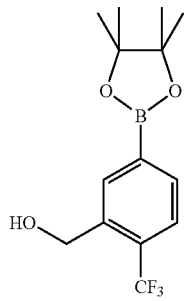 [SMILES: CC1(C)OB(c2ccc(C(F)(F)F)c(CO)c2)OC1(C)C]

To a solution of (5-bromo-2-(trifluoromethyl)phenyl)methanol (0.870 g, 3.41 mmol) in 1,4-Dioxane (13 mL) in a 20 mL microwave reaction vessel was added bis(pinacolato)diboron (1.040 g, 4.09 mmol) and potassium acetate (1.004 g, 10.23 mmol) The solution was degassed with nitrogen for 5 min and then $PdCl_2$(dppf) with DCM (0.167 g, 0.205 mmol) was added. The reaction was heated on the Biotage microwave reactor at 150° C. for 20 min. The reaction was filtered through a pad of celite, concentrated and redissolved in EtOAc (50 mL). The reaction washed with water (4×20 mL), brine (20 mL) and dried over $Mg_2SO_4$. The residue was purified via silica gel chromatography with hexanes and EtOAc to yield (5-(4,4,5,5-tetramethyl-1,3,2-dioxaborolan-2-yl)-2-(trifluoromethyl)phenyl) methanol (800 mg, 2.383 mmol, 69.9% yield) as a clear oil. LC-MS m/z 303.1 (M+H)$^+$, 1.07 min (ret. time).

Ethyl 5-(1-ethyl-1H-1,2,3-triazol-4-yl)-3-(3-(hydroxymethyl)-4-(trifluoromethyl) phenyl)pentanoate

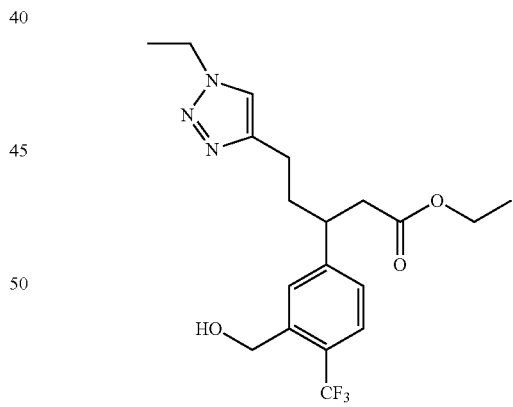

To a solution of (E)-ethyl 5-(1-ethyl-1H-1,2,3-triazol-4-yl)pent-2-enoate (282 mg, 1.263 mmol) and in 1,4-dioxane (10 mL) and water (6.67 mL) was added $Et_3N$ (0.264 mL, 1.895 mmol), (5-(4,4,5,5-tetramethyl-1,3,2-dioxaborolan-2-yl)-2-(trifluoromethyl)phenyl)methanol (401 mg, 1.326 mmol) and [RhCl(cod)]$_2$ (34.9 mg, 0.071 mmol). The reaction was heated to 95° C. and stirred for 2 h. The reaction was cooled and filtered through a pad of celite. The filtrate was concentrated in vacuo and purified via silica gel chromatography with DCM and MeOH to yield ethyl 5-(1-ethyl-1H-1,2,3-triazol-4-yl)-3-(3-(hydroxymethyl)-4-(trifluoromethyl)phenyl)pentanoate (314 mg, 0.377 mmol, 29.9% yield) as a colorless oil. LC-MS m/z 400.1 (M+H)+, 0.91 min (ret. time).

Ethyl 5-(1-ethyl-1H-1,2,3-triazol-4-yl)-3-(3-((4-methyl-1,1-dioxido-4,5-dihydrobenzo[f][1,2]thiazepin-2(3H)-yl)methyl)-4-(trifluoromethyl)phenyl)pentanoate

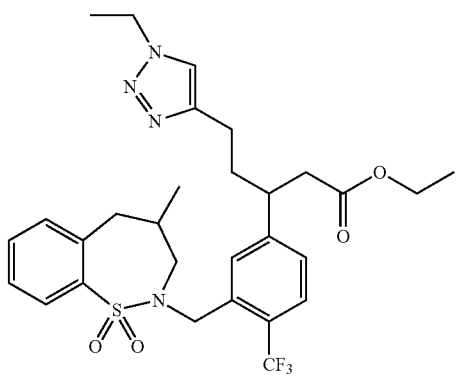 [SMILES: CCOC(=O)CC(CCc1cn(CC)nn1)c1ccc(C(F)(F)F)c(CN2CC(C)Cc3ccccc3S2(=O)=O)c1]

To a solution of ethyl 5-(1-ethyl-1H-1,2,3-triazol-4-yl)-3-(3-(hydroxymethyl)-4-(trifluoromethyl)phenyl)pentanoate (80 mg, 0.100 mmol), 4-methyl-2,3,4,5-tetrahydrobenzo[f][1,2]thiazepine 1,1-dioxide (22.22 mg, 0.105 mmol) and ADDP (50.5 mg, 0.200 mmol) in dry THF (3 mL) was added tributylphosphine (40.5 mg, 0.200 mmol) After 15 min the reaction became cloudy. The reaction was stirred for an additional 18 h and the reaction mixture was concentrated. The reaction mixture was redissolved in a minimal amount of MeOH and purified via reverse-phase HPLC CH₃CN/H₂O (0.1% TFA) to yield ethyl 5-(1-ethyl-1H-1,2,3-triazol-4-yl)-3-(3-((4-methyl-1,1-dioxido-4,5-dihydrobenzo[f][1,2]thiazepin-2(3H)-yl)methyl)-4-(trifluoromethyl)phenyl)pentanoate (32 mg, 0.047 mmol, 46.9% yield) as a clear oil. LC-MS m/z 593.2 (M+H)+, 1.25 min (ret. time).

5-(1-Ethyl-1H-1,2,3-triazol-4-yl)-3-(3-((4-methyl-1,1-dioxido-4,5-dihydrobenzo[f][1,2]thiazepin-2(3H)-yl)methyl)-4-(trifluoromethyl)phenyl)pentanoic acid

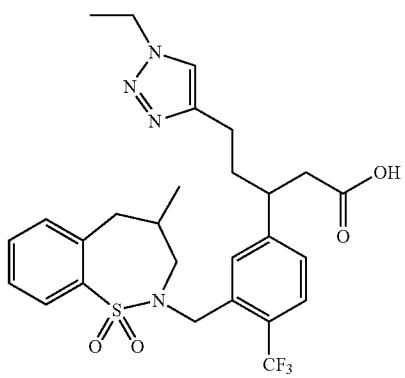 [SMILES: CCn1cc(CCC(CC(=O)O)c2ccc(C(F)(F)F)c(CN3CC(C)Cc4ccccc4S3(=O)=O)c2)nn1]

To a solution of ethyl 5-(1-ethyl-1H-1,2,3-triazol-4-yl)-3-(3-((4-methyl-1,1-dioxido-4,5-dihydrobenzo[f][1,2]thiazepin-2(3H)-yl)methyl)-4-(trifluoromethyl)phenyl)pentanoate (25 mg, 0.042 mmol) in THF (3 mL) was added LiOH (10.10 mg, 0.422 mmol) and water (3.00 mL). The reaction was stirred at RT for 21 h. The reaction was almost complete after 5 h but it was continued overnight to ensure completion. The reaction was concentrated and purified via reverse-phase HPLC CH₃CN/H₂O (neutral) to yield 5-(1-ethyl-1H-1,2,3-triazol-4-yl)-3-(3-((4-methyl-1,1-dioxido-4,5-dihydrobenzo[f][1,2]thiazepin-2(3H)-yl)methyl)-4-(trifluoromethyl)phenyl)pentanoic acid (15 mg, 0.027 mmol, 63.0% yield) as a white solid. LC-MS m/z 565.4 (M+H)+, 1.11 min (ret. time).

Example 199

3-(3-(((R)-4-Ethyl-1,1-dioxido-3,4-dihydro-2H-pyrido[4,3-b][1,4,5]oxathiazepin-2-yl)methyl)-4-methylphenyl)-5-(1-ethyl-1H-1,2,3-triazol-4-yl)pentanoic acid

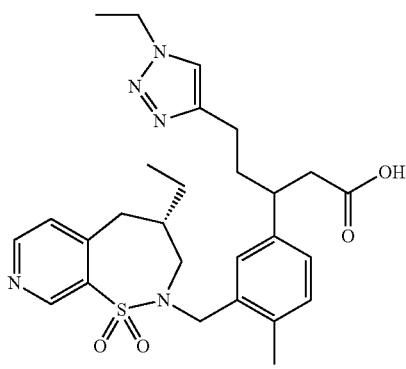 [SMILES: CC[C@H]1Cc2ccncc2S(=O)(=O)N(Cc2cc(C(CCc3cn(CC)nn3)CC(=O)O)ccc2C)C1]

Ethyl 5-(1-ethyl-1H-1,2,3-triazol-4-yl)-3-(3-(hydroxymethyl)-4-methylphenyl)pentanoate

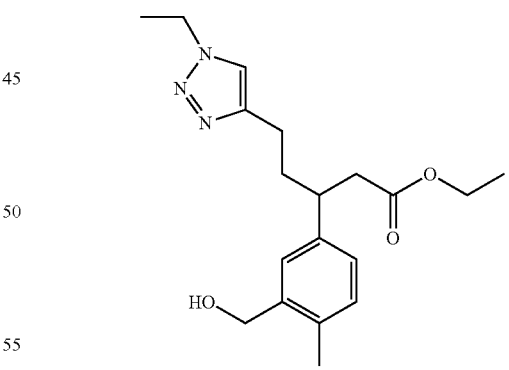

To a solution of (E)-ethyl 5-(1-ethyl-1H-1,2,3-triazol-4-yl)pent-2-enoate (700 mg, 3.14 mmol) and in 1,4-dioxane (10 mL) and water (6.67 mL) was added Et₃N (0.655 mL, 4.70 mmol), (2-methyl-5-(4,4,5,5-tetramethyl-1,3,2-dioxaborolan-2-yl)phenyl)methanol (817 mg, 3.29 mmol) and [RhCl(cod)]₂ (87 mg, 0.176 mmol). The reaction was heated to 95° C. and stirred for 2 h. The reaction was cooled and filtered through a pad of celite. The filtrate was concentrated in vacuo and purified via silica gel chromatography with DCM and MeOH to yield ethyl H-1,2,3-triazol-4-yl)-3-(3-

(hydroxymethyl)-4-methylphenyl)pentanoate (720 mg, 2.084 mmol, 66.5% yield) as a colorless oil. LC-MS m/z 346.1 (M+H)+, 0.83 min (ret. time).

Ethyl 3-(3-(((R)-4-ethyl-1,1-dioxido-3,4-dihydro-2H-pyrido[4,3-b][1,4,5]oxathiazepin-2-yl)methyl)-4-methylphenyl)-5-(1-ethyl-1H-1,2,3-triazol-4-yl)pentanoate

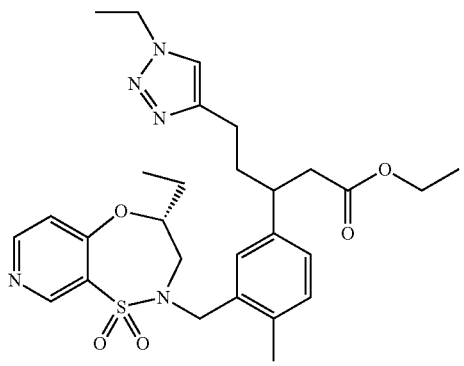 [SMILES: CCOC(=O)CC(CCc1cn(CC)nn1)c1ccc(C)c(CN2C[C@@H](CC)Oc3ccncc3S2(=O)=O)c1]

To a solution of ethyl 5-(1-ethyl-1H-1,2,3-triazol-4-yl)-3-(3-(hydroxymethyl)-4-methylphenyl)pentanoate (80 mg, 0.213 mmol), (R)-4-ethyl-3,4-dihydro-2H-pyrido[4,3-b][1,4,5]oxathiazepine 1,1-dioxide (51.1 mg, 0.224 mmol) and ADDP (323 mg, 1.278 mmol) in dry THF (5 mL) was added tributylphosphine (259 mg, 1.278 mmol) After 15 min the reaction became cloudy. The reaction was stirred for an additional 20 h and the reaction mixture was concentrated. The reaction mixture was redissolved in a minimal amount of MeOH and purified via reverse-phase HPLC CH₃CN/H₂O (neutral) to yield ethyl 3-(3-(((R)-4-ethyl-1,1-dioxido-3,4-dihydro-2H-pyrido[4,3-b][1,4,5]oxathiazepin-2-yl)methyl)-4-methylphenyl)-5-(1-ethyl-1H-1,2,3-triazol-4-yl)pentanoate (110 mg, 0.143 mmol, 66.9% yield) as a clear oil. LC-MS m/z 556.2 (M+H)+, 1.04 min (ret. time).

3-(3-(((R)-4-Ethyl-1,1-dioxido-3,4-dihydro-2H-pyrido[4,3-b][1,4,5]oxathiazepin-2-yl)methyl)-4-methylphenyl)-5-(1-ethyl-1H-1,2,3-triazol-4-yl)pentanoic acid

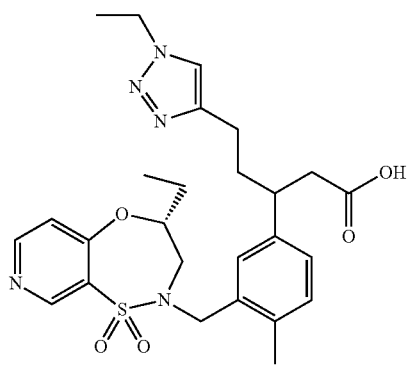 [SMILES: CC[C@@H]1CN(Cc2cc(C(CCc3cn(CC)nn3)CC(=O)O)ccc2C)S(=O)(=O)c2cnccc2O1]

To a solution of ethyl 3-(3-(((R)-4-ethyl-1,1-dioxido-3,4-dihydro-2H-pyrido[4,3-b][1,4,5]oxathiazepin-2-yl)methyl)-4-methylphenyl)-5-(1-ethyl-1H-1,2,3-triazol-4-yl)pentano-ate (100 mg, 0.180 mmol) in THF (3 mL) was added LiOH (43.1 mg, 1.800 mmol) and water (3.00 mL). The reaction was stirred at RT for 21 h. The reaction was almost complete after 5 h but it was continued overnight to ensure completion. The reaction was concentrated and purified via reverse-phase HPLC CH₃CN/H₂O (neutral) to yield 3-(3-(((R)-4-ethyl-1,1-dioxido-3,4-dihydro-2H-pyrido[4,3-b][1,4,5]oxathiazepin-2-yl)methyl)-4-methylphenyl)-5-(1-ethyl-1H-1,2,3-triazol-4-yl)pentanoic acid (54.1 mg, 0.103 mmol, 57.0% yield) as a white solid. LC-MS m/z 528.3 (M+H)+, 0.87 min (ret. time).

Example 200

3-(3-(((R)-4-Ethyl-1,1-dioxido-3,4-dihydro-2H-benzo[b][1,4,5]oxathiazepin-2-yl)methyl)-4-(trifluoromethyl)phenyl)-5-(1-ethyl-1H-1,2,3-triazol-4-yl)pentanoic acid

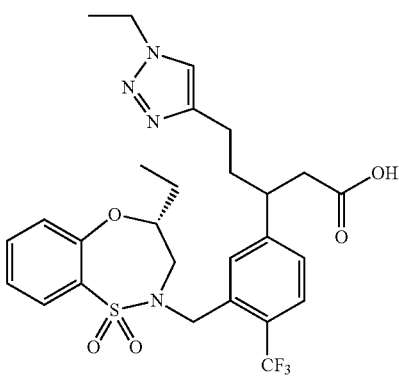 [SMILES: CC[C@@H]1CN(Cc2cc(C(CCc3cn(CC)nn3)CC(=O)O)ccc2C(F)(F)F)S(=O)(=O)c2ccccc2O1]

(5-(4,4,5,5-Tetramethyl-1,3,2-dioxaborolan-2-yl)-2-(trifluoromethyl)phenyl)methanol

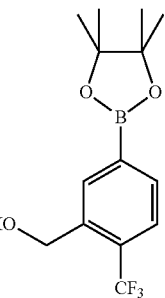

To a solution of (5-bromo-2-(trifluoromethyl)phenyl)methanol (0.870 g, 3.41 mmol) in 1,4-dioxane (13 mL) in a 20 mL microwave reaction vessel was added bis(pinacolato)diboron (1.040 g, 4.09 mmol) and potassium acetate (1.004 g, 10.23 mmol) The solution was degassed with nitrogen for 5 min and then PdCl₂(dppf) with DCM (0.167 g, 0.205 mmol) was added. The reaction was heated on the Biotage microwave reactor at 150° C. for 20 min. After 20 min the reaction turned black. The reaction was filtered through a pad of celite, concentrated and redissolved in EtOAc (50 mL). The reaction washed with water (4×20 mL), brine (20 mL) and dried over Mg₂SO₄. The residue was purified via silica gel chromatography with hexanes and EtOAc to yield (5-(4,4,5,5-tetramethyl-1,3,2-dioxaborolan-2-yl)-2-(trifluoromethyl)phenyl)methanol (800 mg, 2.383 mmol, 69.9% yield) as a clear oil. LC-MS m/z 303.1 (M+H)+, 1.07 min (ret. time).

Ethyl 5-(1-ethyl-1H-1,2,3-triazol-4-yl)-3-(3-(hydroxymethyl)-4-(trifluoromethyl)phenyl)pentanoate

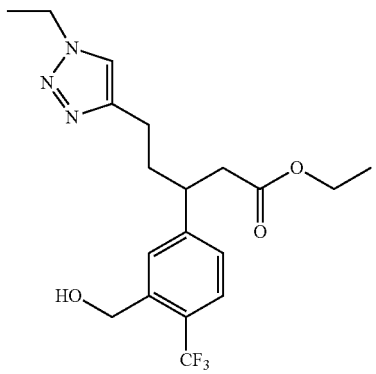 [SMILES: CCOC(=O)CC(CCc1cn(CC)nn1)c1ccc(C(F)(F)F)c(CO)c1]

To a solution of (E)-ethyl 5-(1-ethyl-1H-1,2,3-triazol-4-yl)pent-2-enoate (282 mg, 1.263 mmol) and in 1,4-dioxane (10 mL) and water (6.67 mL) was added Et$_3$N (0.264 mL, 1.895 mmol), (5-(4,4,5,5-tetramethyl-1,3,2-dioxaborolan-2-yl)-2-(trifluoromethyl)phenyl)methanol (401 mg, 1.326 mmol) and [RhCl(cod)]$_2$ (34.9 mg, 0.071 mmol). The reaction was heated to 95° C. and stirred for 2 h. The reaction was cooled and filtered through a pad of celite. The filtrate was concentrated in vacuo and purified via silica gel chromatography with DCM and MeOH to yield ethyl 5-(1-ethyl-1H-1,2,3-triazol-4-yl)-3-(3-(hydroxymethyl)-4-(trifluoromethyl)phenyl)pentanoate (314 mg, 0.377 mmol, 29.9% yield) as a colorless oil. LC-MS m/z 400.1 (M+H)+, 0.91 min (ret. time).

Ethyl 3-(3-(((R)-4-ethyl-1,1-dioxido-3,4-dihydro-2H-benzo[b][1,4,5]oxathiazepin-2-yl)methyl)-4-(trifluoromethyl)phenyl)-5-(1-ethyl-1H-1,2,3-triazol-4-yl)pentanoate

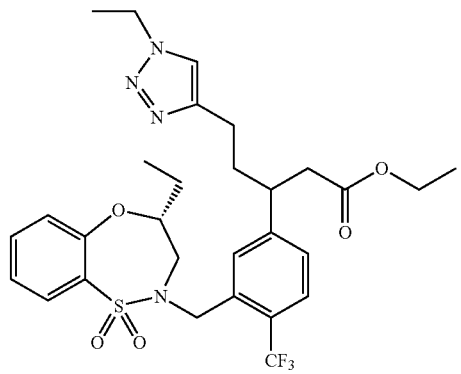 [SMILES: CCOC(=O)CC(CCc1cn(CC)nn1)c1ccc(C(F)(F)F)c(CN2C[C@@H](CC)Oc3ccccc3S2(=O)=O)c1]

To a solution of ethyl 5-(1-ethyl-1H-1,2,3-triazol-4-yl)-3-(3-(hydroxymethyl)-4-(trifluoromethyl)phenyl)pentanoate (80 mg, 0.100 mmol), (R)-4-ethyl-3,4-dihydro-2H-benzo[b][1,4,5]oxathiazepine 1,1-dioxide (23.90 mg, 0.105 mmol) and ADDP (152 mg, 0.601 mmol) in dry THF (3 mL) was added tributylphosphine (0.148 mL, 0.601 mmol). After 15 min the reaction became cloudy. The reaction was stirred for an additional 18 h. The reaction was then concentrated and redissolved in a minimal amount of MeOH and purified via reverse-phase HPLC CH$_3$CN/H$_2$O for purification to give ethyl 3-(3-(((R)-4-ethyl-1,1-dioxido-3,4-dihydro-2H-benzo[b][1,4,5]oxathiazepin-2-yl)methyl)-4-(trifluoromethyl)phenyl)-5-(1-ethyl-1H-1,2,3-triazol-4-yl)pentanoate (60 mg, 0.078 mmol, 78% yield) as a clear oil. LC-MS m/z 609.3 (M+H)+, 1.26 min (ret. time).

3-(3-(((R)-4-Ethyl-1,1-dioxido-3,4-dihydro-2H-benzo[b][1,4,5]oxathiazepin-2-yl)methyl)-4-(trifluoromethyl)phenyl)-5-(1-ethyl-1H-1,2,3-triazol-4-yl)pentanoic acid

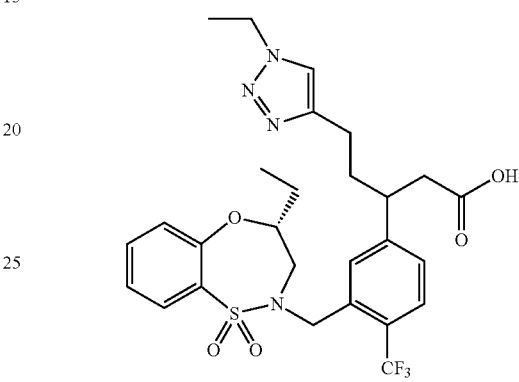

To a solution of ethyl 3-(3-(((R)-4-ethyl-1,1-dioxido-3,4-dihydro-2H-triazol-4-yl)pentanoate (50 mg, 0.065 mmol) in THF (3 mL) was added LiOH (15.54 mg, 0.649 mmol) and water (3.00 mL) The reaction was stirred at RT for 21 h. The reaction was almost complete after 5 h but it was continued overnight to ensure completion. The reaction was concentrated and purified via reverse-phase HPLC CH$_3$CN/H$_2$O (neutral) to yield 3-(3-(((R)-4-ethyl-1,1-dioxido-3,4-dihydro-2H-benzo[b][1,4,5]oxathiazepin-2-yl)methyl)-4-(trifluoromethyl)phenyl)-5-(1-ethyl-1H-1,2,3-triazol-4-yl)pentanoic acid (26 mg, 0.045 mmol, 69.0% yield) as a white solid. LC-MS m/z 581.3 (M+H)+, 1.08 min (ret. time).

Example 201

3-(4-methyl-3-(((R)-4-methyl-1,1-dioxido-3,4-dihydro-2H-benzo[b][1,4,5]oxathiazepin-2-yl)methyl)phenyl)-5-(1-propyl-1H-1,2,3-triazol-4-yl)pentanoic acid

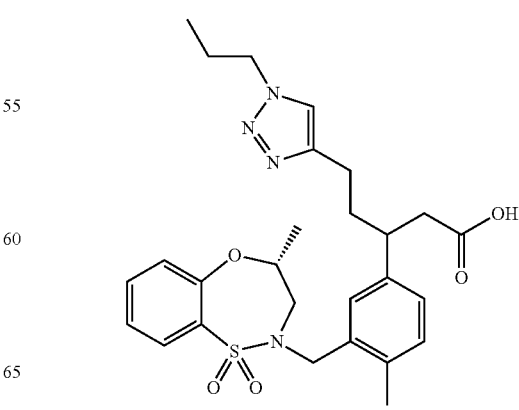

Ethyl 3-(4-methyl-3-(((R)-4-methyl-1,1-dioxido-3,4-dihydro-2H-benzo[b][1,4,5]oxathiazepin-2-yl)methyl)phenyl)-5-(1-propyl-1H-1,2,3-triazol-4-yl)pentanoate

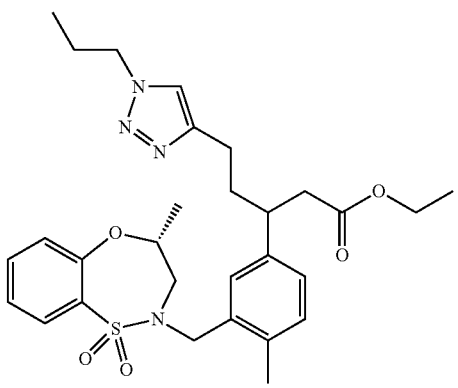 [SMILES: CCCn1cc(CCC(CC(=O)OCC)c2ccc(C)c(CN3C[C@@H](C)Oc4ccccc4S3(=O)=O)c2)nn1]

To a solution of (E)-ethyl 5-(1-propyl-1H-1,2,3-triazol-4-yl)pent-2-enoate (150 mg, 0.632 mmol) and in 1,4-dioxane (10 mL) and water (6.67 mL) was added Et$_3$N (0.132 mL, 0.948 mmol), (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (294 mg, 0.664 mmol) and [RhCl(cod)]$_2$ (17.45 mg, 0.035 mmol). The reaction was heated to 75° C. and stirred for 2 h. The reaction was cooled and filtered through a pad of celite. The filtrate was concentrated in vacuo and purified via reverse-phase HPLC CH$_3$CN/H$_2$O (0.1% TFA) to yield ethyl 3-(4-methyl-3-(((R)-4-methyl-1,1-dioxido-3,4-dihydro-2H-benzo[b][1,4,5]oxathiazepin-2-yl)methyl)phenyl)-5-(1-propyl-1H-1,2,3-triazol-4-yl)pentanoate (136 mg, 0.245 mmol, 38.8% yield) as a colorless oil. LC-MS m/z 555.4 (M+H)$^+$, 1.16 min (ret. time).

3-(4-methyl-3-(((R)-4-methyl-1,1-dioxido-3,4-dihydro-2H-benzo[b][1,4,5]oxathiazepin-2-yl)methyl)phenyl)-5-(1-propyl-1H-1,2,3-triazol-4-yl)pentanoic acid

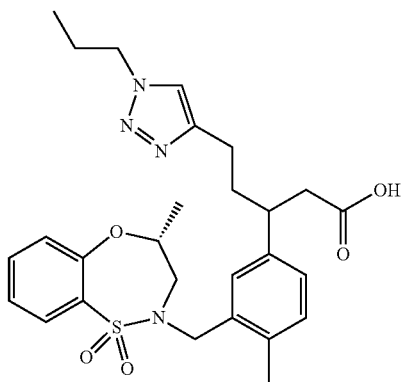 [SMILES: CCCn1cc(CCC(CC(=O)O)c2ccc(C)c(CN3C[C@@H](C)Oc4ccccc4S3(=O)=O)c2)nn1]

To a solution of ethyl 3-(4-methyl-3-(((R)-4-methyl-1,1-dioxido-3,4-dihydro-2H-benzo[b][1,4,5]oxathiazepin-2-yl)methyl)phenyl)-5-(1-propyl-1H-1,2,3-triazol-4-yl)pentanoate (139 mg, 0.251 mmol) in THF (3 mL) was added LiOH (60.0 mg, 2.506 mmol) and water (3.00 mL). The reaction was stirred at RT for 21 h. The reaction was almost complete after 5 h but it was continued overnight to ensure completion. The reaction was concentrated, dissolved in a minimal amount of DMSO and purified via reverse-phase HPLC CH$_3$CN/H$_2$O (neutral) to yield 3-(4-methyl-3-(((R)-4-methyl-1,1-dioxido-3,4-dihydro-2H-benzo[b][1,4,5]oxathiazepin-2-yl)methyl)phenyl)-5-(1-propyl-1H-1,2,3-triazol-4-yl)pentanoic acid (60 mg, 0.111 mmol, 44.1% yield) as a white solid. LC-MS m/z 527.2 (M+H)$^+$, 1.17 min (ret. time).

Example 202

3-(3-(((R)-4-Ethyl-1,1-dioxido-3,4-dihydro-2H-benzo[b][1,4,5]oxathiazepin-2-yl)methyl)-4-methylphenyl)-5-(1-propyl-1H-1,2,3-triazol-4-yl)pentanoic acid

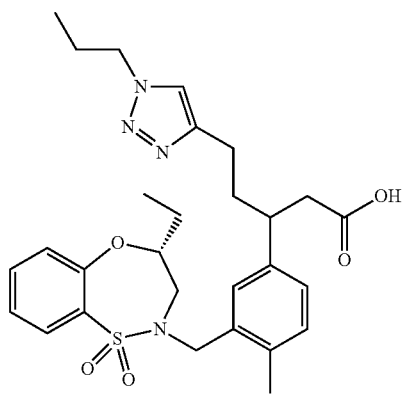 [SMILES: CCCn1cc(CCC(CC(=O)O)c2ccc(C)c(CN3C[C@@H](CC)Oc4ccccc4S3(=O)=O)c2)nn1]

Ethyl 3-(3-(((R)-4-ethyl-1,1-dioxido-3,4-dihydro-2H-benzo[b][1,4,5]oxathiazepin-2-yl)methyl)-4-methylphenyl)-5-(1-propyl-1H-1,2,3-triazol-4-yl)pentanoate

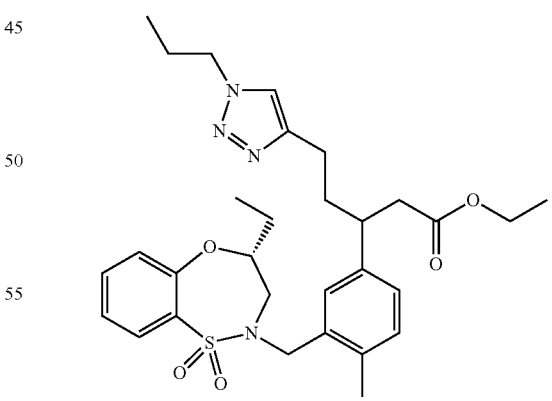

To a solution of (E)-ethyl 5-(1-propyl-1H-1,2,3-triazol-4-yl)pent-2-enoate (150 mg, 0.632 mmol) and in 1,4-dioxane (10 mL) and water (6.67 mL) was added Et$_3$N (0.132 mL, 0.948 mmol), (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (304 mg, 0.664 mmol) and [RhCl(cod)]$_2$ (17.45 mg, 0.035 mmol) The reaction was heated to 75° C. and stirred for 2 h. The reaction was cooled and filtered through a pad of celite. The filtrate was concentrated in vacuo and purified via reverse-phase HPLC CH₃CN/H₂O (0.1% TFA) to yield ethyl 3-(3-(((R)-4-ethyl-1,1-dioxido-3,4-dihydro-2H-benzo[b][1,4,5] oxathiazepin-2-yl)methyl)-4-methylphenyl)-5-(1-propyl-1H-1,2,3-triazol-4-yl)pentanoate (290 mg, 0.474 mmol, 75% yield) as a colorless oil. LC-MS m/z 569.2 (M+H)⁺, 1.24 min (ret. time).

3-(3-(((R)-4-Ethyl-1,1-dioxido-3,4-dihydro-2H-benzo[b][1,4,5]oxathiazepin-2-yl)methyl)-4-methylphenyl)-5-(1-propyl-1H-1,2,3-triazol-4-yl)pentanoic acid

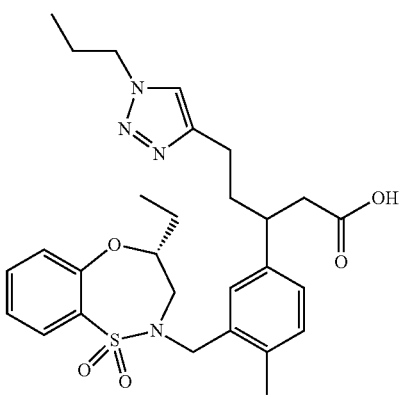 [SMILES: CCCn1cc(CCC(CC(=O)O)c2ccc(C)c(CN3C[C@@H](CC)Oc4ccccc4S3(=O)=O)c2)nn1]

To a solution of ethyl 3-(3-(((R)-4-ethyl-1,1-dioxido-3,4-dihydro-2H-benzo[b][1,4,5]oxathiazepin-2-yl)methyl)-4-methylphenyl)-5-(1-propyl-1H-1,2,3-triazol-4-yl)pentanoate (290 mg, 0.510 mmol) in THF (3 mL) was added LiOH (122 mg, 5.10 mmol) and water (3.00 mL) The reaction was stirred at RT for 21 h. The reaction was almost complete after 5 h but it was continued overnight to ensure completion. The reaction was concentrated and purified via reverse-phase HPLC CH₃CN/H₂O (neutral) to yield 3-(3-(((R)-4-ethyl-1,1-dioxido-3,4-dihydro-2H-benzo[b][1,4,5] oxathiazepin-2-yl)methyl)-4-methylphenyl)-5-(1-propyl-1H-1,2,3-triazol-4-yl)pentanoic acid (85 mg, 0.157 mmol, 30.8% yield) as a white solid. LC-MS m/z 541.2 (M+H)⁺, 1.19 min (ret. time).

Example 203

5-(1-Isopropyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid

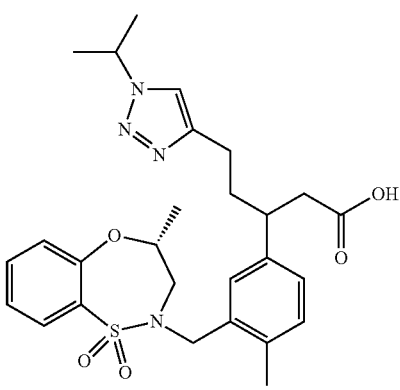 [SMILES: Cc1ccc(C(CCc2cn(C(C)C)nn2)CC(=O)O)cc1CN1C[C@@H](C)Oc2ccccc2S1(=O)=O]

Ethyl 5-(1-isopropyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl) pentanoate

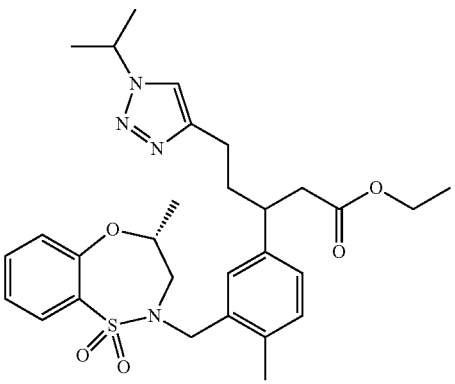 [SMILES: CCOC(=O)CC(CCc1cn(C(C)C)nn1)c1ccc(C)c(CN2C[C@@H](C)Oc3ccccc3S2(=O)=O)c1]

To a solution of (E)-ethyl 5-(1-isopropyl-1H-1,2,3-triazol-4-yl)pent-2-enoate (150 mg, 0.632 mmol) and in 1,4-dioxane (3 mL) and water (2.000 mL) was added Et₃N (0.132 mL, 0.948 mmol), (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (294 mg, 0.664 mmol) and [RhCl(cod)]₂ (17.45 mg, 0.035 mmol). The reaction was heated to 75° C. and stirred for 2 h. The reaction was cooled and filtered through a pad of celite. The filtrate was concentrated in vacuo and purified via silica gel chromatography with hexanes and EtOAc to yield ethyl 5-(1-isopropyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate (249 mg, 0.395 mmol, 62.5% yield) as a colorless oil. LC-MS m/z 555.2 (M+H)⁺, 1.18 min (ret. time).

5-(1-Isopropyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid

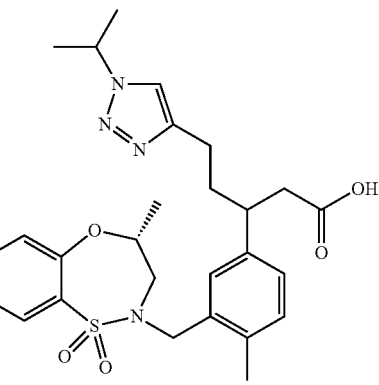

To a solution of ethyl 5-(1-isopropyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoate (245 mg, 0.442 mmol) in THF (3 mL) was added LiOH (106 mg, 4.42 mmol) and water (3.00 mL). The reaction was stirred at RT for 21 h. The reaction was concentrated, redissolved in a minimal amount of DMSO and purified via reverse-phase HPLC CH$_3$CN/H$_2$O (neutral) to yield 5-(1-isopropyl-1H-1,2,3-triazol-4-yl)-3-(4-methyl-3-(((R)-4-methyl-1,1-dioxido-3,4-dihydro-2H-benzo[b][1,4,5]oxathiazepin-2-yl)methyl)phenyl)pentanoic acid (150 mg, 0.285 mmol, 64.5% yield) as a white solid. LC-MS m/z 527.2 (M+H)$^+$, 1.01 min (ret. time).

Example 204

3-(3-(((R)-4-Ethyl-1,1-dioxido-3,4-dihydro-2H-benzo[b][1,4,5]oxathiazepin-2-yl)methyl)-4-methylphenyl)-5-(1-isopropyl-1H-1,2,3-triazol-4-yl)pentanoic acid

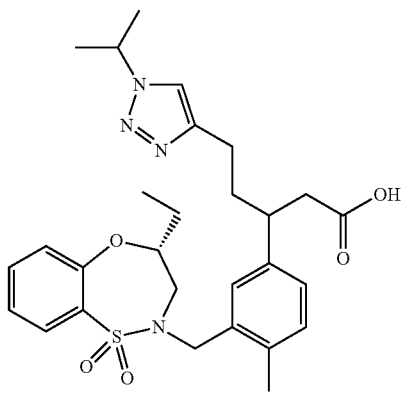 [SMILES: CC[C@@H]1CN(Cc2cc(C(CCc3cn(C(C)C)nn3)CC(=O)O)ccc2C)S(=O)(=O)c2ccccc2O1]

Ethyl 3-(3-(((R)-4-ethyl-1,1-dioxido-3,4-dihydro-2H-benzo[b][1,4,5]oxathiazepin-2-yl)methyl)-4-methylphenyl)-5-(1-isopropyl-1H-1,2,3-triazol-4-yl)pentanoate

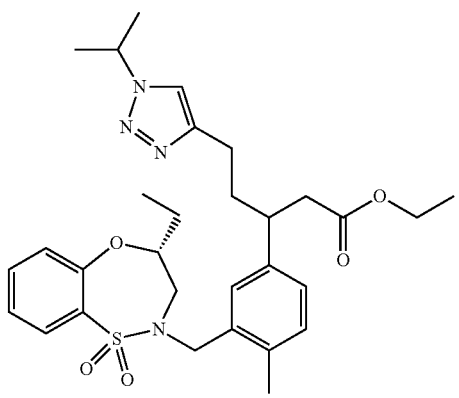 [SMILES: CCOC(=O)CC(CCc1cn(C(C)C)nn1)c1ccc(C)c(CN2C[C@@H](CC)Oc3ccccc3S2(=O)=O)c1]

To a solution of (E)-ethyl 5-(1-isopropyl-1H-1,2,3-triazol-4-yl)pent-2-enoate (150 mg, 0.632 mmol) and in 1,4-dioxane (3 mL) and water (2.000 mL) was added Et$_3$N (0.132 mL, 0.948 mmol), (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (304 mg, 0.664 mmol) and [RhCl(cod)]$_2$ (17.45 mg, 0.035 mmol). The reaction was heated to 75° C. and stirred for 2 h. The reaction was cooled and filtered through a pad of celite. The residue was purified via reverse-phase HPLC CH$_3$CN/H$_2$O (neutral) to yield ethyl 3-(3-(((R)-4-ethyl-1,1-dioxido-3,4-dihydro-2H-benzo[b][1,4,5]oxathiazepin-2-yl)methyl)-4-methylphenyl)-5-(1-isopropyl-1H-1,2,3-triazol-4-yl)pentanoate (225 mg, 0.380 mmol, 60.1% yield) as a colorless oil. LC-MS m/z 569.2 (M+H)$^+$, 1.23 min (ret. time).

3-(3-(((R)-4-Ethyl-1,1-dioxido-3,4-dihydro-2H-benzo[b][1,4,5]oxathiazepin-2-yl)methyl)-4-methylphenyl)-5-(1-isopropyl-1H-1,2,3-triazol-4-yl)pentanoic acid

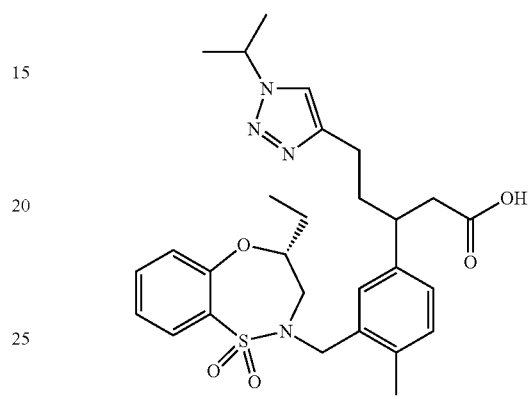

To a solution of ethyl 3-(3-(((R)-4-ethyl-1,1-dioxido-3,4-dihydro-2H-benzo[b][1,4,5]oxathiazepin-2-yl)methyl)-4-methylphenyl)-5-(1-isopropyl-1H-1,2,3-triazol-4-yl)pentanoate (225 mg, 0.396 mmol) in THF (3 mL) was added LiOH (95 mg, 3.96 mmol) and water (3.00 mL). The reaction was stirred at RT for 21 h. The reaction was concentrated, redissolved in a minimal amount of DMSO and purified via reverse-phase HPLC CH$_3$CN/H$_2$O (neutral) to yield 3-(3-(((R)-4-ethyl-1,1-dioxido-3,4-dihydro-2H-benzo[b][1,4,5]oxathiazepin-2-yl)methyl)-4-methylphenyl)-5-(1-isopropyl-1H-1,2,3-triazol-4-yl)pentanoic acid (125 mg, 0.231 mmol, 58.4% yield) as a white solid. LC-MS m/z 541.2 (M+H)$^+$, 1.06 min (ret. time).

Example 205

3-(3-(((R)-4-Ethyl-1,1-dioxido-3,4-dihydro-2H-pyrido[4,3-b][1,4,5]oxathiazepin-2-yl)methyl)-4-methylphenyl)-5-(1-propyl-1H-1,2,3-triazol-4-yl)pentanoic acid

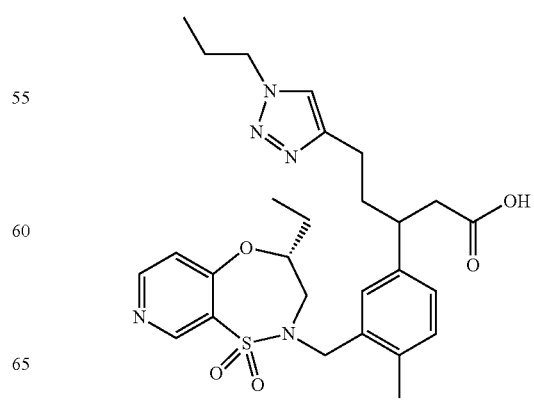

455

Ethyl 3-(3-(hydroxymethyl)-4-methylphenyl)-5-(1-propyl-1H-1,2,3-triazol-4-yl)pentanoate

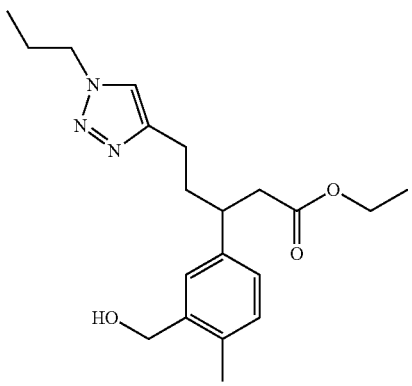 [SMILES: CCCn1cc(CCC(CC(=O)OCC)c2ccc(C)c(CO)c2)nn1]

To a solution of (E)-ethyl 5-(1-propyl-1H-1,2,3-triazol-4-yl)pent-2-enoate (200 mg, 0.843 mmol) and in 1,4-dioxane (10 mL) and water (6.67 mL) was added Et$_3$N (0.176 mL, 1.264 mmol) (2-methyl-5-(4,4,5,5-tetramethyl-1,3,2-dioxaborolan-2-yl)phenyl)methanol (220 mg, 0.885 mmol) and [RhCl(cod)]$_2$ (23.27 mg, 0.047 mmol) The reaction was heated to 75° C. and stirred for 2 h. The reaction was cooled and filtered through a pad of celite. The filtrate was concentrated in vacuo and purified via reverse-phase HPLC CH$_3$CN/H$_2$O (0.1% TFA) to yield ethyl 3-(3-(hydroxymethyl)-4-methylphenyl)-5-(1-propyl-1H-1,2,3-triazol-4-yl)pentanoate (200 mg, 0.406 mmol, 48.2% yield) as a colorless oil. LC-MS m/z 360.2 (M+H)$^+$, 0.89 min (ret. time).

Ethyl 3-(3-(((R)-4-ethyl-1,1-dioxido-3,4-dihydro-2H-pyrido[4,3-b][1,4,5]oxathiazepin-2-yl)methyl)-4-methylphenyl)-5-(1-propyl-1H-1,2,3-triazol-4-yl)pentanoate

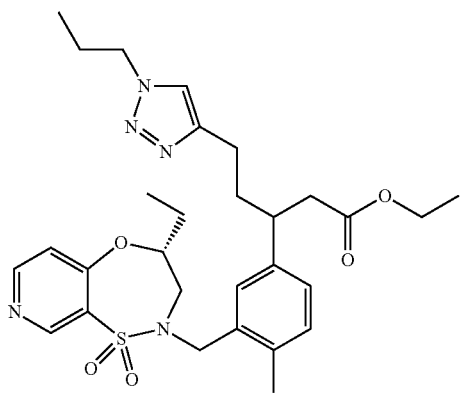 [SMILES: CCCn1cc(CCC(CC(=O)OCC)c2ccc(C)c(CN3C[C@@H](CC)Oc4ccncc4S3(=O)=O)c2)nn1]

To a solution of ethyl 3-(3-(hydroxymethyl)-4-methylphenyl)-5-(1-propyl-1H-1,2,3-triazol-4-yl)pentanoate (120 mg, 0.167 mmol) (R)-4-ethyl-3,4-dihydro-2H-pyrido[4,3-b][1,4,5]oxathiazepine 1,1-dioxide (40.0 mg, 0.175 mmol) and ADDP (253 mg, 1.001 mmol) in dry THF (3 mL) was added tributylphosphine (0.247 mL, 1.001 mmol) After 15 min the reaction became cloudy. The reaction was stirred for an additional 18 h. The reaction was then concentrated and redissolved in a minimal amount of DMSO and purified via reverse-phase HPLC CH$_3$CN/H$_2$O (0.1% TFA) to yield ethyl 3-(3-(((R)-4-ethyl-1,1-dioxido-3,4-dihydro-2H-pyrido[4,3-b][1,4,5]oxathiazepin-2-yl)methyl)-4-methylphenyl)-5-(1-propyl-1H-1,2,3-triazol-4-yl)pentanoate (75 mg, 0.104 mmol, 62.3% yield) as a clear oil. LC-MS m/z 570.4 (M+H)$^+$, 1.10 min (ret. time).

3-(3-(((R)-4-Ethyl-1,1-dioxido-3,4-dihydro-2H-pyrido[4,3-b][1,4,5]oxathiazepin-2-yl)methyl)-4-methylphenyl)-5-(1-propyl-1H-1,2,3-triazol-4-yl)pentanoic acid

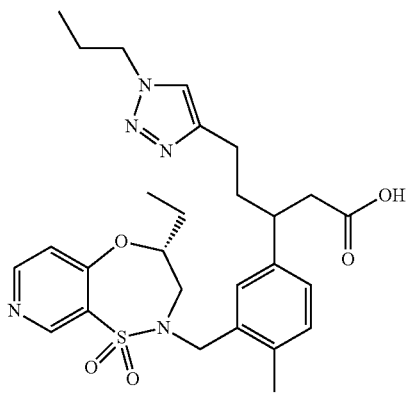 [SMILES: CCCn1cc(CCC(CC(=O)O)c2ccc(C)c(CN3C[C@@H](CC)Oc4ccncc4S3(=O)=O)c2)nn1]

To a solution of ethyl 3-(3-(((R)-4-ethyl-1,1-dioxido-3,4-dihydro-2H-pyrido[4,3-b][1,4,5]oxathiazepin-2-yl)methyl)-4-methylphenyl)-5-(1-propyl-1H-1,2,3-triazol-4-yl)pentanoate (58 mg, 0.102 mmol) in THF (2.000 mL) was added LiOH (7.31 mg, 0.305 mmol) and water (2 mL). The reaction was stirred at RT for 21 h. The reaction was concentrated, dissolved in a minimal amount of DMSO and purified via reverse-phase HPLC CH$_3$CN/H$_2$O (neutral) to yield 3-(3-(((R)-4-ethyl-1,1-dioxido-3,4-dihydro-2H-pyrido[4,3-b][1,4,5]oxathiazepin-2-yl)methyl)-4-methylphenyl)-5-(1-propyl-1H-1,2,3-triazol-4-yl)pentanoic acid (28 mg, 0.052 mmol, 50.8% yield) as a white solid. LC-MS m/z 542.2 (M+H)$^+$, 0.95 min (ret. time).

Example 206

3-(3-(((R)-4-Ethyl-1,1-dioxido-3,4-dihydro-2H-pyrido[4,3-b][1,4,5]oxathiazepin-2-yl)methyl)-4-methylphenyl)-5-(1-isopropyl-1H-1,2,3-triazol-4-yl)pentanoic acid

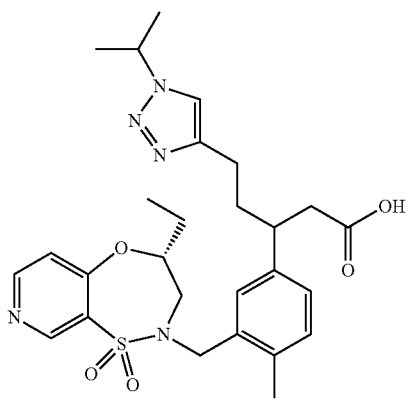 [SMILES: CC[C@@H]1CN(Cc2cc(C(CCc3cn(C(C)C)nn3)CC(=O)O)ccc2C)S(=O)(=O)c2cnccc2O1]

Ethyl 3-(3-(hydroxymethyl)-4-methylphenyl)-5-(1-isopropyl-1H-1,2,3-triazol-4-yl)pentanoate

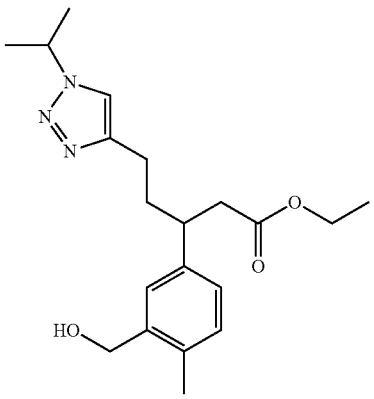 [SMILES: CCOC(=O)CC(CCc1cn(C(C)C)nn1)c1ccc(C)c(CO)c1]

To a solution of (E)-ethyl 5-(1-isopropyl-1H-1,2,3-triazol-4-yl)pent-2-enoate (200 mg, 0.843 mmol) in 1,4-dioxane (10 mL) and water (6.67 mL) was added Et$_3$N (128 mg, 1.264 mmol) (2-methyl-5-(4,4,5,5-tetramethyl-1,3,2-dioxaborolan-2-yl)phenyl)methanol (220 mg, 0.885 mmol) and [RhCl(cod)]$_2$ (23.27 mg, 0.047 mmol) The reaction was heated to 75° C. and stirred for 2 h. The reaction was cooled and filtered through a pad of celite. The filtrate was concentrated in vacuo and purified via reverse-phase HPLC CH$_3$CN/H$_2$O (neutral) to yield ethyl 3-(3-(hydroxymethyl)-4-methylphenyl)-5-(1-isopropyl-1H-1,2,3-triazol-4-yl)pentanoate (195 mg, 0.505 mmol, 59.9% yield) as a yellow oil. LC-MS m/z 360.1 (M+H)$^+$, 0.86 min (ret. time).

Ethyl 3-(3-(((R)-4-ethyl-1,1-dioxido-3,4-dihydro-2H-pyrido[4,3-b][1,4,5]oxathiazepin-2-yl)methyl)-4-methylphenyl)-5-(1-isopropyl-1H-1,2,3-triazol-4-yl)pentanoate

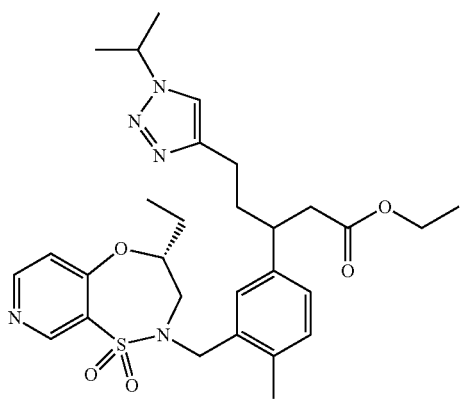 [SMILES: CCOC(=O)CC(CCc1cn(C(C)C)nn1)c1ccc(C)c(CN2C[C@@H](CC)Oc3ccncc3S2(=O)=O)c1]

To a solution of ethyl 3-(3-(hydroxymethyl)-4-methylphenyl)-5-(1-isopropyl-1H-1,2,3-triazol-4-yl)pentanoate (190 mg, 0.529 mmol) (R)-4-ethyl-3,4-dihydro-2H-pyrido[4,3-b][1,4,5]oxathiazepine 1,1-dioxide (127 mg, 0.555 mmol) and ADDP (533 mg, 2.114 mmol) in dry THF (5 mL) was added tributylphosphine (0.522 mL, 2.114 mmol) After 15 min the reaction became cloudy. The reaction was stirred for an additional 18 h. The reaction was then concentrated and redissolved in a minimal amount of DMSO and purified via reverse-phase HPLC CH$_3$CN/H$_2$O (neutral) for purification to give ethyl 3-(3-(((R)-4-ethyl-1,1-dioxido-3,4-dihydro-2H-pyrido[4,3-b][1,4,5]oxathiazepin-2-yl)methyl)-4-methylphenyl)-5-(1-isopropyl-1H-1,2,3-triazol-4-yl)pentanoate as a clear oil. LC-MS m/z 570.3 (M+H)$^+$, 1.07 min (ret. time).

3-(3-(((R)-4-Ethyl-1,1-dioxido-3,4-dihydro-2H-pyrido[4,3-b][1,4,5]oxathiazepin-2-yl)methyl)-4-methylphenyl)-5-(1-isopropyl-1H-1,2,3-triazol-4-yl)pentanoic acid

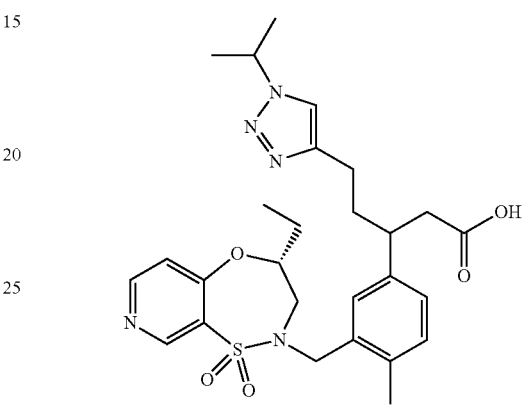

To a solution of ethyl 3-(3-(((R)-4-ethyl-1,1-dioxido-3,4-dihydro-2H-pyrido[4,3-b][1,4,5]oxathiazepin-2-yl)methyl)-4-methylphenyl)-5-(1-isopropyl-1H-1,2,3-triazol-4-yl)pentanoate (290 mg, 0.509 mmol) in THF (2.000 mL) was added LiOH (36.6 mg, 1.527 mmol) and water (2 mL) The reaction was stirred at RT for 21 h. The reaction was concentrated, redissolved in a minimal amount of DMSO and purified via reverse-phase HPLC CH$_3$CN/H$_2$O (neutral) to yield 3-(3-(((R)-4-ethyl-1,1-dioxido-3,4-dihydro-2H-pyrido[4,3-b][1,4,5]oxathiazepin-2-yl)methyl)-4-methylphenyl)-5-(1-isopropyl-1H-1,2,3-triazol-4-yl)pentanoic acid (160 mg, 0.295 mmol, 58.0% yield) as a white solid. LC-MS m/z 542.2 (M+H)$^+$, 0.92 min (ret. time).

Example 207

3-(3-(((R)-4-Ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)hexanoic acid (peak 1)

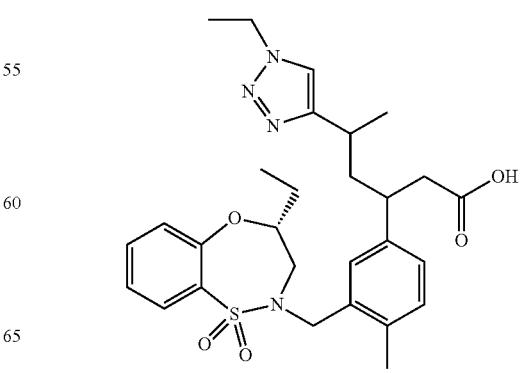

(E)-Ethyl 5-methyl-7-(triisopropylsilyl)hept-2-en-6-ynoate

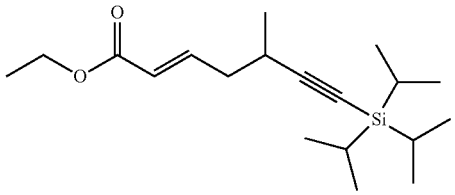 [SMILES: CCOC(=O)/C=C/CC(C)C#C[Si](C(C)C)(C(C)C)C(C)C]

A mixture of cobalt(II)acetate tetrahydrate (0.178 g, 0.713 mmol), 1,2-bis(diphenylphosphino)ethane (0.284 g, 0.713 mmol), and zinc (0.093 g, 1.427 mmol) in dimethyl sulfoxide (DMSO) (3.6 mL) and tert-butanol (3.60 mL) was stirred at RT for 15 min (the reaction turned a pastel purple color). To the mixture was added α,β,γ,δ-unsaturated ester (2E,4E)-ethyl hexa-2,4-dienoate (0.523 mL, 3.57 mmol) and triisopropylsilyl acetylene (1.600 mL, 7.13 mmol) and stirred at 80° C. for 20 h (the reaction turned black). The mixture was passed through a short column of silica gel (2 g) with Et$_2$O as eluent. The organic layer was concentrated and the residue was purified via silica gel chromatography with hexanes and EtOAc to yield (E)-ethyl 5-methyl-7-(triisopropylsilyl)hept-2-en-6-ynoate (350 mg, 1.074 mmol, 30.1% yield) as a clear oil. LC-MS m/z 323.2 (M+H)$^+$, 1.71 min (ret. time).

(E)-Ethyl 5-methylhept-2-en-6-ynoate

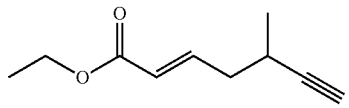

To a solution of (E)-ethyl 5-methyl-7-(triisopropylsilyl)hept-2-en-6-ynoate (190 mg, 0.300 mmol) in THF (20 mL) was added dropwise TBAF (0.300 mL, 0.300 mmol) at RT. The reaction was allowed to stir for 1 h. The reaction was concentrated then redissolved in DCM (10 mL) and water (10 mL). The layers separated, dried over Na$_2$SO$_4$ and concentrated. The compound was taken to the next step without further purification. NMR shows product as well as leftover TBAF. $^1$H NMR (400 MHz, CHLOROFORM-d) δ ppm 0.97-1.16 (m, 29H) 1.20-1.38 (m, 9H) 1.41-1.55 (m, 1H) 1.60-1.78 (m, 1H) 2.12 (s, 1H) 2.39 (d, J=2.51 Hz, 2H) 2.56-2.72 (m, 1H) 3.22-3.41 (m, 1H) 4.22 (d, J=7.28 Hz, 3H) 5.85-5.99 (m, 1H) 6.92-7.07 (m, 1H)

(E)-Ethyl 5-(1-ethyl-1H-1,2,3-triazol-4-yl)hex-2-enoate

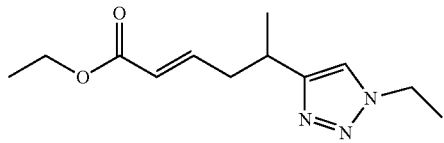 [SMILES: CCOC(=O)/C=C/CC(C)c1cn(CC)nn1]

To a solution of (E)-ethyl 5-methylhept-2-en-6-ynoate (950 mg, 5.72 mmol) in tert-butanol (10.00 mL), water (10 mL), was added NaN$_3$ (557 mg, 8.57 mmol), and iodoethane (0.686 mL, 8.57 mmol). The solution was allowed to stir for 30 min and then copper(II) sulfate (365 mg, 2.286 mmol) and sodium ascorbate (453 mg, 2.286 mmol) were added. This was stirred for 18 h at RT, with a vent and in the absence of light. The reaction was continued for an additional 24 h and concentrated. The residue was redissolved in a minimal amount of DMSO and purified via reverse-phase HPLC CH$_3$CN/H$_2$O (neutral) to yield (E)-ethyl 5-(1-ethyl-1H-1,2,3-triazol-4-yl)hex-2-enoate (650 mg, 2.137 mmol, 37.4% yield) as a clear oil. LC-MS m/z 237.9 (M+H)$^+$, 0.74 min (ret. time).

Ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)hexanoate

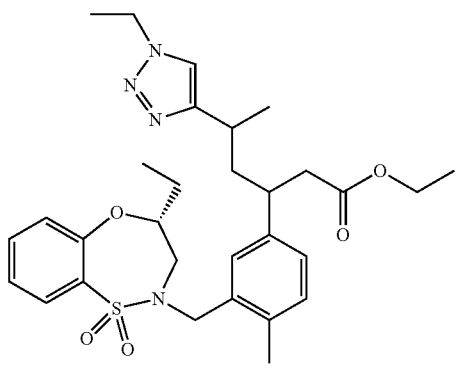 [SMILES: CCOC(=O)CC(CC(C)c1cn(CC)nn1)c1ccc(C)c(CN2C[C@@H](CC)Oc3ccccc3S2(=O)=O)c1]

To a solution of (E)-ethyl 5-(1-ethyl-1H-1,2,3-triazol-4-yl)hex-2-enoate (88 mg, 0.371 mmol) in 1,4-dioxane (3.00 mL) and water (2 mL) was added Et$_3$N (0.078 mL, 0.556 mmol), (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (178 mg, 0.389 mmol) and [RhCl(cod)]$_2$ (10.24 mg, 0.021 mmol) The reaction was heated to 75° C. and stirred for 2 h. The reaction was cooled and filtered through a pad of celite. The filtrate was concentrated in vacuo and purified via reverse-phase HPLC CH$_3$CN/H$_2$O (0.1% TFA) to yield ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)hexanoate (22.1 mg, 0.039 mmol, 10.48% yield) LC-MS m/z 569.2 (M+H)$^+$, 1.24 min (ret. time) and ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)hexanoate (27.2 mg, 0.039 mmol, 12.90% yield) LC-MS m/z 569.2 (M+H)$^+$, 1.26 min (ret. time) as colorless oils. The two peaks were separated on the reverse-phase HPLC and carried on separately.

461

3-(3-(((R)-4-Ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)hexanoic acid

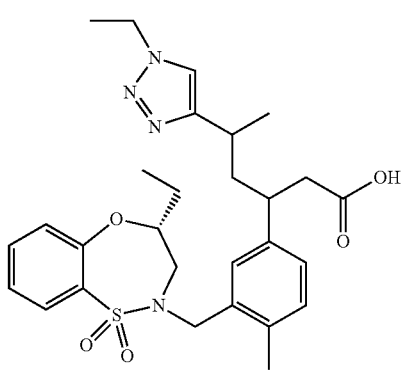

To a stirred solution of ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)hexanoate (22.7 mg, 0.040 mmol) in THF (1 mL) and water (1.000 mL) was added LiOH (2.87 mg, 0.120 mmol) The reaction was allowed to stir for 18 h and quenched with a minimal amount of 1 N HCl (0.5 mL). The sample was purified via reverse-phase HPLC CH$_3$CN/H$_2$O (0.1% TFA) to yield 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)hexanoic acid (14.3 mg, 0.026 mmol, 66.3% yield) as a white solid. LC-MS m/z 541.2 (M+H)$^+$, 1.07 min (ret. time).

Example 208

3-(3-(((R)-4-Ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)hexanoic acid (Isomer M1 and Isomer N1)

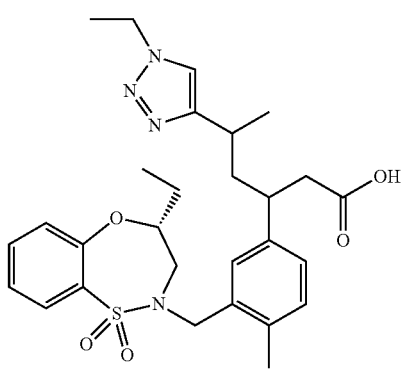

Isomer M1

462

-continued

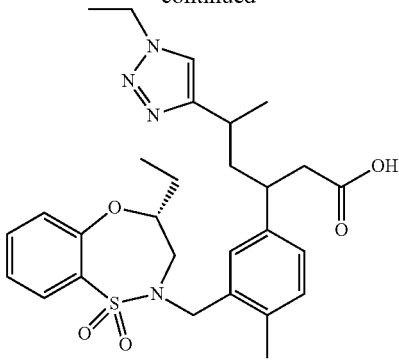

Isomer N1

3-(3-(((R)-4-Ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)hexanoic acid (Isomer M1 and Isomer N1)

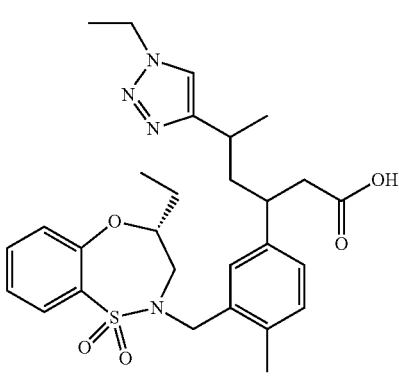 [SMILES: CC[C@@H]1CN(Cc2cc(C(CC(=O)O)CC(C)c3cn(CC)nn3)ccc2C)S(=O)(=O)c2ccccc2O1]

Isomer M1

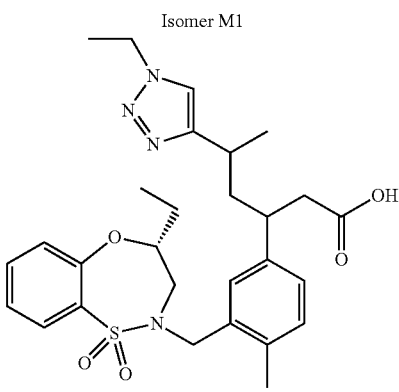

Isomer N1

To a solution of ethyl 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)hexanoate (27.2 mg, 0.048 mmol) in THF (1 mL) and water (1.000 mL) was added LiOH (3.44 mg, 0.143 mmol). The reaction was allowed to stir for 18 h and the reaction was quenched with a minimal amount of 1 N HCl (0.5 mL). The sample was purified via reverse-phase HPLC CH$_3$CN/H$_2$O (0.1% TFA) to yield 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)hexanoic acid (5.5 mg, 10.17 µmol, 21.27% yield) and 3-(3-(((R)-4-ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)hexanoic acid (10.8 mg, 0.020 mmol, 41.8% yield) as white solids. LC-MS m/z 541.2 (M+H)+, 1.10 min (ret. time) and LC-MS m/z 541.2 (M+H)+, 1.10 min (ret. time) respectively.

Example 209

3-(1,4-Dimethyl-1H-benzo[d][1,2,3]triazol-5-yl)-3-(3-((1,1-dioxido-4,5-dihydrobenzo[f][1,2]thiazepin-2(3H)-yl)methyl)-4-methylphenyl)propanoic acid

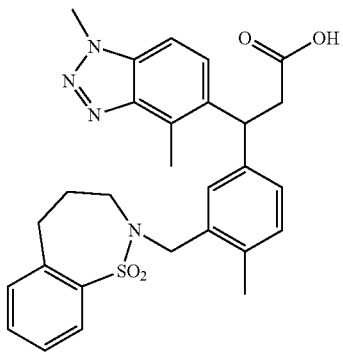 [SMILES: Cc1ccc(C(CC(=O)O)c2ccc3c(nnn3C)c2C)cc1CN1CCCc2ccccc2S1(=O)=O]

N-Allyl-2-bromobenzenesulfonamide

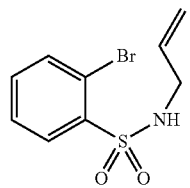

To a solution of 2-bromobenzene-1-sulfonyl chloride (5 g, 19.6 mmol) in DCM (100 mL) was added TEA (5.5 mL, 39.2 mmol) at 0° C. After 10 min, allylamine (1.3 g, 21.5 mmol) was added and stirred at RT overnight. The reaction mixture was diluted with water (70 mL) and extracted with DCM (2×75 mL). The combined organic layer washed with brine, dried over anhydrous Na2SO4, filtered and concentrated to give the title compound (3.5 g, 65%) as solid. LC-MS m/z 274.01 (M)+, 1.888 min (ret. time)

2,3,4,5-Tetrahydrobenzo[f][1,2]thiazepine 1,1-dioxide

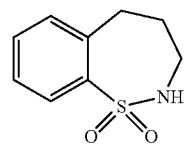 [SMILES: O=S1(=O)NCCCc2ccccc21]

To a solution of N-allyl-2-bromobenzenesulfonamide (4.0 g, 14.5 mmol) in toluene (40 mL) was added AlBN (0.47 g, 2.9 mmol) at RT. The reaction mixture was heated to 75° C., then Bu3SnH (4.65 g, 15.9 mmol) was added at 75° C. The reaction mixture was heated to 110° C. after addition for 5 h. The reaction mixture was concentrated and purified by silica gel chromatography (15% EtOAc in hexane) to give the title compound (560 mg, 22%). LC-MS m/z 198.04 (M+H)+, 1.644 min (ret. time)

Ethyl 3-(1,4-dimethyl-1H-benzo[d][1,2,3]triazol-5-yl)-3-(3-((1,1-dioxido-4,5-dihydrobenzo[f][1,2]thiazepin-2(3H)-yl)methyl)-4-methylphenyl)propanoate

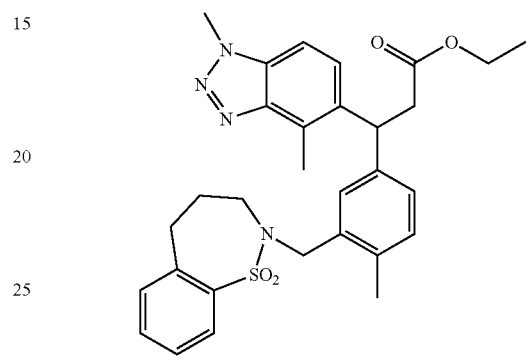

To a solution of ethyl 3-(1,4-dimethyl-1H-benzo[d][1,2,3]triazol-5-yl)-3-(3-(hydroxymethyl)-4-methylphenyl)propanoate (80 mg, 0.218 mmol), 2,3,4,5-tetrahydrobenzo[f][1,2]thiazepine 1,1-dioxide (45.1 mg, 0.229 mmol), and 1,1'-(azodicarbonyl)dipiperidine (110 mg, 0.435 mmol) in THF (10 mL) at RT was added tri-n-butylphosphine (0.107 mL, 0.435 mmol). The reaction mixture was stirred at RT for 20 h. The solvent was removed and the crude product purified on silica gel chromatography. The desired fractions were concentrated under reduced pressure to give the title compound (100 mg, 0.178 mmol, 82% yield) as oil. LC-MS m/z 547.4 (M+H)+, 1.18 min (ret. time)

3-(1,4-Dimethyl-1H-benzo[d][1,2,3]triazol-5-yl)-3-(3-((1,1-dioxido-4,5-dihydrobenzo[f][1,2]thiazepin-2(3H)-yl)methyl)-4-methylphenyl)propanoic acid

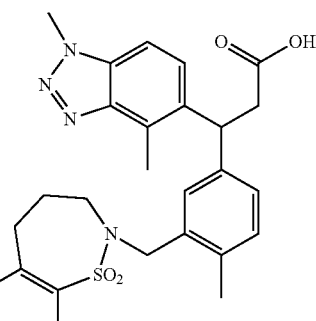

To a solution of ethyl 3-(1,4-dimethyl-1H-benzo[d][1,2,3]triazol-5-yl)-3-(3-((1,1-dioxido-4,5-dihydrobenzo[f][1,2]thiazepin-2(3H)-yl)methyl)-4-methylphenyl)propanoate (101 mg, 0.185 mmol), ethyl 3-(1,4-dimethyl-1H-benzo[d][1,2,3]triazol-5-yl)-3-(4-methyl-3-((4-methyl-1,1-dioxido- 4,5-dihydrobenzo[f][1,2]thiazepin-2(3H)-yl)methyl)phenyl)propanoate (100 mg, 0.178 mmol) in MeOH (2 mL) at RT was added 2 M LiOH (0.554 mL, 1.109 mmol). The reaction mixture was heated in a Biotage microwave at high absorption for 30 min at 85° C. 1N HCl (1.109 mL, 1.109 mmol) and 1 mL of DMSO were added and concentrated. The reaction mixture was purified with reverse-phase HPLC under acidic conditions to give the title compound (82.2 mg, 0.154 mmol, 84% yield). LC-MS m/z 519.2 (M+H)+, 1.05 min (ret. time)

2-Bromo-N-(2-methylallyl)benzenesulfonamide

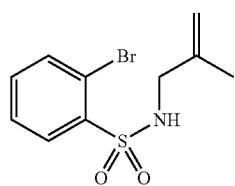

To a solution of 2-bromobenzene-1-sulfonyl chloride (5 g, 19.6 mmol) in DCM (100 mL) was added TEA (5.5 mL, 39.2 mmol) at 0° C. After 10 min, 2-methyl allylamine (1.3 g, 21.5 mmol) was added at 0° C., then stirred at RT overnight. The reaction mixture was diluted with water (100 mL) and extracted with DCM (2×100 mL). The combined organic layer washed with brine, dried over anhydrous Na₂SO₄, filtered and concentrated to give the title compound (3.5 g, 62%) as solid. LC-MS m/z 287.99 (M)+, 1.993 min (ret. time)

4-Methyl-2,3,4,5-tetrahydrobenzo[f][1,2]thiazepine 1,1-dioxide

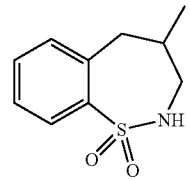

To a solution of N-(2-methylallyl)benzenesulfonamide (4.0 g, 13.8 mmol) in toluene (40 mL) was added AIBN (0.45 g, 2.76 mmol) at RT. The reaction mixture was heated to 75° C., then Bu₃SnH (4.4 g, 15.2 mmol) was added at 75° C. The reaction mixture was heated to 110° C. for 5 h. The reaction mixture was concentrated and purified by silica gel chromatography (15% EtOAc in hexane) to give the title compound (660 mg, 26.4%). LC-MS m/z 211.02 (M+H)+, 1.782 min (ret. time)

The compounds listed in the table below were prepared in a similar manner as above

| Reagent | Product Name | Product Structure | (M + H)+ | Ret. Time (min) | Comment |
|---------|--------------|-------------------|----------|-----------------|---------|
| MeO-phenyl-Br-SO₂Cl | 7-Methoxy-4-methyl-2,3,4,5-tetrahydrobenzo[f][1,2]thiazepine 1,1-dioxide | | 242.19 | 1.844 | |
| F-phenyl-Br-SO₂Cl | 7-Fluoro-4-methyl-2,3,4,5-tetrahydrobenzo[f][1,2]thiazepine 1,1-dioxide | | 228.0 | 1.75 | (M − H)+ |
| F₃C-phenyl-Br-SO₂Cl | 4-Methyl-7-(trifluoromethyl)-2,3,4,5-tetrahydrobenzo[f][1,2]thiazepine 1,1-dioxide | | 278.0 | 1.871 | (M − H)+ |
| F₃CO-phenyl-Br-SO₂Cl | 4-Methyl-7-(trifluoromethoxy)-2,3,4,5-tetrahydrobenzo[f][1,2]thiazepine 1,1-dioxide | | 296.0 | 1.897 | |

-continued

| Reagent | Product Name | Product Structure | (M + H)⁺ | Ret. Time (min) | Comment |
|---|---|---|---|---|---|
| 2-bromo-5-fluorobenzenesulfonyl chloride | 8-Fluoro-4-methyl-2,3,4,5-tetrahydrobenzo[f][1,2]thiazepine 1,1-dioxide | | 229.98 | 2.106 | |
| 2,4-dibromobenzenesulfonyl chloride | 7-Bromo-4-methyl-2,3,4,5-tetrahydrobenzo[f][1,2]thiazepine 1,1-dioxide | | 290.11 | 2.222 | M⁺ |
| 2,5-dibromobenzenesulfonyl chloride | 8-Bromo-4-methyl-2,3,4,5-tetrahydrobenzo[f][1,2]thiazepine 1,1-dioxide | | 290.02 | 2.167 | M |
| 2-bromo-5-(trifluoromethyl)benzenesulfonyl chloride | 4-Methyl-8-(trifluoromethyl)-2,3,4,5-tetrahydrobenzo[f][1,2]thiazepine 1,1-dioxide | | 278.08 | 3.488 | |
| 2-chloropyridine-3-sulfonyl chloride | 4-Methyl-2,3,4,5-tetrahydropyrido[2,3-f][1,2]thiazepine 1,1-dioxide | | 213.04 | 1.346 | |
| 4-chloropyridine-3-sulfonyl chloride | 4-Methyl-2,3,4,5-tetrahydropyrido[4,3-f][1,2]thiazepine 1,1-dioxide | | 213.16 | 2.494 | |

Example 210

3-(1,4-Dimethyl-1H-benzo[d][1,2,3]triazol-5-yl)-3-(4-methyl-3-((4-methyl-1,1-dioxido-4,5-dihydrobenzo[f][1,2]thiazepin-2(3H)-yl)methyl)phenyl)propanoic acid

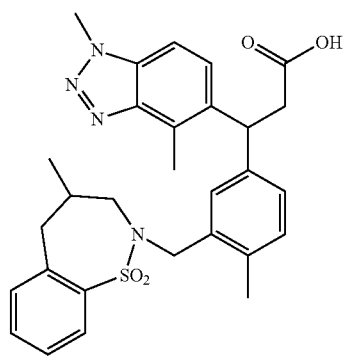 [SMILES: Cc1ccc(C(CC(=O)O)c2ccc3c(nnn3C)c2C)cc1CN1CC(C)Cc2ccccc2S1(=O)=O]

Ethyl 3-(1,4-dimethyl-1H-benzo[d][1,2,3]triazol-5-yl)-3-(4-methyl-3-((4-methyl-1,1-dioxido-4,5-dihydrobenzo[f][1,2]thiazepin-2(3H)-yl)methyl)phenyl)propanoate

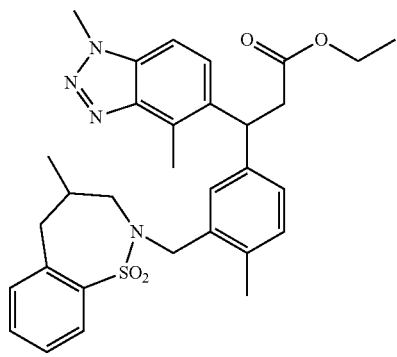 [SMILES: CCOC(=O)CC(c1ccc(C)c(CN2CC(C)Cc3ccccc3S2(=O)=O)c1)c1ccc2c(nnn2C)c1C]

To a solution of ethyl 3-(1,4-dimethyl-1H-benzo[d][1,2,3]triazol-5-yl)-3-(3-(hydroxymethyl)-4-methylphenyl)propanoate (80 mg, 0.218 mmol), 4-methyl-2,3,4,5-tetrahydrobenzo[f][1,2]thiazepine 1,1-dioxide (46.0 mg, 0.218 mmol) and 1,1'-(azodicarbonyl)dipiperidine (110 mg, 0.435 mmol) in THF (10 mL) at RT was added tri-n-butylphosphine (0.107 mL, 0.435 mmol). The reaction mixture was stirred at RT for 20 h. The solvent was removed and the crude product purified by silica gel chromatography (product came out at 50% EtOAc in hexane). The desired fractions were concentrated under reduced pressure to give the title compound (100 mg, 0.178 mmol, 82% yield) as oil. LC-MS m/z 561.1 (M+H)$^+$, 1.24 min (ret. time)

3-(1,4-Dimethyl-1H-benzo[d][1,2,3]triazol-5-yl)-3-(4-methyl-3-((4-methyl-1,1-dioxido-4,5-dihydrobenzo[f][1,2]thiazepin-2(3H)-yl)methyl)phenyl)propanoic acid

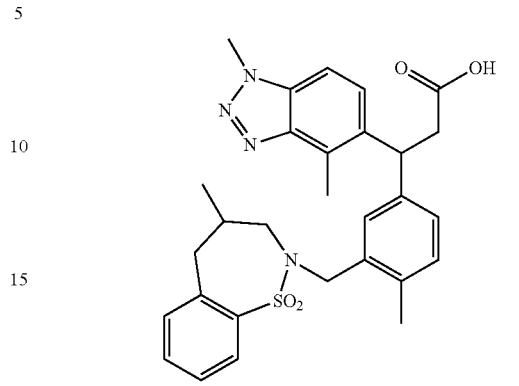

To a solution of ethyl 3-(1,4-dimethyl-1H-benzo[d][1,2,3]triazol-5-yl)-3-(4-methyl-3-((4-methyl-1,1-dioxido-4,5-dihydrobenzo[f][1,2]thiazepin-2(3H)-yl)methyl)phenyl)propanoate (100 mg, 0.178 mmol) in MeOH (2 mL) at RT was added 2 M LiOH (0.549 mL, 1.098 mmol). The reaction mixture was heated in a Biotage microwave at high absorption for 30 min at 85° C. 1N HCl (1.109 mL, 1.109 mmol) and 1 mL of DMSO were added and concentrated. The reaction mixture was purified with reverse-phase HPLC under acidic conditions to give the title compound (82.2 mg, 0.154 mmol, 84% yield). LC-MS m/z 533.2 (M+H)$^+$, 1.07 min (ret. time)

Example 211

3-(1,4-Dimethyl-1H-benzo[d][1,2,3]triazol-5-yl)-3-(3-(((R)-9-fluoro-4-methyl-1,1-dioxido-3,4-dihydro-2H-benzo[b][1,4,5]oxathiazepin-2-yl)methyl)-4-methylphenyl)propanoic acid

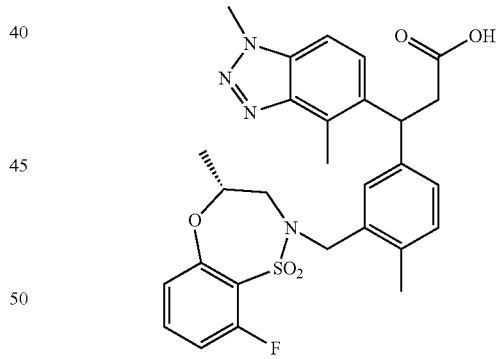

(R)-2,6-Difluoro-N-(2-hydroxypropyl)benzenesulfonamide

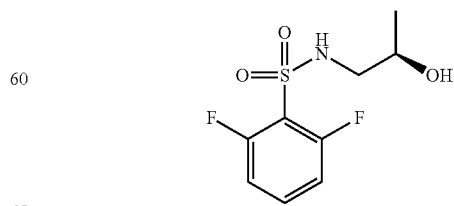

(R)-1-Amino-2-propanol (4.44 mL, 57.5 mmol) in THF (60 mL) and water (15 mL) was added K$_2$CO$_3$ (7.95 g, 57.5 mmol) and then 2,6-difluorobenzene-1-sulfonyl chloride (5 mL, 36.9 mmol) slowly. The resulting reaction mixture was stirred at RT for 1.5 h. The reaction mixture was diluted with H$_2$O (30 mL) and extracted with EtOAc (2×60 mL). The combined organic layer washed with brine, dried over Na$_2$SO$_4$, filtered, concentrated to afford the title compound (10.3 g, 41.0 mmol, 71.3% yield). LC-MS m/z 252.1 (M+H)$^+$, 0.64 min (ret. time)

(R)-9-Fluoro-4-methyl-3,4-dihydro-2H-benzo[b][1,4,5]oxathiazepine 1,1-dioxide

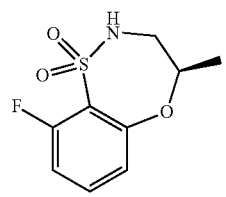

(R)-2,6-Difluoro-N-(2-hydroxypropyl)benzenesulfonamide (10.3 g, 41.0 mmol) in dimethyl sulfoxide (DMSO) (100 mL) was added KOt-Bu (6.90 g, 61.5 mmol). The result reaction mixture was heated at 80° C. for 1.5 h, 19 h at 80° C. More KOt-Bu (4.60 g, 41.0 mmol) and 50 mL DMSO were added and heated at 80° C. for 2 h. The reaction mixture was diluted with H$_2$O (200 mL), acidified with HCl (2N) to pH ~6, and extracted with EtOAc (2×500 mL). The combined organic layer was washed with brine (400 mL), and concentrated. It was purified by silica gel chromatography. Desired fractions were concentrated and then triturated with ether to give the title compound (2.46 g, 10.64 mmol, 25.9% yield) as white solid. LC-MS m/z 232.0 (M+H)$^+$, 0.69 min (ret. time)

3-(1,4-Dimethyl-1H-benzo[d][1,2,3]triazol-5-yl)-3-(3-(((R)-9-fluoro-4-methyl-1,1-dioxido-3,4-dihydro-2H-benzo[b][1,4,5]oxathiazepin-2-yl)methyl)-4-methylphenyl)propanoic acid

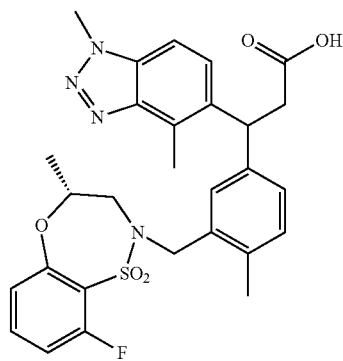 [SMILES: Cc1ccc(C(CC(=O)O)c2ccc3c(nnn3C)c2C)cc1CN1C[C@@H](C)Oc2cccc(F)c2S1(=O)=O]

To a solution of ethyl 3-(1,4-dimethyl-1H-benzo[d][1,2,3]triazol-5-yl)-3-(3-(hydroxymethyl)-4-methylphenyl)propanoate (50 mg, 0.136 mmol), (R)-9-fluoro-4-methyl-3,4-dihydro-2H-benzo[b][1,4,5]oxathiazepine 1,1-dioxide (33.0 mg, 0.143 mmol), and 1,1'-(azodicarbonyl)dipiperidine (68.7 mg, 0.272 mmol) in THF (3 mL) at RT was added tri-n-butylphosphine (0.067 mL, 0.272 mmol). The reaction mixture was stirred at RT for 4 h. The solvent was removed and the crude product purified by silica gel chromatography (product came out at 50% EtOAc in hexane). The desired fractions were concentrated under reduced pressure to give the intermediate ethyl 3-(1,4-dimethyl-1H-benzo[d][1,2,3]triazol-5-yl)-3-(3-(((R)-9-fluoro-4-methyl-1,1-dioxido-3,4-dihydro-2H-benzo[b][1,4,5]oxathiazepin-2-yl)methyl)-4-methylphenyl)propanoate. It was dissolved in MeOH (2 mL), 2 M LiOH (0.408 mL, 0.816 mmol) was added and the reaction mixture was heated in a Biotage microwave at 85° C. for 30 min. then stirred at RT for 19 h. 0.8 mL of 1 N HCl and 1.5 mL of DMSO were added. Most solvents were dried and the sample was purified with reverse-phase HPLC with acidic condition to give the title compound (55.72 mg, 0.101 mmol, 74.1% yield). LC-MS m/z 553.4 (M+H)$^+$, 1.05 min (ret. time)

Example 212

(S)-3-(7-Methoxy-1-methyl-1H-benzo[d][1,2,3]triazol-5-yl)-3-(4-methyl-3-(((R)-4-methyl-1,1-dioxido-4,5-dihydrobenzo[f][1,2]thiazepin-2(3H)-yl)methyl)phenyl)propanoic acid

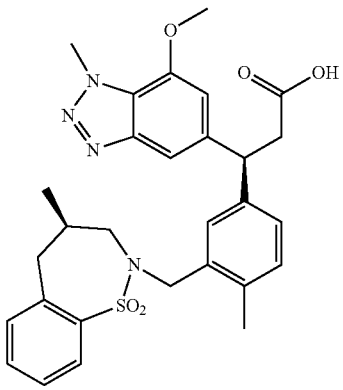 [SMILES: COc1cc([C@@H](CC(=O)O)c2ccc(C)c(CN3C[C@H](C)Cc4ccccc4S3(=O)=O)c2)cc2nnn(C)c12]

(R)-4-Methyl-2,3,4,5-tetrahydrobenzo[f][1,2]thiazepine 1,1-dioxide & (S)-4-methyl-2,3,4,5-tetrahydrobenzo[f][1,2]thiazepine 1,1-dioxide

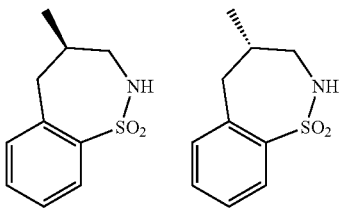

4-Methyl-2,3,4,5-tetrahydrobenzo[f][1,2]thiazepine 1,1-dioxide (500 mg, 2.367 mmol) was separated by Chiral SFC method (Column: Chiralpak AD, 20×250 mm, 5 u; Co-solvent: 20% MeOH:IPA; Flow rate: 50 g/min; Back Pressure: 100 bar). Desired fractions were concentrated to give (R)-4-methyl-2,3,4,5-tetrahydrobenzo[f][1,2]thiazepine 1,1-dioxide (222 mg, 1.051 mmol, 89% yield) and (S)-4-methyl-2,3,4,5-tetrahydrobenzo[f][1,2]thiazepine 1,1-dioxide (232 mg, 1.098 mmol, 93% yield). LC-MS m/z 212.0 (M+H)$^+$, 0.85 min (ret. time) (R isomer) LC-MS m/z 211.9 (M+H)$^+$, 0.83 min (ret. time) (S isomer)

(S)-Ethyl 3-(3-(hydroxymethyl)-4-methylphenyl)-3-(7-methoxy-1-methyl-1H-benzo[d][1,2,3]triazol-5-yl)propanoate

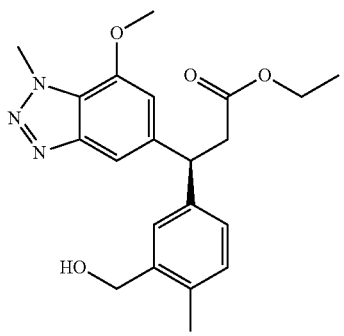 [SMILES: CCOC(=O)C[C@@H](c1ccc(C)c(CO)c1)c1cc(OC)c2c(c1)nnn2C]

(E)-Ethyl 3-(7-methoxy-1-methyl-1H-benzo[d][1,2,3]triazol-5-yl)acrylate (200 mg, 0.765 mmol), (3-(hydroxymethyl)-4-methylphenyl)boronic acid (381 mg, 2.296 mmol), (Rh(nbd)Cl)$_2$ (35.3 mg, 0.077 mmol), (2R,3R)-butane-2,3-diylbis(diphenylphosphine) (35.9 mg, 0.084 mmol), 1,4-dioxane (5 mL), 1M potassium hydroxide (0.765 mL, 0.765 mmol) were combined in a Schlenk tube and a stream of Ar was bubbled through the mixture for ~6 min. The reaction was stirred under argon for 3 h. After 4 h the reaction was diluted with EtOAc (50 mL) and water (20 mL) and the phases were separated. The aqueous was extracted again with EtOAc (50 mL) and the combined EtOAc washed with water (25 mL) and satd aq NaCl (25 mL) and dried (Na$_2$SO$_4$) and filtered and stood in solution overnight. A small amount of additional precipitate formed and the solid was filtered off through a glass fiber filter. The residue was concentrated to afford a yellow oil. The crude product was purified by silica gel chromatography with a gradient running from DCM to 70% EtOAc/DCM over 30 min. The desired fractions were concentrated to afford the title compound (223 mg, 0.582 mmol, 76% yield) as a waxy off white solid. The sample showed ~92% e.e. (isomer ratio is 96% of the major and 4% of the minor). LC-MS m/z 384.1 (M+H)$^+$, 0.94 min (ret. time)

(S)-3-(7-Methoxy-1-methyl-1H-benzo[d][1,2,3]triazol-5-yl)-3-(4-methyl-3-(((R)-4-methyl-1,1-dioxido-4,5-dihydrobenzo[f][1,2]thiazepin-2(3H)-yl)methyl)phenyl)propanoic acid

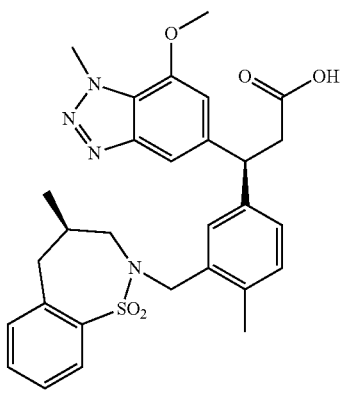 [SMILES: COc1cc([C@@H](CC(=O)O)c2ccc(C)c(CN3C[C@H](C)Cc4ccccc4S3(=O)=O)c2)cc2nnn(C)c12]

To a solution of (S)-ethyl 3-(3-(hydroxymethyl)-4-methylphenyl)-3-(7-methoxy-1-methyl-1H-benzo[d][1,2,3]triazol-5-yl)propanoate (50 mg, 0.130 mmol), (R)-4-methyl-2,3,4,5-tetrahydrobenzo[f][1,2]thiazepine 1,1-dioxide (27.6 mg, 0.130 mmol), and 1,1'-(azodicarbonyl)dipiperidine (65.8 mg, 0.261 mmol) in THF (3 mL) at RT was added tri-n-butylphosphine (0.064 mL, 0.261 mmol). The reaction mixture was stirred at RT for 20 h. The solvent was removed and the crude product purified by silica gel chromatography (product came out at 50% EtOAc in hexane). The desired fractions were concentrated under reduced pressure to give desired intermediate as oil. It was redissolved in MeOH (2 mL), 2M LiOH (0.391 mL, 0.782 mmol) was added and the reaction mixture was heated in a Biotage microwave at high absorption for 30 min at 85° C. 0.8 mL of 1 N HCl and 1.5 mL of DMSO were added. Most solvents were removed and the sample was purified with reverse-phase HPLC with acidic condition to give the title compound (46.1 mg, 0.084 mmol, 64.4% yield). LC-MS m/z 549.4 (M+H)$^+$, 1.19 min (ret. time)

Example 213

(S)-3-(7-Methoxy-1-methyl-1H-benzo[d][1,2,3]triazol-5-yl)-3-(4-methyl-3-(((S)-4-methyl-1,1-dioxido-4,5-dihydrobenzo[f][1,2]thiazepin-2(3H)-yl)methyl)phenyl)propanoic acid

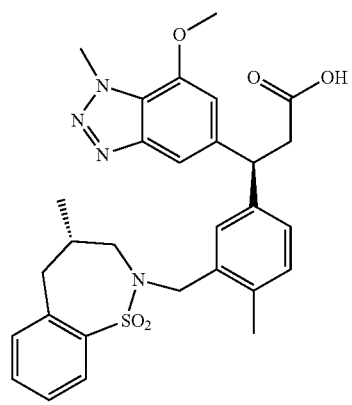 [SMILES: COc1cc([C@@H](CC(=O)O)c2ccc(C)c(CN3C[C@@H](C)Cc4ccccc4S3(=O)=O)c2)cc2nnn(C)c12]

To a solution of (S)-ethyl 3-(3-(hydroxymethyl)-4-methylphenyl)-3-(7-methoxy-1-methyl-1H-benzo[d][1,2,3]triazol-5-yl)propanoate (50 mg, 0.130 mmol), (S)-4-methyl-2,3,4,5-tetrahydrobenzo[f][1,2]thiazepine 1,1-dioxide (27.6 mg, 0.130 mmol), and 1,1'-(azodicarbonyl)dipiperidine (65.8 mg, 0.261 mmol) in THF (3 mL) at RT was added tri-n-butylphosphine (0.064 mL, 0.261 mmol). The reaction mixture was stirred at RT for 20 h. The solvent was removed and the crude product purified by silica gel chromatography (product came out at 50% EtOAc in hexane). The desired fractions were concentrated under reduced pressure to give desired intermediate as oil. It was redissolved in MeOH (2 mL), 2M LiOH (0.391 mL, 0.782 mmol) was added and the reaction mixture was heated in a Biotage microwave at high absorption for 30 min at 85° C. 0.8 mL of 1 N HCl and 1.5 mL of DMSO were added. Most solvents were removed and the sample was purified with reverse-phase HPLC with acidic condition to give the title compound (69.3 mg, 0.126 mmol, 97% yield). LC-MS m/z 549.3 (M+H)$^+$, 1.20 min (ret. time)

Example 214

3-(4-Cyano-2-methylphenyl)-3-(4-methyl-3-((4-methyl-1,1-dioxido-4,5-dihydrobenzo[f][1,2]thiazepin-2(3H)-yl)methyl)phenyl)propanoic acid

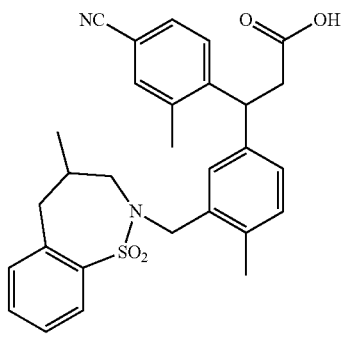 [SMILES: Cc1ccc(C(CC(=O)O)c2ccc(C#N)cc2C)cc1CN1CC(C)Cc2ccccc2S1(=O)=O]

To a solution of methyl 3-(4-cyano-2-methylphenyl)-3-(3-(hydroxymethyl)-4-methylphenyl)propanoate (80 mg, 0.247 mmol), 4-methyl-2,3,4,5-tetrahydrobenzo[f][1,2]thiazepine 1,1-dioxide (52.3 mg, 0.247 mmol), and 1,1'-(azodicarbonyl)dipiperidine (110 mg, 0.435 mmol) in THF (10 mL) at RT was added tri-n-butylphosphine (0.107 mL, 0.435 mmol). The reaction mixture was stirred at RT for 75 h. The solvent was removed and the crude product purified by silica gel chromatography (product came out at 30% EtOAc in hexane). The desired fractions were concentrated under reduced pressure to give the intermediate methyl 3-(4-cyano-2-methylphenyl)-3-(4-methyl-3-((4-methyl-1,1-dioxido-4,5-dihydrobenzo[f][1,2]thiazepin-2(3H)-yl)methyl)phenyl)propanoate. It was redissolved in MeOH (2 mL), 2M LiOH (0.742 mL, 1.484 mmol) was added and the reaction mixture was heated in a Biotage microwave at high absorption for 30 min at 85° C. 0.8 mL of 1 N HCl and 1 mL of DMSO were added. Most solvents were removed and the sample was purified with reverse-phase HPLC with acidic condition to give the title compound (96.3 mg, 77%) as solid. LC-MS m/z 503.1 (M+H)$^+$, 1.15 min (ret. time)

The compounds listed in the table below were prepared in a similar manner as above.

| Example # | Name | Structure | (M + H)$^+$ | Ret. Time (min) |
|---|---|---|---|---|
| Example 215 | 3-(4-Cyano-2-methylphenyl)-3-(3-((7-fluoro-4-methyl-1,1-dioxido-4,5-dihydrobenzo[f][1,2]thiazepin-2(3H)-yl)methyl)-4-methylphenyl)propanoic acid | 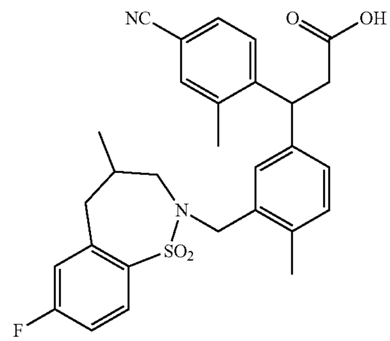 [SMILES: Cc1ccc(C(CC(=O)O)c2ccc(C#N)cc2C)cc1CN1CC(C)Cc2cc(F)ccc2S1(=O)=O] | 521.3 | 1.22 |
| Example 216 | 3-(4-Cyano-2-methylphenyl)-3-(3-((7-methoxy-4-methyl-1,1-dioxido-4,5-dihydrobenzo[f][1,2]thiazepin-2(3H)-yl)methyl)-4-methylphenyl)propanoic acid | 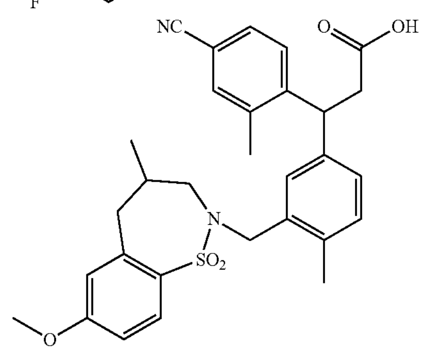 | 533.1 | 1.20 |
| Example 217 | 3-(4-Cyano-2-methylphenyl)-3-(4-methyl-3-((4-methyl-1,1-dioxido-7-(trifluoromethyl)-4,5-dihydrobenzo[f][1,2]thiazepin-2(3H)-yl)methyl)phenyl)propanoic acid | 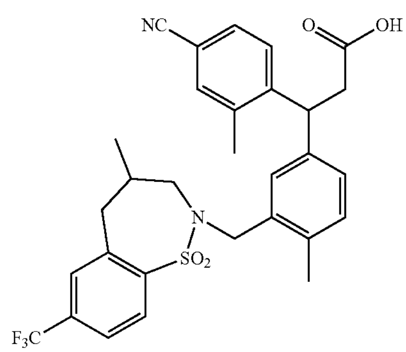 [SMILES: Cc1ccc(C(CC(=O)O)c2ccc(C#N)cc2C)cc1CN1CC(C)Cc2cc(C(F)(F)F)ccc2S1(=O)=O] | 571.5 | 1.32 |

| Example # | Name | Structure | (M + H)⁺ | Ret. Time (min) |
|---|---|---|---|---|
| Example 218 | 3-(4-Cyano-2-methylphenyl)-3-(4-methyl-3-((4-methyl-1,1-dioxido-7-(trifluoromethoxy)-4,5-dihydrobenzo[f][1,2]thiazepin-2(3H)-yl)methyl)phenyl)propanoic acid | 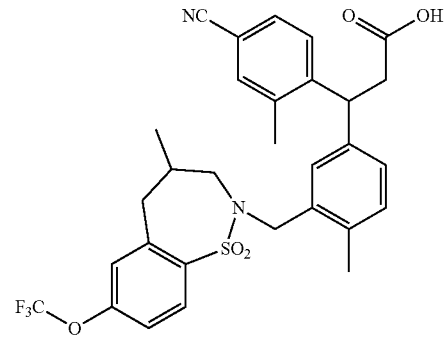 [SMILES: Cc1ccc(C(CC(=O)O)c2ccc(C#N)cc2C)cc1CN1CC(C)Cc2cc(OC(F)(F)F)ccc2S1(=O)=O] | 587.0 | 1.32 |

Example 219

3-(4-Cyano-2-methoxyphenyl)-3-(3-(((R)-4-ethyl-1,1-dioxido-3,4-dihydro-2H-benzo[b][1,4,5]oxathiazepin-2-yl)methyl)-4-methylphenyl)propanoic acid

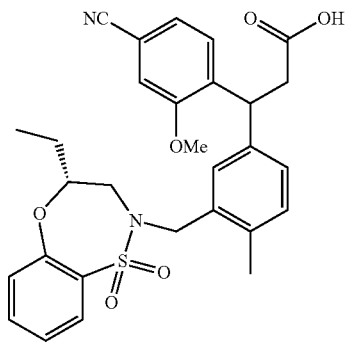 [SMILES: CC[C@@H]1CN(Cc2cc(C(CC(=O)O)c3ccc(C#N)cc3OC)ccc2C)S(=O)(=O)c2ccccc2O1]

(E)-Methyl 3-(4-cyano-2-methoxyphenyl)acrylate

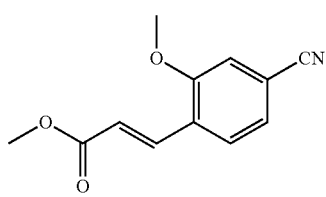 [SMILES: COC(=O)/C=C/c1ccc(C#N)cc1OC]

To a solution of 4-bromo-3-methoxybenzonitrile (1000 mg, 4.72 mmol) in DMF (7 mL) was added methyl acrylate (2.137 mL, 23.58 mmol), DIPEA (2.059 mL, 11.79 mmol), Pd(OAc)₂ (106 mg, 0.472 mmol), and tri-o-tolylphosphine (287 mg, 0.943 mmol). The reaction vessel was heated in a Biotage Initiator microwave at high absorption for 1 h at 150° C. The reaction mixture was concentrated, filtered through celite, then diluted with water, extracted with EtOAc twice. The combined organic layer was concentrated under reduced pressure with a rotavap evaporator. The crude product was purified by silica gel chromatography. Those fractions were combined and concentrated to give the title compound (1.135 g, 5.23 mmol, 111% yield). It was carried it to next step without further purification. LC-MS m/z 218.2 (M+H)⁺, 0.96 min (ret. time)

3-(4-Cyano-2-methoxyphenyl)-3-(3-(((R)-4-ethyl-1,1-dioxido-3,4-dihydro-2H-benzo[b][1,4,5]oxathiazepin-2-yl)methyl)-4-methylphenyl)propanoic acid To a suspension of (E)-methyl 3-(4-cyano-2-methoxyphenyl)acrylate (100 mg, 0.460 mmol), (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (253 mg, 0.552 mmol), and [RhCl(cod)]₂ (22.70 mg, 0.046 mmol) in 1,4-dioxane (2 mL) and water (1 mL) at RT was added Et₃N (0.192 mL, 1.381 mmol). The resulting suspension was heated in a Biotage microwave at high absorption for 30 min at 100° C. The reaction mixture was passed through celite and washed with EtOAc. The organic layer was collected and concentrated to give the crude product. The reaction mixture was purified with reverse-phase HPLC under neutral condition to give the intermediate methyl 3-(4-cyano-2-methoxyphenyl)-3-(3-(((R)-4-ethyl-1,1-dioxido-3,4-dihydro-2H-benzo[b][1,4,5]oxathiazepin-2-yl)methyl)-4-methylphenyl)propanoate. It was redissolved in MeOH (2 mL), 2M LiOH (1.381 mL, 2.76 mmol) was added and the reaction mixture was heated in a Biotage microwave at high absorption for 30 min at 80° C. It was acidified with 1N HCl to pH2, 1 mL of DMSO was added. Most solvents were removed and the sample was purified with reverse-phase HPLC with acidic condition to give the title compound (55.6 mg, 0.104 mmol, 22.59%) as solid. LC-MS: m/z 535.1 (M+H)⁺, Rt 1.12 min. ¹H NMR (400 MHz, DMSO-d₆) δ=12.14 (br. s., 1H), 7.78 (d, J=6.5 Hz, 1H), 7.68 (t, J=7.7 Hz, 1H), 7.51-7.29 (m, 5H), 7.23 (m, 1H), 7.19-7.06 (m, 2H), 4.83-4.72 (m, 1H), 4.41 (dd, J=6.5, 14.1 Hz, 1H), 4.19-4.04 (m, 1H), 3.89-3.77 (m, 4H), 3.71-3.58 (m, 1H), 3.04-2.93 (m, 2H), 2.89-2.68 (m, 1H), 2.24 (s., 3H), 1.63-1.48 (m, 1H), 1.46-1.20 (m, 1H), 1.11-0.96 (m, 3H)

Example 220

3-(4-Cyano-3-methoxyphenyl)-3-(3-(((R)-4-ethyl-1,1-dioxido-3,4-dihydro-2H-benzo[b][1,4,5]oxathiazepin-2-yl)methyl)-4-methylphenyl)propanoic acid

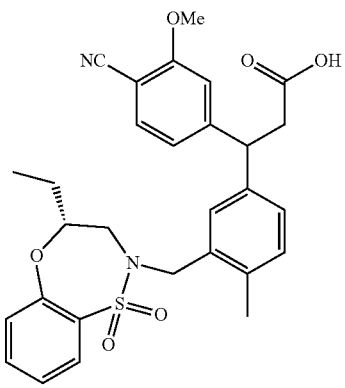 [SMILES: CC[C@@H]1CN(Cc2cc(C(CC(=O)O)c3ccc(C#N)c(OC)c3)ccc2C)S(=O)(=O)c2ccccc2O1]

(E)-Methyl 3-(4-cyano-3-methoxyphenyl)acrylate

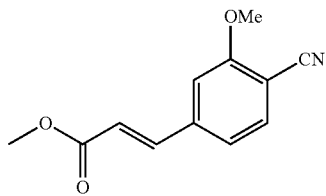 [SMILES: COC(=O)/C=C/c1ccc(C#N)c(OC)c1]

To a solution of 4-bromo-2-methoxybenzonitrile (500 mg, 2.358 mmol) in DMF (7 mL) was added methyl acrylate (2.137 mL, 23.58 mmol), DIPEA (2.059 mL, 11.79 mmol), Pd(OAc)$_2$ (106 mg, 0.472 mmol), and tri-o-tolylphosphine (287 mg, 0.943 mmol). The reaction vessel was heated in a Biotage Initiator microwave at high absorption for 1 h at 150° C. The reaction mixture was concentrated, filtered through celite, then diluted with water, extracted with EtOAc twice. The combined organic layer was concentrated to give the title compound (1.342 g, 6.18 mmol, 131% yield). It was carried it to next step without further purification. LC-MS m/z 218.2 (M+H)$^+$, 0.85 min (ret. time)

3-(4-Cyano-3-methoxyphenyl)-3-(3-(((R)-4-ethyl-1,1-dioxido-3,4-dihydro-2H-benzo[b][1,4,5]oxathiazepin-2-yl)methyl)-4-methylphenyl)propanoic acid

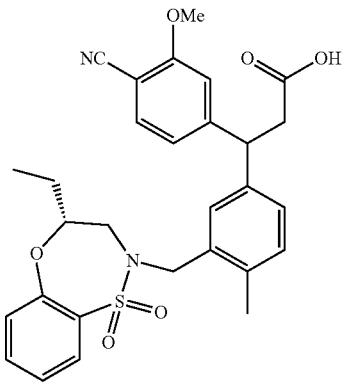 [SMILES: CC[C@@H]1CN(Cc2cc(C(CC(=O)O)c3ccc(C#N)c(OC)c3)ccc2C)S(=O)(=O)c2ccccc2O1]

To a suspension of (E)-methyl 3-(4-cyano-3-methoxyphenyl)acrylate (100 mg, 0.460 mmol), (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (253 mg, 0.552 mmol), and [RhCl(cod)]$_2$ (22.70 mg, 0.046 mmol) in 1,4-dioxane (2 mL) and water (1 mL) at RT was added Et$_3$N (0.192 mL, 1.381 mmol). The resulting suspension was heated at 55° C. for 1 h. The reaction mixture was passed through celite and washed with EtOAc. The organic layer was collected and concentrated to give the crude product. The reaction mixture was purified with reverse-phase HPLC under neutral condition to give the intermediate methyl 3-(4-cyano-3-methoxyphenyl)-3-(3-(((R)-4-ethyl-1,1-dioxido-3,4-dihydro-2H-benzo[b][1,4,5]oxathiazepin-2-yl)methyl)-4-methylphenyl)propanoate. It was redissolved in MeOH (2 mL), 2M LiOH (1.381 mL, 2.76 mmol) was added and the reaction mixture was heated in a Biotage microwave at high absorption for 30 min at 80° C. It was acidified with 1N HCl to pH 2, 1 mL of DMSO was added. Most solvents were removed and the sample was purified with reverse-phase HPLC with acidic condition to give the title compound (57.57 mg, 0.108 mmol, 23.39% yield) as white solid. LC-MS: m/z 535.1 (M+H)$^+$, Rt 1.10 min. $^1$H NMR (400 MHz, DMSO-d$_6$) δ=12.19 (br. s., 1H), 7.79 (d, J=7.5 Hz, 1H), 7.68 (t, J=7.7 Hz, 1H), 7.60 (d, J=7.8 Hz, 1H), 7.42-7.18 (m, 5H), 7.15 (m, 1H), 7.00 (t, J=7.7 Hz, 1H), 4.53-4.40 (m, 2H), 4.11 (m., 1H), 3.91 (d, J=4.3 Hz, 3H), 3.80 (dd, J=3.8, 14.1 Hz, 1H), 3.63 (dd, J=10.4, 15.2 Hz, 1H), 3.13-2.99 (m, 2H), 2.85-2.66 (m, 1H), 2.26 (s., 3H), 1.61-1.44 (m, 1H), 1.40-1.17 (m, 1H), 1.07-0.96 (m, 3H)

Example 221

3-(4-Cyano-2-fluorophenyl)-3-(3-(((R)-4-ethyl-1,1-dioxido-3,4-dihydro-2H-benzo[b][1,4,5]oxathiazepin-2-yl)methyl)-4-methylphenyl)propanoic acid

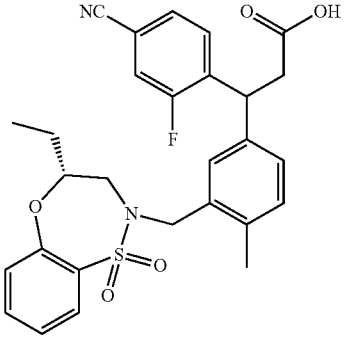 [SMILES: CC[C@@H]1CN(Cc2cc(C(CC(=O)O)c3ccc(C#N)cc3F)ccc2C)S(=O)(=O)c2ccccc2O1]

(E)-Methyl 3-(4-cyano-2-fluorophenyl)acrylate

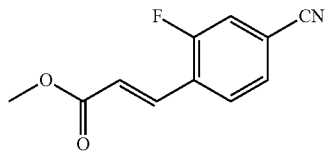

To a solution of 4-bromo-3-fluorobenzonitrile (943 mg, 4.72 mmol) in DMF (7 mL) was added methyl acrylate (2.137 mL, 23.58 mmol), DIPEA (2.059 mL, 11.79 mmol), Pd(OAc)$_2$ (106 mg, 0.472 mmol), and tri-o-tolylphosphine (287 mg, 0.943 mmol). The reaction vessel was heated in a Biotage Initiator microwave at high absorption for 1 h at 150° C. The reaction mixture was concentrated, filtered through celite, then diluted with water, extracted with EtOAc twice. The combined organic layer was concentrated to give the title compound (1.509 g, 7.35 mmol, 156% yield). It was carried it to next step without further purification. LC-MS m/z 206.0 (M+H)$^+$, 0.84 min (ret. time)

481

3-(4-Cyano-2-fluorophenyl)-3-(3-(((R)-4-ethyl-1,1-dioxido-3,4-dihydro-2H-benzo[b][1,4,5]oxathiazepin-2-yl)methyl)-4-methylphenyl)propanoic acid

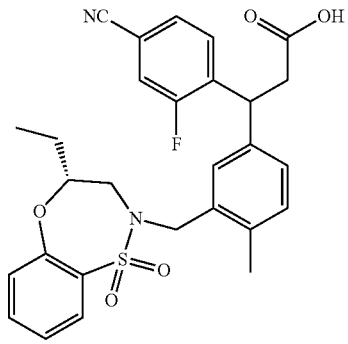 [SMILES: CC[C@@H]1CN(Cc2cc(C(CC(=O)O)c3ccc(C#N)cc3F)ccc2C)S(=O)(=O)c2ccccc2O1]

To a suspension of (E)-methyl 3-(4-cyano-2-fluorophenyl)acrylate (100 mg, 0.487 mmol), (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (267 mg, 0.585 mmol), and [RhCl(cod)]$_2$ (24.03 mg, 0.049 mmol) in 1,4-dioxane (2 mL) and water (1 mL) at RT was added Et$_3$N (0.204 mL, 1.462 mmol). The resulting suspension was heated in a Biotage microwave at high absorption for 30 min at 100° C. The reaction mixture was passed through celite and washed with EtOAc. The organic layer was collected and concentrated to give the crude product. The reaction mixture was purified with reverse-phase HPLC under neutral condition to give the intermediate. It was redissolved in MeOH (2 mL), 2M LiOH (1.462 mL, 2.92 mmol) was added and the reaction mixture was heated in a Biotage microwave at high absorption for 30 min at 80° C. The reaction mixture was stirred at RT for 4 h. It was acidified with 1N HCl to pH2, 1 mL of DMSO was added. Most solvents were removed and the sample was purified with reverse-phase HPLC with acidic condition to give the title compound (12 mg, 0.023 mmol, 4.71% yield) and 3-(4-carbamoyl-2-fluorophenyl)-3-(3-(((R)-4-ethyl-1,1-dioxido-3,4-dihydro-2H-benzo[b][1,4,5]oxathiazepin-2-yl)methyl)-4-methylphenyl)propanoic acid (73 mg, 0.135 mmol, 27.7% yield) as solid. LC-MS: m/z 523.3 (M+H)$^+$, 1.12 min. (ret. time).

Example 222

5-(1-Ethyl-1H-1,2,3-triazol-4-yl)-3-(4-methyl-3-(((S)-4-methyl-1,1-dioxido-4,5-dihydrobenzo[f][1,2]thiazepin-2(3H)-yl)methyl)phenyl)pentanoic acid

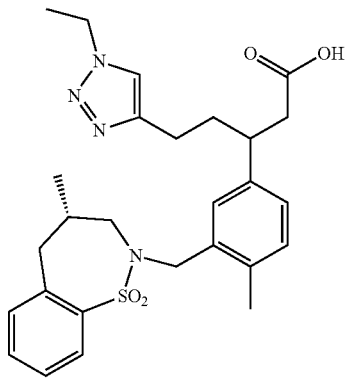 [SMILES: CCn1cc(CCC(CC(=O)O)c2ccc(C)c(CN3C[C@@H](C)Cc4ccccc4S3(=O)=O)c2)nn1]

482

Ethyl 5-(1-ethyl-1H-1,2,3-triazol-4-yl)-3-(3-(hydroxymethyl)-4-methylphenyl)pentanoate

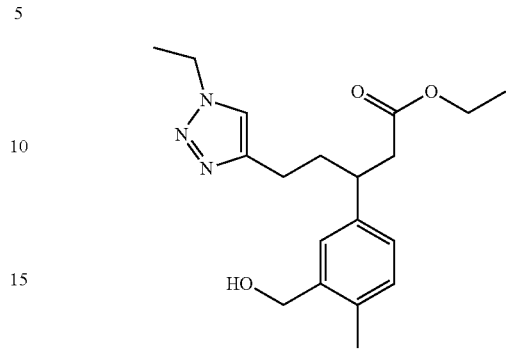

To a suspension of (Z)-ethyl 5-(1-ethyl-1H-1,2,3-triazol-4-yl)pent-2-enoate (500 mg, 2.239 mmol), (2-methyl-5-(4,4,5,5-tetramethyl-1,3,2-dioxaborolan-2-yl)phenyl)methanol (667 mg, 2.69 mmol), and [RhCl(cod)]$_2$ (110 mg, 0.224 mmol) in 1,4-dioxane (2 mL) and water (1 mL) at RT was added Et$_3$N (0.936 mL, 6.72 mmol). The resulting suspension was heated at 90° C. for 1 h. The reaction mixture was passed through celite and washed with EtOAc. The organic layer was collected and concentrated to give the crude product. The reaction mixture was purified by silica gel chromatography (product came out at 100% EtOAc in hexane). The desired fractions were concentrated under reduced pressure to give the title compound ethyl 5-(1-ethyl-1H-1,2,3-triazol-4-yl)-3-(3-(hydroxymethyl)-4-methylphenyl)pentanoate (685 mg, 1.983 mmol, 89% yield) as oil. LC-MS: m/z 346.1 (M+H)$^+$, 0.83 min. (ret. time)

5-(1-Ethyl-1H-1,2,3-triazol-4-yl)-3-(4-methyl-3-(((S)-4-methyl-1,1-dioxido-4,5-dihydrobenzo[f][1,2]thiazepin-2(3H)-yl)methyl)phenyl)pentanoic acid

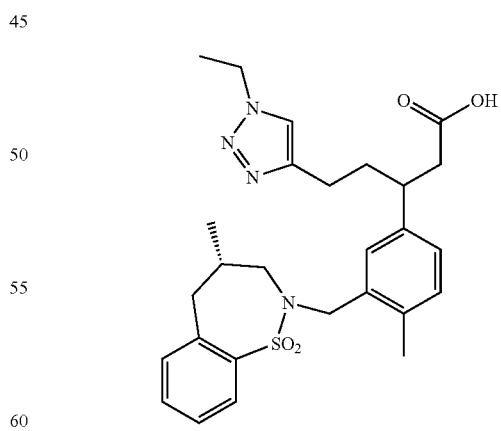

To a solution of ethyl 5-(1-ethyl-1H-1,2,3-triazol-4-yl)-3-(3-(hydroxymethyl)-4-methylphenyl)pentanoate (50 mg, 0.145 mmol), (S)-4-methyl-2,3,4,5-tetrahydrobenzo[f][1,2]thiazepine 1,1-dioxide (30.6 mg, 0.145 mmol), and 1,1'-(azodicarbonyl)dipiperidine (73.0 mg, 0.289 mmol) in THF (3 mL) at RT was added tri-n-butylphosphine (0.071 mL, 0.289 mmol). The reaction mixture was stirred at RT for 20 h. The solvent was removed and the crude product purified with reverse-phase HPLC under neutral conditions to give the desired intermediate. It was redissolved in MeOH (2 mL), 2M LiOH (0.434 mL, 0.868 mmol) was added and the reaction mixture was heated in a Biotage microwave at high absorption for 30 min at 80° C. 0.8 mL of 1 N HCl and 1.5 mL of DMSO were added. Most solvents were removed and the sample was purified with reverse-phase HPLC with acidic condition to give the title compound (60.6 mg, 0.119 mmol, 82% yield). LC-MS m/z 511.4 (M+H)$^+$, 1.00 min (ret. time)

Example 223

3-(3-(((R)-4-Ethyl-1,1-dioxido-3,4-dihydro-2H-benzo[b][1,4,5]oxathiazepin-2-yl)methyl)-4-methylphenyl)-5-(1-ethyl-1H-1,2,3-triazol-4-yl)pentanoic acid

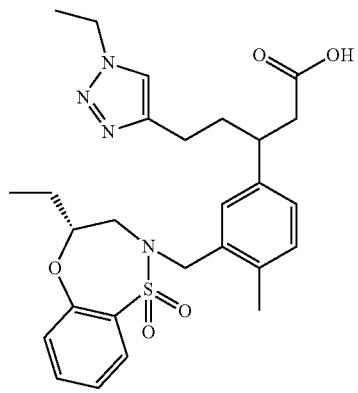 [SMILES: CC[C@@H]1CN(Cc2cc(C(CCc3cn(CC)nn3)CC(=O)O)ccc2C)S(=O)(=O)c2ccccc2O1]

To a suspension of (Z)-ethyl 5-(1-ethyl-1H-1,2,3-triazol-4-yl)pent-2-enoate (230 mg, 1.030 mmol), (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (565 mg, 1.236 mmol), and [RhCl(cod)]$_2$ (50.8 mg, 0.103 mmol) in 1,4-dioxane (2 mL) and water (1 mL) at RT was added Et$_3$N (0.431 mL, 3.09 mmol). The resulting suspension was heated at 90° C. for 1 h. The reaction mixture was passed through celite and washed with EtOAc. The organic layer was collected and concentrated to give the crude product. The reaction mixture was purified by silica gel chromatography (product came out at 70% EtOAc in hexane). The desired fractions were concentrated under reduced pressure to give the intermediate (481 mg, 0.867 mmol, 84% yield) as oil. 60 mg of intermediate was dissolved in 2 mL MeOH. 2M LiOH (3.09 mL, 6.18 mmol) was added and the reaction mixture was heated in a Biotage microwave at high absorption for 30 min at 80° C. 0.8 mL of 1 N HCl and 1.5 mL of DMSO were added. Most solvents were removed and the sample was purified with reverse-phase HPLC with acidic condition to give the title compound (62 mg). LC-MS: m/z 527.3 (M+H)$^+$, 1.03 min. (ret. time)

Example 224

3-(3-((1,1-Dioxido-4,5-dihydrobenzo[f][1,2]thiazepin-2(3H)-yl)methyl)-4-methylphenyl)-5-(1-ethyl-1H-1,2,3-triazol-4-yl)pentanoic acid

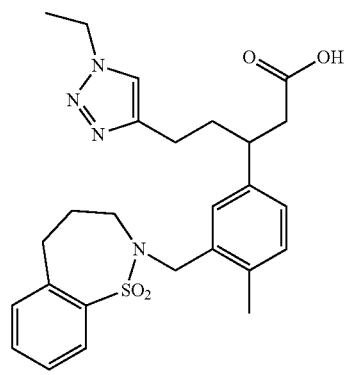 [SMILES: CCn1cc(CCC(CC(=O)O)c2ccc(C)c(CN3CCCc4ccccc4S3(=O)=O)c2)nn1]

To a solution of ethyl 5-(1-ethyl-1H-1,2,3-triazol-4-yl)-3-(3-(hydroxymethyl)-4-methylphenyl)pentanoate (150 mg, 0.434 mmol), 2,3,4,5-tetrahydrobenzo[f][1,2]thiazepine 1,1-dioxide (86 mg, 0.434 mmol), and 1,1'-(azodicarbonyl)dipiperidine (219 mg, 0.868 mmol) in THF (5 mL) at RT was added tri-n-butylphosphine (0.214 mL, 0.868 mmol). The reaction mixture was stirred at RT for 20 h. The solvent was removed and the crude product purified with reverse-phase HPLC under neutral conditions to give desired intermediate. It was redissolved in MeOH (2 mL), 2M LiOH (1.303 mL, 2.61 mmol) was added and the reaction mixture was heated in a Biotage microwave at high absorption for 30 min at 80° C. 0.8 mL of 1 N HCl and 1.5 mL of DMSO were added. Most solvents were removed and the sample was purified with reverse-phase HPLC with acidic condition to give the title compound (48.5 mg, 0.098 mmol, 22.49% yield). LC-MS m/z 497.4 (M+H)$^+$, 0.96 min (ret. time)

Example 225

3-(3-(((R)-4-Ethyl-1,1-dioxido-3,4-dihydro-2H-pyrido[2,3-b][1,4,5]oxathiazepin-2-yl)methyl)-4-methylphenyl)-5-(1-ethyl-1H-1,2,3-triazol-4-yl)pentanoic acid

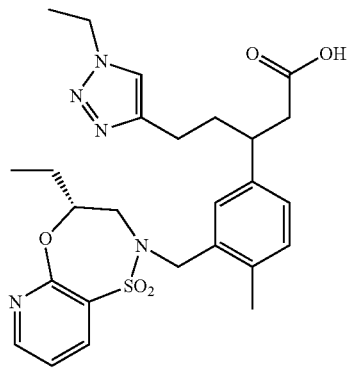 [SMILES: CC[C@@H]1CN(Cc2cc(C(CCc3cn(CC)nn3)CC(=O)O)ccc2C)S(=O)(=O)c2cccnc2O1]

To a solution of ethyl 5-(1-ethyl-1H-1,2,3-triazol-4-yl)-3-(3-(hydroxymethyl)-4-methylphenyl)pentanoate (50 mg, 0.145 mmol), (R)-4-ethyl-3,4-dihydro-2H-pyrido[2,3-b][1,4,5]oxathiazepine 1,1-dioxide (33.0 mg, 0.145 mmol), and 1,1'-(azodicarbonyl)dipiperidine (73.0 mg, 0.289 mmol) in THF (3 mL) at RT was added tri-n-butylphosphine (0.071 mL, 0.289 mmol). The reaction mixture was stirred at RT for 20 h. The solvent was removed and the crude product purified with reverse-phase HPLC under neutral conditions to give the desired intermediate as oil. It was redissolved in MeOH (2 mL), 2M LiOH (0.434 mL, 0.868 mmol) was added and the reaction mixture was heated in a Biotage microwave at high absorption for 30 min at 80° C. 0.8 mL of 1 N HCl and 1.5 mL of DMSO were added. Most solvents were removed and the sample was purified with reverse-phase HPLC with acidic condition to give the title compound (52 mg, 0.099 mmol, 68.1% yield). LC-MS m/z 528.2 (M+H)+, 0.87 min (ret. time)

Example 226

5-(1-Ethyl-1H-1,2,3-triazol-4-yl)-3-(4-methyl-3-(((R)-4-methyl-1,1-dioxido-4,5-dihydrobenzo[f][1,2]thiazepin-2(3H)-yl)methyl)phenyl)pentanoic acid

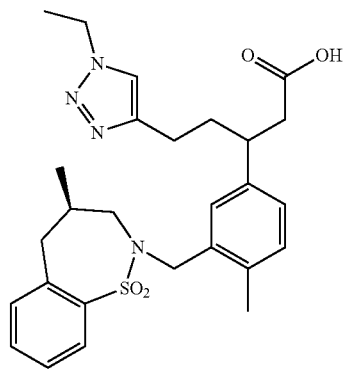 [SMILES: CCn1cc(CCC(CC(=O)O)c2ccc(C)c(CN3C[C@H](C)Cc4ccccc4S3(=O)=O)c2)nn1]

To a suspension of ethyl 5-(1-ethyl-1H-1,2,3-triazol-4-yl)-3-(3-(hydroxymethyl)-4-methylphenyl)pentanoate (80 mg, 0.232 mmol), (R)-4-methyl-2,3,4,5-tetrahydrobenzo[f][1,2]thiazepine 1,1-dioxide (48.9 mg, 0.232 mmol), and ADDP (117 mg, 0.463 mmol) in THF (3 mL) at RT was added tributylphosphine (0.128 mL, 0.463 mmol). The reaction mixture was stirred at RT for 20 h. The solvent was removed and the crude product purified with reverse-phase HPLC under neutral conditions to give desired intermediate. It was redissolved in MeOH (2 mL), 2 M LiOH (0.695 mL, 1.390 mmol) was added and the reaction mixture was heated in a Biotage microwave at high absorption for 30 min at 80° C. 0.8 mL of 1 N HCl and 1.5 mL of DMSO were added. Most solvents were removed and the sample was purified with reverse-phase HPLC with acidic condition to give the title compound (65.9 mg, 0.129 mmol, 55.7% yield). LC-MS m/z 511.4 (M+H)+, 1.00 min (ret. time)

Example 227

5-(1-Ethyl-1H-1,2,3-triazol-4-yl)-3-(3-((8-fluoro-4-methyl-1,1-dioxido-4,5-dihydrobenzo[f][1,2]thiazepin-2(3H)-yl)methyl)-4-methylphenyl)pentanoic acid

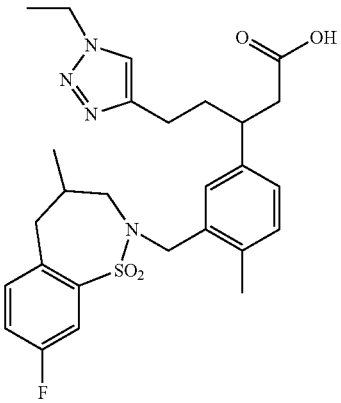 [SMILES: CCn1cc(CCC(CC(=O)O)c2ccc(C)c(CN3CC(C)Cc4ccc(F)cc4S3(=O)=O)c2)nn1]

Ethyl 5-(1-ethyl-1H-1,2,3-triazol-4-yl)-3-(3-((8-fluoro-4-methyl-1,1-dioxido-4,5-dihydrobenzo[f][1,2]thiazepin-2(3H)-yl)methyl)-4-methylphenyl)pentanoate

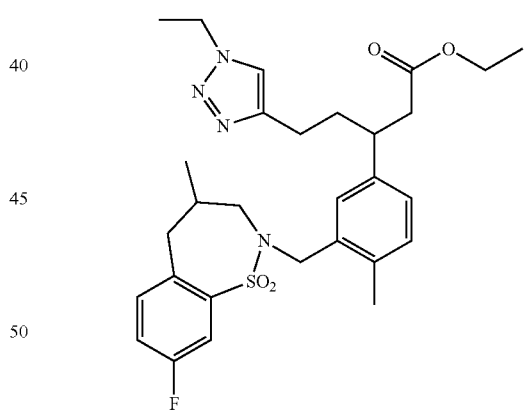

To a solution of ethyl 5-(1-ethyl-1H-1,2,3-triazol-4-yl)-3-(3-(hydroxymethyl)-4-methylphenyl)pentanoate (70 mg, 0.203 mmol), 8-fluoro-4-methyl-2,3,4,5-tetrahydrobenzo[f][1,2]thiazepine 1,1-dioxide (46.5 mg, 0.203 mmol), and 1,1'-(azodicarbonyl)dipiperidine (102 mg, 0.405 mmol) in THF (3 mL) at RT was added tri-n-butylphosphine (0.100 mL, 0.405 mmol). The reaction mixture was stirred at RT for 70 h. The solvent was removed and the crude product purified with reverse-phase HPLC under neutral conditions to give the title compound (70 mg, 0.126 mmol, 62.1% yield) was obtained. LC-MS m/z 557.0 (M+H)+, 1.21 min (ret. time)

5-(1-Ethyl-1H-1,2,3-triazol-4-yl)-3-(3-((8-fluoro-4-methyl-1,1-dioxido-4,5-dihydrobenzo[f][1,2]thiazepin-2(3H)-yl)methyl)-4-methylphenyl)pentanoic acid

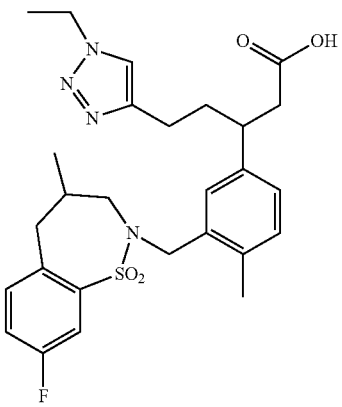 [SMILES: CCn1cc(CCC(CC(=O)O)c2ccc(C)c(CN3CC(C)Cc4ccc(F)cc4S3(=O)=O)c2)nn1]

To a solution of ethyl 5-(1-ethyl-1H-1,2,3-triazol-4-yl)-3-(3-((8-fluoro-4-methyl-1,1-dioxido-4,5-dihydrobenzo[f][1,2]thiazepin-2(3H)-yl)methyl)-4-methylphenyl)pentanoate (70 mg, 0.126 mmol) in MeOH (2 mL) was added 2M LiOH (0.440 mL, 0.880 mmol). The reaction mixture was heated in Biotage microwave at high absorption for 30 min at 80° C. 0.8 mL of 1 N HCl and 1.5 mL of DMSO were added. Most solvents were removed and the sample was purified with reverse-phase HPLC with acidic condition to give the title compound (56.7 mg, 0.107 mmol, 85% yield). LC-MS m/z 529.1 (M+H)$^+$, 1.04 min (ret. time)

Example 228

3-(3-((7-(3-Aminopropyl)-4-methyl-1,1-dioxido-4,5-dihydrobenzo[f][1,2]thiazepin-2(3H)-yl)methyl)-4-methylphenyl)-3-(1-methyl-1H-benzo[d][1,2,3]triazol-5-yl)propanoic acid trifluoroacetic acid salt

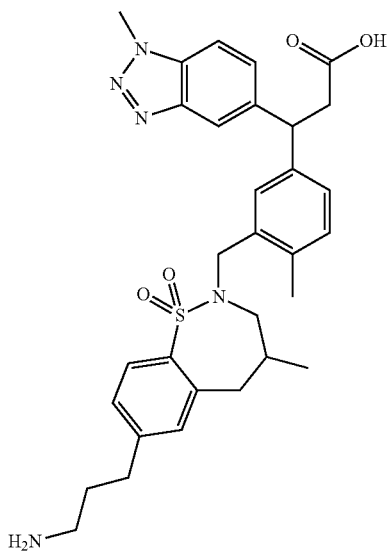 [SMILES: Cc1ccc(C(CC(=O)O)c2ccc3c(c2)nnn3C)cc1CN1CC(C)Cc2cc(CCCN)ccc2S1(=O)=O]

3-(3-((7-(3-((tert-Butoxycarbonyl)amino)propyl)-4-methyl-1,1-dioxido-4,5-dihydrobenzo[f][1,2]thiazepin-2

(3H)-yl)methyl)-4-methylphenyl)-3-(1-methyl-1H-benzo[d][1,2,3]triazol-5-yl)propanoic acid (80 mg, 0.118 mmol) in 1,4-dioxane (0.5 mL) was added 4 M HCl in dioxane (0.296 mL, 1.184 mmol). The resulting reaction mixture was stirred at RT for 19 h. More 4 M HCl in dioxane (0.296 mL, 1.184 mmol) was added and then stirred at RT for 24 h. The reaction mixture was concentrated and the sample was purified with reverse-phase HPLC with acidic condition to give the title compound (77.6 mg, 0.113 mmol, 95% yield) was obtained. LC-MS m/z 576.3 (M+H)$^+$, 0.79 min (ret. time)

Example 229

3-(4-Cyano-2-methylphenyl)-3-(3-((4-ethyl-1,1-dioxido-3,4-dihydro-2H-benzo[b][1,4,5]oxathiazepin-2-yl)methyl)-4-methylphenyl)propanoic acid

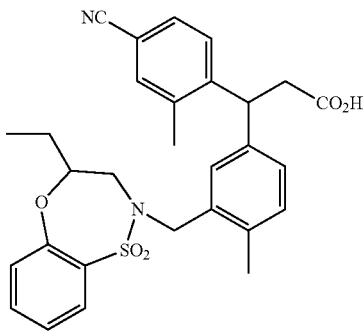 [SMILES: CCC1CN(Cc2cc(C(CC(=O)O)c3ccc(C#N)cc3C)ccc2C)S(=O)(=O)c2ccccc2O1]

(E)-methyl 3-(4-cyano-2-methylphenyl)acrylate

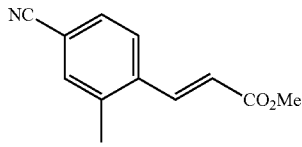

To a solution of 4-bromo-3-methylbenzonitrile (0.784 g, 4 mmol) in DMF (20 mL) was added methyl acrylate (1.812 mL, 20.00 mmol), DIPEA (1.747 mL, 10.00 mmol), Pd(OAc)$_2$ (0.090 g, 0.400 mmol) and tri-o-tolylphosphine (0.243 g, 0.800 mmol). The reaction mixture was then heated with microwave irradiation at 150° C. under N$_2$ atmosphere for 1 h. The reaction mixture was evaporated under vacuum to remove remaining methyl acrylate, then diluted with H$_2$O (20 mL), extracted with EtOAc (3×40 mL). The combined organic layer was washed with brine (50 mL), dried over MgSO$_4$, filtered, evaporated down under vacuum, and purified by flash chromatography to afford desired product (E)-methyl 3-(4-cyano-2-methylphenyl) acrylate (0.8815 g, 4.38 mmol, 110% yield). $^1$H-NMR (400 MHz, CHLOROFORM-d) δ ppm 2.47 (s, 3H) 3.84 (s, 3H) 6.43 (d, J=15.81 Hz, 1H) 7.47-7.55 (m, 2H) 7.61 (d, J=8.53 Hz, 1H) 7.92 (d, J=15.81 Hz, 1H).

489

Methyl 3-(4-cyano-2-methylphenyl)-3-(3-(hydroxymethyl)-4-methylphenyl)propanoate

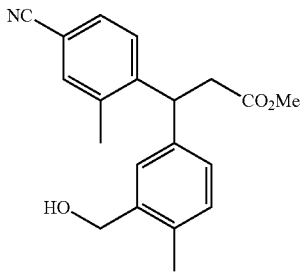 [SMILES: COC(=O)CC(c1ccc(C)c(CO)c1)c1ccc(C#N)cc1C]

To a solution of (E)-methyl 3-(4-cyano-2-methylphenyl)acrylate (0.88 g, 4.37 mmol) in 1,4-dioxane (25 mL) and water (8 mL) was added (3-(hydroxymethyl)-4-methylphenyl)boronic acid (1.452 g, 8.75 mmol), Et$_3$N (2.438 mL, 17.49 mmol) and [RhCl(cod)]$_2$ (0.108 g, 0.219 mmol). The resulting reaction mixture was stirred at 90° C. for 1 h. The reaction mixture was extracted with EtOAc (3×30 mL). The combined organic layer was dried over MgSO$_4$, filtered, evaporated down under vacuum, and purified by flash chromatography to afford desired product methyl 3-(4-cyano-2-methylphenyl)-3-(3-(hydroxymethyl)-4-methylphenyl)propanoate (1.2015 g, 3.72 mmol, 85% yield). LC-MS m/z 306.2 (M−OH)$^+$, 0.94 min (ret. time).

4-Ethyl-3,4-dihydro-2H-benzo[b][1,4,5]oxathiazepine 1,1-dioxide

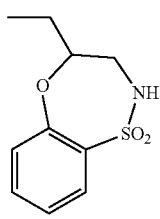

To a solution of 1-amino-2-butanol (1.897 mL, 20.00 mmol) in THF (40 mL) and water (10 mL) was added K$_2$CO$_3$ (2.76 g, 20.00 mmol) then 2-fluorobenzene-1-sulfonyl chloride (2.65 mL, 20 mmol). The resulting reaction mixture was stirred at RT for 20 h. The reaction mixture was diluted with H$_2$O (40 mL) and extracted with EtOAc (80+2×40 mL). The combined organic layer was washed with brine (60 mL), dried over MgSO$_4$, filtered, evaporated down under vacuum, dried under high vacuum. This intermediate was dissolved in dimethyl sulfoxide (80 mL) and was added KOtBu (6.73 g, 60.0 mmol). The resulting reaction was stirred at 80° C. for 17.5 h. The reaction mixture was diluted with H$_2$O (80 mL) and HCl (40 mL, 1 N) then extracted with EtOAc (200+2×100 mL). The combined organic layer was washed with brine (100 mL), dried over MgSO$_4$, filtered, evaporated down under vacuum, and purified by flash chromatography to afford desired product 4-ethyl-3,4-dihydro-2H-benzo[b][1,4,5]oxathiazepine 1,1-dioxide (4.1306 g, 18.17 mmol, 91% yield). LC-MS m/z 228.1 (M+H)$^+$, 0.75 min (ret. time).

490

3-(4-Cyano-2-methylphenyl)-3-(3-((4-ethyl-1,1-dioxido-3,4-dihydro-2H-benzo[b] [1,4,5]oxathiazepin-2-yl)methyl)-4-methylphenyl)propanoic acid

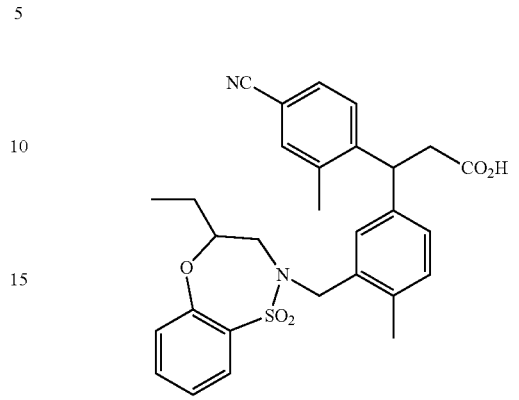

To a solution of methyl 3-(4-cyano-2-methylphenyl)-3-(3-(hydroxymethyl)-4-methylphenyl)propanoate (50 mg, 0.155 mmol) in THF (2 mL) was added 4-ethyl-3,4-dihydro-2H-benzo[b][1,4,5]oxathiazepine 1,1-dioxide (52.7 mg, 0.232 mmol), PS—PPh$_3$ (193 mg, 0.309 mmol) and DIAD (0.060 mL, 0.309 mmol). The resulting reaction mixture was stirred at RT for 50 min. The reaction mixture was filtered and evaporated down. This intermediate was redissolved in MeOH (2.0 mL). To the resulting solution was added NaOH (2 N) (0.387 mL, 0.773 mmol) and the mixture heated with microwave irradiation at 80° C. for 20 min. The reaction mixture was acidified with HCl (1 N) to pH ~5, evaporated down under vacuum, and purified with reverse phase HPLC to afford desired product 3-(4-cyano-2-methylphenyl)-3-(3-((4-ethyl-1,1-dioxido-3,4-dihydro-2H-benzo[b][1,4,5]oxathiazepin-2-yl)methyl)-4-methylphenyl)propanoic acid (42.7 mg, 0.082 mmol, 53.3% yield). LC-MS m/z 519.2 (M+H)$^+$, 1.13 min (ret. time).

Example 230

3-(4-Cyano-2-methylphenyl)-3-(3-((4-ethyl-1,1-dioxido-3,4-dihydro-2H-pyrido[2,3-b][1,4,5]oxathiazepin-2-yl)methyl)-4-methylphenyl)propanoic acid

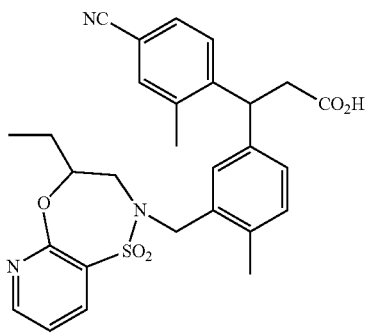 [SMILES: CCC1CN(Cc2cc(C(CC(=O)O)c3ccc(C#N)cc3C)ccc2C)S(=O)(=O)c2cccnc2O1]

4-Ethyl-3,4-dihydro-2H-pyrido[2,3-b][1,4,5]oxathiazepine 1,1-dioxide

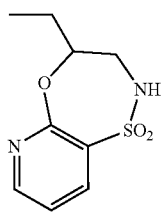

To a solution of 1-amino-2-butanol (1.897 mL, 20.00 mmol) in THF (40 mL) and water (10 mL) was added K₂CO₃ (2.76 g, 20.00 mmol) then 2-chloropyridine-3-sulfonyl chloride (2.89 mL, 20 mmol). The resulting reaction mixture was stirred at RT for 1 h. The reaction mixture was diluted with H2O and extracted with EtOAc (80+2×40 mL). The combined organic layer was washed with brine (60 mL), dried over MgSO₄, filtered, evaporated down under vacuum, dried under high vacuum. This intermediate was dissolved in dimethyl sulfoxide (80 mL) and was added KOtBu (6.73 g, 60.0 mmol). The resulting reaction was stirred at 80° C. for 90 min. The reaction mixture was diluted with H₂O (80 mL) before was added HCl (40 mL, 1 N) then extracted with EtOAc (200+2×100 mL). The combined organic layer was washed with brine (100 mL), dried over MgSO₄, filtered, evaporated down under vacuum, and purified by flash chromatography to afford desired product 4-ethyl-3,4-dihydro-2H-pyrido[2,3-b][1,4,5]oxathiazepine 1,1-dioxide (4.4145 g, 19.34 mmol, 97% yield). LC-MS m/z 229.2 (M+H)⁺, 0.45 min (ret. time).

3-(4-Cyano-2-methylphenyl)-3-(3-((4-ethyl-1,1-dioxido-3,4-dihydro-2H-pyrido[2,3-b][1,4,5]oxathiazepin-2-yl)methyl)-4-methylphenyl)propanoic acid

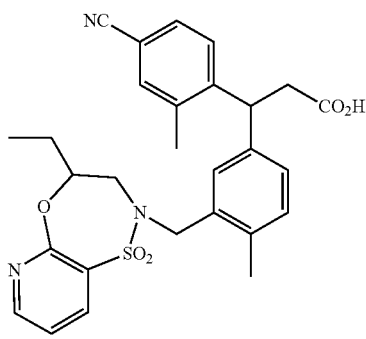 [SMILES: CCC1CN(Cc2cc(C(CC(=O)O)c3ccc(C#N)cc3C)ccc2C)S(=O)(=O)c2cccnc2O1]

To a solution of methyl 3-(4-cyano-2-methylphenyl)-3-(3-(hydroxymethyl)-4-methylphenyl)propanoate (50 mg, 0.155 mmol) in THF (2 mL) was added 4-ethyl-3,4-dihydro-2H-pyrido[2,3-b][1,4,5]oxathiazepine 1,1-dioxide (52.9 mg, 0.232 mmol), PS—PPh₃ (193 mg, 0.309 mmol) and DIAD (0.060 mL, 0.309 mmol). The resulting reaction mixture was stirred at RT for 50 min. The reaction mixture was filtered and evaporated down. This intermediate was redissolved in MeOH (2.000 mL). To the resulting solution was added NaOH (2 N) (0.387 mL, 0.773 mmol) and the mixture heated with microwave irradiation at 80° C. for 20 min. The reaction mixture was acidified with HCl (1 N) to pH ~5, evaporated down under vacuum, and purified with reverse phase HPLC to afford desired product 3-(4-cyano-2-methylphenyl)-3-(3-((4-ethyl-1,1-dioxido-3,4-dihydro-2H-pyrido[2,3-b][1,4,5]oxathiazepin-2-yl)methyl)-4-methylphenyl)propanoic acid (43.8 mg, 0.084 mmol, 54.5% yield). LC-MS m/z 520.1 (M+H)⁺, 1.03 min (ret. time).

Example 231

3-(4-Cyano-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid

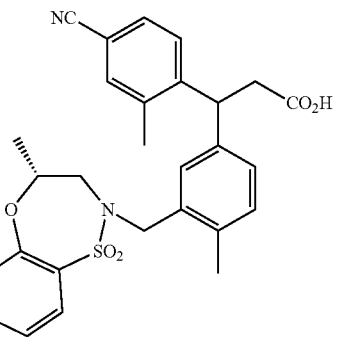

To a solution of methyl 3-(4-cyano-2-methylphenyl)-3-(3-(hydroxymethyl)-4-methylphenyl)propanoate (50 mg, 0.155 mmol) in THF (2 mL) was added (R)-4-methyl-3,4-dihydro-2H-benzo[b][1,4,5]oxathiazepine 1,1-dioxide (49.5 mg, 0.232 mmol), PS—PPh₃ (193 mg, 0.309 mmol) and DIAD (0.060 mL, 0.309 mmol). The resulting reaction mixture was stirred at RT for 50 min before was filtered then evaporated down. This intermediate was redissolved in MeOH (2.0 mL) before was added NaOH (2 N) (0.387 mL, 0.773 mmol) and the mixture heated with microwave irradiation at 80° C. for 20 min. The reaction mixture was acidified with HCl (1 N) to pH ~5 before was evaporated down under vacuum, and purified with reverse phase HPLC to afford desired product 3-(4-cyano-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid (33.5 mg, 0.066 mmol, 42.9% yield). LC-MS m/z 505.1 (M+H)⁺, 1.09 min (ret. time).

Example 232

3-(3,4-Difluorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid

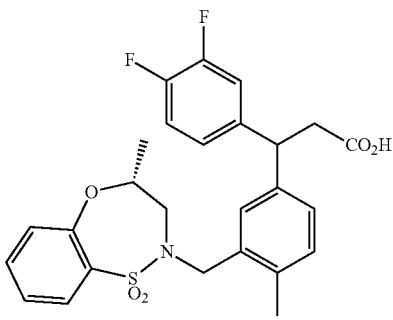 [SMILES: Cc1ccc(C(CC(=O)O)c2ccc(F)c(F)c2)cc1CN1C[C@@H](C)Oc2ccccc2S1(=O)=O]

(E)-methyl 3-(3-(hydroxymethyl)-4-methylphenyl)acrylate

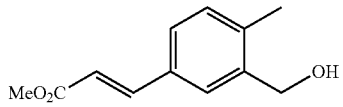

To a solution of (5-bromo-2-methylphenyl)methanol (1.82 g, 5.88 mmol) in DMF (20 mL) was added methyl acrylate (2.67 mL, 29.4 mmol), DIPEA (2.57 mL, 14.71 mmol), Pd(OAc)$_2$ (0.132 g, 0.588 mmol) and tri-o-tolylphosphine (0.358 g, 1.177 mmol). The reaction mixture was then heated with microwave irradiation at 130° C. under N$_2$ atmosphere for 1 h, heated again with microwave at 150° C. for 1 h. The reaction mixture was evaporated down under vacuum. The residue was purified by flash chromatography to afford desired product (E)-methyl 3-(3-(hydroxymethyl)-4-methylphenyl)acrylate (1.0271 g, 4.98 mmol, 85% yield). LC-MS m/z 207.1 (M+H)$^+$, 0.76 min (ret. time).

(R,E)-methyl 3-(4-methyl-3-((4-methyl-1,1-dioxido-3,4-dihydro-2H-benzo[b][1,4,5]oxathiazepin-2-yl)methyl)phenyl)acrylate

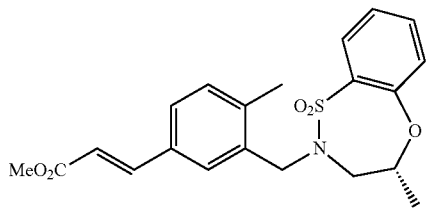 [SMILES: COC(=O)/C=C/c1ccc(C)c(CN2C[C@@H](C)Oc3ccccc3S2(=O)=O)c1]

To a solution of (E)-methyl 3-(3-(hydroxymethyl)-4-methylphenyl)acrylate (1.02 g, 4.95 mmol) in THF (100 mL) was added (R)-4-methyl-3,4-dihydro-2H-benzo[b][1,4,5]oxathiazepine 1,1-dioxide (1.371 g, 6.43 mmol), PS—PPh$_3$ (4.64 g, 7.42 mmol) then DIAD (1.442 mL, 7.42 mmol). The resulting reaction mixture was stirred at RT for 30 min. The reaction mixture was filtered. The filtrate was evaporated down under vacuum, and purified by flash chromatography to afford desired product (R,E)-methyl 3-(4-methyl-3-((4-methyl-1,1-dioxido-3,4-dihydro-2H-benzo[b][1,4,5]oxathiazepin-2-yl)methyl)phenyl)acrylate (1.0552 g, 2.63 mmol, 53.1% yield). LC-MS m/z 402.1 (M+H)$^+$, 1.12 min (ret. time).

3-(3,4-Difluorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid

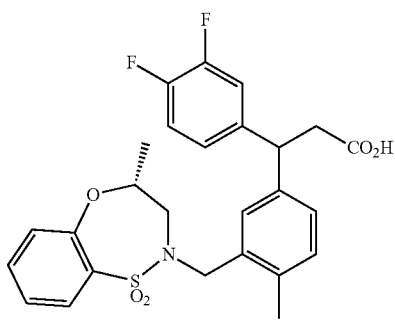 [SMILES: Cc1ccc(C(CC(=O)O)c2ccc(F)c(F)c2)cc1CN1C[C@@H](C)Oc2ccccc2S1(=O)=O]

To a solution of (R)-methyl 3-(4-methyl-3-((4-methyl-1,1-dioxido-3,4-dihydro-2H-benzo[b][1,4,5]oxathiazepin-2-yl)methyl)phenyl)acrylate (60.2 mg, 0.15 mmol) in 1,4-dioxane (2 mL) and water (0.7 mL) was added (3,4-difluorophenyl)boronic acid (47.4 mg, 0.300 mmol), Et$_3$N (0.084 mL, 0.600 mmol) and [RhCl(cod)]$_2$ (3.70 mg, 7.50 µmol). The resulting reaction mixture was stirred at 90° C. for 23 h. To the reaction mixture was added more Et$_3$N (0.042 mL, 0.300 mmol) and (3,4-difluorophenyl)boronic acid (23.69 mg, 0.150 mmol). The reaction mixture was stirred at 90° C. for 90 min. To the reaction mixture was added more [RhCl(cod)]$_2$ (3.70 mg, 7.50 µmol). The reaction mixture was stirred at 90° C. for 110 min. The reaction mixture was evaporated down under vacuum. This intermediate was redissolved in MeOH (2 mL). To the resulting solution was added NaOH (2 N) (0.375 mL, 0.750 mmol) and the mixture heated with microwave irradiation at 80° C. for 20 min. To the reaction mixture was added more NaOH (2 N) (0.150 mL, 0.300 mmol) and then heated with microwave irradiation at 80° C. for 20 min. The reaction mixture was acidified with HCl (3 N) to pH 4-5, evaporated down under vacuum, and purified with reverse phase HPLC to afford desired product 3-(3,4-difluorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid (46.1 mg, 0.092 mmol, 61.3% yield). LC-MS m/z 502.1 (M+H)$^+$, 1.15 min (ret. time).

Example 233

3-(4-Methyl-3-(((R)-4-methyl-1,1-dioxido-3,4-dihydro-2H-benzo[b][1,4,5]oxathiazepin-2-yl)methyl)phenyl)-3-(3,4,5-trifluorophenyl)propanoic acid

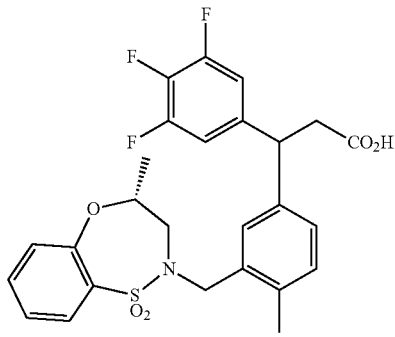 [SMILES: Cc1ccc(C(CC(=O)O)c2cc(F)c(F)c(F)c2)cc1CN1C[C@@H](C)Oc2ccccc2S1(=O)=O]

To a solution of (R,E)-methyl 3-(4-methyl-3-((4-methyl-1,1-dioxido-3,4-dihydro-2H-benzo[b][1,4,5]oxathiazepin-2-yl)methyl)phenyl)acrylate (60.2 mg, 0.15 mmol) in 1,4-dioxane (2 mL) and water (0.7 mL) was added (3,4,5-trifluorophenyl)boronic acid (52.8 mg, 0.300 mmol), Et$_3$N (0.084 mL, 0.600 mmol) and [RhCl(cod)]$_2$ (3.70 mg, 7.50 µmol). The resulting reaction mixture was stirred at 90° C. for 90 min. The reaction mixture was evaporated down under vacuum. This intermediate was redissolved in MeOH (2 mL). To the resulting solution was added NaOH (3 N) (0.400 mL, 1.200 mmol) and the mixture heated with microwave irradiation at 80° C. for 20 min. The reaction mixture was acidified with HCl (3 N) to pH 4-5, evaporated down under vacuum, and purified with reverse phase HPLC to afford desired product 3-(4-methyl-3-(((R)-4-methyl-1,1-dioxido-3,4-dihydro-2H-benzo[b][1,4,5]oxathiazepin-2-yl)methyl)phenyl)-3-(3,4,5-trifluorophenyl)propanoic acid

Example 234

3-(3-Fluorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid

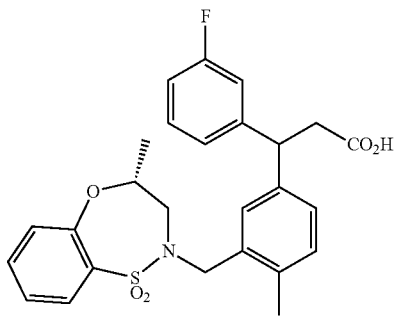 [SMILES: Cc1ccc(C(CC(=O)O)c2cccc(F)c2)cc1CN1C[C@@H](C)Oc2ccccc2S1(=O)=O]

To a solution of (R,E)-methyl 3-(4-methyl-3-((4-methyl-1,1-dioxido-3,4-dihydro-2H-benzo[b][1,4,5]oxathiazepin-2-yl)methyl)phenyl)acrylate (60.2 mg, 0.15 mmol) in 1,4-dioxane (2 mL) and water (0.7 mL) was added (3-fluorophenyl)boronic acid (42.0 mg, 0.300 mmol), Et₃N (0.084 mL, 0.600 mmol) and [RhCl(cod)]₂ (3.70 mg, 7.50 µmol). The resulting reaction mixture was stirred at 90° C. for 90 min. The reaction mixture was evaporated down under vacuum. This intermediate was redissolved in MeOH (2 mL). To the resulting solution was added NaOH (3 N) (0.400 mL, 1.200 mmol) and the mixture heated with microwave irradiation at 80° C. for 20 min. The reaction mixture was acidified with HCl (3 N) to pH 4-5, evaporated down under vacuum, and purified with reverse phase HPLC to afford desired product 3-(3-fluorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid (53.9 mg, 0.111 mmol, 74.3% yield). LC-MS m/z 484.3 (M+H)⁺, 1.12 min (ret. time).

Example 235

3-(4-Methyl-3-(((R)-4-methyl-1,1-dioxido-3,4-dihydro-2H-benzo[b][1,4,5]oxathiazepin-2-yl)methyl)phenyl)-3-phenylpropanoic acid

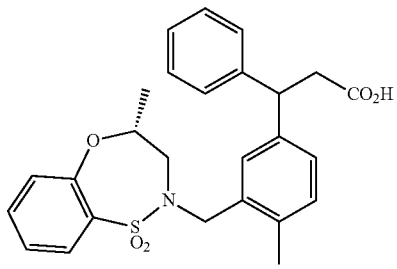 [SMILES: Cc1ccc(C(CC(=O)O)c2ccccc2)cc1CN1C[C@@H](C)Oc2ccccc2S1(=O)=O]

To a solution of (R,E)-methyl 3-(4-methyl-3-((4-methyl-1,1-dioxido-3,4-dihydro-2H-benzo[b][1,4,5]oxathiazepin-2-yl)methyl)phenyl)acrylate (60.2 mg, 0.15 mmol) in 1,4-dioxane (2 mL) and water (0.7 mL) was added phenylboronic acid (36.6 mg, 0.300 mmol), Et₃N (0.084 mL, 0.600 mmol) and [RhCl(cod)]₂ (3.70 mg, 7.50 µmol). The resulting reaction mixture was stirred at 90° C. for 1 h. The reaction mixture was evaporated down under vacuum. This intermediate was redissolved in MeOH (2 mL). To the resulting solution was added NaOH (3 N) (0.400 mL, 1.200 mmol) and the mixture heated with microwave irradiation at 80° C. for 20 min. The reaction mixture was acidified with HCl (3 N) to pH 4-5, evaporated down under vacuum, and purified with reverse phase HPLC to afford desired product 3-(4-methyl-3-(((R)-4-methyl-1,1-dioxido-3,4-dihydro-2H-benzo[b][1,4,5]oxathiazepin-2-yl)methyl)phenyl)-3-phenylpropanoic acid (48.6 mg, 0.104 mmol, 69.6% yield). LC-MS m/z 466.3 (M+H)⁺, 1.14 min (ret. time).

Example 236

3-(4-Methyl-3-(((R)-4-methyl-1,1-dioxido-3,4-dihydro-2H-benzo[b][1,4,5]oxathiazepin-2-yl)methyl)phenyl)-3-(o-tolyl)propanoic acid

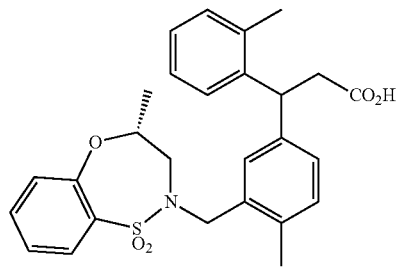 [SMILES: Cc1ccc(C(CC(=O)O)c2ccccc2C)cc1CN1C[C@@H](C)Oc2ccccc2S1(=O)=O]

To a solution of (R,E)-methyl 3-(4-methyl-3-((4-methyl-1,1-dioxido-3,4-dihydro-2H-benzo[b][1,4,5]oxathiazepin-2-yl)methyl)phenyl)acrylate (60.2 mg, 0.15 mmol) in 1,4-dioxane (2 mL) and water (0.7 mL) was added o-tolylboronic acid (40.8 mg, 0.300 mmol), Et₃N (0.084 mL, 0.600 mmol) and [RhCl(cod)]₂ (3.70 mg, 7.50 µmol). The resulting reaction mixture was stirred at 90° C. for 1 h. The reaction mixture was then heated with microwave irradiation at 130° C. for 30 min. The resulting reaction mixture was evaporated down under vacuum. This intermediate was redissolved in MeOH (2 mL). To the resulting solution was added NaOH (3 N) (0.400 mL, 1.200 mmol) and the mixture heated with microwave irradiation at 80° C. for 20 min. The reaction mixture was acidified with HCl (3 N) to pH 4-5, evaporated down under vacuum, and purified with reverse phase HPLC to afford desired product 3-(4-methyl-3-(((R)-4-methyl-1,1-dioxido-3,4-dihydro-2H-benzo[b][1,4,5]oxathiazepin-2-yl)methyl)phenyl)-3-(o-tolyl)propanoic acid (31.4 mg, 0.065 mmol, 43.6% yield). LC-MS m/z 480.1 (M+H)⁺, 1.18 min (ret. time).

Example 237

3-(4-Fluorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid

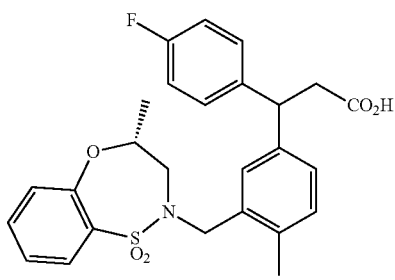 [SMILES: Cc1ccc(C(CC(=O)O)c2ccc(F)cc2)cc1CN1C[C@@H](C)Oc2ccccc2S1(=O)=O]

To a solution of (R,E)-methyl 3-(4-methyl-3-((4-methyl-1,1-dioxido-3,4-dihydro-2H-benzo[b][1,4,5]oxathiazepin-2-yl)methyl)phenyl)acrylate (60.2 mg, 0.15 mmol) in 1,4-dioxane (2 mL) and water (0.7 mL) was added (4-fluorophenyl)boronic acid (42.0 mg, 0.300 mmol), $Et_3N$ (0.084 mL, 0.600 mmol) and $[RhCl(cod)]_2$ (3.70 mg, 7.50 μmol). The resulting reaction mixture was stirred at 90° C. for 1 h. The reaction mixture was evaporated down under vacuum. This intermediate was redissolved in MeOH (2 mL). To the resulting solution was added NaOH (3 N) (0.400 mL, 1.200 mmol) and the mixture heated with microwave irradiation at 80° C. for 20 min. The reaction mixture was acidified with HCl (3 N) to pH 4-5, evaporated down under vacuum, and purified with reverse phase HPLC to afford desired product 3-(4-fluorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid (41.5 mg, 0.086 mmol, 57.2% yield). LC-MS m/z 484.3 (M+H)$^+$, 1.14 min (ret. time).

Example 238

3-(4-Fluoro-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid

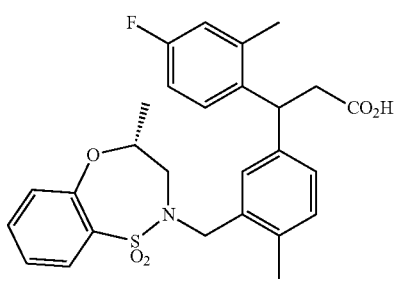 [SMILES: Cc1ccc(C(CC(=O)O)c2ccc(F)cc2C)cc1CN1C[C@@H](C)Oc2ccccc2S1(=O)=O]

To a solution of (R,E)-methyl 3-(4-methyl-3-((4-methyl-1,1-dioxido-3,4-dihydro-2H-benzo[b][1,4,5]oxathiazepin-2-yl)methyl)phenyl)acrylate (60.2 mg, 0.15 mmol) in 1,4-dioxane (2 mL) and water (0.7 mL) was added (4-fluoro-2-methylphenyl)boronic acid (46.2 mg, 0.300 mmol), $Et_3N$ (0.084 mL, 0.600 mmol) and $[RhCl(cod)]_2$ (3.70 mg, 7.50 μmol). The resulting reaction mixture was stirred at 90° C. for 1 h. The reaction mixture was then heated with microwave irradiation at 130° C. for 30 min. The reaction mixture was evaporated down under vacuum. This intermediate was redissolved in MeOH (2 mL). To the resulting solution was added NaOH (3 N) (0.400 mL, 1.200 mmol) and the mixture heated with microwave irradiation at 80° C. for 20 min. The reaction mixture was acidified with HCl (3 N) to pH 4-5, evaporated down under vacuum, and purified with reverse phase HPLC to afford desired product 3-(4-fluoro-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid (12.4 mg, 0.025 mmol, 16.61% yield). LC-MS m/z 498.5 (M+H)$^+$, 1.20 min (ret. time).

Example 239

3-(4-Chloro-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid

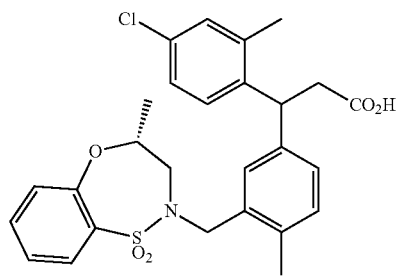 [SMILES: Cc1ccc(C(CC(=O)O)c2ccc(Cl)cc2C)cc1CN1C[C@@H](C)Oc2ccccc2S1(=O)=O]

To a solution of (R,E)-methyl 3-(4-methyl-3-((4-methyl-1,1-dioxido-3,4-dihydro-2H-benzo[b][1,4,5]oxathiazepin-2-yl)methyl)phenyl)acrylate (60.2 mg, 0.15 mmol) in 1,4-dioxane (2 mL) and water (0.7 mL) was added (4-chloro-2-methylphenyl)boronic acid (51.1 mg, 0.300 mmol), $Et_3N$ (0.084 mL, 0.600 mmol) and $[RhCl(cod)]_2$ (3.70 mg, 7.50 μmol). The resulting reaction mixture was stirred at 90° C. for 2 h. The reaction mixture was evaporated down under vacuum. This intermediate was redissolved in MeOH (2 mL). To the resulting solution was added NaOH (3 N) (0.400 mL, 1.200 mmol) and the mixture heated with microwave irradiation at 80° C. for 20 min. The reaction mixture was acidified with HCl (3 N) to pH 4-5, evaporated down under vacuum, and purified with reverse phase HPLC to afford desired product 3-(4-chloro-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid (15.6 mg, 0.030 mmol, 20.23% yield). LC-MS m/z 514.3 (M+H)$^+$, 1.21 min (ret. time).

Example 240

3-(4-Chlorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid

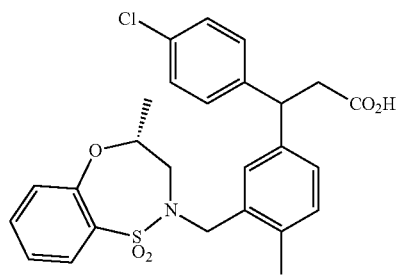

To a solution of (R,E)-methyl 3-(4-methyl-3-((4-methyl-1,1-dioxido-3,4-dihydro-2H-benzo[b][1,4,5]oxathiazepin-2-yl)methyl)phenyl)acrylate (60.2 mg, 0.15 mmol) in 1,4-dioxane (2 mL) and water (0.7 mL) was added (4-chlorophenyl)boronic acid (46.9 mg, 0.300 mmol), Et₃N (0.084 mL, 0.600 mmol) and [RhCl(cod)]₂ (3.70 mg, 7.50 µmol). The resulting reaction mixture was stirred at 90° C. for 2 h. The reaction mixture was evaporated down under vacuum. This intermediate was redissolved in MeOH (2 mL). To the resulting solution was added NaOH (3 N) (0.400 mL, 1.200 mmol) and the mixture heated with microwave irradiation at 80° C. for 20 min. The reaction mixture was acidified with HCl (3 N) to pH 4-5, evaporated down under vacuum, and purified with reverse phase HPLC to afford desired product 3-(4-chlorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid (44.9 mg, 0.090 mmol, 59.9% yield). LC-MS m/z 500.3 (M+H)⁺, 1.18 min (ret. time).

Example 241

3-(4-Carbamoyl-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid

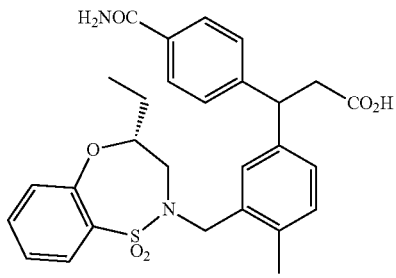 [SMILES: CC[C@@H]1CN(Cc2cc(C(CC(=O)O)c3ccc(C(N)=O)cc3)ccc2C)S(=O)(=O)c2ccccc2O1]

To a solution of methyl 3-(4-cyano-2-methylphenyl)-3-(3-(hydroxymethyl)-4-methylphenyl)propanoate (50 mg, 0.155 mmol) in THF (2 mL) was added (R)-4-ethyl-3,4-dihydro-2H-benzo[b][1,4,5]oxathiazepine 1,1-dioxide (52.7 mg, 0.232 mmol), PS—PPh₃ (193 mg, 0.309 mmol) and DIAD (0.060 mL, 0.309 mmol). The resulting reaction mixture was stirred at RT for 30 min. The reaction mixture was filtered, evaporated down under vacuum. This intermediate was redissolved in EtOH (2 mL). To the resulting solution was added NaOH (2 N) (0.541 mL, 1.082 mmol) and H₂O₂ (~30%) (0.111 mL, 1.082 mmol). The resulting reaction mixture was stirred at RT for 17 h. The reaction mixture was acidified with HCl (1 N) to pH ~5, evaporated down under vacuum, and purified with reverse phase HPLC to afford desired product 3-(4-carbamoyl-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid (29.5 mg, 0.055 mmol, 35.6% yield). LC-MS m/z 537.3 (M+H)⁺, 0.97 min (ret. time).

Example 242

3-(4-Acetylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid

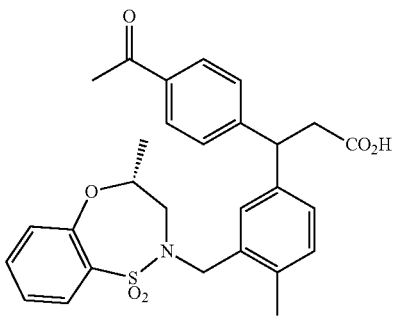 [SMILES: CC(=O)c1ccc(C(CC(=O)O)c2ccc(C)c(CN3C[C@@H](C)Oc4ccccc4S3(=O)=O)c2)cc1]

To a solution of (R,E)-methyl 3-(4-methyl-3-((4-methyl-1,1-dioxido-3,4-dihydro-2H-benzo[b][1,4,5]oxathiazepin-2-yl)methyl)phenyl)acrylate (60.2 mg, 0.15 mmol) in 1,4-dioxane (2 mL) and water (0.7 mL) was added (4-acetylphenyl)boronic acid (49.2 mg, 0.300 mmol), Et₃N (0.084 mL, 0.600 mmol) and [RhCl(cod)]₂ (3.70 mg, 7.50 µmol). The resulting reaction mixture was stirred at 90° C. for 90 min. The reaction mixture was evaporated down under vacuum. This intermediate was redissolved in MeOH (2 mL). To the resulting solution was added NaOH (3 N) (0.400 mL, 1.200 mmol) and the mixture heated with microwave irradiation at 80° C. for 20 min. The reaction mixture was acidified with HCl (3 N) to pH 4-5, evaporated down under vacuum, and purified with reverse phase HPLC to afford desired product 3-(4-acetylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid (52.4 mg, 0.103 mmol, 68.8% yield). LC-MS m/z 508.3 (M+H)⁺, 1.06 min (ret. time).

Example 243

4-(2-Carboxy-1-(4-methyl-3-(((R)-4-methyl-1,1-dioxido-3,4-dihydro-2H-benzo[b][1,4,5]oxathiazepin-2-yl)methyl)phenyl)ethyl)-2-(ethylcarbamoyl)benzoic acid; 5-(2-carboxy-1-(4-methyl-3-(((R)-4-methyl-1,1-dioxido-3,4-dihydro-2H-benzo[b][1,4,5]oxathiazepin-2-yl)methyl)phenyl)ethyl)-2-(ethylcarbamoyl)benzoic acid (unknown ratio mixture)

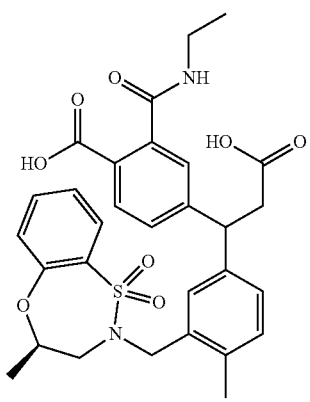

-continued

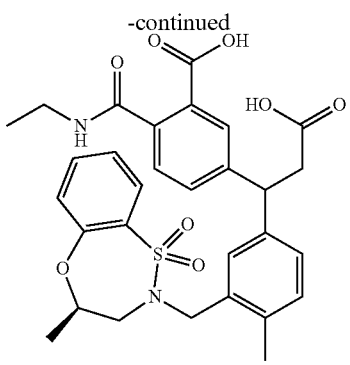

To a solution of (R,E)-methyl 3-(4-methyl-3-((4-methyl-1,1-dioxido-3,4-dihydro-2H-benzo[b][1,4,5]oxathiazepin-2-yl)methyl)phenyl)acrylate (60.2 mg, 0.15 mmol) in 1,4-dioxane (2 mL) and water (0.7 mL) was added (2-ethyl-1,3-dioxoisoindolin-5-yl)boronic acid (65.7 mg, 0.300 mmol), Et$_3$N (0.084 mL, 0.600 mmol) and [RhCl(cod)]$_2$ (3.70 mg, 7.50 µmol). The resulting reaction mixture was stirred at 90° C. for 2.5 h. To the reaction mixture was added more (2-ethyl-1,3-dioxoisoindolin-5-yl)boronic acid (32.9 mg, 0.150 mmol) and then stirred at 90° C. for 90 min. To the reaction mixture was added more Et$_3$N (0.084 mL, 0.600 mmol) and [RhCl(cod)]$_2$ (3.70 mg, 7.50 µmol) then stirred at 90° C. for 30 min. The reaction mixture was evaporated under vacuum. This intermediate was redissolved in MeOH (2 mL). To the resulting solution was added NaOH (3 N) (0.400 mL, 1.200 mmol) and the mixture heated with microwave irradiation at 80° C. for 20 min. The reaction mixture was acidified with HCl (3 N) to pH 4-5, evaporated down under vacuum, and purified with reverse phase HPLC to afford desired product 4-(2-carboxy-1-(4-methyl-3-(((R)-4-methyl-1,1-dioxido-3,4-dihydro-2H-benzo[b][1,4,5]oxathiazepin-2-yl)methyl)phenyl)ethyl)-2-(ethylcarbamoyl)benzoic acid; 5-(2-carboxy-1-(4-methyl-3-(((R)-4-methyl-1,1-dioxido-3,4-dihydro-2H-benzo[b][1,4,5]oxathiazepin-2-yl)methyl)phenyl)ethyl)-2-(ethylcarbamoyl)benzoic acid (unknown ratio mixture) (26.4 mg, 0.023 mmol, 15.16% yield). LC-MS m/z 550.3 (M+H)$^+$, 0.91 min (ret. time).

Example 244

3-(1-(2-((Tert-butoxycarbonyl)amino)ethyl)-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

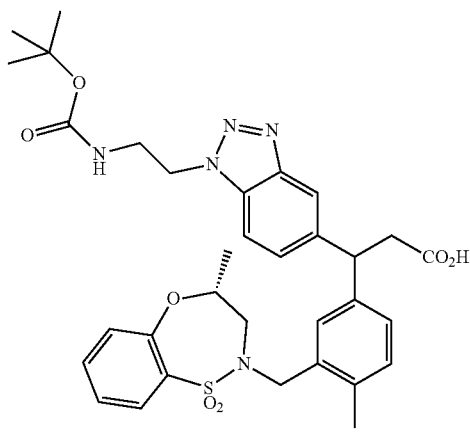 [SMILES: Cc1ccc(C(CC(=O)O)c2ccc3c(c2)nnn3CCNC(=O)OC(C)(C)C)cc1CN1C[C@@H](C)Oc2ccccc2S1(=O)=O]

To a solution of (E)-ethyl 3-(1-(2-((tert-butoxycarbonyl)amino)ethyl)-1H-benzo[d][1,2,3]triazol-5-yl)acrylate (108 mg, 0.3 mmol) in 1,4-dioxane (4 mL) and water (1.4 mL) was added (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (266 mg, 0.600 mmol), Et$_3$N (0.167 mL, 1.200 mmol) and [RhCl(cod)]$_2$ (7.40 mg, 0.015 mmol). The resulting reaction mixture was stirred at 90° C. for 2.5 h. To the reaction mixture was added more (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (133 mg, 0.300 mmol) and then stirred at 90° C. for 90 min. To the reaction mixture was added more Et$_3$N (0.167 mL, 1.200 mmol) and [RhCl(cod)]$_2$ (7.40 mg, 0.015 mmol) then stirred at 90° C. for 30 min. The reaction mixture was evaporated down under vacuum. This intermediate was redissolved in MeOH (4 mL). To the resulting solution was added NaOH (3 N) (0.800 mL, 2.400 mmol) and the mixture heated with microwave irradiation at 80° C. for 20 min before was acidified with HCl (3 N) to pH 4-5, evaporated down under vacuum, and purified with reverse phase HPLC to afford desired product 3-(1-(2-((tert-butoxycarbonyl)amino)ethyl)-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid (155.0 mg, 0.239 mmol, 80% yield). LC-MS m/z 650.5 (M+H)$^+$, 1.02 min (ret. time).

Example 245

3-(4-Methyl-3-(((R)-4-methyl-1,1-dioxido-3,4-dihydro-2H-benzo[b][1,4,5]oxathiazepin-2-yl)methyl)phenyl)-3-(3-oxo-2,3-dihydro-1H-inden-5-yl)propanoic acid

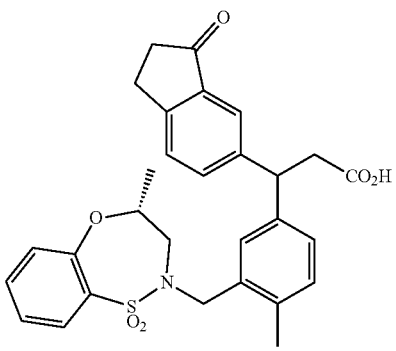 [SMILES: Cc1ccc(C(CC(=O)O)c2ccc3c(c2)C(=O)CC3)cc1CN1C[C@@H](C)Oc2ccccc2S1(=O)=O]

To a solution of (R,E)-methyl 3-(4-methyl-3-((4-methyl-1,1-dioxido-3,4-dihydro-2H-benzo[b][1,4,5]oxathiazepin-2-yl)methyl)phenyl)acrylate (60.2 mg, 0.15 mmol) in 1,4-dioxane (2 mL) and water (0.7 mL) was added 6-(4,4,5,5-tetramethyl-1,3,2-dioxaborolan-2-yl)-2,3-dihydro-1H-inden-1-one (77 mg, 0.300 mmol), Et$_3$N (0.084 mL, 0.600 mmol) and [RhCl(cod)]$_2$ (3.70 mg, 7.50 µmol). The resulting reaction mixture was stirred at 90° C. for 80 min. The reaction mixture was evaporated down under vacuum. This intermediate was redissolved in MeOH (2 mL). To the resulting solution was added NaOH (3 N) (0.400 mL, 1.200 mmol) and the mixture heated with microwave irradiation at 80° C. for 20 min. The reaction mixture was acidified with HCl (3 N) to pH 4-5, evaporated down under vacuum, and purified with reverse phase HPLC to afford desired product 3-(4-methyl-3-(((R)-4-methyl-1,1-dioxido-3,4-dihydro-2H-benzo[b][1,4,5]oxathiazepin-2-yl)methyl)phenyl)-3-(3-oxo-2,3-dihydro-1H-inden-5-yl)propanoic acid (24.1 mg, 0.046 mmol, 30.9% yield). LC-MS m/z 520.1 (M+H)⁺, 1.03 min (ret. time).

Example 246

3-(1-(3-((Tert-butoxycarbonyl)amino)propyl)-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

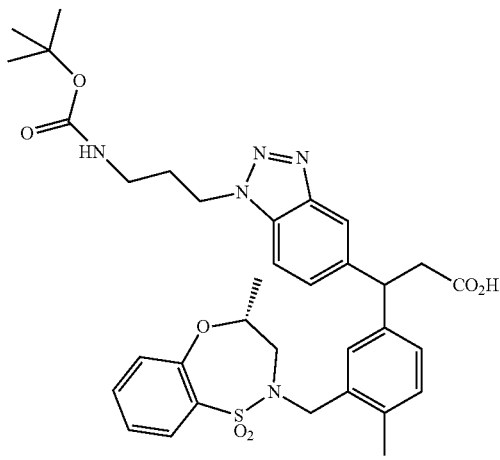 [SMILES: Cc1ccc(C(CC(=O)O)c2ccc3c(c2)nnn3CCCNC(=O)OC(C)(C)C)cc1CN1C[C@@H](C)Oc2ccccc2S1(=O)=O]

To a solution of (E)-ethyl 3-(1-(3-((tert-butoxycarbonyl)amino)propyl)-1H-benzo[d][1,2,3]triazol-5-yl)acrylate (112 mg, 0.3 mmol) in 1,4-dioxane (4 mL) and water (1.4 mL) was added (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (266 mg, 0.600 mmol), Et₃N (0.167 mL, 1.200 mmol) and [RhCl(cod)]₂ (7.40 mg, 0.015 mmol). The resulting reaction mixture was stirred at 90° C. for 80 min. The reaction mixture was evaporated down under vacuum. This intermediate was redissolved in MeOH (4 mL). To the resulting solution was added NaOH (3 N) (0.800 mL, 2.400 mmol) and the mixture heated with microwave irradiation at 80° C. for 20 min before was acidified with HCl (3 N) to pH 4-5, evaporated down under vacuum, and purified with reverse phase HPLC to afford desired product 3-(1-(3-((tert-butoxycarbonyl)amino)propyl)-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid (133.6 mg, 0.201 mmol, 67.1% yield). LC-MS m/z 664.0 (M+H)⁺, 1.09 min (ret. time).

Example 247

3-(4-Methyl-3-(((R)-4-methyl-1,1-dioxido-3,4-dihydro-2H-benzo[b][1,4,5]oxathiazepin-2-yl)methyl)phenyl)-3-(4-(methylthio)phenyl)propanoic acid

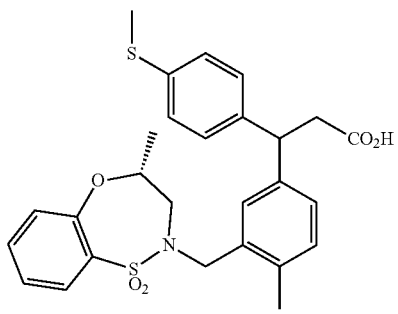 [SMILES: CSc1ccc(C(CC(=O)O)c2ccc(C)c(CN3C[C@@H](C)Oc4ccccc4S3(=O)=O)c2)cc1]

Methyl 3-(4-methyl-3-(((R)-4-methyl-1,1-dioxido-3,4-dihydro-2H-benzo[b][1,4,5]oxathiazepin-2-yl)methyl)phenyl)-3-(4-(methylthio)phenyl)propanoate

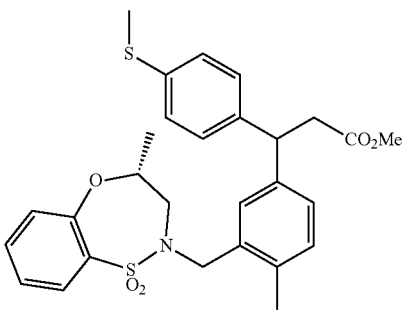 [SMILES: COC(=O)CC(c1ccc(SC)cc1)c1ccc(C)c(CN2C[C@@H](C)Oc3ccccc3S2(=O)=O)c1]

To a solution of (R,E)-methyl 3-(4-methyl-3-((4-methyl-1,1-dioxido-3,4-dihydro-2H-benzo[b][1,4,5]oxathiazepin-2-yl)methyl)phenyl)acrylate (161 mg, 0.4 mmol) in 1,4-dioxane (6 mL) and water (2 mL) was added (4-(methylthio)phenyl)boronic acid (134 mg, 0.800 mmol), Et₃N (0.223 mL, 1.600 mmol) and [RhCl(cod)]₂ (9.86 mg, 0.020 mmol). The resulting reaction mixture was stirred at 90° C. for 100 min. The reaction mixture was evaporated down under vacuum, and purified by flash chromatography to afford desired product methyl 3-(4-methyl-3-(((R)-4-methyl-1,1-dioxido-3,4-dihydro-2H-benzo[b][1,4,5]oxathiazepin-2-yl)methyl)phenyl)-3-(4-(methylthio)phenyl)propanoate (206.5 mg, 0.393 mmol, 98% yield). LC-MS m/z 526.4 (M+H)⁺, 1.30 min (ret. time).

3-(4-Methyl-3-(((R)-4-methyl-1,1-dioxido-3,4-dihydro-2H-benzo[b][1,4,5]oxathiazepin-2-yl)methyl)phenyl)-3-(4-(methylthio)phenyl)propanoic acid

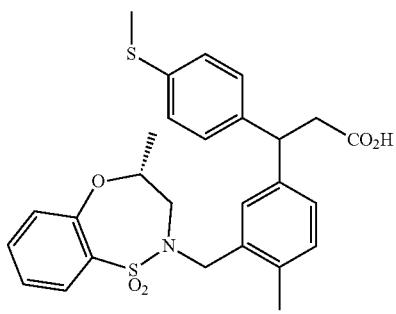 [SMILES: CSc1ccc(C(CC(=O)O)c2ccc(C)c(CN3C[C@@H](C)Oc4ccccc4S3(=O)=O)c2)cc1]

To a solution of methyl 3-(4-methyl-3-(((R)-4-methyl-1,1-dioxido-3,4-dihydro-2H-benzo[b][1,4,5]oxathiazepin-2-yl)methyl)phenyl)-3-(4-(methylthio)phenyl)propanoate (31.5 mg, 0.06 mmol) in MeOH (2.0 mL) was added NaOH (2.0 N) (0.150 mL, 0.300 mmol) and the mixture heated with microwave irradiation at 80° C. for 20 min. The reaction mixture was acidified with HCl (2 N) to pH ~4, evaporated down under vacuum, and purified with reverse phase HPLC to afford desired product 3-(4-methyl-3-(((R)-4-methyl-1,1-dioxido-3,4-dihydro-2H-benzo[b][1,4,5]oxathiazepin-2-yl)methyl)phenyl)-3-(4-(methylthio)phenyl)propanoic acid (19.6 mg, 0.038 mmol, 63.8% yield). LC-MS m/z 512.4 (M+H)$^+$, 1.20 min (ret. time).

Example 248

3-(4-Methyl-3-(((R)-4-methyl-1,1-dioxido-3,4-dihydro-2H-benzo[b][1,4,5]oxathiazepin-2-yl)methyl)phenyl)-3-(1-oxo-2,3-dihydro-1H-inden-5-yl)propanoic acid

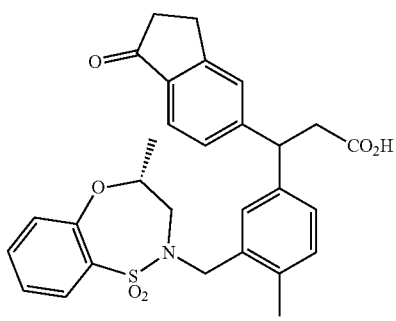 [SMILES: Cc1ccc(C(CC(=O)O)c2ccc3c(c2)CCC3=O)cc1CN1C[C@@H](C)Oc2ccccc2S1(=O)=O]

To a solution of (R,E)-methyl 3-(4-methyl-3-((4-methyl-1,1-dioxido-3,4-dihydro-2H-benzo[b][1,4,5]oxathiazepin-2-yl)methyl)phenyl)acrylate (60.2 mg, 0.15 mmol) in 1,4-dioxane (2 mL) and water (0.7 mL) was added 5-(4,4,5,5-tetramethyl-1,3,2-dioxaborolan-2-yl)-2,3-dihydro-1H-inden-1-one (77 mg, 0.300 mmol), Et$_3$N (0.084 mL, 0.600 mmol) and [RhCl(cod)]$_2$ (3.70 mg, 7.50 μmol). The resulting reaction mixture was stirred at 90° C. for 19 h. The reaction mixture was evaporated down under vacuum. This intermediate was redissolved in MeOH (2 mL). To the resulting solution was added NaOH (3 N) (0.400 mL, 1.200 mmol) and the mixture heated with microwave irradiation at 80° C. for 20 min. The reaction mixture was acidified with HCl (3 N) to pH ~4, evaporated down under vacuum, and purified with reverse phase HPLC to afford desired product 3-(4-methyl-3-(((R)-4-methyl-1,1-dioxido-3,4-dihydro-2H-benzo[b][1,4,5]oxathiazepin-2-yl)methyl)phenyl)-3-(1-oxo-2,3-dihydro-1H-inden-5-yl)propanoic acid (16.4 mg, 0.032 mmol, 21.04% yield). LC-MS m/z 520.2 (M+H)$^+$, 1.02 min (ret. time).

Example 249

3-(2,4-Difluorophenyl)-3-(3-(((R)-4-ethyl-1,1-dioxido-3,4-dihydro-2H-benzo[b][1,4,5]oxathiazepin-2-yl)methyl)-4-methylphenyl)propanoic acid

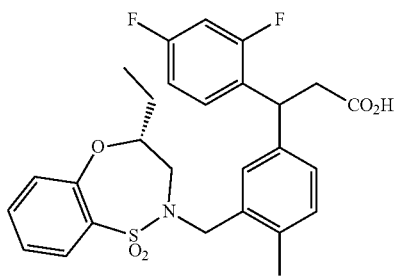 [SMILES: CC[C@@H]1CN(Cc2cc(C(CC(=O)O)c3ccc(F)cc3F)ccc2C)S(=O)(=O)c2ccccc2O1]

(E)-Methyl 3-(2,4-difluorophenyl)acrylate

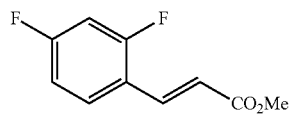

To a solution of trimethyl phosphonoacetate (1.425 mL, 8.80 mmol) in THF (30 mL) was added KOtBu (0.987 g, 8.80 mmol) and stirred at RT for 10 min before was added 2,4-difluorobenzaldehyde (0.875 mL, 8 mmol) in THF (5 mL). The resulting reaction mixture was stirred at RT for 160 min. To the reaction mixture was added more trimethyl phosphonoacetate (0.648 mL, 4.00 mmol) then KOtBu (0.449 g, 4.00 mmol). The resulting reaction mixture was stirred at RT for 30 min. To the reaction mixture was added H$_2$O (20 mL), extracted with EtOAc (3×30 mL). The combined organic layer was washed with brine (20 mL), dried over MgSO$_4$, filtered, evaporated down under vacuum to afford desired intermediate (E)-methyl 3-(2,4-difluorophenyl)acrylate (1.5710 g, 7.93 mmol, 99% yield). LC-MS m/z 199.1 (M+H)$^+$, 0.94 min (ret. time).

507

Methyl 3-(2,4-difluorophenyl)-3-(3-(hydroxymethyl)-4-methylphenyl)propanoate

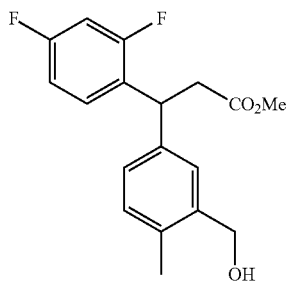 [SMILES: COC(=O)CC(c1ccc(C)c(CO)c1)c1ccc(F)cc1F]

To a solution of (E)-methyl 3-(2,4-difluorophenyl)acrylate (396 mg, 2 mmol) in 1,4-dioxane (10 mL) and water (3 mL) was added (3-(hydroxymethyl)-4-methylphenyl)boronic acid (664 mg, 4.00 mmol), Et₃N (1.115 mL, 8.00 mmol) and [RhCl(cod)]₂ (49.3 mg, 0.100 mmol). The resulting reaction mixture was stirred at 90° C. for 19 h. The reaction mixture was extracted with EtOAc (3×15 mL). The combined organic layer was dried over MgSO₄, filtered, evaporated down under vacuum, and purified by flash chromatography to afford desired product methyl 3-(2,4-difluorophenyl)-3-(3-(hydroxymethyl)-4-methylphenyl)propanoate (522.3 mg, 1.631 mmol, 82% yield). LC-MS m/z 303.1 (M+H)⁺, 0.98 min (ret. time).

3-(2,4-Difluorophenyl)-3-(3-(((R)-4-ethyl-1,1-dioxido-3,4-dihydro-2H-benzo[b][1,4,5]oxathiazepin-2-yl)methyl)-4-methylphenyl)propanoic acid

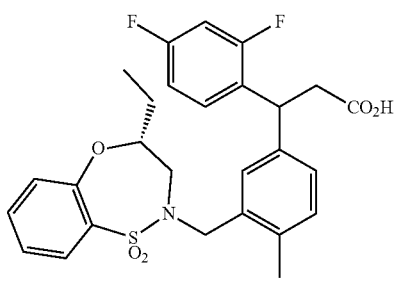 [SMILES: CC[C@@H]1CN(Cc2cc(C(CC(=O)O)c3ccc(F)cc3F)ccc2C)S(=O)(=O)c2ccccc2O1]

To a solution of methyl 3-(2,4-difluorophenyl)-3-(3-(hydroxymethyl)-4-methylphenyl)propanoate (50 mg, 0.156 mmol) in THF (2 mL) was added (R)-4-ethyl-3,4-dihydro-2H-benzo[b][1,4,5]oxathiazepine 1,1-dioxide (53.2 mg, 0.234 mmol), PS—PPh₃ (195 mg, 0.312 mmol) and DIAD (0.061 mL, 0.312 mmol). The resulting reaction mixture was stirred at RT for 45 min. The reaction mixture was filtered and evaporated down. This intermediate was redissolved in MeOH (2.000 mL). To the resulting solution was added NaOH (2 N) (0.390 mL, 0.780 mmol) and the mixture heated with microwave irradiation at 80° C. for 20 min. The reaction mixture was acidified with HCl (1 N) to pH ~5, evaporated down under vacuum, and purified with reverse phase HPLC to afford desired product 3-(2,4-difluorophenyl)-3-(3-(((R)-4-ethyl-1,1-dioxido-3,4-dihydro-2H-benzo[b][1,4,5]oxathiazepin-2-yl)methyl)-4-methylphenyl)propanoic acid (55.3 mg, 0.107 mmol, 68.7% yield). LC-MS m/z 516.3 (M+H)⁺, 1.19 min (ret. time).

508

Example 250

3-(2,4-Difluorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid

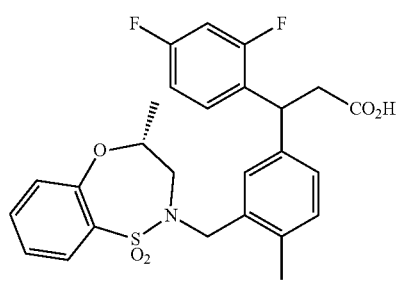 [SMILES: Cc1ccc(C(CC(=O)O)c2ccc(F)cc2F)cc1CN1C[C@@H](C)Oc2ccccc2S1(=O)=O]

To a solution of methyl 3-(2,4-difluorophenyl)-3-(3-(hydroxymethyl)-4-methylphenyl)propanoate (50 mg, 0.156 mmol) in THF (2 mL) was added (R)-4-methyl-3,4-dihydro-2H-benzo[b][1,4,5]oxathiazepine 1,1-dioxide (49.9 mg, 0.234 mmol), PS—PPh₃ (195 mg, 0.312 mmol) and DIAD (0.061 mL, 0.312 mmol). The resulting reaction mixture was stirred at RT for 45 min. The reaction mixture was filtered and evaporated down. This intermediate was redissolved in MeOH (2.000 mL). To the resulting solution was added NaOH (2 N) (0.390 mL, 0.780 mmol) and the mixture heated with microwave irradiation at 80° C. for 20 min. The reaction mixture was acidified with HCl (1 N) to pH ~5, evaporated down under vacuum, and purified with reverse phase HPLC to afford desired product 3-(2,4-difluorophenyl)-3-(4-methyl-3-(((R)-4-methyl-1,1-dioxido-3,4-dihydro-2H-benzo[b][1,4,5]oxathiazepin-2-yl)methyl)phenyl)propanoic acid (54.3 mg, 0.108 mmol, 69.4% yield). LC-MS m/z 502.2 (M+H)⁺, 1.13 min (ret. time).

Example 251

Methyl 3-(1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate

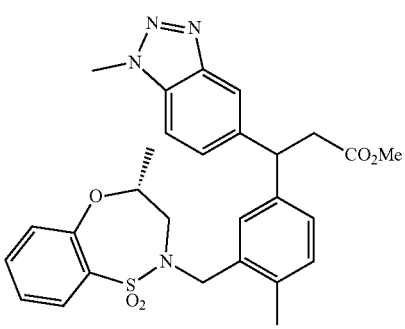 [SMILES: COC(=O)CC(c1ccc(C)c(CN2C[C@@H](C)Oc3ccccc3S2(=O)=O)c1)c1ccc2c(c1)nnn2C]

To a solution of methyl 3-(3-(hydroxymethyl)-4-methylphenyl)-3-(1-methyl-1H-benzo[d][1,2,3]triazol-5-yl)propanoate (204 mg, 0.6 mmol) in THF (10 mL) was added (R)-4-methyl-3,4-dihydro-2H-benzo[b][1,4,5]oxathiazepine 1,1-dioxide (192 mg, 0.900 mmol), PS—PPh₃ (750 mg, 1.200 mmol) and then DIAD (0.233 mL, 1.200 mmol). The resulting reaction mixture was stirred at RT for 19.5 h. To the reaction mixture was added more PS—PPh₃ (375 mg, 0.600 mmol) and stirred at RT for 80 min. To the reaction mixture was added more DIAD (0.117 mL, 0.600 mmol) and stirred at RT for 3 h. The reaction mixture was filtered and the filter cake was washed with EtOAc (2×10 mL). The combined filtrate was washed with H₂O (20 mL) and the aqueous layer was extracted with EtOAc (2×20 mL). The combined organic layer was washed with brine (30 mL), dried over MgSO₄, filtered, evaporated down under vacuum, and purified by flash chromatography before was further purified with reverse phase HPLC to afford desired product methyl 3-(1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate (80.9 mg, 0.151 mmol, 25.2% yield). LC-MS m/z 535.1 (M+H)⁺, 1.35 min (ret. time).

Example 252

3-(4-Acetyl-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid

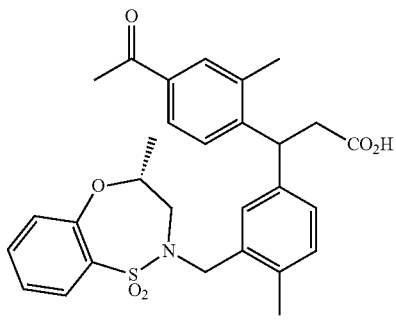 [SMILES: CC(=O)c1ccc(C(CC(=O)O)c2ccc(C)c(CN3C[C@@H](C)Oc4ccccc4S3(=O)=O)c2)c(C)c1]

To a solution of (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (152 mg, 0.344 mmol) in 1,4-dioxane (2 mL) and water (0.7 mL) was added (E)-methyl 3-(4-acetyl-2-methylphenyl)acrylate (50 mg, 0.229 mmol), Et₃N (0.096 mL, 0.687 mmol) and [RhCl(cod)]₂ (5.65 mg, 0.011 mmol). The resulting reaction mixture was stirred at 90° C. for 17 h. The reaction mixture was evaporated down under vacuum. This intermediate was redissolved in MeOH (3 mL). To the resulting solution was added NaOH (3 N) (0.611 mL, 1.833 mmol) and the mixture heated with microwave irradiation at 80° C. for 20 min. The reaction mixture was acidified with HCl (3 N) to pH ~4, evaporated down under vacuum, and purified with reverse phase HPLC to afford desired product 3-(4-acetyl-2-methylphenyl)-3-(4-methyl-3-(((R)-4-methyl-1,1-dioxido-3,4-dihydro-2H-benzo[b][1,4,5]oxathiazepin-2-yl)methyl)phenyl)propanoic acid (64.2 mg, 0.123 mmol, 53.7% yield). LC-MS m/z 522.3 (M+H)⁺, 1.06 min (ret. time).

Example 253

3-(4-Acetyl-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid

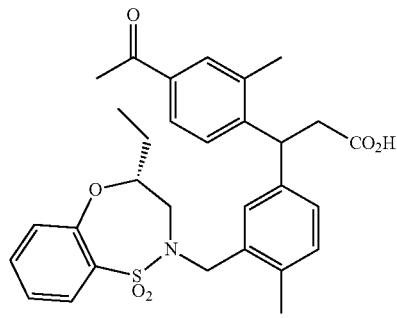 [SMILES: CC[C@@H]1CN(Cc2cc(C(CC(=O)O)c3ccc(C(C)=O)cc3C)ccc2C)S(=O)(=O)c2ccccc2O1]

To a solution of (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (157 mg, 0.344 mmol) in 1,4-dioxane (2 mL) and water (0.7 mL) was added (E)-methyl 3-(4-acetyl-2-methylphenyl)acrylate (50 mg, 0.229 mmol), Et₃N (0.096 mL, 0.687 mmol) and [RhCl(cod)]₂ (5.65 mg, 0.011 mmol). The resulting reaction mixture was stirred at RT for 1 h. The reaction mixture was then heated at 90° C. for 3.5 h. The reaction mixture was evaporated down under vacuum. This intermediate was redissolved in MeOH (3 mL). To the resulting solution was added NaOH (3 N) (0.611 mL, 1.833 mmol) and the mixture heated with microwave irradiation at 80° C. for 20 min. The reaction mixture was acidified with HCl (3 N) to pH ~4, evaporated down under vacuum, and purified with reverse phase HPLC to afford desired product 3-(4-acetyl-2-methylphenyl)-3-(3-(((R)-4-ethyl-1,1-dioxido-3,4-dihydro-2H-benzo[b][1,4,5]oxathiazepin-2-yl)methyl)-4-methylphenyl)propanoic acid (55.1 mg, 0.103 mmol, 44.9% yield). LC-MS m/z 536.2 (M+H)⁺, 1.12 min (ret. time).

Example 254

3-(2-Methyl-1-oxoisoindolin-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

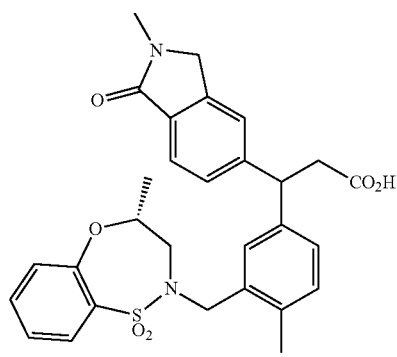 [SMILES: Cc1ccc(C(CC(=O)O)c2ccc3c(c2)CN(C)C3=O)cc1CN1C[C@@H](C)Oc2ccccc2S1(=O)=O]

Methyl 4-bromo-2-methylbenzoate

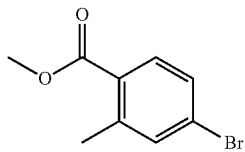

Under nitrogen, 4-bromo-2-methylbenzoic acid (5.0 g, 23.25 mmol) was dissolved in MeOH (100 mL), after which, SOCl$_2$ (1.697 mL, 23.25 mmol) was added dropwise to the solution. The mixture was refluxed at 80° C. for 2 h., and then concentrated to afford methyl 4-bromo-2-methylbenzoate (5.0 g, 20.74 mmol, 89% yield). LC-MS: m/z 229 (M+H)$^+$ 1.28 min (ret. time).

Methyl 4-bromo-2-(bromomethyl)benzoate

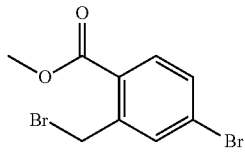

To a solution of methyl 4-bromo-2-methylbenzoate (5.0 g, 21.83 mmol) in chloroform (20 mL), under nitrogen, was added NBS (3.88 g, 21.83 mmol) and benzoyl peroxide (0.264 g, 1.091 mmol). The mixture was refluxed at 100° C. for 2 h., filtered and concentrated to afford methyl 4-bromo-2-(bromomethyl)benzoate (5.0 g, 13.64 mmol, 62.5% yield). LC-MS: m/z 307 (M+H)$^+$ 1.28 min (ret. time).

5-Bromoisoindolin-1-one

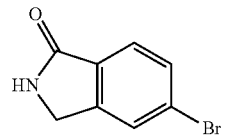 [SMILES: O=C1NCc2cc(Br)ccc21]

A mixture of methyl 4-bromo-2-(bromomethyl)benzoate (5.0 g, 16.24 mmol) and NH$_4$OH (21.07 mL, 162 mmol) under nitrogen was sealed and stirred overnight. The reaction was then filtered to afford 5-bromoisoindolin-1-one (2.5 g, 11.79 mmol, 72.6% yield). LC-MS: m/z 212 (M+H)$^+$ 0.98 min (ret. time).

5-Bromo-2-methylisoindolin-1-one

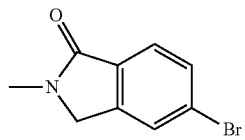

To a solution of 5-bromoisoindolin-1-one (2500 mg, 11.79 mmol) in DMF (20 mL) under nitrogen, at 0° C., was added NaH (566 mg, 14.15 mmol) and the mixture was stirred for 30 min. After which, MeI (0.885 mL, 14.15 mmol) was added dropwise and the mixture was stirred at 0° C. for 2 h. The reaction was quenched with sat. aqueous NH$_4$Cl, and extracted with EtOAc (3×30 mL). The organic layer was washed with brine, dried and concentrated to afford 5-bromo-2-methylisoindolin-1-one (2500 mg, 7.30 mmol, 61.9% yield). LC-MS: m/z 226 (M+H)$^+$ 1.02 min (ret. time).

(E)-Ethyl 3-(2-methyl-1-oxoisoindolin-5-yl)acrylate

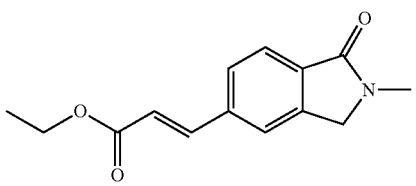 [SMILES: CCOC(=O)/C=C/c1ccc2c(c1)CN(C)C2=O]

A mixture of tri-o-tolylphosphine (0.242 g, 0.796 mmol), ethyl acrylate (1.594 g, 15.92 mmol), 5-bromo-2-methylisoindolin-1-one (1.8 g, 7.96 mmol), Pd(OAc)$_2$ (0.089 g, 0.398 mmol), and TEA (2.220 mL, 15.92 mmol) in CH$_3$CN (25.0 mL) was stirred at 80° C. for 3 h. The reaction was filtered and concentrated and the residue was purified by flash column chromatography eluting with petroleum ether/EtOAc (1/5), to afford (E)-ethyl 3-(2-methyl-1-oxoisoindolin-5-yl)acrylate (1.02 g, 3.95 mmol, 49.6% yield). LC-MS: m/z 247 (M+H)$^+$ 1.50 min (ret. time).

3-(2-Methyl-1-oxoisoindolin-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

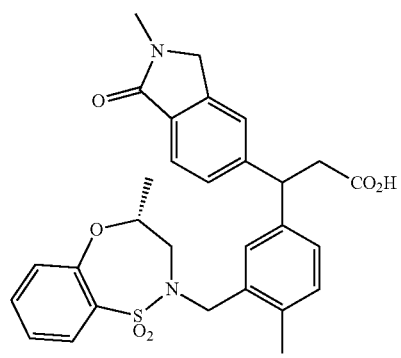 [SMILES: Cc1ccc(C(CC(=O)O)c2ccc3c(c2)CN(C)C3=O)cc1CN1C[C@@H](C)Oc2ccccc2S1(=O)=O]

To a solution of (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (271 mg, 0.612 mmol) in 1,4-dioxane (4 mL) and water (1.3 mL) was added (E)-ethyl 3-(2-methyl-1-oxoisoindolin-5-yl)acrylate (100 mg, 0.408 mmol), Et$_3$N (0.170 mL, 1.223 mmol) and [RhCl(cod)]$_2$ (10.05 mg, 0.020 mmol) and the mixture heated at 90° C. for 18 h. The reaction mixture was evaporated down under vacuum. This intermediate was redissolved in MeOH (6 mL). To the resulting solution was added NaOH (3 N) (1.087 mL, 3.26 mmol) and the mixture heated with microwave irradiation at 80° C. for 20 min (6-2). The reaction mixture was acidified with HCl (3 N) to pH ~4, evaporated down under vacuum, and purified with reverse phase HPLC to afford desired product 3-(2-methyl-1-oxoisoindolin-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid (103.0 mg, 0.193 mmol, 47.3% yield). LC-MS m/z 535.1 (M+H)+, 0.92 min (ret. time).

Example 255

3-(2,2-Dimethyl-1-oxo-2,3-dihydro-1H-inden-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

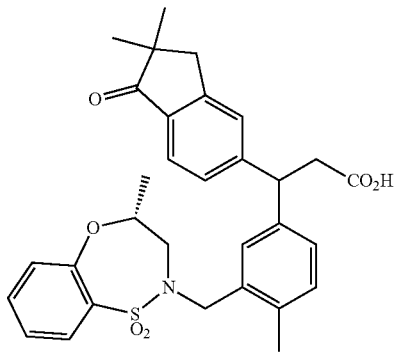 [SMILES: Cc1ccc(C(CC(=O)O)c2ccc3c(c2)CC(C)(C)C3=O)cc1CN1C[C@@H](C)Oc2ccccc2S1(=O)=O]

5-Bromo-2,2-dimethyl-2,3-dihydro-1H-inden-1-one

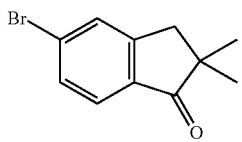

A solution of 1M LiHMDS (95 mL, 95 mmol) was added dropwise to a solution of 5-bromo-2,3-dihydro-1H-inden-1-one (5 g, 23.69 mmol) in THF (100 mL) at −78° C. under a nitrogen atmosphere. The mixture was stirred for 1 h at 0° C. The mixture was then cooled to −78° C., and methyl iodide (7.41 mL, 118 mmol) was added and stirred for another 2 h. The reaction mixture was quenched with saturated aqueous NH4Cl. The combined aqueous layers were extracted with EtOAc. The organic layer was evaporated and the crude product was purified by flash column chromatography eluting with petroleum ether/EtOAc (20/1) to afford 5-bromo-2,2-dimethyl-2,3-dihydro-1H-inden-1-one (5.0 g, 17.36 mmol, 73.3% yield). LC-MS: m/z 239 (M+H)+ 1.78 min (ret. time).

(E)-Ethyl 3-(2,2-dimethyl-1-oxo-2,3-dihydro-1H-inden-5-yl)acrylate

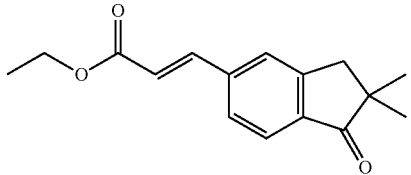 [SMILES: CCOC(=O)/C=C/c1ccc2c(c1)CC(C)(C)C2=O]

To a solution of 5-bromo-2,2-dimethyl-2,3-dihydro-1H-inden-1-one (3.5 g, 14.64 mmol) in Et3N (90 mL, 646 mmol) was added ethyl acrylate (3.66 g, 36.6 mmol), Pd(OAc)2 (0.329 g, 1.464 mmol) and tri-o-tolylphosphine (0.891 g, 2.93 mmol). The reaction mixture was heated to 100° C. under a nitrogen atmosphere for 4 h. The mixture was cooled to RT and the Et3N was evaporated under vacuum. The residue were extracted with EtOAc. The organic layer was dried over MgSO4 and the solvent was removed. The crude product was purified by flash column chromatography eluting with petroleum ether/EtOAc (20/1) to afford (E)-ethyl 3-(2,2-dimethyl-1-oxo-2,3-dihydro-1H-inden-5-yl)acrylate (2.4 g, 9.29 mmol, 63.5% yield). LC-MS: m/z 259 (M+H)+ 1.81 min (ret. time).

3-(2,2-Di methyl-1-oxo-2,3-dihydro-1H-inden-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

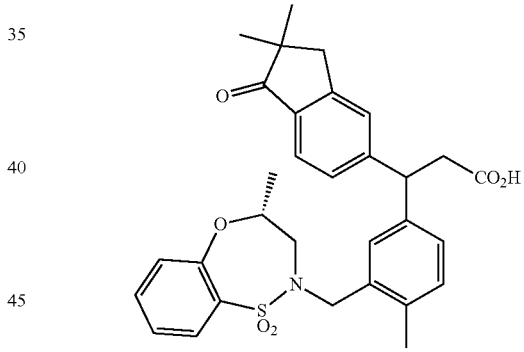

To a solution of (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (257 mg, 0.581 mmol) in 1,4-dioxane (4 mL) and water (1.3 mL) was added (E)-ethyl dimethyl-1-oxo-2,3-dihydro-1H-inden-5-yl)acrylate (100 mg, 0.387 mmol), Et3N (0.162 mL, 1.161 mmol) and [RhCl(cod)]2 (9.54 mg, 0.019 mmol) and the mixture heated at 90° C. for 65 h. The reaction mixture was evaporated down under vacuum. This intermediate was redissolved in MeOH (6 mL). To the resulting solution was added NaOH (3 N) (1.032 mL, 3.10 mmol) and the mixture heated with microwave irradiation at 60° C. for 10 min. The reaction mixture was acidified with HCl (3 N) to pH ~4, evaporated down under vacuum, and purified with reverse phase HPLC to afford desired product 3-(2,2-dimethyl-1-oxo-2,3-dihydro-1H-inden-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid (118.5 mg, 0.216 mmol, 55.9% yield). LC-MS m/z 548.3 (M+H)+, 1.12 min (ret. time).

Example 256

3-(2-Ethyl-1,3-dioxoisoindolin-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

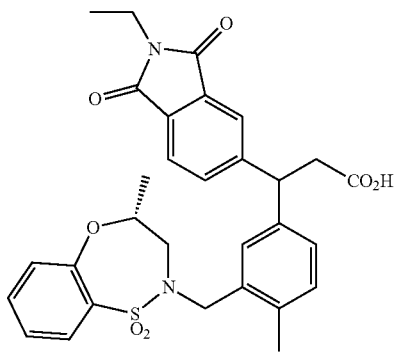 [SMILES: CCN1C(=O)c2ccc(C(CC(=O)O)c3ccc(C)c(CN4C[C@@H](C)Oc5ccccc5S4(=O)=O)c3)cc2C1=O]

5-Bromo-2-ethylisoindoline-1,3-dione

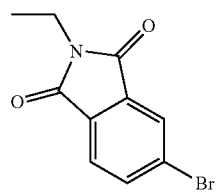

To a solution of 5-bromoisoindoline-1,3-dione (1130 mg, 5 mmol) in THF (25 mL) was added iodoethane (0.606 mL, 7.50 mmol) and then slowly was added NaH (144 mg, 6.00 mmol). The resulting reaction was stirred at RT for 22 h. To the reaction mixture was added DMF (2 mL) then stirred at RT for 23 h. To the reaction mixture was added more DMF (3 mL) then was stirred at RT for 120 h. The reaction mixture was diluted with H$_2$O (20 mL), acidified with HCl (1 mL, 1.0 N), extracted with EtOAc (3×20 mL), washed with brine (20 mL), dried over MgSO$_4$, filtered, evaporated down under vacuum, and purified by flash chromatography to afford desired product 5-bromo-2-ethylisoindoline-1,3-dione (899.7 mg, 3.54 mmol, 70.8% yield). LC-MS m/z 254.1 (M+H)$^+$, 0.90 min (ret. time).

(E)-tert-butyl 3-(2-ethyl-1,3-dioxoisoindolin-5-yl)acrylate

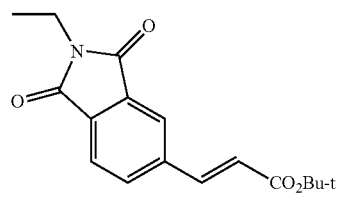

To a solution of 5-bromo-2-ethylisoindoline-1,3-dione (254 mg, 1 mmol) in DMF (5 mL) was added tert-butyl acrylate (0.726 mL, 5.00 mmol), DIPEA (0.437 mL, 2.500 mmol), Pd(OAc)$_2$ (22.45 mg, 0.100 mmol) and tri-o-tolylphosphine (60.9 mg, 0.200 mmol). The reaction mixture was then heated with microwave irradiation at 130° C. under N$_2$ atmosphere for 1 h. The reaction mixture was evaporated down under vacuum, and purified by flash chromatography to afford desired product (E)-tert-butyl 3-(2-ethyl-1,3-dioxoisoindolin-5-yl)acrylate (182.7 mg, 0.606 mmol, 60.6% yield). LC-MS m/z 302.2 (M+H)$^+$, 1.10 min (ret. time).

3-(2-Ethyl-1,3-dioxoisoindolin-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid

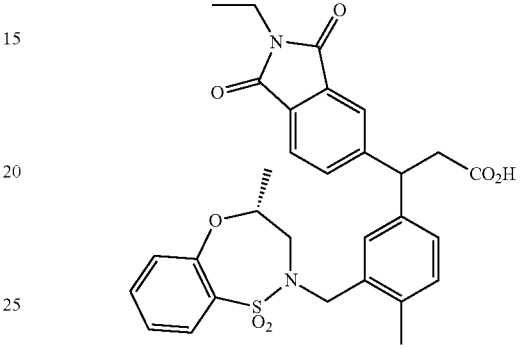

To a solution of (R)-4-methyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (221 mg, 0.498 mmol) in 1,4-dioxane (4 mL) and water (1.3 mL) was added (E)-tert-butyl 3-(2-ethyl-1,3-dioxoisoindolin-5-yl)acrylate (100 mg, 0.332 mmol), Et$_3$N (0.139 mL, 0.996 mmol) and [RhCl(cod)]$_2$ (8.18 mg, 0.017 mmol) and the mixture heated at 90° C. for 65.5 h. The reaction mixture was evaporated down under vacuum. This intermediate was added HCl (4.0 N in p-dioxane) (0.830 mL, 3.32 mmol) and stirred at RT for 5 h. The reaction mixture was evaporated down under vacuum, and purified with reverse phase HPLC to afford desired product 3-(2-ethyl-1,3-dioxoisoindolin-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid (66.2 mg, 0.118 mmol, 35.5% yield). LC-MS m/z 563.2 (M+H)$^+$, 1.09 min (ret. time).

Example 257

3-(3-(((R)-4-ethyl-1,1-dioxido-3,4-dihydro-2H-benzo[b][1,4,5]oxathiazepin-2-yl)methyl)-4-methylphenyl)-3-(2-ethyl-1,3-dioxoisoindolin-5-yl)propanoic acid

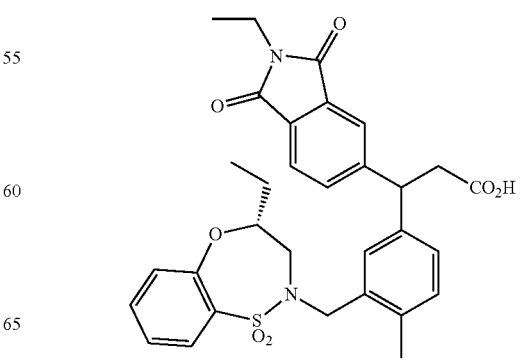

To a solution of (R)-4-ethyl-2-(2-methyl-5-(4,4,5,5-tetramethyl-1,3,2-dioxaborolan-2-yl)benzyl)-3,4-dihydro-2H-benzo[b][1,4,5]oxathiazepine 1,1-dioxide (182 mg, 0.398 mmol) in 1,4-dioxane (4 mL) and water (1.3 mL) was added (E)-tert-butyl 3-(2-ethyl-1,3-dioxoisoindolin-5-yl)acrylate (80 mg, 0.265 mmol), Et$_3$N (0.111 mL, 0.796 mmol) and [RhCl(cod)]$_2$ (6.55 mg, 0.013 mmol) and the mixture heated at 90° C. for 18 h. The reaction mixture was evaporated down under vacuum. To this intermediate was added HCl (4.0 N in p-dioxane) (0.664 mL, 2.65 mmol) and stirred at RT for 25 h. The reaction mixture was evaporated down under vacuum, and purified with reverse phase HPLC to afford desired product 3-(3-(((R)-4-ethyl-1,1-dioxido-3,4-dihydro-2H-benzo[b][1,4,5]oxathiazepin-2-yl)methyl)-4-methylphenyl)-3-(2-ethyl-1,3-dioxoisoindolin-5-yl)propanoic acid (77.5 mg, 0.134 mmol, 50.6% yield). LC-MS m/z 577.4 (M+H)$^+$, 1.13 min (ret. time).

Example 258

3-(1,4-Dimethyl-1H-benzo[d][1,2,3]triazol-5-yl)-3-(3-((R)-4-methyl-1,1-dioxido-3,4-dihydro-2H-benzo[b][1,4,5]oxathiazepin-2-yl)-2,3-dihydro-1H-inden-5-yl)propanoic acid

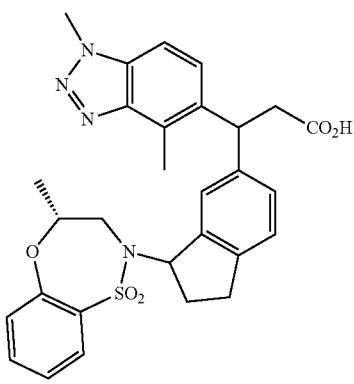 [SMILES: Cc1c(C(CC(=O)O)c2ccc3c(c2)C(N2C[C@@H](C)Oc4ccccc4S2(=O)=O)CC3)ccc2c1nnn2C]

6-(4,4,5,5-Tetramethyl-1,3,2-dioxaborolan-2-yl)-2,3-dihydro-1H-inden-1-one

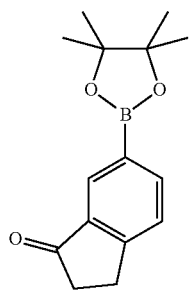 [SMILES: CC1(C)OB(c2ccc3c(c2)C(=O)CC3)OC1(C)C]

To a solution of 6-bromo-2,3-dihydro-1H-inden-1-one (1.688 g, 8 mmol) in DMF (16 mL) was added bis(pinacolato)diboron (3.05 g, 12.00 mmol), KOAc (1.570 g, 16.00 mmol) and PdCl$_2$(dppf) (0.293 g, 0.400 mmol) and the mixture heated with microwave irradiation at 100° C. for 1 h. The reaction mixture was evaporated down under vacuum, and purified by flash chromatography to afford desired product 6-(4,4,5,5-tetramethyl-1,3,2-dioxaborolan-2-yl)-2,3-dihydro-1H-inden-1-one (1.5529 g, 4.81 mmol, 60.2% yield). LC-MS m/z 259.0 (M+H)$^+$, 1.00 min (ret. time).

Ethyl 3-(1,4-dimethyl-1H-benzo[d][1,2,3]triazol-5-yl)-3-(3-oxo-2,3-dihydro-1H-inden-5-yl)propanoate

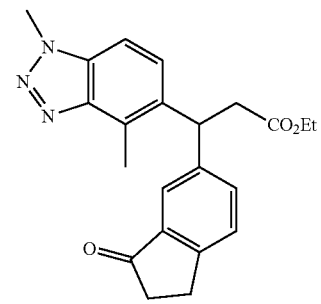 [SMILES: CCOC(=O)CC(c1ccc2c(c1)C(=O)CC2)c1ccc2c(nnn2C)c1C]

To a solution of (E)-ethyl 3-(1,4-dimethyl-1H-benzo[d][1,2,3]triazol-5-yl)acrylate (0.981 g, 4 mmol) in 1,4-dioxane (30 mL) and water (10 mL) was added 6-(4,4,5,5-tetramethyl-1,3,2-dioxaborolan-2-yl)-2,3-dihydro-1H-inden-1-one (1.553 g, 6.02 mmol), Et$_3$N (1.673 mL, 12.00 mmol) and [Rh(cod)Cl]$_2$ (0.099 g, 0.200 mmol). The resulting reaction mixture was stirred at 90° C. for 23 h. The reaction mixture was extracted with EtOAc (3×20 mL). The combined organic layer was dried over MgSO$_4$, filtered, evaporated down under vacuum, and purified by flash chromatography to afford desired product ethyl 3-(1,4-dimethyl-1H-benzo[d][1,2,3]triazol-5-yl)-3-(3-oxo-2,3-dihydro-1H-inden-5-yl)propanoate (0.4515 g, 0.885 mmol, 22.13% yield). LC-MS m/z 378.1 (M+H)$^+$, 0.89 min (ret. time).

Ethyl 3-(1,4-dimethyl-1H-benzo[d][1,2,3]triazol-5-yl)-3-(3-hydroxy-2,3-dihydro-1H-inden-5-yl)propanoate

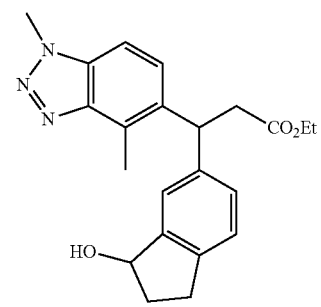 [SMILES: CCOC(=O)CC(c1ccc2c(c1)C(O)CC2)c1ccc2c(nnn2C)c1C]

To a solution of ethyl 3-(1,4-dimethyl-1H-benzo[d][1,2,3]triazol-5-yl)-3-(3-oxo-2,3-dihydro-1H-inden-5-yl)propanoate (0.4515 g, 0.885 mmol) in THF (2.0 mL) was added NaBH$_4$ (0.100 g, 2.66 mmol) then MeOH (500 µl) was added portion wise to the mixture and stirred at RT for 20 h. The reaction mixture was then evaporated down under vacuum, and purified by flash chromatography to afford desired product ethyl 3-(1,4-dimethyl-1H-benzo[d][1,2,3]triazol-5-yl)-3-(3-hydroxy-2,3-dihydro-1H-inden-5-yl)propanoate (0.3837 g, 0.940 mmol, 106% yield). LC-MS m/z 380.1 (M+H)$^+$, 0.90 min (ret. time).

3-(1,4-Dimethyl-1H-benzo[d][1,2,3]triazol-5-yl)-3-(3-((R)-4-methyl-1,1-dioxido-3,4-dihydro-2H-benzo[b][1,4,5]oxathiazepin-2-yl)-2,3-dihydro-1H-inden-5-yl)propanoic acid

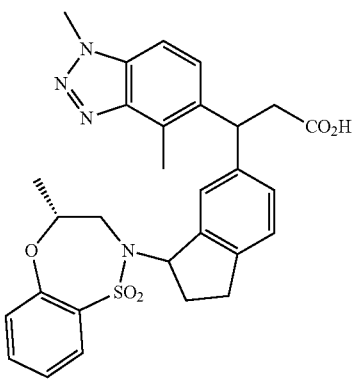 [SMILES: Cc1c(C(CC(=O)O)c2ccc3c(c2)C(N2C[C@@H](C)Oc4ccccc4S2(=O)=O)CC3)ccc2c1nnn2C]

To a solution of ethyl 3-(1,4-dimethyl-1H-benzo[d][1,2,3]triazol-5-yl)-3-(3-hydroxy-2,3-dihydro-1H-inden-5-yl)propanoate (95 mg, 0.250 mmol) in THF (2 mL) was added (R)-4-methyl-3,4-dihydro-2H-benzo[b][1,4,5]oxathiazepine 1,1-dioxide (80 mg, 0.375 mmol), PS—PPh$_3$ (313 mg, 0.500 mmol) and DIAD (0.097 mL, 0.500 mmol). The resulting reaction mixture was stirred at RT for 5 h. The reaction mixture was filtered and evaporated down. This intermediate was redissolved in MeOH (2.000 mL). To the resulting solution was added NaOH (2 N) (0.625 mL, 1.250 mmol) and the mixture heated with microwave irradiation at 80° C. for 30 min. The reaction mixture was acidified with HCl (1 N) to pH ~5, evaporated down under vacuum, and purified with reverse phase HPLC to afford desired product 3-(1,4-dimethyl-1H-benzo[d][1,2,3]triazol-5-yl)-3-(3-((R)-4-methyl-1,1-dioxido-3,4-dihydro-2H-benzo[b][1,4,5]oxathiazepin-2-yl)-2,3-dihydro-1H-inden-5-yl)propanoic acid (54.8 mg, 0.096 mmol, 38.5% yield). LC-MS m/z 547.3 (M+H)$^+$, 0.96 min (ret. time).

Example 259

3-(1,4-Dimethyl-1H-benzo[d][1,2,3]triazol-5-yl)-3-(3-((R)-4-ethyl-1,1-dioxido-3,4-dihydro-2H-benzo[b][1,4,5]oxathiazepin-2-yl)-2,3-dihydro-1H-inden-5-yl)propanoic acid

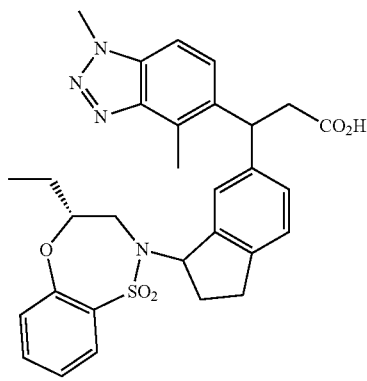 [SMILES: CC[C@@H]1CN(C2CCc3ccc(C(CC(=O)O)c4ccc5c(nnn5C)c4C)cc32)S(=O)(=O)c2ccccc2O1]

To a solution of ethyl 3-(1,4-dimethyl-1H-benzo[d][1,2,3]triazol-5-yl)-3-(3-hydroxy-2,3-dihydro-1H-inden-5-yl)propanoate (190 mg, 0.500 mmol) in THF (4 mL) was added (R)-4-ethyl-3,4-dihydro-2H-benzo[b][1,4,5]oxathiazepine 1,1-dioxide (170 mg, 0.750 mmol), PS—PPh$_3$ (625 mg, 1.000 mmol) and DIAD (0.194 mL, 1.000 mmol). The resulting reaction mixture was stirred at RT for 4 h. Then another portion of PS—PPh$_3$ (0.5 mmol) and DIAD (0.5 mmol) were added. The resulting mixture was stirred for additional 1 h. The reaction mixture was filtered and evaporated down. This intermediate was redissolved in MeOH (3.00 mL). To the resulting solution was added NaOH (2 N) (1.250 mL, 2.500 mmol) and the mixture heated with microwave irradiation at 80° C. for 30 min. The reaction mixture was acidified with HCl (1 N) to pH ~5, evaporated down under vacuum, and purified with reverse phase HPLC to afford desired product 3-(1,4-dimethyl-1H-benzo[d][1,2,3]triazol-5-yl)-3-(3-((R)-4-ethyl-1,1-dioxido-3,4-dihydro-2H-benzo[b][1,4,5]oxathiazepin-2-yl)-2,3-dihydro-1H-inden-5-yl)propanoic acid (61.6 mg, 0.110 mmol, 21.97% yield). LC-MS m/z 561.1 (M+H)$^+$, 1.00 min (ret. time).

Example 260

3-(1,4-Dimethyl-1H-benzo[d][1,2,3]triazol-5-yl)-3-(3-(4-methyl-1,1-dioxido-4,5-dihydrobenzo[f][1,2]thiazepin-2(3H)-yl)-2,3-dihydro-1H-inden-5-yl)propanoic acid

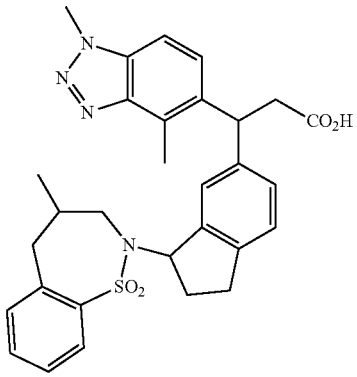 [SMILES: Cc1c(C(CC(=O)O)c2ccc3c(c2)C(N2CC(C)Cc4ccccc4S2(=O)=O)CC3)ccc2c1nnn2C]

To a solution of ethyl 3-(1,4-dimethyl-1H-benzo[d][1,2,3]triazol-5-yl)-3-(3-hydroxy-2,3-dihydro-1H-inden-5-yl)propanoate (0.122 g, 0.322 mmol) in THF (4 mL) was added 4-methyl-2,3,4,5-tetrahydrobenzo[f][1,2]thiazepine 1,1-dioxide (0.102 g, 0.482 mmol), PS—PPh$_3$ (0.603 g, 0.965 mmol) and DIAD (0.188 mL, 0.965 mmol). The resulting reaction mixture was stirred at RT for 1 h. The reaction mixture was filtered and evaporated down. This intermediate was redissolved in MeOH (3.0 mL). To the resulting solution was added NaOH (2 N) (0.804 mL, 1.608 mmol) and the mixture heated with microwave irradiation at 80° C. for 30 min. The reaction mixture was acidified with HCl (1 N) to pH ~5, evaporated down under vacuum, and purified with reverse phase HPLC to afford desired product 3-(1,4-dimethyl-1H-benzo[d][1,2,3]triazol-5-yl)-3-(3-(4-methyl-1,1-dioxido-4,5-dihydrobenzo[f][1,2]thiazepin-2(3H)-yl)-2,3-dihydro-1H-inden-5-yl)propanoic acid (29 mg, 0.053 mmol, 16.56% yield). LC-MS m/z 545.3 (M+H)$^+$, 0.99 min (ret. time).

Example 261

3-(3-(8-Bromo-4-methyl-1,1-dioxido-4,5-dihydrobenzo[f][1,2]thiazepin-2(3H)-yl)-2,3-dihydro-1H-inden-5-yl)-3-(1,4-dimethyl-1H-benzo[d][1,2,3]triazol-5-yl)propanoic acid

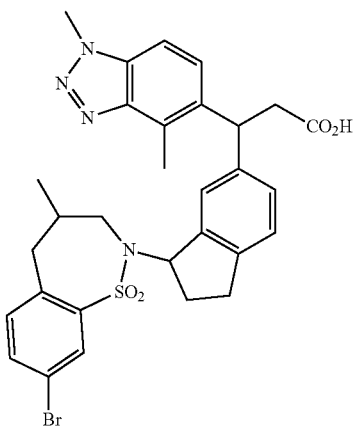 [SMILES: Cc1c(C(CC(=O)O)c2ccc3c(c2)C(N2CC(C)Cc4ccc(Br)cc4S2(=O)=O)CC3)ccc2c1nnn2C]

To a solution of ethyl 3-(1,4-dimethyl-1H-benzo[d][1,2,3]triazol-5-yl)-3-(3-hydroxy-2,3-dihydro-1H-inden-5-yl)propanoate (75 mg, 0.198 mmol) in THF (2 mL) was added 8-bromo-4-methyl-2,3,4,5-tetrahydrobenzo[f][1,2]thiazepine 1,1-dioxide (86 mg, 0.296 mmol), PS—PPh$_3$ (371 mg, 0.593 mmol) and DIAD (0.115 mL, 0.593 mmol). The resulting reaction mixture was stirred at RT for 1 h. The reaction mixture was filtered and evaporated down. This intermediate was redissolved in MeOH (2 mL). To the resulting solution was added NaOH (2 N) (0.494 mL, 0.988 mmol) and the mixture heated with microwave irradiation at 80° C. for 30 min. The reaction mixture was acidified with HCl (1 N) to pH ~5, evaporated down under vacuum, and purified with reverse phase HPLC to afford desired product 3-(3-(8-bromo-4-methyl-1,1-dioxido-4,5-dihydrobenzo[f][1,2]thiazepin-2(3H)-yl)-2,3-dihydro-1H-inden-5-yl)-3-(1,4-dimethyl-1H-benzo[d][1,2,3]triazol-5-yl)propanoic acid (29.4 mg, 0.047 mmol, 23.85% yield). LC-MS m/z 623.4 (M+H)$^+$, 1.17 min (ret. time).

Example 262

3-(3-(8-Bromo-4-methyl-1,1-dioxido-4,5-dihydrobenzo[f][1,2]thiazepin-2(3H)-yl)-2,3-dihydro-1H-inden-5-yl)-3-(1,4-dimethyl-1H-benzo[d][1,2,3]triazol-5-yl)propanoic acid

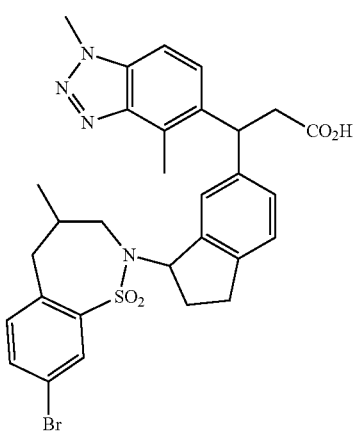 [SMILES: Cc1c(C(CC(=O)O)c2ccc3c(c2)C(N2CC(C)Cc4ccc(Br)cc4S2(=O)=O)CC3)ccc2c1nnn2C]

To a solution of ethyl 3-(1,4-dimethyl-1H-benzo[d][1,2,3]triazol-5-yl)-3-(3-hydroxy-2,3-dihydro-1H-inden-5-yl)propanoate (75 mg, 0.198 mmol) in THF (2 mL) was added 8-bromo-4-methyl-2,3,4,5-tetrahydrobenzo[f][1,2]thiazepine 1,1-dioxide (86 mg, 0.296 mmol), PS—PPh$_3$ (371 mg, 0.593 mmol) and DIAD (0.115 mL, 0.593 mmol). The resulting reaction mixture was stirred at RT for 1 h. The reaction mixture was filtered and evaporated down. This intermediate was redissolved in MeOH (2 mL). To the resulting solution was added NaOH (2 N) (0.494 mL, 0.988 mmol) and the mixture heated with microwave irradiation at 80° C. for 30 min. The reaction mixture was acidified with HCl (1 N) to pH ~5, evaporated down under vacuum, and purified with reverse phase HPLC to afford desired product 3-(3-(8-bromo-4-methyl-1,1-dioxido-4,5-dihydrobenzo[f][1,2]thiazepin-2(3H)-yl)-2,3-dihydro-1H-inden-5-yl)-3-(1,4-dimethyl-1H-benzo[d][1,2,3]triazol-5-yl)propanoic acid (23.2 mg, 0.037 mmol, 18.82% yield). LC-MS m/z 623.3 (M+H)$^+$, 1.09 min (ret. time).

Example 263

2-{34-Methyl-3,3-dioxo-10-oxa-3$\lambda^6$-thia-2,17,18,19-tetraazaheptacyclo[24.5.2.1$^{2,11}$.1$^{20,24}$.0$^{4,9}$.0$^{17,21}$.0$^{29,32}$]pentatriaconta-4(9),5,7,18,20(34),21,23,26(33),27,29(32)-decaen-25-yl}acetic acid

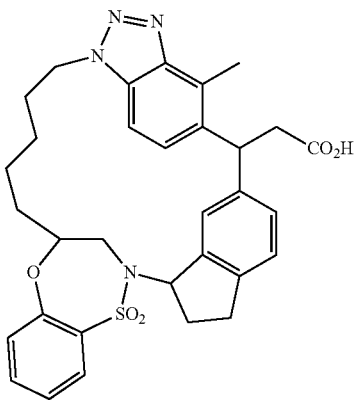 [SMILES: Cc1c2ccc3c1nnn3CCCCCC1CN(C3CCc4ccc(cc43)C2CC(=O)O)S(=O)(=O)c2ccccc2O1]

Tert-Butyl (3-methyl-2-nitrophenyl)carbamate

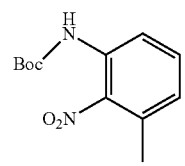

To a solution of 3-methyl-2-nitrobenzoic acid (25 g, 138 mmol) in tert-butanol (250 mL) was added diphenyl phosphorazidate (41.8 g, 152 mmol) and TEA (21.16 mL, 152 mmol) under nitrogen atmosphere and stirred at 90° C. for 18 h. The reaction mixture was then cooled to 0° C., and concentrated to afford the crude compound. The crude compound was purified by flash column chromatography using EtOAc:hexane (5:95) to afford tert-butyl (3-methyl-2-nitrophenyl)carbamate (30 g, 117 mmol, 84% yield). LC-MS: m/z 152 (M-100)$^+$ 2.60 min (ret. time).

tert-Butyl allyl(3-methyl-2-nitrophenyl)carbamate

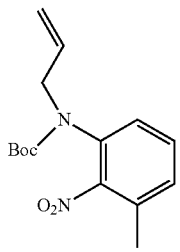 [SMILES: C=CCN(C(=O)OC(C)(C)C)c1cccc(C)c1[N+](=O)[O-]]

To a solution of tert-butyl (3-methyl-2-nitrophenyl)carbamate (5 g, 19.82 mmol) in DMF (50 mL) was added NaH (0.476 g, 19.82 mmol) at 0° C., and stirred for 20 min. Afterwards, 3-bromoprop-1-ene (2.398 g, 19.82 mmol) was added at 0° C. and the reaction mixture was stirred at RT for 3 h. The reaction mixture was then cooled to 0° C., quenched with cold water, and extracted with EtOAc (2×). The combined organic layers were washed with brine, dried under anhydrous $Na_2SO_4$ and filtered to afford tert-butyl allyl(3-methyl-2-nitrophenyl)carbamate (4 g, 13.68 mmol, 69.0% yield). $^1$H NMR (400 MHz, $CDCl_3$) δ ppm 7.35 (t, 1H), 7.23 (d, 1H), 7.14 (bs, 1H), 5.95 (m, 1H), 5.11 (t, 2H), 4.43 (bs, 1H), 3.83 (bs, 1H), 2.38 (s, 3H), 1.39 (bs, 9H).

N-Allyl-3-methyl-2-nitroaniline

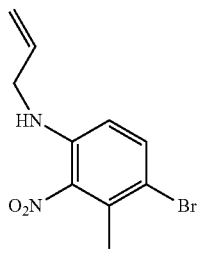

To a solution of tert-butyl allyl(3-methyl-2-nitrophenyl)carbamate (4 g, 13.68 mmol) in DCM (40 mL) was added TFA (3.16 mL, 41.0 mmol) at 0° C. The reaction mixture was stirred at RT for 3 h. The reaction mixture was then concentrated under reduced pressure, quenched with saturated $NaHCO_3$, and extracted with DCM (2×). The combined organic layers were washed with brine, dried under anhydrous $Na_2SO_4$ and filtered. The filtrate was reduced under pressure to afford N-allyl-3-methyl-2-nitroaniline (2 g, 10.24 mmol, 74.8% yield). LC-MS: m/z 193 (M+H)$^+$ 2.59 min (ret. time).

N-Allyl-4-bromo-3-methyl-2-nitroaniline

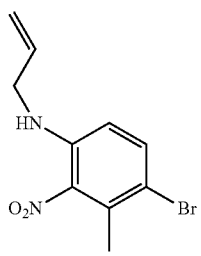

To a solution of N-allyl-3-methyl-2-nitroaniline (2 g, 10.41 mmol) in DMF (25 mL) was added NBS (1.852 g, 10.41 mmol) at 0° C. The reaction mixture was stirred at RT for 16 h. The reaction mixture was then cooled to 0° C., quenched with cold water, and extracted with EtOAc (2×). The combined organic layers were washed with brine, dried under anhydrous $Na_2SO_4$ and filtered. The filtrate was reduced under pressure and it was purified by flash column chromatography by using EtOAc:hexane (2:98) to afford N-allyl-4-bromo-3-methyl-2-nitroaniline (1.4 g, 4.90 mmol, 47.1% yield). LC-MS: m/z 270.93 (M+H)$^+$ 2.84 min (ret. time).

N1-Allyl-4-bromo-3-methylbenzene-1,2-diamine

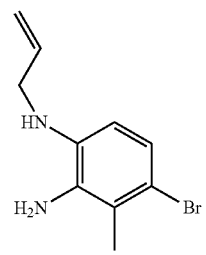

To a solution of N-allyl-4-bromo-3-methyl-2-nitroaniline (1.4 g, 5.16 mmol) in EtOH (20 mL) was added $SnCl_2.2H_2O$ (1.165 g, 5.16 mmol) at 0° C. The reaction mixture was stirred at 90° C. for 3 h. The reaction mixture was then concentrated under vacuum, quenched with cold water, adjusted to pH=10 with a 10% NaOH solution, and extracted with DCM (2×). The combined organic layers were dried under anhydrous $Na_2SO_4$ and filtered to afford N1-allyl-4-bromo-3-methylbenzene-1,2-diamine (1 g, 4.01 mmol, 78% yield). LC-MS: m/z 241 (M+H)$^+$ 2.23 min (ret. time).

1-Allyl-5-bromo-4-methyl-1H-benzo[d][1,2,3]triazole

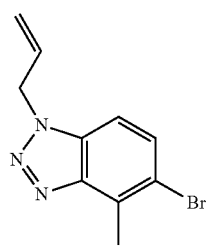

To a solution of N1-allyl-4-bromo-3-methylbenzene-1,2-diamine (7 g, 29.0 mmol) in $H_2SO_4$ (6.19 mL, 116 mmol) was added a saturated solution of sodium nitrate (3.70 g, 43.5 mmol) at 0° C. The reaction mixture was stirred at 0° C. for 3 h. The reaction mixture was then cooled to 0° C., and was quenched with cold water. The observed solid was filtered and dried under vacuum to afford 1-allyl-5-bromo-4-methyl-1H-benzo[d][1,2,3]triazole (4 g, 15.80 mmol, 54.4% yield). LC-MS: m/z 251.89 (M+H)$^+$ 1.08 min (ret. time).

525

(E)-Ethyl 3-(1-allyl-4-methyl-1H-benzo[d][1,2,3]triazol-5-yl)acrylate

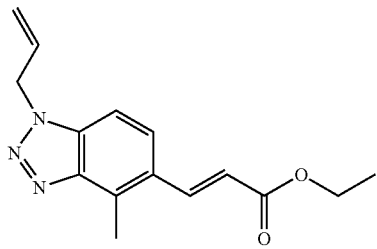 [SMILES: C=CCn1nnc2c(C)c(/C=C/C(=O)OCC)ccc21]

Experiment 1

To solution of 1-allyl-5-bromo-4-methyl-1H-benzo[d][1,2,3]triazole (1 g, 3.97 mmol) in DMF (2 mL) was added ethyl acrylate (1.588 g, 15.87 mmol), tri-o-tolylphosphine (0.362 g, 1.190 mmol) and DIPEA (2.77 mL, 15.87 mmol) degassed with nitrogen for 20 min. After which, Pd(OAc)$_2$ (0.045 g, 0.198 mmol) was added to a microwave reactor. The reaction mixture was stirred at 120° C. for 1 h. The reaction mixture was cooled to 0° C., quenched with cold water, and extracted with EtOAc (2×). The combined organic layers were washed with brine, dried under anhydrous Na$_2$SO$_4$ and filtered. The filtrate was evaporated under reduced pressure and the crude residue was purified on flash column chromatography using EtOAc:hexane (9:91) eluted dried under vacuum to afford (E)-ethyl 3-(1-allyl-4-methyl-1H-benzo[d][1,2,3]triazol-5-yl)acrylate (400 mg, 1.434 mmol, 36.1% yield). LC-MS: m/z 271.98 (M+H)$^+$ 1.06 min (ret. time).

Experiment 2

To solution of 1-allyl-5-bromo-4-methyl-1H-benzo[d][1,2,3]triazole (3 g, 11.90 mmol) in DMF (3 mL) was added ethyl acrylate (4.77 g, 47.6 mmol), tri-o-tolylphosphine (1.087 g, 3.57 mmol) and DIPEA (8.31 mL, 47.6 mmol). The mixture was degassed with nitrogen for 20 min, after which Pd(OAc)$_2$ (0.134 g, 0.595 mmol) was added to a microwave reactor. The reaction mixture was stirred at 120° C. for 1 h. The reaction mixture was cooled to 0° C., quenched with cold water and extracted with EtOAc (2×). The combined organic layers were washed with brine, dried under anhydrous Na$_2$SO$_4$ and filtered. The filtrate was evaporated under reduced pressure and the crude residue was purified on flash column chromatography using EtOAc:hexane (9:91) to afford (E)-ethyl 3-(1-allyl-4-methyl-1H-benzo[d][1,2,3]triazol-5-yl)acrylate (1.7 g, 5.88 mmol, 49.4% yield).

Final purification

The above final products of (E)-ethyl 3-(1-allyl-4-methyl-1H-benzo[d][1,2,3]triazol-5-yl)acrylate were combined and triturated with Et$_2$O to afford (E)-ethyl 3-(1-allyl-4-methyl-1H-benzo[d][1,2,3]triazol-5-yl)acrylate (2.0 g, 7.31 mmol). LC-MS: m/z 272.12 (M+H)$^+$ 2.34 min (ret. time).

526

Ethyl 3-(1-allyl-4-methyl-1H-benzo[d][1,2,3]triazol-5-yl)-3-(3-hydroxy-2,3-dihydro-1H-inden-5-yl)propanoate

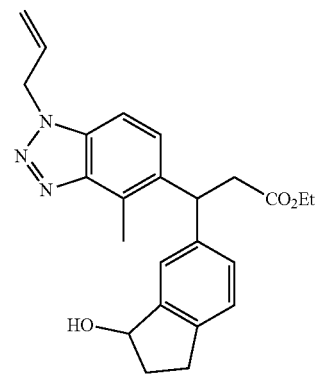 [SMILES: C=CCn1nnc2c(C)c(C(CC(=O)OCC)c3ccc4c(c3)C(O)CC4)ccc21]

To a solution of (E)-ethyl 3-(1-allyl-4-methyl-1H-benzo[d][1,2,3]triazol-5-yl)acrylate (0.250 g, 0.921 mmol) in 1,4-dioxane (9 mL) and water (3 mL) was added 6-(4,4,5,5-tetramethyl-1,3,2-dioxaborolan-2-yl)-2,3-dihydro-1H-inden-1-ol (0.3624 g, 1.393 mmol), Et$_3$N (0.385 mL, 2.76 mmol) and [Rh(cod)Cl]$_2$ (0.023 g, 0.046 mmol). The resulting reaction mixture was stirred at 90° C. for 3 h. The reaction mixture was evaporated down under vacuum, and purified by flash chromatography to afford desired product ethyl 3-(1-allyl-4-methyl-1H-benzo[d][1,2,3]triazol-5-yl)-3-(3-hydroxy-2,3-dihydro-1H-inden-5-yl)propanoate (0.1877 g, 0.463 mmol, 50.2% yield). LC-MS m/z 406.1 (M+H)$^+$, 0.98 min (ret. time).

1-Aminohex-5-en-2-ol

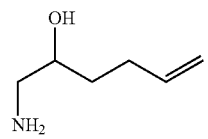

To a solution of 2-(but-3-en-1-yl)oxirane (0.751 mL, 6.65 mmol) in CH$_3$CN (1 mL) was added NH$_4$OH (4.63 mL, 33.3 mmol) at RT. The reaction mixture was heated at 120° C. for 1 h before was evaporated down under vacuum to afford desired product 1-aminohex-5-en-2-ol (0.7165 g, 6.22 mmol, 93% yield). LC-MS m/z 115.8 (M+H)$^+$, 0.18 min (ret. time).

2-Fluoro-N-(2-hydroxyhex-5-en-1-yl)benzenesulfonamide

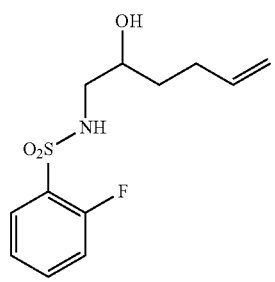 [SMILES: C=CCCC(O)CNS(=O)(=O)c1ccccc1F]

To a solution of 1-aminohex-5-en-2-ol (0.7165 g, 6.22 mmol) in THF (12.00 mL) and water (3 mL) was added potassium carbonate (1.290 g, 9.33 mmol) and 2-fluorobenzene-1-sulfonyl chloride (0.906 mL, 6.84 mmol). The resulting reaction mixture was stirred at RT for 1 h. The reaction mixture was evaporated down under vacuum, and purified by flash chromatography to afford desired product 2-fluoro-N-(2-hydroxyhex-5-en-1-yl)benzenesulfonamide (1.0917 g, 3.99 mmol, 64.2% yield). LC-MS m/z 273.9 (M+H)$^+$, 0.72 min (ret. time).

4-(But-3-en-1-yl)-3,4-dihydro-2H-benzo[b][1,4,5]oxathiazepine 1,1-dioxide

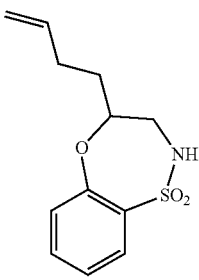 [SMILES: C=CCCC1CNS(=O)(=O)c2ccccc2O1]

To a solution of 2-fluoro-N-(2-hydroxyhex-5-en-1-yl)benzenesulfonamide (0.741 mL, 3.99 mmol) was dissolved in dimethyl sulfoxide (20 mL) and was added KOtBu (1.342 g, 11.96 mmol). The resulting reaction was heated with microwave irradiation at 80° C. for 2 h. The reaction mixture was diluted with H$_2$O (80 mL) and HCl (40 mL, 1 N), extracted with EtOAc (200+2×100 mL). The combined organic layer was washed with brine (100 mL), dried over MgSO$_4$, filtered, evaporated down under vacuum, and purified by flash chromatography to afford desired product 4-(but-3-en-1-yl)-3,4-dihydro-2H-benzo[b][1,4,5]oxathiazepine 1,1-dioxide (0.6525 g, 2.58 mmol, 64.6% yield). LC-MS m/z 253.9 (M+H)$^+$, 0.85 min (ret. time).

Ethyl 3-(1-allyl-4-methyl-1H-benzo[d][1,2,3]triazol-5-yl)-3-(3-(4-(but-3-en-1-yl)-1,1-dioxido-3,4-dihydro-2H-benzo[b][1,4,5]oxathiazepin-2-yl)-2,3-dihydro-1H-inden-5-yl)propanoate

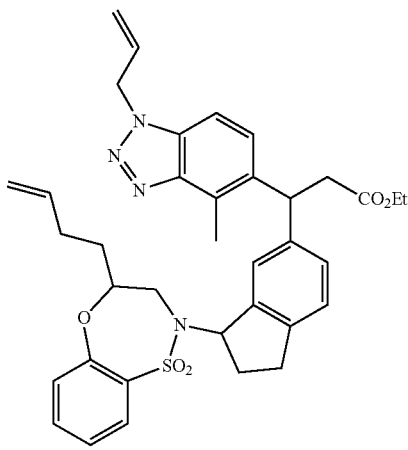 [SMILES: C=CCCC1CN(C2CCc3ccc(C(CC(=O)OCC)c4ccc5c(nnn5CC=C)c4C)cc32)S(=O)(=O)c2ccccc2O1]

To a solution of ethyl 3-(1-allyl-4-methyl-1H-benzo[d][1,2,3]triazol-5-yl)-3-(3-hydroxy-2,3-dihydro-1H-inden-5-yl)propanoate (0.1877 g, 0.463 mmol) in THF (8 mL) was added 4-(but-3-en-1-yl)-3,4-dihydro-2H-benzo[b][1,4,5]oxathiazepine 1,1-dioxide (0.176 g, 0.694 mmol), PS—PPh$_3$ (0.579 g, 0.926 mmol) and DIAD (0.180 mL, 0.926 mmol). The resulting reaction mixture was stirred at RT for 1 h. The reaction mixture was filtered, evaporated down, purified by flash chromatography to afford desired product ethyl 3-(1-allyl-4-methyl-1H-benzo[d][1,2,3]triazol-5-yl)-3-(3-(4-(but-3-en-1-yl)-1,1-dioxido-3,4-dihydro-2H-benzo[b][1,4,5]oxathiazepin-2-yl)-2,3-dihydro-1H-inden-5-yl)propanoate (0.2716 g, 0.424 mmol, 92% yield). LC-MS m/z 641.4 (M+H)$^+$, 1.30 min (ret. time).

Ethyl 2-{34-methyl-3,3-dioxo-10-oxa-3$\lambda^6$-thia-2,17,18,19-tetraazaheptacyclo[24.5.2. 1$^{2,11}$.1$^{2^0,2^4}$.0$^{4,9}$.0$^{1^7,21}$.0$^{2^9,32}$]pentatriaconta-4(9),5, 7,14,18,20(34),21,23,26(33),27,29(32)-undecaen-25-yl}acetate

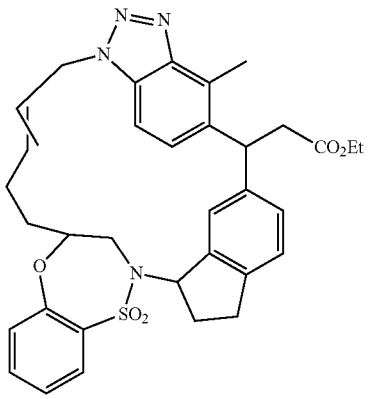 [SMILES: CCCCC1CN(C2CCc3ccc(C(CC(=O)OCC)c4ccc5c(nnn5CCC)c4C)cc32)S(=O)(=O)c2ccccc2O1]

To a solution of ethyl 3-(1-allyl-4-methyl-1H-benzo[d][1,2,3]triazol-5-yl)-3-(3-(4-(but-3-en-1-yl)-1,1-dioxido-3,4-dihydro-2H-benzo[b][1,4,5]oxathiazepin-2-yl)-2,3-dihydro-1H-inden-5-yl)propanoate (0.1358 g, 0.212 mmol) in DCM (100 mL) was added benzylidene-bis(tricyclohexylphosphine)-dichlororuthenium (0.018 g, 0.021 mmol) in DCM (1 mL). The resulting reaction mixture was stirred under reflux for 69 h during which more Grubbs's 2nd generation catalyst (18 mg) was added at 27$^{th}$ h and more Grubbs's 2nd generation catalyst (9 mg) was added at 52$^{nd}$ h. The reaction mixture was evaporated down, purified by flash chromatography to afford desired product ethyl 2-{34-methyl-3,3-dioxo-10-oxa-3$\lambda^6$-thia-2,17,18,19-tetraazaheptacyclo[24.5.2.1$^{2,11}$.1$^{2^0,2^4}$.0$^{4,9}$.0$^{1^7,21}$.0$^{2^9,32}$]pentatriaconta-4(9),5,7,14,18,20(34),21,23,26(33),27,29(32)-undecaen-25-yl}acetate (45.7 mg, 0.075 mmol, 35.2% yield). LC-MS m/z 613.1 (M+H)$^+$, 1.17 and 1.20 min (ret. time).

2-{34-Methyl-3,3-dioxo-10-oxa-3$\lambda^6$-thia-2,17,18,19-tetraazaheptacyclo[24.5.2, 1$^{2,11}$.1$^{2^0,2^4}$.0$^{4,9}$.0$^{1^7,21}$.0$^{2^9,32}$]pentatriaconta-4(9),5, 7,18,20(34),21,23,26(33),27,29(32)-decaen-25-yl}acetic acid

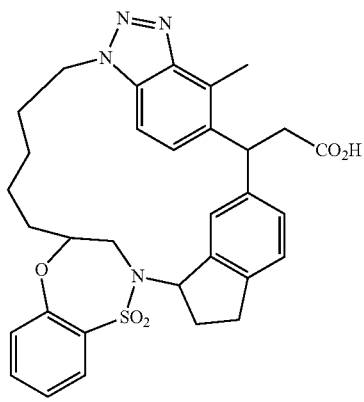 [SMILES: Cc1c2ccc3c1nnn3CCCCCC1CN(C3CCc4ccc(cc43)C2CC(=O)O)S(=O)(=O)c2ccccc2O1]

To a solution of ethyl 2-{34-methyl-3,3-dioxo-10-oxa-3λ⁶-thia-2,17,18,19-tetraazaheptacyclo[24.5.2.1²,¹¹.1²⁰,²⁴.0⁴,⁹.0¹⁷,²¹.0²⁹,³²]pentatriaconta-4(9),5,7,14,18,20(34),21,23,26(33),27,29(32)-undecaen-25-yl}acetate (45 mg, 0.073 mmol) in MeOH (7.00 mL) was added 20% Pd(OH)$_2$ (1.031 mg, 7.34 μmol) and the resulting suspension stirred under an atmosphere of hydrogen for 1 h. The reaction mixture was evaporated down. This intermediate was redissolved in MeOH (3 mL). To the resulting solution was added NaOH (2 N) (14.69 mg, 0.367 mmol) and the mixture heated with microwave irradiation at 80° C. for 30 min. The reaction mixture was acidified with HCl (1 N) to pH ~5, evaporated down under vacuum, and purified with reverse phase HPLC to afford desired product isomer 1 2-{34-methyl-3,3-dioxo-10-oxa-3λ⁶-thia-2,17,18,19-tetraazaheptacyclo[24.5.2.1²,¹¹.1²⁰,²⁴.0⁴,⁹.0¹⁷,²¹.0²⁹,³²]pentatriaconta-4(9),5,7,18,20(34),21,23,26(33),27,29(32)-decaen-25-yl}acetic acid (5.5 mg, 9.37 μmol, 12.76% yield). LC-MS m/z 587.3 (M+H)⁺, 1.03 min (ret. time).

Example 264

2-{34-Methyl-3,3-dioxo-10-oxa-3λ⁶-thia-2,17,18,19-tetraazaheptacyclo[24.5.2.1²,¹¹.1²⁰,²⁴.0⁴,⁹.0¹⁷,²¹.0²⁹,³²]pentatriaconta-4(9),5,7,18,20(34),21,23,26(33),27,29(32)-decaen-25-yl}acetic acid

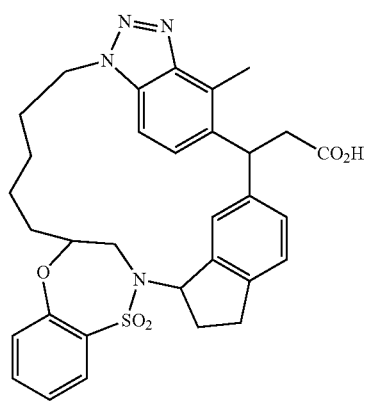 [SMILES: Cc1c2ccc3c1nnn3CCCCCC1CN(C3CCc4ccc(cc43)C2CC(=O)O)S(=O)(=O)c2ccccc2O1]

To a solution of ethyl 2-{34-methyl-3,3-dioxo-10-oxa-3λ⁶-thia-2,17,18,19-tetraazaheptacyclo[24.5.2.1²,¹¹.1²⁰,²⁴.0⁴,⁹.0¹⁷,²¹.0²⁹,³²]pentatriaconta-4(9),5,7,14,18,20(34),21,23,26(33),27,29(32)-undecaen-25-yl}acetate (45 mg, 0.073 mmol) in MeOH (7.00 mL) was added 20% Pd(OH)$_2$ (1.031 mg, 7.34 μmol) and the resulting suspension stirred under an atmosphere of hydrogen for 1 h. The reaction mixture was evaporated down. This intermediate was redissolved in MeOH (3 mL). To the resulting solution was added NaOH (2 N) (14.69 mg, 0.367 mmol) and the mixture heated with microwave irradiation at 80° C. for 30 min. The reaction mixture was acidified with HCl (1 N) to pH ~5, evaporated down under vacuum, and purified with reverse phase HPLC to afford desired product isomer 2 2-{34-methyl-3,3-dioxo-10-oxa-3λ⁶-thia-2,17,18,19-tetraazaheptacyclo[24.5.2.1²,¹¹.1²⁰,²⁴.0⁴,⁹.0¹⁷,²¹.0²⁹,³²]pentatriaconta-4(9),5,7,18,20(34),21,23,26(33),27,29(32)-decaen-25-yl}acetic acid (6.1 mg, 10.40 μmol, 14.16% yield). LC-MS m/z 587.3 (M+H)⁺, 1.03 min (ret. time).

Example 265

2-{4,32-Dimethyl-30,30-dioxo-23-oxa-30λ⁶-thia-1,14,15,16-tetraazahexacyclo[20.8.1.1³,⁷.1⁹,¹³.0¹²,¹⁶.0²⁴,²⁹]tritriaconta-3,5,7(33),9,11,13(32),14,24(29),25,27-decaen-8-yl}acetic acid

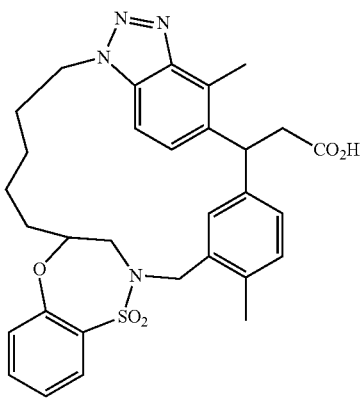 [SMILES: Cc1ccc2cc1CN1CC(CCCCCn3nnc4c(C)c(ccc43)C2CC(=O)O)Oc2ccccc2S1(=O)=O]

Ethyl 3-(1-allyl-4-methyl-1H-benzo[d][1,2,3]triazol-5-yl)-3-(3-(hydroxymethyl)-4-methylphenyl)propanoate

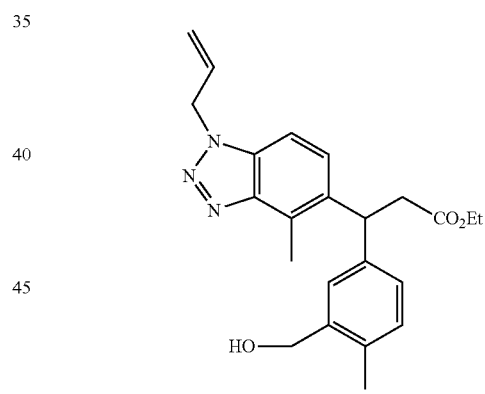

To a solution of (E)-ethyl 3-(1-allyl-4-methyl-1H-benzo[d][1,2,3]triazol-5-yl)acrylate (0.3 g, 1.106 mmol) in 1,4-dioxane (12 mL) and water (4 mL) was added (3-(hydroxymethyl)-4-methylphenyl)boronic acid (0.400 g, 2.410 mmol), Et$_3$N (0.462 mL, 3.32 mmol) and [Rh(cod)Cl]$_2$ (0.027 g, 0.055 mmol). The resulting reaction mixture was stirred at 90° C. for 16 h before was added more (3-(hydroxymethyl)-4-methylphenyl)boronic acid (0.2 g) and stirred at 90° C. for another 1 h. The reaction mixture was evaporated down under vacuum, and purified by flash chromatography to afford desired product ethyl 3-(1-allyl-4-methyl-1H-benzo[d][1,2,3]triazol-5-yl)-3-(3-(hydroxymethyl)-4-methylphenyl)propanoate (0.2107 g, 0.535 mmol, 48.4% yield). LC-MS m/z 394.2 (M+H)⁺, 0.97 min (ret. time).

531

Ethyl 3-(1-allyl-4-methyl-1H-benzo[d][1,2,3]triazol-5-yl)-3-(3-((4-(but-3-en-1-yl)-1,1-dioxido-3,4-dihydro-2H-benzo[b][1,4,5]oxathiazepin-2-yl)methyl)-4-methylphenyl)propanoate

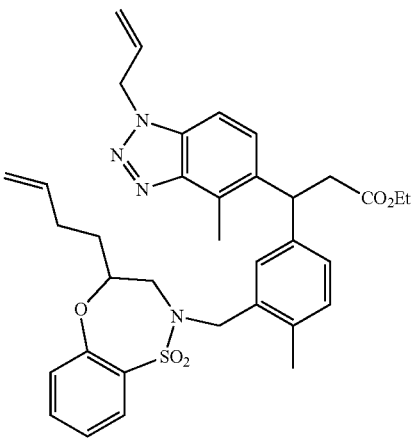 [SMILES: C=CCCC1CN(Cc2cc(C(CC(=O)OCC)c3ccc4c(nnn4CC=C)c3C)ccc2C)S(=O)(=O)c2ccccc2O1]

To a solution of ethyl 3-(1-allyl-4-methyl-1H-benzo[d][1,2,3]triazol-5-yl)-3-(3-(hydroxymethyl)-4-methylphenyl)propanoate (0.2107 g, 0.535 mmol) in THF (8 mL) was added 4-(but-3-en-1-yl)-3,4-dihydro-2H-benzo[b][1,4,5]oxathiazepine 1,1-dioxide (0.203 g, 0.803 mmol), PS—PPh$_3$ (1.004 g, 1.606 mmol) and DIAD (0.312 mL, 1.606 mmol). The resulting reaction mixture was stirred at RT for 1 h. The reaction mixture was filtered, evaporated down to afford crude desired product ethyl 3-(1-allyl-4-methyl-1H-benzo[d][1,2,3]triazol-5-yl)-3-(3-((4-(but-3-en-1-yl)-1,1-dioxido-3,4-dihydro-2H-benzo[b][1,4,5]oxathiazepin-2-yl)methyl)-4-methylphenyl)propanoate (0.4815 g, 0.766 mmol, 143% yield). LC-MS m/z 629.3 (M+H)$^+$, 1.32 min (ret. time).

Ethyl 2-{4,32-dimethyl-30,30-dioxo-23-oxa-30λ$^6$-thia-1,14,15,16-tetraazahexacyclo[20.8.1.1$^{3,7}$.1$^{9,13}$.0$^{12,16}$.0$^{24,29}$]tritriaconta-3,5,7(33),9,11,13(32),14,18,24(29),25,27-undecaen-8-yl}acetate

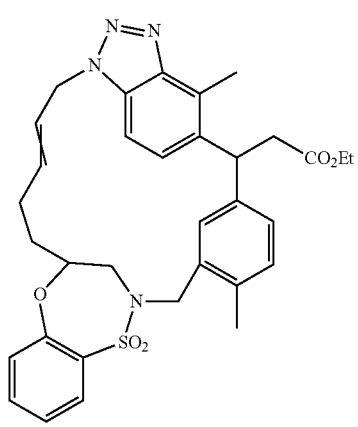 [SMILES: CCOC(=O)CC1c2ccc(C)c(c2)CN2CC(CCC=CCn3nnc4c(C)c1ccc43)Oc1ccccc1S2(=O)=O]

To a solution of ethyl 3-(1-allyl-4-methyl-1H-benzo[d][1,2,3]triazol-5-yl)-3-(3-((4-(but-3-en-1-yl)-1,1-dioxido-3,4-dihydro-2H-benzo[b][1,4,5]oxathiazepin-2-yl)methyl)-4-methylphenyl)propanoate (0.24 g, 0.382 mmol) in DCM (100 mL) was added benzylidene-bis(tricyclohexylphosphine)-dichlororuthenium (0.065 g, 0.076 mmol) in DCM (1 mL). The resulting reaction mixture was stirred at reflux for 45 h during which more Grubbs's 2nd generation catalyst (65 mg) was added at 21$^{st}$ h. The reaction mixture was evaporated down, purified by flash chromatography before further purified with reverse phase HPLC to afford desired product ethyl 2-{4,32-dimethyl-30,30-dioxo-23-oxa-30λ$^6$-thia-1,14,15,16-tetraazahexacyclo[20.8.1.1$^{3,7}$.1$^{9,13}$.0$^{12,16}$.0$^{24,29}$]tritriaconta-3,5,7(33),9,11,13(32),14,18,24(29),25,27-undecaen-8-yl}acetate (106.7 mg, 0.178 mmol, 46.5% yield). LC-MS m/z 601.1 (M+H)$^+$, 1.16 and 1.21 min (ret. time).

2-{4,32-Dimethyl-30,30-dioxo-23-oxa-30λ$^6$-thia-1,14,15,16-tetraazahexacyclo[20.8.1.1$^{3,7}$.1$^{9,13}$.0$^{12,16}$.0$^{24,29}$]tritriaconta-3,5,7(33),9,11,13(32),14,24(29),25,27-decaen-8-yl}acetic acid

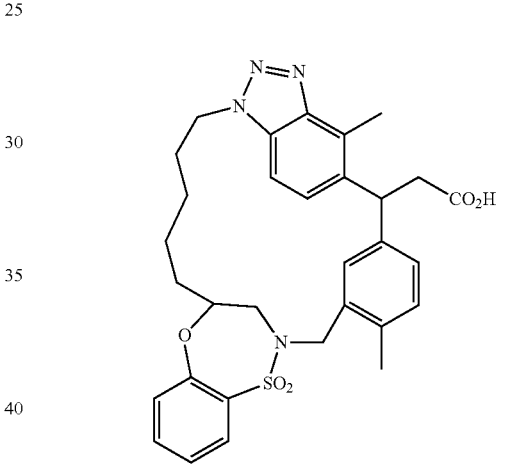

To a solution of ethyl 2-{4,32-dimethyl-30,30-dioxo-23-oxa-30λ$^6$-thia-1,14,15,16-tetraazahexacyclo[20.8.1.1$^{3,7}$.1$^{9,13}$.0$^{12,16}$.0$^{24,29}$]tritriaconta-3,5,7(33),9,11,13(32),14,18,24(29),25,27-undecaen-8-yl}acetate (56.7 mg, 0.094 mmol) was reduced by 20% Pd(OH)$_2$ (13.26 mg, 0.094 mmol) under an atmosphere of hydrogen in the mixture of MeOH (30 mL) and DCM (5.0 mL) using H-CUBE. The reaction mixture was then evaporated down. This intermediate was redissolved in MeOH (2 mL) then added NaOH (2 N) (18.88 mg, 0.472 mmol) before was heated with microwave irradiation at 80° C. for 30 min. The reaction mixture was acidified with HCl (1 N) to pH ~5, evaporated down under vacuum, and purified with reverse phase HPLC to afford desired product isomer 1 2-{4,32-dimethyl-30,30-dioxo-23-oxa-30λ$^6$-thia-1,14,15,16-tetraazahexacyclo[20.8.1.1$^{3,7}$.1$^{9,13}$.0$^{12,16}$.0$^{24,29}$]tritriaconta-3,5,7(33),9,11,13(32),14,24(29),25,27-decaen-8-yl}acetic acid (24.6 mg, 0.043 mmol, 45.4% yield). LC-MS m/z 575.4 (M+H)$^+$, 1.00 min (ret. time).

Example 266

2-{4,32-Dimethyl-30,30-dioxo-23-oxa-30λ6-thia-1,14,15,16-tetraazahexacyclo[20.8.1.1$^{3,7}$.1$^{9,13}$.0$^{12,1^6}$.0$^{24,29}$]tritriaconta-3,5,7(33),9,11,13(32),14,18,24(29),25,27-undecaen-8-yl}acetic acid

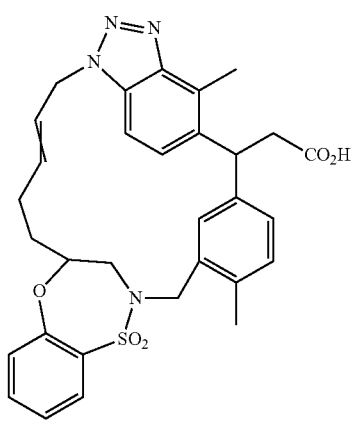 [SMILES: Cc1ccc2cc1CN1CC(CCC=CCn3nnc4c(C)c(ccc43)C2CC(=O)O)Oc2ccccc2S1(=O)=O]

To a solution of ethyl 2-{4,32-dimethyl-30,30-dioxo-23-oxa-30λ$^6$-thia-1,14,15,16-tetraazahexacyclo[20.8.1.1$^{3,7}$.1$^{9,13}$.0$^{12,1^6}$.0$^{24,29}$]tritriaconta-3,5,7(33),9,11,13(32),14,18,24(29),25,27-undecaen-8-yl}acetate (50 mg, 0.083 mmol) in MeOH (2 mL) was added NaOH (2 N) (16.65 mg, 0.416 mmol) and the resulting suspension was heated with microwave irradiation at 80° C. for 30 min. The reaction mixture was acidified with HCl (1 N) to pH ~5, evaporated down under vacuum, and purified with reverse phase HPLC to afford desired product isomer 1 2-{4,32-dimethyl-30,30-dioxo-23-oxa-30λ$^6$-thia-1,14,15,16-tetraazahexacyclo[20.8.1.1$^{3,7}$.1$^{9,13}$.0$^{12,1^6}$.0$^{24,29}$]tritriaconta-3,5,7(33),9,11,13(32),14,18,24(29),25,27-undecaen-8-yl}acetic acid (8.2 mg, 0.014 mmol, 17.20% yield). LC-MS m/z 573.3 (M+H)$^+$, 1.00 min (ret. time).

Example 267

2-{34-Methyl-3,3-dioxo-10-oxa-3λ$^6$-thia-2,17,18,19-tetraazaheptacyclo[24.5.2.1$^{2,11}$.1$^{2^0,2^4}$.0$^{4,9}$.0$^{1^7,21}$.0$^{2^9,3^2}$]pentatriaconta-4(9),5,7,14,18,20(34),21,23,26(33),27,29(32)-undecaen-25-yl}acetic acid

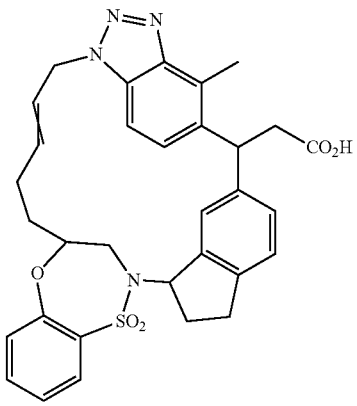 [SMILES: Cc1c2ccc3c1nnn3CC=CCCC1CN(C3CCc4ccc(cc43)C2CC(=O)O)S(=O)(=O)c2ccccc2O1]

Ethyl 2-{34-methyl-3,3-dioxo-10-oxa-3λ$^6$-thia-2,17,18,19-tetraazaheptacyclo[24.5.2.1$^{2,11}$.1$^{2^0,2^4}$.0$^{4,9}$.0$^{1^7,21}$.0$^{2^9,3^2}$]pentatriaconta-4(9),5,7,14,18,20(34),21,23,26(33),27,29(32)-undecaen-25-yl}acetate

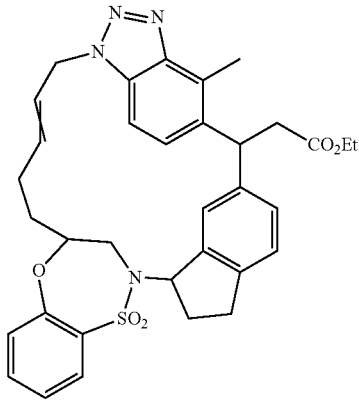 [SMILES: CCOC(=O)CC1c2ccc3c(c2)C(CC3)N2CC(CCC=CCn3nnc4c(C)c1ccc43)Oc1ccccc1S2(=O)=O]

To a solution of ethyl 3-(1-allyl-4-methyl-1H-benzo[d][1,2,3]triazol-5-yl)-3-(3-(4-(but-3-en-1-yl)-1,1-dioxido-3,4-dihydro-2H-benzo[b][1,4,5]oxathiazepin-2-yl)-2,3-dihydro-1H-inden-5-yl)propanoate (0.3442 g, 0.537 mmol) in DCM (50 mL) was added benzylidene-bis(tricyclohexylphosphine)-dichlororuthenium (0.046 g, 0.054 mmol) in DCM (1 mL). The resulting reaction mixture was stirred at reflux for 48 h during which more Grubbs's 2nd generation catalyst (46 mg) was added at 24$^{th}$ h. The reaction mixture was evaporated down, purified by flash chromatography to afford desired product ethyl 2-{34-methyl-3,3-dioxo-10-oxa-3λ$^6$-thia-2,17,18,19-tetraazaheptacyclo[24.5.2.1$^{2,11}$.1$^{2^0,2^4}$.0$^{4,9}$.0$^{1^7,21}$.0$^{2^9,3^2}$]pentatriaconta-4(9),5,7,14,18,20(34),21,23,26(33),27,29(32)-undecaen-25-yl}acetate (42.7 mg, 0.070 mmol, 12.97% yield). LC-MS m/z 613.1 (M+H)$^+$, 1.20 min (ret. time).

2-{34-Methyl-3,3-dioxo-10-oxa-3λ$^6$-thia-2,17,18,19-tetraazaheptacyclo[24.5.2.1$^{2,11}$.1$^{2^0,2^4}$.0$^{4,9}$.0$^{1^7,21}$.0$^{2^9,3^2}$]pentatriaconta-4(9),5,7,14,18,20(34),21,23,26(33),27,29(32)-undecaen-25-yl}acetic acid

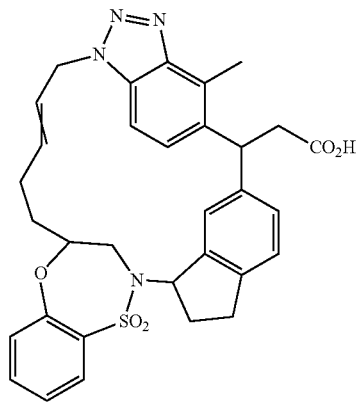 [SMILES: Cc1c2ccc3c1nnn3CC=CCCC1CN(C3CCc4ccc(cc43)C2CC(=O)O)S(=O)(=O)c2ccccc2O1]

To a solution of ethyl 2-{34-methyl-3,3-dioxo-10-oxa-3λ$^6$-thia-2,17,18,19-tetraazaheptacyclo[24.5.2.1$^{2,11}$.1$^{20,24}$.0$^{4,9}$.0$^{17,21}$.0$^{29,32}$]pentatriaconta-4(9),5,7,14,18,20(34),21,23,26(33),27,29(32)-undecaen-25-yl}acetate (45 mg, 0.073 mmol) in MeOH (2 mL) was added NaOH (2 N) (14.69 mg, 0.367 mmol) and the resulting suspension was stirred at 80° C. for 0.5 h. The reaction mixture was acidified with HCl (1 N) to pH ~5, evaporated down under vacuum, and purified with reverse phase HPLC to afford the desired product isomer 1 2-{34-methyl-3,3-dioxo-10-oxa-3λ$^6$-thia-2,17,18,19-tetraazaheptacyclo[24.5.2.1$^{2,11}$.1$^{20,24}$.0$^{4,9}$.0$^{17,21}$.0$^{29,32}$]pentatriaconta-4(9),5,7,14,18,20(34),21,23,26(33),27,29(32)-undecaen-25-yl}acetic acid (5.4 mg, 9.24 μmol, 12.58% yield). LC-MS m/z 585.3 (M+H)$^+$, 0.94 min (ret. time).

Example 268

3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid

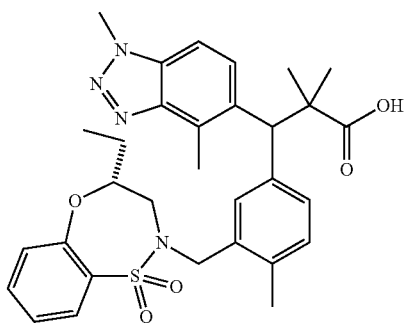 [SMILES: CC[C@@H]1CN(Cc2cc(C(c3ccc4c(nnn4C)c3C)C(C)(C)C(=O)O)ccc2C)S(=O)(=O)c2ccccc2O1]

1,4-dimethyl-1H-benzo[d][1,2,3]triazole-5-carbaldehyde

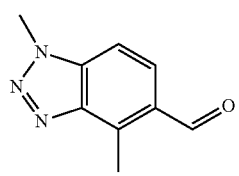

A solution of n-BuLi (1.6M in hexane) (7.36 mL, 11.78 mmol) and ethylmagnesium bromide (1.0 M in hexane) (8.49 mL, 8.49 mmol) was diluted with toluene (30 mL) and cooled to −78° C. The solution was stirred at −78° C. for 40 min after which time a solution of 5-bromo-1,4-dimethyl-1Hbenzo[d][1,2,3]triazole (2.4 g, 10.62 mmol) in THF (10.00 mL) was added. The resulting dark colored solution was allowed to stir for 1 h during which time the cooling bath warmed to −15° C. To this solution was added DMF (4.97 mL, 64.2 mmol) and the resulting solution was stirred at −15 to −10° C. for 1 h and then the cooling bath was removed. After a further 1.5 h the reaction was quenched via the addition of saturated NH$_4$Cl solution dropwise (25 mL) and diluted with water (50 mL) and EtOAc (50 mL). The layers were separated and the aqueous phase extracted with EtOAc (100 mL). The combined organics were dried over Na$_2$SO$_4$ and concentrated. The residue was purified via silica gel chromatography with hexane ethylacetate to yield 1,4-dimethyl-1H-benzo[d][1,2,3]triazole-5-carbaldehyde (1.07 g, 5.92 mmol, 55.8% yield) as an amber solid. LC-MS m/z 175.9 (M+H)$^+$, 0.58 min (ret. time).

(5-bromo-2-methylphenyl)methanol

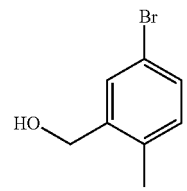

To a stirred solution of 5-bromo-2-methylbenzoic acid (10.0 g, 46.5 mmol) in THF (50 mL) was added LAH (46.5 mL, 46.5 mmol, 1 M in THF) dropwise at 0° C. After 0.5 h the reaction turned a milky white color and then stirred for another 1.5 h. The reaction was then quenched with the dropwise addition of saturated Na$_2$SO$_4$ in water at 0° C. The reaction was diluted with Et$_2$O (100 mL) and water (100 mL). The organic phase was separated from the aqueous phase, dried over Na$_2$SO$_4$ and concentrated in vacuo. The residue was purified via silica gel chromatography with hexane ethylacetate to yield (5-bromo-2-methylphenyl)methanol (7.3 g, 34.1 mmol, 73.4% yield) as a white solid. LC-MS m/z 182.8 (M−OH)$^+$, 0.78 min (ret. time).

(R)-2-(5-bromo-2-methylbenzyl)-4-ethyl-3,4-dihydro-2H-benzo[b][1,4,5]oxathiazepine 1,1-dioxide

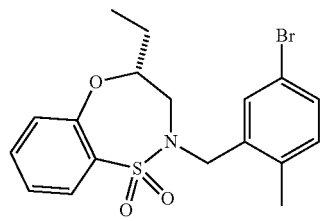 [SMILES: CC[C@@H]1CN(Cc2cc(Br)ccc2C)S(=O)(=O)c2ccccc2O1]

To a solution of (R)-4-ethyl-3,4-dihydro-2H-benzo[b][1,4,5]oxathiazepine 1,1-dioxide (593 mg, 2.61 mmol), (5-bromo-2-methylphenyl)methanol (500 mg, 2.487 mmol) and ADDP (1255 mg, 4.97 mmol) in dry THF (35 mL) was added tributylphosphine (1.227 mL, 4.97 mmol). After 15 min the reaction became cloudy. The reaction was stirred for an additional 18 h. The reaction was then concentrated and the residue purified via silica gel chromatography with hexane EtOAc to yield (R)-2-(5-bromo-2-methylbenzyl)-4-ethyl-3,4-dihydro-2H-benzo[b][1,4,5]oxathiazepine 1,1-dioxide (825 mg, 1.608 mmol, 64.7% yield) as a white solid. LC-MS m/z 410.0 (M+H)$^+$, 1.31 min (ret. time).

(4R)-2-(5-((1,4-dimethyl-1H-benzo[d][1,2,3]triazol-5-yl)(hydroxy)methyl)-2-methylbenzyl)-4-ethyl-3,4-dihydro-2H-benzo[b][1,4,5]oxathiazepine 1,1-dioxide

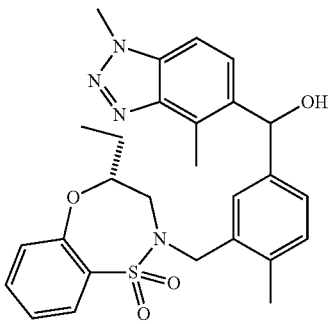 [SMILES: CC[C@@H]1CN(Cc2cc(C(O)c3ccc4c(nnn4C)c3C)ccc2C)S(=O)(=O)c2ccccc2O1]

To a stirred solution of (R)-2-(5-bromo-2-methylbenzyl)-4-ethyl-3,4-dihydro-2Hbenzo[b][1,4,5]oxathiazepine 1,1-dioxide (360 mg, 0.877 mmol) in dry THF (24 mL) was added n-BuLi (0.658 mL, 1.053 mmol) at −78° C. The reaction mixture was stirred at −78° C. for 30 min then 1,4-dimethyl-1H-benzo[d][1,2,3]triazole-5-carbaldehyde (184 mg, 1.053 mmol) was added. The reaction was stirred at −78° C. for 1 h and gradually warmed to 0° C. over the next 30 min. Then let it stir at RT for 1 h. The reaction mixture was quenched with saturated NH$_4$Cl (10 mL) and diluted with EtOAc (20 mL). The two phases were separated and the organic phase was concentrated in vacuo. The residue was purified with reverse-phase HPLC CH$_3$CN/H$_2$O (0.1% TFA) to yield (4R)-2-(5-((1,4-dimethyl-1H-benzo[d][1,2,3]triazol-5-yl)(hydroxy)methyl)-2-methylbenzyl)-4-ethyl-3,4-dihydro-2H-benzo[b][1,4,5]oxathiazepine 1,1-dioxide (250 mg, 0.395 mmol, 45.0% yield) as a white foam. LC-MS m/z 507.1 (M+H)$^+$, 1.06 min (ret. time).

Methyl 3-(1,4-dimethyl-1H-benzo[d][1,2,3]triazol-5-yl)-3-(3-(((R)-4-ethyl-1,1-dioxido-3,4-dihydro-2Hbenzo[b][1,4,5]oxathiazepin-2-yl)methyl)-4-methylphenyl)-2,2-dimethylpropanoate

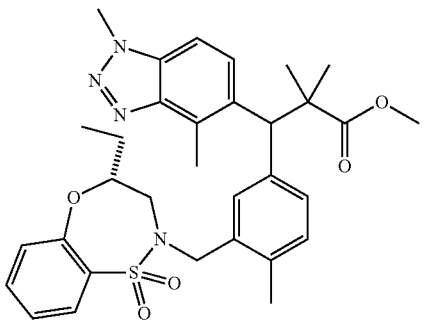 [SMILES: CC[C@@H]1CN(Cc2cc(C(c3ccc4c(nnn4C)c3C)C(C)(C)C(=O)OC)ccc2C)S(=O)(=O)c2ccccc2O1]

To a solution of (4R)-2-(5-((1,4-dimethyl-1H-benzo[d][1,2,3]triazol-5-yl)(hydroxy)methyl)-2-methylbenzyl)-4-ethyl-3,4-dihydro-2H-benzo[b][1,4,5]oxathiazepine 1,1-dioxide (50 mg, 0.099 mmol) in dry DCM (2 mL) was added titanium tetrachloride (0.099 mL, 0.099 mmol) at 0° C. The reaction was stirred for 10 min and ((1-methoxy-2-methylprop-1-en-1-yl)oxy)trimethylsilane (0.040 mL, 0.197 mmol) was added maintaining the reaction at 0° C. and stirred for another 20 min. The reaction was then quenched with the addition of saturated NaHCO$_3$ solution and a white precipitate formed. The reaction mixture was then diluted with DCM (10 mL) and the organic layer was separated and concentrated. The residue was purified via silica gel chromatography with hexane ethylacetate to yield methyl 3-(1,4-dimethyl-1H-benzo[d][1,2,3]triazol-5-yl)-3-(3-(((R)-4-ethyl-1,1-dioxido-3,4-dihydro-2Hbenzo[b][1,4,5]oxathiazepin-2-yl)methyl)-4-methylphenyl)-2,2-dimethylpropanoate (49 mg, 0.083 mmol, 84% yield) as a colorless solid. LC-MS m/z 591.2 (M+H)$^+$, 1.30 min (ret. time).

3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid

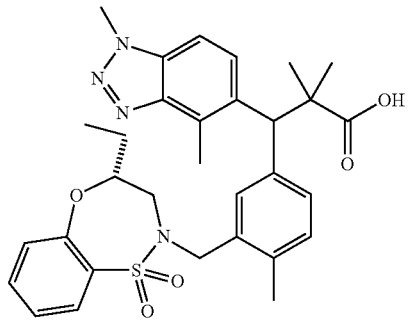 [SMILES: CC[C@@H]1CN(Cc2cc(C(c3ccc4c(nnn4C)c3C)C(C)(C)C(=O)O)ccc2C)S(=O)(=O)c2ccccc2O1]

To a stirred solution of methyl 3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoate (55 mg, 0.093 mmol) in THF (2 mL) and water (2.000 mL) was added LiOH (2.230 mg, 0.093 mmol) stirred for 18 h at RT. The reaction did not proceed so the reaction was heated to 80° C. for 4 h. Again the reaction did not proceed. The reaction was transferred to a 20 mL microwave vial and heated to 100° C. for 30 min. The reaction went only about 30% so the reaction was put into the microwave reactor again and this time heated to 125° C. for 60 min. The reaction was neutralized with 1 N HCl and purified reverse-phase HPLC CH$_3$CN/H$_2$O (0.1% TFA) to yield 3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid (30 mg, 0.052 mmol, 55.9% yield) as a white solid. LC-MS m/z 577.2 (M+H)$^+$, 1.13 min (ret. time).

3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid (Alternative Synthesis)

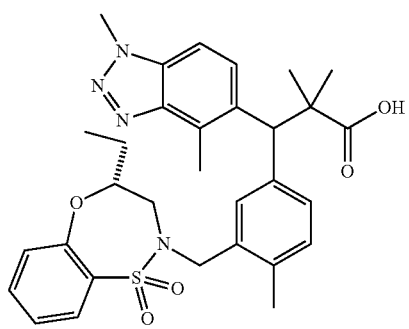 [SMILES: CC[C@@H]1CN(Cc2cc(C(c3ccc4c(nnn4C)c3C)C(C)(C)C(=O)O)ccc2C)S(=O)(=O)c2ccccc2O1]

To a solution of (4R)-2-(5-((1,4-dimethyl-1H-benzo[d][1,2,3]triazol-5-yl)(hydroxy)methyl)-2-methylbenzyl)-4-ethyl-3,4-dihydro-2H-benzo[b][1,4,5]oxathiazepine 1,1-dioxide (170 mg, 0.336 mmol) in dry DCM (6 mL) was added ((1-methoxy-2-methylprop-1-en-1-yl)oxy)trimethylsilane (0.136 mL, 0.671 mmol) and titanium tetrachloride (0.336 mL, 0.336 mmol) at 0° C. The reaction was stirred for 30 min at which time the reaction mixture was concentrated and redissolved in MeOH (6 mL) and transferred to a microwave vial. Then a solution of LiOH (48.2 mg, 2.013 mmol) in water (3 mL) was added to the solution. A white cloudy mixture formed so THF (3 mL) was added to dissolve the intermediate better. The reaction mixture was then heated in the microwave at 125° C. for 5 h. The reaction mixture was acidified using formic acid and concentrated. The residue was purified via reverse-phase HPLC CH$_3$CN/H$_2$O (0.1% TFA) to yield H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid (75.2 mg, 0.130 mmol, 38.9% yield) as a white solid. LC-MS m/z 577.2 (M+H)$^+$, 1.13 min (ret time).

Example 269

(S)-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid

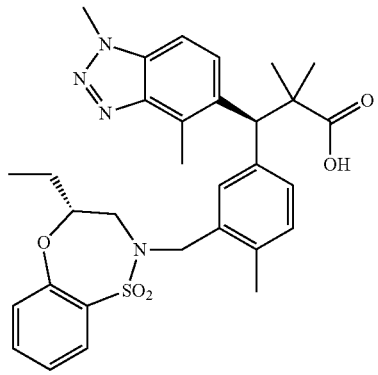 [SMILES: CC[C@@H]1CN(Cc2cc([C@@H](c3ccc4c(nnn4C)c3C)C(C)(C)C(=O)O)ccc2C)S(=O)(=O)c2ccccc2O1]

4-Bromo-2-(((4-methoxybenzyl)oxy)methyl)-1-methylbenzene

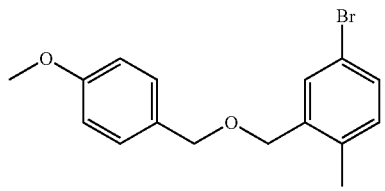 [SMILES: COc1ccc(COCc2cc(Br)ccc2C)cc1]

To a stirred solution of (5-bromo-2-methylphenyl)methanol (100 g, 497 mmol) in dry DMF (800 mL) was added NaH (21.88 g, 547 mmol). After the reaction mixture was stirred for 30 minutes, 1-(chloromethyl)-4-methoxybenzene (82 g, 522 mmol) was added at 0° C. and the reaction mixture was stirred for another 2 h at RT. The reaction was then diluted with Et$_2$O (200 mL) and water (200 mL). The organic phase was washed with brine (300 mL) and dried with Na$_2$SO$_4$ and concentrated under reduced pressure. The residue was purified via silica gel column (petroleum ether:EtOAc=10:1) to yield 4-bromo-2-(((4-methoxybenzyl)oxy)methyl)-1-methylbenzene (140 g, 436 mmol, 88% yield) as a clear oil. $^1$H NMR (400 MHz, CHLOROFORM-d) δ ppm 2.27 (s, 3H) 3.84 (s, 3H) 4.49 (s, 2H), 4.54 (s, 2H), 6.92 (d, J=8.8, 2H), 6.94 (d, J=8.4, 1H), 7.31-7.35 (m, 3H), 7.54 (d, J=2, 1H).

3-(4-Methoxybenzyl)oxy)methyl)-4-methyl benzaldehyde

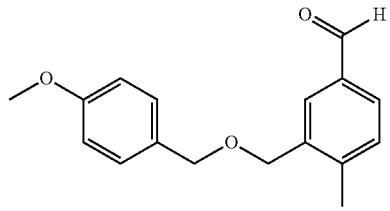 [SMILES: COc1ccc(COCc2cc(C=O)ccc2C)cc1]

To a stirred solution of 4-bromo-2-(((4-methoxybenzyl)oxy)methyl)-1-methylbenzene (80 g, 249 mmol) in THF (800 mL) at −78° C. under N$_2$, n-BuLi (120 mL, 299 mmol) was carefully added. The reaction mixture was stirred at −78° C. for 65 min, and then DMF (38.6 mL, 498 mmol) was added. The reaction mixture was stirred at −78° C. to 25° C. for another 30 min. The mixture was quenched with sat. NH$_4$Cl (300 mL), and extracted with EtOAc (2×500 mL), the organic layer was washed with water (300 mL) and brine (2×100 mL), dried (Na$_2$SO$_4$) and concentrated. The residue was washed with petroleum ether:EtOAc=10/1 (2000 mL) to give the desired product 3-(((4-methoxybenzyl)oxy)methyl)-4-methylbenzaldehyde (50 g, 185 mmol, 74.3% yield) as a solid. LC-MS m/z 288.1 (M+H$_2$O)$^+$, 2.04 min (ret. time).

(1,4-dimethyl-1H-benzo[d][1,2,3]triazol-5-yl)(3-(((4-methoxybenzyl)oxy)methyl)-4-methylphenyl)methanol

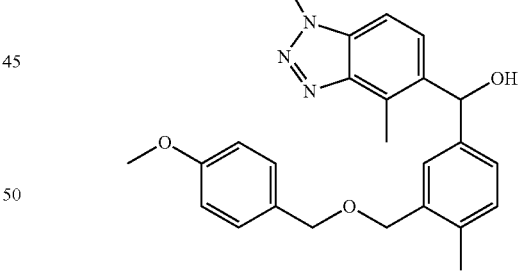

To a stirred solution of 5-bromo-1,4-dimethyl-1H-benzo[d][1,2,3]triazole (36 g, 159 mmol) in dry THF (500 mL) was added t-butyl lithium (147 mL, 191 mmol) at −78° C. under the protection of N$_2$. The reaction was stirred at −78° C. for 0.5 h after which time a solution of 3-(((4-methoxybenzyl)oxy)methyl)-4-methylbenzaldehyde (43.0 g, 159 mmol) in dry THF (500 mL) was added. It was stirred at −78° C. for 1.5 hours then warmed to RT and continually stirred for 1 h. After the reaction was complete, saturated NH$_4$Cl aqueous solution (100 mL) was added to the mixture and the mixture extracted with EtOAc (2×300 mL). The combined the organic layers were washed with brine and dried with MgSO$_4$ and concentrated. The crude product was obtained as an oil and was purified by silica gel chromatography (EtOAc:petroleum ether=1:5) to get (1,4-dimethyl-1H-benzo[d][1,2,3]triazol-5-yl)(3-(((4-methoxybenzyl)oxy)methyl)-4-methylphenyl)methanol (24 g, 57.5 mmol, 36.1% yield) as clear oil. LC-MS m/z 418.2 (M+H)$^+$, 2.05 (ret. time).

Methyl 3-(1,4-dimethyl-1H-benzo[d][1,2,3]triazol-5-yl)-3-(3-(hydroxymethyl)-4-methylphenyl)-2,2-dimethylpropanoate

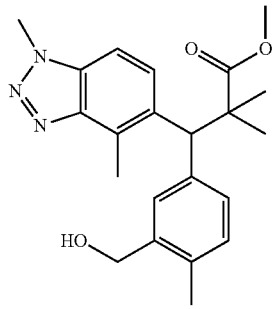 [SMILES: COC(=O)C(C)(C)C(c1ccc(C)c(CO)c1)c1ccc2c(nnn2C)c1C]

To a solution of (1,4-dimethyl-1H-benzo[d][1,2,3]triazol-5-yl)(3-(((4-methoxybenzyl)oxy)methyl)-4-methylphenyl)methanol (15.0 g, 35.9 mmol) in DCM (250.0 mL) was added ((1-methoxy-2-methylprop-1-en-1-yl)oxy)trimethylsilane (12.53 g, 71.9 mmol). Titanium tetrachloride (3.96 mL, 35.9 mmol) in DCM (20 ml) was slowly added to the reaction at 0° C. under N$_2$ protection. The mixture was stirred at 0° C. for 0.5 h under N$_2$ protection, then was warmed to RT and continuously stirred for 4 h. The reaction was poured into 100 mL of saturated NaHCO$_3$ solution at 0° C. and the organic layer was separated. The aqueous layer was extracted with DCM (3×50 mL). The combined organic layers were washed with brine and dried over anhydrous Na$_2$SO$_4$. After filtration and concentration, the residue was purified with a short silica column (eluted with petroleum ether:EtOAc=1:1) to give methyl 3-(1,4-dimethyl-1H-benzo[d][1,2,3]triazol-5-yl)-3-(3-(hydroxymethyl)-4-methylphenyl)-2,2-dimethylpropanoate (3.0 g, 7.63 mmol, 21.23% yield) as a solid. LC-MS m/z 382.2 (M+H)$^+$, 1.82 (ret.time).

(S)-Methyl 3-(1,4-dimethyl-1H-benzo[d][1,2,3]triazol-5-yl)-3-(3-(hydroxymethyl)-4-methylphenyl)-2,2-dimethylpropanoate and (R)-methyl 3-(1,4-dimethyl-1H-benzo[d][1,2,3]triazol-5-yl)-3-(3-(hydroxymethyl)-4-methylphenyl)-2,2-dimethylpropanoate isomer 1

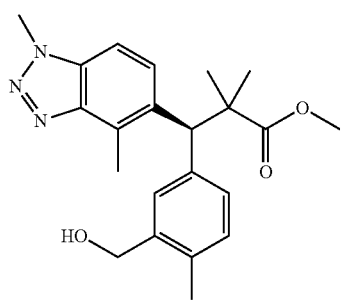

isomer 2

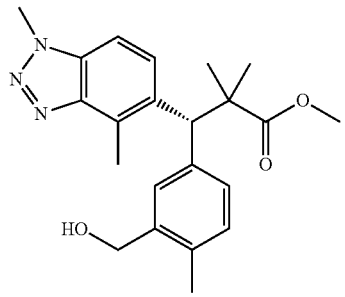

Methyl 3-(1,4-dimethyl-1H-benzo[d][1,2,3]triazol-5-yl)-3-(3-(hydroxymethyl)-4-methylphenyl)-2,2-dimethylpropanoate (4.5 g, 11.80 mmoL) was separated by chiral SFC to afford (S)-methyl 3-(1,4-dimethyl-1H-benzo[d][1,2,3]triazol-5-yl)-3-(3-(hydroxymethyl)-4-methylphenyl)-2,2-dimethylpropanoate (1.4 g, 29.6%, isomer 1) and (R)-methyl 3-(1,4-dimethyl-1H-benzo[d][1,2,3]triazol-5-yl)-3-(3-(hydroxymethyl)-4-methylphenyl)-2,2-dimethylpropanoate (1.1 g, 23.22%, isomer 2).

Isomer 1 $^1$H NMR (400 MHz, CHLOROFORM-d) δ ppm 1.32 (s, 3H), 1.41 (s, 3H), 2.29 (s, 3H), 2.82 (s, 3H), 3.50 (s, 3H), 4.25 (s, 3H), 4.64 (s, 2H), 4.89 (s, 1H), 7.07 (m, 2H), 7.22 (d, J=1.2, 1H), 7.28 (m, 1H), 7.63 (d, J=9.2, 1H).

Isomer 2 $^1$H NMR (400 MHz, CHLOROFORM-d) δ ppm 1.24 (s, 3H), 1.41 (s, 3H), 2.29 (s, 3H), 2.82 (s, 3H), 3.50 (s, 3H), 4.26 (s, 3H), 4.64 (s, 2H), 4.89 (s, 1H), 7.07 (m, 2H), 7.22 (d, J=1.2, 1H), 7.28 (m, 1H), 7.63 (d, J=8.4, 1H).

(S)-3-(1,4-dimethyl-1H-benzo[d][1,2,3]triazol-5-yl)-3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid

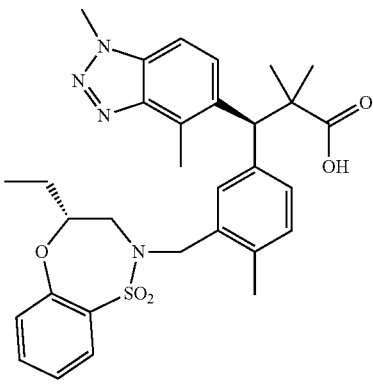 [SMILES: CC[C@@H]1CN(Cc2cc([C@@H](c3ccc4c(nnn4C)c3C)C(C)(C)C(=O)O)ccc2C)S(=O)(=O)c2ccccc2O1]

To a solution of (S)-methyl 3-(1,4-dimethyl-1H-benzo[d][1,2,3]triazol-5-yl)-3-(3-(hydroxymethyl)-4-methylphenyl)-2,2-dimethylpropanoate (150 mg, 0.393 mmol) in THF (5 mL) was added (R)-4-ethyl-3,4-dihydro-2H-benzo[b][1,4,5]oxathiazepine 1,1-dioxide (134 mg, 0.590 mmol), PS—PPh$_3$ (492 mg, 0.786 mmol) and then DIAD (0.153 mL, 0.786 mmol). The resulting reaction mixture was stirred at RT for 1 h. The reaction mixture was filtered, concentrated under vacuum, and redissolved in MeOH (6.00 mL). To this solution was added NaOH (3 N) (0.786 mL, 2.359 mmol). The resulting reaction mixture was heated with microwave irradiation at 130° C. for 2 h. To the reaction mixture was added THF (2 mL) and the mixture heated with microwave irradiation at 130° C. for 1 h. To the reaction mixture was added LiOH (47.1 mg, 1.966 mmol) and heated with microwave irradiation at 130° C. for 1 h, then at 140° C. for 2 h, and again at 140° C. for an additional 2 h. The reaction mixture was acidified with HCl (3 N) to pH 4-5, concentrated under vacuum, and purified with reverse phase HPLC to afford desired product (S)-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid (106.1 mg, 0.184 mmol, 46.8% yield). LC-MS m/z 577.4 (M+H)+, 1.12 min (ret. time).

Example 270

(R)-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid

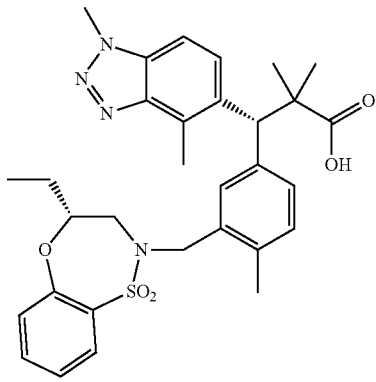 [SMILES: CC[C@@H]1CN(Cc2cc([C@H](c3ccc4c(nnn4C)c3C)C(C)(C)C(=O)O)ccc2C)S(=O)(=O)c2ccccc2O1]

To a solution of (R)-methyl 3-(1,4-dimethyl-1H-benzo[d][1,2,3]triazol-5-yl)-3-(3-(hydroxymethyl)-4-methylphenyl)-2,2-dimethylpropanoate (50 mg, 0.131 mmol) in THF (2 mL) was added (R)-4-ethyl-3,4-dihydro-2H-benzo[b][1,4,5]oxathiazepine 1,1-dioxide (44.7 mg, 0.197 mmol), PS—PPh$_3$ (164 mg, 0.262 mmol) and then DIAD (0.051 mL, 0.262 mmol). The resulting reaction mixture was stirred at RT for 18 h, filtered, and concentrated under vacuum. The resulting residue was redissolved in MeOH (2.00 mL) and THF (1 mL). To this solution was added NaOH (3 N) (0.262 mL, 0.786 mmol) and LiOH (15.69 mg, 0.655 mmol). The resulting reaction mixture was heated with microwave irradiation at 140° C. for 2 h. The reaction mixture was acidified with HCl (3 N) to pH 4-5, concentrated under vacuum, and purified with reverse phase HPLC to afford the desired product (R)-3-(1,4-dimethyl-1H-benzo[d][1,2,3]triazol-5-yl)-3-(3-(((R)-4-ethyl-1,1-dioxido-3,4-dihydro-2H-benzo[b][1,4,5]oxathiazepin-2-yl)methyl)-4-methylphenyl)-2,2-dimethylpropanoic acid (25.2 mg, 0.044 mmol, 33.3% yield). LC-MS m/z 577.4 (M+H)+, 1.07 min (ret. time).

The invention claimed is:

1. A compound which is 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid or a pharmaceutically acceptable salt thereof.

2. A pharmaceutical composition comprising the compound or pharmaceutically acceptable salt thereof according to claim 1 and a pharmaceutically acceptable excipient.

3. A method of activating Nrf2 in a human in need thereof comprising administering to said human a therapeutically effective amount of the compound or pharmaceutically acceptable salt thereof according to claim 1.

4. A compound which is (R)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid or a pharmaceutically acceptable salt thereof.

5. A pharmaceutical composition comprising the compound or pharmaceutically acceptable salt thereof according to claim 4 and a pharmaceutically acceptable excipient.

6. A method of activating Nrf2 in a human in need thereof comprising administering to said human a therapeutically effective amount of the compound or pharmaceutically acceptable salt thereof according to claim 4.

7. A compound which is (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid or a pharmaceutically acceptable salt thereof.

8. A method of activating Nrf2 in a human in need thereof comprising administering to said human a therapeutically effective amount of the compound or pharmaceutically acceptable salt thereof according to claim 7.

9. A pharmaceutical composition comprising the compound or pharmaceutically acceptable salt thereof according to claim 7 and a pharmaceutically acceptable carrier or excipient.

10. A compound which is (S)-3-(3-(((R)-4-ethyl-1, 1-dioxide-3,4-dihyrdro-2H-pyrido [2,3-b][1,4,5]oxathiazepin-2-yl)methyl)-4-methylphenyl) -3-(1-ethyl-4-methyl-1H-benzo[d][1,2,3]triazol-5-yl)propanoic acid.

11. A pharmaceutical composition comprising the compound according to claim 10 and a pharmaceutically acceptable excipient.

12. A method of activating Nrf2 in a human in need thererof comprising administering to said human a therapeutically effective amount of the compound according to claim 10.

* * * * *